(12) United States Patent
Cullen et al.

(10) Patent No.: US 9,850,262 B2
(45) Date of Patent: Dec. 26, 2017

(54) PROTEASOME ACTIVITY ENHANCING COMPOUNDS

(71) Applicant: Proteostasis Therapeutics, Inc., Cambridge, MA (US)

(72) Inventors: Matthew Cullen, Braintree, MA (US); Sheila Hauck, Lincoln, MA (US); Bolin Geng, Andover, MA (US); Megan Foley, Cambridge, MA (US); Cecilia M. Bastos, S. Grafton, MA (US); Benito Munoz, Newtonville, MA (US); Markus Haeberlein, Wellesley, MA (US)

(73) Assignee: Proteostasis Therapeutics, Inc., Cambridge, MA (US)

( * ) Notice: Subject to any disclaimer, the term of this patent is extended or adjusted under 35 U.S.C. 154(b) by 0 days.

(21) Appl. No.: 15/153,379

(22) Filed: May 12, 2016

(65) Prior Publication Data

US 2016/0333031 A1 Nov. 17, 2016

Related U.S. Application Data

(63) Continuation of application No. PCT/US2014/065204, filed on Nov. 12, 2014.

(60) Provisional application No. 61/903,330, filed on Nov. 12, 2013.

(51) Int. Cl.
| | | |
|---|---|---|
| *C07F 7/18* | (2006.01) | |
| *C07D 417/14* | (2006.01) | |
| *C07D 519/00* | (2006.01) | |
| *C07B 59/00* | (2006.01) | |
| *C07D 209/14* | (2006.01) | |
| *C07D 401/14* | (2006.01) | |
| *C07D 209/12* | (2006.01) | |
| *C07D 471/04* | (2006.01) | |
| *C07D 403/06* | (2006.01) | |
| *C07D 401/06* | (2006.01) | |

(52) U.S. Cl.
CPC .......... *C07F 7/1856* (2013.01); *C07B 59/002* (2013.01); *C07D 209/12* (2013.01); *C07D 209/14* (2013.01); *C07D 401/06* (2013.01); *C07D 401/14* (2013.01); *C07D 403/06* (2013.01); *C07D 417/14* (2013.01); *C07D 471/04* (2013.01); *C07D 519/00* (2013.01); *C07B 2200/05* (2013.01)

(58) Field of Classification Search
CPC . C07F 7/1856; C07B 59/002; C07B 2200/05; C07D 519/00; C07D 417/14; C07D 209/14; C07D 401/06; C07D 401/14; C07D 403/06; C07D 471/04; C07D 209/12

See application file for complete search history.

(56) References Cited

U.S. PATENT DOCUMENTS

| | | |
|---|---|---|
| 4,148,895 A | 4/1979 | Lattrell et al. |
| 4,290,940 A | 9/1981 | Wirth et al. |
| 4,814,344 A | 3/1989 | Humber et al. |
| 5,561,149 A | 10/1996 | Azria et al. |
| 5,852,046 A | 12/1998 | Lang et al. |
| 5,859,035 A | 1/1999 | Anthony et al. |
| 6,063,782 A | 5/2000 | Kimura et al. |
| 6,201,129 B1 | 3/2001 | Chuncharprasert et al. |
| 6,310,217 B1 | 10/2001 | Lehr |
| 6,469,171 B1 | 10/2002 | Banwell et al. |
| 6,500,853 B1 | 12/2002 | Seehra et al. |
| 6,589,954 B1 | 7/2003 | Mavunkel et al. |
| 6,627,645 B2 | 9/2003 | Andersson et al. |
| 6,828,344 B1 | 12/2004 | Bemis et al. |
| 6,867,209 B1 | 3/2005 | Mavunkel et al. |
| 7,238,713 B2 | 7/2007 | Anderson et al. |
| 7,417,063 B2 | 8/2008 | Smallheer et al. |
| 7,425,642 B2 | 9/2008 | Watanabe et al. |
| 7,482,354 B2 | 1/2009 | Traquandi et al. |
| 7,528,165 B2 | 5/2009 | Hsieh et al. |
| 7,576,206 B2 | 8/2009 | Bernardini et al. |
| 7,632,955 B2 | 12/2009 | Hsieh et al. |
| 7,767,817 B2 | 8/2010 | Wang et al. |
| 7,781,479 B2 | 8/2010 | Takahashi et al. |
| 8,097,644 B2 | 1/2012 | Beard et al. |
| 8,197,819 B2 | 6/2012 | Srivastava et al. |
| 8,293,781 B2 * | 10/2012 | Tomoo ................ C07D 209/08 514/415 |
| 2002/0037887 A1 | 3/2002 | Pintor et al. |
| 2004/0122096 A1 | 6/2004 | Lang et al. |
| 2005/0075348 A1 | 4/2005 | Harriman et al. |

(Continued)

FOREIGN PATENT DOCUMENTS

| | | |
|---|---|---|
| CN | 101016294 A | 8/2007 |
| DE | 4325204 A1 | 2/1995 |

(Continued)

OTHER PUBLICATIONS

Trader, D.J., "Establishment of a suite of assays that support the discovery of proteasome stimulators." Biochimica et Biophysica Acta (BBA)—General Subjects (2017) 1861: 892-899.*
Jaung, J., "Synthesis and keto-enol isomerism of 1-alkyl-2-methyl-5, 6-dicyano-3-[2-(5-alkylamino-2, 3-dicyanopyrazin-6-yl)-1-hydroxyethenyl]-pyrrolo [2, 3-b] pyrazine." Dyes and pigments 48.2 (2001): 133-141.*
JP 2001151771 A English Machine Translation ProQuest Dialog Feb. 9, 2017 p. 1-81.*

(Continued)

*Primary Examiner* — Matt Mauro
(74) *Attorney, Agent, or Firm* — Elmore Patent Law Group, P.C.; Mahreen Chaudhry Hoda; Carolyn S. Elmore

(57) ABSTRACT

The present invention is directed to compounds having the Formula (I), (II), (III), (IV), and (V), compositions thereof, and methods for the treatment of a condition associated with a dysfunction in proteostasis.

25 Claims, No Drawings

(56) References Cited

U.S. PATENT DOCUMENTS

| | | |
|---|---|---|
| 2005/0113357 A1 | 5/2005 | Anderson et al. |
| 2006/0116379 A1 | 6/2006 | Ogawa et al. |
| 2006/0135540 A1 | 6/2006 | Lin et al. |
| 2007/0185184 A1 | 8/2007 | Hanson et al. |
| 2007/0203121 A1 | 8/2007 | Merce Vidal et al. |
| 2008/0171772 A1 | 7/2008 | Beard et al. |
| 2008/0188453 A1 | 8/2008 | Adams et al. |
| 2009/0047246 A1 | 2/2009 | Beigelman et al. |
| 2009/0118503 A1 | 5/2009 | Sprott et al. |
| 2009/0143371 A1 | 6/2009 | Buettelmann et al. |
| 2009/0163545 A1 | 6/2009 | Goldfarb |
| 2009/0215750 A1 | 8/2009 | Bamberg et al. |
| 2009/0227538 A1 | 9/2009 | Fruchtel et al. |
| 2009/0264384 A1 | 10/2009 | Didsbury et al. |
| 2009/0264457 A1 | 10/2009 | Codony-Soler et al. |
| 2009/0318446 A1 | 12/2009 | Fischer et al. |
| 2010/0074955 A1 | 3/2010 | Buschmann et al. |
| 2010/0087415 A1 | 4/2010 | Whitten et al. |
| 2010/0087446 A1 | 4/2010 | Chakravarty et al. |
| 2010/0099726 A1 | 4/2010 | Cantley et al. |
| 2010/0113777 A1 | 5/2010 | Tomoo et al. |
| 2010/0190768 A1 | 7/2010 | Sone et al. |
| 2010/0197708 A1 | 8/2010 | Talley et al. |
| 2010/0204282 A1 | 8/2010 | Hutchinson et al. |
| 2010/0249069 A1 | 9/2010 | Donello et al. |
| 2010/0331297 A1 | 12/2010 | Bulawa et al. |
| 2011/0009453 A1 | 1/2011 | Donello et al. |
| 2011/0098483 A1 | 4/2011 | Petasis et al. |
| 2011/0144090 A1 | 6/2011 | Elder et al. |
| 2011/0319403 A1 | 12/2011 | Aslanian et al. |
| 2012/0006417 A1 | 1/2012 | Folk |
| 2012/0022057 A1 | 1/2012 | Aslanian et al. |
| 2012/0064175 A1 | 3/2012 | Vukovic et al. |
| 2012/0071448 A1 | 3/2012 | Donello et al. |
| 2012/0245186 A1 | 9/2012 | Blackman et al. |
| 2012/0316193 A1 | 12/2012 | Foley et al. |
| 2013/0029948 A1 | 1/2013 | Roppe et al. |
| 2013/0045992 A1 | 2/2013 | Finley et al. |
| 2013/0150385 A1 | 6/2013 | Blackman et al. |
| 2013/0156755 A1 | 6/2013 | Blackman et al. |
| 2013/0171105 A1 | 7/2013 | Blackman et al. |
| 2016/0214989 A1 | 7/2016 | Finley et al. |

FOREIGN PATENT DOCUMENTS

| | | | |
|---|---|---|---|
| EP | 562832 | 9/1993 | |
| EP | 639573 | 2/1995 | |
| EP | 1837329 A1 | 9/2007 | |
| EP | 2020230 A1 | 2/2009 | |
| EP | 2141148 A1 | 1/2010 | |
| EP | 2141163 A1 | 1/2010 | |
| GB | 1073521 | 6/1967 | |
| GB | 1410783 | 10/1975 | |
| JE | 07-133274 A | 5/1995 | |
| JP | 08-225535 A | 9/1996 | |
| JP | 10-508321 A | 8/1998 | |
| JP | 11-503445 A | 3/1999 | |
| JP | 11-503758 A | 3/1999 | |
| JP | 2000063354 | 2/2000 | |
| JP | 2001151771 A * | 6/2001 | B62H 1/12 |
| JP | 2002-510622 A | 4/2002 | |
| JP | 2003-501476 A | 1/2003 | |
| JP | 2007-519631 A | 7/2007 | |
| JP | WO 2008120818 A1 * | 10/2008 | C07D 209/08 |
| JP | 2009179589 A | 8/2009 | |
| WO | 9513266 A1 | 5/1995 | |
| WO | 96/32379 A1 | 10/1996 | |
| WO | 9736881 A1 | 10/1997 | |
| WO | 9746226 A2 | 12/1997 | |
| WO | 98/27089 A1 | 6/1998 | |
| WO | 9943672 A1 | 9/1999 | |
| WO | 0144182 A1 | 6/2001 | |
| WO | 03041644 A2 | 5/2003 | |
| WO | 2004/020409 A1 | 3/2004 | |
| WO | 2004/104007 | 12/2004 | |
| WO | 2005/021558 | 3/2005 | |
| WO | 2005/025515 | 3/2005 | |
| WO | 2005/066126 A1 | 7/2005 | |
| WO | 2005/121175 A2 | 12/2005 | |
| WO | 2006/087355 | 8/2006 | |
| WO | 2006/125324 A1 | 11/2006 | |
| WO | 2007095561 A2 | 8/2007 | |
| WO | 2008/024978 A2 | 2/2008 | |
| WO | 2008/100867 A2 | 8/2008 | |
| WO | 2008/109702 A1 | 9/2008 | |
| WO | 2008/147536 | 12/2008 | |
| WO | 2009013010 A2 | 1/2009 | |
| WO | 2009/023623 A1 | 2/2009 | |
| WO | 2009/062118 | 5/2009 | |
| WO | 2009/071577 | 6/2009 | |
| WO | 2009/073620 | 6/2009 | |
| WO | 2009/097141 | 8/2009 | |
| WO | 2009/108551 | 9/2009 | |
| WO | 2009/117676 | 9/2009 | |
| WO | 2009/127686 A1 | 10/2009 | |
| WO | 2009/130481 A1 | 10/2009 | |
| WO | 2009118292 A1 | 10/2009 | |
| WO | 2009/136175 | 11/2009 | |
| WO | 2009/158011 | 12/2009 | |
| WO | 2009/158371 | 12/2009 | |
| WO | 2010/006234 A2 | 1/2010 | |
| WO | 2010/015816 A2 | 2/2010 | |
| WO | 2010/019391 A1 | 2/2010 | |
| WO | 2010015816 A2 | 2/2010 | |
| WO | 2010/067123 A1 | 6/2010 | |
| WO | 2010/139982 A1 | 12/2010 | |
| WO | 2011038579 A1 | 4/2011 | |
| WO | 2011094545 A2 | 8/2011 | |
| WO | 2011/127333 A2 | 10/2011 | |
| WO | 2011/133653 A1 | 10/2011 | |
| WO | 2012/012712 | 1/2012 | |
| WO | 2012078757 A2 | 6/2012 | |
| WO | 2012096919 A1 | 7/2012 | |
| WO | 2012106343 A2 | 8/2012 | |
| WO | 2012116061 A1 | 8/2012 | |
| WO | 2012116247 A1 | 8/2012 | |
| WO | 2012141796 A2 | 10/2012 | |
| WO | 2012162293 A1 | 11/2012 | |
| WO | 2012162372 A1 | 11/2012 | |
| WO | 2012162584 A1 | 11/2012 | |
| WO | 2013006864 A2 | 1/2013 | |
| WO | 2013014104 A1 | 1/2013 | |
| WO | 2013/074594 A1 | 5/2013 | |
| WO | 2013067162 A1 | 5/2013 | |
| WO | 2013067165 A1 | 5/2013 | |

OTHER PUBLICATIONS

De Freitas, G., B.L., et al., "Development of Co MFA and CoMSIA models of affinity and selectivity for indole ligands of cannabinoid CB1 and CB2 receptors," European Journal of Medicinal Chemistry, 44: 2482-2496 (2009).

Lee, B. H. et al., "Enhancement of proteasome activity by a small-molecule inhibitor of USP14", Nature, 2010, 467, 179-184.

CAS RN 784194-52-1, STN Entry Date Nov. 19, 2004.

CAS RN 133674-62-1, STN Entry Date May 10, 1991.

CAS RN 57248-18-7, STN Entry Date Nov. 16, 1984.

CAS RN 169501-21-7, STN Entry Date Nov. 1, 1995.

Gadaginamath, G. S., et al., "Synthesis and antimicrobial activity of 4-isogramines, 4-arylthiomethyl and 3-aminoacetyl derivatives of 2-methylindoles," Revue Roumaine de Chimie, 40(3): 265-273 (1995).

Iwaki, T., et al., "Water-Soluble Melatonins: Syntheses of Melatonins Carrying a Glycosyl Group at the 1-Position," Heterocyles, 60(6): 1411-1418 (2003).

Aparoy, P., et al., "Pharmacophore modeling and virtual screening for designing potential 5-Lipoxygenase inhibitors," Bioorganic & Medicinal Chemistry Letters, 20(3):1013-1018 (2010).

Van Zandt, M. C., et al., "Discovery of 3-[(4,5,7-Trifluorobenzothiazol-2-yl)methyl]indole-N-acetic Acid (Lidorestat) and Congeners as Highly Potent and Selective Inhibitors of Aldose Reductase for Treatment of Chronic Diabetic Complications," J. Med. Chem., 48: 3141-3152 (2005).

(56) References Cited

OTHER PUBLICATIONS

Liu, W., et al., "Discovery of a Peroxisome Proliferator Activated Receptor γ (PPARγ) Modulator with Balanced PPARα Activity for the Treatment of Type 2 Diabetes and Dyslipidemia," J. Med. Chem., 52(14): 4443-4453 (2009).
Stearns, B. A., et al., "Synthesis and biological evaluation of 6-aryl-6H-pyrrolo[3,4-d]pyridazine derivatives: high-affinity ligands to the α2δ subunit of voltage gated calcium channels," Bioorganic & Medicinal Chemistry Letters, 14(5): 1295-1298 (2004).
Vidovic, D., et al., "A Combined Ligand- and Structure-Based Virtual Screening Protocol Identifies Submicromolar PPAR[γ] Partial Agonists," Chem Med Chem, 6(1): 94-103 (2011).
Marchand, P., et al., "Synthesis and structure-activity relationships of N-aryl(indol-3-yl)glyoxamides as antitumor agents", Bioorganic & Medicinal Chemistry, 17(18): 6715-6727 (2009).
Preobrazhenskaya, M. N., et al., "Synthesis and Study of the Pharmacological Activity of 1-(Indolyl-3')-2-Alikylaminoethanols", Pharmaceutical Chemistry Journal, pp. 532-536 (1970). Retrieved from the Internet: URL:http://rd.springer.com/content/pdf/10.1007/BF00763238.pdf [retrieved on Oct. 7, 2014].
Abdel-Motaleb, R., M., et al., "Studies with azoles and benzoazoles: A novel simple approach for synthesis of 3-functionally substituted 3-acylindoles", Journal of Heterocyclic Chemistry, 44 (1): 109-114 (2007).
Rao, R. K., et al., "An efficient, mild, and selective Ullmann-type N-arylation of indoles catalyzed by copper(I) complex", Tetrahedron, 65(23): 4619-4624 (2009).
Gitto, R. et al., "Development of 3-substituted-1H-indole derivatives as NR2B/NMDA receptor antagonists", Bioorganic & Medicinal Chemistry, 17(4): 1640-1647 (2009).
Gadaginamath, et al., "Synthesis and Antimicrobial Activity of Novel 3-Thiazolyl/Imidazo (2, 1-b)-1 ,3,4-Thiadiazolyi/Anilinoacetyi/PhenoxyacetylIndole Derivatives," Indian Journal of Heterocyclic Chemistry, 9(1 ):33-38 (1999).
Kang, et al., "Cell Cycle Arrest and Cytochrome c-mediated Apoptotic Induction in A549 Human Lung Cancer Cells by MCS-C2, an Analog of Sangivamycin," Journal of Microbiology and Biotechnology, 20(2):428-432 (2010).
Registry (STN) CAS Registration No. 380907-35-7.
Registry (STN) CAS Registration No. 314261-13-7.
Registry (STN) CAS Registration No. 325742-01-6.
Registry (STN) CAS Registration No. 670268-20-9.
Supplementary European Search Report from EP 11 73 7731 dated Jul. 3, 2014.
International Search Report dated Oct. 24, 2011, from PCT/US2011/022929.
Office Action dated Aug. 18, 2014 from U.S. Appl. No. 13/575,812.
Office Action dated Feb. 5, 2015 from U.S. Appl. No. 13/575,812.
Kumar, D., et al., "A facile and regioselective synthesis of 1,4-disubstituted 1,2,3-triazoles using click chemistry," Tetrahedron Letters, 50(18): 2065-2068 (2009).
STN International, File Registry [online] RN 1266216-33-4, RN 1266208-38-1, RN 1266193-66-1, RN 1266184-43-3, RN 1266168-16-4, RN 1266155-14-9, RN 1266153-33-6, RN 1266150-22-4, RN 1266137-42-1, RN 1266131-49-0.
Machine Translation of JP2001151771A, p. 1-40, retrieved from https://www4.j-platpat.inpit.go.jp/cgi-bin/trao_web_cgi_ejje?u=http://www4.j-platpat.inpit . . . .
CAS Registry No. 500774-96-9, STN Entry Date Mar. 27, 2003.
CAS Registry No. 1027660-19-0, STN Entry Date Jun. 12, 2008.
CAS Registry No. 1026840-66-3, STN Entry Date Jun. 9, 2008.
CAplus Accession No. 1929:33387.
CAS Registry No. 857810-06-1, STN Entry Date Aug. 1, 2005.
Cavalli, A., et al., "Toward a Pharmacophore for Drugs Inducing the Long QT Syndrome: Insights from a CoMFA Study of HERG K+ Channel Blockers", Journal of Medicinal Chemistry, vol. 45, No. 18, Aug. 1, 2002 (Aug. 1, 2002), pp. 3844-3853, XP055281643.
Brana, M. F., et al., "Synthesis and biological activity of N,N-dialkylaminoalkyl-substituted bisindolyl and diphenyl pyrazolone derivatives", Bioorganic & Medicinal Chemistry, Pergamon, GB, vol. 14, No. 1, Jan. 1, 2006 (Jan. 1, 2006), pp. 9-16, XP027992247.
Office Action dated Jul. 14, 2014 from U.S. Appl. No. 13/468,757.
Office Action dated Dec. 31, 2014 from U.S. Appl. No. 13/468,757.
Wolff, Burger's medicinal Chemistry and Drug Discovery, vol. 1, Principles and Practice, John Wiley & sons, New York, 1997.
Foley, et al., U.S. Appl. No. 15/402,628, filed Jan. 10, 2017.

\* cited by examiner

PROTEASOME ACTIVITY ENHANCING COMPOUNDS

RELATED APPLICATIONS

This application is a continuation of International Application No. PCT/US2014/065204, which designated the United States and was filed on Nov. 12, 2014, published in English, which claims the benefit of U.S. Provisional Application No. 61/903,330 filed Nov. 12, 2013. The entire teachings of the above applications are incorporated herein by reference.

BACKGROUND OF THE INVENTION

Cells normally maintain a balance between protein synthesis, folding, trafficking, aggregation, and degradation, referred to as protein homeostasis, utilizing sensors and networks of pathways [Sitia et al., *Nature* 426: 891-894, 2003; Ron et al., *Nat Rev Mol Cell Biol* 8: 519-529, 2007]. The cellular maintenance of protein homeostasis, or proteostasis, refers to controlling the conformation, binding interactions, location and concentration of individual proteins making up the proteome. Protein folding in vivo is accomplished through interactions between the folding polypeptide chain and macromolecular cellular components, including multiple classes of chaperones and folding enzymes, which minimize aggregation [Wiseman et al., *Cell* 131: 809-821, 2007]. Whether a given protein folds in a certain cell type depends on the distribution, concentration, and subcellular localization of chaperones, folding enzymes, metabolites and the like [Wiseman et al.]. Human loss of function diseases are often the result of a disruption of normal protein homeostasis, typically caused by a mutation in a given protein that compromises its cellular folding, leading to efficient degradation [Cohen et al., *Nature* 426: 905-909, 2003]. Human gain of function diseases are similarly frequently the result of a disruption in protein homeostasis, such as the accumulation of misfolded proteins, leading to protein aggregation [Balch et al. (2003), *Science* 319: 916-919].

The proteasome is a large protein complex of multiple subunits which acts as a protease to degrade misfolded proteins. Most proteasome substrates are targeted for degradation by the covalent attachment of ubiquitin moieties which are recognized by the proteasome [Lee et al. (2010), *Nature* 467(7312): 179-184]. Proteins with longer ubiquitin chains tend to have a stronger association with the proteasome than those with smaller chains [Lee et al. (2010); Proctor et al. (2007), *BMC Systems Biology* 1: 17]. The length of the abiquitin chains is modulated, in part, by proteasome-associated deubiquitinating enzymes. One such mammalian deubiquitinating enzyme is Usp14 which has been shown to act as an inhibitor of the proteasome [Lee et al. (2010)].

Both proteasome dysfunction and dysfunction in proteostasis have been implicated in a diverse range of diseases including for example, neurodegenerative disease, metabolic diseases, inflammatory diseases, and cancer. In many such diseases and conditions, the proteasome has decreased ability to degrade misfolded or abnormal proteins, leading to the presence of toxic protein aggregates. In addition, the enhancement of proteasome activity can be therapeutic for any disease characterized by deficient proteasome activity, or deficient activity of other components of the ubiquitin-proteasome pathway including, but not limited to, von Hippel-Lindau disease, spinocerebellar ataxia 1, Angelman syndrome, giant axon neuropathy, inclusion body myopathy with Paget disease of bone and frontotemporal dementia (IBMPFD), and others [Lehman, N. L., (2009), *Acta Neuropathologica*, 118(3), 329-347; Weihl et al., (2007), *Neuromuscular Disorders*, 17, 87-87]. Enhancing proteasome activity is also therapeutic for diseases in which proteasome substrates are involved and contribute to pathology, but which do not satisfy a strict definition of proteinopathies. For example, numerous oncoproteins are proteasome substrates and their ability to promote cancer can potentially be attenuated by enhancing proteasome activity.

Therefore, there is a need for compounds and pharmaceutical compositions to treat conditions associated with proteostasis dysfunction and/or that provide therapies based on enhancing proteasome activity.

SUMMARY OF THE INVENTION

The present invention is based, in part, on the discovery that compounds of the invention inhibit Usp14. The present invention is directed to compounds encompassed by the Formulae (I), (II), (III), (IV), and (V), or a pharmaceutically acceptable salt, solvate, clathrate or prodrug of any of thereof, compositions thereof, methods for the treatment of a condition associated with a dysfunction in proteostasis, methods for enhancing proteasome activity and methods for treating cancer or tumor.

In one embodiment, the invention is directed to a compound having the Formula (I):

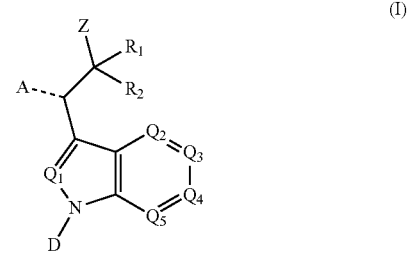

(I)

or a pharmaceutically acceptable salt, solvate, clathrate or prodrug thereof; wherein:

D is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_d$-$S(O)_nR_c$, $S(O)_nR_c$, $S(O)_nNR_dR_d$, $OC(O)OR_c$, $(C=NR_d)R_c$, optionally substituted heterocyclic and optionally substituted heteroaryl;

-A is selected from the group consisting of, =O, —OH, —$C_1$-$C_{10}$ alkyl and —$C_2$-$C_{12}$ alkenyl, wherein the —$C_1$-$C_{10}$ alkyl and —$C_2$-$C_{12}$ alkenyl are each optionally substituted;

$Q_1$ is $C(R_a)$ or nitrogen;

Each of $Q_2$, $Q_3$, $Q_4$ and $Q_5$ is independently selected from the group consisting of $C(R_3)$ and nitrogen; wherein at least two of $Q_2$, $Q_3$, $Q_4$ and $Q_5$ are each independently $C(R_3)$;

Each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl;

Each $R_3$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $N_3$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl;

Z is selected from the group consisting of $NR_bR_b$, optionally substituted aryl, optionally substituted heterocyclic, optionally substituted heteroaryl, optionally substituted $C_3$-$C_{12}$ cycloalkyl, optionally substituted $C_3$-$C_{12}$ cycloalkenyl, and $OR_e$;

Each $R_a$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl;

Each $R_b$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

Each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

Each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or two geminal $R_d$ groups are taken together with the nitrogen atom to which they are attached to form an optionally substituted heterocyclic or an optionally substituted heteroaryl;

Each $R_e$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally sub-stituted heterocyclic, optionally substituted aryl and optionally substituted heteroaryl; and each n is independently 0, 1 or 2.

In yet an additional embodiment, the invention is directed to a compound having the Formula (II):

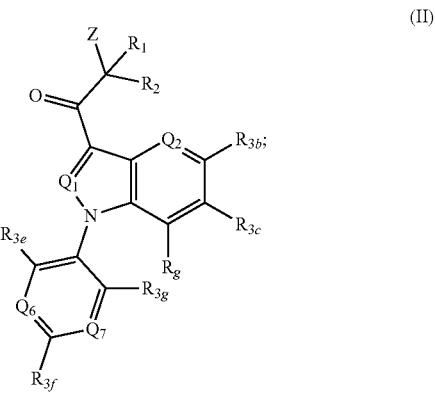

(II)

wherein $Q_1$, $R_a$, $Q_2$, $R_1$, $R_2$, $R_3$, Z, $R_b$, $R_c$, $R_d$, $R_e$, and n are as defined above for Formula (I);

$Q_6$ and $Q_7$ are each independently selected from the group consisting of $C(R_h)$ and nitrogen;

Each $R_h$ is independently selected from the group consisting of independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl;

$R_{3e}$, $R_{3f}$ and $R_{3g}$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl;

Each of $R_{3b}$ and $R_{3c}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl; and $R_g$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl.

In yet another embodiment, the invention is directed to a compound having the Formula (III):

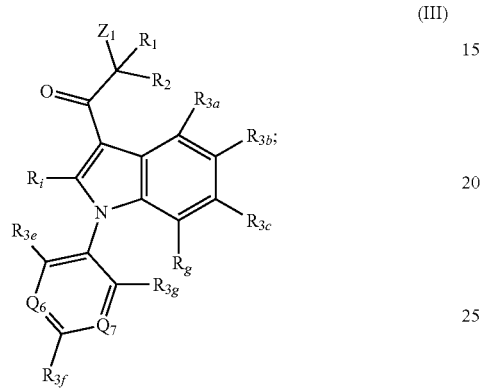

(III)

wherein:

$R_1$, $R_2$, $R_b$, $R_c$, $R_d$, $R_{3e}$, $R_{3f}$, $R_{3g}$, $R_g$, $R_{3b}$, $R_{3c}$, $Q_6$, $Q_7$ and n and are as defined above for Formula (II);

$R_{3a}$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl; and $Z_1$ is selected from the group consisting of $NR_bR_b$ and N-heterocyclic; and $R_i$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl.

In a further embodiment, the invention is directed to a compound having the Formula (IV):

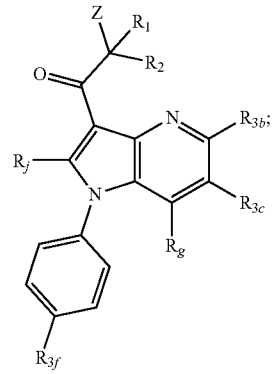

(IV)

wherein $R_1$, $R_2$, $R_b$, $R_c$, $R_d$, $R_{3f}$, $R_g$, $R_{3b}$, $R_{3c}$ and Z are as defined above for Formula (II);

$R_j$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl.

In an additional embodiment, the invention is directed to a compound having the Formula (V):

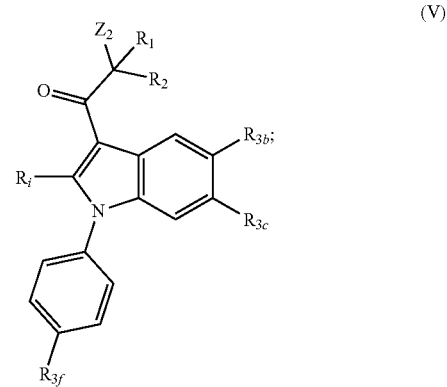

(V)

wherein $R_1$, $R_2$, $R_c$, $R_d$, $R_i$, $R_{3f}$ and n are as defined above for Formula (III);

one of $R_{3b}$ and $R_{3c}$ is hydrogen and the other of $R_{3b}$ and $R_{3c}$ is selected from the group consisting of optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl; and $Z_2$ is optionally substituted 1-pyrrolidinyl or optionally substituted 1-piperidinyl.

In additional embodiments, the invention is directed to a pharmaceutical composition comprising a pharmaceutically acceptable carrier or excipient and a compound of Formula (I), (II), (III), (IV), or (V), or a pharmaceutically acceptable salt, solvate, clathrate or prodrug thereof.

In an additional aspect, the invention is directed to a method of inhibiting deubiquitination activity of a Usp14 protein comprising contacting the Usp14 protein with an effective amount of a compound of Formula (I), (II), (III), (IV), or (V), or a pharmaceutically acceptable salt, solvate, clathrate or prodrug thereof, in an amount sufficient to inhibit deubiquitination activity of the Usp14 protein.

In yet another embodiment, the invention is directed to a method of enhancing protein degradation by a proteasome in a cell comprising contacting the cell with an effective amount of a compound of Formula (I), (II), (III), (IV), or (V) or a pharmaceutically acceptable salt, solvate, clathrate or prodrug thereof, in an amount sufficient to enhance protein degradation by the proteasome.

In additional embodiments, the invention encompasses a method of treating a patient suffering from a condition associated with a dysfunction in proteostasis comprising administering to said patient an effective amount of a compound of Formula (I), (II), (III), (IV), or (V), or a pharmaceutically acceptable salt, solvate, clathrate or prodrug thereof.

In another aspect, the invention is directed to a method of enhancing proteasome function in a subject in need thereof comprising administering to said subject an effective amount of a compound of Formula (I), (II), (III), (IV), or (V), or a pharmaceutically acceptable salt, solvate, clathrate or prodrug thereof.

In a further embodiment, the invention is directed to a method for treating a condition characterized by deficient proteasome activity or deficiency of other components of the ubiquitin-proteasome pathway in a subject comprising administering to said subject an effective amount of a compound of Formula (I), (II), (III), (IV), or (V), or a pharmaceutically acceptable salt, solvate, clathrate or prodrug thereof.

In yet another embodiment, the invention encompasses a method of treating cancer or a tumor in a subject in need thereof comprising administering to said subject an effective amount of a compound of Formula (I), (II), (III), (IV), or (V), a pharmaceutically acceptable salt, solvate, clathrate or prodrug thereof.

In a further aspect, the invention is a pharmaceutical composition comprising:

a pharmaceutically acceptable carrier or excipient;

an agent selected from the group consisting of a proteostasis regulator and a pharmacologic chaperone; and a compound of Formula (I), (II), (III), (IV), or (V), or a pharmaceutically acceptable salt, solvate, clathrate or prodrug thereof.

DETAILED DESCRIPTION OF THE INVENTION

A description of preferred embodiments of the invention follows.

As used herein, the words "a" and "an" are meant to include one or more unless otherwise specified. For example, the term "a cell" encompasses both a single cell and a combination of two or more cells.

As discussed above, the present invention is directed to compounds of Formulae (I), (II), (III), (IV) and (V), or a pharmaceutically acceptable salt, solvate, clathrate or prodrug thereof, pharmaceutical compositions thereof, methods of use thereof in the treatment of conditions associated with a dysfunction in proteostasis, methods of enhancing proteasome activity and methods for treating cancer or a tumor.

In some embodiments, the invention is directed to a compound of Formula (I), provided that when D is 4-chlorophenyl, -A is =O, $Q_1$ is $C(R_a)$, $R_a$ is methyl, Z is 1-piperidinyl, 4-hydroxy-1-piperidinyl or 1-pyrrolidinyl, and each of $R_1$ and $R_2$ is hydrogen, then at least one of $Q_2$, $Q_3$, $Q_4$, and $Q_5$ is not CH; and provided that when D is selected from the group consisting of phenyl, 4-chlorophenyl, 4-methylphenyl and 4-methoxyphenyl, -A is =O, $Q_1$ is $C(R_a)$, $R_a$ is methyl, Z is 1-piperidinyl or 4-morpholinyl, each of $R_1$ and $R_2$ is hydrogen, and $Q_2$ and $Q_5$ are each CH, then $Q_3$ and $Q_4$ are not $C(OCH_3)$ and $C(Br)$, respectively.

The invention encompasses a compound having the Formula (I), or a pharmaceutically acceptable salt, solvate, clathrate or prodrug thereof. In certain aspects, the compound has the Formula (I), wherein -A is =O, or is a pharmaceutically acceptable salt, solvate, clathrate or prodrug thereof. In certain additional embodiments, the compound has the Formula (I), wherein -A is —OH, or is a pharmaceutically acceptable salt, solvate, clathrate or prodrug thereof. In yet additional embodiments, the compound has the Formula (I), wherein -A is —$C_1$-$C_{10}$ alkyl, optionally substituted, or is a pharmaceutically acceptable salt, solvate, clathrate or prodrug thereof. In a further embodiment, the compound has the Formula (I), wherein -A is —$C_2$-$C_{12}$ alkenyl, optionally substituted, or is a pharmaceutically acceptable salt, solvate, clathrate or prodrug thereof.

In some embodiments, the compound has the Formula (I), wherein each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl. In additional embodiments, the compound has the Formula (I), wherein $R_1$ and $R_2$ are each independently selected from hydrogen and optionally substituted $C_1$-$C_{10}$ alkyl, or is a pharmaceutically acceptable salt, solvate, clathrate or prodrug thereof. In some embodiments, $R_1$ and $R_2$ are each hydrogen.

In additional aspects, the compound has the Formula (I), wherein D is optionally substituted $C_3$-$C_{12}$ cycloalkyl, optionally substituted $C_3$-$C_{12}$ cycloalkenyl, optionally substituted aryl, optionally substituted heteroaryl, or optionally substituted heterocyclic, or is a pharmaceutically acceptable salt, solvate, clathrate or prodrug thereof. In some embodiments, D is optionally substituted aryl or an optionally substituted heteroaryl. In yet additional embodiments, D is an optionally substituted heteroaryl. In further embodiments, D is an optionally substituted heteroaryl, wherein said heteroaryl comprises at least one ring nitrogen atom. In another embodiment, D is an optionally substituted pyridinyl or an optionally substituted pyrimidinyl. In yet an additional embodiment, D is optionally substituted phenyl.

In an additional aspect, the compound has the Formula (I), wherein $Q_1$ is $C(R_a)$, and $R_a$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl, or is a pharmaceutically acceptable salt, solvate, clathrate or prodrug thereof. In yet an additional embodiment, $R_a$ is selected from hydrogen and optionally substituted $C_1$-$C_{10}$ alkyl. In some embodiments, $R_a$ is an optionally substituted $C_1$-$C_4$ alkyl. In yet additional embodiments, $R_a$ is methyl.

In yet an additional embodiment, the compound has the Formula (I), wherein one or two of $Q_2$, $Q_3$, $Q_4$ and $Q_5$ is nitrogen and the remaining of $Q_2$, $Q_3$, $Q_4$ and $Q_5$ are each independently $C(R_3)$, or is a pharmaceutically acceptable salt, solvate, clathrate or prodrug thereof. In some embodiments, $Q_2$ is nitrogen and $Q_3$, $Q_4$ and $Q_5$ are each independently $C(R_3)$. In certain aspects, $Q_3$, $Q_4$ and $Q_5$ are each CH. In certain additional embodiments, both $Q_2$ and $Q_3$ are nitrogen and $Q_4$ and $Q_5$ are each independently $C(R_3)$. In yet additional embodiments, $Q_3$ is nitrogen and $Q_2$, $Q_4$ and $Q_5$ are each independently $C(R_3)$. In a further embodiment, $Q_4$ is nitrogen and $Q_2$, $Q_3$ and $Q_5$ are each independently $C(R_3)$. In an additional embodiment, Q5 is nitrogen and $Q_2$, $Q_3$ and $Q_4$ are each independently $C(R_3)$.

In some embodiments, the compound has the Formula (I), wherein $Q_3$ is $C(R_{3b})$ and $R_{3b}$ is selected from the group consisting of hydrogen, halo, $NR_dR_d$, $NO_2$, CN, optionally substituted $C_1$-$C_{10}$ alkyl, $C(O)OR_c$, $C(O)R_c$, $NR_dC(O)R_c$, and $OR_c$, or is a pharmaceutically acceptable salt, solvate, clathrate or prodrug thereof. In yet additional aspects, $Q_4$ and $Q_5$ are each CH.

In yet additional embodiments, the compound has the Formula (I), wherein each of $Q_2$, $Q_3$, $Q_4$ and $Q_5$ is $C(R_3)$.

In some embodiments, the compound has the Formula (I), wherein Z is an optionally substituted heterocyclic containing at least one ring nitrogen atom or $NR_bR_b$, or is a pharmaceutically acceptable salt, solvate, clathrate or prodrug thereof. In certain aspects, Z is an optionally substituted N-heterocyclic. In additional aspects, Z is selected from optionally substituted pyrrolidinyl and optionally substituted piperidinyl. In yet additional embodiments, Z is selected from optionally substituted 1-pyrrolidinyl and optionally substituted 1-piperidinyl. In a further embodiment, Z is optionally substituted 1-piperidinyl.

In yet additional embodiments, the compound has the Formula (I), wherein Z is:

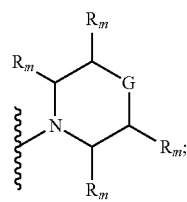

wherein G is absent, $C(R_n)$, O or S; each $R_m$ and $R_n$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl, and wherein n, $R_c$, and $R_d$ are as defined above, or is a pharmaceutically acceptable salt, solvate, clathrate or prodrug thereof. In some embodiments, G is O. In yet additional embodiments, G is S.

In yet additional embodiments, the compound has the Formula (I), wherein Z is an optionally substituted cycloalkyl, or is a pharmaceutically acceptable salt, solvate, clathrate or prodrug thereof.

In some embodiments, the invention is directed to a compound having the Formula (II), or a pharmaceutically acceptable salt, solvate, clathrate or prodrug thereof.

In some embodiments, the compound has the Formula (II), wherein $R_1$ and $R_2$ are each independently selected from hydrogen and optionally substituted $C_1$-$C_{10}$ alkyl, or is a pharmaceutically acceptable salt, solvate, clathrate or prodrug thereof. In additional embodiments, $R_1$ and $R_2$ are each hydrogen.

In additional embodiments, the compound has the Formula (II), wherein $Q_1$ is $C(R_a)$ and $Q_2$ is $C(R_3)$ or nitrogen, wherein each of $R_a$ and $R_3$ is independently selected from the group consisting of hydrogen and optionally substituted $C_1$-$C_{10}$ alkyl, or is a pharmaceutically acceptable salt, solvate, clathrate or prodrug thereof. In some embodiments, $R_a$ is an optionally substituted $C_1$-$C_4$ alkyl. In yet additional embodiments, $R_a$ is methyl.

In yet additional embodiments, the compound has the Formula (II), wherein each of $R_{3b}$ and $R_{3c}$ is independently selected from the group consisting of hydrogen, halo, $NR_dR_d$, $NO_2$, CN, optionally substituted $C_1$-$C_{10}$ alkyl, $C(O)OR_c$, $C(O)R_c$, $NR_dC(O)R_c$, and $OR_c$, or is a pharmaceutically acceptable salt, solvate, clathrate or prodrug thereof.

In some aspects, the compound has the Formula (II), wherein Z is an optionally substituted heterocyclic containing at least one ring nitrogen atom or $NR_bR_b$, or is a pharmaceutically acceptable salt, solvate, clathrate or prodrug thereof. In some embodiments, Z is an optionally substituted N-heterocyclic or $NR_bR_b$. In additional embodiments, Z is an optionally substituted N-heterocyclic. In yet additional embodiments, Z is selected from optionally substituted pyrrolidinyl and optionally substituted piperidinyl. In further embodiments, Z is selected from optionally substituted 1-pyrrolidinyl and optionally substituted 1-piperidinyl. In some aspects, Z is optionally substituted 1-piperidinyl.

In yet additional embodiments, the compound has the Formula (II), wherein one of $Q_6$ and $Q_7$ is nitrogen and the other is $C(R_a)$, or is a pharmaceutically acceptable salt, solvate, clathrate or prodrug thereof.

In additional aspects, the compound has the Formula (II), wherein each of $Q_6$ and $Q_7$ is $C(R_a)$, or is a pharmaceutically acceptable salt, solvate, clathrate or prodrug thereof.

In some aspects of the invention, the compound has the Formula (II), wherein $R_{3f}$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl, or is a pharmaceutically acceptable salt, solvate, clathrate or prodrug thereof. In additional embodiments, $R_{3e}$ and $R_{3g}$ are each hydrogen. In yet additional aspects, $R_{3f}$ is selected from the group consisting of hydrogen, halo, $N_3$, $C(O)OR_c$, CN, $C(O)R_c$, $C(O)C(O)R_c$, $C(O)NR_dR_d$, $NO_2$ and $NR_dR_d$. In further embodiments, $R_{3f}$ is selected from the group consisting of halo, $N_3$, $C(O)OR_c$, CN, $C(O)R_c$, $C(O)C(O)R_c$, $C(O)NR_dR_c$, $NO_2$ and $NR_dR_d$.

In some aspects of the invention, the compound has the Formula (III), or a pharmaceutically acceptable salt, solvate, clathrate or prodrug thereof.

In some embodiments, the compound has the Formula (III), wherein $R_i$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl, or is a pharmaceutically acceptable salt, solvate, clathrate or prodrug thereof. In certain embodiments, the compound has the Formula (III), wherein $R_i$ is optionally substituted $C_1$-$C_4$ alkyl.

In additional embodiments, the compound has the Formula (III), wherein $R_1$ and $R_2$ are each independently selected from hydrogen and optionally substituted $C_1$-$C_{10}$ alkyl, or is a pharmaceutically acceptable salt, solvate, clathrate or prodrug thereof. In some embodiments, $R_1$ and $R_2$ are each hydrogen.

In some embodiments, the compound has the Formula (III), wherein at least one of $R_{3a}$, $R_{3b}$, $R_{3c}$ and $R_g$ is not hydrogen, or is a pharmaceutically acceptable salt, solvate, clathrate or prodrug thereof. In additional embodiments, the compound has the Formula (III), provided that when $R_{3c}$ is bromo, then $R_{3b}$ is not methoxy.

In yet additional embodiments, the compound has the Formula (III), wherein each of $R_{3b}$ and $R_{3c}$ is independently selected from the group consisting of hydrogen, halo, $NR_dR_d$, $NO_2$, CN, optionally substituted $C_1$-$C_{10}$ alkyl, $C(O)OR_c$, $C(O)R_cNR_dC(O)R_c$, $OC(O)R_c$ and $OR_c$, or is a pharmaceutically acceptable salt, solvate, clathrate or prodrug thereof. In yet additional embodiments, the compound has the Formula (III), wherein each of $R_{3b}$ and $R_{3c}$ is independently selected from the group consisting of hydrogen, halo, $NR_dR_d$, $NO_2$, CN, optionally substituted $C_1$-$C_{10}$ alkyl, $C(O)OR_c$, $C(O)R_c$, $NR_dC(O)R_c$, $OC(O)R_c$, $OR_c$, optionally substituted $C_3$-$C_6$ cycloalkyl, optionally substituted heterocyclic and optionally substituted heteroaryl. In a further embodiment, one of $R_{3b}$ and $R_{3c}$ is hydrogen and the other of $R_{3b}$ and $R_{3c}$ is selected from the group consisting of halo, $NR_dR_d$, $NO_2$, CN, optionally substituted $C_1$-$C_{10}$ alkyl, $C(O)OR_c$, $C(O)R_c$, $NR_dC(O)R_c$, $OC(O)R_c$, $OR_c$, optionally substituted $C_3$-$C_6$ cycloalkyl, optionally substituted heterocyclic and optionally substituted heteroaryl. In yet additional embodiments, one of $R_{3b}$ and $R_{3c}$ is hydrogen, and the other of $R_{3b}$ and $R_{3c}$ is $C_1$-$C_{10}$ alkyl optionally substituted with one or more substituents selected from the group consisting of halo, $C(O)OR'$, $C(O)NR''R''$, $S(O)_2$, $S(O)_2NR''R''$, $NR''(O)_2R_c$, $NR''C(O)R_c$, $NR''C(O)OR'$, $NR''C(O)NR''R''$, CN, $OR'$, $NR''R''$, optionally substituted heterocyclic, and optionally substituted heteroaryl, and optionally further substituted; wherein each R' is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; and each R" is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or two geminal R" groups are taken together with the nitrogen atom to which they are attached to form an optionally substituted heterocyclic or an optionally substituted heteroaryl.

In further aspects, the compound has the Formula (III), wherein one of $Q_6$ and $Q_7$ is nitrogen and the other is $C(R_h)$, or is a pharmaceutically acceptable salt, solvate, clathrate or prodrug thereof.

In yet additional embodiments, the compound has the Formula (III), wherein $Q_6$ and $Q_7$ are each independently $C(R_h)$, or is a pharmaceutically acceptable salt, solvate, clathrate or prodrug thereof.

In additional embodiments, the compound has the Formula (III), wherein $R_{3b}$, $R_{3c}$ and $R_g$ are each hydrogen and $R_{3a}$ is selected from the group consisting of halo, $NR_dR_d$, $NO_2$, CN, optionally substituted $C_1$-$C_{10}$ alkyl, $C(O)OR_c$, $C(O)R_c NR_dC(O)R_c$, $OC(O)R$ and $OR_c$. In further aspects, $Q_6$ and $Q_7$ are each independently $C(R_h)$, or is a pharmaceutically acceptable salt, solvate, clathrate or prodrug thereof. In yet further embodiments, wherein $Q_6$ and $Q_7$ are each independently $C(R_h)$ and Z is selected from optionally substituted 1-pyrrolidinyl and optionally substituted 1-piperidinyl.

In yet additional embodiments, the compound has the Formula (III), wherein $R_{3f}$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl, or is a pharmaceutically acceptable salt, solvate, clathrate or prodrug thereof. In some embodiments, $R_{3e}$ and $R_{3g}$ are each hydrogen. In yet additional aspects, $R_{3f}$ is selected from the group consisting of hydrogen, halo, $N_3$, $C(O)OR_c$, CN, $C(O)R_c$, $C(O)C(O)R_c$, $C(O)NR_dR_d$, $NO_2$ and $NR_dR_d$. In yet additional embodiments, $R_{3f}$ is selected from the group consisting of halo, $N_3$, $C(O)OR_c$, CN, $C(O)R_c$, $C(O)C(O)R_c$, $C(O)NR_dR_d$, $NO_2$ and $NR_dR_d$.

In additional embodiments, the compound has the Formula (III), wherein $Z_1$ is selected from optionally substituted 1-pyrrolidinyl and optionally substituted 1-piperidinyl, or is a pharmaceutically acceptable salt, solvate, clathrate or prodrug thereof. In some embodiments, $Z_1$ is optionally substituted 1-piperidinyl. In yet further embodiments, $Z_1$ is an optionally substituted 1-pyrrolidinyl.

In other embodiments of the invention, the invention is directed to a compound having the Formula (IV), or a pharmaceutically acceptable salt, solvate, clathrate or prodrug thereof.

In some embodiments, the compound has the Formula (IV), wherein $R_j$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_n$-$NR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl, or is a pharmaceutically acceptable salt, solvate, clathrate or prodrug thereof. In some aspects, the compound has the Formula (IV), wherein $R_j$ is optionally substituted $C_1$-$C_4$ alkyl. In certain embodiments, $R_j$ is optionally substituted methyl. In yet other embodiments, $R_j$ is methyl.

In certain aspects, the compound has the Formula (IV), wherein $R_1$ and $R_2$ are each independently selected from hydrogen and optionally substituted $C_1$-$C_{10}$ alkyl, or is a pharmaceutically acceptable salt, solvate, clathrate or prodrug thereof. In yet an additional embodiment, $R_1$ and $R_2$ are each hydrogen.

In additional embodiments, the compound has the Formula (IV), wherein each of $R_{3b}$ and $R_{3c}$ is independently selected from the group consisting of hydrogen, halo, $NR_dR_d$, $NO_2$, CN, optionally substituted $C_1$-$C_{10}$ alkyl, $C(O)OR_c$, $C(O)R_c$, $NR_dC(O)R_c$, $OC(O)R_c$, and $OR_c$, or is a pharmaceutically acceptable salt, solvate, clathrate or prodrug thereof. In yet additional embodiments, the compound has the Formula (IV), wherein each of $R_{3b}$ and $R_{3c}$ is independently selected from the group consisting of hydrogen, halo, $NR_dR_d$, $NO_2$, CN, optionally substituted $C_1$-$C_{10}$ alkyl, $C(O)OR_c$, $C(O)R_c$, $NR_dC(O)R_c$, $OC(O)R_c$, $OR_c$, optionally substituted $C_3$-$C_6$ cycloalkyl, optionally substituted heterocyclic and optionally substituted heteroaryl. In a further embodiment, one of $R_{3b}$ and $R_{3c}$ is hydrogen and the other of $R_{3b}$ and $R_{3c}$ is selected from the group consisting of halo, $NR_dR_d$, $NO_2$, CN, optionally substituted $C_1$-$C_{10}$ alkyl, $C(O)OR_c$, $C(O)R_c$, $NR_dC(O)R_c$, $OC(O)R_c$, $OR_c$, optionally substituted $C_3$-$C_6$ cycloalkyl, optionally substituted heterocyclic, and optionally substituted heteroaryl. In yet additional embodiments, one of $R_{3b}$ and $R_{3c}$ is hydrogen, and the other of $R_{3b}$ and $R_{3c}$ is $C_1$-$C_{10}$ alkyl optionally substituted with one or more substituents selected from the group consisting of halo, C(O)OR', C(O)NR"R", $S(O)_2$, $S(O)_2$NR"R", NR"S(O)$_2R_c$, NR"C(O)$R_c$, NR"C(O)OR', NR"C(O)NR"R", OR', NR"R", CN, optionally substituted heterocyclic, and optionally substituted heteroaryl, and is optionally further substituted; wherein each R' is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; and each R" is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or two geminal R groups are taken together with the nitrogen atom to which they are attached to form an optionally substituted heterocyclic or an optionally substituted heteroaryl.

In a further embodiment, the compound has the Formula (IV), wherein $R_{3f}$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_n$-$NR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl, or is a pharmaceutically acceptable salt, solvate, clathrate or prodrug thereof. In additional embodiments, $R_{3f}$ is selected from the group consisting of hydrogen, halo, $N_3$, $C(O)OR_c$, CN, $C(O)R_c$, $C(O)C(O)R_c$, $C(O)NR_dR_d$, $NO_2$ and $NR_dR_d$. In yet additional embodiments, $R_{3f}$ is selected from the group consisting of halo, $N_3$, $C(O)OR_c$, CN, $C(O)R_c$, $C(O)C(O)R_c$, $C(O)NR_dR_d$, $NO_2$ and $NR_dR_d$. In a further embodiment, $R_{3f}$ is selected from the group consisting of halo and CN. In yet another embodiment, $R_{3f}$ is selected from chloro and CN. In yet additional embodiments, $R_{3f}$ is CN. In further embodiments, $R_{3f}$ is chloro.

In a further embodiment, $R_j$ is methyl, and $R_{3f}$ is selected from the group consisting of halo, $N_3$, $C(O)OR_c$, CN, $C(O)R_c$, $C(O)C(O)R_c$, $C(O)NR_dR_d$, $NO_2$ and $NR_dR_d$.

In yet additional aspects, the compound has the Formula (IV), wherein $R_g$ and $R_{3b}$ are both hydrogen and $R_3$, is optionally substituted $C_1$-$C_6$ alkyl, CN and $OR_c$, or is a pharmaceutically acceptable salt, solvate, clathrate or prodrug thereof. In some embodiments, $R_{3c}$ is methyl optionally substituted with an $NR_dR_d$, $NR_dC(O)R_c$, $OR_c$, $CR_cR_cC(O)OR_c$, and $CR_cR_cC(O)NR_dR_d$.

In some embodiments, the compound has the Formula (IV), wherein $R_g$ and $R_{3c}$ are both hydrogen and $R_{3b}$ is optionally substituted $C_1$-$C_6$ alkyl, CN and $OR_c$, or is a pharmaceutically acceptable salt, solvate, clathrate or prodrug thereof.

In yet additional embodiments, the compound has the Formula (IV), wherein Z is selected from optionally substituted 1-pyrrolidinyl and optionally substituted 1-piperidinyl, or is a pharmaceutically acceptable salt, solvate, clathrate or prodrug thereof. In yet an additional aspect, Z is optionally substituted 1-piperidinyl. In a further aspect, Z is an optionally substituted 1-pyrrolidinyl.

In yet additional embodiments, the compound has the Formula (IV), wherein Z is:

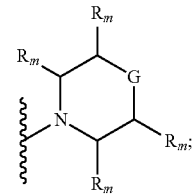

wherein G is absent, $C(R_n)$, O or S; each $R_m$ and $R_n$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_n$ $NR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl, and wherein n, $R_c$, and $R_d$ are as defined above, or is a pharmaceutically acceptable salt, solvate, clathrate or prodrug thereof. In some embodiments, G is O. In yet additional embodiments, G is S. In yet an additional embodiment, the invention is directed to a compound having the Formula (V), or a pharmaceutically acceptable salt, solvate, clathrate or prodrug thereof.

In additional embodiments, the compound has the Formula (V), wherein $Z_2$ is an optionally substituted 1-piperidinyl, or is a pharmaceutically acceptable salt, solvate, clathrate or prodrug thereof.

In some embodiments, the compound has the Formula (V), wherein $Z_2$ is an optionally substituted 1-pyrrolidinyl, or is a pharmaceutically acceptable salt, solvate, clathrate or prodrug thereof.

In some embodiments, the compound has the Formula (V), wherein $R_i$ is an optionally substituted $C_1$-$C_4$ alkyl, or is a pharmaceutically acceptable salt, solvate, clathrate or prodrug thereof. In certain aspects, $R_i$ is an optionally substituted methyl or optionally substituted ethyl. In certain additional aspects, $R_i$ is methyl.

In yet additional aspects, the compound has the Formula (V), wherein $R_{3f}$ is selected from the group consisting of hydrogen, halo, $N_3$, C(O)O$R_c$, CN, C(O)$R_c$, C(O)C(O)$R_c$, C(O)N$R_d R_d$, $NO_2$ and N$R_d R_d$, or is a pharmaceutically acceptable salt, solvate, clathrate or prodrug thereof. In yet additional embodiments, $R_{3f}$ is selected from the group consisting of halo, $N_3$, C(O)O$R_c$, CN, C(O)$R_c$, C(O)C(O)$R_c$, C(O)N$R_d R_d$, $NO_2$ and N$R_d R_d$.

In yet additional aspects, the compound has the Formula (V), wherein $R_{3b}$ is hydrogen, and $R_{3c}$ is selected from the group consisting of optionally substituted $C_1$-$C_6$ alkyl, CN and O$R_c$, or is a pharmaceutically acceptable salt, solvate, clathrate or prodrug thereof.

In further aspects, the compound has the Formula (V), wherein $R_{3c}$ is hydrogen, and $R_{3b}$ is selected from the group consisting of optionally substituted $C_1$-$C_6$ alkyl, CN and O$R_c$, or is a pharmaceutically acceptable salt, solvate, clathrate or prodrug thereof.

In an additional embodiment, the compound has the Formula (V), wherein $R_i$ is methyl, $R_{3f}$ is selected from the group consisting of halo, $N_3$, C(O)O$R_c$, CN, C(O)$R_c$, C(O)C(O)$R_c$, C(O)N$R_d R_d$, $NO_2$ and N$R_d R_d$, and $Z_2$ is an optionally substituted 1-piperidinyl, or is a pharmaceutically acceptable salt, solvate, clathrate or prodrug thereof. In yet additional embodiments, $R_i$ is methyl, $R_{3f}$ is halo or CN, and $Z_2$ is an optionally substituted 1-piperidinyl.

It is to be understood that the specific embodiments described herein can be taken in combination with other specific embodiments delineated herein. For example, for compounds of Formula (I), Z was described as 1-piperidinyl in certain embodiments, $Q_1$ was described as C($R_a$) in certain embodiments, and D was described as optionally substituted phenyl in some embodiments. It is thus to be understood that the invention specifically encompasses compounds of Formula (I), wherein Z is 1-piperidinyl, $Q_1$ is C($R_a$) and D is optionally substituted phenyl.

The present invention additionally encompasses the compounds shown below in Table 1:

TABLE 1

| Compound No. | Chemical Structure |
|---|---|
| 30 | 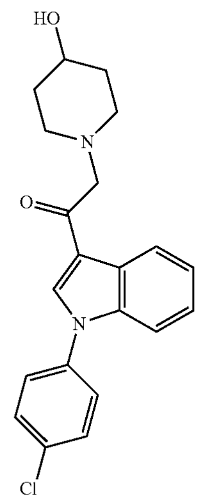 [SMILES: O=C(CN1CCC(O)CC1)c1cn(-c2ccc(Cl)cc2)c2ccccc12] |
| 31 | 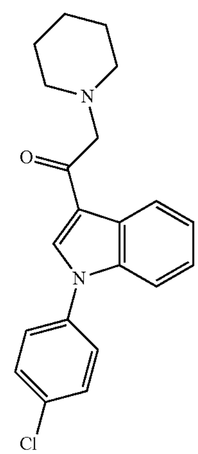 [SMILES: O=C(CN1CCCCC1)c1cn(-c2ccc(Cl)cc2)c2ccccc12] |
| 34 | 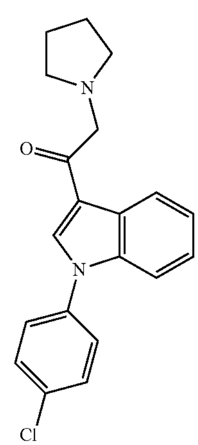 [SMILES: O=C(CN1CCCC1)c1cn(-c2ccc(Cl)cc2)c2ccccc12] |

TABLE 1-continued
| Compound No. | Chemical Structure |
| --- | --- |
| 86 | 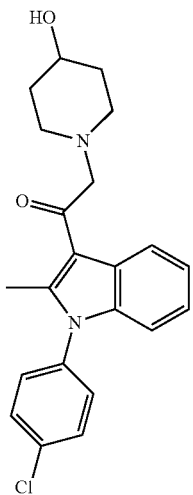 [SMILES: Cc1c(C(=O)CN2CCC(O)CC2)c2ccccc2n1-c1ccc(Cl)cc1] |
| 87 | 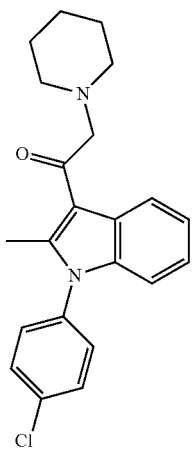 [SMILES: Cc1c(C(=O)CN2CCCCC2)c2ccccc2n1-c1ccc(Cl)cc1] |
| 88 | 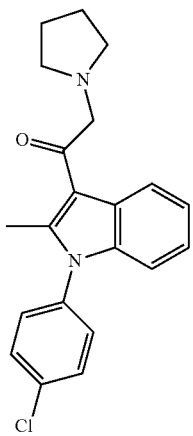 [SMILES: Cc1c(C(=O)CN2CCCC2)c2ccccc2n1-c1ccc(Cl)cc1] |
TABLE 1-continued
| Compound No. | Chemical Structure |
| --- | --- |
| 98 | 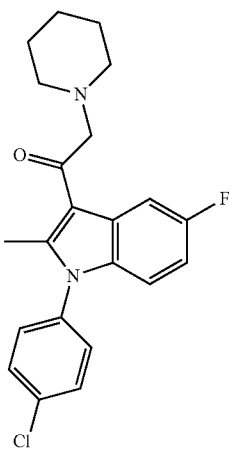 |
| 104 | 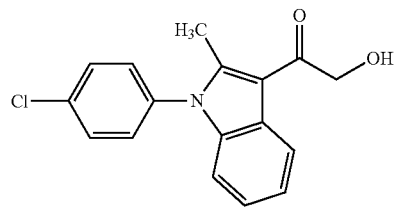 [SMILES: Cc1c(C(=O)CO)c2ccccc2n1-c1ccc(Cl)cc1] |
| 106 | 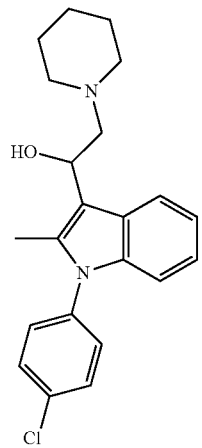 [SMILES: Cc1c(C(O)CN2CCCCC2)c2ccccc2n1-c1ccc(Cl)cc1] |

TABLE 1-continued

| Compound No. | Chemical Structure |
|---|---|
| 108 | 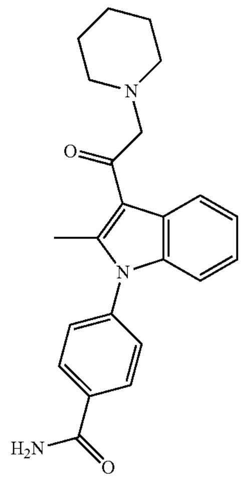 [SMILES: Cc1c(C(=O)CN2CCCCC2)c2ccccc2n1-c1ccc(C(N)=O)cc1] |
| 109 | 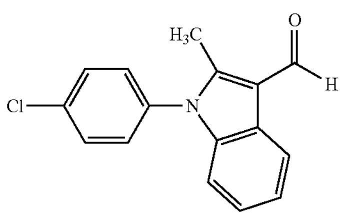 [SMILES: Cc1c(C=O)c2ccccc2n1-c1ccc(Cl)cc1] |
| 115 | 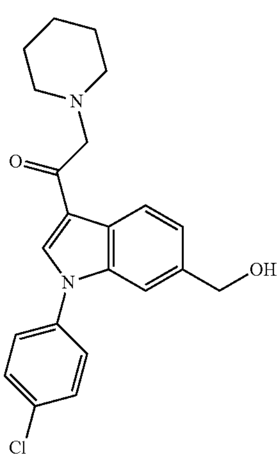 [SMILES: O=C(CN1CCCCC1)c1cn(-c2ccc(Cl)cc2)c2cc(CO)ccc12] |
| 116 | 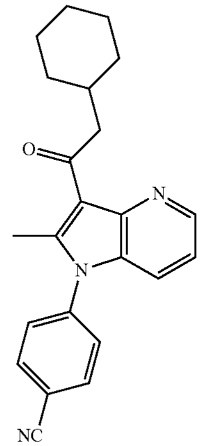 [SMILES: Cc1c(C(=O)CC2CCCCC2)c2ncccc2n1-c1ccc(C#N)cc1] |
| 118 | 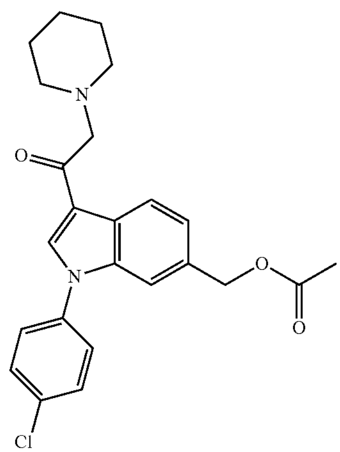 [SMILES: CC(=O)OCc1ccc2c(C(=O)CN3CCCCC3)cn(-c3ccc(Cl)cc3)c2c1] |
| 119 | 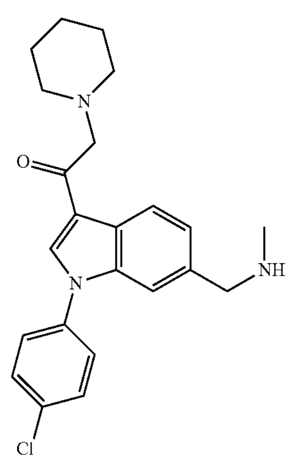 [SMILES: CNCc1ccc2c(C(=O)CN3CCCCC3)cn(-c3ccc(Cl)cc3)c2c1] |

TABLE 1-continued
| Compound No. | Chemical Structure |
|---|---|
| 120 | 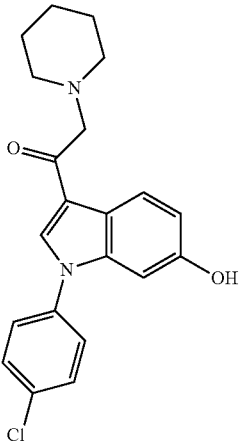 [SMILES: O=C(CN1CCCCC1)c1cn(-c2ccc(Cl)cc2)c2cc(O)ccc12] |
| 123 | 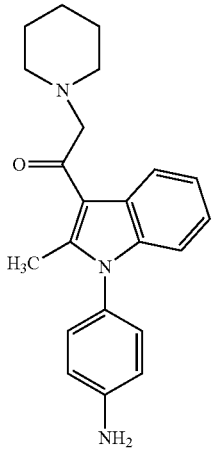 [SMILES: Cc1c(C(=O)CN2CCCCC2)c2ccccc2n1-c1ccc(N)cc1] |
| 125 | 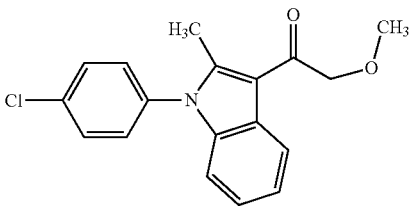 [SMILES: COCC(=O)c1c(C)n(-c2ccc(Cl)cc2)c2ccccc12] |
| 126 | 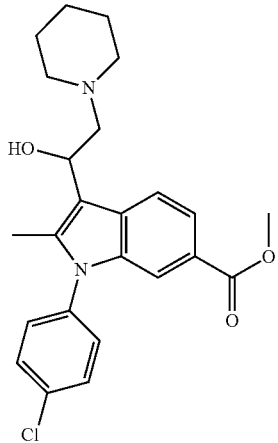 |
TABLE 1-continued
| Compound No. | Chemical Structure |
|---|---|
| 127 | 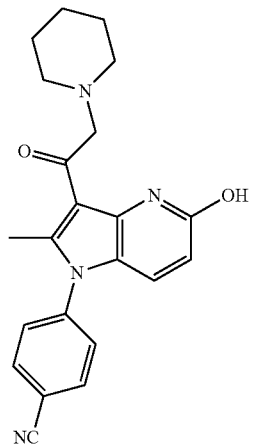 [SMILES: Cc1c(C(=O)CN2CCCCC2)c2nc(O)ccc2n1-c1ccc(C#N)cc1] |
| 128 | 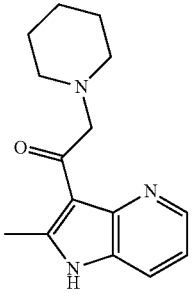 |
| 130 | 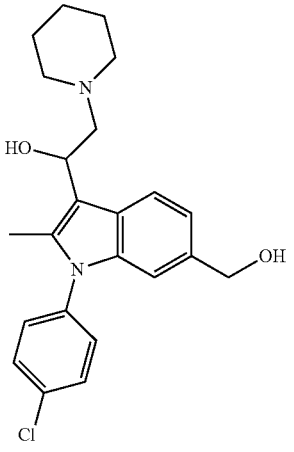 [SMILES: Cc1c(C(O)CN2CCCCC2)c2ccc(CO)cc2n1-c1ccc(Cl)cc1] |

TABLE 1-continued
| Compound No. | Chemical Structure |
|---|---|
| 131 | 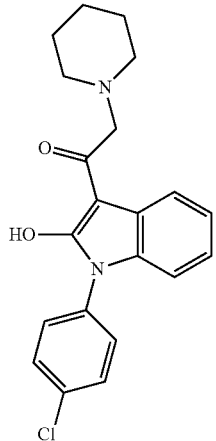 [SMILES: O=C(CN1CCCCC1)c1c(O)n(-c2ccc(Cl)cc2)c2ccccc12] |
| 132 | 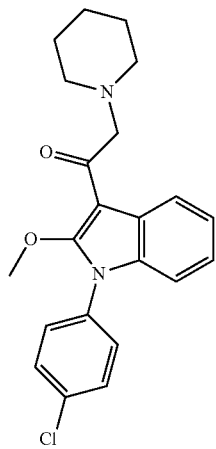 [SMILES: COc1c(C(=O)CN2CCCCC2)c2ccccc2n1-c1ccc(Cl)cc1] |
| 133 | 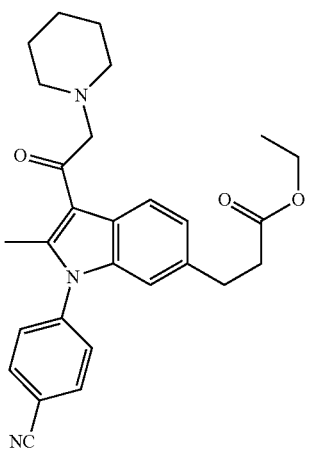 [SMILES: CCOC(=O)CCc1ccc2c(C(=O)CN3CCCCC3)c(C)n(-c3ccc(C#N)cc3)c2c1] |
TABLE 1-continued
| Compound No. | Chemical Structure |
|---|---|
| 141 | 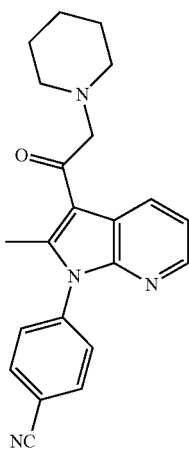 [SMILES: Cc1c(C(=O)CN2CCCCC2)c2cccnc2n1-c1ccc(C#N)cc1] |
| 142 | 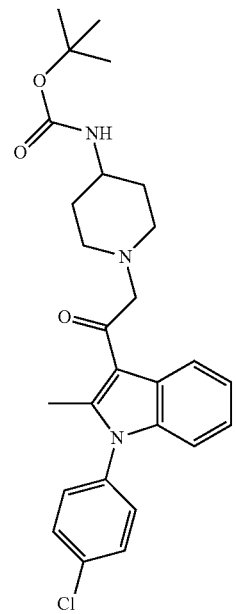 [SMILES: Cc1c(C(=O)CN2CCC(NC(=O)OC(C)(C)C)CC2)c2ccccc2n1-c1ccc(Cl)cc1] |
| 144 | 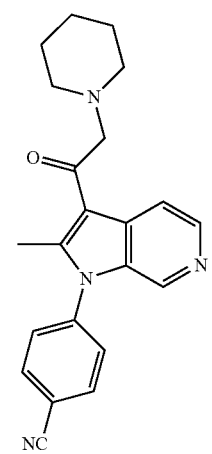 [SMILES: Cc1c(C(=O)CN2CCCCC2)c2ccncc2n1-c1ccc(C#N)cc1] |

TABLE 1-continued

| Compound No. | Chemical Structure |
|---|---|
| 145 | 2-methyl-1-(4-chlorophenyl)-5-phenoxy-3-(2-(piperidin-1-yl)acetyl)-1H-indole |
| 146 | 4-(2-methyl-7-methoxy-3-(2-(piperidin-1-yl)acetyl)-1H-indol-1-yl)benzonitrile |
| 147 | 4-azido-N-(1-(2-(2-methyl-1-(4-chlorophenyl)-1H-indol-3-yl)-2-oxoethyl)piperidin-4-yl)benzamide |
| 148 | 2-methyl-1-(4-chlorophenyl)-6-hydroxy-3-(2-(piperidin-1-yl)acetyl)-1H-indole |
| 149 | 2-methyl-1-(6-chloropyridin-3-yl)-3-(2-(piperidin-1-yl)acetyl)-1H-pyrrolo[3,2-b]pyridine |
| 150 | 2-methyl-1-(4-chlorophenyl)-5-nitro-3-(2-(piperidin-1-yl)acetyl)-1H-indole |

TABLE 1-continued
| Compound No. | Chemical Structure |
|---|---|
| 151 | 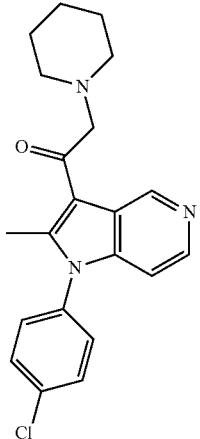 [SMILES: Cc1c(C(=O)CN2CCCCC2)c2cnccc2n1-c1ccc(Cl)cc1] |
| 152 | 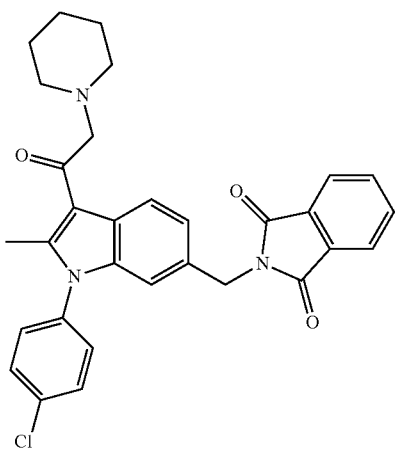 [SMILES: Cc1c(C(=O)CN2CCCCC2)c2ccc(CN3C(=O)c4ccccc4C3=O)cc2n1-c1ccc(Cl)cc1] |
| 153 | 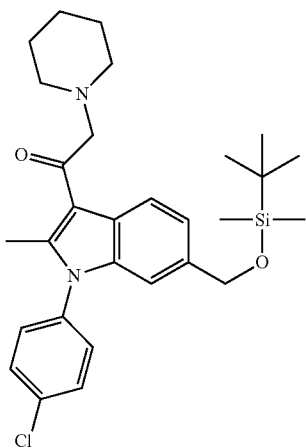 |
| 154 | 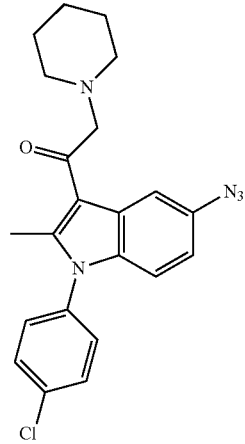 [SMILES: Cc1c(C(=O)CN2CCCCC2)c2cc(N=[N+]=[N-])ccc2n1-c1ccc(Cl)cc1] |
| 155 | 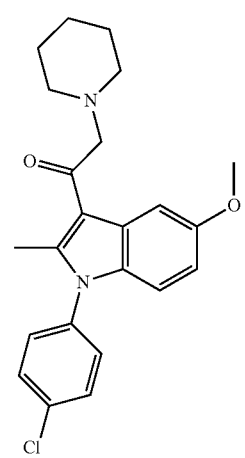 |
| 156 | 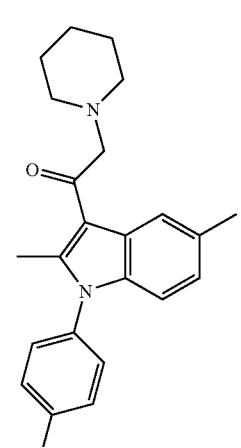 |

TABLE 1-continued

| Compound No. | Chemical Structure |
|---|---|
| 160 | 1-(1-(4-cyanophenyl)-2-methyl-1H-indol-3-yl)-2-(piperidin-1-yl)ethanone |
| 161 | 1-(1-(4-chlorophenyl)-2-methyl-1H-pyrrolo[3,2-b]pyridin-3-yl)-2-(piperidin-1-yl)ethanone |
| 162 | 1-(1-(4-cyanophenyl)-2-methyl-1H-pyrrolo[3,2-b]pyridin-3-yl)-2-(piperidin-1-yl)ethanone |
| 163 | 5-cyano-1-(4-cyanophenyl)-2-methyl-3-(2-(piperidin-1-yl)acetyl)-1H-indole |
| 164 | 2-methyl-1-(4-nitrophenyl)-3-(2-(piperidin-1-yl)acetyl)-1H-indole |
| 165 | 1-(1-(4-cyanophenyl)-5-fluoro-2-methyl-1H-pyrrolo[3,2-b]pyridin-3-yl)-2-(piperidin-1-yl)ethanone |

TABLE 1-continued
| Compound No. | Chemical Structure |
|---|---|
| 166 | 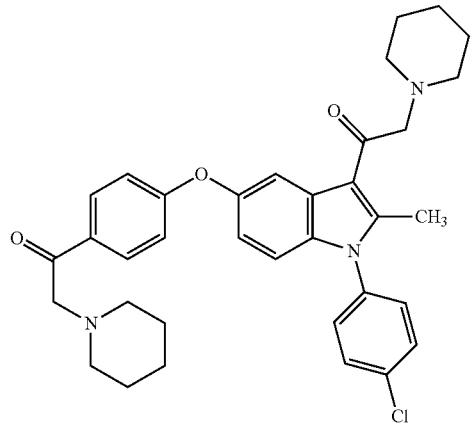 [SMILES: Cc1c(C(=O)CN2CCCCC2)c2cc(Oc3ccc(C(=O)CN4CCCCC4)cc3)ccc2n1-c1ccc(Cl)cc1] |
| 167 | 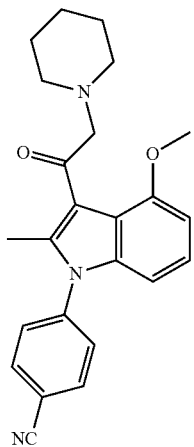 |
| 168 | 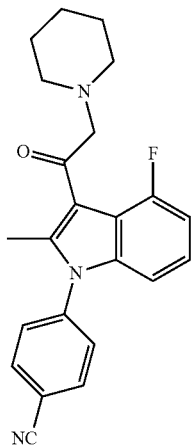 [SMILES: Cc1c(C(=O)CN2CCCCC2)c2c(F)cccc2n1-c1ccc(C#N)cc1] |
| 169 | 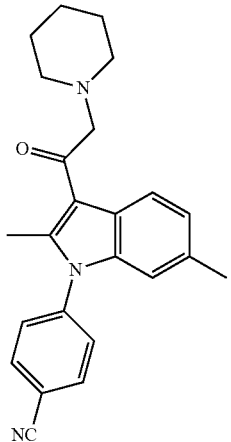 |
| 170 | 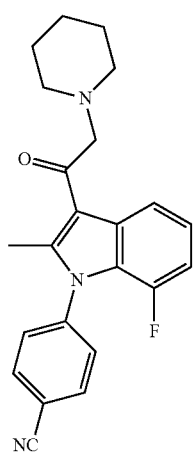 [SMILES: Cc1c(C(=O)CN2CCCCC2)c2cccc(F)c2n1-c1ccc(C#N)cc1] |
| 171 | 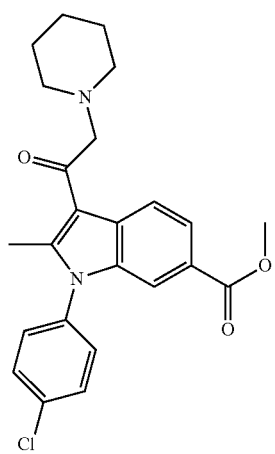 |

TABLE 1-continued
| Compound No. | Chemical Structure |
|---|---|
| 172 | 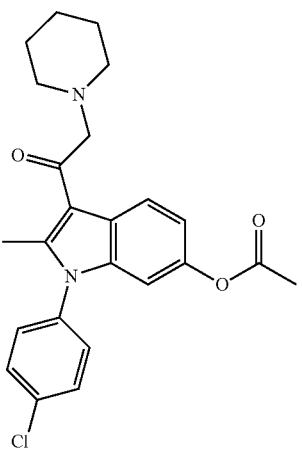 [SMILES: CC(=O)Oc1ccc2c(C(=O)CN3CCCCC3)c(C)n(-c3ccc(Cl)cc3)c2c1] |
| 173 | 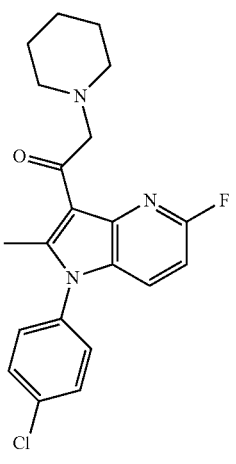 [SMILES: Cc1c(C(=O)CN2CCCCC2)c2nc(F)ccc2n1-c1ccc(Cl)cc1] |
| 174 | 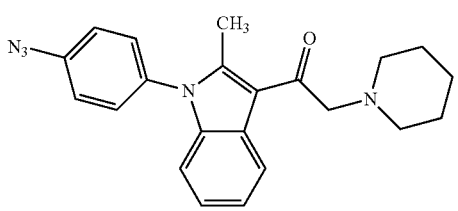 [SMILES: Cc1c(C(=O)CN2CCCCC2)c2ccccc2n1-c1ccc(N=[N+]=[N-])cc1] |
| 175 | 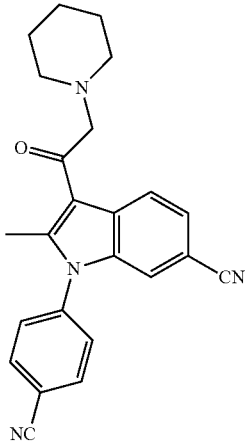 [SMILES: Cc1c(C(=O)CN2CCCCC2)c2ccc(C#N)cc2n1-c1ccc(C#N)cc1] |
| 176 | 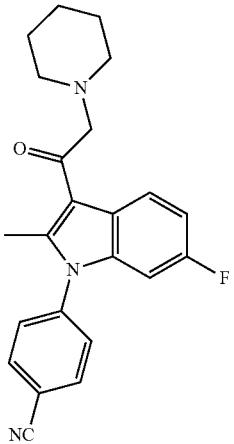 [SMILES: Cc1c(C(=O)CN2CCCCC2)c2ccc(F)cc2n1-c1ccc(C#N)cc1] |
| 177 | 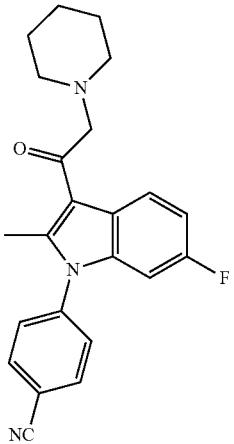 [SMILES: Cc1c(C(=O)CN2CCCCC2)c2ccc(F)cc2n1-c1ccc(C#N)cc1] |
| 178 | 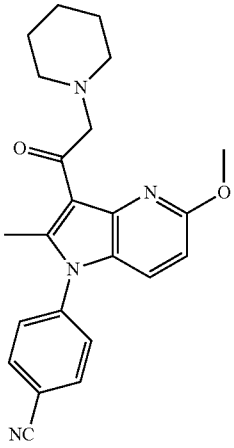 |

TABLE 1-continued
| Compound No. | Chemical Structure |
|---|---|
| 179 | 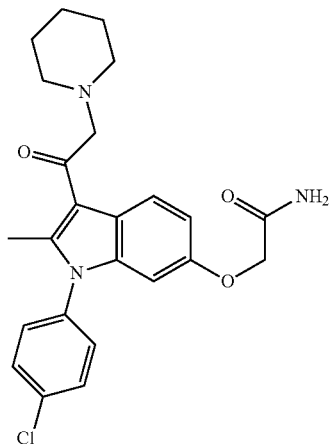 [SMILES: Cc1c(C(=O)CN2CCCCC2)c2ccc(OCC(N)=O)cc2n1-c1ccc(Cl)cc1] |
| 180 | 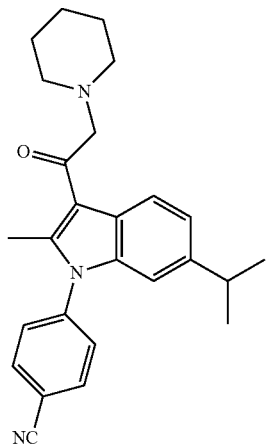 [SMILES: Cc1c(C(=O)CN2CCCCC2)c2ccc(C(C)C)cc2n1-c1ccc(C#N)cc1] |
| 181 | 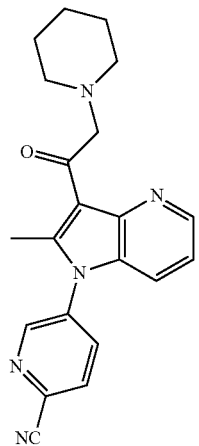 |
| 182 | 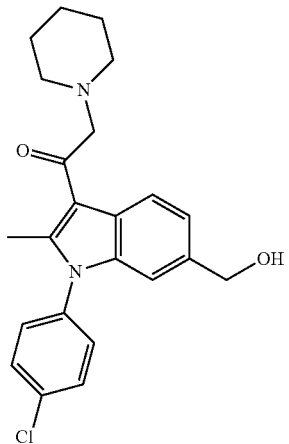 [SMILES: Cc1c(C(=O)CN2CCCCC2)c2ccc(CO)cc2n1-c1ccc(Cl)cc1] |
| 183 | 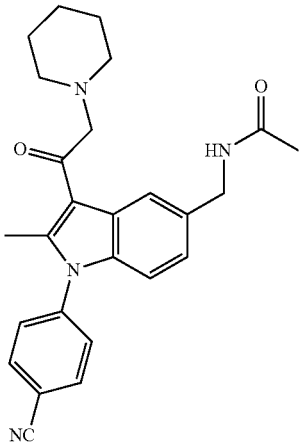 [SMILES: CC(=O)NCc1ccc2c(c1)c(C(=O)CN1CCCCC1)c(C)n2-c1ccc(C#N)cc1] |
| 184 | 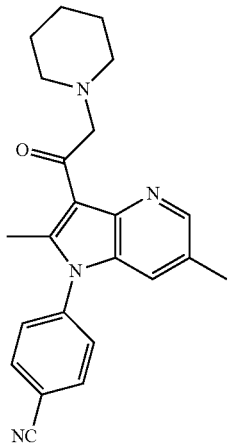 |

TABLE 1-continued
| Compound No. | Chemical Structure |
|---|---|
| 185 | 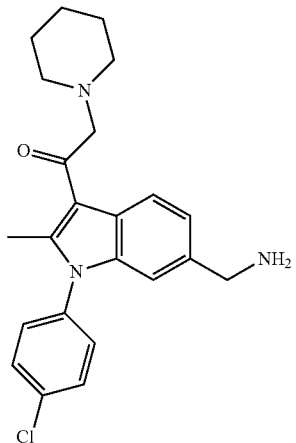 [SMILES: Cc1c(C(=O)CN2CCCCC2)c2ccc(CN)cc2n1-c1ccc(Cl)cc1] |
| 186 | 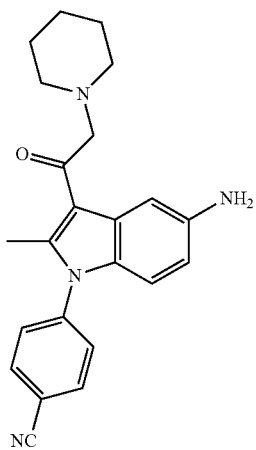 [SMILES: Cc1c(C(=O)CN2CCCCC2)c2cc(N)ccc2n1-c1ccc(C#N)cc1] |
| 187 | 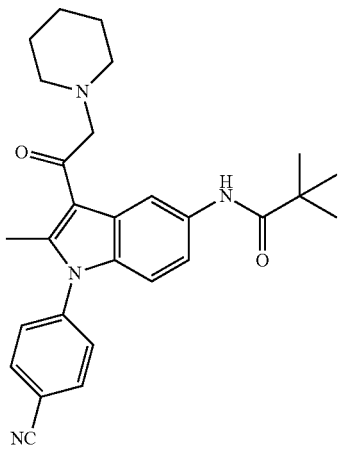 [SMILES: Cc1c(C(=O)CN2CCCCC2)c2cc(NC(=O)C(C)(C)C)ccc2n1-c1ccc(C#N)cc1] |
| 188 | 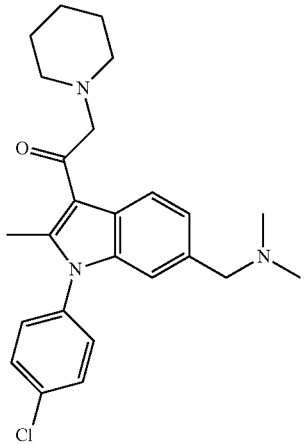 |
| 189 | 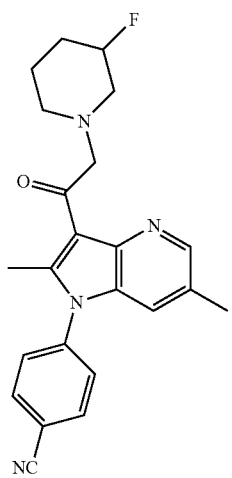 |
| 190 | 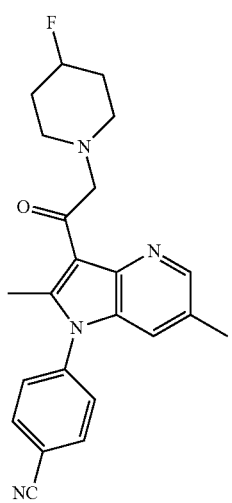 |

TABLE 1-continued
| Compound No. | Chemical Structure |
|---|---|
| 191 | 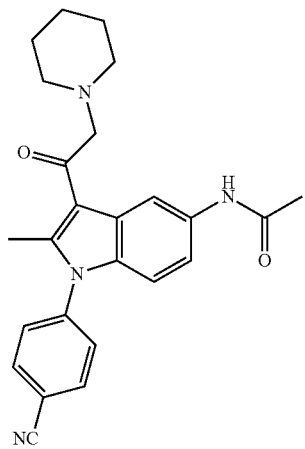 [SMILES: CC(=O)Nc1ccc2c(c1)c(C(=O)CN1CCCCC1)c(C)n2-c1ccc(C#N)cc1] |
| 192 | 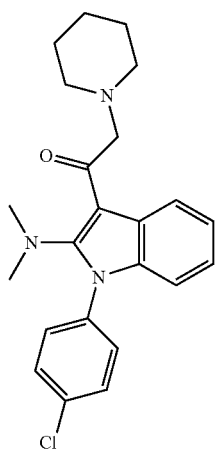 [SMILES: CN(C)c1c(C(=O)CN2CCCCC2)c2ccccc2n1-c1ccc(Cl)cc1] |
| 193 | 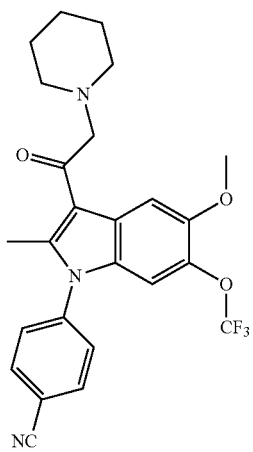 [SMILES: COc1cc2c(C(=O)CN3CCCCC3)c(C)n(-c3ccc(C#N)cc3)c2cc1OC(F)(F)F] |
| 194 | 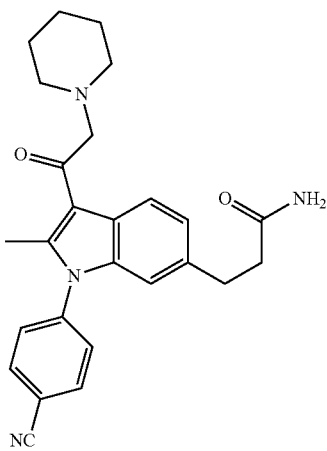 |
| 195 | 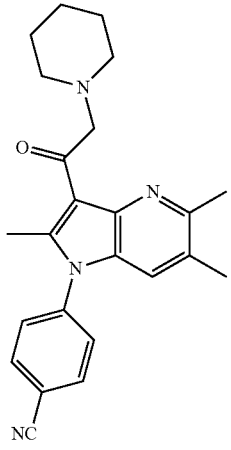 |
| 196 | 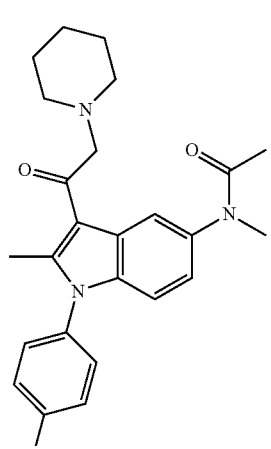 |

TABLE 1-continued

| Compound No. | Chemical Structure |
|---|---|
| 197 | 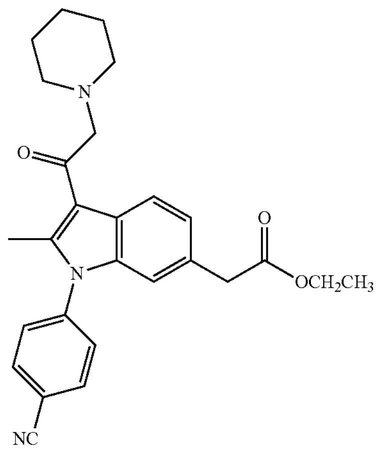 [SMILES: CCOC(=O)Cc1ccc2c(C(=O)CN3CCCCC3)c(C)n(-c3ccc(C#N)cc3)c2c1] |
| 198 | 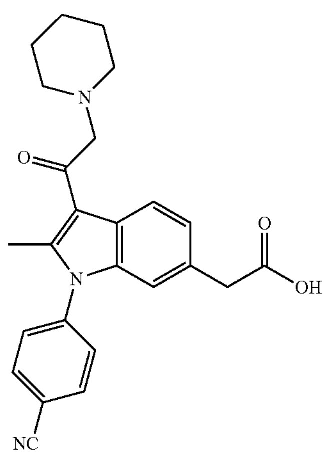 [SMILES: Cc1c(C(=O)CN2CCCCC2)c2ccc(CC(=O)O)cc2n1-c1ccc(C#N)cc1] |
| 199 | 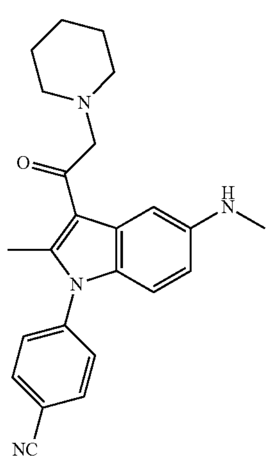 |
| 200 | |
| 201 | |
| 202 | |

TABLE 1-continued
| Compound No. | Chemical Structure |
|---|---|
| 203 | 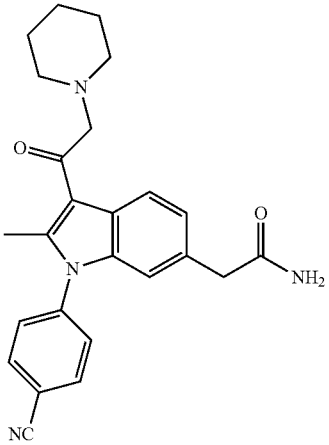 [SMILES: Cc1c(C(=O)CN2CCCCC2)c2ccc(CC(N)=O)cc2n1-c1ccc(C#N)cc1] |
| 204 | 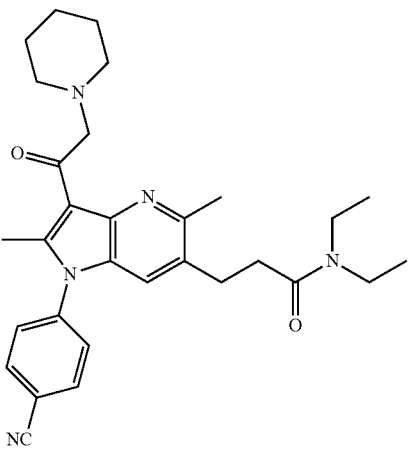 [SMILES: CCN(CC)C(=O)CCc1cc2c(nc1C)c(C(=O)CN1CCCCC1)c(C)n2-c1ccc(C#N)cc1] |
| 205 | 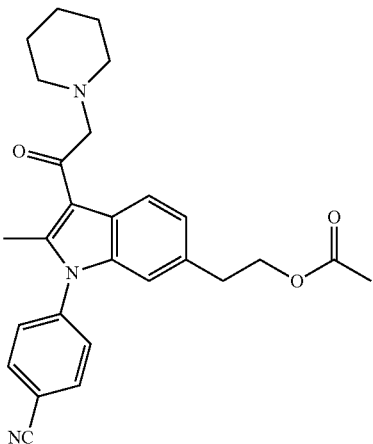 [SMILES: CC(=O)OCCc1ccc2c(C(=O)CN3CCCCC3)c(C)n(-c3ccc(C#N)cc3)c2c1] |
| 206 | 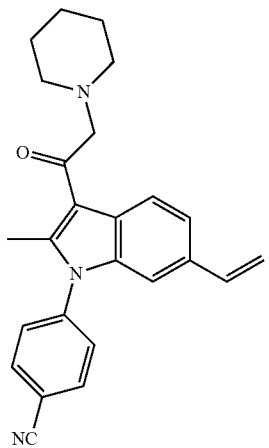 [SMILES: C=Cc1ccc2c(C(=O)CN3CCCCC3)c(C)n(-c3ccc(C#N)cc3)c2c1] |
| 207 | 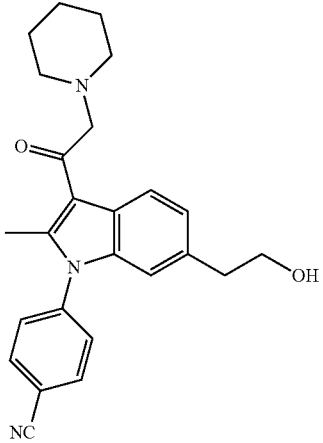 [SMILES: Cc1c(C(=O)CN2CCCCC2)c2ccc(CCO)cc2n1-c1ccc(C#N)cc1] |
| 208 | 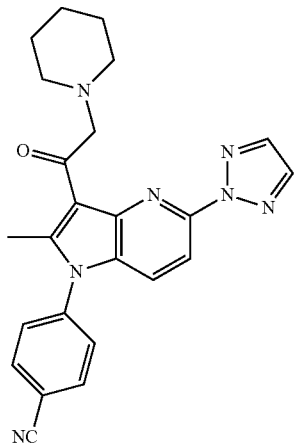 [SMILES: Cc1c(C(=O)CN2CCCCC2)c2nc(-n3nccn3)ccc2n1-c1ccc(C#N)cc1] |

TABLE 1-continued
| Compound No. | Chemical Structure |
|---|---|
| 209 | 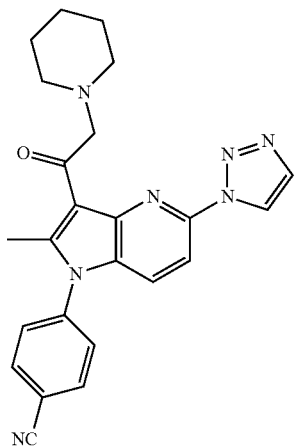 [SMILES: Cc1c(C(=O)CN2CCCCC2)c2nc(-n3ccnn3)ccc2n1-c1ccc(C#N)cc1] |
| 210 | 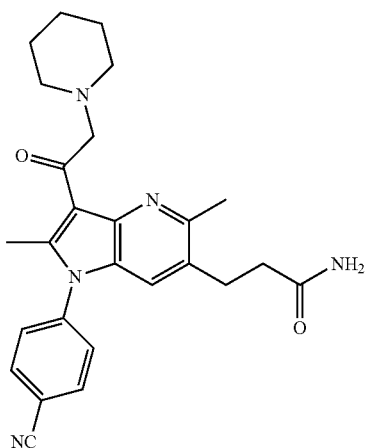 [SMILES: Cc1nc2c(C(=O)CN3CCCCC3)c(C)n(-c3ccc(C#N)cc3)c2cc1CCC(N)=O] |
| 211 | 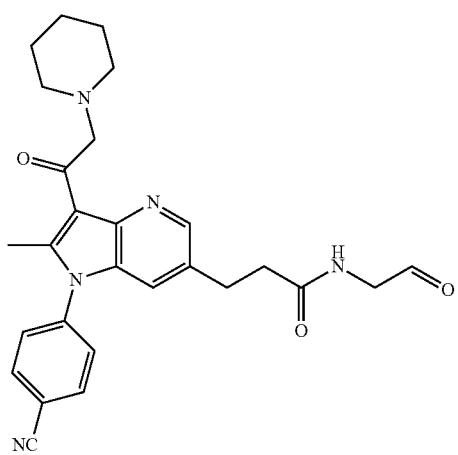 [SMILES: Cc1c(C(=O)CN2CCCCC2)c2ncc(CCC(=O)NCC=O)cc2n1-c1ccc(C#N)cc1] |
| 212 | 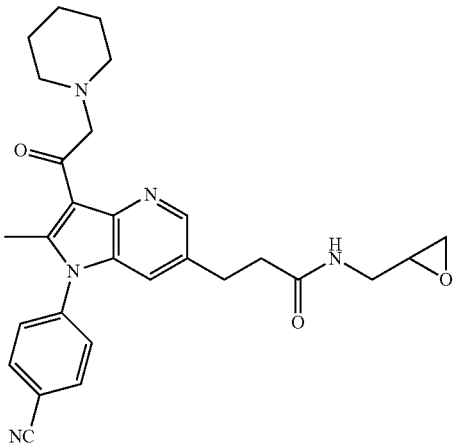 [SMILES: Cc1c(C(=O)CN2CCCCC2)c2ncc(CCC(=O)NCC3CO3)cc2n1-c1ccc(C#N)cc1] |
| 213 | 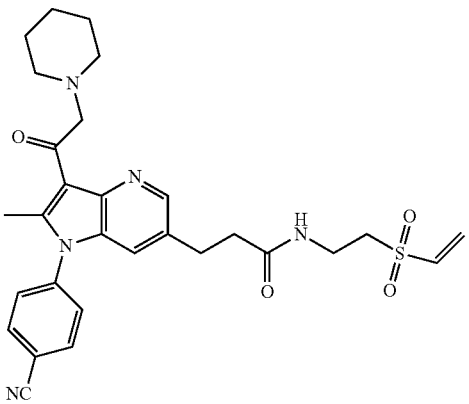 [SMILES: C=CS(=O)(=O)CCNC(=O)CCc1cnc2c(C(=O)CN3CCCCC3)c(C)n(-c3ccc(C#N)cc3)c2c1] |
| 214 | 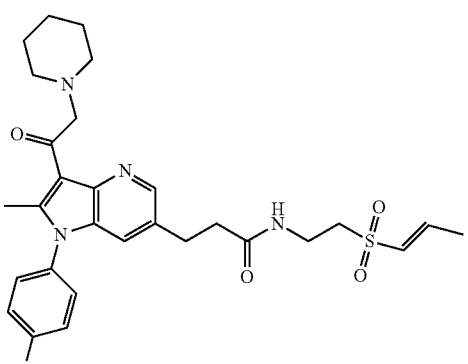 |

TABLE 1-continued
| Compound No. | Chemical Structure |
|---|---|
| 215 | 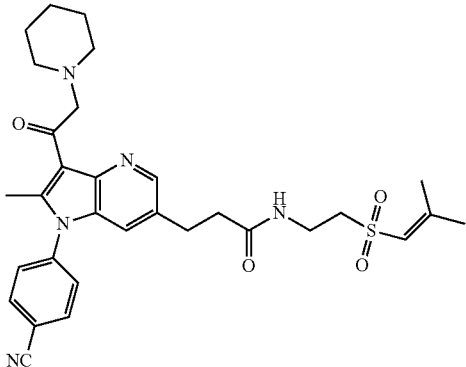 [SMILES: CC(C)=CS(=O)(=O)CCNC(=O)CCc1cnc2c(C(=O)CN3CCCCC3)c(C)n(-c3ccc(C#N)cc3)c2c1] |
| 216 | 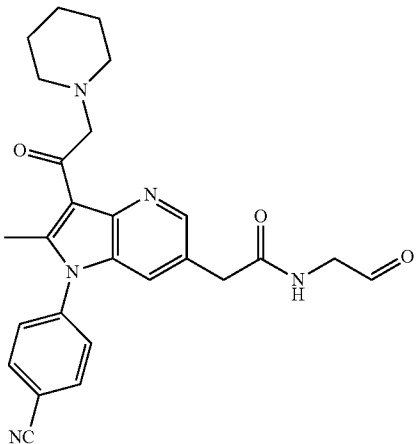 [SMILES: Cc1c(C(=O)CN2CCCCC2)c2ncc(CC(=O)NCC=O)cc2n1-c1ccc(C#N)cc1] |
| 217 | 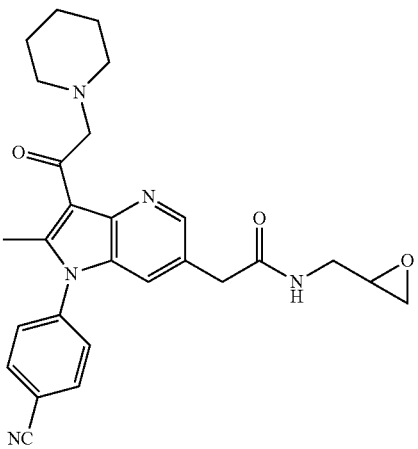 [SMILES: Cc1c(C(=O)CN2CCCCC2)c2ncc(CC(=O)NCC3CO3)cc2n1-c1ccc(C#N)cc1] |
| 218 | 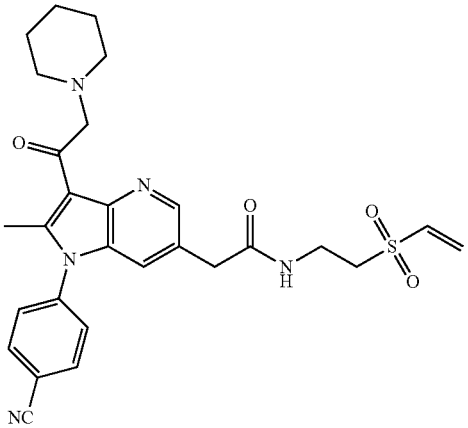 [SMILES: C=CS(=O)(=O)CCNC(=O)Cc1cnc2c(C(=O)CN3CCCCC3)c(C)n(-c3ccc(C#N)cc3)c2c1] |
| 219 | 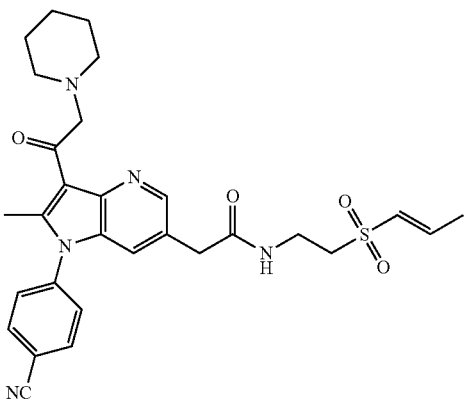 [SMILES: C/C=C/S(=O)(=O)CCNC(=O)Cc1cnc2c(C(=O)CN3CCCCC3)c(C)n(-c3ccc(C#N)cc3)c2c1] |
| 220 | 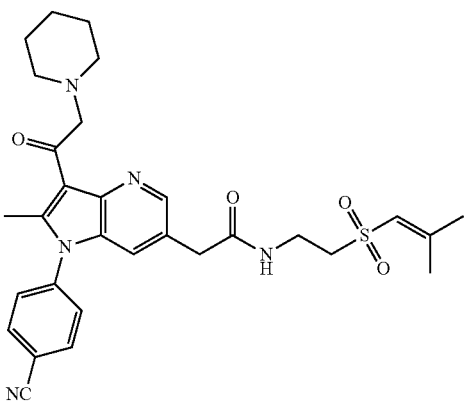 [SMILES: CC(C)=CS(=O)(=O)CCNC(=O)Cc1cnc2c(C(=O)CN3CCCCC3)c(C)n(-c3ccc(C#N)cc3)c2c1] |

TABLE 1-continued
| Compound No. | Chemical Structure |
|---|---|
| 230 | 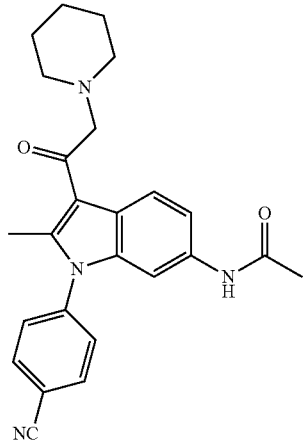 [SMILES: CC(=O)Nc1ccc2c(C(=O)CN3CCCCC3)c(C)n(-c3ccc(C#N)cc3)c2c1] |
| 231 | 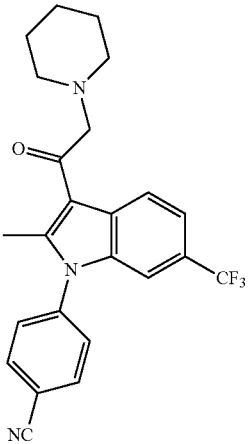 [SMILES: Cc1c(C(=O)CN2CCCCC2)c2ccc(C(F)(F)F)cc2n1-c1ccc(C#N)cc1] |
| 233 | 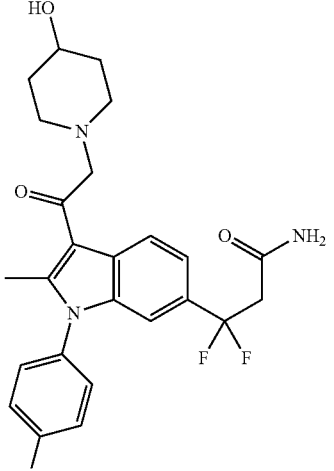 |
| 234 | 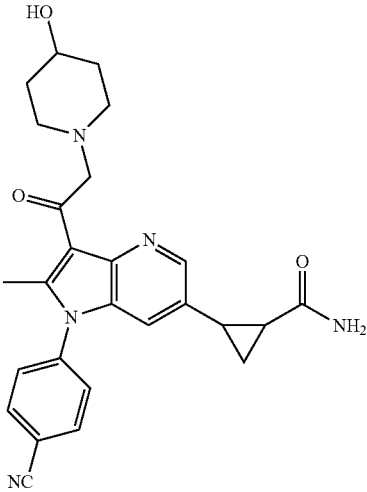 [SMILES: Cc1c(C(=O)CN2CCC(O)CC2)c2ncc(C3CC3C(N)=O)cc2n1-c1ccc(C#N)cc1] |
| 235 | 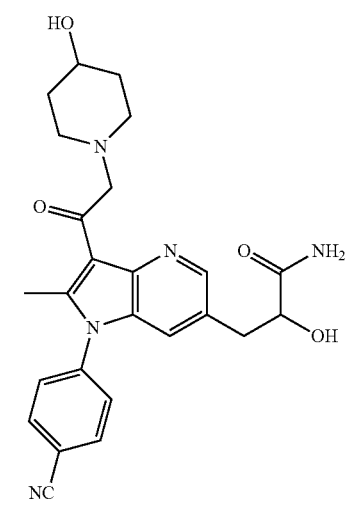 [SMILES: Cc1c(C(=O)CN2CCC(O)CC2)c2ncc(CC(O)C(N)=O)cc2n1-c1ccc(C#N)cc1] |
| 236 | 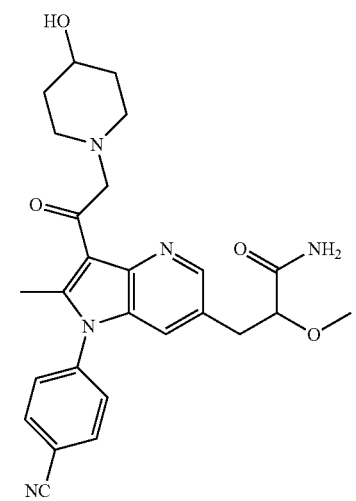 |

TABLE 1-continued
| Compound No. | Chemical Structure |
|---|---|
| 237 | 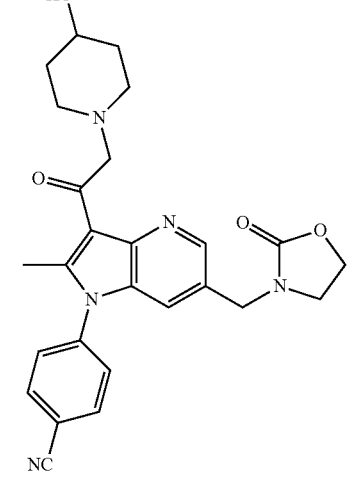 |
| 238 | 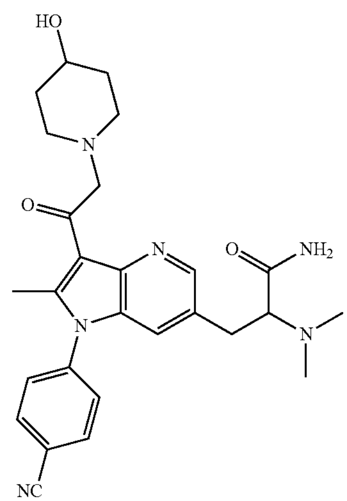 |
| 239 | 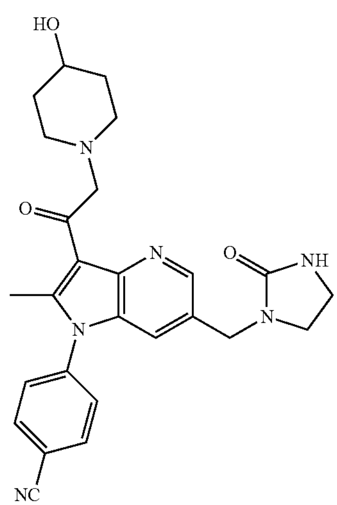 [SMILES: Cc1c(C(=O)CN2CCC(O)CC2)c2ncc(CN3CCNC3=O)cc2n1-c1ccc(C#N)cc1] |
| 240 | |
| 241 | |
| 242 | |

TABLE 1-continued
| Compound No. | Chemical Structure |
|---|---|
| 243 | 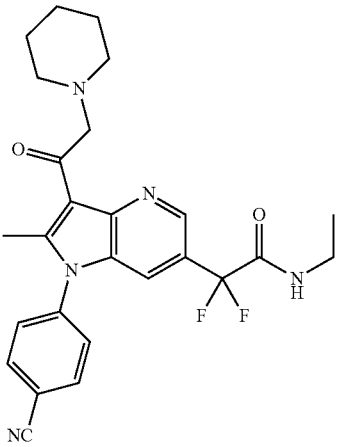 [SMILES: CCNC(=O)C(F)(F)c1cnc2c(C(=O)CN3CCCCC3)c(C)n(-c3ccc(C#N)cc3)c2c1] |
| 244 | 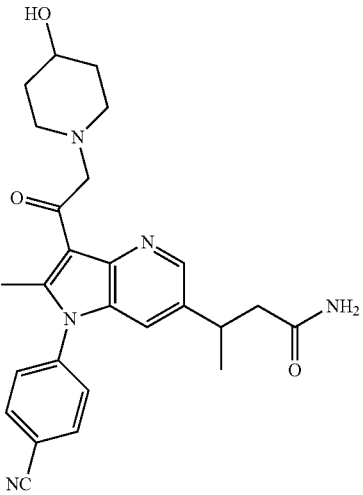 [SMILES: Cc1c(C(=O)CN2CCC(O)CC2)c2ncc(C(C)CC(N)=O)cc2n1-c1ccc(C#N)cc1] |
| 245 | 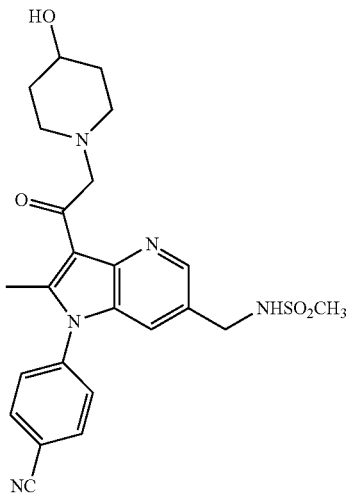 |
| 246 | 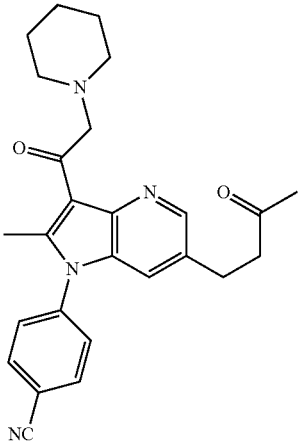 [SMILES: CC(=O)CCc1cnc2c(C(=O)CN3CCCCC3)c(C)n(-c3ccc(C#N)cc3)c2c1] |
| 247 | 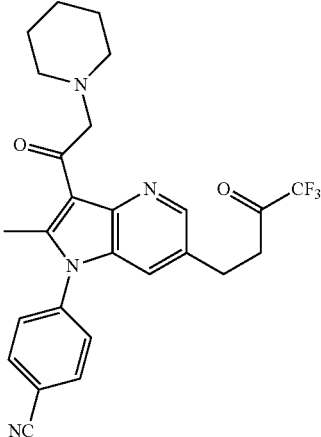 [SMILES: Cc1c(C(=O)CN2CCCCC2)c2ncc(CCC(=O)C(F)(F)F)cc2n1-c1ccc(C#N)cc1] |
| 248 | 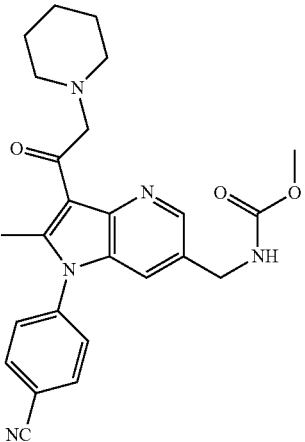 |

TABLE 1-continued
| Compound No. | Chemical Structure |
|---|---|
| 249 | 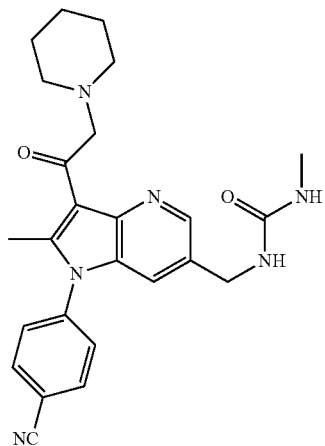 |
| 250 | 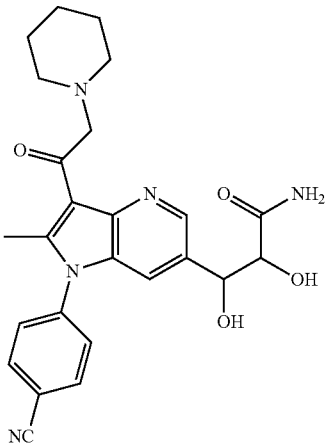 [SMILES: Cc1c(C(=O)CN2CCCCC2)c2ncc(C(O)C(O)C(N)=O)cc2n1-c1ccc(C#N)cc1] |
| 251 | 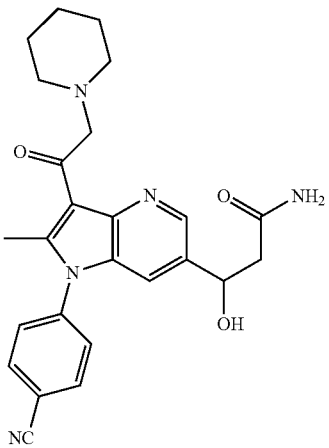 [SMILES: Cc1c(C(=O)CN2CCCCC2)c2ncc(C(O)CC(N)=O)cc2n1-c1ccc(C#N)cc1] |
| 252 | 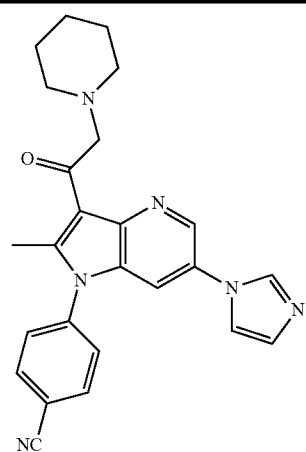 |
| 253 | 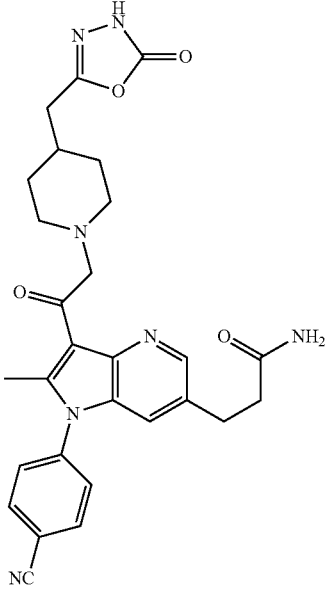 [SMILES: Cc1c(C(=O)CN2CCC(Cc3n[nH]c(=O)o3)CC2)c2ncc(CCC(N)=O)cc2n1-c1ccc(C#N)cc1] |
| 254 | 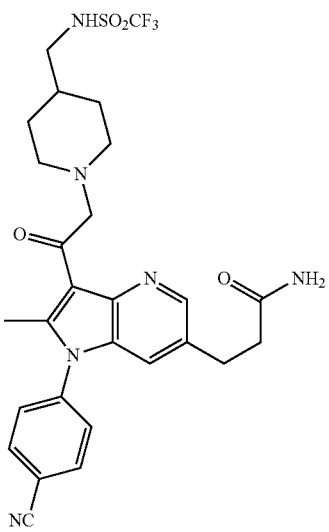 |

TABLE 1-continued

| Compound No. | Chemical Structure |
|---|---|
| 255 | 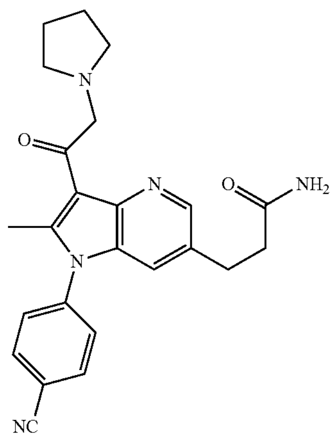 [SMILES: Cc1c(C(=O)CN2CCCC2)c2ncc(CCC(N)=O)cc2n1-c1ccc(C#N)cc1] |
| 256 | 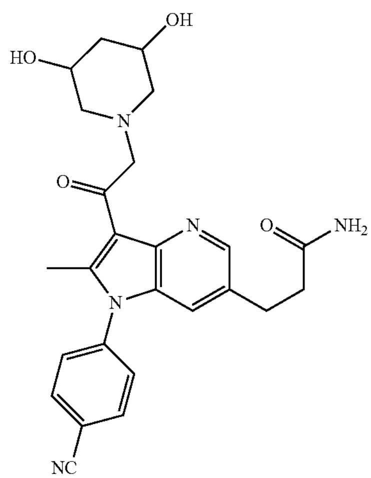 [SMILES: Cc1c(C(=O)CN2CC(O)CC(O)C2)c2ncc(CCC(N)=O)cc2n1-c1ccc(C#N)cc1] |
| 257 | 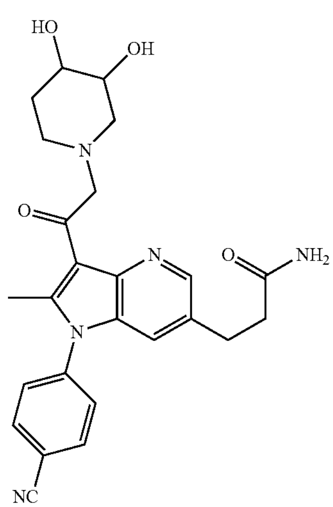 [SMILES: Cc1c(C(=O)CN2CCC(O)C(O)C2)c2ncc(CCC(N)=O)cc2n1-c1ccc(C#N)cc1] |
| 258 | |
| 259 | |
| 260 | |

TABLE 1-continued

| Compound No. | Chemical Structure |
|---|---|
| 261 | 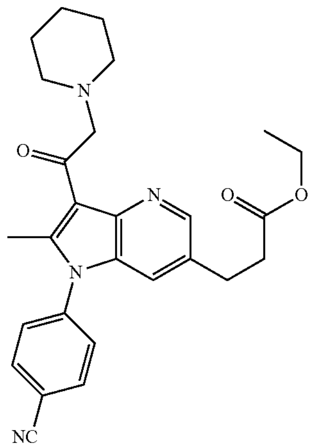 [SMILES: CCOC(=O)CCc1cnc2c(C(=O)CN3CCCCC3)c(C)n(-c3ccc(C#N)cc3)c2c1] |
| 262 | 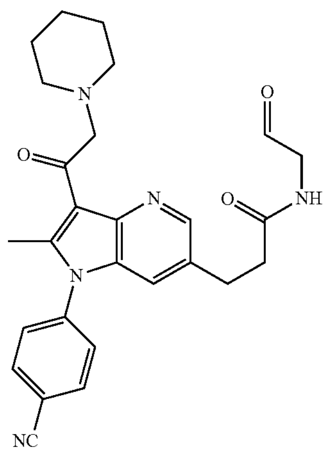 [SMILES: Cc1c(C(=O)CN2CCCCC2)c2ncc(CCC(=O)NCC=O)cc2n1-c1ccc(C#N)cc1] |
| 263 | 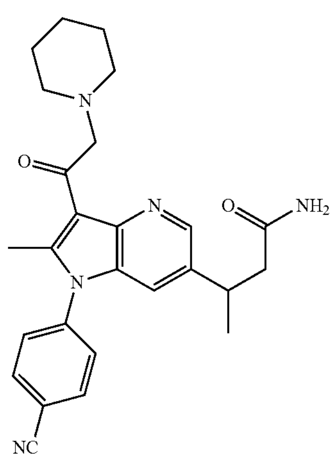 [SMILES: Cc1c(C(=O)CN2CCCCC2)c2ncc(C(C)CC(N)=O)cc2n1-c1ccc(C#N)cc1] |
| 264 | 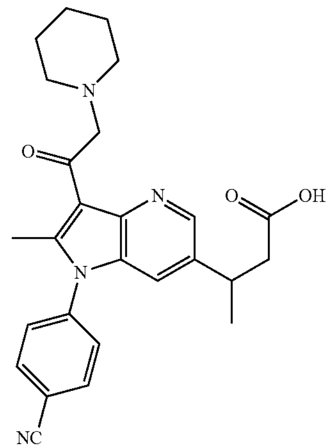 [SMILES: Cc1c(C(=O)CN2CCCCC2)c2ncc(C(C)CC(=O)O)cc2n1-c1ccc(C#N)cc1] |
| 265 | 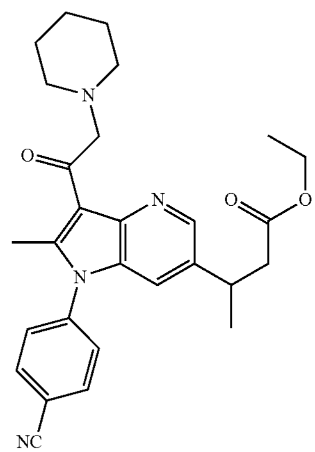 [SMILES: CCOC(=O)CC(C)c1cnc2c(C(=O)CN3CCCCC3)c(C)n(-c3ccc(C#N)cc3)c2c1] |
| 266 | 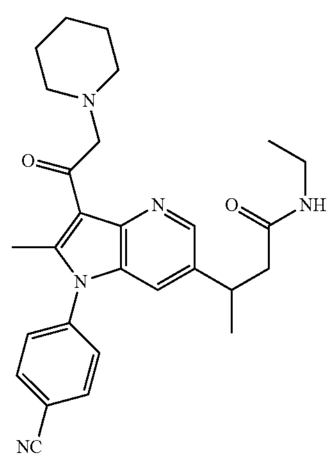 [SMILES: CCNC(=O)CC(C)c1cnc2c(C(=O)CN3CCCCC3)c(C)n(-c3ccc(C#N)cc3)c2c1] |

TABLE 1-continued
| Compound No. | Chemical Structure |
| --- | --- |
| 267 | 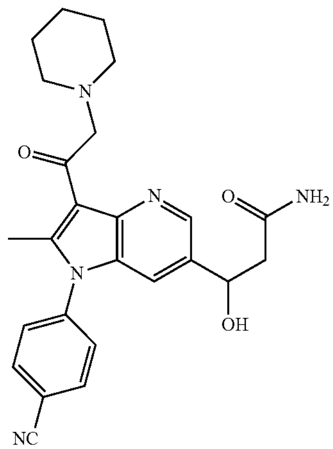 [SMILES: Cc1c(C(=O)CN2CCCCC2)c2ncc(C(O)CC(N)=O)cc2n1-c1ccc(C#N)cc1] |
| 268 | 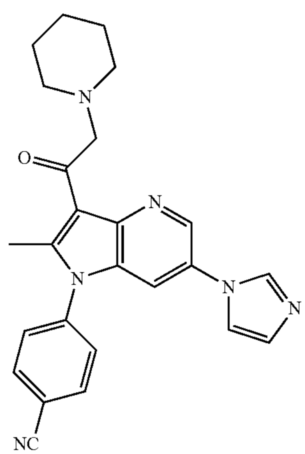 [SMILES: Cc1c(C(=O)CN2CCCCC2)c2ncc(-n3ccnc3)cc2n1-c1ccc(C#N)cc1] |
| 269 | 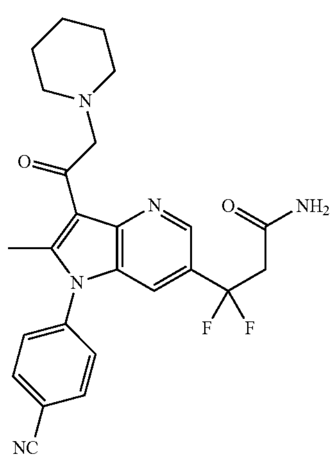 [SMILES: Cc1c(C(=O)CN2CCCCC2)c2ncc(C(F)(F)CC(N)=O)cc2n1-c1ccc(C#N)cc1] |
| 270 | |
| 271 | |
| 272 | |
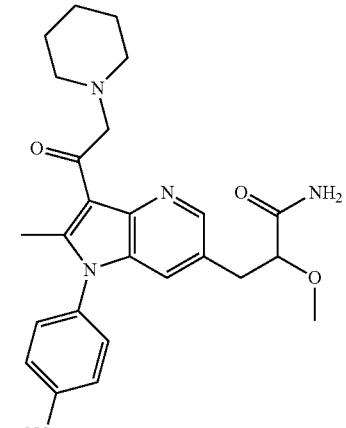

TABLE 1-continued
| Compound No. | Chemical Structure |
|---|---|
| 273 | 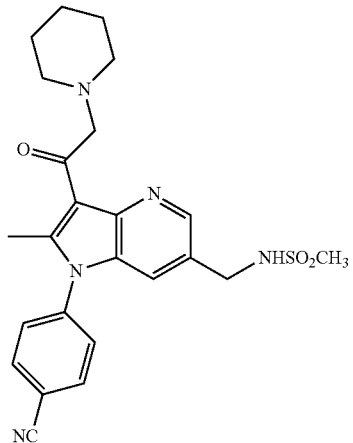 |
| 274 | 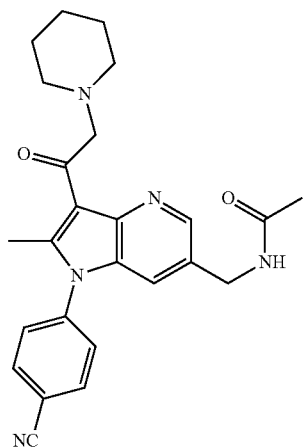 [SMILES: CC(=O)NCc1cnc2c(C(=O)CN3CCCCC3)c(C)n(-c3ccc(C#N)cc3)c2c1] |
| 275 | 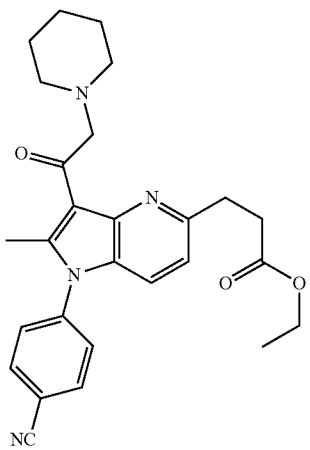 [SMILES: CCOC(=O)CCc1ccc2c(n1)c(C(=O)CN1CCCCC1)c(C)n2-c1ccc(C#N)cc1] |
| 276 | 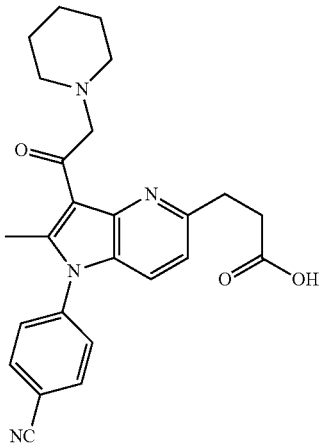 [SMILES: Cc1c(C(=O)CN2CCCCC2)c2nc(CCC(=O)O)ccc2n1-c1ccc(C#N)cc1] |
| 277 | 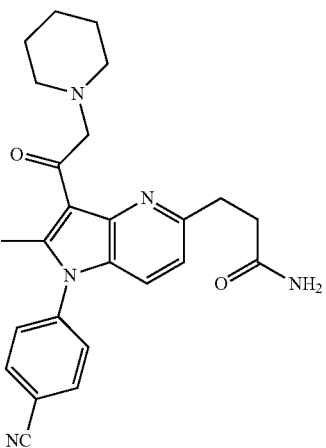 [SMILES: Cc1c(C(=O)CN2CCCCC2)c2nc(CCC(N)=O)ccc2n1-c1ccc(C#N)cc1] |
| 278 | 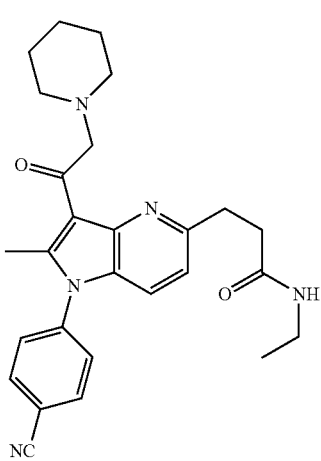 [SMILES: CCNC(=O)CCc1ccc2c(n1)c(C(=O)CN1CCCCC1)c(C)n2-c1ccc(C#N)cc1] |

TABLE 1-continued
| Compound No. | Chemical Structure |
|---|---|
| 279 | 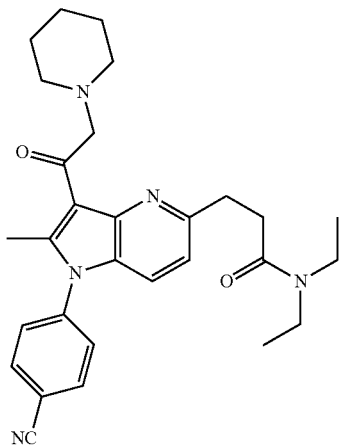 [SMILES: CCN(CC)C(=O)CCc1ccc2c(n1)c(C(=O)CN1CCCCC1)c(C)n2-c1ccc(C#N)cc1] |
| 280 | 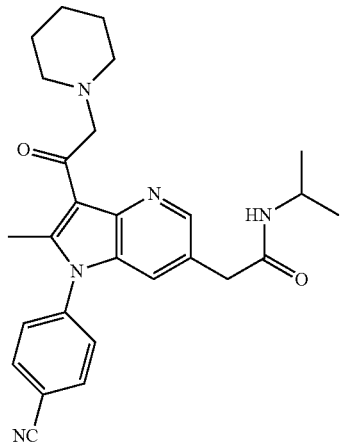 [SMILES: Cc1c(C(=O)CN2CCCCC2)c2ncc(CC(=O)NC(C)C)cc2n1-c1ccc(C#N)cc1] |
| 281 | 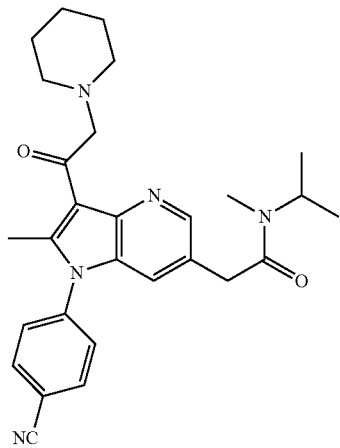 [SMILES: Cc1c(C(=O)CN2CCCCC2)c2ncc(CC(=O)N(C)C(C)C)cc2n1-c1ccc(C#N)cc1] |
| 282 | 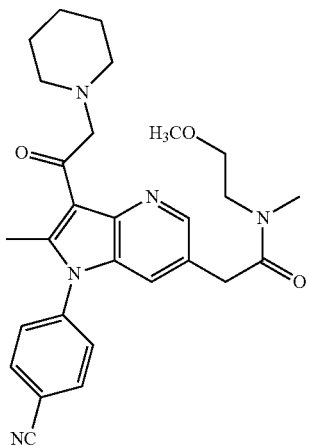 |
| 283 | 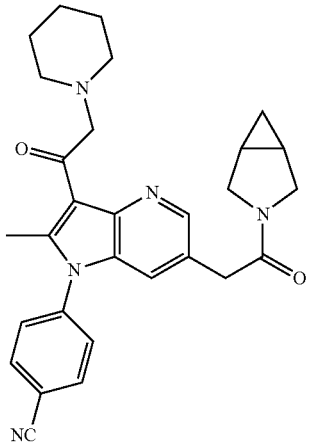 [SMILES: Cc1c(C(=O)CN2CCCCC2)c2ncc(CC(=O)N3CC4CC4C3)cc2n1-c1ccc(C#N)cc1] |
| 284 | 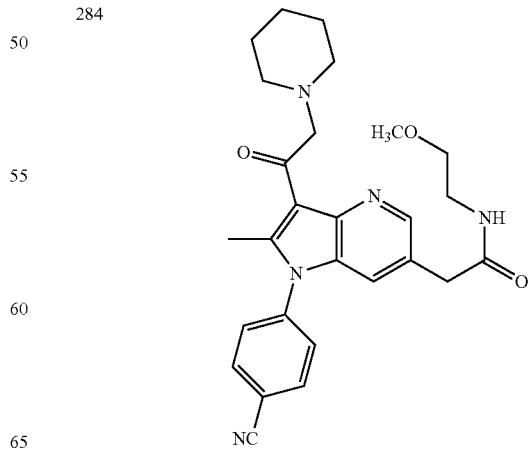 |

TABLE 1-continued
| Compound No. | Chemical Structure |
|---|---|
| 285 | 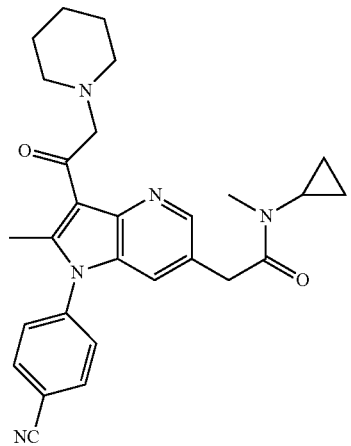 [SMILES: Cc1c(C(=O)CN2CCCCC2)c2ncc(CC(=O)N(C)C3CC3)cc2n1-c1ccc(C#N)cc1] |
| 286 | 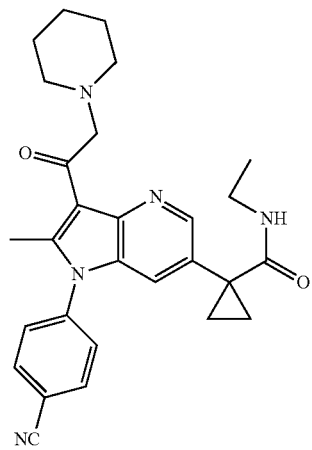 [SMILES: CCNC(=O)C1(c2cnc3c(C(=O)CN4CCCCC4)c(C)n(-c4ccc(C#N)cc4)c3c2)CC1] |
| 287 | 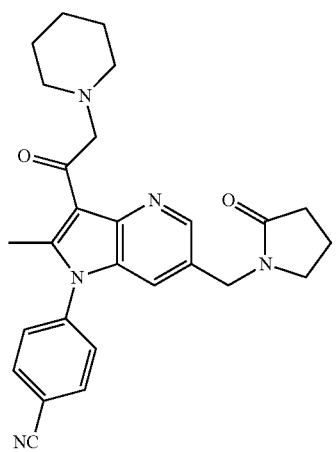 |
| 288 | 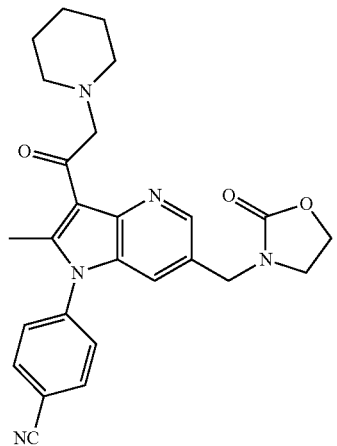 |
| 289 | 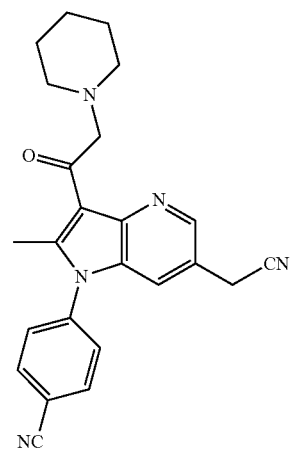 [SMILES: Cc1c(C(=O)CN2CCCCC2)c2ncc(CC#N)cc2n1-c1ccc(C#N)cc1] |
| 290 | 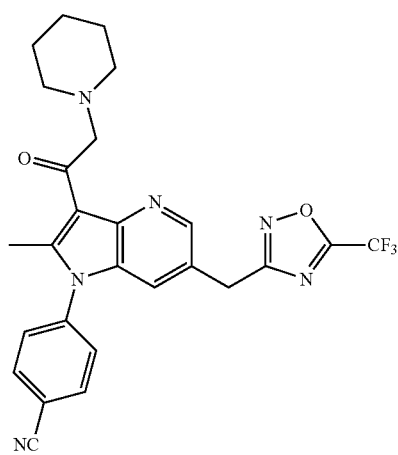 [SMILES: Cc1c(C(=O)CN2CCCCC2)c2ncc(Cc3noc(C(F)(F)F)n3)cc2n1-c1ccc(C#N)cc1] |

TABLE 1-continued
| Compound No. | Chemical Structure |
|---|---|
| 291 | 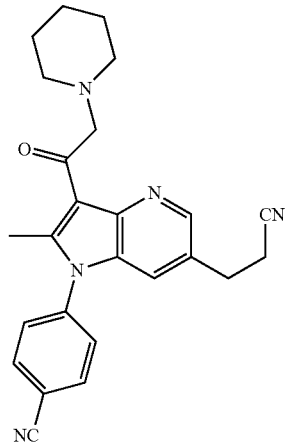 [SMILES: Cc1c(C(=O)CN2CCCCC2)c2ncc(CCC#N)cc2n1-c1ccc(C#N)cc1] |
| 292 | 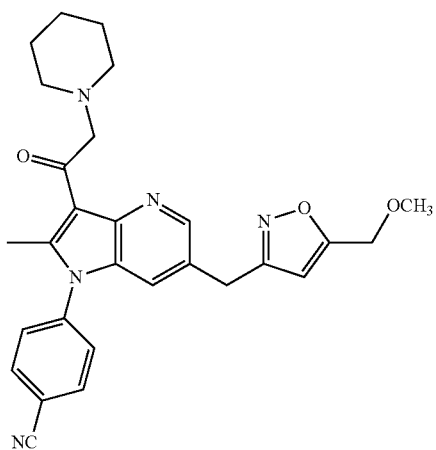 [SMILES: COCc1cc(Cc2cnc3c(C(=O)CN4CCCCC4)c(C)n(-c4ccc(C#N)cc4)c3c2)no1] |
| 294 | 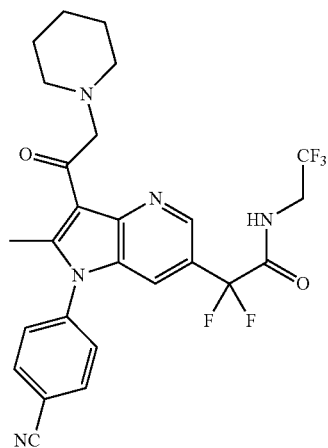 [SMILES: Cc1c(C(=O)CN2CCCCC2)c2ncc(C(F)(F)C(=O)NCC(F)(F)F)cc2n1-c1ccc(C#N)cc1] |
TABLE 1-continued
| Compound No. | Chemical Structure |
|---|---|
| 295 | 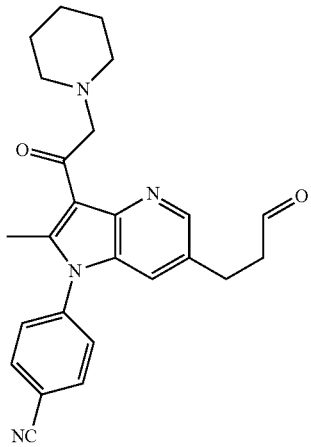 [SMILES: Cc1c(C(=O)CN2CCCCC2)c2ncc(CCC=O)cc2n1-c1ccc(C#N)cc1] |
| 296 | 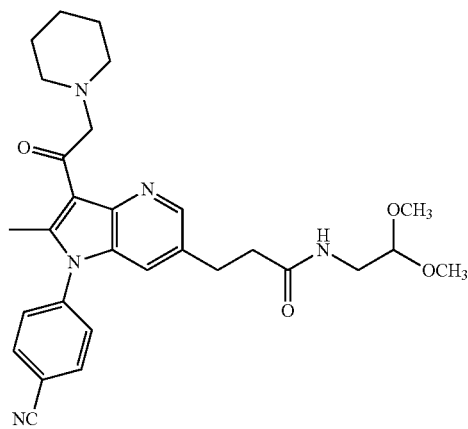 [SMILES: COC(CNC(=O)CCc1cnc2c(C(=O)CN3CCCCC3)c(C)n(-c3ccc(C#N)cc3)c2c1)OC] |
| 297 | 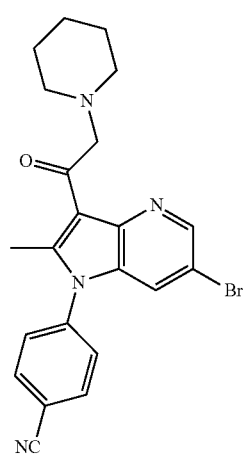 [SMILES: Cc1c(C(=O)CN2CCCCC2)c2ncc(Br)cc2n1-c1ccc(C#N)cc1] |

TABLE 1-continued
| Compound No. | Chemical Structure |
|---|---|
| 298 | 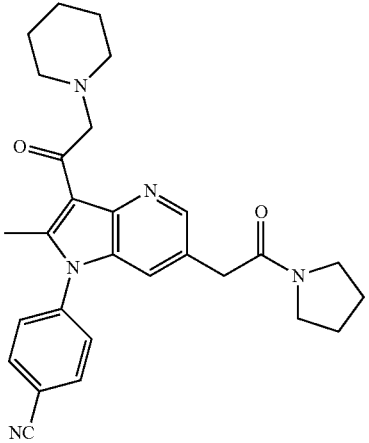 [SMILES: Cc1c(C(=O)CN2CCCCC2)c2ncc(CC(=O)N3CCCC3)cc2n1-c1ccc(C#N)cc1] |
| 299 | 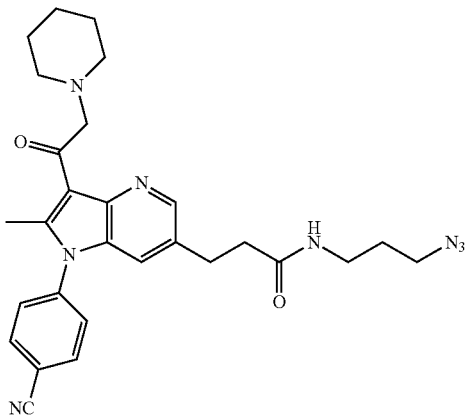 [SMILES: Cc1c(C(=O)CN2CCCCC2)c2ncc(CCC(=O)NCCCN=[N+]=[N-])cc2n1-c1ccc(C#N)cc1] |
| 300 | 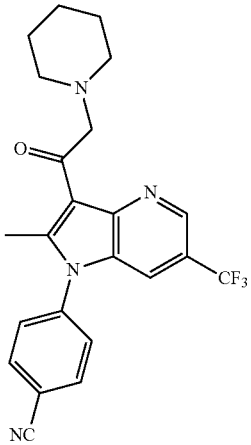 [SMILES: Cc1c(C(=O)CN2CCCCC2)c2ncc(C(F)(F)F)cc2n1-c1ccc(C#N)cc1] |
| 301 | 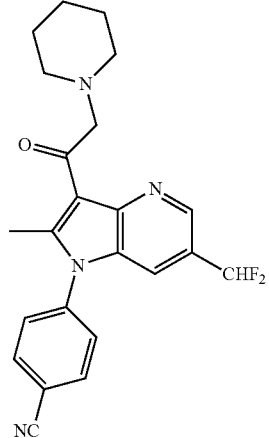 [SMILES: Cc1c(C(=O)CN2CCCCC2)c2ncc(C(F)F)cc2n1-c1ccc(C#N)cc1] |
| 302 | 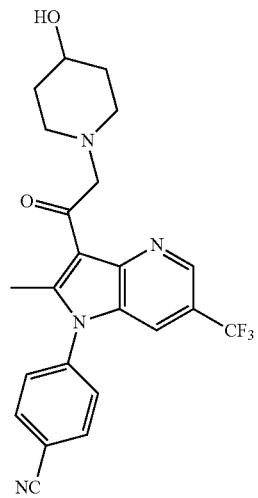 [SMILES: Cc1c(C(=O)CN2CCC(O)CC2)c2ncc(C(F)(F)F)cc2n1-c1ccc(C#N)cc1] |
| 303 | 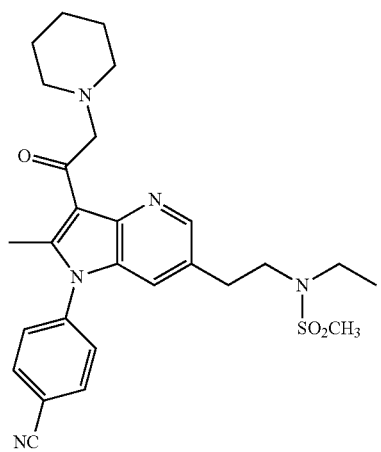 [SMILES: CCN(CCc1cnc2c(C(=O)CN3CCCCC3)c(C)n(-c3ccc(C#N)cc3)c2c1)S(C)(=O)=O] |

US 9,850,262 B2
TABLE 1-continued
| Compound No. | Chemical Structure |
|---|---|
| 304 | 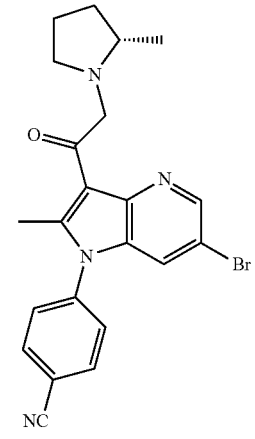 |
| 305 | 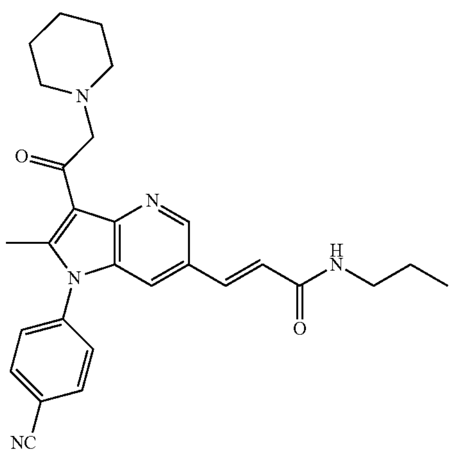 [SMILES: CCCNC(=O)/C=C/c1cnc2c(C(=O)CN3CCCCC3)c(C)n(-c3ccc(C#N)cc3)c2c1] |
| 306 | 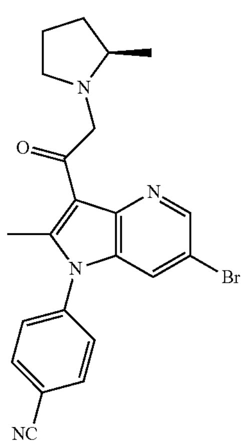 [SMILES: Cc1c(C(=O)CN2CCC[C@H]2C)c2ncc(Br)cc2n1-c1ccc(C#N)cc1] |
TABLE 1-continued
| Compound No. | Chemical Structure |
|---|---|
| 307 | 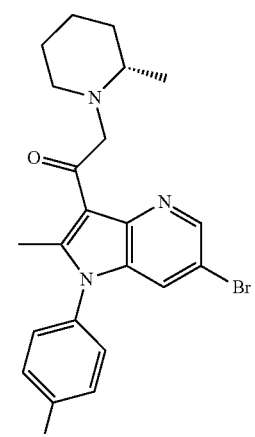 |
| 308 | 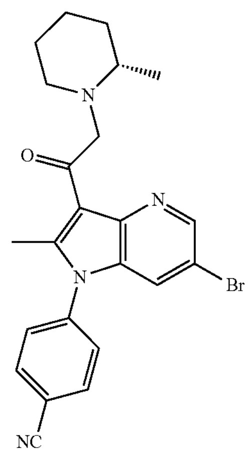 [SMILES: Cc1c(C(=O)CN2CCCC[C@@H]2C)c2ncc(Br)cc2n1-c1ccc(C#N)cc1] |
| 309 | 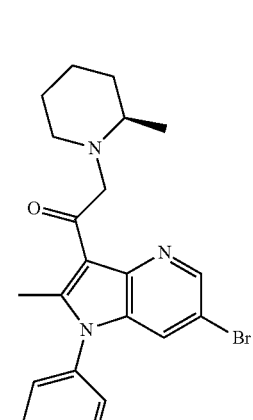 |

TABLE 1-continued

| Compound No. | Chemical Structure |
|---|---|
| 310 | (2,2-dimethylpyrrolidin-1-yl)methyl ketone attached to 2-methyl-6-bromo-1-(4-cyanophenyl)pyrrolo[3,2-b]pyridine |
| 311 | (4-methoxypiperidin-1-yl)methyl ketone attached to 2-methyl-6-bromo-1-(4-cyanophenyl)pyrrolo[3,2-b]pyridine |
| 312 | (4-(hydroxymethyl)piperidin-1-yl)methyl ketone attached to 2-methyl-6-bromo-1-(4-cyanophenyl)pyrrolo[3,2-b]pyridine |
| 314 | (3,6-dihydro-2H-pyridin-1-yl)methyl ketone attached to 2-methyl-6-bromo-1-(4-cyanophenyl)pyrrolo[3,2-b]pyridine |
| 315 | (2,5-dihydro-1H-pyrrol-1-yl)methyl ketone attached to 2-methyl-6-bromo-1-(4-cyanophenyl)pyrrolo[3,2-b]pyridine |
| 318 | (2,2-dimethylpiperidin-1-yl)methyl ketone attached to 2-methyl-6-bromo-1-(4-cyanophenyl)pyrrolo[3,2-b]pyridine |

TABLE 1-continued
| Compound No. | Chemical Structure |
|---|---|
| 319 | 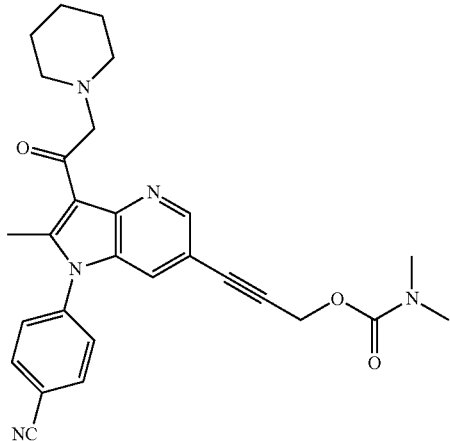 |
| 320 | 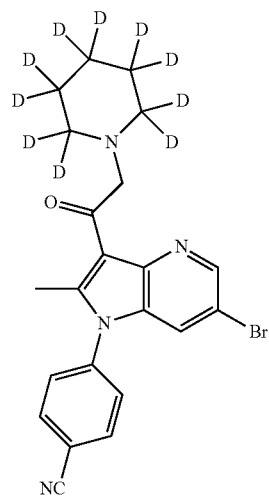 [SMILES: [2H]C1([2H])N(CC(=O)c2c(C)n(-c3ccc(C#N)cc3)c3cc(Br)cnc23)C([2H])([2H])C([2H])([2H])C([2H])([2H])C1([2H])[2H]] |
| 321 | 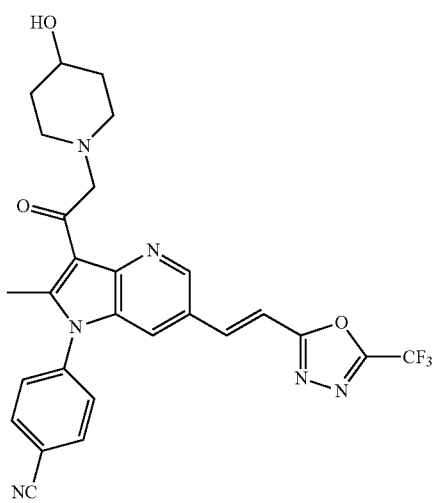 [SMILES: Cc1c(C(=O)CN2CCC(O)CC2)c2ncc(/C=C/c3nnc(C(F)(F)F)o3)cc2n1-c1ccc(C#N)cc1] |
TABLE 1-continued
| Compound No. | Chemical Structure |
|---|---|
| 324 | 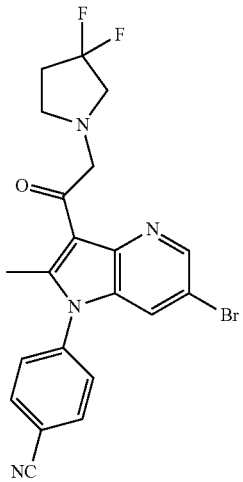 [SMILES: Cc1c(C(=O)CN2CCC(F)(F)C2)c2ncc(Br)cc2n1-c1ccc(C#N)cc1] |
| 325 | 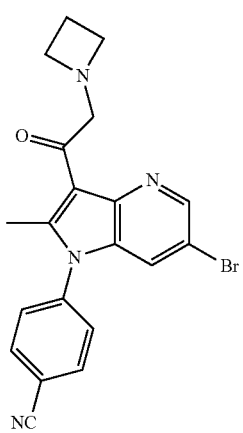 [SMILES: Cc1c(C(=O)CN2CCC2)c2ncc(Br)cc2n1-c1ccc(C#N)cc1] |
| 326 | 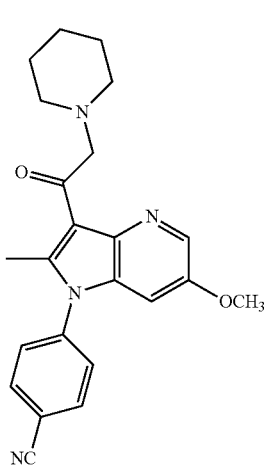 [SMILES: COc1cnc2c(C(=O)CN3CCCCC3)c(C)n(-c3ccc(C#N)cc3)c2c1] |

TABLE 1-continued
| Compound No. | Chemical Structure |
|---|---|
| 327 | 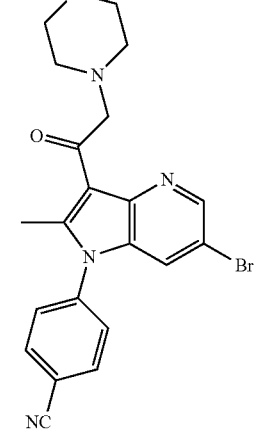 |
| 328 | 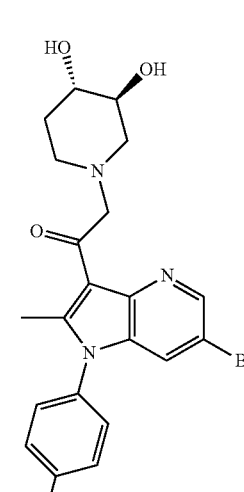 |
| 329 | 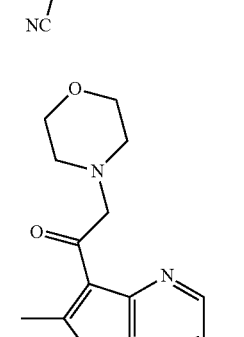 |
| 330 | 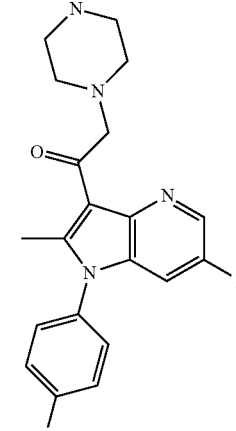 |
| 331 | 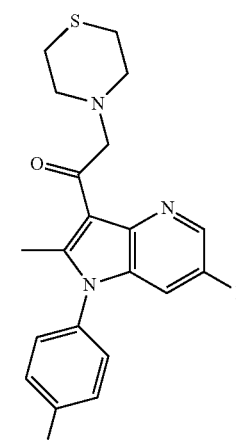 |
| 332 | 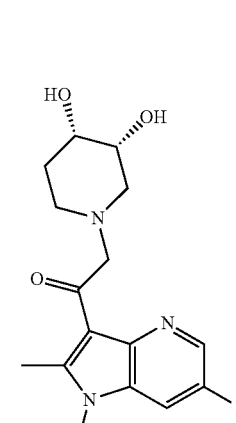 |

TABLE 1-continued

| Compound No. | Chemical Structure |
|---|---|
| 335 | 1-(4-cyanophenyl)-3-[2-(4-hydroxypiperidin-1-yl)acetyl]-2-methyl-1H-pyrrolo[3,2-b]pyridine |
| 336 | 1-(4-cyanophenyl)-2-isopropyl-3-[2-(piperidin-1-yl)acetyl]-1H-pyrrolo[3,2-b]pyridine |
| 337 | 1-(4-cyanophenyl)-3-[2-(4-hydroxypiperidin-1-yl)acetyl]-2-methyl-1H-indole |
| 338 | 1-(4-cyanophenyl)-3-[2-((3R,5S)-3,5-dimethylpiperidin-1-yl)acetyl]-6-bromo-2-methyl-1H-pyrrolo[3,2-b]pyridine |
| 339 | 1-(4-cyanophenyl)-3-[2-(4-hydroxypiperidin-1-yl)acetyl]-6-methoxy-2-methyl-1H-pyrrolo[3,2-b]pyridine |
| 340 | 1-(4-cyanophenyl)-6-ethoxy-3-[2-(4-hydroxypiperidin-1-yl)acetyl]-2-methyl-1H-pyrrolo[3,2-b]pyridine |

TABLE 1-continued
| Compound No. | Chemical Structure |
|---|---|
| 341 | 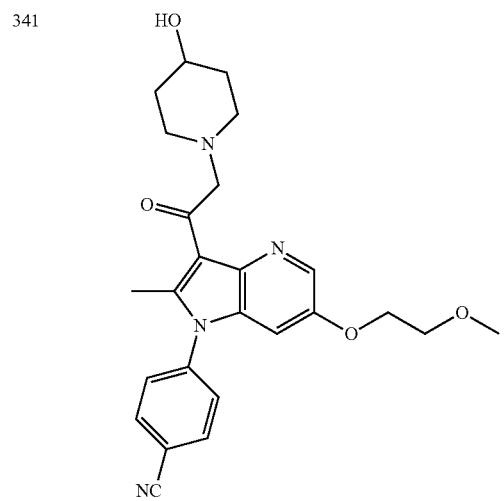 |
| 342 | 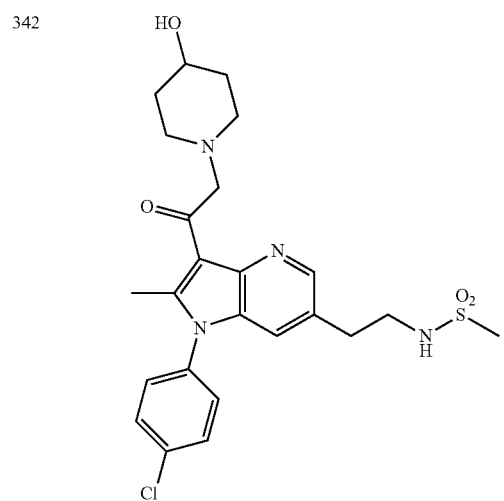 |
| 343 | 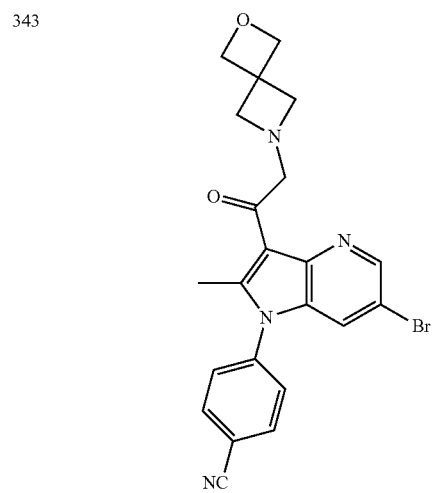 |
| 344 | 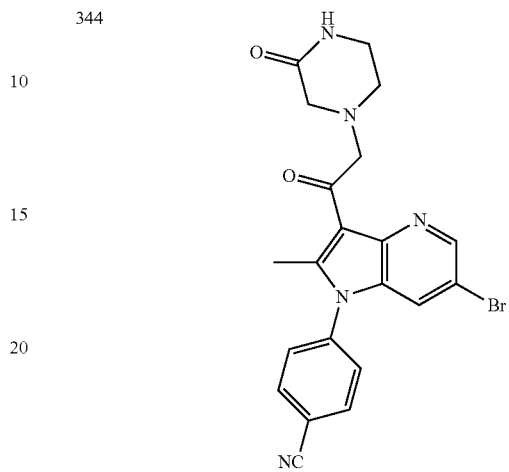 |
| 345 | 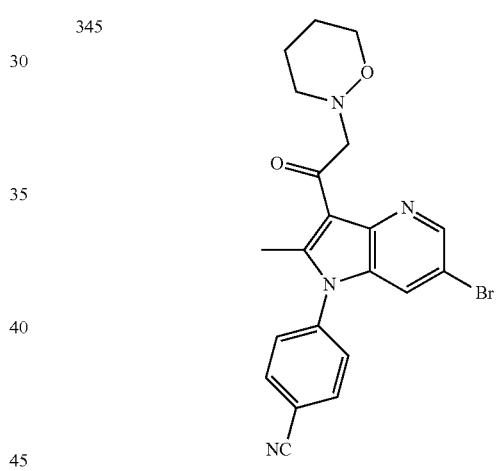 |
| 346 | 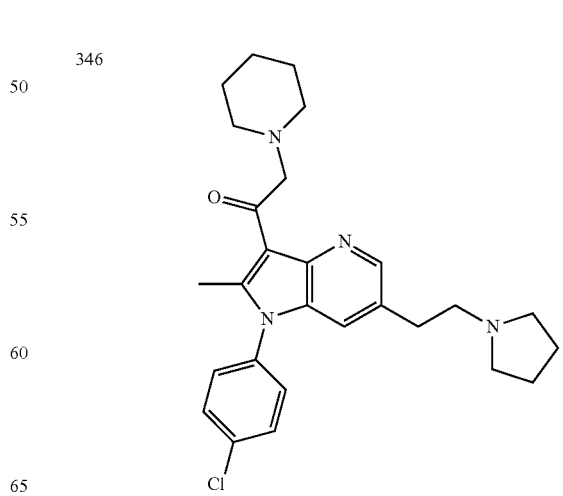 |

TABLE 1-continued

| Compound No. | Chemical Structure |
|---|---|
| 347 | 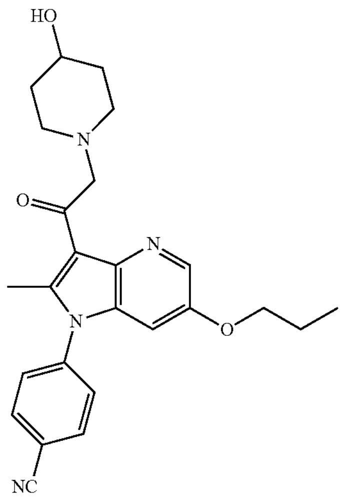 [SMILES: CCCOc1cnc2c(C(=O)CN3CCC(O)CC3)c(C)n(-c3ccc(C#N)cc3)c2c1] |
| 348 | 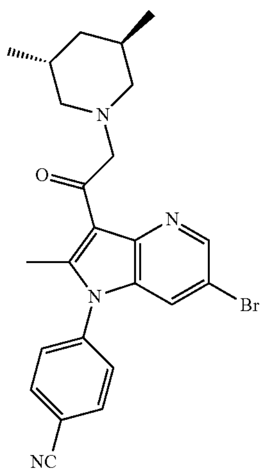 [SMILES: Cc1c(C(=O)CN2C[C@H](C)C[C@@H](C)C2)c2ncc(Br)cc2n1-c1ccc(C#N)cc1] |
| 349 | 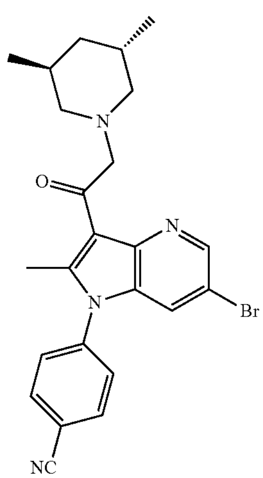 [SMILES: Cc1c(C(=O)CN2C[C@@H](C)C[C@H](C)C2)c2ncc(Br)cc2n1-c1ccc(C#N)cc1] |
| 350 | |
| 351 | |
| 352 | |

TABLE 1-continued

| Compound No. | Chemical Structure |
|---|---|
| 353 | 4-hydroxypiperidine-N-CH2-C(=O)- at 3-position of 2-methyl-6-bromo-1-(4-cyanophenyl)-pyrrolo[3,2-b]pyridine |
| 354 | 4-(aminomethyl)piperidine-N-CH2-C(=O)- at 3-position of 2-methyl-6-bromo-1-(4-cyanophenyl)-pyrrolo[3,2-b]pyridine |
| 355 | (3R,4S)-3,4-dihydroxypiperidine-N-CH2-C(=O)- at 3-position of 2-methyl-6-bromo-1-(4-cyanophenyl)-pyrrolo[3,2-b]pyridine |
| 356 | (3S,4R)-3,4-dihydroxypiperidine-N-CH2-C(=O)- at 3-position of 2-methyl-6-bromo-1-(4-cyanophenyl)-pyrrolo[3,2-b]pyridine |
| 357 | 4-hydroxypiperidine-N-CH2-C(=O)- at 3-position of 2-methyl-6-(2-sulfamoylethyl)-1-(4-chlorophenyl)-pyrrolo[3,2-b]pyridine |
| 359 | 2-azaspiro[3.3]heptan-2-yl-CH2-C(=O)- at 3-position of 2-methyl-6-bromo-1-(4-cyanophenyl)-pyrrolo[3,2-b]pyridine · TFA |

TABLE 1-continued
| Compound No. | Chemical Structure |
|---|---|
| 360 | 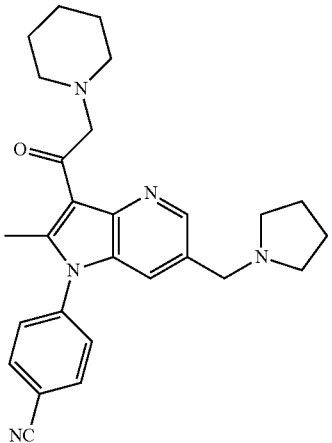 [SMILES: Cc1c(C(=O)CN2CCCCC2)c2ncc(CN3CCCC3)cc2n1-c1ccc(C#N)cc1] |
| 361 | 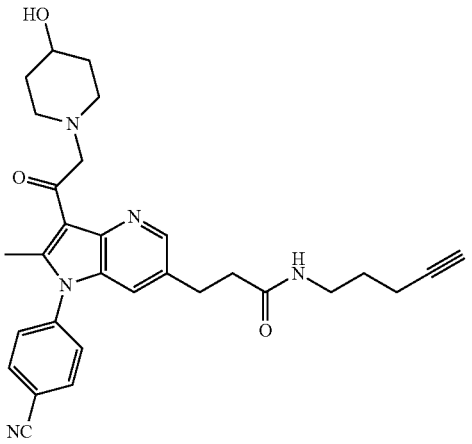 [SMILES: C#CCCCNC(=O)CCc1cnc2c(C(=O)CN3CCC(O)CC3)c(C)n(-c3ccc(C#N)cc3)c2c1] |
| 362 | 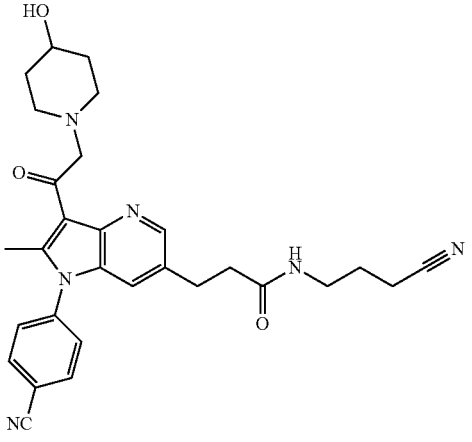 [SMILES: Cc1c(C(=O)CN2CCC(O)CC2)c2ncc(CCC(=O)NCCCC#N)cc2n1-c1ccc(C#N)cc1] |
| 363 | 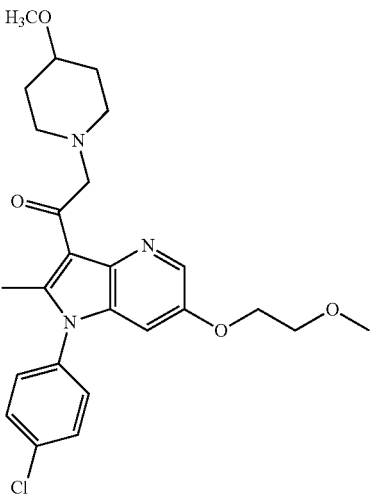 |
| 364 | 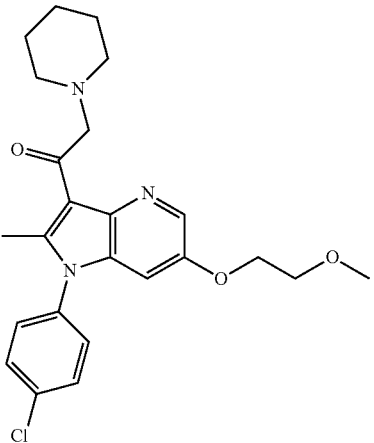 |
| 365 | 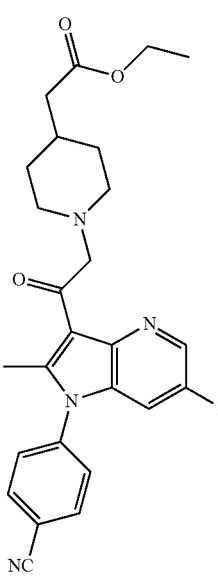 |

TABLE 1-continued
| Compound No. | Chemical Structure |
|---|---|
| 366 | 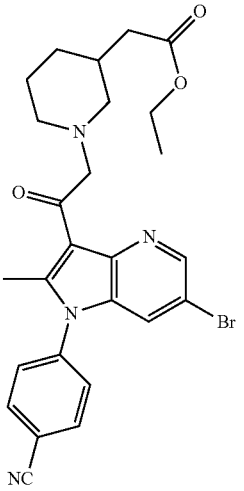 [SMILES: CCOC(=O)CC1CCCN(CC(=O)c2c(C)n(-c3ccc(C#N)cc3)c3cc(Br)cnc23)C1] |
| 367 | 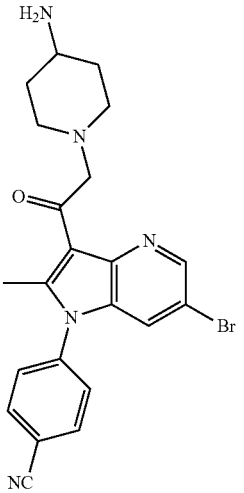 [SMILES: Cc1c(C(=O)CN2CCC(N)CC2)c2ncc(Br)cc2n1-c1ccc(C#N)cc1] |
| 368 | 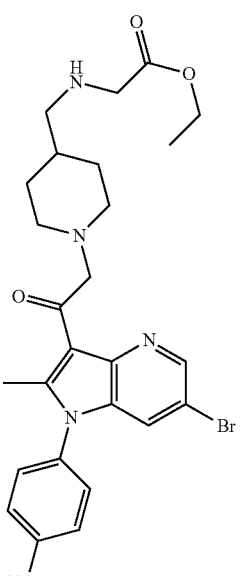 |
TABLE 1-continued
| Compound No. | Chemical Structure |
|---|---|
| 369 | 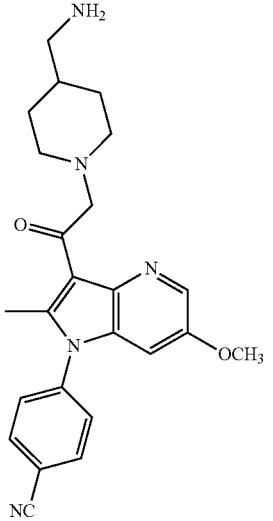 [SMILES: COc1cnc2c(C(=O)CN3CCC(CN)CC3)c(C)n(-c3ccc(C#N)cc3)c2c1] |
| 370 | 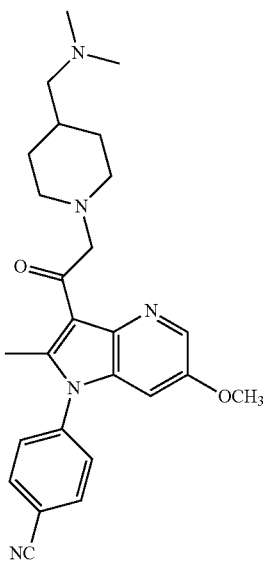 [SMILES: COc1cnc2c(C(=O)CN3CCC(CN(C)C)CC3)c(C)n(-c3ccc(C#N)cc3)c2c1] |

TABLE 1-continued
| Compound No. | Chemical Structure |
|---|---|
| 371 | 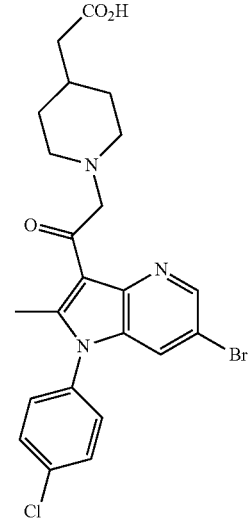 [SMILES: Cc1c(C(=O)CN2CCC(CC(=O)O)CC2)c2ncc(Br)cc2n1-c1ccc(Cl)cc1] |
| 372 | 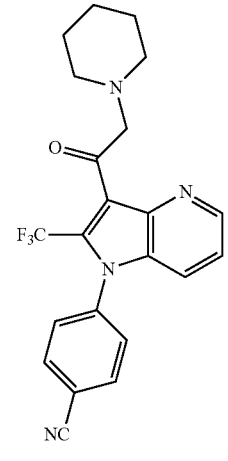 |
| 373 | 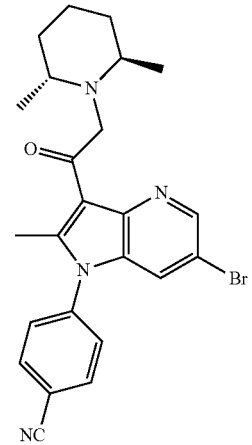 [SMILES: Cc1c(C(=O)CN2[C@H](C)CCC[C@H]2C)c2ncc(Br)cc2n1-c1ccc(C#N)cc1] |
| 374 | 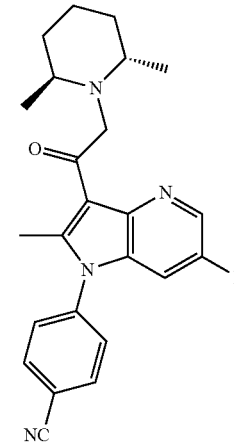 |
| 381 | 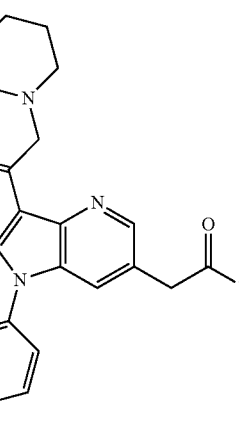 |
| 382 | 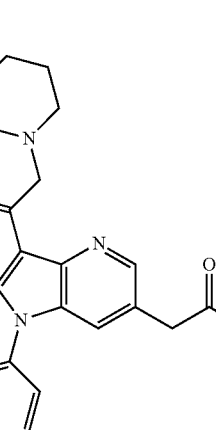 |

TABLE 1-continued
| Compound No. | Chemical Structure |
|---|---|
| 383 | 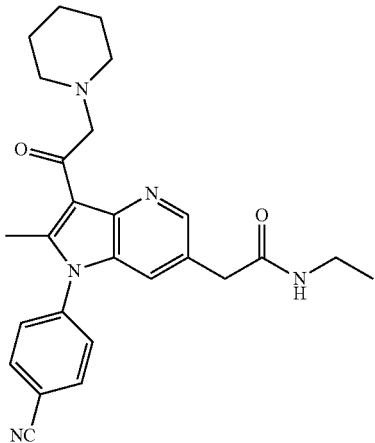 [SMILES: CCNC(=O)Cc1cnc2c(C(=O)CN3CCCCC3)c(C)n(-c3ccc(C#N)cc3)c2c1] |
| 384 | 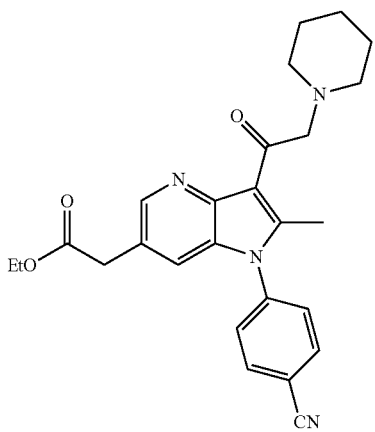 [SMILES: CCOC(=O)Cc1cnc2c(C(=O)CN3CCCCC3)c(C)n(-c3ccc(C#N)cc3)c2c1] |
| 385 | 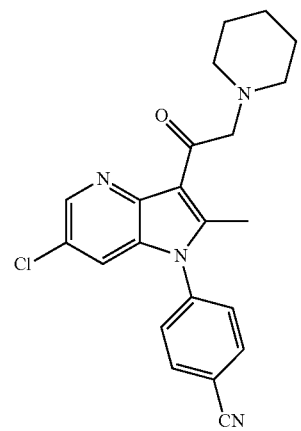 [SMILES: Cc1c(C(=O)CN2CCCCC2)c2ncc(Cl)cc2n1-c1ccc(C#N)cc1] |
| 386 | 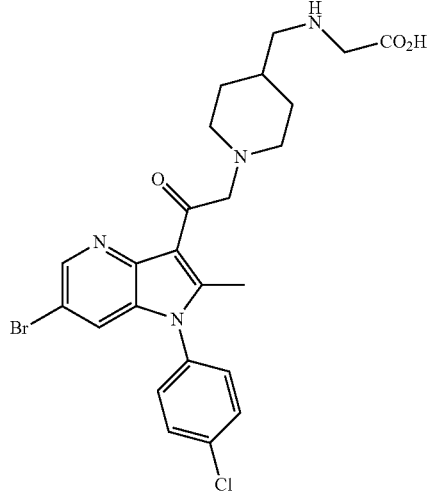 [SMILES: Cc1c(C(=O)CN2CCC(CNCC(=O)O)CC2)c2ncc(Br)cc2n1-c1ccc(Cl)cc1] |
| 387 | 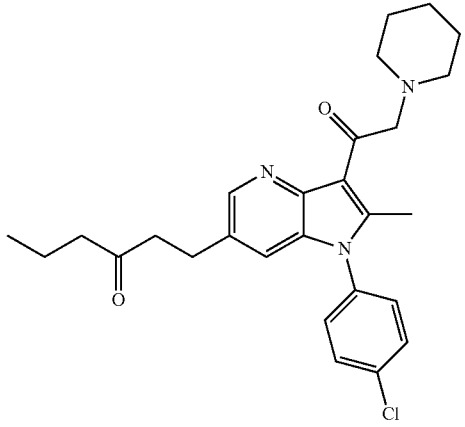 [SMILES: CCCC(=O)CCc1cnc2c(C(=O)CN3CCCCC3)c(C)n(-c3ccc(Cl)cc3)c2c1] |
| 388 | 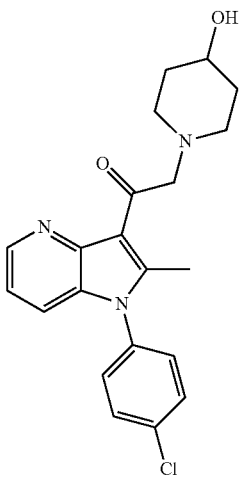 |

TABLE 1-continued
| Compound No. | Chemical Structure |
|---|---|
| 389 | 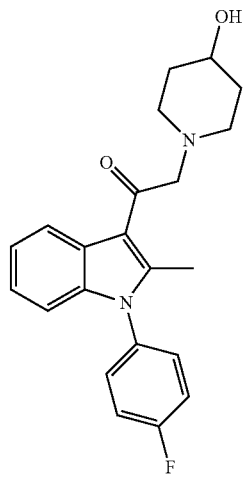 [SMILES: Cc1c(C(=O)CN2CCC(O)CC2)c2ccccc2n1-c1ccc(F)cc1] |
| 390 | 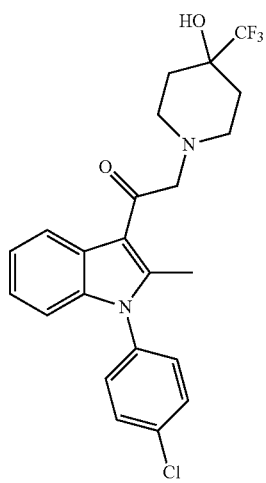 [SMILES: Cc1c(C(=O)CN2CCC(O)(C(F)(F)F)CC2)c2ccccc2n1-c1ccc(Cl)cc1] |
| 391 | 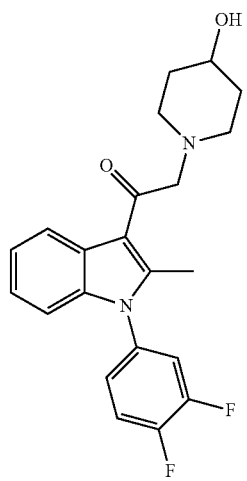 [SMILES: Cc1c(C(=O)CN2CCC(O)CC2)c2ccccc2n1-c1ccc(F)c(F)c1] |
| 392 | 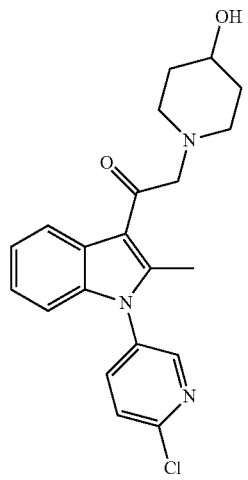 [SMILES: Cc1c(C(=O)CN2CCC(O)CC2)c2ccccc2n1-c1ccc(Cl)nc1] |
| 393 | 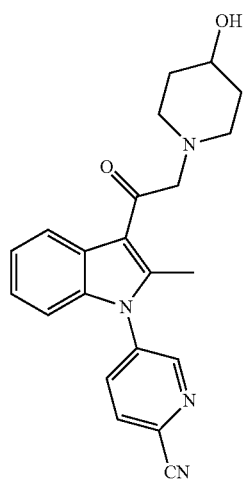 |
| 394 | 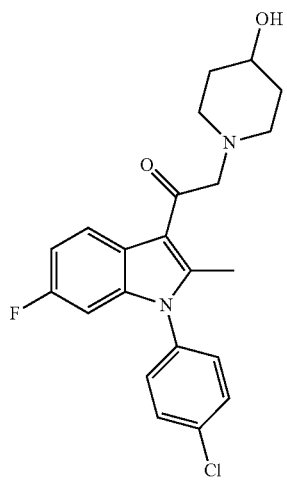 [SMILES: Cc1c(C(=O)CN2CCC(O)CC2)c2ccc(F)cc2n1-c1ccc(Cl)cc1] |

TABLE 1-continued
| Compound No. | Chemical Structure |
|---|---|
| 395 | 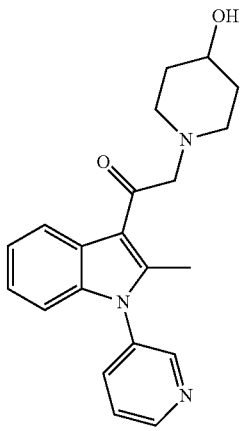 [SMILES: Cc1c(C(=O)CN2CCC(O)CC2)c2ccccc2n1-c1cccnc1] |
| 396 | 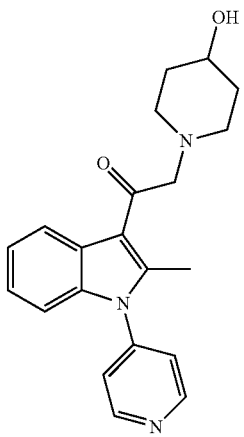 [SMILES: Cc1c(C(=O)CN2CCC(O)CC2)c2ccccc2n1-c1ccncc1] |
| 397 | 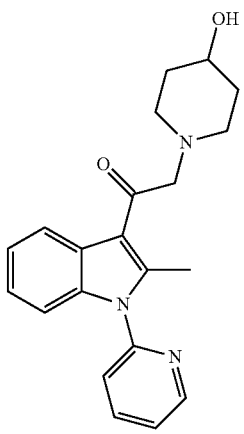 |
TABLE 1-continued
| Compound No. | Chemical Structure |
|---|---|
| 398 | 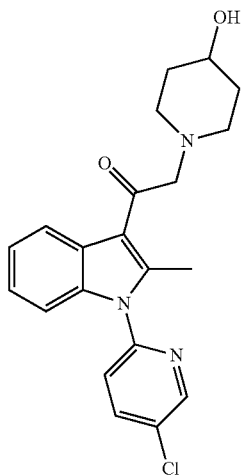 [SMILES: Cc1c(C(=O)CN2CCC(O)CC2)c2ccccc2n1-c1ccc(Cl)cn1] |
| 399 | 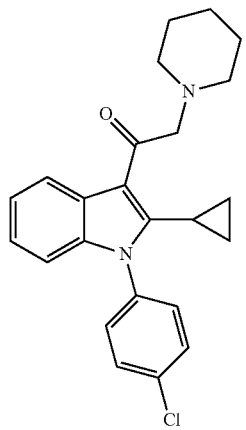 [SMILES: O=C(CN1CCCCC1)c1c(C2CC2)n(-c2ccc(Cl)cc2)c2ccccc12] |
| 400 | 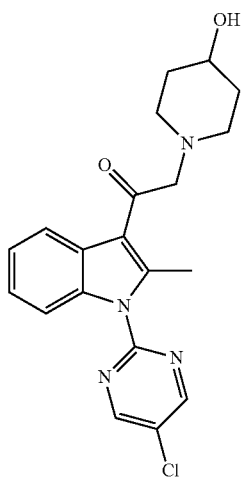 |

TABLE 1-continued

| Compound No. | Chemical Structure |
|---|---|
| 401 | (structure: 1-(4-chlorophenyl)-2-ethyl-3-(2-(piperidin-1-yl)acetyl)-1H-indole) |
| 402 | (structure: 1-(5-chlorothiazol-2-yl)-3-(2-(4-hydroxypiperidin-1-yl)acetyl)-2-methyl-1H-indole) |

The term "alkyl", as used herein, unless otherwise indicated, refers to both branched and straight-chain saturated aliphatic hydrocarbon groups having the specified number of carbon atoms; for example, "$C_1$-$C_{10}$ alkyl" denotes alkyl having 1 to 10 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

The term, "alkenyl", as used herein, refers to both straight and branched-chain moieties having the specified number of carbon atoms and having at least one carbon-carbon double bond.

The term, "alkynyl", as used herein, refers to both straight and branched-chain moieties having the specified number or carbon atoms and having at least one carbon-carbon triple bond.

The term "cycloalkyl," as used herein, refers to cyclic alkyl moieties having 3 or more carbon atoms. Examples of cycloalkyl include, but are not limited to, cyclopropyl, cyclobutyl, cyclopentyl, cyclohexyl, cycloheptyl and adamantyl.

The term "cycloalkenyl," as used herein, refers to cyclic alkenyl moieties having 3 or more carbon atoms.

The term "cycloalkynyl," as used herein, refers to cyclic alkynyl moieties having 5 or more carbon atoms.

The term "heterocyclic" encompasses heterocycloalkyl, heterocycloalkenyl, heterobicycloalkyl, heterobicycloalkenyl, heteropolycycloalkyl, heteropolycycloalkenyl, and the like. Heterocycloalkyl refers to cycloalkyl groups containing one or more heteroatoms (O, S, or N) within the ring. Heterocycloalkenyl as used herein refers to cycloalkenyl groups containing one or more heteroatoms (O, S or N) within the ring. Heterobicycloalkyl refers to bicycloalkyl groups containing one or more heteroatoms (O, S or N) within a ring. Heterobicycloalkenyl as used herein refers to bicycloalkenyl groups containing one or more heteroatoms (O, S or N) within a ring. The foregoing heterocyclic groups may be C-attached or heteroatom-attached (where such is possible). As used herein, the term N-heterocyclic denotes that the heterocyclic group is N-attached. For example, when Z is N-heterocyclic, it is N-attached to the carbon to which $R_1$ and $R_2$ are attached. Representative examples of N-heterocyclic include, but are not limited to, pyrrolind-1-yl (1-pyrrolidinyl), piperidin-1-yl (1-piperidinyl), piperazin-1-yl (1-piperazinyl) and morpholin-1-yl (1-morpholinyl).

Cycloalkyl, cycloalkenyl, heterocyclic, groups also include groups similar to those described above for each of these respective categories, but which are substituted with one or more oxo moieties.

The term "aryl", as used herein, refers to mono- or polycyclic aromatic carbocyclic ring systems. A polycyclic aryl is a polycyclic ring system that comprises at least one aromatic ring. Polycyclic aryls can comprise fused rings, covalently attached rings or a combination thereof. The term "aryl" embraces aromatic radicals, such as, phenyl, naphthyl, indenyl, tetrahydronaphthyl, and indanyl. An aryl group may be substituted or unsubstituted. In some embodiments, the aryl is a $C_4$-$C_{10}$ aryl.

The term "heteroaryl", as used herein, refers to aromatic carbocyclic groups containing one or more heteroatoms (O, S, or N) within a ring. A heteroaryl group can be monocyclic or polycyclic. A heteroaryl group may additionally be substituted or unsubstituted. The heteroaryl groups of this invention can also include ring systems substituted with one or more oxo moieties. A polycyclic heteroaryl can comprise fused rings, covalently attached rings or a combination thereof. A polycyclic heteroaryl is a polycyclic ring system that comprises at least one aromatic ring containing one or more heteroatoms within a ring. Polycyclic aryls can comprise fused rings, covalently attached rings or a combination thereof. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, thiazolopyridinyl, oxazolopyridinyl and azaindolyl. The foregoing heteroaryl groups may be C-attached or heteroatom-attached (where such is possible). For instance, a group derived from pyrrole may be pyrrol-1-yl (N-attached) or pyrrol-3-yl (C-attached). In some embodiments, the heteroaryl is 4- to 10-membered heteroaryl.

The term "substituted" refers to substitution by independent replacement of one, two, or three or more of the hydrogen atoms with substituents including, but not limited to, —$C_1$-$C_{12}$ alkyl, —$C_2$-$C_{12}$ alkenyl, —$C_2$-$C_{12}$ alkynyl, —$C_3$-$C_{12}$ cycloalkyl, —$C_3$-$C_{12}$ cycloalkenyl, $C_3$-$C_{12}$ cycloalkynyl, -heterocyclic, —F, —Cl, —Br, —I, —OH, —$NO_2$, —$N_3$, —CN, —$NH_2$, oxo, thioxo, —$NHR_x$, —$NR_xR_x$, dialkylamino, -diarylamino, -diheteroarylamino, —$OR_x$, —C(O)$R_y$, —C(O)C(O)$R_y$, —$OCO_2R_y$, —OC(O)$R_y$, OC(O)C(O)$R_y$, —NHC(O)$R_y$, —$NHCO_2R_y$, —NHC(O)C(O)$R_y$, NHC(S)$NH_2$, —NHC(S)$NHR_x$, —NHC(NH)$NH_2$, —NHC(NH)$NHR_x$, —NHC(NH)$R_x$, —C(NH)$NHR_x$, and (C=$NR_x$)$R_x$; —NRxC(O)$R_x$, —$NR_xC(O)N(R_x)_2$, —$NRxCO_2R_y$, —NRxC(O)C(O)$R_y$, —$NR_xC(S)NH_2$, —$NR_xC(S)NHR_x$, —$NR_xC(NH)NH_2$, —$NR_xC(NH)NHR_x$, —NRxC(NH)$R_x$, —C(NRx)$NHR_x$ —S(O)$R_y$, —$NHSO_2R_x$, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, -polyalkoxyalkyl, -polyalkoxy, -methoxymethoxy, -methoxyethoxy, —SH, —S—$R_x$, or -methylthiomethyl, wherein $R_x$ is selected from the group consisting of hydrogen, —$C_1$-$C_{12}$ alkyl, —$C_2$-$C_{12}$ alkenyl, —$C_2$-$C_2$ alkynyl, —$C_3$-$C_{12}$ cycloalkyl, -aryl, -heteroaryl and -heterocyclic and —$R_y$ is selected from the group consisting of hydrogen, —$C_1$-$C_{12}$ alkyl, —$C_2$-$C_{12}$ alkenyl, —$C_2$-$C_{12}$ alkynyl, —$C_3$-$C_{12}$ cycloalkyl, -aryl, -heteroaryl, -heterocyclic, —$NH_2$, —NH—$C_1$-$C_{12}$ alkyl, —NH—$C_2$-$C_{12}$ alkenyl, —NH—$C_2$-$C_{12}$-alkynyl, —NH—$C_3$-$C_{12}$ cycloalkyl, —NH-aryl, —NH— heteroaryl and —NH-heterocyclic. It is understood that the aryls, heteroaryls, alkyls, and the like can be further substituted.

The term "haloalkyl" as used herein refers to an alkyl group having 1 to (2n+1) substituent(s) independently selected from F, Cl, Br or I, where n is the maximum number of carbon atoms in the alkyl group.

As will be understood by the skilled artisan, "H" is the symbol for hydrogen, "N" is the symbol for nitrogen, "S" is the symbol for sulfur, and "O" is the symbol for oxygen. "Me" is an abbreviation for methyl.

Non-limiting examples of optionally substituted aryl are phenyl, substituted phenyl, napthyl and substituted naphthyl.

Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. "Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. When the compounds described herein contain olefinic double bonds or other centers of geometric asymmetry, and unless specified otherwise, it is intended that the compounds include both E and Z geometric isomers. Likewise, all tautomeric forms are also intended to be included.

The term "enantiomerically pure" means a stereomerically pure composition of a compound. For example, a stereochemically pure composition is a composition that is free or substantially free of other stereoisomers of that compound. In another example, for a compound having one chiral center, an enantiomerically pure composition of the compound is free or substantially free of the other enantiomer. In yet another example, for a compound having two chiral centers, an enantiomerically pure composition is free or substantially free of the other diastereomers.

Where a particular stereochemistry is described or depicted it is intended to mean that a particular enantiomer is present in excess relative to the other enantiomer. A compound has an R-configuration at a specific position when it is present in excess compared to the compound having an S-configuration at that position. A compound has an S-configuration at a specific position when it is present in excess compared to the compound having an R-configuration at that position.

Likewise, all tautomeric forms are also intended to be included. Where a particular compound is described or depicted, it is intended to encompass that chemical structure as well as tautomers of that structure.

It is to be understood that atoms making up the compounds of the present invention are intended to include isotopic forms of such atoms. Isotopes, as used herein, include those atoms having the same atomic number but different mass numbers. Isotopes of hydrogen include, for example, tritium and deuterium, and isotopes of carbon include, for example, $^{13}C$ and $^{14}C$. The invention therefore encompasses embodiments in which one or more of the hydrogen atoms in Formula (I), (II), (III), (IV), and (V), or a compound described herein, are replaced with deuterium. The invention also encompasses embodiments wherein one or more of the carbon atoms in Formula (I), (II), (III), (IV), and (V), is replaced with silicon atoms.

The invention additionally encompasses embodiment wherein one or more of the nitrogen atoms in Formula (I), (II), (III), (IV), and (V), or a compound described herein are oxidized to N-oxide.

Methods that can be used for the synthesis of the compounds described herein have been reported in the literature, for example in: 1) Zhu, L. et al. "Simple Copper Salt-Catalyzed N-Arylation of Nitrogen-Containing Heterocycles with Aryl and Heteroaryl Halides" *J. Org. Chem.* 2007, 72, 8535; 2) Zhang, H. et al. "Amino Acid Promoted CuI-Catalyzed C—N Bond Formation between Aryl Halides and Amines or N-Containing Heterocycles" *J. Org. Chem.* 2005, 70, 5164; 3) Murakami, Y. et al. "Chemical confirmation of the structure of a mutagenic aminophenylnorharman, 9-(4'-aminophenyl)-9H-pyrido[3,4-b]indole: an authentic synthesis of 9-(4'-nitrophenyl)-9H-pyrido[3,4-b] indole as its relay compound" *Heterocycles,* 2010, 80, 455; 4) Wang, L. et al. "Gold-Catalyzed Deacylative Cycloisomerization Reactions of 3-Acylindole/ynes: A New Approach for Carbazole Synthesis" *Org. Lett.* 2011, 13, 3786; 5) Golubeva, G. A. et al. "Electrophilic substitution in alkylated 2-aminoindoles" *Khimiya Geterotsiklicheskikh Soedinenii* 1985, 7, 946; 6) Sawada, Y. et al. "Eight-Membered Oxygen Hetercycles by Brook Rearrangement-mediated [3+4] Annulation" *Org. Lett.* 2004, 6, 2277; 7) Aubé, J. et al. "Synthetic Aspects of an Asymmetric Nitrogen-Insertion Process: Preparation of Chiral, Non-Racemic Caprolactams and Valerolactams. Total Synthesis of (−)-

Alloyohimbane" *J. Am. Chem. Soc.* 1990, 112, 4879; 8) Antila, J. C. et al. "The Copper-Catalyzed N-Arylation of Indoles" *J. Am. Chem. Soc.* 2002, 124, 11684; 9) Larock, R. C. et al. "Synthesis of 2,3-Disubstituted Indoles via Palladium-Catalyzed Annulation of Internal Alkynes" *J. Org. Chem.* 1998, 63, 7652; 10) Harcken, C. et al. "A general and efficient synthesis of azaindoles and diazaindoles" *Synlett.* 2005, 20, 3121; 11) Wei, Y. et al. "Palladium-Catalyzed Aerobic Oxidative Cyclization of N-Aryl Imines: Indole Synthesis from Anilines and Ketones" *J. Am. Chem. Soc.* 2012, 134, 9098; 12) Kaila, N. et al. "Diazine Indole Acetic Acids as Potent, Selective, and Orally Bioavailable Antagonists of Chemoattractant Receptor Homologous Molecule Expressed on Th2 Cells (CRTH2) for the Treatment of Allergic Inflammatory Diseases" *J. Med. Chem.* 2012, 55, 5088; 13) Carpita, A. et al. "Microwave-assisted synthesis of indole- and azaindole-derivatives in water via cycloisomerization of 2-alkynylanilines and alkynylpyridinamines promoted by amines or catalytic amounts of neutral or basic salts" *Tetrahedron.* 2010, 66, 7169; 14) Pabba, C. et al. "Microwave-assisted synthesis of 1-aryl-1H-indazoles via one-pot two-step Cu-catalyzed intramolecular N-arylation of aryl hydrazones" *Tetrahedron Lett.* 2005, 46, 7553.

Exemplary synthetic routes for the preparation of compounds of the invention are shown in the Schemes I to IV below. As will be understood by the skilled artisan, diastereomers can be separated from the reaction mixture using column chromatography.

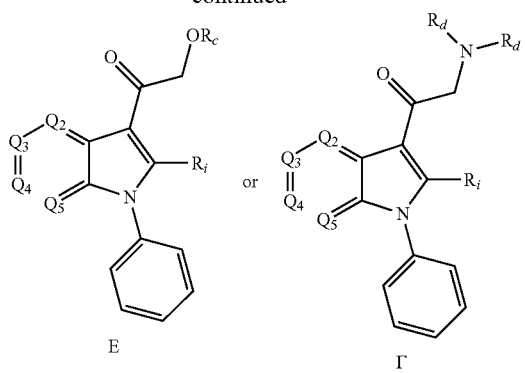

A copper-catalyzed arylation of substituted indole or aza-indole of type A with substituted halobezenes affords intermediate B (Scheme I).[1,2] Additionally, nucleophilic-aromatic substitution of electron poor benzenes with indole A affords product B.[3] A Friedel-Crafts acylation with an acyl chloride or chloro acetyl chloride, in conjunction with an aluminum-based Lewis acid and/or pyridine provides compounds X[4] or Δ.[5] In intermediate Δ the chloride is easily displaced with a variety of O[6] and N[7]-based nucleophiles, followed in some instances by further modifications, to provide desired compounds of type E and Γ, respectively.

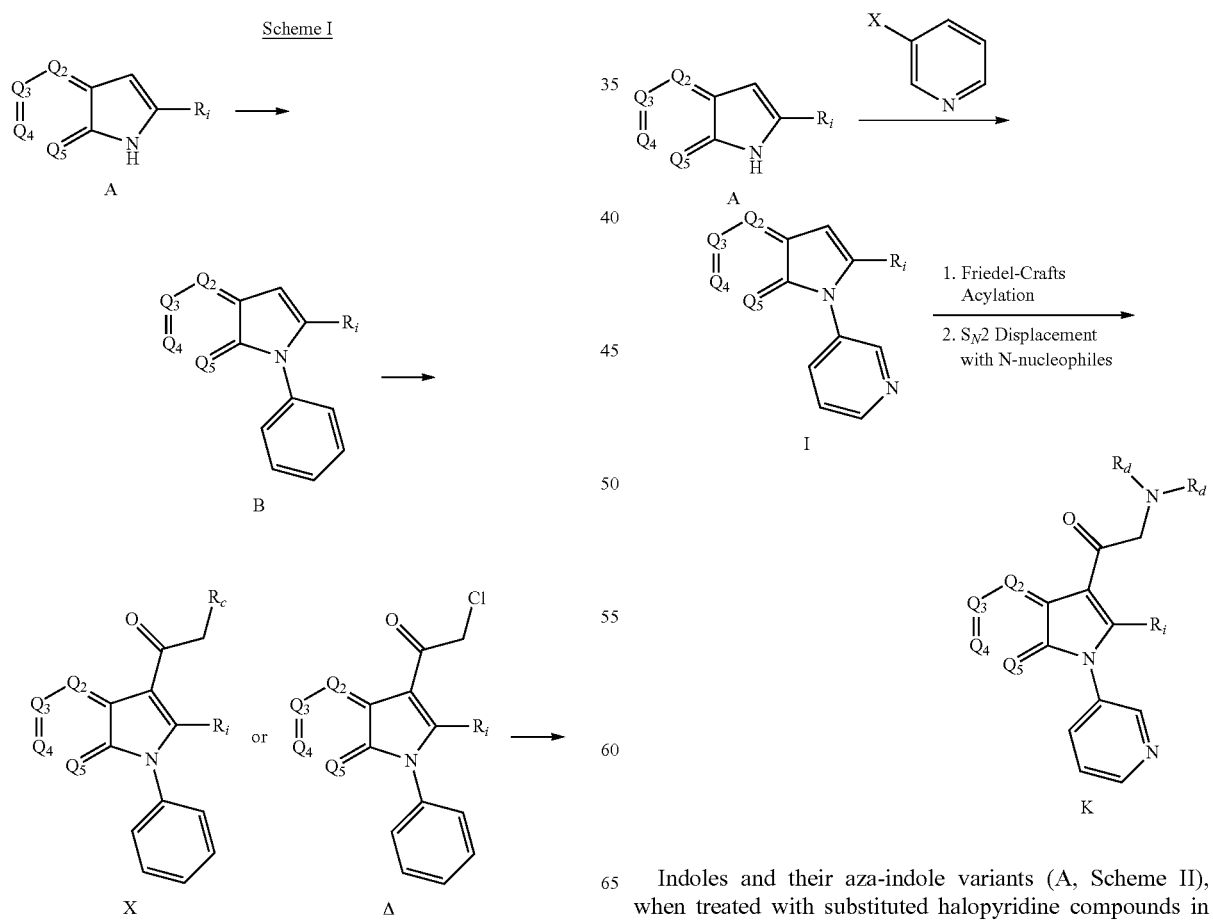

Indoles and their aza-indole variants (A, Scheme II), when treated with substituted halopyridine compounds in the presence of copper (I) reagents, affords intermediates I.[8]

Intermediates like I can be further modified through processes analogous to those described above (Scheme 1) to afford compounds of type K.

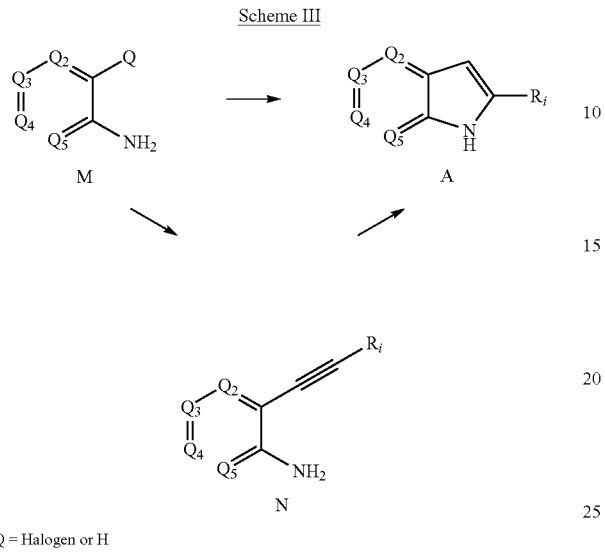

Q = Halogen or H

Substituted indoles and aza-indoles of type A (Scheme III) are prepared via a Larock indole synthesis from substituted alkynes and halogenated anilines or aminopyridines of type M.[9,10] Compounds of type A are also be prepared directly from compounds of type M by treating with ketones, copper (II) salts, and palladium (II) salts.[10] Alternatively, compounds of type A are also prepared in a step-wise fashion from compounds of type M through Sonogoshira couplings with terminal alkynes to afford compounds of type N,[11,12] which are then cyclized by treating with a base to compounds of type A.[12]

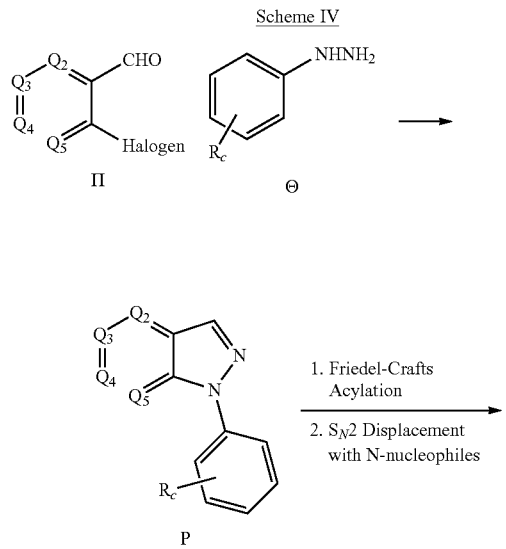

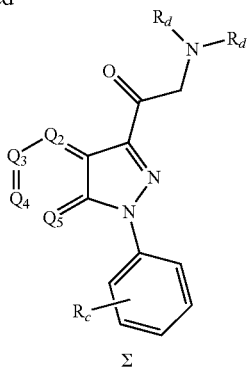

Indazole compounds of type P will be made via copper (I)-catalyzed annulations of substituted aldehydes (I) and substituted aryl hydrazines ($\Theta$).[13] Intermediates like P will be further modified through processes analogous to those described above (Scheme 1) to afford compounds of type $\Sigma$.

The invention encompasses pharmaceutically acceptable salts of the compounds described herein. Thus, in certain aspects, the invention is directed to pharmaceutically acceptable salts of compounds of the invention and pharmaceutical compositions thereof. A "pharmaceutically acceptable salt" includes an ionic bond-containing product of the reaction between the disclosed compound with either an acid or a base, suitable for administering to a subject. Pharmaceutically acceptable salts are well known in the art and are described, for example, in Berge et al. (1977), Pharmaceutical Salts. Journal of Pharmaceutical Sciences, 69(1): 1-19, the contents of which are herein incorporated by reference. A non-limiting example of a pharmaceutically acceptable salt is an acid salt of a compound containing an amine or other basic group which can be obtained by reacting the compound with a suitable organic or inorganic acid. Examples of pharmaceutically acceptable salts also can be metallic salts including, but not limited to, sodium, magnesium, calcium, lithium and aluminum salts. Further examples of pharmaceutically acceptable salts include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, trifluoroacetates, benzoates and salts with amino acids such as glutamic acid. Salts can also be formed with suitable organic bases when the compound comprises an acid functional group such as —C(O)OH or —SO$_3$H. Such bases suitable for the formation of a pharmaceutically acceptable base addition salts with compounds of the present invention include organic bases that are nontoxic and strong enough to react with the acid functional group. Such organic bases are well known in the art and include amino acids such as arginine and lysine, mono-, di-, and triethanolamine, choline, mono-, di-, and trialkylamine, such as methylamine, dimethylamine, and trimethylamine, guanidine, N-benzylphenethylamine, N-methylglucosamine, N-methylpiperazine, morpholine, ethylendiamine, tris(hydroxymethyl)aminomethane and the like.

The invention also includes hydrates of the compounds described herein, including, for example, solvates of the compounds described herein, pharmaceutical compositions comprising the solvates and methods of use of the solvates. In some embodiments, the invention is a solvate of a compound of Formula (I), (II), (III), (IV), or (V), or a compound described herein, or a pharmaceutical composition thereof.

Also included in the present invention are prodrugs of the compounds described herein, for example, prodrugs of a compound of Formula (I), (II), (III), (IV), or (V), or a compound described herein, or a pharmaceutical composition of any of thereof or method of use of the prodrug.

The invention additionally includes clathrates of the compounds described herein, pharmaceutical compositions comprising the clathrates, and methods of use of the clathrates. In some embodiments, the invention is directed to clathrates of a compound of Formula (I), (II), (III), (IV), or (V), or a compound described herein, or a pharmaceutical composition thereof.

The invention encompasses a method of inhibiting deubiquitination activity of a Usp14 protein comprising contacting the Usp14 protein with a compound described herein, or a pharmaceutically acceptable salt, solvate, clathrate or prodrug thereof, in an amount sufficient to inhibit deubiquitination activity of the Usp14 protein. In certain embodiments, a cell is contacted with the compound described herein or a pharmaceutically acceptable salt, solvate, clathrate or prodrug thereof, in an amount sufficient to inhibit deubiquitination activity of the Usp14 protein.

The invention also encompasses a method of enhancing protein degradation by a proteasome in a cell comprising contacting the cell with a compound of a compound described herein, or a pharmaceutically acceptable salt, solvate, clathrate or prodrug thereof, in an amount sufficient to enhance protein degradation by the proteasome.

As discussed above, the invention includes pharmaceutical compositions comprising a pharmaceutically acceptable carrier or excipient and a compound described herein. The compounds of Formulae (I), (II), (III), (IV), and (V), or a pharmaceutically acceptable salt, solvate, clathrate or prodrug, or a compound described herein, can be administered in pharmaceutical compositions comprising a pharmaceutically acceptable carrier or excipient. The excipient can be chosen based on the expected route of administration of the composition in therapeutic applications. The route of administration of the composition depends on the condition to be treated. For example, intravenous injection may be preferred for treatment of a systemic disorder and oral administration may be preferred to treat a gastrointestinal disorder. The route of administration and the dosage of the composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms.

Pharmaceutical compositions comprising compounds of Formulae (I), (II), (III), (IV), and (V), or a pharmaceutically acceptable salt, solvate, clathrate or prodrug, or a compound described herein, can be administered by a variety of routes including, but not limited to, parenteral, oral, pulmonary, ophthalmic, nasal, rectal, vaginal, aural, topical, buccal, transdermal, intravenous, intramuscular, subcutaneous, intradermal, intraocular, intracerebral, intralymphatic, intraarticular, intrathecal and intraperitoneal.

The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the pharmacologic agent or composition. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Pharmaceutical compositions can also include large, slowly metabolized macromolecules such as proteins, polysaccharides such as chitosan, polylactic acids, polyglycolic acids and copolymers (such as latex functionalized SEPHAROSE™, agarose, cellulose, and the like), polymeric amino acids, amino acid copolymers, and lipid aggregates (such as oil droplets or liposomes).

The compositions can be administered parenterally such as, for example, by intravenous, intramuscular, intrathecal or subcutaneous injection. Parenteral administration can be accomplished by incorporating a composition into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Injectable formulations can be prepared either as liquid solutions or suspensions; solid forms suitable for solution in, or suspension in, liquid vehicles prior to injection can also be prepared. The preparation also can also be emulsified or encapsulated in liposomes or micro particles such as polylactide, polyglycolide, or copolymer for enhanced adjuvant effect, as discussed above [Langer, *Science* 249: 1527, 1990 and Hanes, *Advanced Drug Delivery Reviews* 28: 97-119, 1997]. The compositions and pharmacologic agents described herein can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, transdermal applications and ocular delivery. For suppositories, binders and carriers include, for example, polyalkylene glycols or triglycerides; such suppositories can be formed from mixtures containing the active ingredient in the range of about 0.5% to about 10%, preferably about 1% to about 2%. Oral formulations include excipients, such as pharmaceutical grades of mannitol, lactose, starch, magnesium stearate, sodium saccharine, cellulose, and magnesium carbonate. Topical application can result in transdermal or intradermal delivery. Transdermal delivery can be achieved using a skin patch or using transferosomes. [Paul et al., *Eur. J. Immunol.* 25: 3521-24, 1995; Cevc et al., *Biochem. Biophys. Acta* 1368: 201-15, 1998].

For the purpose of oral therapeutic administration, the pharmaceutical compositions can be incorporated with excipients and used in the form of tablets, troches, capsules, elixirs, suspensions, syrups, wafers, chewing gums and the like. Tablets, pills, capsules, troches and the like may also contain binders, excipients, disintegrating agent, lubricants, glidants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and non-toxic in the amounts used. In another embodiment, the composition is administered as a tablet or a capsule.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor, and the like. For vaginal administration, a pharmaceutical composition may be presented as pessaries, tampons, creams, gels, pastes, foams or spray.

The pharmaceutical composition can also be administered by nasal administration. As used herein, nasally administering or nasal administration includes administering the composition to the mucus membranes of the nasal passage or nasal cavity of the patient. As used herein, pharmaceutical compositions for nasal administration of a composition include therapeutically effective amounts of the compounds prepared by well-known methods to be administered, for example, as a nasal spray, nasal drop, suspension, gel, ointment, cream or powder. Administration of the composition may also take place using a nasal tampon or nasal sponge.

For topical administration, suitable formulations may include biocompatible oil, wax, gel, powder, polymer, or other liquid or solid carriers. Such formulations may be administered by applying directly to affected tissues, for example, a liquid formulation to treat infection of conjunctival tissue can be administered dropwise to the subject's eye, or a cream formulation can be administered to the skin.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the pharmaceutical composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

In addition to the usual meaning of administering the formulations described herein to any part, tissue or organ whose primary function is gas exchange with the external environment, for purposes of the present invention, "pulmonary" will also mean to include a tissue or cavity that is contingent to the respiratory tract, in particular, the sinuses.

For pulmonary administration, an aerosol formulation containing the active agent, a manual pump spray, nebulizer or pressurized metered-dose inhaler as well as dry powder formulations are contemplated. Suitable formulations of this type can also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the compound intended for pulmonary administration is dissolved, suspended or emulsified in a mixture of a solvent, surfactant and propellant. The mixture is maintained under pressure in a canister that has been sealed with a metering valve.

The invention also encompasses a method of treating a patient suffering from a condition associated with a dysfunction in protein homeostasis comprising administering to said patient a therapeutically effective amount of a compound described herein.

"Treating" or "treatment" includes preventing or delaying the onset of the symptoms, complications, or biochemical indicia of a disease, alleviating or ameliorating the symptoms or arresting or inhibiting further development of the disease, condition, or disorder. A "subject" is an animal to be treated or in need of treatment. A "patient" is a human subject in need of treatment.

An "effective amount" refers to that amount of an agent that is sufficient to achieve a desired and/or recited effect. In the context of a therapeutic agent, an "effective amount" of the therapeutic agent that is sufficient to ameliorate of one or more symptoms of a disorder and/or prevent advancement of a disorder, cause regression of the disorder and/or to achieve a desired effect.

As used herein, the term "inhibiting" or "decreasing" encompasses causing a net decrease by either direct or indirect means. The term "increasing" or "enhancing" means to cause a net gain by either direct or indirect means.

The invention encompasses the treatment of a condition associated with a dysfunction in proteostasis. Proteostasis refers to protein homeostasis. Dysfunction in protein homeostasis is a result of protein misfolding, protein aggregation, defective protein trafficking or protein degradation. Exemplary proteins of which there can be a dysfunction in proteostasis, for example that can exist in a misfolded state, include, but are not limited to, glucocerebrosidase, hexosamine A, cystic fibrosis transmembrane conductance regulator, aspartylglucsaminidase, α-galactosidase A, cysteine transporter, acid ceremidase, acid α-L-fucosidase, protective protein, cathepsin A, acid β-glucosidase, acid β-galactosidase, iduronate 2-sulfatase, α-L-iduronidase, galactocerebrosidase, acid α-mannosidase, acid β-mannosidase, arylsulfatase B, arylsulfatase A, N-acetylgalactosamine-6-sulfate sulfatase, acid β-galactosidase, N-acetyl-glucosamine-1-phosphotransferase, acid sphingmyelinase, NPC-1, acid α-glucosidase, β-hexosamine B, heparin N-sulfatase, α-N-acetylglucosaminidase, α-glucosaminide N-acetyltransferase, N-acetylglucosamine-6-sulfate sulfatase, α-N-acetylgalactosaminidase, islet amyloid polypeptide (IAPP or amylin), α-neuramidase, β-glucuronidase, β-hexosamine A and acid lipase, polyglutamine, α-synuclein, Aβ peptide, tau protein, transthyretin, insulin, TAR DNA-binding protein 43 (TDP-43), ataxin-3, superoxide dismutase (SOD), and rhodopsin.

In certain embodiments, the protein is selected from the group consisting of huntingtin, tau, alpha-synuclein, 1 antitrypsin and superoxide dismutase.

Protein conformational diseases encompass gain of function disorders and loss of function disorders. In one embodiment, the protein conformational disease is a gain of function disorder. The terms "gain of function disorder," "gain of function disease," "gain of toxic function disorder" and "gain of toxic function disease" are used interchangeably herein. A gain of function disorder is a disease characterized by increased aggregation-associated proteotoxicity. In these diseases, aggregation exceeds clearance inside and/or outside of the cell. Gain of function diseases include, but are not limited to neurodegenerative diseases associated with aggregation of polyglutamine, Lewy body diseases, amyotrophic lateral sclerosis, transthyretin-associated aggregation diseases, Alzheimer's disease, Machado-Joseph disease, cerebral B-amyloid angiopathy, retinal ganglion cell degeneration, tautopathies (progressive supranuclear palsy, corticobasal degeration, frontotemporal lobar degeneration), cerebral hemorrhage with amyloidosis, Alexander disease, Serpinopathies, familial amyloidotic neuropathy, senile systemic amyloidosis, ApoAI amyloidosis, ApoAII amyloidosis, ApoAIV amyloidosis, familial amyloidosis of the Finnish type, lysoyzme amyloidosis, fibrinogen amyloidosis, dialysis amyloidosis, inclusion body myositis/myopathy, cataracts, medullary thyroid carcinoma, cardiac atrial amyloidosis, pituitary prolactinoma, hereditary lattice corneal dystrophy, cutaneous lichen amyloidosis, corneal lactoferrin amyloidosis, corneal lactoferrin amyloidosis, pulmonary alveolar proteinosis, odontogenic tumor amyloid, seminal vesical amyloid, sickle cell disease, critical illness myopathy, von Hippel-Lindau disease, spinocerebellar ataxia 1, Angelman syndrome, giant axon neuropathy, inclusion body myopathy with Paget disease of bone, frontotemporal dementia (IBMPFD) and prion diseases. Neurodegenerative diseases associated with aggregation of polyglutamine include, but are not limited to, Huntington's disease, dentatorubral and pallidoluysian atrophy, several forms of spino-cerebellar ataxia, and spinal and bulbar muscular atrophy. Alzheimer's disease is characterized by the formation of two types of aggregates: extracellular aggregates of Aβ peptide and intracellular aggregates of the microtubule associated protein tau. Transthyretin-associated aggregation diseases include, for example, senile systemic amyloidoses and familial amyloidotic neuropathy. Lewy body diseases are characterized by an aggregation of α-synuclein protein and include, for example, Parkinson's disease. Prion diseases (also known as transmissible spongiform encephalopathies or TSEs) are characterized by aggregation of prion proteins. Exemplary human prion diseases are Creutzfeldt-Jakob Disease (CJD), Variant Creutzfeldt-Jakob Disease, Gerstmann-Straussler-Scheinker Syndrome, Fatal Familial Insomnia and Kuru. Additional neurodegenerative diseases include tauopathies, Frontal Lobe Dementia (FLD), Dementias (including, but not limited to, Dementia with Lewy bodies (DLB), familial dementia, Serpinopathies, Down's Syndrome dementia), Multiple Sclerosis, and Neuropathic pain.

In a further embodiment, the protein conformation disease is a loss of function disorder. The terms "loss of function disease" and "loss of function disorder" are used interchangeably herein. Loss of function diseases are a group of diseases characterized by inefficient folding of a protein resulting in excessive degradation of the protein. Loss of function diseases include, for example, lysosomal storage diseases. Lysosomal storage diseases are a group of diseases characterized by a specific lysosomal enzyme deficiency which may occur in a variety of tissues, resulting in the build-up of molecules normally degraded by the deficient enzyme. The lysosomal enzyme deficiency can be in a lysosomal hydrolase or a protein involved in the lysosomal trafficking. Lysosomal storage diseases include, but are not limited to, aspartylglucosaminuria, Fabry's disease, Batten disease, Cystinosis, Farber, Fucosidosis, Galactasidosialidosis, Gaucher's disease (including Types 1, 2 and 3), Gml gangliosidosis, Hunter's disease, Hurler-Scheie's disease, Krabbe's disease, α-Mannosidosis, β-Mannosidosis, Maroteaux-Lamy's disease, Metachromatic Leukodystrophy, Morquio A syndrome, Morquio B syndrome, Mucolipidosis II, Mucolipidosis III, Neimann-Pick Disease (including Types A, B and C), Pompe's disease, Sandhoff disease, Sanfilippo syndrome (including Types A, B, C and D), Schindler disease, Schindler-Kanzaki disease, Sialidosis, Sly syndrome, Tay-Sach's disease and Wolman disease.

In yet an additional embodiment, the disease associated with a dysfunction in proteostasis is a myopathy. In some embodiments, the myopathy is selected from the group consisting of Duchenne muscular dystrophy (DMD), Becker's muscular dystrophy (BMD), Spinal muscular atrophy (SMA), Spinal-Bulbar Muscular Atrophy (SBMA), Inclusion body myositis, Freidreich's Ataxia, multiple systems atrophy, spinocerebellar ataxias and seipinopathies.

In another embodiment, the disease associated with a dysfunction in proteostasis is a cardiovascular disease. Cardiovascular diseases include, but are not limited to, coronary artery disease, myocardial infarction, stroke, restenosis and arteriosclerosis. Conditions associated with a dysfunction of proteostasis also include ischemic conditions, such as, ischemia/reperfusion injury, myocardial ischemia, stable angina, unstable angina, stroke, ischemic heart disease and cerebral ischemia.

In yet another embodiment, the disease associated with a dysfunction in proteostasis is diabetes and/or complications of diabetes, including, but not limited to, diabetic retinopathy, cardiomyopathy, neuropathy, nephropathy, and impaired wound healing.

In a further embodiment, the disease associated with a dysfunction in proteostasis is an ocular disease including, but not limited to, age-related macular degeneration (AMD), diabetic macular edema (DME), diabetic retinopathy, glaucoma, cataracts, retinitis pigmentosa (RP) and dry macular degeneration.

In some embodiments, the condition associated with a dysfunction in proteostasis is selected from the group consisting of Huntington's disease, Alzheimer's disease, Parkinson's disease, amyotrophic lateral sclerosis, diabetes and complications thereof, ocular diseases and cancer or tumor.

Additional conditions associated with a dysfunction of proteostasis include hemoglobinopathies, inflammatory diseases, intermediate filament diseases, drug-induced lung damage and hearing loss. The invention also encompasses methods for the treatment of hemoglobinopathies (such as sickle cell anemia), an inflammatory disease (such as inflammatory bowel disease, colitis, ankylosing spondylitis), intermediate filament diseases (such as non-alcoholic and alcoholic fatty liver disease) and drug induced lung damage (such as methotrexate-induced lung damage). The invention additionally encompasses methods for treating hearing loss, such as noise-induced hearing loss, aminoglycoside-induced hearing loss, and cisplatin-induced hearing loss.

In addition to conditions associated with a dysfunction in proteostasis, the compound of the present invention can be used to treat a disease or condition characterized by deficient proteasome activity or deficient activity of other components of the ubiquitin-proteasome pathway. Such conditions include, for example, Hippel-Lindau disease, spino-cerebellar ataxia 1, Angelman syndrome, giant axon neuropathy, inclusion body myopathy with Paget disease, and frontotemporal dementia.

In certain embodiments, the invention encompasses a method for the treatment of a condition selected from the group consisting of Parkinson's disease, Alzheimer's disease, Frontotemporal lobar dementia (FTLD), Progressive Supranuclear Palsy (PSP), Amyotrophic lateral sclerosis (ALS), Spinocerebellar ataxia (SCA), Retinitis pigmentosum, prion diseases and autism.

In certain embodiments, the invention includes methods for the treatment of a condition associated with a dysfunction in proteostasis comprising administering to a patient in need thereof an effective amount of a compound of Formula (I), (II), (III), (IV), or (V), or a pharmaceutically acceptable salt, solvate, clathrate or prodrug, or the compounds described herein, and a second agent (e.g., a second therapeutic agent). Co-administered agents, compounds, or therapeutics need not be administered at exactly the same time. In certain embodiments, however, the compound encompassed by Formula (I), (II), (III), (IV), or (V), or a pharmaceutically acceptable salt, solvate, clathrate or prodrug, or a compound described herein, is administered substantially simultaneously as the second agent. By "substantially simultaneously," it is meant that the compound of (I), (II), (III), (IV), or (V), or a pharmaceutically acceptable salt, solvate, clathrate or prodrug, or a compound described herein, is administered before, at the same time, and/or after the administration of the second agent, and encompasses, for example, administration within the same treatment session or as part of the same treatment regimen. Exemplary second agents include pharmacologic chaperones and proteostasis regulators (such as, those described below).

In yet additional aspects, the invention encompasses a method for treating a condition characterized by deficient proteasome activity or deficiency of other components of the ubiquitin-proteasome pathway in a subject comprising administering to said subject an effective amount of a compound of the invention, or a pharmaceutically acceptable salt, solvate, clathrate or prodrug thereof.

In an additional embodiment, the invention is directed to a pharmaceutical composition comprising a compound of (I), (II), (III), (IV), or (V), or a pharmaceutically acceptable salt, solvate, clathrate or prodrug thereof, or a compound described herein, and a second agent, wherein the second agent is selected from the group consisting of a pharmacologic chaperone and a proteostasis regulator. The invention also encompasses a method of treating a patient suffering from a condition associated with a dysfunction in proteostasis comprising administering a therapeutically effective amount of a compound of the invention and a second agent, wherein the second agent is a pharmacologic chaperone. Pharmacologic chaperones or kinetic stabilizers refer to compounds that bind an existing steady state level of the folded mutant protein and chemically enhance the folding equilibrium by stabilizing the fold [Bouvier, *Chem Biol* 14: 241-242, 2007; Fan et al., *Nat Med* 5: 112-115, 1999; Sawkar et al., *Proc Natl Acad Sci USA* 99:15428-15433, 2002; Johnson and Kelly, *Accounts of Chemical Research* 38: 911-921, 2005]. The pharmacologic chaperone is administered in an amount that in combination with a compound described herein in an amount that is sufficient to treat a patient suffering from a condition associated with a dysfunction in proteostasis. Exemplary pharmacologic chaperones are described in U.S. Patent Application Publication No's. 20080056994, 20080009516, 20070281975, 20050130972, 20050137223, 20050203019, 20060264467 and 20060287358, the contents of each of which are incorporated by reference herein.

In another embodiment, the invention is a method of treating a patient suffering from a condition associated with a dysfunction in proteostasis comprising administering to said patient an effective amount of a compound described herein or a pharmaceutically acceptable salt, solvate, clathrate or prodrug, of any of thereof, and a second agent, wherein the second agent is a proteostasis regulator. The term "proteostasis regulator" refers to small molecules, siRNA and biologicals (including, for example, proteins) that enhance cellular protein homeostasis. For example, proteostasis regulators can be agents that influence protein synthesis, folding, trafficking and degradation pathways. Proteostasis regulators encompass pharmacologic agents that stimulate the heat shock response (HSR) signaling activity. Proteostasis regulators function by manipulating signaling pathways, including, but not limited to, the heat shock response or the unfolded protein response, or both, resulting in transcription and translation of proteostasis network components. Proteostasis regulators can enhance the folding, trafficking and function of proteins (for example, mutated proteins). Proteostasis regulators can also regulate protein chaperones by upregulating transcription or translation of the protein chaperone, or inhibiting degradation of the protein chaperone. Proteostasis regulators can influence the biology of folding, often by the coordinated increase in chaperone and folding enzyme levels and macromolecules that bind to partially folded conformational ensembles, thus enabling their progression to intermediates with more native structure and ultimately increasing the concentration of folded mutant protein for export. In one aspect, the proteostasis regulator is distinct from a chaperone in that the proteostasis regulator can enhance the homeostasis of a mutated protein but does not bind the mutated protein. In addition, proteostasis regulators can upregulate an aggregation pathway or a disaggregase activity. Exemplary proteostasis regulators are the celastrols, MG-132 and L-type $Ca^{2+}$ channel blockers (e.g., dilitiazem and verapamil). The term "celastrols" refers to celastrol and derivatives or analogs thereof, including, but not limited to, those celastrol derivatives described in Westerheide et al., J Biol Chem, 2004. 279(53): p. 56053-60, the contents of which are expressly incorporated by reference herein. Celastrol derivatives include, for example, celastrol methyl ester, dihydrocelastrol diacetate, celastrol butyl ether, dihydrocelastrol, celastrol benzyl ester, primesterol, primesterol diacetate and triacetate of celastrol. In certain aspects, the proteostasis regulator is a heat shock response activator. A heat shock response activator is an agent that indirectly or directly activates the heat shock response, for example, by directly or indirectly activating heat shock transcription factor 1 (HSF 1), inhibiting Hsp90, and/or activating chaperone expression (Westerheide et al., J Biol Chem, 2004. 279(53): p. 56053-60, the contents of which are expressly incorporated by reference herein). The terms "heat shock response activator," "heat shock activator," "heat shock response inducer," and "heat shock inducer" are used interchangeably herein. Non-limiting examples of heat shock response activators are celastrols, non-steroidal anti-inflammatory drugs, ansamycin, geldenamycin, radiciol, glucuronic acid, and tributylin. Heat shock response activators have also been described, for example, in U.S. Patent Application Publication No's. 20070259820, 20070207992, 20070179087, 20060148767, the contents of each of which are expressly incorporated by reference herein. In some embodiments, the heat shock response activator is a small molecule heat shock response activator.

The invention also encompasses a method of treating cancer or a tumor in a patient in need thereof comprising administering to said patient an effective amount of a compound of Formula (I), (II), (III), (IV), or (V), or a compound described herein or a pharmaceutically acceptable salt, solvate, clathrate or prodrug, of any of thereof. The invention additionally encompasses a method of treating cancer or a tumor in a patient in need thereof comprising administering to said patient an effective amount of a compound described herein. Cancers that can be treated according to methods of the present invention include, but are not limited to, breast cancer, colon cancer, pancreatic cancer, prostate cancer, lung cancer, ovarian cancer, cervical cancer, multiple myeloma, basal cell carcinoma, neuroblastoma, hematologic cancer, rhabdomyosarcoma, liver cancer, skin cancer, leukemia, basal cell carcinoma, bladder cancer, endometrial cancer, glioma, lymphoma, and gastrointestinal cancer.

In another embodiment, the invention is a method of treating cancer or a tumor comprising administering a compound of Formula (I), (II), (III), (IV), or (V), or a compound described herein or a pharmaceutically acceptable salt, solvate, clathrate or prodrug, or any of thereof, in combination with the administration of a chemotherapeutic agent. Chemotherapeutic agents that can be utilized include, but are not limited to, alkylating agents such as cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

In a further embodiment, the invention is a method of treating cancer or a tumor comprising administering to a patient in need thereof an effective amount of a compound of Formula (I), (II), (III), (IV), or (V), or a compound described herein or a pharmaceutically acceptable salt, solvate, clathrate or prodrug, of any of thereof, in combination with radiation therapy.

In yet an additional embodiment, the invention is a method of treating a viral infection comprising administering to a subject in need thereof an effective amount of a compound of Formula (I), (II), (III), (IV), or (V), or a compound described herein or a pharmaceutically acceptable salt, solvate, clathrate or prodrug, or any of thereof. In certain embodiments, the viral infection is an infection from a virus of the flavivirus family. Examples of viruses in the flavivirus family include, for example, Dengue virus, West Nile virus, Japanese encephalitis virus, yellow fever virus and tick-borne encephalitis viruses. In an additional embodiment, the virus is the La Crosse virus. In another embodiment, the virus is Dengue virus or West Nile virus.

The invention is illustrated by the following examples which are not meant to be limiting in any way.

EXEMPLIFICATION

General Synthetic Route 1

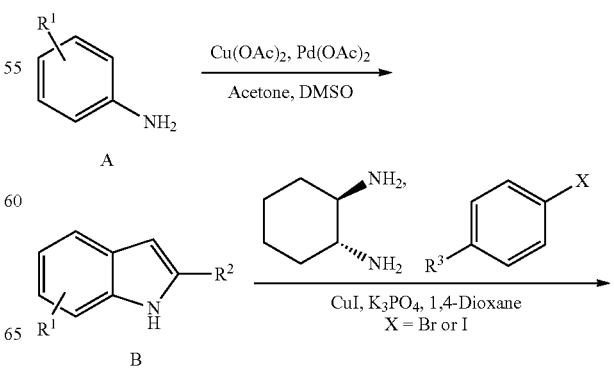

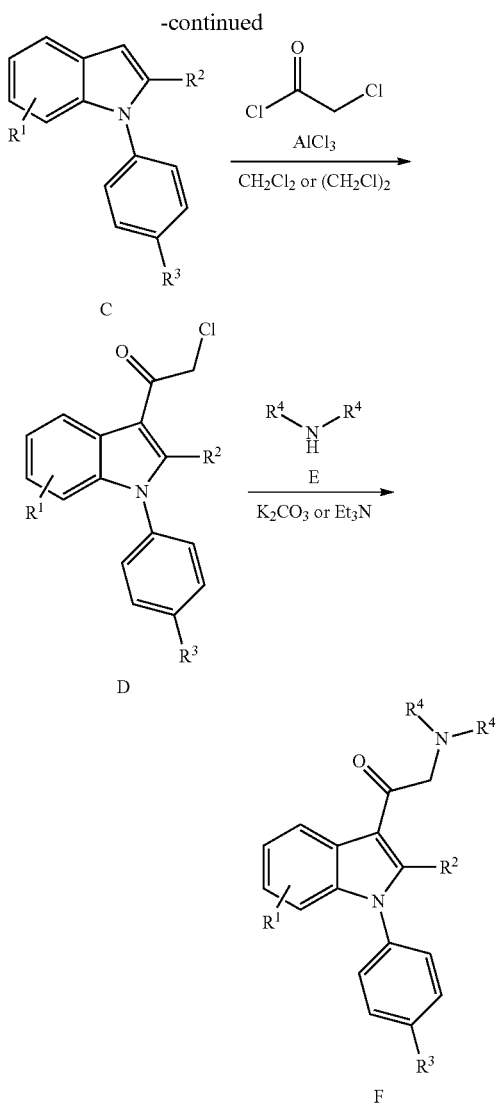

Method of Preparing Intermediate B: In a sealed tube, a mixture of aniline A (1 equiv. 0.046 mol), anhydrous copper (II) acetate (2 equiv.), palladium(II) acetate (0.02 equiv.) and acetone (1.8 M relative to aniline A) in dimethylsulfoxide (1.8 M relative to aniline A) is heated at 90° C. The progress of the reaction is monitored by TLC and HPLC. After cooling to room temperature, the reaction mixture is poured into cold water and then extracted with ethyl acetate. The organic layer is separated and then washed with water and brine. The organic layer is dried over anhydrous sodium sulfate and concentrated under reduced pressure to afford the crude product mixture, which is purified by column chromatography on (100-200 mesh) silica gel to afford intermediate B.

Method of Preparing General Intermediate C: In a sealed tube, a mixture of a substituted 2-methylindole (1 equiv.) or substituted indole B (1 equiv.), copper (I) iodide (0.05 equiv.), and potassium phosphate (1.70 equiv.) in 1,4-dioxane (0.2 M) is sparged with nitrogen gas for 0.5 h. Then trans-(+/−)-1,2-cyclohexanediamine (0.05 equiv.) and aryl halide (1 equiv.) are then added to the flask at room temperature and the resulting reaction mixture is heated at 110° C. for one to two days. After cooling to room temperature, the reaction mixture is filtered through celite and the filter pad is washed with ethyl acetate. The filtrate is concentrated to afford the crude product mixture, which is purified by column chromatography on silica gel (100-200 mesh) to intermediate C.

Alternative Method of Preparing General Intermediate C: A mixture of a substituted 2-methylindole B (1 equiv.) or alternatively substituted indole B (1 equiv.), 4-fluoro substituted benzene (2 equiv.), 18-crown-6 (2 equiv.) and 37%-potassium fluoride/aluminum oxide (15:1 w/w relative to indole) in dimethylsulfoxide (0.15 M) is heated at 100° C. The progress of the reaction is followed by TLC and HPLC. After cooling to room temperature, the reaction mixture is filtered and the filtrate is extracted with ethyl acetate. The organic extract is washed with water and brine. The organic phase is then dried over sodium sulfate and concentrated to obtain the crude product mixture. The crude product is purified by column chromatography on (100-200 mesh) silica to afford Intermediate C.

Alternative Method of Preparing General Intermediate C: A mixture of indole B (1 equiv.), aryl halide (1.2 equiv.), cesium fluoride (2.50 equiv.), copper(I) iodide (0.05 equiv.) and N,N-dimethylethylenediamine (0.10 equiv.) is prepared in dry tetrahydrofuran (0.6 M relative to indole B) and then stirred at 70° C. under an inert atmosphere atmosphere. After cooling to room temperature the reaction mixture is diluted with water and extracted with ethyl acetate. The organic extracts are combined, washed with water and brine, dried over sodium sulfate and then concentrated to afford crude product. The crude product is purified by the column chromatography using (100-200 mesh) silica gel to obtain intermediate C.

Alternative Method of Preparing General Intermediate C: Within a sealed tube, a solution of intermediate B (1 equiv.) in dimethyl sulfoxide (0.07 M relative to B) is treated with potassium carbonate (2.5 equiv.), aryl halide (2.5 equiv.), and 8-hydroxy quinnoline (0.2 equiv.). The sealed tube is then purged with nitrogen for 30 min at room temperature. Solid copper(I) iodide (0.2 equiv.) is then added to the reaction mixture and the sealed system is heated at 110° C. The progress of the reaction is followed by HPLC and TLC. After cooling to room temperature, cold water is added to the reaction mixture, which is then extracted with ethyl acetate. The combined organic extracts are washed with brine and then dried over anhydrous sodium sulfate. The organic phase is concentrated under reduced pressure and the crude product purified by by column chromatography on silica gel (100-200 mesh) to afford intermediate C.

Method of Preparing General Intermediate D: A stirred suspension of aluminum trichloride (1.5 equiv.) in dichloromethane (0.1 M relative to C) is cooled to 0° C. Neat chloro acetyl chloride (1.5 equiv.) is added to the reaction mixture in a drop-wise manner and the resulting mixture is stirred at 0° C. for 0.5 h. Intermediate C (1 equiv.) is dissolved in dichloromethane (0.6 M) and then added to the reaction mixture. The mixture is allowed to warm to room temperature and is then heated at reflux. The progress of the reaction is monitored by TLC and HPLC. After cooling to room temperature, the reaction mixture is poured into ice water and the mixture is extracted with dichloromethane. The organic extracts are combined and washed with water and brine. The organic phase is then dried over sodium sulfate and concentrated to obtain the crude product mixture. The crude product is purified by column chromatography on (230-400 mesh) silica gel to afford intermediate D.

Method of Preparing Target Compound F: To a cold solution of intermediate D (1 equiv.) in anhydrous N,N-dimethylformamide (0.08 M) is added solid potassium carbonate (3 equiv.) and amine E (2 equiv.) or triethylamine (3 equiv.) and amine E (2 equiv.) in anhydrous acetonitrile (0.08 M). The mixture is allowed to warm to room temperature and the progress of the reaction is monitored by HPLC and TLC. The reaction mixture is then poured into ice cold water and the resulting precipitate is collected by filtration. The solids are washed with water and then dried to afford target compound F.

Example 1

4-(2-Methyl-3-(2-(piperidin-1-yl)acetyl)-1H-indol-1-yl)benzonitrile (Compound 160)

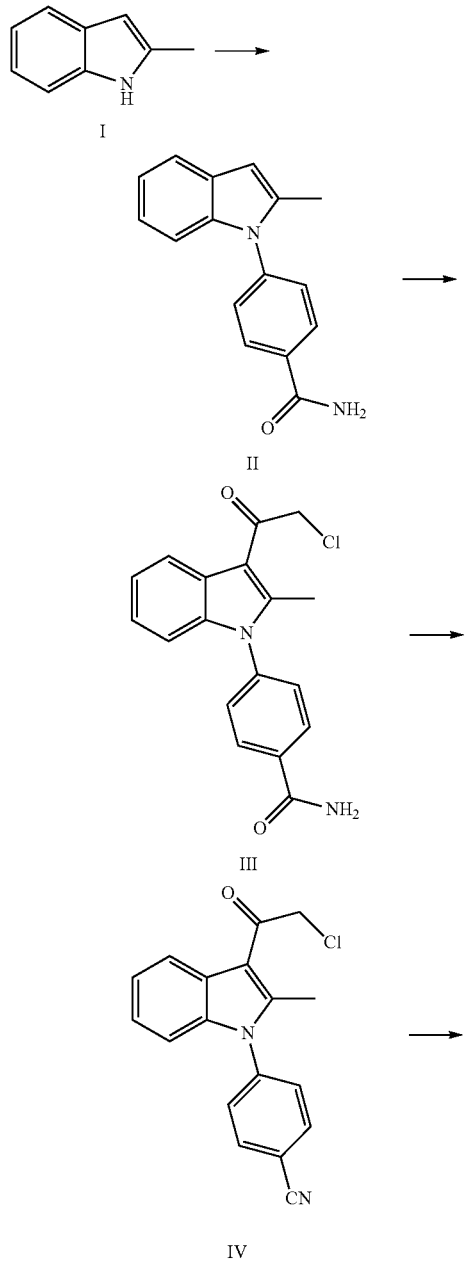

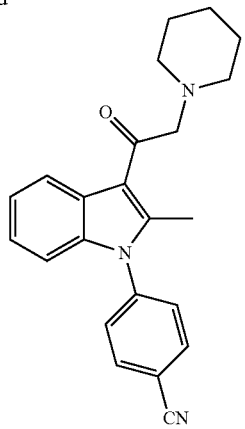

Synthesis of 4-(2-Methyl-indol-1-yl)-benzamide (II): A mixture of commercially available 2-methylindole (2.00 g, 0.015 mol), 4-fluorobenzonitrile (3.60 g, 0.030 mol), 18-crown-6 (8.06 g, 0.030 mol) and 37%-potassium fluoride/$Al_2O_3$ (30.0 g) in dimethylsulfoxide (100 mL) was heated at 100° C. for 3 hr. After cooling to room temperature, the reaction mixture was filtered and the filtrate was extracted with ethyl acetate (25 mL). The organic extract was washed with water (2×50 mL) and brine. The organic phase was then dried over sodium sulfate and concentrated to obtain the crude product mixture. The crude product was purified by column chromatography on (100-200 mesh) silica using 2% methanol in dichloromethane as the eluant to afford product II (1.40 g, 37%) as a white solid. $^1$H NMR (400 MHz, DMSO-$d_6$): δ 8.13 (s, 1H), 8.06 (d, J=8.5, 2.1 Hz, 2H), 7.53 (dd, J=8.5, 2.1 Hz, 2H), 7.50 (s, 1H), 7.03-7.09 (m, 3H), 6.45 (s, 1H), 2.30 (s, 3H); MS (ESI, positive mode) m/z 251 (MH$^-$).

Synthesis of 4-[3-(2-Chloro-acetyl)-2-methyl-indol-1-yl]-benzamide (III): A stirred suspension of aluminum trichloride (1.23 g, 9.20 mmol) in dichloromethane (50 mL) was cooled to 0° C. Chloro acetyl chloride (1.04 g, 9.20 mmol) was added to the reaction mixture in a drop-wise manner and the resulting mixture was stirred at 0° C. for 0.5 h. Intermediate II (1.43 g, 6.16 mmol) was dissolved in dichloromethane (10 mL) and then added to the reaction mixture. The mixture was allowed to warm to room temperature and then heated at reflux for 16 h, before being allowed to cool to room temperature. The reaction was quenched with ice water and the mixture was extracted with dichloromethane (50 mL×3). The organic extracts were combined and washed with water and brine. The organic phase was then dried over sodium sulfate and concentrated to obtain the crude product mixture. The crude product was purified by column chromatography on (230-400 mesh) silica gel using 3% methanol in dichloromethane to afford III (0.400 g, 22%) as an off white solid. $^1$H NMR (400 MHz, DMSO-$d_6$): δ 8.17 (s, 1H); 8.10 (d, J=8.5 Hz, 2H), 8.07 (d, J=8.1 Hz, 1H), 7.56 (bd, J=8.4 Hz, 2H), 7.26 (t, J=7.2 Hz, 1H), 7.18 (t, J=7.2 Hz, 1H), 6.98 (d, J=8.0 Hz, 1H), 5.03 (s, 2H), 2.53 (s, 3H); MS (ESI, negative mode) m/z 325/327 (M$^-$-H, $^{35/37}$Cl).

Synthesis of 4-[3-(2-Chloro-acetyl)-2-methyl-indol-1-yl]-benzonitrile (IV): To a stirred suspension of compound III (0.150 g, 0.460 mmol) in 1,2-dichloroethane (5 mL) was added propylphosphonic acid anhydride (0.438 g, 0.690 mmol) and then the reaction mixture was heated at reflux for 12 h. After cooling to room temperature, the reaction mixture was poured into ice-cold water (20 mL) and the mixture was extracted with dichloromethane (20 mL×2). The organic layer was washed with water and brine, before it was dried over sodium sulfate and concentrated to obtain the crude product mixture. The crude product was purified by the column chromatography on (230-400 mesh) silica using 16% ethyl acetate in hexanes as the eluant to afford IV (0.050 g, 34%) as an off-white solid. $^1$H NMR (400 MHz, CDCl$_3$): δ 7.92 (d, J=8.4 Hz, 2H), 7.91 (d, J=8 Hz, 1H), 7.49 (d, J=8.4 Hz, 2H), 7.35 (t, J=7.1 Hz, 1H), 7.18-7.25 (m, 1H), 7.02 (d, J=8.2 Hz, 1H), 4.76 (s, 2H), 2.62 (s, 3H); MS (ESI, negative mode) m/z 307/309 (M$^-$-H, $^{35/37}$Cl).

Synthesis of 4-[2-Methyl-3-(2-piperidin-1-yl-acetyl)-indol-1-yl]-benzonitrile (160): To a solution of piperidine (0.020 g, 0.243 mmol) in N,N-dimethylformamide (2 mL) being maintained at 0° C. was added solid potassium carbonate (0.055 g, 0.405 mmol). The suspension was stirred at the reduced temperature for 0.5 h and then compound IV (0.050 g, 0.162 mmol) was added to the reaction mixture. The resulting mixture was allowed to warm to room temperature and stir for 1 h. The reaction was quenched with ice water and then extracted with ethyl acetate (20 mL×2). The combined organic extracts were washed with water and brine, before being dried over sodium sulfate and concentrated to afford the crude product mixture. The crude product was purified by the column chromatography on (230-400 mesh) silica using 2% methanol in dichloromethane as the eluant to obtain 160 (0.013 g, 23%) as an off-white solid. $^1$H NMR (400 MHz, CDCl$_3$): δ 8.03 (d, J=8.2 Hz, 1H), 7.90 (d, J=8.4 Hz, 2H), 7.48 (d, J=8.4 Hz, 2H), 7.30 (t, J=8 Hz, 1H), 7.19 (t, J=7.4 Hz, 1H), 6.99 (d, J=8.2 Hz, 1H), 3.79 (s, 2H), 2.57-2.65 (bs, 7H), 1.62-1.70 (m, 4H), 1.42-1.50 (bm, 2H); MS (ESI, positive mode) m/z 358 (MH$^+$).

Example 2

4-(2,6-Dimethyl-3-(2-(piperidin-1-yl)acetyl)-1H-indol-1-yl)benzonitrile (Compound 169)

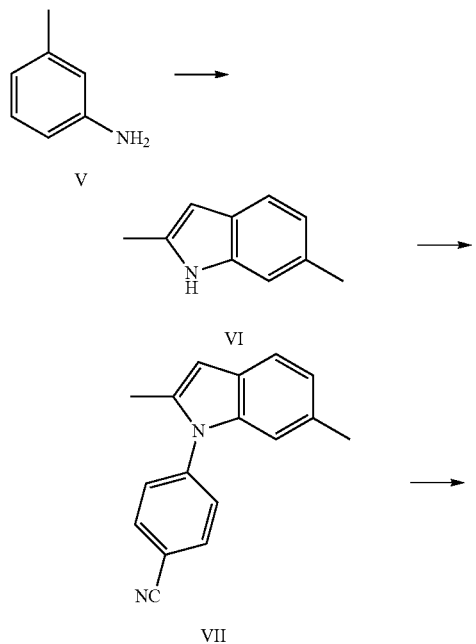

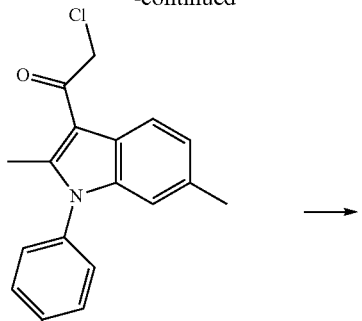

VIII

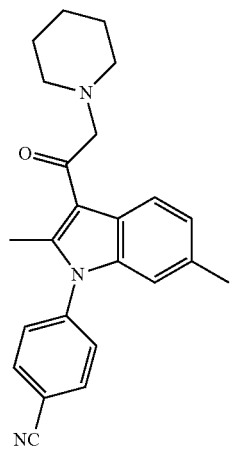

169

Synthesis of 2,6-Dimethyl-1H-indole (VI): In a sealed tube, a mixture of m-toludine (5.00 g, 0.046 mol), anhydrous copper (II) acetate (18.6 g, 0.093 mol), palladium (II) acetate (0.208 g, 0.930 mmol) and acetone (25 mL) in dimethylsulfoxide (25 mL) was heated at 90° C. for 18 h. After cooling to room temperature, the reaction mixture was poured into cold water and then extracted with ethyl acetate (2×250 mL). The organic layer was separated and then washed with water and brine. The organic layer was dried over anhydrous sodium sulfate and then concentrated under reduced pressure to afford the crude product mixture, which was purified by column chromatography on (100-200 mesh) silica gel using an ethyl acetate/hexane gradient to afford compound VI (1.0 g, 15%). $^1$H NMR (400 MHz, CDCl$_3$): δ 10.70 (s, 1H), 7.23 (d, J=8.00 Hz, 1H), 7.02 (s, 1H), 6.72 (d, J=7.8 Hz, 1H), 6.01 (s, 1H), 2.34 (s, 6H); MS (ESI, positive mode) m/z 146 (MH$^+$).

Synthesis of 4-(2,6-Dimethyl-indol-1-yl)-benzonitrile (VII): In a sealed tube, a solution of compound VI (0.800 g, 5.50 mmol) in 1,4-dioxane (50 mL) was treated with potassium phosphate (2.10 g, 9.90 mmol) and 4-iodo-benzonitrile (1.38 g, 0.006 mol). The mixture was sparged with nitrogen gas for 0.5 h at room temperature. Then copper (I) iodide (0.052 g, 0.270 mmol) and trans-(+/−)-1,2-diaminocyclohexane (0.056 g, 0.490 mmol) were added before the tube was sealed. The reaction mixture was heated at 110° C., with stirring, for 16 h. After cooling the reaction mixture was poured into cold water and extracted with ethyl acetate (2×100 mL). The combined organic extracts were dried over anhydrous sodium sulfate and then concentrated under reduced pressure to afford the crude product mixture. The crude product was purified by column chromatography on (100-200 mesh) silica gel using an ethyl acetate/hexane gradient to afford compound VII (0.500 g, 36%). $^1$H NMR (400 MHz, CDCl$_3$): δ 7.83 (dt, J=8.6, 2 Hz, 2H), 7.47 (dt, J=8.6, 2 Hz, 2H), 7.43 (d, J=8 Hz, 1H), 6.96 (d, J=8 Hz, 1H), 6.91 (bs, 1H), 6.38 (s, 1H), 2.38 (s, 3H), 2.30 (s, 3H); MS (ESI, positive mode) m/z 247 (MH$^-$).

Synthesis of 4-[3-(2-Chloro-acetyl)-2,6-dimethyl-indol-1-yl]-benzonitrile (VIII): To a cooled (0° C.) suspension of anhydrous aluminum chloride (0.810 g, 6.10 mmol) in anhydrous dichloromethane (20 mL), being maintained under a nitrogen atmosphere, was added chloro-acetyl chloride (0.690 g, 6.10 mmol). The reaction mixture was allowed to warm to room temperature and stir for 0.5 h. A solution of compound VII (0.500 g, 2.00 mmol) in anhydrous dichloromethane (5 mL) was then added to the flask and the resulting mixture was heated at 45° C. for 18 h. After cooling, the reaction mixture was poured into cold water and then extracted with dichloromethane (2×50 mL). The combined organic extracts were dried over anhydrous sodium sulfate and then concentrated under reduced pressure to afford the crude product mixture. The crude product was purified by column chromatography on (100-200 mesh) silica gel using an ethyl acetate/hexanes gradient to afford product VIII (0.05 g). $^1$H NMR (400 MHz, CDCl$_3$): δ 7.92 (d, J=8.6 Hz, 2H), 7.76 (d, J=8.2 Hz, 1H), 7.48 (d, J=8.6 Hz, 2H), 7.16 (d, J=8.2 Hz, 1H), 6.79 (s, 1H), 4.74 (s, 2H), 2.59 (s, 3H), 2.38 (s, 3H); MS (ESI, positive mode) m/z 323 (MH$^+$).

Synthesis of 4-[2,6-Dimethyl-3-(2-piperidin-1-yl-acetyl)-indol-1-yl]-benzonitrile (169): A mixture of compound VIII (0.050 g, 0.150 mmol), triethylamine (0.025 g, 0.230 mmol), and piperidine (0.014 g, 0.170 mmol) in anhydrous acetonitrile (5 mL) was maintained under a nitrogen atmosphere and allowed to stir at room temperature for 1 h. The volatiles were removed under vacuum and the remaining material was poured into cold water. The precipitate that formed was collected by filtration and washed with water. Drying the solids afforded compound 169 (30 mg, 52%) as a pale-brown solid. $^1$H NMR (400 MHz, CDCl$_3$): δ 7.95-7.87 (m, 3H), 7.46 (d, J=6.7 Hz, 2H), 7.12 (d, J=8.3 Hz, 1H), 6.77 (s, 1H), 3.78 (s, 2H), 2.60-2.57 (bm, 7H), 2.38 (s, 3H), 1.68-1.62 (m, 4H), 1.50-1.46 (bm, 2H); MS (ESI, positive mode) m/z 372 (MH$^+$).

Example 3

4-(6-Isopropyl-2-methyl-3-(2-(piperidin-1-yl) acetyl)-1H-indol-1-yl)benzonitrile (Compound 180)

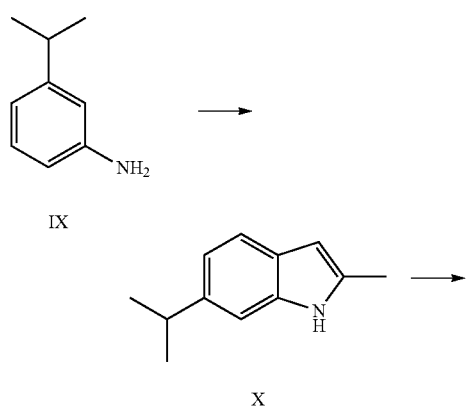

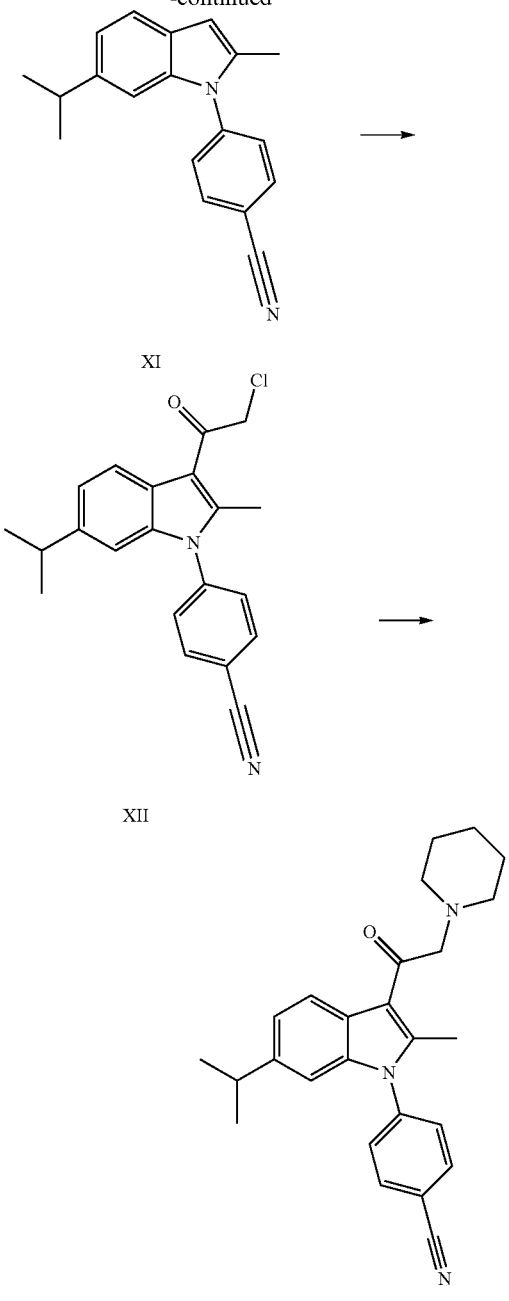

Synthesis of 6-Isopropyl-2-methyl-1H-indole (X): In a screw-cap vial was prepared a mixture of commercially available IX (5.00 g, 0.037 mol), copper (II) acetate-monohydrate (22.0 g, 0.110 mol), dimethylsulfoxide (30 mL), and acetone (200 mL). The reaction mixture was sparged with nitrogen gas for 30 min and then palladium (II) acetate (0.170 g, 0.740 mmol) was added. The vial was sealed tightly and then heated to 95-100° C. for 16 h. After cooling to room temperature the reaction mixture was filtered through celite. The filter pad was washed with ethyl acetate (50 mL) and the filtrate was evaporated in vacuo to afford an oil. The oil was poured over ice-water (200 mL) and then extracted with ethyl acetate (3×150 mL). The combined extracts were washed with water (3×500 mL) and then dried over anhydrous sodium sulfate. The organic layer was then concentrated in vacuum and remaining residue was purified by flash chromatography on silica gel using 3% ethyl acetate/hexanes as the eluent to afford X as an off-white fluffy solid. $^1$H NMR (400 MHz, CDCl$_3$): δ 7.73 (bs, 1H), 7.41 (d, J=8.1 Hz, 1H), 7.12 (s, 1H), 6.95 (dd, J=8.1, 1.4 Hz, 1H), 6.15 (s, 1H), 2.97 (hept, J=6.9 Hz, 1H), 2.41 (s, 3H), 1.28 (d, J=7.0 Hz, 6H); MS (ESI, positive mode) m/z 174 (MH$^+$).

Synthesis of 4-(6-Isopropyl-2-methyl-indol-1-yl)-benzonitrile (XI). A mixture of X (330 mg, 1.90 mmol), 4-iodobenzonitrile (527 mg, 2.30 mmol), and potassium phosphate (726 mg, 3.40 mmol) in 1,4-dioxane (80 mL) was sparged with nitrogen gas for 30 min in a screw cap bottle. Then (+/−)-trans-1,2-diaminocyclohexane (20 mg, 0.17 mmol) and copper (I) iodide (2 mg, 0.095 mmol) were added to the mixture and the bottle was sealed tightly. The system was heated to 110° C. for 16 h and was then allowed to cool to room temperature. The mixture was concentrated in vacuo and the remaining residue was poured into ice-water (20 mL). The aqueous mixture was then extracted with ethyl acetate (3×30 mL) and the combined organic extracts were dried over anhydrous sodium sulfate. The organic layer was then concentrated under vacuum to afford a crude mass, which was purified by flash chromatography on silica gel using 2% ethyl acetate in hexanes as the eluant to afford compound XI as an off-white solid (230 mg, 44%); $^1$H NMR (400 MHz, CDCl$_3$): δ 7.84 (dt, J=8.4, 2.1 Hz, 2H), 7.46-7.51 (m, 3H), 7.04 (dd, J=8.1, 1.4 Hz, 1H), 6.94 (s, 1H), 6.39 (s, 1H), 2.93 (hept, J=6.9 Hz, 1H), 2.29 (s, 3H), 1.23 (d, J=6.9 Hz, 6H); MS (ESI, positive mode) m/z 275 (MH$^-$).

Synthesis of 4-[3-(2-Chloro-acetyl)-6-isopropyl-2-methyl-indol-1-yl]-benzonitrile (XII): To an ice-cold suspension of anhydrous aluminum trichloride (60 mg, 0.440 mmol) in dry dichloromethane (5 mL) was added a solution of chloroacetyl chloride (50 mg, 0.44 mmol) in dry dichloromethane (1 mL) in a drop-wise manner. The resulting mixture was allowed to stir for 30 min at 0° C. and then a solution of compound XI (100 mg, 0.36 mmol) in dry dichloromethane (1 mL) was added to the flask in a single portion. The reaction was allowed to warm to room temperature and stir for 5 h before it was quenched over ice-water (20 mL). The aqueous mixture was then basified with an aqueous, saturated solution of sodium bicarbonate and then extracted with dichloromethane (3×10 mL). The combined organic extracts were dried over anhydrous sodium sulfate and then evaporated in vacuo. The resulting crude product mixture was purified by column chromatography on (60-120 mesh) silica gel using ethyl acetate as the eluant. The material obtained after column chromatography was washed with n-pentane and (2×2 mL) and then allowed to dry to afford XII as an off-white solid; $^1$H NMR (400 MHz, CDCl$_3$): δ 7.93 (d, J=8.4 Hz, 2H), 7.80 (d, J=8.4 Hz, 1H), 7.48 (d, J=8.3 Hz, 2H), 7.23 (s, 1H), 6.82 (s, 1H), 4.74 (s, 2H), 2.94 (hept, J=6.9 Hz, 1H), 2.59 (s, 3H), 1.23 (d, J=6.9 Hz, 6H); MS (ESI, positive mode) m/z 351 (MH$^+$).

Synthesis of 4-[6-Isopropyl-2-methyl-3-(2-piperidin-1-yl-acetyl)-indol-1-yl]-benzonitrile (180). To a cold (0° C.) solution of compound XII (40 mg, 0.110 mmol) in dry N,N-dimethylformamide (1 mL) was added piperidine (22 mg, 0.220 mmol) and the resulting mixture was allowed to stir for 30 min at the reduced temperature. Then the reaction mixture was poured over crushed ice (10 mL) and the mixture was stirred for 15 min. The precipitate that formed was collected by filtration, washed with water (30 mL), and then dried in vacuo afforded 180 as an off-white solid (20 mg, 44%); $^1$H NMR (400 MHz, CDCl$_3$): δ 7.89-7.95 (m, 3H), 7.46 (d, J=8.2 Hz, 2H), 7.20 (d, J=8.5 Hz, 1H), 6.80 (s, 1H), 3.78 (s, 2H), 2.87-2.94 (bm, 1H), 2.57-2.65 (bm, 7H), 1.63-1.67 (bm, 4H), 1.47 (bs, 2H), 1.21 (d, J=6.9 Hz, 6H); MS (ESI, positive mode) m/z 400 (MH$^+$).

Examples 4-5

(1-(4-Chlorophenyl)-3-(2-(piperidin-1-yl)acetyl)-1H-indol-6-yl)methyl Acetate (Compound 118), 1-(1-(4-Chlorophenyl)-6-(hydroxymethyl)-1H-indol-3-yl)-2-(piperidin-1-yl)ethan-1-one (Compound 115)

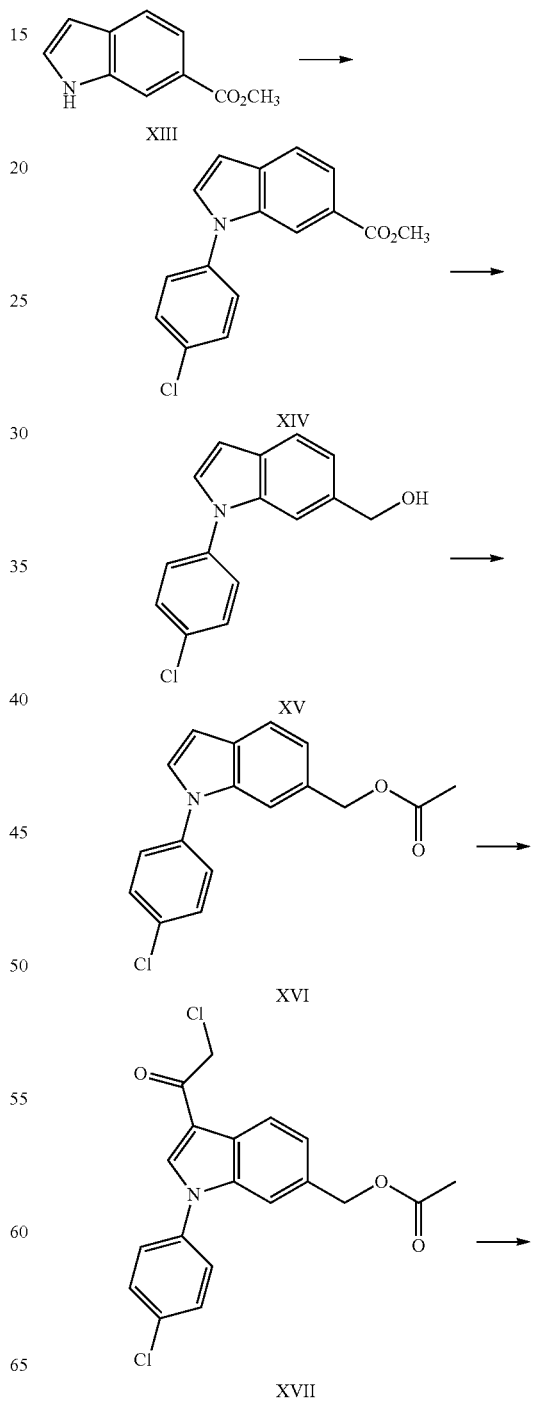

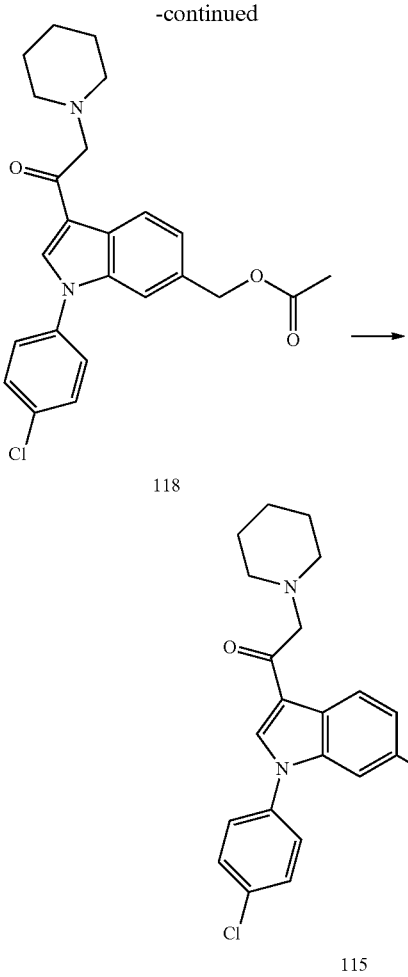

118

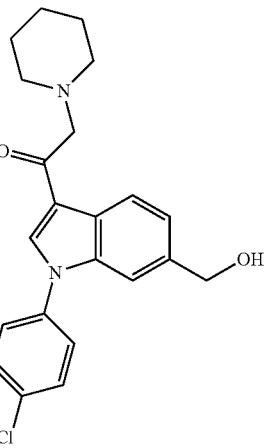

115

Synthesis of 1-(4-Chloro-phenyl)-1H-indole-6-carboxylic acid Methyl Ester (XIV): To a mixture of XIII (5 g, 0.028 mol), 4-chloro-iodobenzene (8.2 g, 0.034 mol), copper(I) iodide (0.27 g, 1.42 mmol), cesium fluoride (10.8 g, 71.3 mmol), and anhydrous tetrahydrofuran (100 mL) being maintained under a nitrogen atmosphere was added N,N-dimethyl ethylenediamine (0.4 mL, 2.85 mmol). The reaction mixture was heated at 85° C. for 18 h and then allowed to cool to room temperature. The reaction mixture was poured onto cold water (250 mL) and the mixture was extracted with ethyl acetate (2×250 mL). The organic layer was washed with brine, dried over anhydrous sodium sulfate, and then concentrated under reduced pressure to obtain the crude product mixture. The crude product was purified by column chromatography on 100-200 mesh silica gel using an ethyl acetate-hexanes gradient as the eluant to afford XIV (3.5 g, 44%) as a white solid. $^1$H NMR (400 MHz, CDCl$_3$): δ 8.19 (brs, 1H), 7.86 (dd, J=8.3, 1.4 Hz, 1H), 7.69 (d, J=8.3 Hz, 1H), 7.54-7.50 (m, 2H), 7.42-7.48 (m, 3H), 6.72 (dd, J=3.2, 0.72 Hz, 1H), 3.90 (s, 3H); MS (ESI, positive mode) m/z 286 (MH$^+$, $^{35/37}$Cl).

Synthesis of [1-(4-Chloro-phenyl)-1H-indol-6-yl]-methanol (XV): Lithium aluminum hydride (1.06 g, 2.80 mol) was added in a portionwise manner to a solution of XIV (2.0 g, 0.007 mol) in anhydrous tetrahydrofuran (50 mL) being maintained at 0° C. under nitrogen atmosphere. The resulting mixture was allowed to warm to room temperature and stir for 4 h. The reaction mixture was quenched through the addition of ethyl acetate (100 mL) at 0° C. and the resulting mixture was allowed to stir for 0.5 h. The mixture was filtered through a pad of celite and the filter pad was washed with ethyl acetate (2×100 mL). The combined organic layers were concentrated under reduced pressure to afford the crude product mixture, which was purified by column chromatography on 100-200 mesh silica gel using and ethyl acetate-hexanes gradient to afford XV (1.5 g, 83%) as a white solid. $^1$H NMR (400 MHz, CDCl$_3$): δ 7.66 (d, J=8.1 Hz, 1H), 7.47-7.54 (m, 3H), 7.45-7.42 (m, 2H), 7.29 (d, J=3.2 Hz, 1H), 7.17 (dd, J=8.1, 1.3 Hz, 1H), 6.67 (dd, J=2.6 Hz, 1H), 4.77 (s, 2H), 3.70 (s, 1H); MS (ESI, positive mode) m/z 258/260 (MH$^+$, $^{35/37}$Cl).

Synthesis of (1-(4-Chlorophenyl)-1H-indol-6-yl)methyl Acetate (XVI): To a solution of XV (1.5 g, 5.80 mmol) in dry dichloromethane (100 mL) being maintained under a nitrogen atmosphere was added acetic anhydride (1.2 g, 11.6 mmol) and triethylamine (1.2 g, 11.6 mmol). The resulting mixture was allowed to stir for 3 h at room temperature, before it was poured onto cold water (50 mL) and extracted with ethyl acetate (2×100 mL). The organic layer was washed with brine, dried over anhydrous sodium sulfate, and concentrated under reduced pressure to obtain the crude product mixture. The crude product was purified by column chromatography on 100-200 mesh silica gel using an ethyl acetate-hexanes gradient to afford XVI (0.9 g, 53%) as colorless liquid. $^1$H NMR (400 MHz, CDCl$_3$): δ 7.67 (d, J=8.2 Hz, 1H), 7.55-7.46 (m, 3H), 7.45-7.36 (m, 2H), 7.29 (d, J=3.2 Hz, 1H), 7.18 (dd, J=8.2, 1.4 Hz, 1H), 6.67 (d, J=3.2 Hz, 1H), 5.17 (s, 2H), 2.06 (s, 3H); MS (ESI, positive mode) m/z 300/302 (MH$^+$, $^{35/37}$Cl).

Synthesis of (3-(2-Chloroacetyl)-1-(4-chlorophenyl)-1H-indol-6-yl)methyl Acetate (XVII): To a suspension of anhydrous aluminum chloride (0.67 g, 0.005 mol) in dry dichloromethane (15 mL) being maintained at 0° C. under a nitrogen atmosphere was added chloro-acetyl chloride (0.57 g, 0.005 mol). The resulting mixture was allowed to warm to room temperature and stir for 0.5 h. A solution of intermediate XVI (0.4 mL, 0.00285 mol) in dry dichloromethane (10 mL) was then added to the reaction mixture and allowed to stir for 1 h. The reaction mixture was then poured onto cold water (50 mL) and the mixture was extracted with ethyl acetate (2×100 mL). The combined organic layers were washed with brine, dried over anhydrous sodium sulfate, and concentrated under reduced pressure to afford the crude product mixture. The crude product was purified by column chromatography on 100-200 mesh silica gel using an ethyl acetate-hexanes gradient to afford product XVII (0.9 g, 72%) as a brown solid. $^1$H NMR (400 MHz, CDCl$_3$): δ 8.40 (d, J=8.2 Hz, 1H), 8.01 (s, 1H), 7.57 (d, J=8.7 Hz, 2H), 7.46 (d, J=8.7 Hz, 2H), 7.40 (brs, 1H), 7.39 (dd, J=8.3, 1.4 Hz, 1H), 5.17 (s, 2H), 4.54 (s, 2H), 2.07 (s, 3H); MS (ESI, positive mode) m/z 376/378 (MH$^+$, $^{35/37}$Cl).

Synthesis of (1-(4-Chlorophenyl)-3-(2-(piperidin-1-yl)acetyl)-1H-indol-6-yl)methyl Acetate (118): A mixture of XVII (0.15 g, 0.39 mmol), triethylamine (0.1 mL, 0.78 mmol) and piperidine (0.06 mL, 0.59 mmol) in dry acetonitrile (10 mL) was allowed to stir for 1 h, at room temperature, under a nitrogen atmosphere. The reaction mixture was then poured onto cold water (50 mL) and extracted with ethyl acetate (2×100 mL). The combined organic layers were washed with brine, dried over anhydrous sodium sulfate, and concentrated under reduced pressure to obtain the crude product mixture. The crude product was purified by column chromatography on 100-200 mesh silica gel using an ethyl acetate-hexanes gradient to afford product 118 (0.100 g, 59%) as a brown liquid, which solidified into an amorphous mass upon standing. ¹H NMR (400 MHz, CDCl₃): δ 8.52 (s, 1H), 8.46 (d, J=8.3 Hz, 1H), 7.57 (d, J=8.6 Hz, 2H), 7.46 (d, J=8.6 Hz, 2H), 7.40 (s, 1H), 7.35 (dd, J=8.2, 1.3 Hz, 1H), 5.18 (s, 2H), 3.58 (s, 2H), 2.52 (brs, 4H), 2.05 (s, 3H), 1.65-1.55 (m, 4H), 1.45 (brs, 2H); MS (ESI, positive mode) m/z 425/427 (MH⁺, ³⁵/³⁷Cl).

Synthesis of 1-(1-(4-Chlorophenyl)-6-(hydroxymethyl)-1H-indol-3-yl)-2-(piperidin-1-yl)ethan-1-one (115): To a solution of 118 (0.1 g, 0.235 mmol) in wet tetrahydrofuran (20 mL) was added lithium hydroxide (0.03 g, 0.705 mmol).

purified by column chromatography on 100-200 mesh silica gel using an ethyl acetate-hexanes gradient to afford product 115 (50 mg, 55%) as an off white solid. ¹H NMR (400 MHz, CDCl₃): δ 8.48 (s, 1H), 8.44 (d, J=8.2 Hz, 1H), 7.55 (d, J=8.5 Hz, 2H), 7.45 (d, J=8.3 Hz, 2H), 7.31 (d, J=8.0 Hz, 1H), 4.78 (s, 2H), 3.58 (s, 2H), 2.52 (brs, 4H), 1.65-1.54 (m, 4H), 1.45 (brs, 2H); MS (ESI, positive mode) m/z 383/385 (MH⁺, ³⁵/³⁷Cl).

General Synthetic Route 2

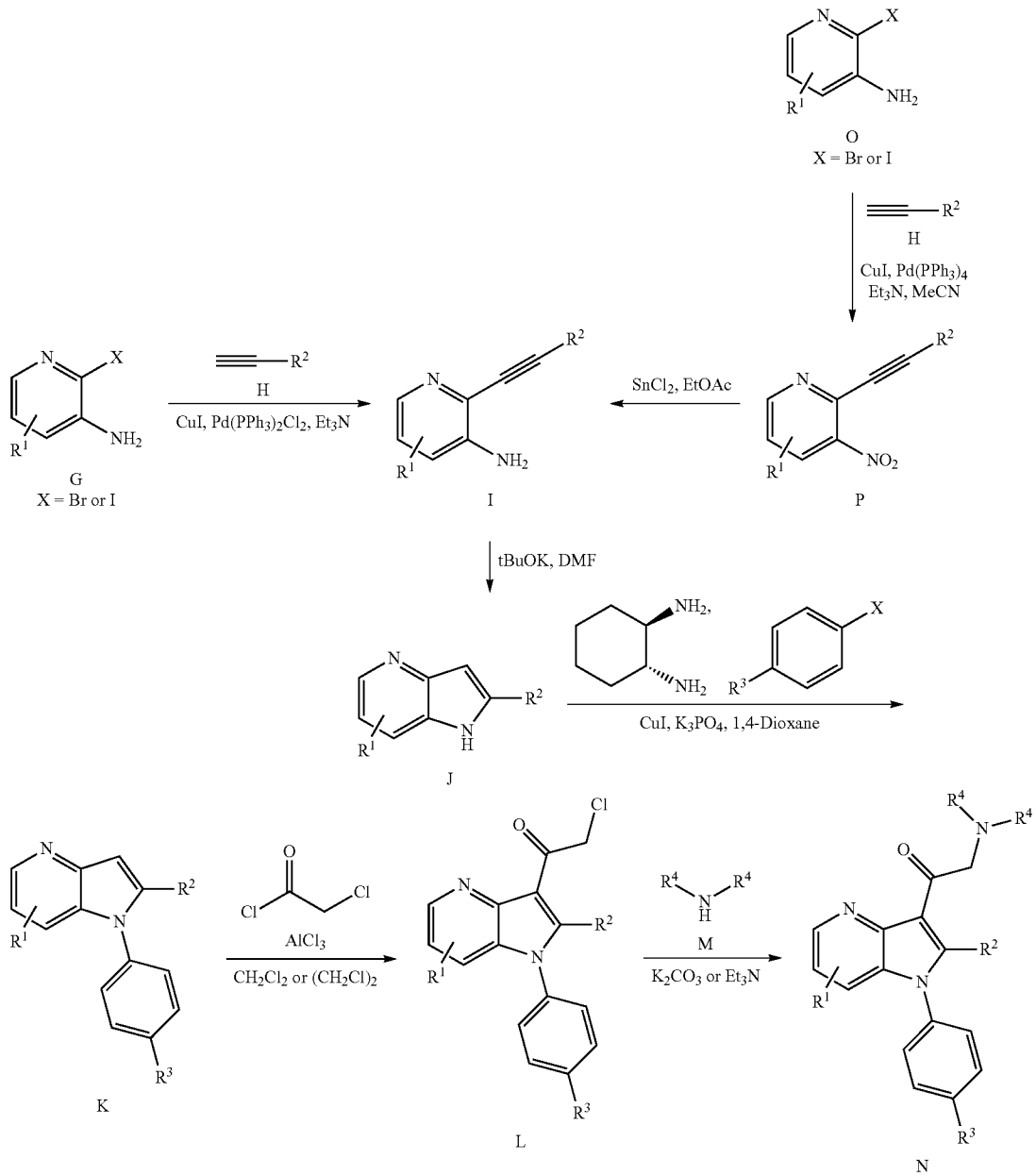

Method of Preparing General Intermediate I from G: A mixture of copper (I) iodide (0.05 equiv.) and 3-amino-2-halo-pyridine (0.012 mol) in triethylamine (0.5 M) is sparged with nitrogen gas for 15 minutes. Then bis(triphenylphosphine)palladium(II) dichloride (0.05 mmol) is added at room temperature followed by alkyne H (1-8

The resulting mixture was allowed to stir at room temperature for 1 h, before it was poured onto cold water (50 mL) and extracted with ethyl acetate (2×100 mL). The combined organic layers were washed with brine, dried over anhydrous sodium sulfate, and concentrated under reduced pressure to obtain the crude product mixture. The crude product was equiv.). The reaction mixture is allowed to stir at room temperature and the progress of the reaction was monitored by HPLC and TLC. The reaction mixture is then diluted with water and filtered through celite. The filter pad is washed with ethyl acetate and the filtrates are separated. The organic layer is dried over anhydrous sodium sulfate and then concentrated under vacuum to afford the crude product mixture. The crude product is purified by column chromatography on silica gel (100-200 mesh) to afford intermediate I.

Method of Preparing General Intermediate J: To a cold solution of intermediate I (1 equiv.) in anhydrous N,N-dimethylformamide (0.3 M) is added solid potassium tert-butoxide or sodium tert-butoxide (2.0 equiv.) in a portion-wise manner. The resulting mixture is allowed to stir at room temperature and the progress of the reaction is monitored by HPLC and TLC. The reaction mixture is then poured into cold water and extracted with diethyl ether. The organic layer is then dried over anhydrous sodium sulfate and then concentrated under vacuum to afford intermediate J.

Method of Preparing General Intermediate K: In a sealed tube, a mixture of copper (I) iodide (0.05 equiv.), intermediate J (1 equiv.) and potassium phosphate (1.70 equiv.) in 1,4-dioxane (0.2 M) is sparged with nitrogen gas for 0.5 h. Then trans-(+/−)-1,2-cyclohexanediamine (0.05 equiv.) and aryl halide (1 equiv.) are then added to the flask at room temperature and the resulting reaction mixture is heated at 110° C. The progress of the reaction is monitored by HPLC and TLC. After cooling to room temperature, the reaction mixture is filtered through celite and the filter pad is washed with ethyl acetate. The filtrate is concentrated to afford the crude product mixture, which is purified by column chromatography on silica gel (100-200 mesh) to intermediate K.

Alternative Method of Preparing General Intermediate K: Within a sealed tube, a solution of intermediate J (1 equiv.) in dimethyl sulfoxide (0.07 M relative to J) is treated with potassium carbonate (2.5 equiv.), aryl halide (2.5 equiv.), and 8-hydroxy quinnoline (0.2 equiv.). The sealed tube is then purged with nitrogen for 30 min at room temperature. Solid copper(I) iodide (0.2 equiv.) is then added to the reaction mixture and the sealed system is heated at 110° C. The progress of the reaction is followed by HPLC and TLC. After cooling to room temperature, cold water is added to the reaction mixture, which is then extracted with ethyl acetate. The combined organic extracts are washed with brine and then dried over anhydrous sodium sulfate. The organic phase is concentrated under reduced pressure and the crude product purified by by column chromatography on silica gel (100-200 mesh) to afford intermediate K.

Method of Preparing General Intermediate L: To a cooled solution (0° C.) of intermediate K (1 equiv.) in dichloromethane or 1,2-dichloroethane (0.1 M) is added solid aluminum trichloride (3 equiv.). Then neat chloro-acetyl chloride (3 equiv.) is added to the reaction mixture. The resulting mixture is allowed to warm to room temperature and stir for one to two days. The reaction mixture is poured into ice cold water and then extracted with dichloromethane. The combined organic extracts are washed with water and brine, before being dried over sodium sulfate. The organic phase is then filtered and concentrated under vacuum to afford the crude product mixture. The crude product is chromatographed on silica gel (100-200 mesh) to obtain intermediate L.

Alternative Method of Preparing General Intermediate L: To an ice cooled suspension of aluminum trichloride (5 equiv.) in dry 1,4-dioxane (0.2 M relative to K) is added chloro acetyl chloride (5 equiv.) followed by pyridine (1.4 equiv.). The resultant reaction mixture is stirred at room temperature for 30 min and then to the reaction mixture is added intermediate K (0.86 mmol, 1 equiv.) in dry 1,4-dioxane (0.2 M). The resulting mixture is heated at 60° C. The progress of the reaction is followed by TLC and HPLC. After cooling to room temperature the volatiles are removed under reduced pressure and the crude reaction mixture is partitioned between aqueous saturated ammonium chloride and ethyl acetate. The organic layer is dried over anhydrous sodium sulfate and then concentrated under reduced pressure. The crude product is purified by column chromatography on silica to afford Intermediate L.

Method of Preparing Target Compound N: To a cold solution of intermediate L (1 equiv.) in anhydrous N,N-dimethylformamide (0.08 M) is added solid potassium carbonate (3 equiv.) and amine M (2 equiv.) or triethylamine (3 equiv.) and amine M (2 equiv.) in anhydrous acetonitrile (0.08 M). The mixture is allowed to warm to room temperature and the progress of the reaction is monitored by HPLC and TLC. The reaction mixture is then poured into ice cold water and the resulting precipitate is collected by filtration. The solids are washed with water and then dried to afford target compound N.

Method of Preparing Intermediate P: In a sealed tube, a mixture of 2-halo-3-nitro-pyridine O (1 equiv.), triethylamine (1 M if used as solvent relative to nitropyridine), copper (I) iodide (0.2 equiv.) and acetonitrile (0.3 M if used as solvent relative to nitropyridine) is sparged with nitrogen gas for 15 min. Tetrakis(triphenylphospine)palladium(0) (0.1 equiv.) is added to the reaction mixture, which is again degassed for 10 min. The alkyne is then added to reaction mixture (1-10 equiv.) and the tube is sealed. The progress of the reaction is followed by TLC and HPLC. The reaction mixture is then diluted with water and extracted with ethyl acetate. The combined organic extracts are washed with water and brine solution before drying over sodium sulfate. The crude product mixture is purified by the column chromatography using (100-200 mesh) silica gel to afford compound P.

Method of Preparing Intermediate I from P: To a stirred solution of compound P (1 equiv.) in ethyl acetate (0.15 M) is added stannous chloride (5 equiv.). The reaction mixture is heated at reflux for 2 h, allowed to cool to room temperature, and then basified with a saturated, aqueous solution of sodium bicarbonate. The mixture is then extracted with ethyl acetate and the combined organic extracts are washed with a brine solution. The organic phase is dried over sodium sulfate and concentrated under vacuum to afford crude product I. In the crude product mixture of I is occasionally found some amount of cyclized J.

Example 6

4-(2-Methyl-3-(2-(piperidin-1-yl)acetyl)-1H-pyrrolo[3,2-b]pyridin-1-yl)benzonitrile (Compound 162)

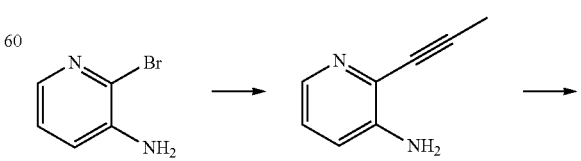

XVIII          XIX

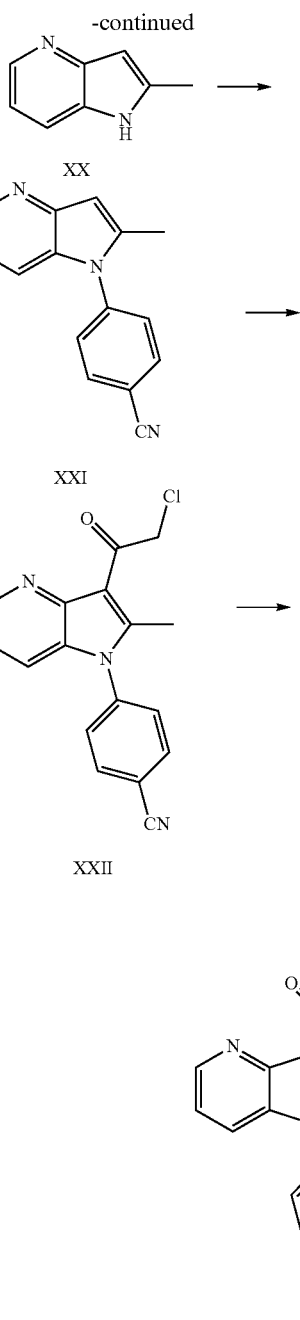

Synthesis of 2-Prop-1-ynyl-pyridin-3-ylamine (XIX): A mixture of copper (I) iodide (110 mg, 0.578 mmol) and commercially available 3-amino-2-bromo-pyridine XVIII (2.00 g, 0.012 mol) in triethylamine (30 mL) was sparged with nitrogen gas for 15 minutes. Then bis(triphenylphosphine)palladium(II) dichloride (450 mg, 0.578 mmol) was added at room temperature. The resulting mixture was cooled to −78° C. and then sparged with propyne gas (7.2 g, 0.092 mol). The reaction mixture was allowed to warm to room temperature and stir for 18 h. The reaction mixture was diluted with water (50 mL) and then filtered through celite. The filter pad was washed with ethyl acetate and the filtrates were separated. The organic layer was dried over anhydrous sodium sulfate and then concentrated under vacuum to afford the crude product mixture. The crude product was chromatographed on silica gel (100-200 mesh) using 50% ethyl acetate in hexanes to obtain XIX (0.75 g) as an off-white solid. $^1$H NMR (400 MHz, CDCl$_3$): δ 7.95 (dd, J=4.3, 1.7 Hz, 1H), 6.92-7.00 (m, 2H), 4.13 (s, 2H), 2.13 (s, 3H); MS (ESI, positive mode) m/z 133 (MH$^+$).

Synthesis of 2-Methyl-1H-pyrrolo[3,2-b]pyridine (XX): To a cold solution of compound XIX (200 mg, 1.50 mmol) in anhydrous N,N-dimethylformamide (5 mL) was added solid potassium tert-butoxide (170 mg, 3.02 mmol) in a portion-wise manner. The resulting mixture was allowed to stir at room temperature for 4 h. The reaction mixture was poured into cold water (10 mL) and then extracted with diethyl ether (2×10 mL). The organic layer was dried over anhydrous sodium sulfate and then concentrated under vacuum to afford product XX (0.150 g) as an off-white solid. $^1$H NMR (400 MHz, DMSO-d$_6$): δ 11.13 (s, 1H), 8.19 (dd, J=4.8, 1 Hz, 1H), 7.59 (d, J=8.1 Hz, 1H), 6.97 (dd, J=8, 4.6 Hz, 1H), 6.24 (s, 1H), 2.42 (s, 3H); MS (ESI, positive mode) m/z 133 (MH$^+$).

Synthesis of 4-(2-Methyl-pyrrolo[3,2-b]pyridin-1-yl)-benzonitrile (XXI): In a sealed tube, a mixture of copper (1) iodide (43 mg, 0.226 mmol), compound XX (0.600 g, 4.53 mmol) and potassium phosphate (1.60 g, 7.70 mmol) in 1,4-dioxane (20 mL) was sparged with nitrogen gas for 0.5 h. Then trans-(+/−)-1,2-cyclohexanediamine (26 mg, 0.226 mmol) and 4-iodo-benzonitrile (1.00 g, 4.53 mmol) where then added to the flask at room temperature and the resulting reaction mixture was heated at 110° C. for 38 h. After cooling to room temperature, the reaction mixture was filtered through celite and the filter pad was washed with ethyl acetate. The filtrate was concentrated to afford the crude product mixture. The crude was purified by column chromatography on silica gel (100-200 mesh) using 30% ethyl acetate in hexane as the eluant to obtain product XXI (0.4 g) as an off-white solid. $^1$H NMR (400 MHz, CDCl$_3$): δ 8.45 (dd, J=5.2, 1 Hz, 1H), 7.93 (d, J=8.6 Hz, 2H), 7.60 (d, J=8.2 Hz, 1H), 7.52 (d, J=8.5 Hz, 2H), 7.21 (dd, J=8.3, 5.2 Hz, 1H), 6.94 (s, 1H), 2.43 (s, 3H), MS (ESI, positive mode) m/z 234 (MH$^+$).

Synthesis of 4-[3-(2-Chloro-acetyl)-2-methyl-pyrrolo[3,2-b]pyridin-1-yl]-benzonitrile (XXII): To a cooled solution (0° C.) of compound XXI (300 mg, 1.28 mmol) in dichloromethane (15 mL) was added solid aluminum trichloride (517 mg, 3.86 mmol). Then neat chloro-acetyl chloride (0.35 mL, 3.86 mmol) was added to the reaction mixture. The resulting mixture was allowed to warm to room temperature and stir for 16 h. The reaction mixture was poured into ice cold water (10 mL) and was then extracted with dichloromethane (2×10 mL). The combined organic extracts were washed with water (2×10 mL) and brine before being dried over sodium sulfate. The organic phase was then filtered and concentrated under vacuum to afford the crude product mixture. The crude product was chromatographed on silica gel (100-200 mesh) using 30% ethyl acetate in hexanes as the eluant to obtain product XXII (120 mg) as an off-white solid. $^1$H NMR (400 MHz, CDCl$_3$): δ 8.59 (dd, J=4.7, 1.4 Hz, 1H), 7.93 (dd, J=6.6, 1.9 Hz, 2H), 7.50 (dd, J=6.7, 2 Hz, 2H), 7.34 (dd, J=8.3, 1.4 Hz, 1H), 7.16 (dd, J=8.3, 4.7 Hz, 1H), 5.33 (s, 2H), 2.70 (s, 3H), MS (ESI, positive mode) m/z 310 (MH$^-$).

Synthesis of 4-[2-Methyl-3-(2-piperidin-1-yl-acetyl)-pyrrolo[3,2-b]pyridin-1-yl]-benzonitrile (162): To a cold solution of compound XXII (120 mg, 0.388 mmol) in anhydrous N,N-dimethylformamide (5 mL) was added solid potassium carbonate (161 mg, 1.16 mmol) and piperidine (0.078 mL, 0.776 mmol). The mixture was allowed to warm to room temperature and stir for 2 h. The reaction mixture was poured into ice cold water (10 mL) and the resulting precipitate was collected by filtration. The solids were washed with water and dried to afford product 162 (90 mg, 65%) as an off-white solid. $^1$H NMR (400 MHz, CDCl$_3$): δ 8.59 (dd, J=4.7, 1.3 Hz, 1H), 7.90 (d, J=8.5 Hz, 2H), 7.47 (d, J=8.5 Hz, 2H), 7.31 (dd, J=8.3, 1.3 Hz, 1H), 7.11 (dd, J=8.2, 4.7 Hz, 1H), 4.33 (s, 2H), 2.64-2.68 (bm, 7H), 1.64-1.72 (m, 4H), 1.42-1.50 (bm, 2H); MS (ESI, positive mode) m/z 359 (MH$^+$).

Examples 7

5-(2-Methyl-3-(2-(piperidin-1-yl)acetyl)-1H-pyrrolo[3,2-b]pyridin-1-yl)picolinonitrile (Compound 181)

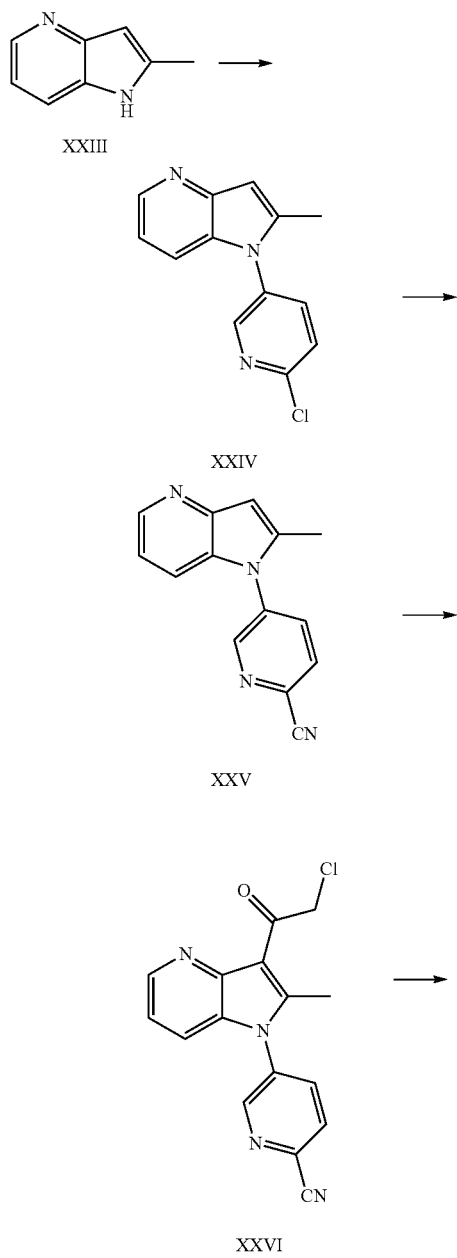

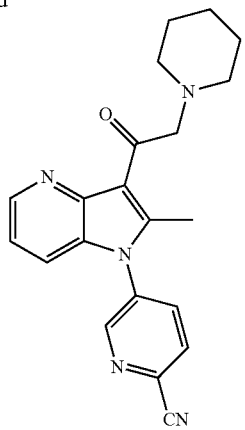

Synthesis of 1-(6-Chloropyridin-3-yl)-2-methyl-1H-pyrrolo[3,2-b]pyridine (XXIV). In a sealed tube, a solution of compound XXIII (Example 2) (0.500 g, 3.70 mmol) in dimethylsulfoxide (50 mL) was treated with potassium carbonate (1.30 g, 9.40 mmol), 2-chloro 5-iodo pyridine (0.906 g, 3.78 mmol), and 8-hydroxy quinnoline (0.109 g, 7.00 mmol). The mixture was sparged with nitrogen gas for 30 min and then copper (I) iodide (0.085 g, 0.700 mmol) was added to the reaction mixture. The system was sealed and then heated at 110° C. for 8 h. After cooling to room temperature, the reaction mixture was diluted with cold water (100 mL) and extracted with ethyl acetate (3×250 mL). The combined organic extracts were washed with brine (25 mL) and then dried over anhydrous sodium sulfate. The organic layer was then concentrated under reduced pressure and the remaining residue was purified by chromatography on silica to afford XXIV (0.4 g, 49%) as yellow solid; $^1$H NMR (400 MHz, CDCl$_3$) δ 8.46-8.43 (m, 2H), 7.66 (dd, J=8.4, 2.6 Hz, 1H), 7.54 (d, J=8.4 Hz, 1H), 7.31 (d, J=8.2 Hz, 1H), 7.04 (dd, J=8.2, 4.8 Hz 1H), 6.66 (s, 1H), 2.36 (s, 3H); MS (ESI, positive mode) m/z 244 (MH$^+$)

Synthesis of 5-(2-Methyl-1H-pyrrolo[3,2-b]pyridin-1-yl)picolinonitrile (XXV). To a solution of compound XXIV (0.240 g, 0.900 mmol) in N,N-dimethylformamide (10 mL) was added zinc (II) cyanide (0.230 g, 1.90 mmol). The resulting mixture was sparged with nitrogen gas for 15 min and then bis-diphenylphosphinoferrocene (0.054 g, 0.090 mmol) and Pd$_2$(dba)$_3$ (0.090 g, 0.096 mmol) were added. The mixture was again sparged with nitrogen gas for 15 min before being heated at 130-140° C. for 2 h. After cooling to room temperature the reaction mixture was diluted with water (50 mL) and then extracted with ethyl acetate (3×50 mL). The combined organic extracts were washed with brine (25 mL) and then dried over anhydrous sodium sulfate. The organic layer was, concentrated under reduced pressure to afford a brown liquid as the crude product mixture. The crude product was purified by column chromatography on silica using 80% ethyl acetate in hexanes as the eluant to afford compound XXV (0.130 g, 57%) as brown solid; $^1$H NMR (400 MHz, CDCl$_3$) δ 8.79 (d, J=2.9 Hz, 1H), 8.49 (d, J=4.2 Hz, 1H) 7.92 (d, J=8.2 Hz, 1H), 7.85 (d, J=8.2 Hz, 1H), 7.39 (d, J=8.2 Hz, 1H), 7.09-7.06 (m, 1H), 6.71 (s, 1H) 2.42 (s, 3H); MS (ESI, positive mode) m/z 235 (MH$^+$).

Synthesis of 5-(3-(2-Chloroacetyl)-2-methyl-1H-pyrrolo[3,2-b]pyridin-1-yl)picolinonitrile (XXVI): To a cold (0° C.) solution of anhydrous aluminum chloride (0.730 g, 0.005 mol) in dichloromethane (10 mL), being maintained under a nitrogen atmosphere, was added neat chloroacetyl chloride (0.600 g, 0.005 mol) in a drop wise manner. The resulting mixture was allowed to stir at the reduced temperature for 1h and then compound XXV (0.130 g, 0.500 mmol) was added. The reaction mixture was allowed to warm to room temperature and was then heated to reflux at 50-60° C. for 24 h. After cooling to room temperature, the reaction mixture was diluted with water (50 mL) and then extracted with ethyl acetate (2×100 mL). The combined organic extracts were washed with brine (2×50 mL) and then dried over anhydrous sodium sulfate. The organic layer was concentrated under reduced pressure and the remaining residue was purified by column chromatography on silica using 35% ethyl acetate in hexanes as the eluant to afford compound XXVI (0.050 g, 29%) as a white solid; $^1$H NMR (400 MHz, CDCl$_3$) δ 8.78 (d, J=2.3 Hz, 1H), 8.62 (d, J=4.7 Hz, 1H), 7.99, (d, J=8.3 Hz, 1H), 7.89 (dd, J=8.2, 2.4 Hz, 1H), 7.35 (d, J=8.3 Hz, 1H), 7.21-7.18 (m, 1H), 5.33 (s, 2H), 2.72 (s, 3H); MS (ESI, positive mode) m/z 311 (MH$^+$).

Synthesis of 5-(2-Methyl-3-(2-(piperidin-1-yl)acetyl)-1H-pyrrolo[3,2-b]pyridin-1-yl)picolinonitrile (181). A mixture of compound XXVI (0.050 g, 1.60 mmol) and triethylamine (0.044 g, 0.300 mmol) in acetonitrile (3 mL), being maintained under an atmosphere of nitrogen, was treated with piperidine (0.023 g, 0.200 mmol). The resulting mixture was allowed to stir for 2 h at room temperature before being diluted with cold water (10 mL). The precipitate that formed was collected by filtration and then washed with both water and hexanes. Drying the material in air afforded 181 (0.030 g, 53%) as an off-white solid; $^1$H NMR (400 MHz, CDCl$_3$) δ 8.76 (d, J=2.2 Hz, 1H), 8.62 (d, J=4.7 Hz, 1H), 7.97 (d, J=8.2 Hz, 1H), 7.86 (d, J=8.2 Hz, 1H), 7.32 (d, J=8.3 Hz, 1H), 7.17-7.13 (m, 1H), 2.68-2.68 (s, 3H), 2.66 (brs, 4H), 1.71-1.66 (m, 4H), 1.49 (brs, 2H); MS (ESI, positive mode) m/z 360 (MH$^+$).

Example 8

4-(2,6-Dimethyl-3-(2-(piperidin-1-yl)acetyl)-1H-pyrrolo[3,2-b]pyridin-1-yl)benzonitrile (Compound 184)

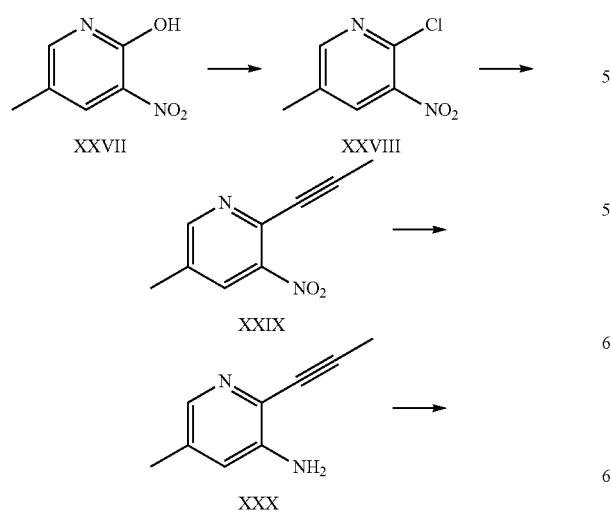

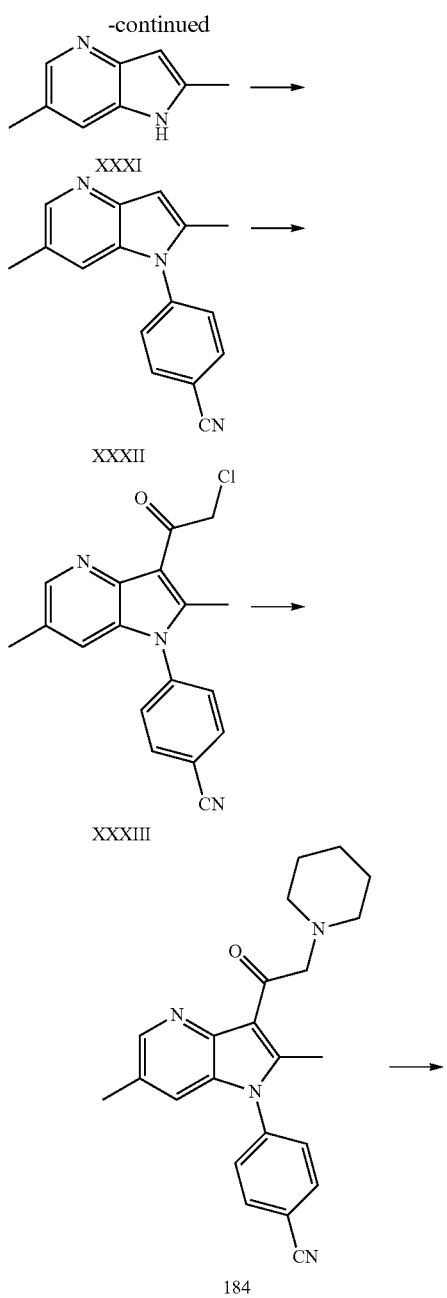

Synthesis of 2-Chloro-5-methyl-3-nitro-pyridine (XXVIII): To a cold (0° C.) solution of commercially available 2-hydroxy-5-methyl-3-nitro pyridine (5.00 g, 0.032 mol) in N,N-dimethylformamide (30 mL) was added phosphoryl chloride (7.4 g, 0.049 mol). The reaction mixture was allowed to slowly warm to room temperature and was then heated at 80° C. for 4 h. After cooling to room temperature, the reaction was quenched with ice water and then extracted with ethyl acetate (3×50 mL). The combined organic extracts were washed with water and brine solution. The organic layer was then dried over anhydrous sodium sulfate and concentrated under reduced pressure to obtain the crude product mixture. The crude product was purified by column chromatography on silica to afford compound XXVIII (3.30 g, 59%) as a pale yellow solid. $^1$H NMR (400 MHz, CDCl$_3$): δ 8.43 (d, J=1.5 Hz, 1H), 8.03 (d, J=1.5 Hz, 1H), 2.45 (s, 3H); MS (ESI, positive mode) m/z 173 (MH$^+$).

Synthesis of 5-Methyl-3-nitro-2-prop-1-ynyl-pyridine (XXIX): In a sealed tube, a suspension of compound XXVIII (3.30 g, 0.019 mol), triethylamine (15 mL), and copper (I) iodide (0.720 g, 3.80 mmol) in acetonitrile (30 mL) was sparged with nitrogen gas for 20 min. Then tetrakis(triphenylphosphine)palladium (0) (2.21 g, 1.90 mmol) was added to the reaction mixture, which was again sparged with nitrogen gas for 10 min. The reaction mixture was cooled to −20° C. and then sparged with propyne gas (6.12 g, 0.152 mol). The reaction mixture was allowed to slowly warm to room temperature and stir for 16 h. The volatiles were removed under vacuum and the remaining material was poured into cold water (80 mL) before extracting with ethyl acetate (3×50 mL). The combined organic extracts were dried over anhydrous sodium sulfate and then concentrated under reduced pressure to obtain the crude product mixture. The crude product was purified by column chromatography on silica to afford compound XXIX (1.20 g, 36%) as a pale-brown solid. $^1$H NMR (400 MHz, CDCl$_3$): δ 8.57 (d, J=1.3 Hz, 1H), 8.07 (d, J=0.8 Hz, 1H), 2.44 (s, 3H), 2.15 (s, 3H); MS (ESI, positive mode) m/z 177 (MH$^+$).

Synthesis of 5-Methyl-2-(prop-1-yn-1-yl)pyridin-3-amine (XXX): To a stirred solution of compound XXIX (1.20 g, 0.008 mol) in ethyl acetate (30 mL) was added stannous chloride dihydrate (3.70 g, 0.016 mol). The reaction mixture was heated at reflux for 2 h and then allowed to cool to room temperature. The reaction mixture was basified with an aqueous sodium carbonate solution and then extracted with ethyl acetate (3×30 mL). The combined organic layers were washed with water and brine solution, before being dried over anhydrous sodium sulfate. The organic layer was concentrated under reduced pressure to obtain the crude product mixture, which was then washed with n-pentane and dried to afford semi-crude XXX (0.9 g, 90%) as a brown solid. Compound XXX was used directly in the next step. $^1$H NMR (400 MHz, CDCl$_3$): δ 7.78 (s, 1H), 6.78 (s, H), 4.07 (bs, 2H), 2.22 (s, 3H), 2.11 (s, 3H); (ESI, positive mode) m/z 146 (MH$^+$).

Synthesis of 2,6-Dimethyl-1H-pyrrolo[3,2-b]pyridine (XXXI): A cold (0° C.) stirred solution of compound XXX (1.20 g, 0.008 mol) in N,N-dimethylformamide (15 mL) was treated with solid potassium tert-butoxide (1.84 g, 0.016 mol) in a portion-wise manner. The reaction mixture was allowed to warm to room temperature and stir for 5 h. The reaction mixture was diluted with water and then extracted with ethyl acetate (3×30 mL). The combined organic extracts were washed with water and brine solution, before being dried over anhydrous sodium sulfate. The organic layer was concentrated under reduced pressure to obtain crude product, which was then washed with n-pentane and dried well to afford compound XXXI (0.700 g, 78%) as a brown solid. $^1$H NMR (400 MHz, DMSO-d$_6$): δ 10.96 (bs, 1H), 8.05 (s, 1H), 7.39 (s, 1H), 6.16 (s, 1H), 2.39 (s, 3H), 2.35 (s, 3H); MS (ESI, positive mode) m/z 147 (MH$^−$).

Synthesis of 4-(2,6-Dimethyl-pyrrolo [3,2-b] pyridin-1-yl)-benzonitrile (XXXII): In a sealed tube, a mixture of compound XXXI (0.600 g, 4.10 mmol), 4-iodo-benzonitrile (1.41 g, 6.10 mmol) and potassium phosphate (1.48 g, 6.90 mmol) in 1,4-dioxane (20 mL) was sparged with nitrogen gas for 0.5 h. Then copper (I) iodide (0.04 g, 0.200 mmol) and trans-(+/−)-1,2-diaminocyclohexane (0.023 g, 0.200 mmol) were added to the reaction mixture. The system was sealed and then heated at 110° C. for 24 h. After cooling to room temperature, the reaction mixture was filtered through a pad of celite and the filter pad was washed with ethyl acetate. The filtrate was concentrated under reduced pressure to obtain crude product mixture, which was then purified by column chromatography on silica and eluted with 50% ethyl acetate in hexanes to afford compound XXXII (0.6 g, 60%) as an off-white solid. $^1$H NMR (400 MHz, CDCl$_3$): δ 8.29 (s, 1H), 7.85 (d, J=8.3 Hz, 2H), 7.46 (d, J=8.3 Hz, 2H), 7.17 (s, 1H), 6.59 (s, 1H), 2.37 (s, 3H), 2.36 (s, 3H); MS (ESI, positive mode) m/z 248 (MH$^+$).

Synthesis of N-[3-(2-Chloro-acetyl)-1-(4-cyano-phenyl)-2-methyl-1H-indol-5-ylmethyl]-acetamide (XXXIII): To a cold (0° C.) suspension of aluminum trichloride (1.61 g, 12.1 mmol) in 1,2-dichloro-ethane (20 mL) was added chloro-acetyl chloride (1.37 g, 12.1 mmol). The resulting mixture was allowed to stir at the reduced temperature for 0.5 h and then a solution of compound XXXII (0.6 g, 0.0024 mol) in 1,2-dichloro-ethane (5 mL) was added to the reaction mixture. The reaction mixture was allowed to warm to room temperature and was further warmed at 80° C. for 18 h. After cooling again to room temperature, the reaction mixture was poured into ice cold water and then extracted with dichloromethane (3×30 mL). The combined organic extracts were washed with water and brine solution, before being dried over anhydrous sodium sulfate. The organic layer was then concentrated under vacuum to obtain the crude product mixture, which was then purified by column chromatography on (100-200 mesh) silica gel using 50% ethyl acetate in hexanes as the eluant to afford compound XXXIII (0.35 g, 45%) as a pale-brown solid. $^1$H NMR (400 MHz, CDCl$_3$): δ 8.42 (s, 1H), 7.93 (d, J=8.3 Hz, 2H), 7.48 (d, J=8.3 Hz, 2H), 7.12 (s, 1H), 5.30 (s, 2H), 2.67 (s, 3H), 2.40 (s, 3H); MS (ESI, positive mode) m/z 324 (MH$^+$).

Synthesis of 4-[2,6-Dimethyl-3-(2-piperidin-1-yl-acetyl)-pyrrolo[3,2-b]pyridin-1-yl]-benzonitrile (184): To a solution of compound XXXIII (0.125 g, 0.380 mmol) in acetonitrile (2 mL) was added piperidine (0.065 g, 0.770 mmol) and triethylamine (0.077 g, 0.770 mmol). The resulting mixture was then allowed to stir at room temperature for 2 h. The reaction mixture was then poured into ice cold water and the resulting precipitate was collected by filtration. The solids were washed with water and then dried to afford product 184 (0.040 g, 28%) as a pale-brown solid. $^1$H NMR (400 MHz, CDCl$_3$): δ 8.42 (s, 1H), 7.90 (d, J=8.3 Hz, 2H), 7.46 (d, J=8.3 Hz, 2H), 7.09 (s, 1H), 4.35 (s, 2H), 2.69 (bs, 2H), 2.64 (s, 3H), 2.39 (s, 3H), 1.70 (bs, 4H), 1.61 (brs, 4H); MS (ESI, positive mode) m/z 374 (MH$^+$).

Examples 9-10

4-(5-Methoxy-2-methyl-3-(2-(piperidin-1-yl)acetyl)-1H-pyrrolo[3,2-b]pyridin-1-yl)benzonitrile (Compound 177), 4-(5-Hydroxy-2-methyl-3-(2-(piperidin-1-yl)acetyl)-1H-pyrrolo[3,2-b]pyridin-1-yl)benzonitrile (Compound 127)

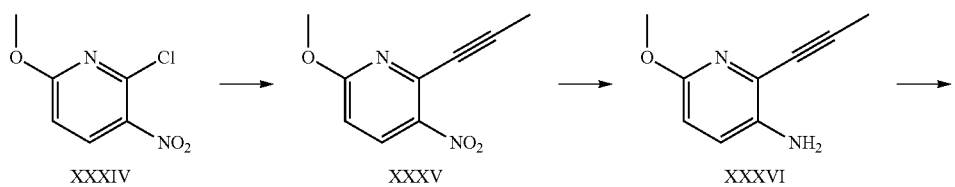

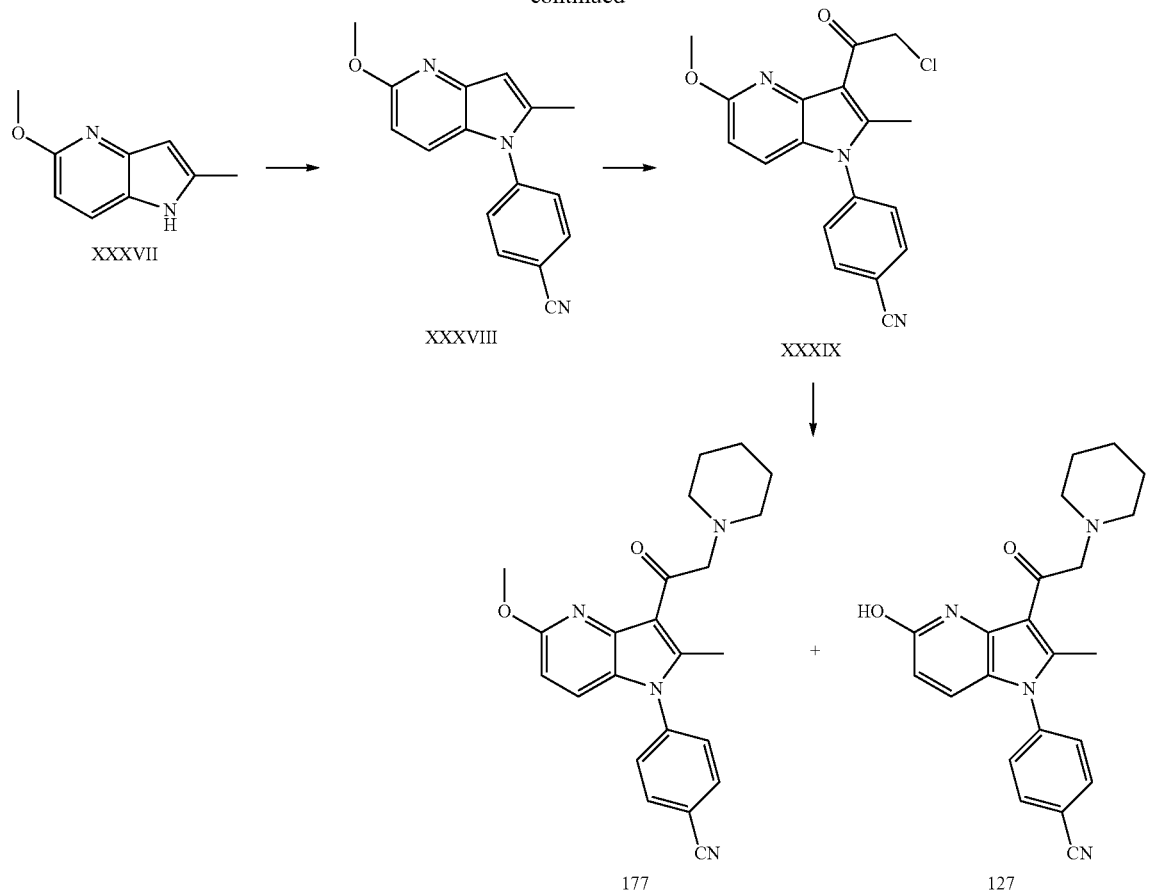

Synthesis of 6-Methoxy-3-nitro-2-prop-1-ynyl-pyridine (XXXV): In a 250 mL sealed tube, a mixture of 2-chloro-6-methoxy-3-nitro-pyridine (2.0 g, 10.4 mmol), triethylamine (10 mL), copper(I) iodide (0.4 g, 2.00 mmol) and acetonitrile (30 mL) was sparged with nitrogen for 15 min. Then tetrakis(triphenylphospine)palladium(0) (1.21 g, 1.00 mmol) was added to the flask. The mixture was, again, sparged with nitrogen for 10 min and then cooled to −20° C. Propyne gas (5.03 g, 0.125 mol) was bubbled into the reaction mixture and then the tube was sealed. The reaction mixture was allowed to slowly warm to room temperature and then stir for 12 h. The progress of the reaction was monitored by TLC. Upon completion the reaction mixture was diluted with water and extracted with ethyl acetate (3×50 mL). The combined organic layers were washed with water, brine, and then dried over sodium sulfate. After filtration the organic layer was concentrated in vacuo. The remaining crude product mixture was purified by the column chromatography using 100-200 mesh silica gel and eluted with 30% ethyl acetate in hexanes to afford compound XXXV (1.0 g, 50%) as an off-white solid. $^1$H NMR (400 MHz, CDCl$_3$) δ 8.23 (d, J=9.1 Hz, 1H), 6.72 (d, J=9.1 Hz, 1H), 4.02 (s, 1H), 2.19 (s, 1H); MS (ESI, positive mode) m/z 193 (MH$^+$).

Synthesis of 6-Methoxy-2-prop-1-ynyl-pyridin-3-ylamine (XXXVI): To a stirred solution of compound XXXV (1.0 g, 5.20 mmol) in ethyl acetate (30 mL) was added stannous chloride (5.87 g, 0.026 mol). The reaction mixture was heated at reflux for 2 h and then allowed to cool to room temperature. The reaction mixture was basified with a saturated aqueous solution of sodium bicarbonate and the resulting mixture was extracted with ethyl acetate (3×30 mL). The combined organic extracts were washed with water, brine, and then dried over sodium sulfate. Concentrating the mixture afforded a brown sticky mass (0.80 g crude, 80%), which was used crude directly in the next step.

Synthesis of 5-Methoxy-2-methyl-1H-pyrrolo[3,2-b]pyridine (XXXVII): To a stirred solution of compound XXXVI (0.8 g, 0.005 mol) in N,N-dimethylformamide (10 mL), which was kept at 0° C., was added solid potassium tert-butoxide (1.1 g, 9.8 mmol) in a portion-wise matter. The reaction mixture was allowed to warm to room temperature and then stir for 5 h. The progress of the reaction was monitored by TLC. Upon completion the reaction mixture was diluted with water (30 mL) and then extracted with ethyl acetate (3×30 mL). The combined organic layers were washed with water, brine, and then dried over sodium sulfate. The organic layer was then concentrated in vacuo and the crude product mixture was purified by column chromatography using 100-200 mesh silica gel and 20% ethyl acetate in hexanes as the eluant. The yellow material obtained after purification was a mixture of compounds XXXVI and XXXVII (0.45 g, 56%). The mixture was used without any further purification.

Synthesis of 4-(5-Methoxy-2-methyl-pyrrolo[3,2-b]pyridin-1-yl)-benzonitrile (XXXVIII): To a stirred solution of compound XXXVII (0.35 g, 2.10 mmol) in 1,4-dioxane (10 mL) were added 4-iodobenzonitrile (0.495 g, 2.10 mmol), copper(I) iodide (0.20 g, 0.001 mol), and then potassium triphosphate (0.77 g, 0.0036 mol). The mixture was sparged with nitrogen for 10 min and then racemic trans-1,2-diamino cyclohexane (0.012 g, 0.10 mmol) was added to the reaction mixture. The mixture was, again, sparged with nitrogen for 5 min and then heated at reflux for 18 h. After cooling to room temperature the reaction mixture was concentrated under the vacuum and the crude product mixture was diluted with water. The aqueous mixture was extracted with ethyl acetate (3×30 mL) and the combined organic extracts were washed with water and brine. The organic layer was then dried over sodium sulfate and concentrated under vacuum. The crude product mixture was purified by column chromatography on 100-200 mesh silica gel using 20% ethyl acetate in hexanes as the eluant to afford compound XXXVIII (0.40 g, 70%) as a yellow solid. $^1$H NMR (400 MHz, CDCl$_3$) δ 7.83 (d, J=8.6 Hz, 2H), 7.45 (d, J=8.4 Hz, 2H), 7.30 (d, J=8.8 Hz, 1H), 6.51 (d, J=8.8 Hz, 1H), 6.50 (s, 1H), 3.99 (s, 1H), 2.36 (s, 3H); MS (ESI, positive mode) m/z 264 (MH$^+$).

Synthesis of 4-[3-(2-Chloro-acetyl)-5-methoxy-2-methyl-pyrrolo[3,2-b]pyridin-1-yl]-benzonitrile (XXXIX): To a stirred suspension of aluminum trichloride (0.81 g, 0.006 mol) in 1,2-dichloroethane (10 mL), which was kept at 0° C., was added chloro acetyl chloride (0.68 g, 6.00 mmol) in a drop-wise manner. The reaction mixture was allowed to stir at 0° C. for 30 min and then a solution of compound XXXVIII (0.40 g, 1.50 mmol) in 1,2-dichloroethane (5 mL) was added. The reaction mixture was allowed to slowly warm to room temperature and was then heated at reflux for 18 h. After cooling to room temperature the reaction mixture was quenched by pouring into ice water and the resulting mixture was extracted with dichloromethane (2×20 mL). The combined organic layers were washed with water, brine, and then concentrated under vacuum. The crude, brown solid XXXIX (0.130 g, 25%) was was used directly in the next step.

Synthesis of 4-(5-Methoxy-2-methyl-3-(2-(piperidin-1-yl)acetyl)-1H-pyrrolo[3,2-b]pyridin-1-yl)benzonitrile (177) and 4-(5-Hydroxy-2-methyl-3-(2-(piperidin-1-yl)acetyl)-1H-pyrrolo[3,2-b]pyridin-1-yl)benzonitrile (127): To a stirred solution of compound XXXIX (0.130 g, 0.380 mmol) in acetonitrile (5 mL) was added triethylamine (0.11 g, 0.0011 mol), followed by piperdine (0.065 g, 0.760 mmol). The reaction mixture was allowed to stir at room temperature for 3 h before it was concentrated under vacuum. The remaining brown, sticky mass was diluted with water and then extracted with dichloromethane (2×20 mL). The combined organic layers were washed with water, brine solution and then concentrated under the vacuum. Crude product was purified by the column chromatography on 100-200 mesh silica gel using 5% methanol in dichloromethane as the eluant. During column chromatography, demethylation of methyl ether was observed, which afforded a mixture of compounds 177 and 127. The product mixture was further purified by prep-HPLC to afford compound 177 (12 mg, 8%) and compound 127 (10 mg, 7%). Analytical data for 177—$^1$H NMR (400 MHz, CDCl$_3$) δ 7.89 (d, J=8.0 Hz, 2H), 7.46 (d, J=8.1 Hz, 2H), 7.23 (d, occluded by solvent, 1H), 6.59 (d, J=8.9 Hz, 1H), 4.45 (brs, 2H), 4.06 (s, 3H), 2.79 (brs, 2H), 2.64 (s, 3H), 1.77 (brs, 4H), 1.61 (brs, 4H); MS (ESI, positive mode) m/z 389 (MH$^+$).

Analytical data for 127—$^1$H NMR (400 MHz, CDCl$_3$) δ: 7.89 (d, J=8.0 Hz, 2H), 7.44 (d, J=8.0 Hz, 2H), 7.10 (d, J=9.5 Hz, 1H), 6.30 (d, J=9.4 Hz, 1H), 3.49 (brs, 2H), 2.64 (brs, 2H), 2.51 (s, 3H), 1.81 (brs, 4H), 1.62-1.54 (m, 4H); MS (ESI, positive mode) m/z 375 (MH$^+$).

General Synthetic Route 3

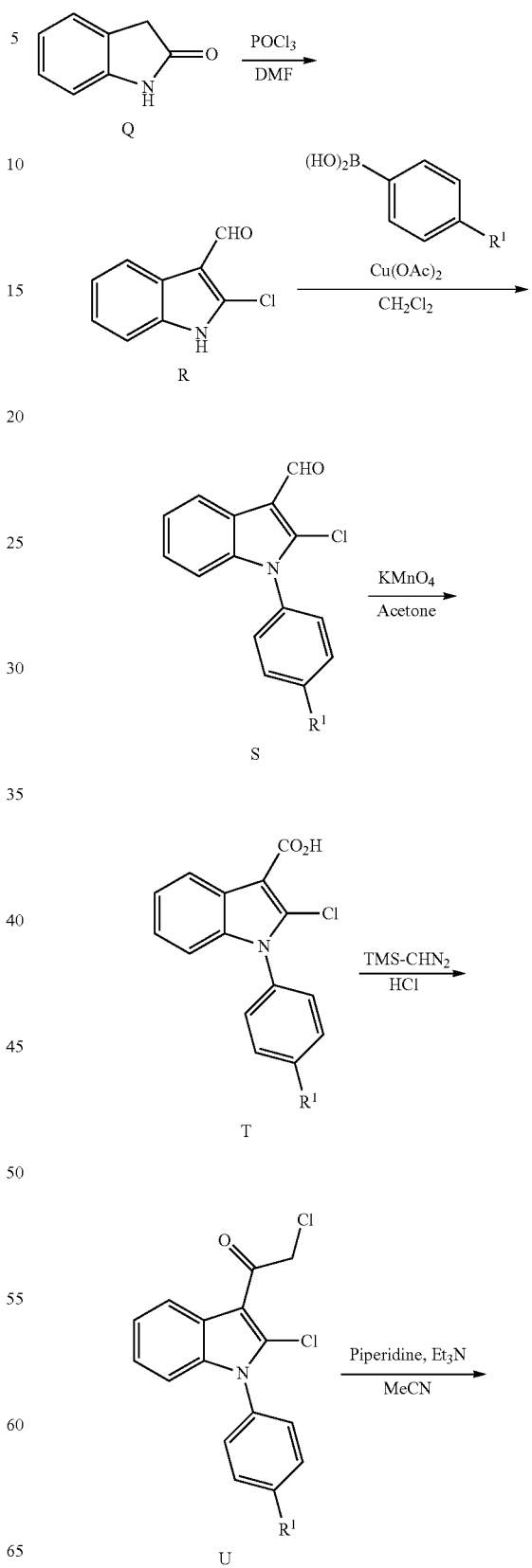

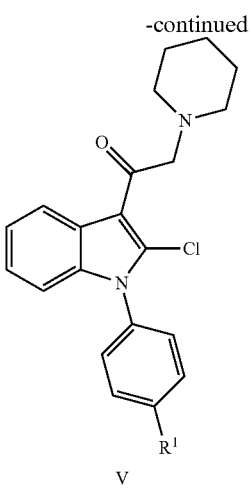

V

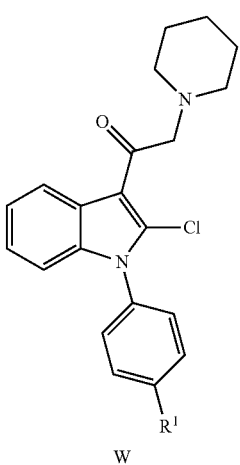

W

Method of Preparing General Intermediate R: A flask of N,N-dimethylformamide (0.125 M relative to Q) is maintained under a nitrogen atmosphere at 0° C. and is then treated with phosphorus oxychloride (2.5 equiv.). The reaction mixture is allowed to stir at the reduced temperature for 30 min and then warmed to room temperature over 1 h. The mixture is cooled back down to 0° C. and solid 2-oxyindole (Q, 1 equiv.) is added. The reaction mixture is allowed to warm to room temperature and stir. The progress of the reaction is monitored by TLC and HPLC. The reaction is quenched through the addition of a saturated aqueous solution of sodium acetate and the resulting mixture is allowed to stir for an additional 2 h. The precipitate that is formed is collected by filtration and washed with water (100 mL). The solid is allowed to dry in a stream of air to afford intermediate R.

Method of Preparing General Intermediate S: To a stirred solution of intermediate R (1 equiv.) in dichloromethane (0.05 M relative to R) is added a substituted boronic acid (2 equiv.), 3 Å molecular sieves (5.5 g), pyridine (0.6 M relative to R), and copper(II) acetate (2 equiv.). The resulting mixture is allowed to stir open to air for 24 h at room temperature. The reaction mixture is then filtered through a pad of celite and the filtrate is evaporated. The remaining crude product mixture is purified by column chromatography on 100-200 mesh silica gel to afford intermediate S.

Method of Preparing General Intermediate T: To a stirred solution of intermediate S (1 equiv.) in acetone (0.01 M relative to S), being maintained at 0° C., is added potassium permanganate (24 equiv.). The reaction mixture is allowed to warm to room temperature and the progress of the reaction is monitored by TLC and HPLC. The reaction mixture is then cooled in an ice water bath and slowly quenched through the addition of aqueous 10% hydrogen peroxide solution. After complete disappearance of color, the mixture is further diluted with 10% hydrochloric acid. The precipitate that is formed is collected by filtration and washed with water. The solid is allowed to dry in a stream of air before purification by column chromatography on 100-200 mesh silica gel to afford intermediate T.

Method of Preparing General Intermediate U: To a stirred solution of intermediate T (1 equiv.) in dichloromethane (0.06 M relative to T), kept at 0° C., is added oxalyl chloride (1.5 equiv.) and N,N-dimethyl formamide (2 drops). The reaction mixture is allowed to warm to room temperature and stir for 1 h before it is condensed in vacuo. The crude mixture is diluted with acetonitrile (0.06 M relative to T) and then treated with a solution of trimethylsilyl diazomethane (2 equiv.). The reaction mixture is allowed to stir at room temperature for 3 h and is then treated with 6N hydrochloric acid (10 mL; effervescence was seen during addition of acid). The reaction mixture is diluted with water and extracted with ethyl acetate. The combined organic extracts are dried over sodium sulfate and condensed in vacuo. The crude product mixture is purified by column chromatography on 100-200 mesh silica gel to afford intermediate U.

Method of Preparing General Intermediate V: To a stirred solution of intermediate U (1 equiv.) in acetonitrile (0.05 M relative to U) is added piperidine (1.5 equiv.) and triethylamine (2 equiv.). The reaction mixture is allowed to stir at room temperature and the progress of the reaction is monitored by HPLC and TLC. Upon completion, the reaction mixture is diluted with water and the precipitate that forms is collected via filtration. Drying the material in air affords intermediate V.

Method of Preparing Target Compound W: To a stirred solution of intermediate V (0.250 mmol, 1 equiv.) in either methanol:water (1:1; 0.01 M relative to V) or acetonitrile (0.01 M relative to V) is added the desired nucleophile or nucleophilic precursor (3 equiv.) and any additional reagents required to generate a competent nucleophile. The progress of the reaction is monitored by TLC and HPLC. Upon completion the reaction mixture is condensed in vacuo and the the remaining mixture is acidified with dilute hydrochloric acid. The mixture is extracted with ethyl acetate and the combined organic extracts are dried over sodium sulfate. After condensing, the crude product is purified by preparative HPLC to afford target compound W.

Examples 11-12

1-(1-(4-Chlorophenyl)-2-hydroxy-1H-indol-3-yl)-2-(piperidin-1-yl)ethan-1-one (Compound 131), 1-(1-(4-Chlorophenyl)-2-methoxy-1H-indol-3-yl)-2-(piperidin-1-yl)ethan-1-one (Compound 132)

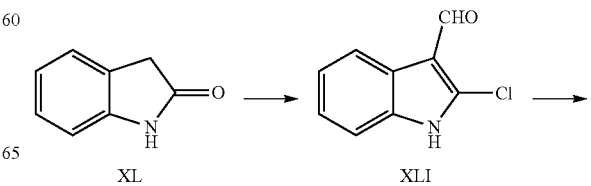

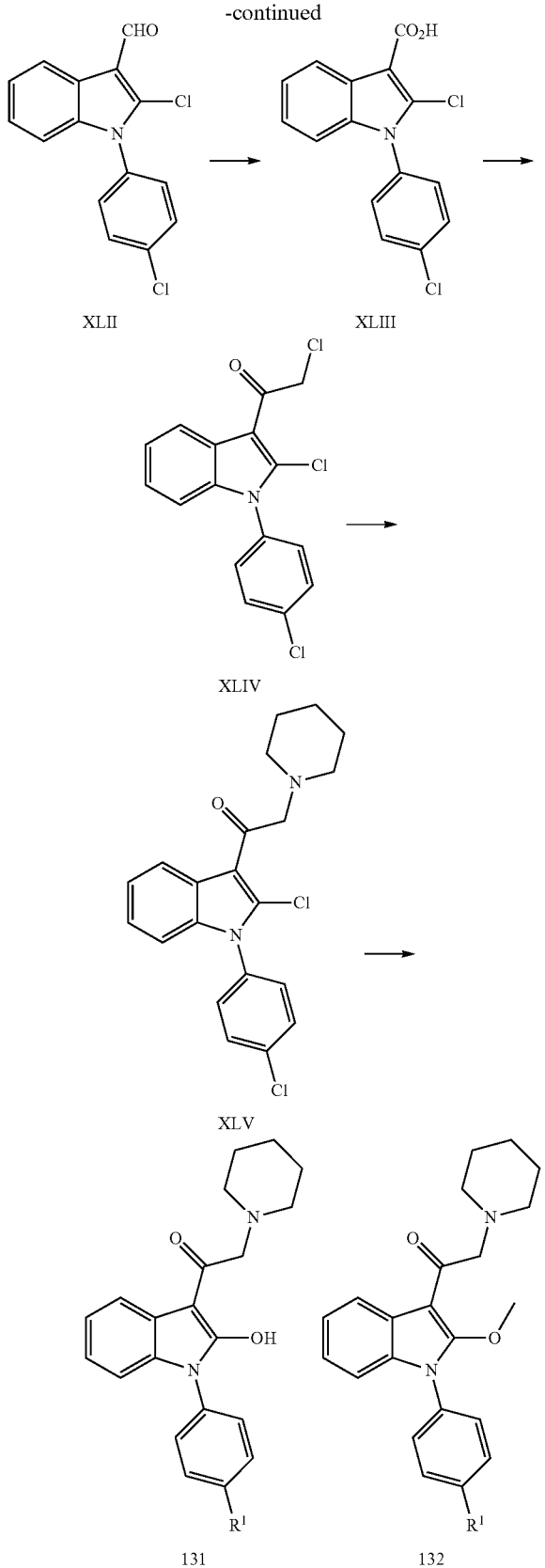

Synthesis of 2-Chloro-1H-indole-3-carbaldehyde (XLI): A flask of N,N-dimethylformamide (30 mL) being maintained under a nitrogen atmosphere at 0° C. was treated with phosphorus oxychloride (9.0 mL, 9.40 mmol). The reaction mixture was allowed to stir at the reduced temperature for 30 min and then warm to room temperature over 1 h. The mixture was cooled back down to 0° C. and solid 2-oxyindole (XL, 5.0 g, 3.76 mmol) was added. The reaction mixture was allowed to warm to room temperature and stir for 4 h. The reaction was quenched through the addition of a saturated aqueous solution of sodium acetate (200 mL) and the resulting mixture was allowed to stir for 2 h. The precipitate that formed was collected by filtration and washed with water (100 mL). Solid was allowed to dry in a stream of air to afford compound XLI (4.5 g, 67%) as an orange colored solid. Compound was used without further purification. $^1$H NMR (400 MHz, DMSO-$d_6$) δ 9.99 (s, 1H), 8.05 (dt, J=8.3, 1.4 Hz, 1H), 7.42 (dt, J=7.2, 1.4 Hz, 1H), 7.21-7.30 (m, 2H); MS (ESI, positive mode) m/z 180/182 (MH$^+$, $^{35/37}$Cl).

Synthesis of 2-Chloro-1-(4-chloro-phenyl)-1H-indole-3-carbaldehyde (XLII): To a stirred solution of compound XLI (5.5 g, 3.07 mmol) in dichloromethane (60 mL) were added 4-chlorophenyl boronic acid (9.6 g, 0.0615 mol), 3 Å molecular sieves (5.5 g), pyridine (5.5 mL), and copper(II) acetate (12 g, 0.0615 mol). The resulting mixture was allowed to stir open to air for 24 h at room temperature. The reaction mixture was then filtered through a pad of celite and the filtrate was evaporated. The remaining crude product mixture was purified by column chromatography on 100-200 mesh silica gel using 10% ethyl acetate in hexanes as the eluant to afford compound XLII (1.8 g, 20%) as a pale yellow solid. $^1$H NMR (400 MHz, DMSO-$d_6$) δ 10.20 (s, 1H), 8.34 (d, J=7.8 Hz, 1H), 7.58 (dt, J=8.7, 2 Hz, 2H), 7.32-7.39 (m, 3H), 7.27-7.29 (m, 1H), 7.07 (d, J=8.3 Hz, 1H); MS (ESI, positive mode) m/z 290/292 (MH$^+$, $^{35/37}$Cl).

Synthesis of 2-Chloro-1-(4-chloro-phenyl)-1H-indole-3-carboxylic acid (XLIII): To a stirred solution of compound XLII (1.8 g, 0.620 mmol) in acetone (50 mL), being maintained at 0° C., was added potassium permanganate (2.3 g, 0.015 mol). The reaction mixture was allowed to warm to room temperature and stir for 4 h. The reaction mixture was then cooled in an ice water bath and slowly quenched through the addition of an aqueous 10% hydrogen peroxide solution. After complete disappearance of color, the mixture was further diluted with 10% hydrochloric acid. The precipitate that formed was collected by filtration and washed with water. The solid was allowed to dry in a stream of air before it was purified by column chromatography on 100-200 mesh silica gel, using 30% ethyl acetate in hexanes as the eluant. Compound XLIII (1.0 g, 53%) was obtained as a pale yellow solid. $^1$H NMR (400 MHz, DMSO-$d_6$) δ 12.75 (s, 1H), 8.10 (dd, J=7.0, 1.1 Hz, 1H), 7.71-7.76 (m, 2H), 7.59-7.63 (m, 2H), 7.23-7.32 (m, 2H), 7.06 (d, J=9.7 Hz, 1H); MS (ESI, positive mode) m/z 306/308 (MH$^+$, $^{35/37}$Cl).

Synthesis of 2-Chloro-1-[2-chloro-1-(4-chloro-phenyl)-1H-indol-3-yl]-ethanone (XLIV): To a stirred solution of compound XLIII (1.0 g, 3.27 mmol) in dichloromethane (50 mL) kept at 0° C. was added oxalyl chloride (0.4 mL, 4.86 mmol) and N,N-dimethyl formamide (2 drops). The reaction mixture was allowed to warm to room temperature and stir for 1 h. The reaction mixture was condensed in vacuo and then maintained under an atmosphere of nitrogen. The crude mixture was diluted with acetonitrile (50 mL) and then treated with a solution of trimethylsilyl diazomethane (0.84 g, 3.3 mL, 6.52 mmol). The reaction mixture was allowed to stir at room temperature for 3 h and was then treated with 6N hydrochloric acid (10 mL; effervescence was seen during addition of acid). The reaction mixture was diluted with water (10 mL) and then extracted with ethyl acetate (25 mL×3). The combined organic extracts were dried over sodium sulfate and condensed in vacuo. The crude product mixture was purified by column chromatography on 100-200 mesh silica gel using 10% ethyl acetate in hexanes as the eluant to afford compound XLV (0.15 g, 7%) as a pale yellow solid. $^1$H NMR (400 MHz, DMSO-d$_6$) δ 8.27 (d, J=7.9 Hz, 1H), 7.76 (d, J=8.6 Hz, 2H), 7.62 (d, J=8.6 Hz, 2H), 7.37 (t, J=7.4, 1H), 7.31 (t, J=7.4 Hz, 1H), 7.07 (d, J=8.0 Hz, 1H), 5.07 (s, 2H); MS (ESI, positive mode) m/z 338/340/342/344 (MH$^+$, $^{35/37}$Cl).

Synthesis of 1-[2-Chloro-1-(4-chloro-phenyl)-1H-indol-3-yl]-2-piperidin-1-yl-ethanone (XLV): To a stirred solution of compound XLIV (0.50 g, 1.40 mmol) in acetonitrile (30 mL) was added piperidine (0.22 mL, 2.20 mmol) and triethylamine (0.38 mL, 2.80 mmol). The reaction mixture was allowed to stir at room temperature for 4 h, after which the reaction mixture was diluted with water. The precipitate that formed was collected via filtration and allowed to dry in air to afford compound XLV (0.50 g, 93%) as a pale yellow solid. $^1$H NMR (400 MHz, DMSO-d$_6$): δ 8.25 (d, J=7.5 Hz, 1H), 7.74 (d, J=8.6 Hz, 2H), 7.61 (d, J=8.6 Hz, 2H), 7.32 (t, J=7.2 Hz, 1H), 7.25 (t, J=7.2 Hz, 1H), 7.04 (d, J=8.3 Hz, 1H), 3.74 (s, 2H), 3.32 (m, occluded by solvent, 4H), 1.49 (brs, 4H), 1.39 (brs, 2H); MS (ESI, positive mode) m/z 387/389/392 (MH$^+$, $^{35/37}$Cl).

Synthesis of 1-[1-(4-Chloro-phenyl)-2-hydroxy-1H-indol-3-yl]-2-piperidin-1-yl-ethanone (131): To a stirred solution of compound XLV (0.1 g, 0.250 mmol) in methanol:water (20 mL; 1:1) was added solid sodium hydroxide (0.051 g, 1.20 mmol). The system was heated at reflux for 2 h and then allowed to cool to room temperature. Excess methanol was removed under reduced pressure and the remaining mixture was acidified with dilute hydrochloric acid. The mixture was extracted with ethyl acetate (3×20 mL) and the combined organic extracts were dried over sodium sulfate. After condensing the ethyl acetate the crude product was purified by preparative HPLC to afford 131 (12 mg, 13%) as a pale yellow solid; $^1$H NMR (400 MHz, DMSO-d$_6$) δ 9.89 (brs, 1H), 7.95 (d, J=7.4 Hz, 1H), 7.54 (d, J=8.6 Hz, 2H), 7.45 (d, J=8.6 Hz, 2H), 6.90-6.85 (m, 1H), 6.81-6.75 (m, 2H), 4.29 (s, 2H), 3.04 (brs, 4H), 1.76 (brs, 4H), 1.54 (brs, 2H); MS (ESI, positive mode) m/z 369/371 (MH$^+$, $^{35/37}$Cl).

Synthesis of 1-[1-(4-Chloro-phenyl)-2-methoxy-1H-indol-3-yl]-2-piperidin-1-yl-ethanone (132): To a stirred solution of sodium methoxide (anhydrous methanol, 5 mL; sodium, 0.011 g) was added a solution of compound XLV (0.100 g, 2.50 mmol) in anhydrous methanol (2 mL). The resulting mixture was heated at reflux for 6 h and then allowed to cool to room temperature. The reaction mixture was condensed in vacuo and the remaining material was diluted with water. The aqueous mixture was extracted with dichloromethane (3×20 mL) and the combined organic extracts were dried over sodium sulfate before being condensed in vacuo. Analyses of the crude product mixture revealed that some of 131 was present so the crude mixture was redissolved in anhydrous N,N-dimethyl formamide (5 mL). Solid potassium carbonate (0.108 g, 0.770 mmol) and methyl iodide (0.03 mL, 0.510 mmol) were added to the flask and the resulting mixture was allowed to stir for 2 h.

The reaction mixture was diluted with water and then extracted with ethyl acetate (3×10 mL). The combined organic extracts were dried over sodium sulfate and then condensed under reduced pressure. The crude product was purified by preparative HPLC to afford 132 (9 mg, 10%) as a pale brown solid. $^1$H NMR (400 MHz, DMSO-d$_6$) 8.15 (d, J=6.7 Hz, 1H), 7.51-7.40 (m, 4H), 7.05 (t, J=7.4 Hz, 1H), 6.98 (t, J=7.4 Hz, 1H), 6.84 (d, J=7.8 Hz, 1H), 4.90 (s, 2H), 3.92-3.83 (m, 2H), 3.37-3.31 (m, 5H), 2.05 (brs, 2H), 1.89 (brs, 2H), 1.74-1.64 (brm, 2H); MS (ESI, positive mode) m/z 383/385 (MH, $^{35/37}$Cl).

General Synthetic Route 4

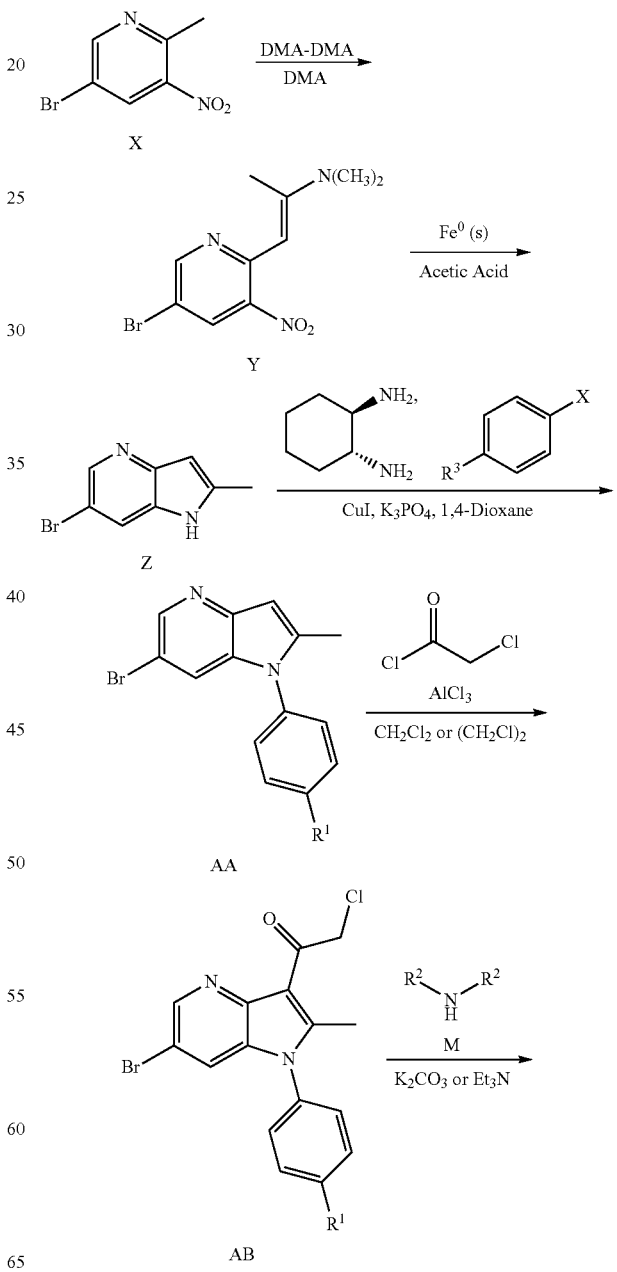

-continued

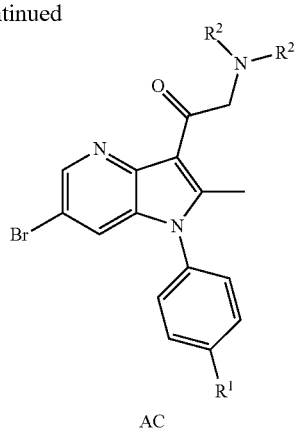

AC

Method of Preparing General Intermediate Y from 5-Bromo-2-methyl-3-nitropyridine (X): 5-Bromo-2-methyl-3-nitro pyridine (1 equiv.) is dissolved in dimethyl acetamide (9 M relative to X) and then dimethylacetamide dimethyl acetal (2 equiv.) is added. The resulting mixture is then heated at 80° C. before cooling to room temperature. The progress of the reaction is monitored by TLC and HPLC. The reaction mixture is concentrated under reduced pressure and the remaining mixture is diluted with water. The mixture is extracted with ethyl acetate and the combined organic extracts are washed with water and brine. The organic phase is dried over sodium sulfate and concentrated under reduced pressure to obtain the crude product as a brown solid, which is used without any further purification.

Method of Preparing General Intermediate Z: Crude intermediate Y (1 equiv.) is dissolved in acetic acid (0.5 M relative to Y) and the resulting solution is treated with iron powder (300 mesh, 8 equiv.). The mixture is heated at 80° C. and then allowed to cool to room temperature. The progress of the reaction is monitored by TLC and HPLC. The reaction is quenched through the addition of aqueous sodium bicarbonate solution and the resulting mixture is filtered through a celite bed. The filtrate is extracted with ethyl acetate and the combined organic extracts are washed with water and brine. The organic layer is dried over sodium sulfate, filtered, and then concentrated under reduced pressure. The crude product is purified by column chromatography on neutral alumina to afford intermediate Z.

Method of Preparing General Intermediate AA: In a sealed tube, a mixture of a substituted 2-methylindole (1 equiv.) or substituted indole Z (1 equiv.), copper(I) iodide (0.05 equiv.), and potassium phosphate (1.70 equiv.) in 1,4-dioxane (0.2 M) is sparged with nitrogen gas for 0.5 h. Then trans-(+/−)-1,2-cyclohexanediamine (0.05 equiv.) and aryl halide (1 equiv.) are then added to the flask at room temperature and the resulting reaction mixture is heated at 110° C. for one to two days. After cooling to room temperature, the reaction mixture is filtered through celite and the filter pad is washed with ethyl acetate. The filtrate is concentrated to afford the crude product mixture, which is purified by column chromatography on silica gel (100-200 mesh) to intermediate AA.

Alternative Method of Preparing General Intermediate AA: A mixture of a substituted 2-methylindole Z (1 equiv.) or alternatively substituted indole Z (1 equiv.), 4-fluoro substituted benzene (2 equiv.), 18-crown-6 (2 equiv.) and 37%-potassium fluoride/aluminum oxide (15:1 w/w relative to indole) in dimethylsulfoxide (0.15 M) is heated at 100° C. The progress of the reaction is followed by TLC and HPLC.

After cooling to room temperature, the reaction mixture is filtered and the filtrate is extracted with ethyl acetate. The organic extract is washed with water and brine. The organic phase is then dried over sodium sulfate and concentrated to obtain the crude product mixture. The crude product is purified by column chromatography on (100-200 mesh) silica to afford Intermediate AA.

Alternative Method of Preparing General Intermediate AA: A mixture of indole Z (1 equiv.), aryl halide (1.2 equiv.), cesium fluoride (2.50 equiv.), copper(I) iodide (0.05 equiv.) and N,N-dimethylethylenediamine (0.10 equiv.) is prepared in dry tetrahydrofuran (0.6 M relative to indole Z) and then stirred at 70° C. under an inert atmosphere atmosphere. After cooling to room temperature the reaction mixture is diluted with water and extracted with ethyl acetate. The organic extracts are combined, washed with water and brine, dried over sodium sulfate and then concentrated to afford crude product. The crude product is purified by the column chromatography using 100-200 mesh silica gel to obtain intermediate AA.

Alternative Method of Preparing General Intermediate AA: Within a sealed tube, a solution of intermediate Z (1 equiv.) in dimethyl sulfoxide (0.07 M relative to Z) is treated with potassium carbonate (2.5 equiv.), aryl halide (2.5 equiv.), and 8-hydroxy quinnoline (0.2 equiv.). The sealed tube is then purged with nitrogen for 30 min at room temperature. Solid copper(I) iodide (0.2 equiv.) is then added to the reaction mixture and the sealed system is heated at 110° C. The progress of the reaction is followed by HPLC and TLC. After cooling to room temperature, cold water is added to the reaction mixture, which is then extracted with ethyl acetate. The combined organic extracts are washed with brine and then dried over anhydrous sodium sulfate. The organic phase is concentrated under reduced pressure and the crude product purified by by column chromatography on silica gel (100-200 mesh) to afford intermediate AA.

Method of Preparing General Intermediate AB: A stirred suspension of aluminum trichloride (1.5 equiv.) in dichloromethane (0.1 M relative to AA) is cooled to 0° C. Neat chloro acetyl chloride (1.5 equiv.) is added to the reaction mixture in a drop-wise manner and the resulting mixture is stirred at 0° C. for 0.5 h. Intermediate AA (1 equiv.) is dissolved in dichloromethane (0.6 M) and then added to the reaction mixture. The mixture is allowed to warm to room temperature and is then heated at reflux. The progress of the reaction is monitored by TLC and HPLC. After cooling to room temperature, the reaction mixture is poured into ice water and the mixture is extracted with dichloromethane. The organic extracts are combined and washed with water and brine. The organic phase is then dried over sodium sulfate and concentrated to obtain the crude product mixture. The crude product is purified by column chromatography on (230-400 mesh) silica gel to afford intermediate AB.

Method of Preparing Target Compound AC: To a cold solution of intermediate AB (1 equiv.) in anhydrous N,N-dimethylformamide (0.08 M) is added solid potassium carbonate (3 equiv.) and amine M (2 equiv.) or triethylamine (3 equiv.) and amine M (2 equiv.) in anhydrous acetonitrile (0.08 M). The mixture is allowed to warm to room temperature and the progress of the reaction is monitored by HPLC and TLC. The reaction mixture is then poured into ice cold water and the resulting precipitate is collected by filtration. The solids are washed with water and then dried to afford target compound AC.

Example 13

4-(6-Bromo-2-methyl-3-(2-(piperidin-1-yl)acetyl)-1H-pyrrolo[3,2-b]pyridin-1-yl)benzonitrile (Compound 297)

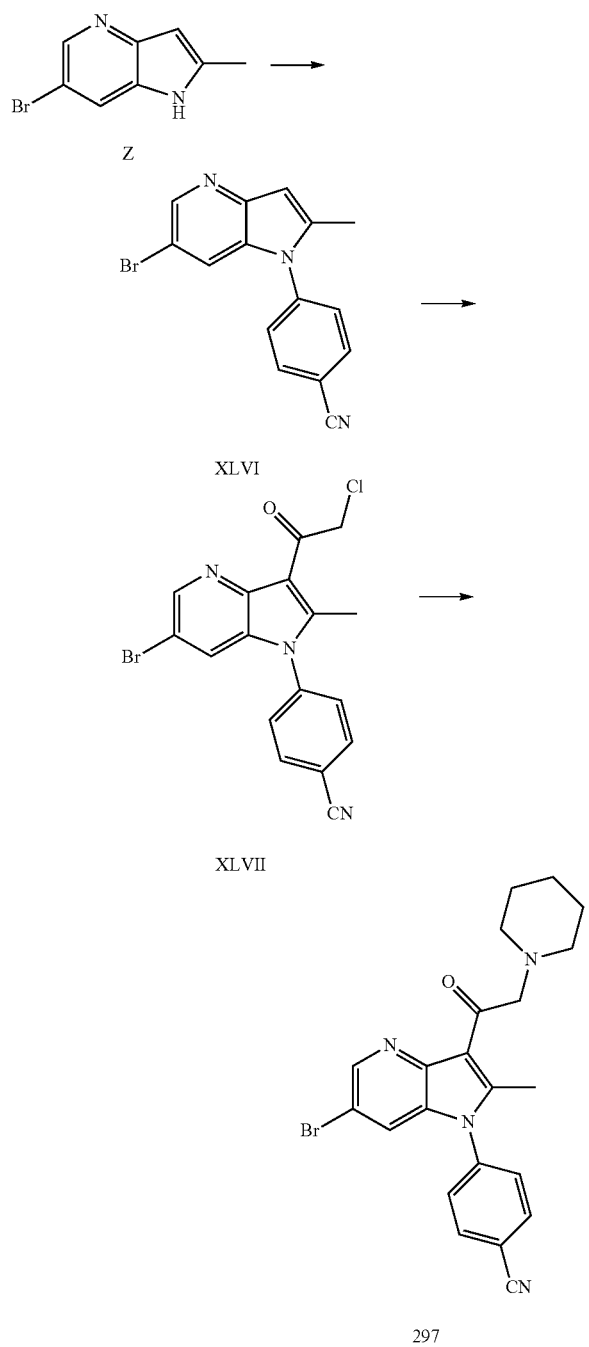

Synthesis of 4-(6-Bromo-2-methyl-pyrrolo[3,2-b]pyridin-1-yl)-benzonitrile (XLVI): To a solution of compound Z (5.0 g, 0.024 mol) in N,N-dimethyl formamide (40 mL), cooled to 0° C., was added sodium hydride (1.90 g, 0.047 mol). The resulting mixture was allowed to slowly warm to room temperature and stir for 1 h. The reaction mixture was again cooled to 0° C. and then 4-fluorobenzonitrile (6.31 g, 0.052 mol) was added. The reaction mixture was heated at 80° C. for 12 h and allowed to cool to room temperature. The reaction mixture was poured over ice and the resulting mixture was extracted with ethyl acetate (2×100 mL). The combined organic extracts were evaporated under reduced pressure and the crude product mixture was purified by column chromatography on 100-200 mesh silica using 2% acetone in dichloromethane as the eluant to afford compound XLVI (3 g, 55%) as a white solid. $^1$H NMR (400 MHz, CDCl$_3$) δ 8.48 (d, 1H, J=1.96 Hz), 7.90-7.87 (m, 2H), 7.53-7.45 (m, 3H), 7.26-7.25 (m, 1H), 7.17-7.15 (m, 1H), 6.62 (s, 1H), 2.36 (s, 3H); MS (ESI, positive mode) m/z 312/314 (MH$^+$, $^{79/81}$Br).

Synthesis of 4-[6-Bromo-3-(2-chloro-acetyl)-2-methyl-pyrrolo[3,2-b]pyridin-1-yl]-benzonitrile (XLVII): To a solution of aluminum chloride (2.1 g, 0.016 mol) in dichloroethane (25 mL), kept at 0° C., was added chloroacetyl chloride (1.6 mL, 0.016 mol). The resulting mixture was allowed to warm to room temperature and stir for 1 h. The reaction mixture was again cooled to 0° C. and was then treated with a solution of compound XLVI (0.5 g, 1.60 mmol) in dichloroethane (10 mL). The reaction mixture was heated at 80° C. for 6 h and then allowed to cool to room temperature. The reaction mixture was concentrated under reduced pressure and the remaining crude product was treated with ice cold water (10 mL), followed by an aqueous saturated sodium bicarbonate solution (10 mL). The mixture was extracted with ethyl acetate (2×100 mL) and the combined organic extracts were evaporated under reduced pressure. The crude product mixture was purified by column chromatography using 100-200 mesh silica using 10% ethyl acetate in hexanes as the eluant to afford compound XLVII (0.25 g, 40%) as a white solid; $^1$H NMR (400 MHz, CDCl$_3$) δ 8.62 (d, 1H, J=1.96 Hz), 7.95 (m, 2H, J=8.56 Hz), 7.52-7.47 (m, 3H), 5.24 (s, 2H), 2.67 (s, 3H).

Synthesis of 4-[6-Bromo-2-methyl-3-(2-piperidin-1-yl-acetyl)-pyrrolo[3,2-b]pyridin-1-yl]-benzonitrile (297): To a solution of compound XLVII (0.25 g, 0.643 mmol) in N,N-dimethyl formamide (4 mL) was added piperidine (0.19 mL 1.93 mmol). The resulting mixture was allowed to stir for 30 min at room temperature, before it was poured into cold water. The brown precipitate that formed was collected via filtration and washed with n-pentane. Drying the solid in a stream of air afforded 297 (0.15 g, 53%) as an off-white solid. $^1$H NMR (400 MHz, CDCl$_3$) δ 8.61 (d, 1H, J=1.9 Hz), 7.93 (d, 2H, J=8.4 Hz), 7.46 (d, 2H, J=8.4 Hz), 7.44 (d, 1H, J=2.0 Hz), 4.26 (s, 2H), 2.72-2.70 (m, 4H), 2.64 (s, 3H), 1.69-1.67 (m, 4H), 1.49-1.48 (m, 2H); MS (ESI, positive mode) m/z 437/439 (MH$^+$, $^{79/81}$Br).

General Synthetic Route 5

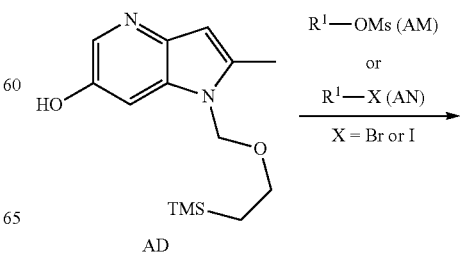

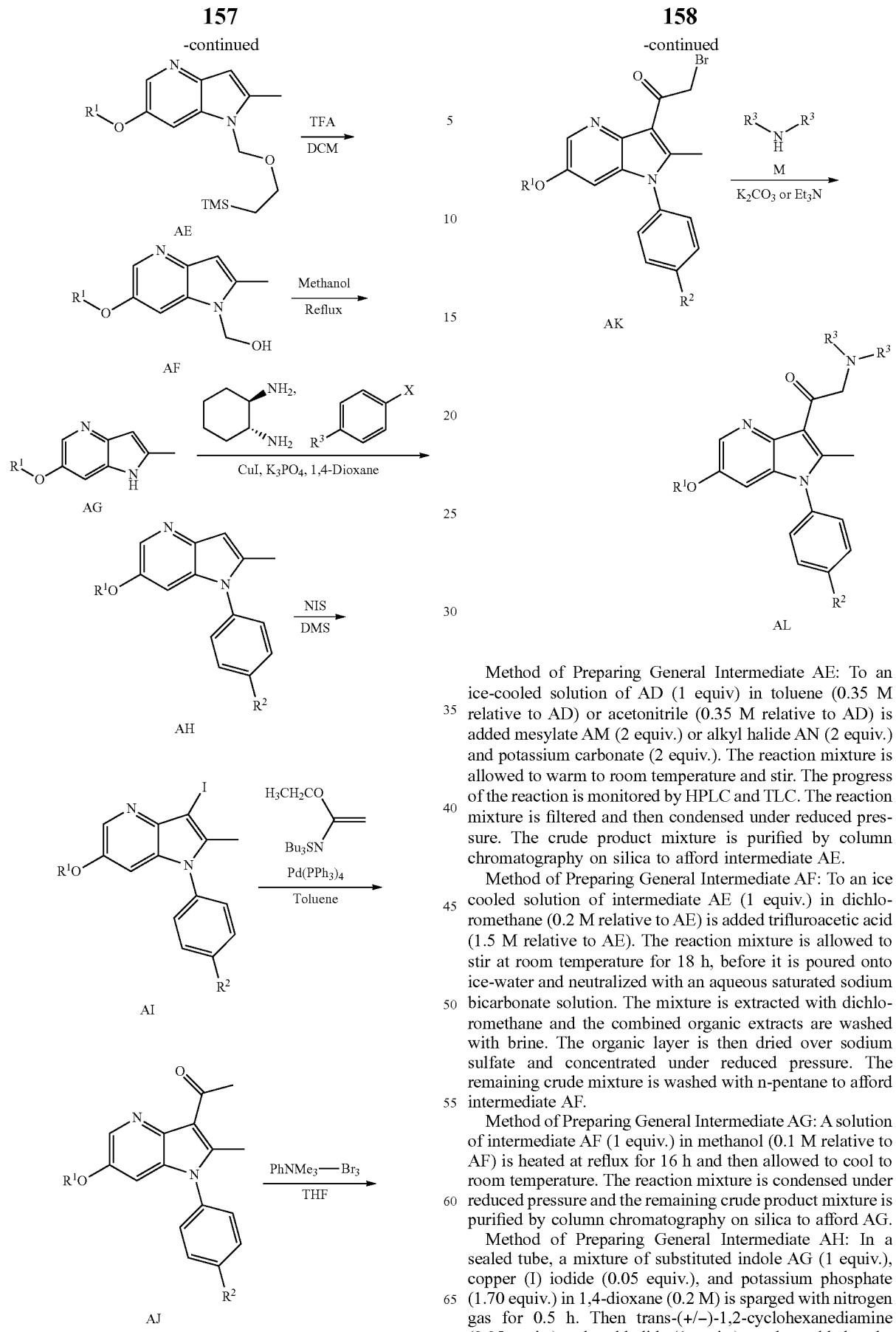

Method of Preparing General Intermediate AE: To an ice-cooled solution of AD (1 equiv) in toluene (0.35 M relative to AD) or acetonitrile (0.35 M relative to AD) is added mesylate AM (2 equiv.) or alkyl halide AN (2 equiv.) and potassium carbonate (2 equiv.). The reaction mixture is allowed to warm to room temperature and stir. The progress of the reaction is monitored by HPLC and TLC. The reaction mixture is filtered and then condensed under reduced pressure. The crude product mixture is purified by column chromatography on silica to afford intermediate AE.

Method of Preparing General Intermediate AF: To an ice cooled solution of intermediate AE (1 equiv.) in dichloromethane (0.2 M relative to AE) is added trifluroacetic acid (1.5 M relative to AE). The reaction mixture is allowed to stir at room temperature for 18 h, before it is poured onto ice-water and neutralized with an aqueous saturated sodium bicarbonate solution. The mixture is extracted with dichloromethane and the combined organic extracts are washed with brine. The organic layer is then dried over sodium sulfate and concentrated under reduced pressure. The remaining crude mixture is washed with n-pentane to afford intermediate AF.

Method of Preparing General Intermediate AG: A solution of intermediate AF (1 equiv.) in methanol (0.1 M relative to AF) is heated at reflux for 16 h and then allowed to cool to room temperature. The reaction mixture is condensed under reduced pressure and the remaining crude product mixture is purified by column chromatography on silica to afford AG.

Method of Preparing General Intermediate AH: In a sealed tube, a mixture of substituted indole AG (1 equiv.), copper (I) iodide (0.05 equiv.), and potassium phosphate (1.70 equiv.) in 1,4-dioxane (0.2 M) is sparged with nitrogen gas for 0.5 h. Then trans-(+/−)-1,2-cyclohexanediamine (0.05 equiv.) and aryl halide (1 equiv.) are then added to the flask at room temperature and the resulting reaction mixture is heated at 110° C. for one to two days. After cooling to room temperature, the reaction mixture is filtered through celite and the filter pad is washed with ethyl acetate. The filtrate is concentrated to afford the crude product mixture, which is purified by column chromatography on silica gel (100-200 mesh) to intermediate AH.

Alternative Method of Preparing General Intermediate AH: A mixture of substituted indole AG (1 equiv.), 4-fluoro substituted benzene (2 equiv.), 18-crown-6 (2 equiv.) and 37%-potassium fluoride/aluminum oxide (15:1 w/w relative to indole) in dimethylsulfoxide (0.15 M) is heated at 100° C. The progress of the reaction is followed by TLC and HPLC. After cooling to room temperature, the reaction mixture is filtered and the filtrate is extracted with ethyl acetate. The organic extract is washed with water and brine. The organic phase is then dried over sodium sulfate and concentrated to obtain the crude product mixture. The crude product is purified by column chromatography on (100-200 mesh) silica to afford Intermediate AH.

Alternative Method of Preparing General Intermediate AH: A mixture of indole AG (1 equiv.), aryl halide (1.2 equiv.), cesium fluoride (2.50 equiv.), copper (I) iodide (0.05 equiv.) and N,N-dimethylethylenediamine (0.10 equiv.) is prepared in dry tetrahydrofuran (0.6 M relative to indole AG) and then stirred at 70° C. under an inert atmosphere atmosphere. After cooling to room temperature the reaction mixture is diluted with water and extracted with ethyl acetate. The organic extracts are combined, washed with water and brine, dried over sodium sulfate and then concentrated to afford crude product. The crude product is purified by the column chromatography using 100-200 mesh silica gel to obtain intermediate AH.

Alternative Method of Preparing General Intermediate AH: Within a sealed tube, a solution of intermediate AG (1 equiv.) in dimethyl sulfoxide (0.07 M relative to AG) is treated with potassium carbonate (2.5 equiv.), aryl halide (2.5 equiv.), and 8-hydroxy quinnoline (0.2 equiv.). The sealed tube is then purged with nitrogen for 30 min at room temperature. Solid copper(I) iodide (0.2 equiv.) is then added to the reaction mixture and the sealed system is heated at 110° C. The progress of the reaction is followed by HPLC and TLC. After cooling to room temperature, cold water is added to the reaction mixture, which is then extracted with ethyl acetate. The combined organic extracts are washed with brine and then dried over anhydrous sodium sulfate. The organic phase is concentrated under reduced pressure and the crude product purified by by column chromatography on silica gel (100-200 mesh) to afford intermediate AH.

Method of Preparing General Intermediate AI: To an ice cooled solution of intermediate AH (0.009 mol, 1 equiv.) in N,N-dimethyl formamide (0.2 M relative to AH) is added N-iodosuccinimide (1.2 equiv.). The reaction mixture is allowed to warm to room temperature and stir. The progress of the reaction is monitored by HPLC and TLC. The reaction mixture is then poured onto ice-water and filtered. The filtered precipitate is allowed to dry in a stream of air to afford intermediate AI.

Method of Preparing General Intermediate AJ: To an ice cooled solution of intermediate AI (1 equiv.) in toluene (0.15 M relative to AI), being maintained under a nitrogen atmosphere, is added tributyl (1-ethoxyvinyl) stannane (1.3 equiv.) and tetrakistriphenylphosphine palladium(0) (0.05 equiv.). The reaction mixture is allowed to warm to room temperature and is then heated at reflux. The progress of the reaction is monitored by HPLC and TLC. After cooling to room temperature, the reaction mixture is poured onto ice-water and acidified with 2M hydrochloride acid. The phases are separated and the aqueous phase is neutralized through the addition of a sodium bicarbonate solution. The aqueous mixture is extracted with ethyl acetate and the combined organic extracts are washed with brine. The organic layer is then dried over sodium sulfate, concentrated under reduced pressure, and the remaining crude product mixture is purified by column chromatography on silica to afford intermediate AJ.

Method of Preparing General Intermediate AK: To a solution of intermediate AJ (1 equiv.) in tetrahydrofuran (0.04 M relative to AJ) is added phenyltrimethylammonium tribromide (1 equiv.). The reaction mixture is heated at reflux and then allowed to cool to room temperature. The progress of the reaction is monitored by HPLC and TLC. The reaction mixture is then poured onto ice-water and the mixture is extracted with ethyl acetate. The combined organic extracts are washed with brine, dried over sodium sulfate, and then concentrated under reduced pressure to obtain AK.

Method of Preparing Target Compound AL: To a cold solution of intermediate AK (1 equiv.) in anhydrous N,N-dimethylformamide (0.08 M) is added solid potassium carbonate (3 equiv.) and amine M (2 equiv.) or triethylamine (3 equiv.) and amine M (2 equiv.) in anhydrous acetonitrile (0.08 M). The mixture is allowed to warm to room temperature and the progress of the reaction is monitored by HPLC and TLC. The reaction mixture is then poured into ice cold water and the resulting precipitate is collected by filtration. The solids are washed with water and then dried to afford target compound AL.

Example 14

4-(6-Methoxy-2-methyl-3-(2-(piperidin-1-yl)acetyl)-1H-pyrrolo[3,2-b]pyridin-1-yl)benzonitrile (Compound 326)

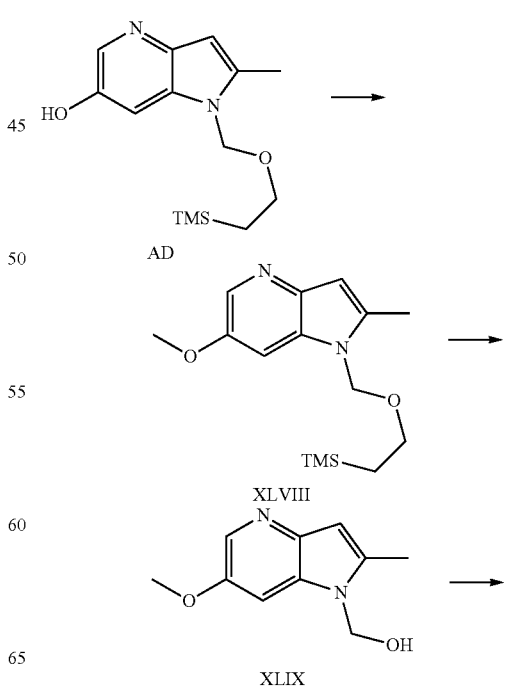

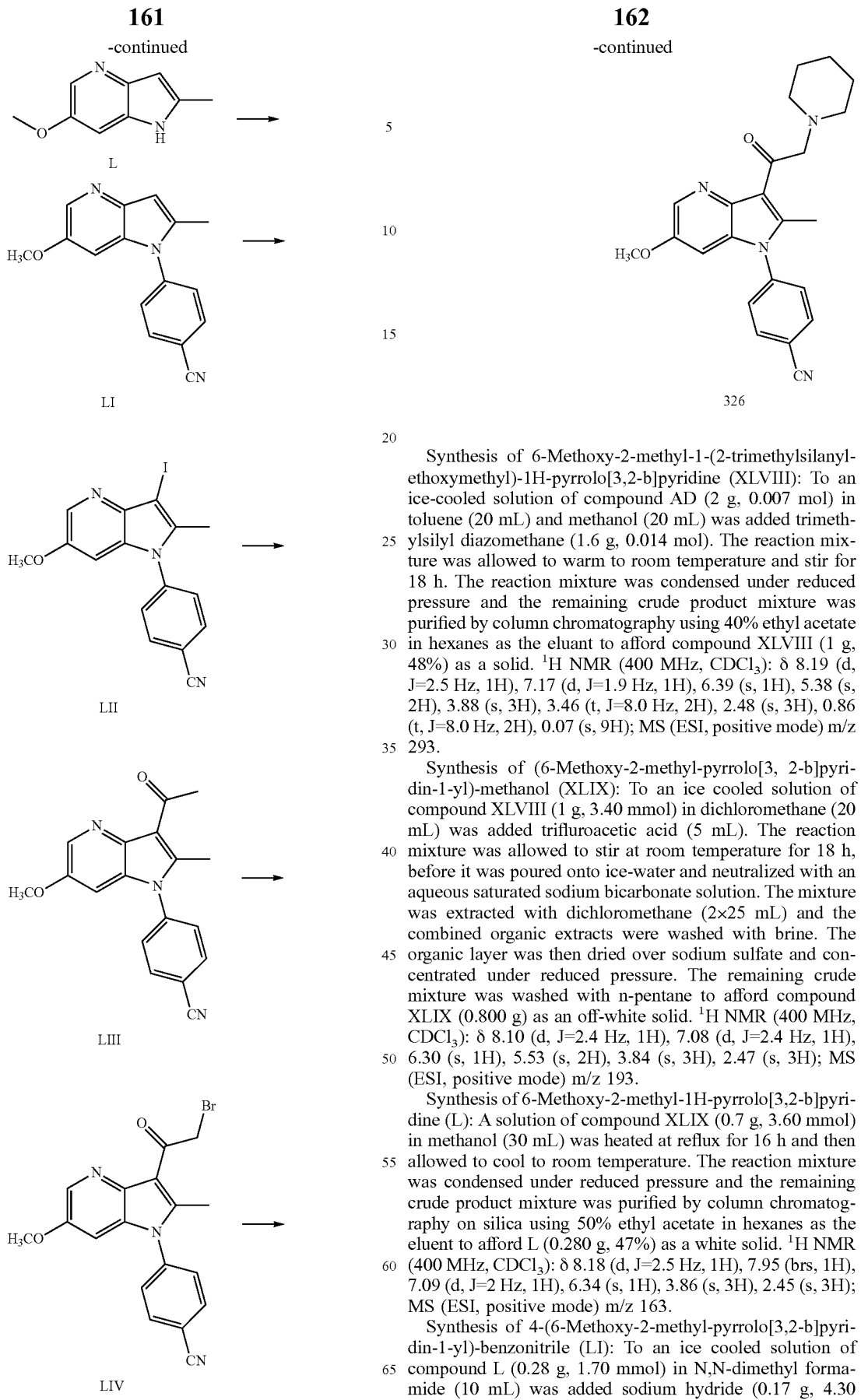

Synthesis of 6-Methoxy-2-methyl-1-(2-trimethylsilanyl-ethoxymethyl)-1H-pyrrolo[3,2-b]pyridine (XLVIII): To an ice-cooled solution of compound AD (2 g, 0.007 mol) in toluene (20 mL) and methanol (20 mL) was added trimethylsilyl diazomethane (1.6 g, 0.014 mol). The reaction mixture was allowed to warm to room temperature and stir for 18 h. The reaction mixture was condensed under reduced pressure and the remaining crude product mixture was purified by column chromatography using 40% ethyl acetate in hexanes as the eluant to afford compound XLVIII (1 g, 48%) as a solid. $^1$H NMR (400 MHz, CDCl$_3$): δ 8.19 (d, J=2.5 Hz, 1H), 7.17 (d, J=1.9 Hz, 1H), 6.39 (s, 1H), 5.38 (s, 2H), 3.88 (s, 3H), 3.46 (t, J=8.0 Hz, 2H), 2.48 (s, 3H), 0.86 (t, J=8.0 Hz, 2H), 0.07 (s, 9H); MS (ESI, positive mode) m/z 293.

Synthesis of (6-Methoxy-2-methyl-pyrrolo[3, 2-b]pyridin-1-yl)-methanol (XLIX): To an ice cooled solution of compound XLVIII (1 g, 3.40 mmol) in dichloromethane (20 mL) was added trifluroacetic acid (5 mL). The reaction mixture was allowed to stir at room temperature for 18 h, before it was poured onto ice-water and neutralized with an aqueous saturated sodium bicarbonate solution. The mixture was extracted with dichloromethane (2×25 mL) and the combined organic extracts were washed with brine. The organic layer was then dried over sodium sulfate and concentrated under reduced pressure. The remaining crude mixture was washed with n-pentane to afford compound XLIX (0.800 g) as an off-white solid. $^1$H NMR (400 MHz, CDCl$_3$): δ 8.10 (d, J=2.4 Hz, 1H), 7.08 (d, J=2.4 Hz, 1H), 6.30 (s, 1H), 5.53 (s, 2H), 3.84 (s, 3H), 2.47 (s, 3H); MS (ESI, positive mode) m/z 193.

Synthesis of 6-Methoxy-2-methyl-1H-pyrrolo[3,2-b]pyridine (L): A solution of compound XLIX (0.7 g, 3.60 mmol) in methanol (30 mL) was heated at reflux for 16 h and then allowed to cool to room temperature. The reaction mixture was condensed under reduced pressure and the remaining crude product mixture was purified by column chromatography on silica using 50% ethyl acetate in hexanes as the eluent to afford L (0.280 g, 47%) as a white solid. $^1$H NMR (400 MHz, CDCl$_3$): δ 8.18 (d, J=2.5 Hz, 1H), 7.95 (brs, 1H), 7.09 (d, J=2 Hz, 1H), 6.34 (s, 1H), 3.86 (s, 3H), 2.45 (s, 3H); MS (ESI, positive mode) m/z 163.

Synthesis of 4-(6-Methoxy-2-methyl-pyrrolo[3,2-b]pyridin-1-yl)-benzonitrile (LI): To an ice cooled solution of compound L (0.28 g, 1.70 mmol) in N,N-dimethyl formamide (10 mL) was added sodium hydride (0.17 g, 4.30 mmol). The reaction mixture was allowed to warm to room temperature and stir for 45 min. The resulting reaction mixture was again cooled to 0° C. and 4-fluorobenzonitrile (0.46 g, 3.70 mmol) was added. The reaction mixture was heated to 80° C. for 10 h and then allowed to cool to room temperature. The reaction mixture was poured onto ice-water and the mixture was extracted with ethyl acetate (2×50 mL). The combined organic extracts were washed with brine, dried over sodium sulfate, and concentrated under reduced pressure to obtain the crude product mixture. The product was purified by column chromatography on silica to afford LI (0.250 g, 62%) as a brown solid. $^1$H NMR (400 MHz, CDCl$_3$): δ 8.24 (d, J=2.5 Hz, 1H), 7.87 (d, J=6.6 Hz, 2H), 7.49 (d, J=6.6 Hz, 2H), 6.88 (d, J=2.4 Hz, 1H), 6.57 (s, 1H), 3.81 (s, 3H), 2.34 (s, 3H); MS (ESI, positive mode) m/z 264.

Synthesis of 4-(3-Iodo-6-methoxy-2-methyl-pyrrolo [3,2-b]pyridin-1-yl)-benzonitrile (LII): To an ice cooled solution of compound LI (0.25 g, 0.009 mol) in N,N-dimethyl formamide (5 mL) was added N-iodosuccinimide (0.25 g, 1.10 mmol). The reaction mixture was allowed to warm to room temperature and stir for 2 h. The reaction mixture was then poured onto ice-water and filtered. The filtered precipitate was allowed to dry in a stream of air to afford compound LII (0.28 g, 76%) as a brown solid. $^1$H NMR (400 MHz, CDCl$_3$): δ 8.33 (d, J=2.4 Hz, 1H), 7.90 (d, J=6.6 Hz, 2H), 7.47 (d, J=6.6 Hz, 2H), 6.82 (d, J=2.4 Hz, 1H), 3.81 (s, 3H), 2.41 (s, 3H); MS (ESI, positive mode) m/z 389.

Synthesis of 4-(3-Acetyl-6-methoxy-2-methyl-pyrrolo[3,2-b]pyridin-1-yl)-benzonitrile (LIII): To an ice cooled solution of compound LII (0.28 g, 0.700 mmol) in toluene (5 mL), being maintained under a nitrogen atmosphere, were added tributyl (1-ethoxyvinyl) stannane (0.32 g, 0.900 mmol) and tetrakistriphenylphosphine palladium(0) (0.085 g, 0.030 mmol). The mixture was allowed to warm to room temperature and was then heated at reflux for 10 h. After cooling to room temperature, the reaction mixture was poured onto ice-water and acidified with 2M hydrochloride acid. The phases were separated and the aqueous phase was neutralized through the addition of a sodium bicarbonate solution. The aqueous mixture was extracted with ethyl acetate (2×50 mL) and the combined organic extracts were washed with brine. The organic layer was then dried over sodium sulfate, concentrated under reduced pressure, and the remaining crude product mixture was purified by column chromatography on silica using 30% ethyl acetate in hexanes the eluant to afford compound LIII (0.070 g, 32%) as a brown solid. $^1$H NMR (400 MHz, CDCl$_3$): δ 8.38 (d, J=2.7 Hz, 1H), 7.93 (d, J=6.6 Hz, 2H), 7.48 (d, J=6.6 Hz, 2H), 6.78 (d, J=2.6 Hz, 1H), 3.81 (s, 3H), 2.96 (s, 3H), 2.61 (s, 3H); MS (ESI, positive mode) m/z 306.

Synthesis of 4-[3-(2-Bromo-acetyl)-6-methoxy-2-methyl-pyrrolo[3,2-b]pyridin-1-yl]-benzonitrile (LIV): To a solution of compound LIII (0.070 g, 0.200 mmol) in tetrahydrofuran (5 mL) was added phenyltrimethylammonium tribromide (0.086 g, 0.200 mmol). The reaction mixture was heated at reflux for 10 h and then allowed to cool to room temperature. The reaction mixture was then poured onto ice-water and the mixture was extracted with ethyl acetate (2×50 mL). The combined organic extracts were washed with brine, dried over sodium sulfate, and then concentrated under reduced pressure to obtain LIV (0.070 g), which was used without further purification.

Synthesis of 4-[6-Methoxy-2-methyl-3-(2-piperidin-1-yl-acetyl)-pyrrolo[3,2-b]pyridin-1-yl]-benzonitrile (326): To a suspension of compound LIV (0.070 g, 0.100 mmol) in dichloromethane (10 mL) was added piperidine (0.036 g, 0.300 mmol). The reaction mixture was allowed to stir at room temperature for 4 h and was then poured onto ice-water. The mixture was extracted with ethyl acetate (2×50 mL) and the combined organic extracts were washed with brine. The organic phase was dried over sodium sulfate, concentrated under reduced pressure, and the remaining crude residue was purified by silica gel (100-200 mesh) column chromatography using 5% methanol in dichloromethane as the eluant to afford 326 (0.025 g, 36%) as a brown solid. $^1$H NMR (400 MHz, CDCl$_3$): δ 8.34 (d, J=2.5 Hz, 1H), 7.94 (d, J=8.5 Hz, 2H), 7.48 (d, J=8.5 Hz, 2H), 6.77 (d, J=2.5 Hz, 1H), 4.62 (s, 2H), 3.81 (s, 3H), 3.08 (m, 4H), 2.63 (s, 3H), 1.92 (m, 6H); MS (ESI, positive mode) m/z 389.

Example 15

4-[2-Methyl-3-(2-piperidin-1-yl-acetyl)-pyrrolo[3,2-b]pyridin-1-yl]-benzonitrile (Compound 116)

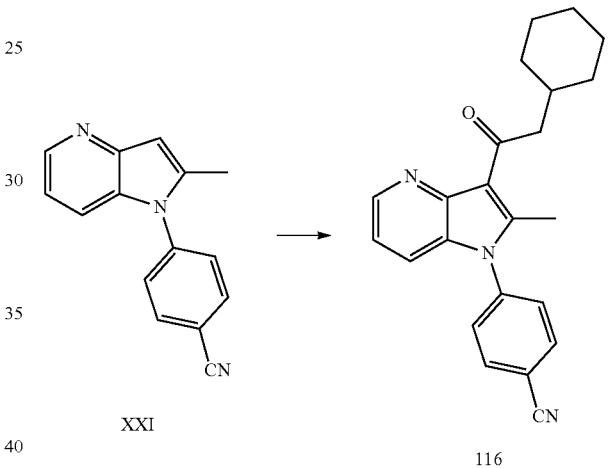

Synthesis of 4-[2-Methyl-3-(2-piperidin-1-yl-acetyl)-pyrrolo[3,2-b]pyridin-1-yl]-benzonitrile (116): To a solution of compound XXI (200 mg, 1.50 mmol) in dichloromethane (10 mL) kept at at 0° C. was added aluminum trichloride (344 mg, 2.57 mmol). After 5 min, neat cyclohexylacetyl chloride (481 mg, 0.003 mol) was added to the reaction mixture. The resulting mixture was allowed to warm to room temperature and stir for 16 h, before it was poured onto ice cold water (10 mL). The mixture was extracted with dichloromethane (2×10 mL) and the combined organic extracts were washed with water (2×10 mL) and brine. The organic layer was dried over sodium sulfate, filtered, and concentrated under vacuum to afford the crude product mixture. The crude product was purified by flash column chromatography on silica gel (100-200 mesh) using 30% ethyl acetate in hexanes as the eluant to afford 116 (110 mg, 21%) as an off-white solid. $^1$H NMR (400 MHz, CDCl$_3$): δ 8.60 (dd, J=4.7, 1.4 Hz, 1H), 7.90 (d, J=8.6 Hz, 2H), 7.48 (d, J=8.6 Hz, 2H), 7.31 (dd, J=8.3, 1.4 Hz, 1H), 7.11 (dd, J=8.3, 4.7 Hz 1H), 3.39 (d, J=6.8 Hz, 2H), 2.65 (s, 3H), 2.08-2.00 (m, 1H), 1.85-1.81 (brm, 2H), 1.72-1.62 (m, 4H), 1.31-1.15 (m, 4H); (ESI, positive mode) m/z 358.

Examples 16-17

Methyl 1-(4-Chlorophenyl)-3-(1-hydroxy-2-(piperidin-1-yl)ethyl)-2-methyl-1H-indole-6-carboxylate (Compound 126), 1-(1-(4-Chlorophenyl)-6-(hydroxymethyl)-2-methyl-1H-indol-3-yl)-2-(piperidin-1-yl)ethan-1-ol (Compound 130)

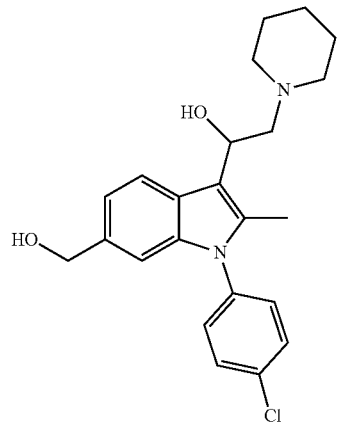

130

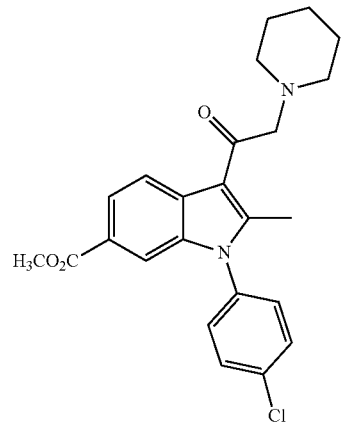

171

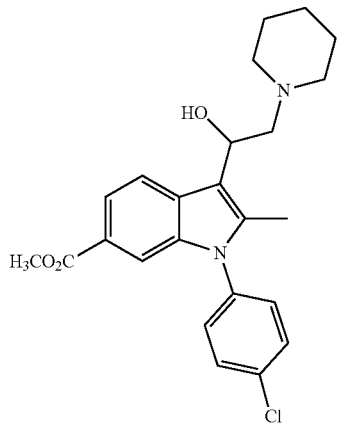

126

Synthesis of Methyl 1-(4-Chlorophenyl)-3-(1-hydroxy-2-(piperidin-1-yl)ethyl)-2-methyl-1H-indole-6-carboxylate (126): To a stirred solution of 171 (0.15 g, 0.350 mmol) in dry tetrahydrofuran (5 mL), kept at 0-5° C., was added lithium borohydride (0.023 g, 1.05 mmol). The reaction mixture was allowed to warm to room temperature and stir for 2 h. The reaction mixture was concentrated under vacuum to dryness and the remaining residue was diluted with water. The aqueous mixture was extracted with dichloromethane and the combined organic extracts were dried over anhydrous sodium sulfate. The organic layer was concentrated and the crude product mixture was purified by column chromatography on silica using 2% methanol in dichloromethane as the eluant to afford 126 (100 mg, 65%) as an off-white solid. $^1$H NMR (400 MHz, CDCl$_3$): δ 7.79 (s, 2H), 7.70 (s, 1H), 7.52 (d, J=8.8 Hz, 2H), 7.24 (d, J=8.8 Hz, 2H), 5.26 (bs, 1H), 3.86 (s, 3H), 3.09 (brs, 1H), 2.87 (brs, 2H), 2.63-2.59 (m, 3H), 2.29 (s, 3H), 1.76 (m, 6H); MS (ESI, positive mode) m/z 427/429 (MH$^+$, $^{35/37}$Cl).

Synthesis of 1-(1-(4-Chlorophenyl)-6-(hydroxymethyl)-2-methyl-1H-indol-3-yl)-2-(piperidin-1-yl)ethan-1-ol (130): To a solution of 171 (0.2 g, 0.470 mmol) in dry tetrahydrofuran (5 mL), kept at 0° C. under a nitrogen atmosphere, was added lithium aluminum hydride (0.05 g, 1.41 mol). The reaction mixture was allowed to warm to room temperature and stir for 2 h. The reaction was quenched through the addition of cold water (10 mL) and the resulting mixture was extracted with ethyl acetate (2×20 mL). The combined organic extracts were washed with brine (10 mL) and dried over sodium sulfate. The organic layer was concentrated under reduced pressure and the crude product mixture was purified by column chromatography on silica using 5% methanol in dichloromethane as the eluant to afford 130 (0.06 g, 32%) as an off white solid; $^1$H NMR (400 MHz, CDCl$_3$) δ 7.77 (d, J=8.1 Hz, 1H), 7.51 (d, J=8.6 Hz, 2H), 7.24 (d, J=10.4 Hz, 2H), 7.11 (d, J=8.0 Hz, 1H), 7.03 (s, 1H), 5.25-5.22 (m, 1H), 4.69 (s, 2H), 3.16-3.10 (m, 1H), 2.86 (bs, 2H), 2.65 (bs, 2H), 2.56-2.52 (m, 1H) 2.26 (s, 3H) 2.08 (s, 1H) 1.75-1.71 (m, 4H) 1.54-1.53 (m, 2H); MS (ESI, positive mode) m/z 399/421 (MH$^+$, $^{35/37}$Cl).

Example 18

1-(1-(4-Chlorophenyl)-2-methyl-1H-indol-3-yl)-2-(piperidin-1-yl)ethan-1-ol (106)

Compound 106 was prepared using methods similar to those described in Examples 16 and 17.

Examples 19-20

1-(6-(((tert-Butyldimethylsilyl)oxy)methyl)-1-(4-chlorophenyl)-2-methyl-1H-indol-3-yl)-2-(piperidin-1-yl)ethan-1-one (Compound 153), 1-(1-(4-Chlorophenyl)-6-(hydroxymethyl)-2-methyl-1H-indol-3-yl)-2-(piperidin-1-yl)ethan-1-one (Compound 182)

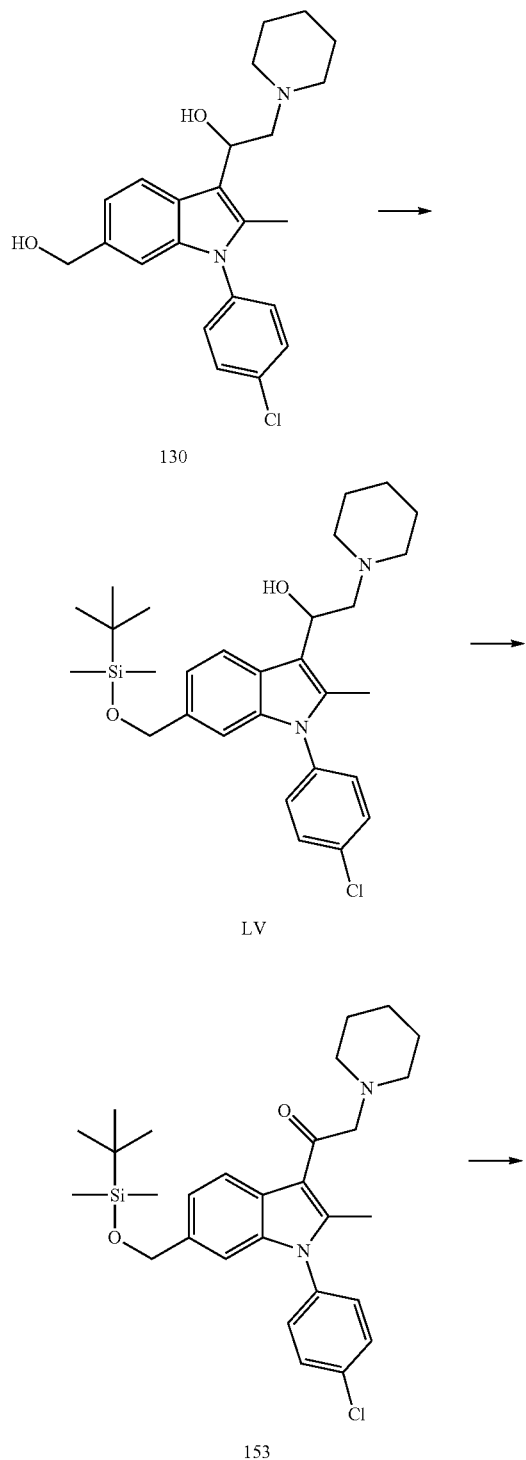

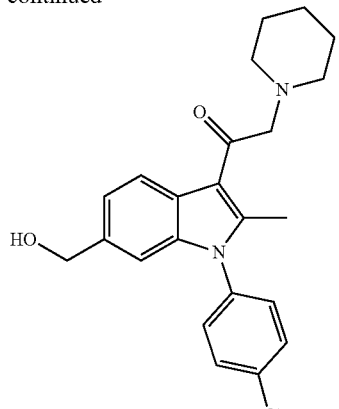

Synthesis of 1: 1-[6-(tert-Butyl-dimethyl-silanyloxymethyl)-1-(4-chloro-phenyl)-2-meth yl-1H-indol-3-yl]-2-piperidin-1-yl-ethanol (LV). To a solution of 130 (0.6 g, 1.50 mmol) in dichloromethane (15 mL), kept under a nitrogen atmosphere at 0° C., was added imidazole (0.35 g, 5.26 mmol). After 10 min, solid tert-butyldimethylsilyl chloride (0.27 g, 1.80 mmol) was added portionwise to the reaction mixture, which was then allowed to warm to room temperature and stir for 3 h. The reaction mixture was diluted with cold water (20 mL) and the mixture was extracted with dichloromethane (2×20 mL). The combined organic extracts were washed with brine (30 mL), dried over anhydrous sodium sulfate, and then concentrated under reduced pressure. The crude product mixture was purified by column chromatography on silica, using 4% methanol in dichloromethane as the eluant, to afford compound LV (0.65 g, 84%) as an off-white solid. $^1$H NMR (400 MHz, CDCl$_3$) δ 7.70 (d, J=8.2 Hz, 1H), 7.47 (d, J=8.7 Hz, 2H), 7.23 (d, J=9.1 Hz, 2H), 7.03 (d, J=8.2 Hz, 1H), 7.00 (s, 1H), 5.14-5.09 (m, 1H), 4.74 (s, 2H), 3.07-2.99 (m, 1H), 2.77 (m, 2H), 2.49-2.43 (m, 2H), 2.24 (s, 3H), 1.66 (brs, 4H), 1.51-1.48 (m, 2H), 0.86 (s, 9H), 0.02 (s, 6H).

Synthesis of 1-[6-(tert-Butyl-dimethyl-silanyloxymethyl)-1-(4-chloro-phenyl)-2-methyl-1H-indol-3-yl]-2-piperidin-1-yl-ethanone (153). To a stirred solution of compound LV (0.6 g, 1.16 mmol) in dichloromethane (20 mL), kept at 0° C. under a nitrogen atmosphere, was added Dess-Martin periodinane (0.74 g, 1.75 mmol). The reaction mixture was allowed to warm to room temperature and stir for 8 h. The reaction mixture was diluted with cold water (20 mL) and then extracted with dichloromethane (3×20 mL). The combined organic extracts were washed with brine (20 mL), dried over anhydrous sodium sulfate, and then concentrated under reduced pressure. The crude product mixture was purified by column chromatography on silica, using 5% methanol in dichloromethane as the eluant, to afford 153 (0.09 g, 15%) as an of-white solid. $^1$H NMR (400 MHz, CDCl$_3$) δ 7.92 (d, J=8.3 Hz, 1H), 7.54 (d, J=8.7 Hz, 2H), 7.24 (d, J=8.7 Hz, 2H), 7.20 (d, J=8.2 Hz, 1H), 6.98 (s, 1H), 4.76 (s, 2H), 3.88 (s, 2H), 2.70 (brs, 4H), 2.58 (s, 3H), 1.71-1.68 (m, 4H), 1.49 (brs, 2H), 0.86 (s, 9H), 0.01 (s, 6H); MS (ESI, positive mode) m/z 511/513 (MH$^+$, $^{35/37}$Cl).

Synthesis of 1-[1-(4-Chloro-phenyl)-6-hydroxymethyl-2-methyl-1H-indol-3-yl]-2-piperidin-1-yl-ethanone (182). To a solution of compound 153 (0.16 g, 0.310 mmol) in dry tetrahydrofuran (5 mL), being kept at 0° C. under a nitrogen atmosphere, was added tetrabutylammonium fluoride solution (1M in THF, 0.47 mL, 0.47 mmol). The reaction mixture was allowed to stir at room temperature for 3 h before it was diluted with cold water (10 mL). The mixture was extracted with ethyl acetate (2×20 mL) and the combined organic extracts were washed with brine (10 mL). The organic layer was dried over anhydrous sodium sulfate and then concentrated under reduced pressure. The remaining crude product mixture was purified by preparative HPLC to afford 153 (0.01 g, 8%) as an off-white solid. $^1$H NMR (400 MHz, CDCl$_3$) δ 7.99 (d, J=8.3 Hz, 1H), 7.55 (d, J=8.5 Hz, 2H), 7.26 (s, 2H), 7.24 (s, 1H), 7.00 (s, 1H), 4.71 (s, 2H), 3.77 (s, 2H), 2.61-2.56 (m, 7H), 1.67-1.61 (m, 4H), 1.46 (brs, 2H); MS (ESI, positive mode) m/z 397/399 (MH$^+$, $^{35/37}$Cl).

Examples 21-23

2-((1-(4-Chlorophenyl)-2-methyl-3-(2-(piperidin-1-yl)acetyl)-1H-indol-6-yl)methyl)isoindoline-1,3-dione (Compound 152), 1-(6-(Aminomethyl)-1-(4-chlorophenyl)-2-methyl-1H-indol-3-yl)-2-(piperidin-1-yl)ethan-1-one (Compound 185), 1-(1-(4-chlorophenyl)-6-((Dimethylamino)methyl)-2-methyl-1H-indol-3-yl)-2-(piperidin-1-yl)ethan-1-one (Compound 188)

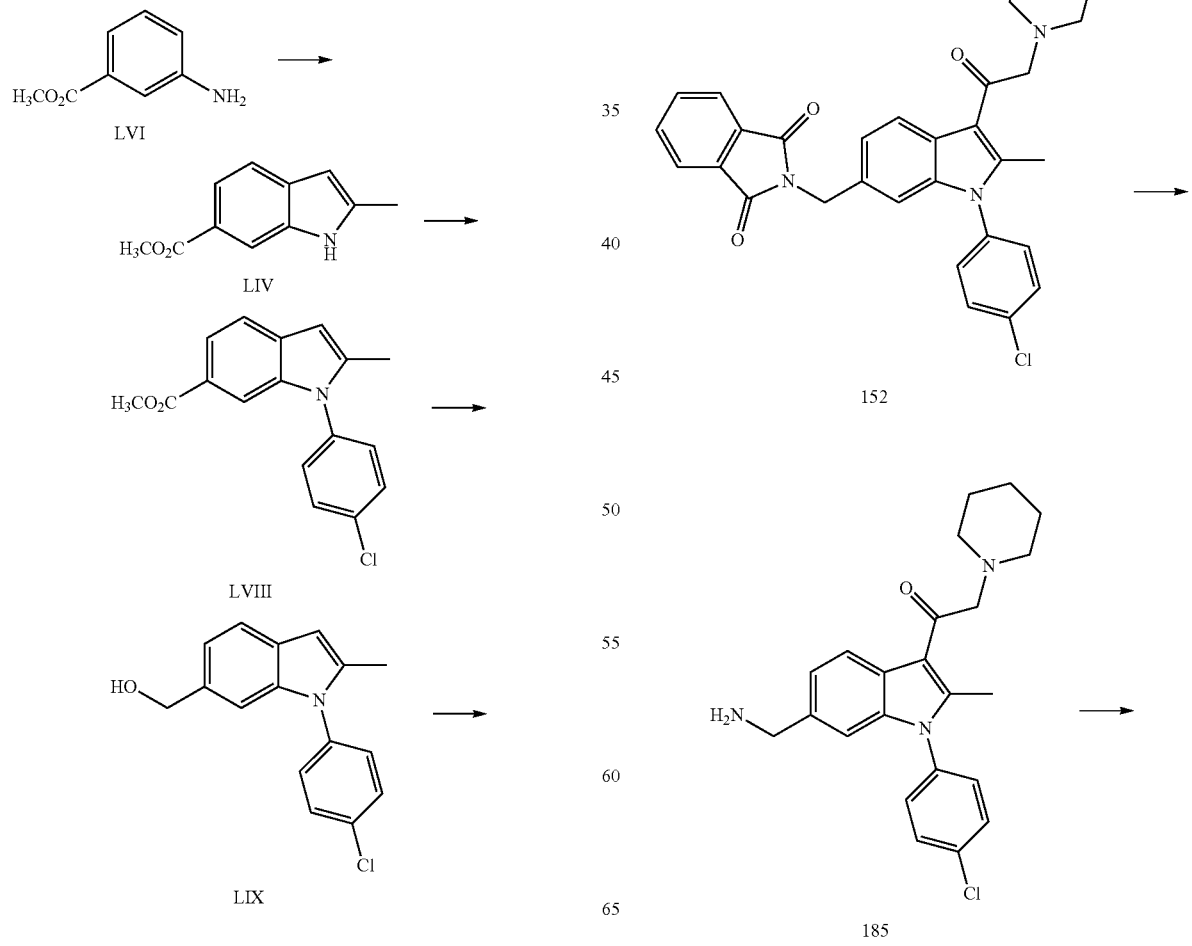

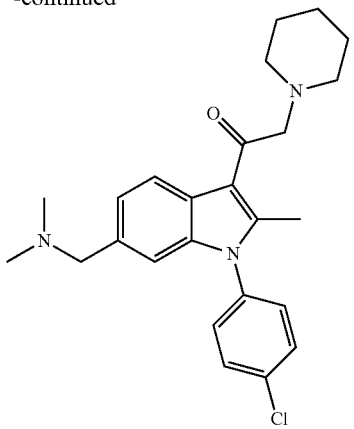

188

Synthesis of Methyl 2-Methyl-1H-indole-6-carboxylate (LVII): In a sealed tube was prepared a degassed mixture of compound LVI (10.0 g, 0.061 mol) and copper(II) acetate monohydrate (36.2 g, 0.182 mol) in dimethylsulfoxide (50 mL). To the flask was added acetone (100 mL), followed by palladium(II) acetate (0.270 g, 0.001 mol), and the resulting reaction mixture was heated at 80° C. for 48 h. After cooling to room temperature, the reaction mixture was filtered through a pad of celite and the filtrate was diluted with water (80 mL). The aqueous mixture was extracted with ethyl acetate (3×100 mL) and the combined organic extracts were dried over anhydrous sodium sulfate. The organic layer was concentrated under reduced pressure to obtain the crude product mixture, which was purified by silica gel chromatography using a gradient of 5-7% ethyl acetate in hexanes as the eluant to afford LVII (4.8 g, 83%) as a pale yellow solid. $^1$H NMR (400 MHz, CDCl$_3$) δ 8.26 (brs, 1H), 8.04 (s, 1H), 7.77 (dd, J=8.3, 3.4 Hz, 1H), 7.50 (d, J=8.3 Hz, 1H), 6.26 (s, 1H), 3.92 (s, 3H), 2.47 (s, 3H); MS (ESI, positive mode) m/z 190 (MH$^+$).

Synthesis of Methyl 1-(4-Chloro-phenyl)-2-methyl-1H-indole-6-carboxylate (LVIII): To a degassed mixture of compound LVII (3.5 g, 0.019 mol), 1-chloro-4-iodobenzene (4.41 g, 0.019 mol), potassium phosphate (6.67 g, 0.031 mol) in 1,4-dioxane (75 mL) were added copper(I) iodide (0.129 g, 0.926 mmol), followed by racemic trans-1,2-diaminocyclohexane (0.105 g, 0.926 mmol). The reaction mixture was heated at 110° C. for 48 h and then allowed to cool to room temperature. The reaction mixture was filtered through bed of celite and the filtrate was condensed under reduced pressure. The remaining crude product mixture was purified by column chromatography (100-200 mesh) on silica gel, using 5% ethyl acetate in hexanes as the eluant to afford LVIII (3.0 g, 86%) as a white solid. $^1$H NMR (400 MHz, CDCl$_3$) δ 7.81 (dd, J=8.3, 1.3 Hz, 1H), 7.75 (s, 1H), 7.57 (s, 1H), 7.53 (d, J=8.7 Hz, 2H), 7.29 (d, J=8.7 Hz, 2H), 6.44 (s, 1H), 3.86 (s, 3H), 2.31 (s, 3H); MS (ESI, positive mode) m/z 300/302 (MH$^+$, $^{35/37}$Cl).

Synthesis of [1-(4-Chloro-phenyl)-2-methyl-1H-indol-6-yl]-methanol (LIX): To an ice-cooled solution of LVIII (1.0 g, 3.34 mmol) in dry tetrahydrofuran (20 mL) was added lithium aluminium hydride (0.380 g, 0.010 mol). The mixture was allowed to warm to room temperature and stir for 2 h. The reaction mixture was carefully quenched through the addition of ice-cold water and the resulting mixture was extracted with ethyl acetate (3×30 mL). The combined organic extracts were washed with a saturated brine solution and dried over sodium sulfate. The mixture was condensed under reduced pressure and the remaining crude product mixture was purified by column chromatography (100-200 mesh) silica gel, using 20% ethyl acetate in hexanes as the eluant, to afford LIX (0.650 g, 65%) as an off-white solid. $^1$H NMR (400 MHz, CDCl$_3$) δ 7.48-7.54 (m, 3H), 7.28 (d, J=8.6 Hz, 2H), 7.10 (dd, J=8.1, 1.2 Hz 1H), 7.07 (s, 1H), 6.38 (s, 1H), 4.69 (s, 2H), 2.29 (s, 3H); MS (ESI, positive mode) m/z 272/274 (MH$^+$, $^{35/37}$Cl).

Synthesis of 2-[1-(4-Chloro-phenyl)-2-methyl-1H-indol-6-ylmethyl]-isoindole-1,3-dione (LX): To a solution of LIX (0.490 g, 1.80 mmol) in dry tetrahydrofuran (20 mL) were added triphenyl phosphine (0.945 g, 3.61 mmol) and phthalimide (0.530 g, 3.61 mmol). The resulting mixture was then treated with di-isopropylazodicarboxylate (0.627 g, 3.61 mmol) in a dropwise manner. The reaction mixture was allowed to stir at room temperature for 4 h before it was poured into ice cold water. The mixture was extracted with ethyl acetate (30 mL) and the combined organic extracts were washed with saturated brine solution, followed by drying over sodium sulfate. The mixture was condensed under reduced pressure and the remaining crude product mixture was purified by column chromatography (100-200 mesh) silica, using 10% ethyl acetate in hexanes as the eluant, to afford LX (0.150 g, 31%) as an off-white solid. $^1$H NMR (400 MHz, CDCl$_3$) δ 7.81-7.78 (m, 2H), 7.68-7.64 (m, 2H), 7.51 (d, J=8.6 Hz, 2H), 7.46 (d, J=8.2 Hz, 1H), 7.27 (d, J=8.6 Hz, 2H), 7.20 (dd, J=8.0, 1.5 Hz, 1H), 7.17 (s, 1H), 6.34 (s, 1H), 4.85 (s, 2H), 2.24 (s, 3H); MS (ESI, positive mode) m/z 401/403 (MH$^+$, $^{35/37}$Cl).

Synthesis of 2-[3-(2-Chloro-acetyl)-1-(4-chloro-phenyl)-2-methyl-1H-indol-6-yl-methyl]-isoindole-dione (LXI): To an ice-cooled suspension of aluminum trichloride (0.297 g, 0.225 mmol) in dichloromethane (20 mL) was added neat chloro acetyl chloride (0.252 g, 0.225 mmol). The mixture was allowed to stir at the reduced temperature for 30 min and then a solution of LX (0.180 g, 0.450 mmol) in dichloromethane (5 mL) was added. The mixture was allowed to warm to room temperature and was then heated at 50° C. for 24 h. The reaction mixture was allowed to cool to room temperature and was then poured into ice cold water. The mixture was extracted extracted with dichloromethane (2×20 mL) and the combined organic extracts were washed with an aqueous saturated solution of sodium bicarbonate. The organic layer was dried over sodium sulfate and condensed in vacuo. The remaining crude product mixture was purified by column chromatography on (100-200 mesh) silica using 20% ethyl acetate in hexanes as the eluant to afford LXI (0.035 g, 19%) as a light pink solid. $^1$H NMR (400 MHz, CDCl$_3$) δ 7.84-7.79 (m, 3H), 7.70-7.67 (m, 2H), 7.59 (d, J=8.5 Hz, 2H), 7.41 (dd, J=8.3, 1.4 Hz, 1H), 7.26 (d, occluded by solvent, 2H), 7.13 (s, 1H), 4.85 (s, 2H), 4.70 (s, 2H), 2.57 (s, H); MS (ESI, positive mode) m/z 477/479 (MH$^+$, $^{35/37}$Cl).

Synthesis of 2-[1-(4-Chloro-phenyl)-2-methyl-3-(2-piperidin-1-yl-acetyl)-1H-indol-6-ylmethyl]-isoindole-1,3-dione (152): To a solution of compound LXI (0.045 g, 0.095 mmol) in acetonitrile (5 mL) was added neat triethylamine (0.019 mL, 0.189 mmol). The reaction mixture was allowed to stir for 10 min and then the reaction mixture was treated with piperidine (0.012 g, 0.142 mol). The reaction mixture was allowed to stir at room temperature for 30 min before it was poured into ice cold water. The resulting precipitate was collected via filtration and allowed to dry in a stream of air to afford a pale yellow solid. The crude solid was further purified by column chromatography on (100-200 mesh) silica gel using 2% methanol in dichloromethane as the eluant to afford 152 (0.009 g, 20%) as a pale yellow solid. $^1$H NMR (400 MHz, CDCl$_3$) δ 7.93 (d, J=9.0 Hz, 1H), 7.82-7.79 (m, 2H), 7.70-7.67 (m, 2H), 7.57 (d, J=8.4 Hz, 2H), 7.37 (d, J=7.3 Hz, 1H), 7.24 (d, occluded by solvent, 2H), 7.10 (s, 1H), 4.85 (s, 2H), 3.79 (brs, 2H), 2.61 (brs, 4H), 2.56 (s, 3H), 1.65 (brs, 4H), 1.49 (brs, 2H); MS (ESI, positive mode) m/z 526/528 (MH$^+$, $^{35/37}$Cl).

Synthesis of 1-[6-Aminomethyl-1-(4-chloro-phenyl)-2-methyl-1H-indol-3-yl]-2-piperidin-1-yl-ethanone (185): To an ice-cooled solution of 152 (0.500 g, 0.952 mmol) in ethanol (15 mL) was added hydrazine hydrate (0.238 g, 4.76 mmol). The resulting mixture was allowed to warm to room temperature and stir for 24 h, before it was condensed in vacuo. The remaining residue was diluted with water (20 mL) and the aqueous mixture was acidified with dilute hydrochloric acid (5 mL). The acidic mixture was washed with ethyl acetate (3×20 mL) and then the aqueous phase was basified using an aqueous, saturated sodium bicarbonate solution. The resulting mixture was extracted with dichloromethane (3×50 mL) and the combined organic extracts were washed with brine (50 mL), dried over sodium sulfate, and concentrated in vacuo. The remaining residue was triturated with pentane (3×5 mL) and then allowed to dry in a stream of air to afford 185 (0.150 g, 40%) as a pale yellow solid. $^1$H NMR (400 MHz, CDCl$_3$): δ 7.96 (d, J=8.2 Hz, 1H), 7.55 (d, J=8.6 Hz, 2H), 7.26 (s, 2H), 7.21 (s, 1H), 6.93 (s, 1H), 3.89 (s, 2H), 3.79 (s, 2H), 2.62 (brs, 4H), 2.57 (s, 3H), 1.66-1.59 (m, 8H); MS (ESI, positive mode) m/z 396/398 (MH$^+$, $^{35/37}$Cl).

Synthesis of 1-[1-(4-Chloro-phenyl)-6-dimethylaminomethyl-2-methyl-1H-indol-3-yl]-2-piperidin-1-yl-ethanone (188): To an ice-cooled solution of 185 (0.050 g, 0.127 mmol) in acetic acid (5 mL) was added paraformaldehyde (0.011 g, 0.380 mmol) and the reaction mixture was allowed to stir at room temperature for 3 h. The reaction mixture was then treated with sodium cyanoborohydride (0.015 g, 0.253 mmol) in a portionwise fashion and allowed to stir for 15 h. The reaction mixture was quenched through the addition of an aqueous saturated sodium bicarbonate solution (100 mL) and the mixture was extracted with ethyl acetate (2×75 mL). The combined organic extracts were washed with brine (75 mL), dried over sodium sulfate and concentrated in vacuo. The remaining crude product mixture was purified by column chromatography on silica using 7% methanol in dichloromethane as the eluent to afford 188 (0.015 g, 28%) as an off-white solid. $^1$H NMR (400 MHz, CDCl$_3$): δ 7.97 (d, J=8.3 Hz, 1H), 7.55 (d, J=8.6 Hz, 2H), 7.27 (d, occluded by solvent, 2H), 7.01 (brs, 1H), 3.82 (s, 2H), 3.57 (brs, 3H) 2.71 (brs, 3H), 2.57 (s, 3H), 2.21 (brs, 6H), 1.70-1.41 (m, 6H); MS (ESI, positive mode) m/z 424/426 (MH$^+$, $^{35/37}$Cl).

Example 24

1-(1-(4-Chlorophenyl)-6-((methylamino)methyl)-1H-indol-3-yl)-2-(piperidin-1-yl)ethan-1-one (119)

Compound 119 was prepared using methods similar to those described in Examples 21-23.

Example 25

1-(2-Methyl-1H-pyrrolo[3,2-b]pyridin-3-yl)-2-(piperidin-1-yl)ethan-1-one (Compound 128)

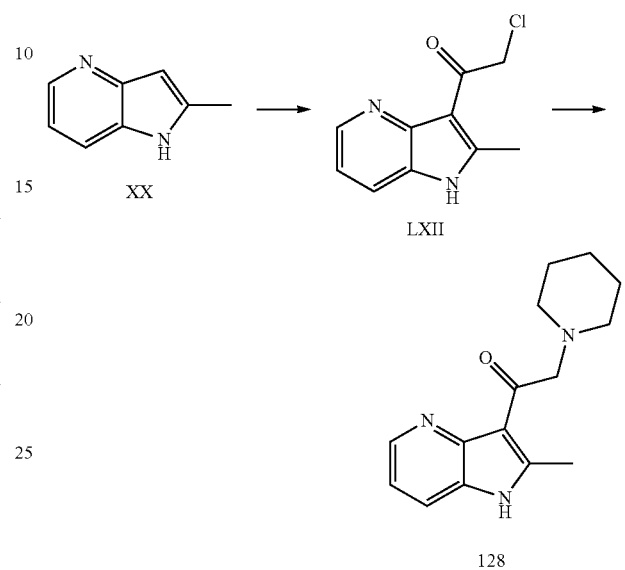

Synthesis of 2-Chloro-1-(2-methyl-1H-pyrrolo[3,2-b]pyridin-3-yl)-ethanone (LXII): To a solution of XX (0.5 g, 3.78 mmol) in dichloromethane (10 mL) was added anhydrous aluminum chloride (2.5 g, 0.018 mol). The mixture was allowed to stir at room temperature for 1 h and then a solution of chloroacetyl chloride (2.1 g, 0.018 mol) in dichloromethane (10 mL) was added dropwise to the reaction mixture. The reaction mixture was allowed to stir under a nitrogen atmosphere, at room temperature, overnight. In the morning the reaction mixture was diluted with methanol (50 mL) and then concentrated in vacuo. The remaining residue was diluted with water (50 mL) and extracted with ethyl acetate (2×100 mL). The combined organic extracts were washed with brine (2×50 mL), dried over anhydrous sodium sulfate, and then concentrated under reduced pressure. The remaining solid material was triturated with n-pentane to afford X (0.5 g, 63%) as a brown solid; $^1$H NMR (400 MHz, DMSO-d$_6$) δ 12.38 (s, 1H), 8.45 (d, J=6.0 Hz, 1H), 7.81 (d, J=9.6 Hz, 1H), 7.20 (d, J=13 Hz, 1H), 5.28 (s, 2H) 2.71 (s, 3H); MS (ESI, positive mode) m/z 209/211 (MH$^+$, $^{35/37}$Cl).

Synthesis of 1-(2-Methyl-1H-pyrrolo [3,2-b]pyridin-3-yl)-2-piperidin-1-yl-ethanone (128). To a solution of compound LXII (0.250 g, 0.0012 mol) and triethylamine (0.333 g, 0.0024 mol) in acetonitrile (5 mL) was added piperidine (0.178 g, 0.00180 mol). The resulting mixture was allowed to stir at room temperature for 6 h, before it was diluted with cold water (10 mL). The precipitate that formed was collected by filtration and washed with additional water and hexanes to afford 128 (0.019 g, 6%) as an off-white solid; $^1$H NMR (400 MHz, CDCl$_3$) δ 8.95 (s, 2H), 8.47 (s, 1H), 7.60 (d, J=7.8 Hz, 1H), 7.08 (d, J=12.8 Hz, 1H), 4.24 (s, 2H), 2.77 (s, 3H), 2.67 (m, 4H), 1.69-1.63 (m, 4H), 1.46 (brs, 2H); MS (ESI, positive mode) m/z 258 (MH$^-$).

Example 26

4-(2-Methyl-3-(2-(piperidin-1-yl)acetyl)-1H-pyrrolo[2,3-b]pyridin-1-yl)benzonitrile (Compound 141)

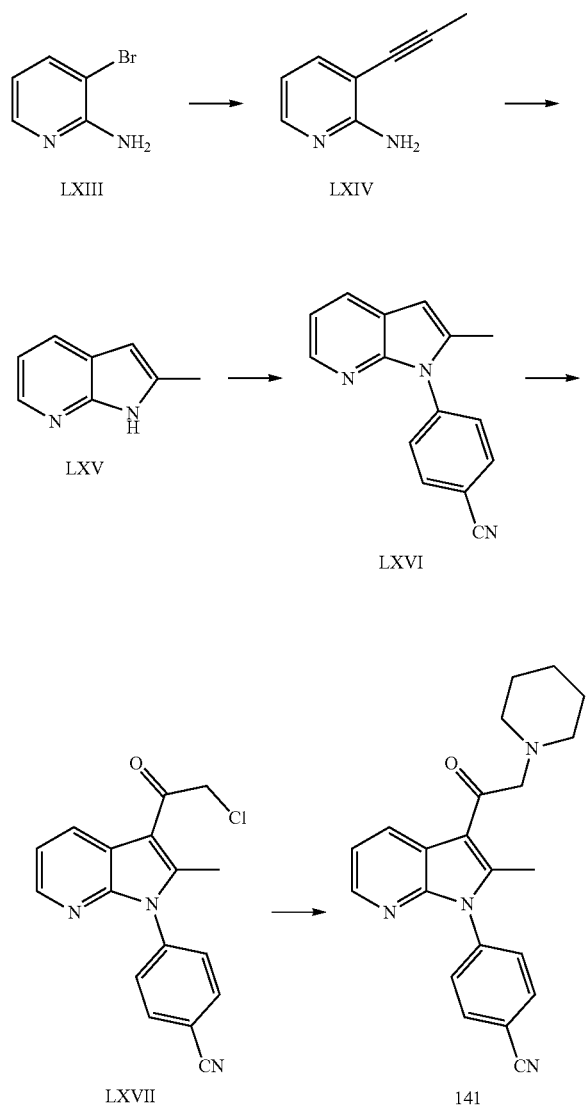

Synthesis of 3-Prop-1-ynyl-pyridin-2-ylamine (LXIV): To a degassed mixture of copper(I) iodide (0.055 g, 0.289 mmol) and 2-amino-3-bromo-pyridine (1 g, 5.78 mmol) in triethylamine (30 mL) was added Pd(PPh$_3$)$_2$Cl$_2$ (0.202 g, 0.289 mmol). The resulting reaction mixture was cooled to −78° C. and purged with propyne gas (3.6 g, 46.0 mmol). The mixture was allowed to warm to room temperature and and stir for 18 h. The reaction mixture was diluted with water (50 mL) and filtered through a pad of celite. The filtrate was extracted with ethyl acetate and the combined organic extracts were dried over anhydrous sodium sulfate. After concentrating in vacuo, the crude product mixture was purified by column chromatography on silica (100-200 mesh) using 50% ethyl acetate in hexanes as the eluent to afford LXIV (0.400 g, 52%) as an off-white solid. $^1$H NMR (400 MHz, CDCl$_3$): δ 7.97 (d, J=3.9 Hz, 1H), 7.46-7.43 (m, 1H), 6.58-6.55 (m, 1H), 4.93 (bs, 2H), 2.09 (s, 3H); MS (ESI, positive mode) m/z 233 (MH$^+$).

Synthesis of 2-Methyl-1H-pyrrolo[2,3-b]pyridine (LXV): To an ice-cooled solution of compound LXIV (0.4 g, 3.02 mmol) in N,N-dimethylformamide (5 mL) was added potassium tert-butoxide (0.68 g, 6.05 mmol) in a portion-wise manner. The resulting mixture was allowed to warm to room temperature and stir for 4 h. The reaction mixture was poured onto cold water (10 mL) and extracted with diethyl ether (2×10 mL). The combined organic extracts were dried over anhydrous sodium sulfate and concentrated in vacuo to get afford LXV (0.3 g, crude) as an off-white solid, which was used without further purification.

Synthesis of 4-(2-Methyl-pyrrolo[2,3-b]pyridin-1-yl)-benzonitrile (LXVI): To a degassed mixture of crude compound LXV (0.35 g), 4-iodobenzene (0.606 g, 2.64 mmol), and potassium phosphate (0.955 g, 4.50 mmol) in 1,4-dioxane (20 mL) were added copper(I) iodide (0.018 g, 0.132 mmol) and trans-(+/−)-1,2-cyclohexanediamine (0.015 g, 0.132 mmol). The reaction mixture was then heated at 110° C. for 38 h, after which it was allowed to cool to room temperature. The reaction mixture was filtered through celite bed and the filtrate was condensed in vacuo. The remaining crude product mixture was purified by column chromatography on silica gel (100-200 mesh) using 30% ethyl acetate in hexanes as the eluent to afford LXVI (0.300 g, 43% after two steps) as an off-white solid. $^1$H NMR (400 MHz, CDCl$_3$): δ 8.20 (dd, J=4.8, 1.5 Hz, 1H), 7.85-7.83 (m, 3H), 7.59-7.56 (m, 2H), 7.11-7.07 (m, 1H), 6.39 (s, 1H), 2.38 (s, 3H); MS (ESI, positive mode) m/z 234 (MH$^+$).

Synthesis of 4-[3-(2-Chloro-acetyl)-2-methyl-pyrrolo-[2,3-b]pyridin-1-yl]-benzonitrile (LXVII): To an ice-cooled solution of compound LXVI (0.3 g, 1.28 mmol) in dichloromethane (15 mL) was added aluminum trichloride (0.517 g, 3.86 mmol). The resulting mixture was allowed to stir for 5 min and was then treated with chloroacetyl chloride (0.35 mL, 3.86 mmol). The reaction mixture was allowed to warm to room temperature and stir for 16 h, before it was poured onto ice cold water (10 mL). The mixture was extracted with dichloromethane (2×10 mL) and the combined organic extracts were washed with water (2×10 mL). The organic layer was dried over sodium sulfate, filtered, and concentrated in vacuo to afford crude product. The crude product mixture was purified by column chromatography on silica gel (100-200 mesh) using 30% ethyl acetate in hexanes as the eluent to afford LXVII (0.1 g, 25%) as an off-white solid. The material was carried forward without any further purification or characterization.

Synthesis of 4-(2-Methyl-3-(2-(piperidin-1-yl)acetyl)-1H-pyrrolo[2,3-b]pyridin-1-yl)benzonitrile (141): To an ice-cooled solution of LXVII (0.1 g, 0.324 mmol) in N,N-dimethylformamide (5 mL) was added potassium carbonate (0.13 g, 0.97 mmol), followed by piperidine (0.041 g, 0.485 mmol). The mixture was allowed to warm to room temperature and stir for 2 h. The reaction mixture was poured onto ice cold water and the precipitate that formed was collected via filtration, washed with water, and dried in a stream of air to afford 141 (0.08 g, 70%) as an off-white solid. $^1$H NMR (400 MHz, CDCl$_3$): δ 8.34 (d, J=8.0 Hz, 1H), 8.27-8.25 (m, 1H), 7.90 (d, J=8.4 Hz, 2H), 7.55 (d, J=8.4 Hz, 2H), 7.28-7.26 (m, 1H), 3.76 (s, 2H), 2.68 (s, 3H), 2.64 (s, 4H), 1.67-1.64 (m, 4H), 1.48 (s, 2H); MS (ESI, positive mode) m/z 359 (MH$^-$).

Example 27

4-(2-Methyl-3-(2-(piperidin-1-yl)acetyl)-1H-pyrrolo[2,3-c]pyridin-1-yl)benzonitrile (Compound 144)

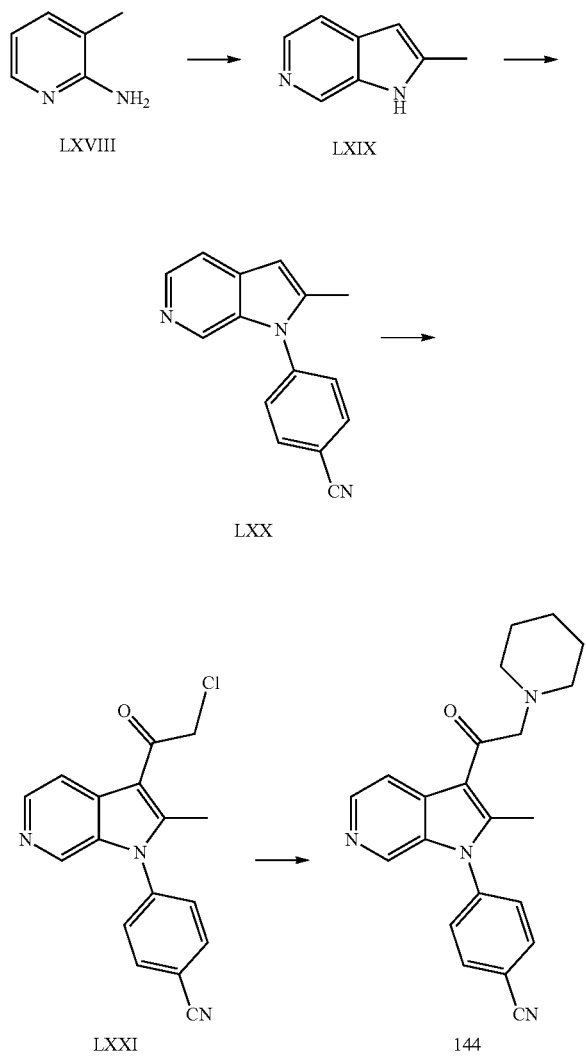

Synthesis of 2-Methyl-1H-pyrrolo[2,3-c]pyridine (LXIX). To a solution of 3-amino-4-methylpyridine (2.16 g, 0.020 mol) in anhydrous tetrahydrofuran (80 mL), maintained at −78° C., was slowly added sec-butyl lithium (59 mL, 0.058 mol, 1.0 M solution in cyclohexane). The reaction mixture was allowed to warm at room temperature and stir for 3 h. The reaction mixture was again cooled to −78° C. and a solution of methyl acetate (0.44 g, 0.006 mol) in tetrahydrofuran (1 mL) was added to the reaction mixture over 5 minutes. The mixture was allowed to warm to −30° C. and stir for 0.5 h. The reaction was quenched with methanol (20 mL) and then allowed warmed to room temperature. After 1 h of additional stirring the reaction mixture was poured onto an aqueous, saturated solution of ammonium chloride (30 mL) and the resulting mixture was extracted with ethyl acetate (3×100 mL). The combined organic extracts were dried over anhydrous sodium sulfate and concentrated under vacuum. The crude product mixture was purified by chromatography on basic alumina using 1.2% methanol in dichloromethane as the eluant to afford compound LXIX (250 mg, 10%). $^1$H NMR (400 MHz, CDCl$_3$): δ 8.88 (brs, 1H), 8.69 (s, 1H), 8.19 (d, J=5.3 Hz, 1H), 7.41 (d, J=5.3 Hz, 1H), 6.24 (s, 1H), 2.49 (s, 3H); MS (ESI, positive mode) m/z 359 (MH$^+$).

Synthesis of 4-(2-Methyl-pyrrolo[2,3-c]pyridin-1-yl)-benzonitrile (LXX): A mixture of LXIX (0.25 g, 1.90 mmol), potassium phosphate (1.42 g, 6.80 mmol) and copper(I) iodide (0.04 g, 0.0032 mol) in 1,4-dioxane (30 mL) was sparged with nitrogen gas for 0.5 h. Then 4-iodobenzonitrile (0.73 g, 3.20 mmol) and (+/−)-trans-1,2-diaminocyclohexane (0.04 g, 0.004 mol) were added to the flask. The resulting mixture was kept under a nitrogen atmosphere and heated at reflux for 48 h. After cooling to room temperature the volatiles were removed under vacuum and the remaining residue was diluted with ice-water. The aqueous mixture was extracted with ethyl acetate (3×20 mL) and the combined organic extracts were washed with brine, dried over anhydrous sodium sulfate, and concentrated under vacuum. The crude product mixture was purified by chromatography on basic alumina using 60% dichloromethane in hexanes as the eluant to obtain LXX (90 mg, 20%) as an off-white solid. $^1$H NMR (400 MHz, CDCl$_3$): δ 8.47 (s, 1H), 8.27 (d, J=4.9 Hz, 1H), 7.87 (dd, J=6.7, 1.8 Hz, 2H), 7.52 (dd, J=6.7, 1.8 Hz, 2H), 7.46 (d, J=4.9 Hz, 1H), 6.46 (s, 1H), 2.36 (s, 3H); MS (ESI, positive mode) m/z 359 (MH$^+$).

Synthesis of 4-[3-(2-Chloro-acetyl)-2-methyl-pyrrolo[2,3-c]pyridin-1-yl]-benzonitrile (LXXI): To an ice-cooled solution of LXX (0.090 g, 0.390 mmol) in dry dichloromethane (7 mL) was added neat chloro acetyl chloride (0.130 g, 1.10 mmol), followed by the addition of powdered anhydrous aluminum trichloride (0.156 g, 1.10 mmol). The reaction mixture was allowed to warm to room temperature and stir for 16 h. The reaction was quenched with ice-water and then neutralized with an aqueous, saturated solution of sodium bicarbonate. The aqueous mixture was extracted with dichloromethane (3×10 mL) and the combined organic extracts were dried over anhydrous sodium sulfate. The organic layer was concentrated under vacuum and the remaining crude product mixture was purified by column chromatography on (100-200 mesh) silica gel, using 5% methanol in dichloromethane as the eluant, to obtain LXXI (0.060 g, 53%) as an off-white solid. $^1$H NMR (400 MHz, CDCl$_3$): δ 8.50 (d, J=5.6 Hz, 1H), 8.42 (s, 1H), 7.96 (dd, J=6.6 Hz, 2H), 7.78 (d, J=5.6 Hz, 1H), 7.53 (dd, J=6.6 Hz, 2H), 4.71 (s, 2H), 2.67 (s, 3H); MS (ESI, positive mode) m/z 310/312 (MH$^+$, $^{35/37}$Cl).

Synthesis of 4-[2-Methyl-3-(2-piperidin-1-yl-acetyl)-pyrrolo[2,3-c]pyridin-1-yl]benzonitrile (144): To an ice-cooled solution of LXXI (60 mg, 0.190 mmol) in dry N,N-dimethylformamide (1 mL) was slowly added neat piperidine (35 mg, 0.380 mmol). The reaction mixture was allowed to stir for 1 h at 0° C. and was then poured into ice-cold water. The precipitate that formed was collected via filtration, washed with water, and allowed to dry under vacuum to afford 144 (25 mg, 36%) as an off-white solid. $^1$H NMR (400 MHz, CDCl$_3$): δ 8.44 (d, J=5.5 Hz, 1H), 8.39 (s, 1H), 7.94 (d, J=8.4 Hz, 2H), 7.87 (d, J=5.5 Hz, 1H), 7.52 (d, J=8.4 Hz, 2H), 3.75 (s, 2H), 2.65 (s, 3H), 2.58 (brs, 4H), 1.67-1.60 (m, 4H), 1.48 (brs, 2H); MS (ESI, positive mode) m/z 359 (MH$^+$).

Example 28

4-(2-Methyl-3-(2-(piperidin-1-yl)acetyl)-1H-pyrrolo[3,2-c]pyridin-1-yl)benzonitrile (Compound 151)

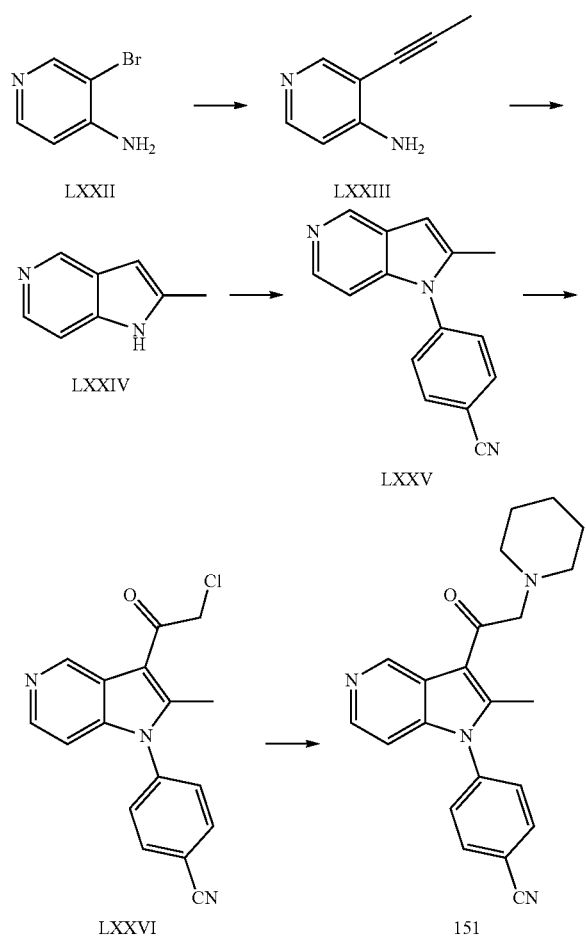

Synthesis of 3-Prop-1-ynyl-pyridin-4-ylamine (LXXIII). To a solution of LXXII (1.5 g, 8.67 mmol) in N,N-dimethylformamide (20 mL) was added solid sodium acetate (2.1 g, 0.02106 mol). The resulting mixture was degassed for 10 min and then [1,1'-bis(diphenylphosphino)ferrocene]dichloropalladium(II) (0.31 g, 0.430 mmol), followed by tributyl (prop-1-yn-1-yl)stannane (3.7 g, 11.3 mmol), were added. The reaction mixture was heated at 100° C. in a sealed tube for 12 h, before being allowed to cool to room temperature. The reaction mixture was poured in to water and the mixture was extracted with ethyl acetate (3×50 mL). The combined organic extracts were dried over sodium sulfate and concentrated in vacuo. The crude product mixture was purified by column chromatography on (100-200 mesh) silica, using 3% methanol in dichloromethane as the eluant to afford LXXIII (1 g, 87%) as a semi solid. $^1$H NMR (400 MHz, CDCl$_3$) δ 8.29 (s, 1H), 8.08 (d, 2H, J=5.7 Hz), 6.50 (d, 2H, J=5.6 Hz), 4.61 (brs, 2H), 2.11 (s, 3H); MS (ESI, positive mode) m/z 133 (MH$^+$).

Synthesis of 2-Methyl-1H-pyrrolo[3,2-c]pyridine (LXXIV). To a solution of LXXIII (900 mg, 6.81 mmol) in N,N-dimethylformamide (10 mL) was added solid potassium tert-butoxide (1.9 g, 0.017 mol). The reaction mixture was allowed to stir at room temperature for 2 h before it was poured into ice-water. The precipitate that formed was collected by filtration and allowed to dry in a stream of air to obtain LXXIV (550 mg, 61%) as an off-white solid. $^1$H NMR (400 MHz, DMSO-d$_6$) δ 11.33 (s, 1H), 8.65 (s, 1H), 8.05 (d, 2H, J=5.5 Hz), 7.23 (d, 2H, J=5.5 Hz), 6.23 (s, 1H), 2.39 (s, 3H); MS (ESI, positive mode) m/z 359 (MH$^+$).

Synthesis of 4-(2-Methyl-pyrrolo[3,2-c]pyridin-1-yl)-benzonitrile (LXXV) In a screw cap bottle was prepared a mixture of compound LXXIV (0.440 g, 3.33 mmol), 4-iodobenzonitrile (1.5 g, 6.66 mmol) and potassium phosphate (2.11 g, 9.99 mmol) in 1,4-dioxane (15 mL). The mixture was sparged with nitrogen gas for 30 min and then (+/−)-trans-1,2-diaminocyclohexane (0.037 g, 0.660 mmol) and copper(I) iodide (~6 mg) was added. The tube was tightly sealed and then heated at 110° C. for 16 h. After cooling to room temperature the excess solvent was removed under vacuum and ice-water (20 mL) was poured over the remaining residue. The aqueous mixture was extracted with ethyl acetate (3×30 mL) and the combined organic extracts were dried over anhydrous sodium sulfate. The organic layer was condensed in vacuo and the remaining crude product mixture was purified by chromatography on basic alumina using 40% ethyl acetate in hexanes as the eluant to afford LXXV (200 mg, 26%) as an off-white solid. $^1$H NMR (400 MHz, CDCl$_3$) δ 8.86 (d, 1H, J=0.5 Hz), 8.2 (d, 1H, J=5.8 Hz), 7.88-7.75 (m, 2H), 7.50-7.47 (m, 2H), 7.01 (d, 1H, J=5.8 Hz), 6.53 (s, 1H), 2.34 (s, 3H); MS (ESI, positive mode) m/z 234 (MH$^-$).

Synthesis of 4-[3-(2-Chloro-acetyl)-2-methyl-pyrrolo[3,2-c]pyridin-1-yl]-benzonitrile (LXXVI). To an ice-cooled suspension of anhydrous aluminum chloride (0.128 g, 0.960 mmol) in dry 1,2-dichloroethane (5 mL) was added neat chloro acetyl chloride (0.15 g, 0.960 mmol) in a dropwise fashion. The reaction mixture was allowed to stir for 30 min at 0° C. and then a solution of LXXV (0.15 g, 0.640 mmol) in dry 1,2-dichloroethane (1 mL) was added in single portion. The reaction mixture was allowed to warm to room temperature and was then heated at 60° C. for 1 h. Additional aluminum chloride (0.5 equiv.) and chloro acetyl chloride (0.5 equiv.) were added to the reaction mixture at 60° C. After 1 h of additional heating, the reaction was poured over ice-water (20 mL) and the aqueous mixture was basified with an aqueous saturated solution of sodium bicarbonate. The mixture was extracted with dichloromethane (3×10 mL) and the combined organic extracts were dried over anhydrous sodium sulfate. Evaporation of the organic layer afforded the crude product mixture, which was purified by column chromatography on neutral alumina using 40% ethyl acetate in hexanes as the eluant to afford a solid. The solid was triturated with n-pentane (2×2 mL) and allowed to dry in a stream of air to afford LXXVI as an off-white solid (85 mg, 43%). $^1$H NMR (400 MHz, CDCl$_3$) δ 9.27 (s, 1H), 8.41 (d, 1H, J=5.6 Hz), 7.95 (d, 2H, J=8.5 Hz), 7.49 (d, 2H, J=8.5 Hz), 6.97 (d, 1H, J=5.6 Hz), 4.74 (s, 2H), 2.16 (s, 3H).

Synthesis of 4-[2-Methyl-3-(2-piperidin-1-yl-acetyl)-pyrrolo[3,2-c]pyridin-1-yl]-benzonitrile (151). To a solution of LXXVI (0.060 g, 0.190 mmol) in dry N,N-dimethylformamide (0.5 mL), kept at 0° C., was added piperidine (0.030 g, 0.380 mmol). The reaction mixture was allowed to warm to room temperature and stir for 30 min. The reaction mixture was then poured into crushed ice (10 mL) and stirred for 15 min. The pale yellow precipitate that formed was collected by filtration and washed with water (10 mL). After drying, the filtered solid was then recrystallized from a mixture of dichloromethane and, n-pentane to afford 151 (20 mg, 29%) as an off-white solid. $^1$H NMR (400 MHz, CDCl$_3$): δ 9.33

(s, 1H), 8.36 (d, 1H, J=5.8 Hz), 7.93 (d, 2H, J=8.6 Hz), 7.48 (d, 2H, J=8.6 Hz), 6.94 (d, J=5.9 Hz, 2H), 3.77 (s, 2H), 2.62 (s, 3H), 2.59 (brs, 4H), 1.66-1.61 (m, 4H), 1.51-1.47 (m, 2H); MS (ESI, positive mode) m/z 359 (MH⁺).
Examples 29-31
1-(4-Chlorophenyl)-2-methyl-3-(2-(piperidin-1-yl)acetyl)-1H-indol-6-yl Acetate (Compound 172), 1-(1-(4-Chlorophenyl)-6-hydroxy-2-methyl-1H-indol-3-yl)-2-(piperidin-1-yl)ethan-1-one (Compound 148), 2-((1-(4-Chlorophenyl)-2-methyl-3-(2-(piperidin-1-yl)acetyl)-1H-indol-6-yl)oxy)acetamide (Compound 179)
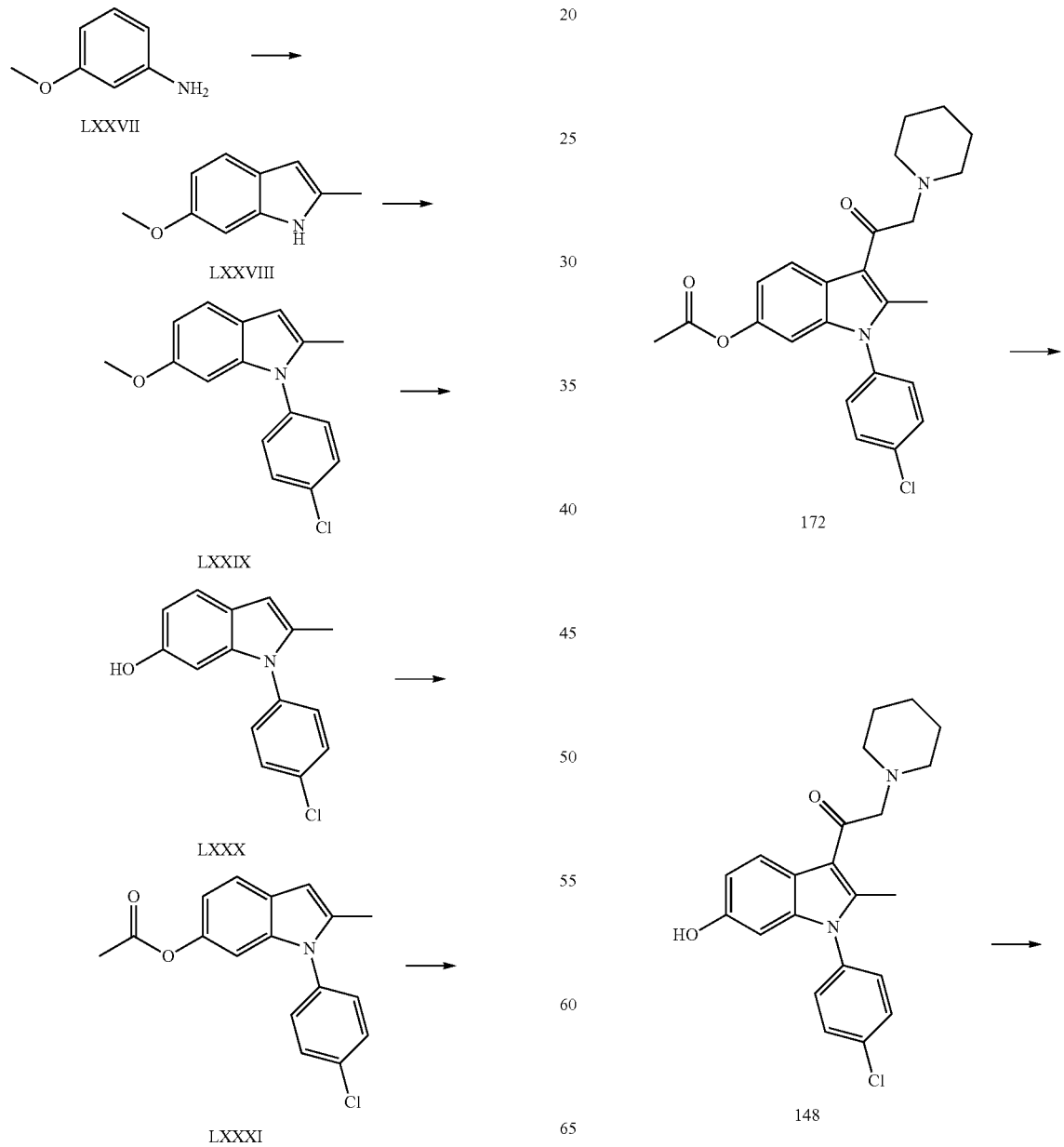

183

-continued

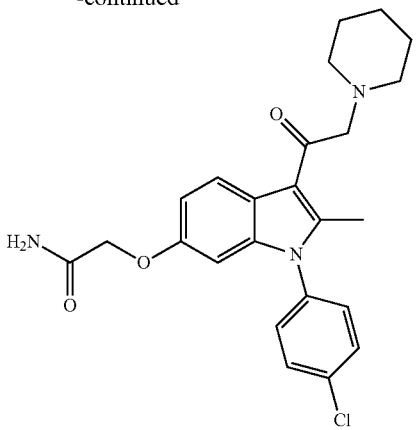

179

Synthesis of 6-Methoxy-2-methyl-1H-indole (LXXVIII): To a solution of 3-methoxyaniline (7.0 g, 0.057 mol) in dimethylsulfoxide (80 mL) was added copper(II) acetate-hydrate (17.0 g, 0.085 mol). The mixture was sparged with nitrogen for 0.5 h and then acetone (100 mL), followed by palladium(II) acetate (0.255 g, 1.13 mmol), were added. The mixture was heated at 80° C. for 48 h, before being allowed to cool to room temperature. The volatiles were removed under vacuum and the remaining residue was poured into cold water (80 mL). The aqueous mixture was extracted with ethyl acetate (3×80 mL) and the combined organic extracts were dried over anhydrous sodium sulfate. The organic layer was concentrated in vacuo and the remaining crude product mixture was purified by column chromatography (100-200 mesh) silica gel using 5% ethyl acetate in hexanes to afford LXXVIII (0.34 g, 4%) as an off-white solid. $^1$HNMR (400 MHz, CDCl$_3$): δ 7.72 (brs, 1H), 7.36 (d, J=8.6 Hz, 1H), 6.80 (s, 1H), 6.72 (dd, J=8.5, 2.3 Hz, 1H), 6.12 (s, 1H), 3.82 (s, 3H), 2.39 (s, 3H); MS (ESI, positive mode) m/z 162 (MH$^+$).

Synthesis of 1-(4-Chloro-phenyl)-6-methoxy-2-methyl-1H-indole (LXXIX): To a degassed solution of LXXVIII (0.650 g, 4.03 mmol) in 1,4-dioxane (50 mL) were added 1-chloro-4-iodo-benzene (0.96 g, 4.03 mmol), potassium phosphate (1.54 g, 7.25 mmol), copper(I) iodide (0.038 g, 0.200 mmol), and trans-(+/−)-1,2-diamino-cyclohexane (0.041 g, 0.362 mmol). The resultant reaction mixture was heated at 110° C. for 24 h, before being allowed to cool to room temperature. The reaction mixture was filtered through a celite bed and the filter cake was washed with ethyl acetate. The filtrate was concentrated in vacuo and the remaining crude product mixture was purified by column chromatography on (100-200 mesh) silica using 5% ethyl acetate in hexanes as the eluant to afford LXXIX (0.550 g, 50%). $^1$H NMR (400 MHz, CDCl$_3$): δ 7.49 (d, J=8.6 Hz, 2H), 7.41 (d, J=8.6 Hz, 1H), 7.28 (d, J=8.6 Hz, 2H), 6.76 (dd, J=8.6, 2.3 Hz, 1H), 6.55 (d, J=2.1 Hz, 1H), 6.30 (s, 1H), 3.74 (s, 3H), 2.23 (s, 3H); MS (ESI, positive mode) m/z 272/274 (MH$^+$, $^{35/37}$Cl).

Synthesis of 1-(4-Chloro-phenyl)-2-methyl-1H-indol-6-ol (LXXX): To an ice-cooled solution of LXXIX (0.200 g, 0.735 mmol) in dichloromethane (12 mL) was added boron tribromide (0.264 g, 1.05 mmol). The mixture was allowed to warm to room temperature and stir for 3 h. The reaction mixture was then poured onto ice-cold water and the mixture was extracted with dichloromethane (3×20 mL). The combined organic extracts were washed with an aqueous saturated solution of sodium bicarbonate and brine. The organic layer was dried over anhydrous sodium sulfate and then concentrated under vacuum to afford crude LXXX (0.150 g, 79%). $^1$H NMR (400 MHz, CDCl$_3$): δ 7.47 (d, J=8.6 Hz, 2H), 7.37 (d, J=8.4 Hz, 1H), 7.25 (d, J=8.6 Hz, 2H), 6.65 (dd, J=8.4, 2.2 Hz, 1H), 6.53 (d, J=2.2 Hz, 1H), 6.30 (s, 1H), 4.54 (s, 1H), 2.23 (s, 3H); MS (ESI, positive mode) m/z 258/260 (MH$^+$, $^{35/37}$Cl).

Synthesis of 1-(4-Chlorophenyl)-2-methyl-1H-indol-6-yl Acetate (LXXXI): To a cold solution of LXXX (0.500 g, 1.94 mmol) in dichloromethane (30 mL) were added acetic anhydride (0.237 g, 2.32 mmol) and triethylamine (0.392 g, 3.88 mmol). The reaction mixture was allowed to warm to room temperature and stir for 3 h. The reaction was quenched with methanol (1 mL) and then washed with brine. The organic layer was dried over anhydrous sodium sulfate and then concentrated under vacuum. The crude product mixture was purified by chromatography on (100-200 mesh) silica gel using 2% ethyl acetate in hexanes to afford LXXXI (0.435 g, 75%). $^1$H NMR (400 MHz, CDCl$_3$): δ 7.51-7.46 (m, 3H), 7.27 (d, J=8.6 Hz, 2H), 6.82 (dd, J=8.4, 2.0 Hz, 1H), 6.77 (d, J=1.8 Hz, 1H), 6.37 (s, 1H), 2.26 (s, 3H), 2.24 (s, 3H); MS (ESI, positive mode) m/z 300/302 (MH$^+$, $^{35/37}$Cl).

Synthesis of 3-(2-Chloroacetyl)-1-(4-chlorophenyl)-2-methyl-1H-indol-6-yl Acetate (LXXXII): To a suspension of aluminum chloride (0.133 g, 0.001 mmol) in dichloromethane (10 mL), kept at 0° C., was added chloro acetyl chloride (0.1230 g, 0.0010 mole). The mixture was allowed to stir at 0° C. for 0.5 h and then a solution of LXXXI (0.150 g, 0.500 mmol) in dichloromethane (5 mL) was added. The reaction mixture was allowed to warm to room temperature and stir for 4 h, after which the system was heated at 50° C. for 1.5 h. After cooling to room temperature the reaction mixture was poured onto ice-cold water and the resulting mixture was extracted with dichloromethane. The combined organic extracts were washed with an aqueous 10%-sodium bicarbonate solution and then dried over sodium sulfate. After condensing the organic layer the crude product mixture was purified by chromatography on (100-200 mesh) silica gel using 5% ethyl acetate in hexanes as the eluant to afford LXXXII (0.090 g, 48%) as a brown solid. $^1$H NMR (400 MHz, CDCl$_3$): δ 7.90 (d, J=8.7 Hz, 1H), 7.56 (d, J=8.6 Hz, 2H), 7.25 (d, occluded by solvent, 2H), 7.04 (dd, J=8.7, 2.2 Hz, 1H), 6.75 (d, J=2.1 Hz, 1H), 4.70 (s, 2H), 2.59 (s, 3H), 2.25 (s, 3H); MS (ESI, positive mode) m/z 376/378 (MH$^+$, $^{35/37}$Cl).

Synthesis of 1-(4-Chlorophenyl)-2-methyl-3-(2-(piperidin-1-yl)acetyl)-1H-indol-6-yl Acetate (172): To a cold solution of LXXXII (0.070 g, 0.186 mmol) in N,N-dimethylformamide (2 mL) was added piperidine (0.019 g, 0.223 mmol). The reaction mixture was allowed to warm to room temperature and stir for 2 h. The reaction mixture was poured onto ice-cold water and the resulting precipitate that formed was collected by filtration. The filtered material was washed with water and allowed to dry in a stream of air to obtain the crude product. The crude solid was triturated with diethyl ether and then dried to afford product 172 (0.014 g, 17%) as an off-white solid. $^1$H NMR (400 MHz, CDCl$_3$): δ 8.02 (d, J=8.7 Hz, 1H), 7.54 (d, J=8.4 Hz, 2H), 7.25 (d, occluded by solvent, 2H), 7.00 (d, J=8.6 Hz, 1H), 6.71 (s, 1H), 3.74 (s, 2H), 2.52-2.64 (m, 7H), 2.26 (s, 3H), 1.58-1.68 (m, 4H), 1.47 (brs, 2H); MS (ESI, positive mode) m/z 376/378 (MH$^+$, $^{35/37}$Cl).

Synthesis of 1-(1-(4-Chlorophenyl)-6-hydroxy-2-methyl-1H-indol-3-yl)-2-(piperidin-1-yl)ethan-1-one (148): To a cold solution of 172 (0.150 g, 0.352 mmol) in ethanol (10 mL) was added solid potassium carbonate (0.058 g, 0.423 mmol). The reaction mixture was allowed to warm to room temperature and stir for 2 h. The reaction mixture was condensed in vacuo and the remaining residue was treated with cold water. The precipitate that formed was collected by filtration, washed with water and allowed to dry in a stream of air. The crude product was triturated with pentane and then dried to afford product 148 (0.070 g, 52%) as an off-white solid. $^1$H NMR (400 MHz, CDCl$_3$): δ 7.87 (d, J=8.7 Hz, 1H), 7.53 (d, J=8.6 Hz, 2H), 7.25 (d, occluded by solvent, 2H), 6.80 (dd, J=8.6, 2.2 Hz, 1H), 6.44 (d, J=2.2 Hz, 1H), 3.73 (s, 2H), 2.60 (brs, 4H), 2.53 (s, 3H), 1.67-1.60 (m, 4H), 1.46 (brs, 2H); MS (ESI, positive mode) m/z 383/385 (MH$^+$, $^{35/37}$Cl).

Synthesis of 2-((1-(4-Chlorophenyl)-2-methyl-3-(2-(piperidin-1-yl)acetyl)-1H-indol-6-yl)oxy)acetamide (179): To a solution of 148 (0.120 g, 0.314 mmol) in N,N-dimethylformamide (5 mL) was added solid cesium carbonate (0.205 g, 0.628 mmol), followed by 2-bromo-acetamide (0.087 g, 0.628 mmol). The reaction mixture was allowed to warm to room temperature and stir for 4 h. The reaction mixture was poured onto ice-water and the precipitate that formed was collected via filtration. The filtered solid was washed with water and dried to afford crude product. The crude solid was triturated with pentane, followed by diethyl ether, and then dried to afford 179 (44 mg, 32%) as an off-white solid. $^1$H NMR (400 MHz, CDCl$_3$): δ 7.99 (d, J=8.8 Hz, 1H), 7.57 (d, J=8.5 Hz, 2H), 7.25 (d, occluded by solvent, 2H), 6.93 (dd, J=8.8, 2.3 Hz, 1H), 6.54 (brs, 1H), 6.47 (d, J=2.3 Hz, 1H), 5.53 (brs, 1H), 4.43 (s, 2H), 3.72 (s, 2H), 2.59 (brs, 4H), 2.55 (s, 3H), 1.60-1.68 (m, 4H), 1.42-1.50 (m, 2H); MS (ESI, positive mode) m/z 440/442 (MH$^+$, $^{35/37}$Cl).

Example 32

N-((1-(4-Cyanophenyl)-2-methyl-3-(2-(piperidin-1-yl)acetyl)-1H-indol-5-yl)methyl)acetamide (Compound 183)

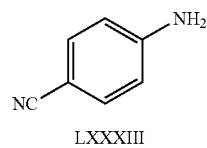

LXXXIII

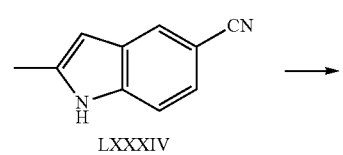

LXXXIV

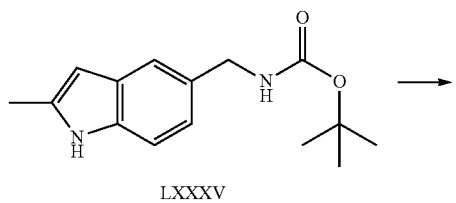

LXXXV

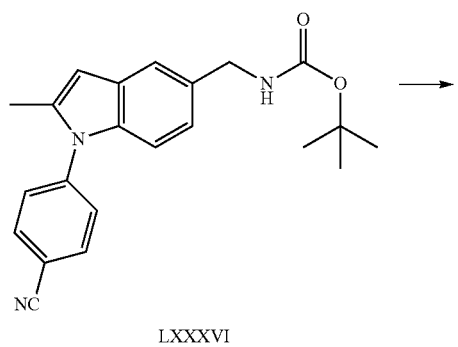

LXXXVI

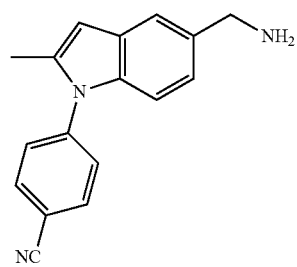

LXXXVII

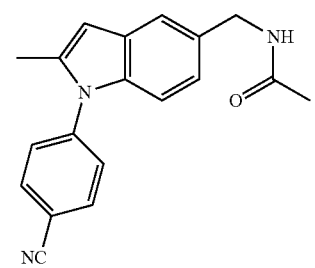

LXXXVIII

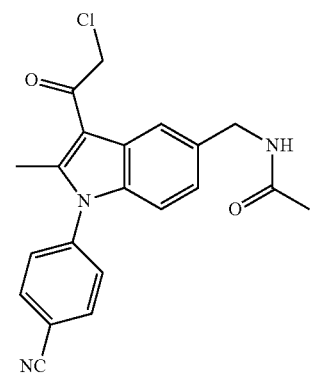

LXXXIX

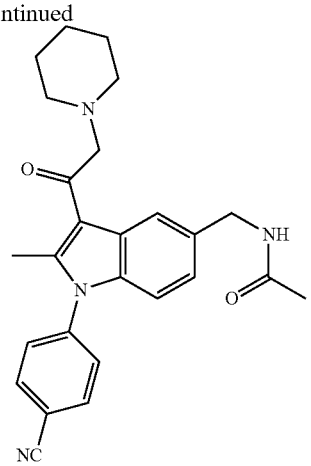

183

Synthesis of 2-Methyl-1H-indole-5-carbonitrile (LXXXIV): In a sealed tube, a suspension of compound LXXXIII (5.0 g, 42.3 mmol) and copper(II) acetate (11.5 g, 63.4 mmol) in dimethylsulfoxide (20 mL) was sparged with nitrogen gas for 0.5 h. Acetone (100 mL) and palladium (II) acetate (0.189 g, 0.840 mmol) were then added to the reaction mixture and the tube was sealed. The system was heated at 85-90° C. for 48 h and then allowed to cool to room temperature. The volatiles were removed under vacuum and the remaining material was poured into cold water (80 mL). The aqueous mixture was extracted with ethyl acetate (3×80 mL) and the combined organic extracts were dried over anhydrous sodium sulfate, before being concentrated under reduced pressure to obtain the crude product mixture. The crude product was purified by flash chromatography on silica to afford compound LXXXIV (1.3 g, 20%) as an off-white solid. $^1$H NMR (400 MHz, CDCl$_3$): δ 8.16 (brs, 1H), 7.83 (s, 1H), 7.36-7.30 (m, 2H), 6.28 (s, 1H), 2.46 (s, 3H); MS (ESI, negative mode) m/z 155 (M$^-$-H).

Synthesis of tert-Butyl ((2-Methyl-1H-indol-5-yl)methyl) carbamate (LXXXV): To a cooled (0° C.) solution of compound LXXXIV (1.20 g, 7.60 mmol) in methanol (50 mL) was added di-tert-butyl-dicarbonate (6.64 g, 30.7 mmol) and nickel (II) chloride-hexahydrate (0.182 g, 0.768 mmol). Subsequently sodium borohydride (2.03 g, 5.37 mmol) was added to the reaction mixture in a portion-wise manner. The resulting mixture was allowed to stir at the reduced temperature for 1.5 h and then warm to room temperature and stir for 6 h. The reaction mixture was concentrated under reduced pressure, diluted with water, and then extracted with ethyl acetate (3×50 mL). The combined organic extracts were dried over anhydrous sodium sulfate and then evaporated to afford the crude product mixture. The crude product was purified by column chromatography on (100-200 mesh) silica gel using 20% ethyl acetate in hexanes as the eluant to afford compound LXXXV (1.30 g, 65%) as a brown, sticky mass. $^1$H NMR (400 MHz, CDCl$_3$): δ 7.85 (brs, 1H), 7.39 (s, 1H), 7.23 (d, J=8.2 Hz, 1H), 7.02 (d, J=8.2 Hz, 1H), 6.16 (s, 1H), 4.76 (brs, 1H), 4.36 (d, J=5.4 Hz, 2H), 2.43 (s, 3H), 1.45 (s, 9H); MS (ESI, positive mode) nm/z 261 (MH$^+$).

Synthesis of tert-Butyl ((1-(4-Cyanophenyl)-2-methyl-1H-indol-5-yl)methyl)carbamate (LXXXVI): In a sealed tube, a mixture of compound LXXXV (1.00 g, 3.84 mmol), 4-iodo-benzonitrile (0.879 g, 3.84 mmol), and potassium phosphate (1.47 g, 6.90 mmol) in 1,4-dioxane (50 mL) was sparged with nitrogen gas for 0.5 h. Then copper (I) iodide (0.036 g, 1.90 mmol) was and trans-(+/−)-1,2-diamino-cyclohexane (0.039 g, 3.40 mmol) were added to the reaction mixture. The vessel was sealed and then heated at 110° C. for 24 h. After cooling to room temperature the reaction mixture was filtered through celite and the filter pad was washed with ethyl acetate. The filtrate was concentrated under vacuum to obtain crude product mixture, which was then chromatographed on (100-200 mesh) silica gel using 20% ethyl acetate in hexanes to afford compound LXXXVI (0.650 g, 47%) as an off-white solid. $^1$H NMR (400 MHz, CDCl$_3$): δ 7.84 (d, J=6.5 Hz, 2H), 7.48-7.46 (m, 3H), 7.06-7.05 (m, 2H), 6.40 (s, 1H), 4.82 (brs, 1H), 4.37 (d, J=5.6 Hz, 2H), 2.31 (s, 3H), 1.45 (s, 9H); MS (ESI, positive mode) m/z 362 (MH$^+$).

Synthesis of 4-(5-Aminomethyl-2-methyl-indol-1-yl)-benzonitrile (LXXXVII): To a cold solution of compound LXXXVI (0.110 g, 0.304 mmol) in 1,4-dioxane (1 mL) was added a 4.0 M solution of hydrochloric acid in 1,4-dioxane (2 mL). The mixture was allowed to warm to room temperature and stir for 1 h. The volatiles were removed under reduced pressure and the remaining material was triturated with n-pentane to afford the hydrochloride salt of compound LXXXVII (0.115 g) as a pale-yellow solid. $^1$H NMR (400 MHz, DMSO-d$_6$): δ 8.16 (brs, 3H), 8.10 (d, J=8.3 Hz, 2H), 7.70 (d, J=8.3 Hz, 2H), 7.63 (s, 1H), 7.17 (s, 2H), 6.53 (s, 1H), 4.08 (d, J=5.6 Hz, 2H), 2.32 (s, 3H); MS (ESI, positive mode) m/z 262 (MH$^+$), 245 (MH$^+$-NH$_3$).

Synthesis of N-[1-(4-Cyano-phenyl)-2-methyl-1H-indol-5-ylmethyl]-acetamide (LXXXVIII): To a cold (0° C.) solution of compound LXXXVII (0.110 g, 0.420 mmol) in dichloromethane (5 mL) was added acetic anhydride (0.051 g, 0.504 mmol) and triethylamine (0.084 g, 0.840 mmol). Reaction mixture was allowed to warm to room temperature and stir for 3 h. The reaction was quenched with methanol (0.5 mL), poured into ice-water, and then extracted with dichloromethane (2×20 mL). The combined organic extracts were dried over anhydrous sodium sulfate and concentrated under vacuum to obtain the crude product mixture. The crude product was purified by column chromatography on neutral alumina using ethyl acetate to afford compound LXXXVIII (0.060 g, 47%) as an off-white solid. $^1$H NMR (400 MHz, CDCl$_3$) δ 7.83 (d, J=6.6 Hz, 2H), 7.48-7.46 (m, 3H), 7.08-7.03 (m, 2H), 6.41 (s, 1H), 5.67 (brs, 1H), 4.50 (d, J=5.5 Hz, 2H), 2.31 (s, 3H), 2.01 (s, 3H); MS (ESI, positive mode) m/z 304 (MH$^+$).

Synthesis of N-[3-(2-Chloro-acetyl)-1-(4-cyano-phenyl)-2-methyl-1H-indol-5-ylmethyl]-acetamide (LXXXIX): To a cold (0° C.) suspension of aluminum chloride (0.240 g, 1.70 mmol) in 1,2-dichloroethane (10 mL) was added chloro-acetyl chloride (0.426 g, 3.46 mmol). The resulting mixture was allowed to warm to room temperature and stir for 0.5 h. After cooling the reaction mixture back to 0° C., a solution of compound LXXXVIII (0.100 g, 0.329 mmol) in 1,2-dichloro-ethane (2 mL) was then added to the reaction mixture. The system was allowed to warm, again, to room temperature and stir for 4 h and warmed further at 60° C. for 1 h. After cooling to room temperature, the reaction mass was poured into ice cold water and extracted with dichloromethane (20 mL). The organic extract was washed with a 10% aqueous sodium bicarbonate solution and then dried over anhydrous sodium sulfate. The organic layer was then concentrated under vacuum to obtain the crude product mixture. The crude was purified by column chromatography on neutral alumina using 50% ethyl acetate in hexanes to afford compound LXXXIX (0.037 g, 30%) as an off-white solid. $^1$H NMR (400 MHz, DMSO-d$_6$): δ 8.38 (t, J=5.7 Hz, 1H), 8.17 (d, J=8.3 Hz, 2H), 8.01 (s, 1H), 7.73 (d, J=8.3 Hz, 2H), 7.12 (d, J=8.3 Hz, 1H), 6.99 (d, J=8.3 Hz, 1H), 5.03 (s, 2H), 4.36 (d, J=5.7 Hz, 2H), 2.59 (s, 3H), 1.86 (s, 3H); MS (ESI, positive mode) m/z 380/382 (MH⁺, ³⁵/³⁷Cl).

Synthesis of N-[1-(4-Cyano-phenyl)-2-methyl-3-(2-piperidin-1-yl-acetyl)-1H-indol-5-ylmethyl]-acetamide (183): To a cold (0° C.) solution of compound LXXXIX (0.037 g, 0.097 mmol) in N,N-dimethylformamide (1 mL) was added piperidine (0.012 g, 0.146 mmol). The mixture was allowed to warm to room temperature and stir for 2 h. The reaction mixture was then poured into ice cold water and the resulting precipitate was collected by filtration. The solids were washed with water and dried to afford product 183 (0.025 g, 61%) as an off white solid. ¹H NMR (400 MHz, DMSO-d₆): δ 8.36 (t, J=5.3 Hz, 1H), 8.15 (d, J=8.3 Hz, 2H), 8.00 (s, 1H), 7.72 (d, J=8.3 Hz, 2H), 7.08 (d, J=8.4 Hz, 1H), 6.96 (d, J=8.3 Hz, 1H), 4.34 (d, J=5.3 Hz, 2H), 3.60 (s, 2H), 2.55 (s, 3H), 2.46 (s, 3H), 1.85 (s, 3H), 1.49-1.08 (m, 4H), 1.39 (brs, 2H); MS (ESI, positive mode) m/z 429 (MH⁺).

Example 33

4-(5-Amino-2-methyl-3-(2-(piperidin-1-yl)acetyl)-1H-indol-1-yl)benzonitrile (Compound 186)

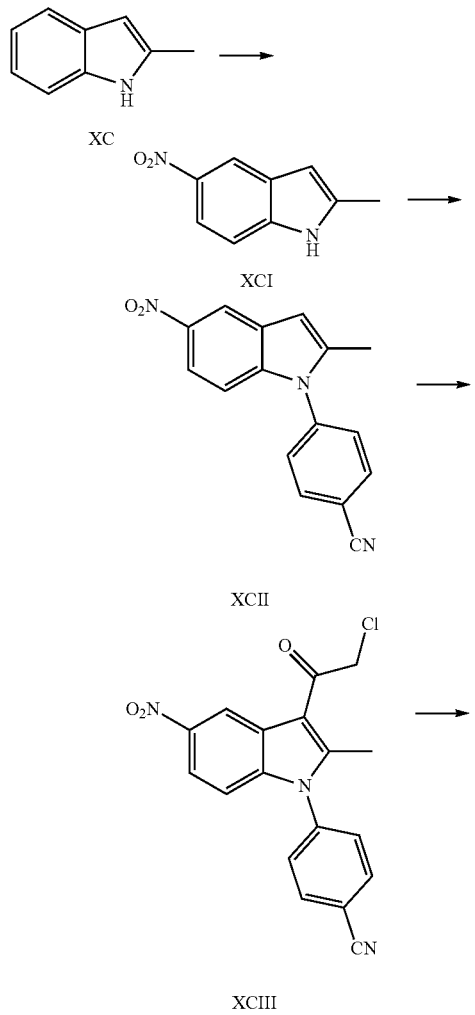

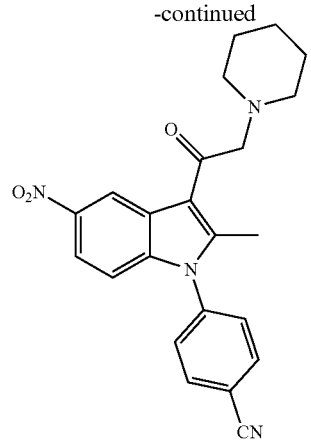

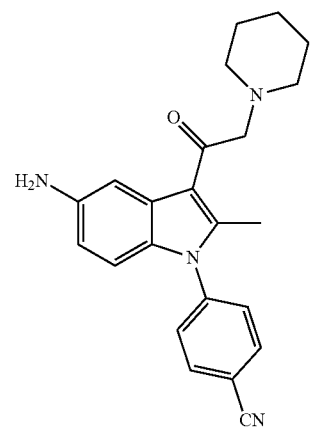

Synthesis of 2-Methyl-5-nitro-1H-indole (XCI): To an ice-cold solution of 2-methyl-1-H-indol (1.0 g, 7.60 mmol) in sulfuric acid (10 mL) was added sodium nitrate (0.78 g, 9.10 mmol) in sulfuric acid (10 mL) in a dropwise fashion. After the addition was completed, the reaction mixture was poured onto crushed ice and the precipitate that formed was collected via filtration. The filtered solid was washed with water and dried in a stream of air to afford XCI (0.5 g, 37%) as a yellow solid. ¹H NMR (400 MHz, CDCl₃+2-drops DMSO-d₆): δ 9.34 (brs, 1H), 8.41 (d, J=1.4 Hz, 1H), 7.96 (dd, J=1.3, 8.4 Hz, 1H), 7.26 (d, J=8.8 Hz, 1H), 6.33 (s, 1H), 2.44 (s, 3H); MS (ESI, positive mode) m/z 175 (MH⁺).

Synthesis of 4-(2-Methyl-5-nitro-indol-1-yl)-benzonitrile (XCII): A mixture of XCI (0.6 g, 3.40 mmol), 4-iodobenzonitrile (1.56 g, 6.80 mmol), potassium carbonate (1.40 g, 10.2 mmol) and 8-hydroxyquinoline (963 mg, 6.42 mmol) in dimethylsulfoxide (30 mL) was sparged with nitrogen gas for 0.5 h in a sealed tube. Then copper(I) iodide (0.65 g, 3.40 mmol) was finally added to the flask and the resulting mixture was heated at 140° C. for 24 h. After cooling to room temperature, the reaction mixture was filtered through celite bed and the filter cake was washed with ethyl acetate and water. The phases of the filtrate were separated and the organic layer was washed with water and brine. The organic layer was then dried over sodium sulfate and concentrated under vacuum to obtain the crude product. The crude product was purified by chromatography on (100-200 mesh) silica gel using 30% ethyl acetate in hexanes as the eluant to afford XCII (0.35 g, 37%) as an off-white solid. $^1$H NMR (400 MHz, CDCl$_3$): δ 8.51 (d, J=2.1 Hz, 1H), 8.02 (dd, J=2.1, 8.4 Hz, 1H), 7.89 (dd, J=1.7, 6.8 Hz, 2H), 7.50 (dd, J=1.8, 6.7 Hz, 2H), 7.08 (d, J=8.4 Hz, 1H), 6.61 (s, 1H), 2.33 (s, 3H); MS (ESI, positive mode) m/z 278 (MH$^+$).

Synthesis of 4-[3-(2-Chloro-acetyl)-2-methyl-5-nitro-indol-1-yl]-benzonitrile (XCIII): To a suspension of aluminum chloride (2.4 g, 0.018 mol) in 1,2-dichloroethane (20 mL), kept at 0° C., was added chloro acetyl chloride (1.6 mL, 0.018 mol). The mixture was allowed to warm to room temperature and stir for 0.5 h. Then the reaction mixture was cooled back to 0° C. and a solution of compound XCII (1.0 g, 3.60 mmol) in 1,2-dichloroethane (10 mL) was added. The resultant mixture was allowed to warm to room temperature and was then heated at 60° C. for 24 h. After cooling, the reaction mixture was poured onto ice cold water and then extracted with dichloromethane (40 mL). The organic layer was washed with an aqueous 10%-sodium bicarbonate solution and dried over anhydrous sodium sulfate. The organic layer was concentrated under vacuum and the remaining crude product mixture was purified by column chromatography on neutral alumina, using 30% ethyl acetate in hexanes as the eluant, to afford product XCIII (0.60 g, 46%) as an off-white solid. $^1$H NMR (400 MHz, CDCl$_3$): δ 8.94 (d, J=2.0 Hz, 1H), 8.13 (dd, J=2.1, 8.4 Hz, 1H), 7.97 (d, J=8.4 Hz, 2H), 7.51 (d, J=8.4 Hz, 2H), 7.06 (d, J=8.4 Hz, 1H), 4.73 (s, 2H), 2.64 (s, 3H); MS (ESI, positive mode) m/z 352 (MH$^+$).

Synthesis of 4-[2-Methyl-5-nitro-3-(2-piperidin-1-yl-acetyl)-indol-1-yl]-benzonitrile (XCIV): To a solution of compound XCIII (0.4 g, 1.13 mmol) in N,N-dimethylformamide (10 mL), kept at 0° C., was added potassium carbonate (0.313 g, 2.20 mmol), followed by piperidine (0.23 mL, 2.20 mmol). The mixture was allowed to stir for 1 h at the reduced temperature and then the reaction mixture was poured onto ice cold water. The precipitate that formed was collected by filtration, washed with water, and dried in a stream of air to afford XCIV (0.25 g, 56%) as an off-white solid. $^1$H NMR (400 MHz, CDCl$_3$): δ 9.11 (d, J=2.1 Hz, 1H), 8.08 (d, J=2.2, 8.4 Hz, 1H), 7.95 (dd, J=2.0, 8.4 Hz, 2H), 7.50 (dd, J=2.4, 8.4 Hz, 2H), 7.02 (d, J=8.6 Hz, 1H), 3.70 (s, 2H), 2.62 (s, 3H), 2.60-2.58 (m, 4H), 1.65-1.61 (m, 4H), 1.47-1.46 (m, 2H); MS (ESI, positive mode) m/z 403 (MH$^+$).

Synthesis of 4-(5-Amino-2-methyl-3-(2-(piperidin-1-yl)acetyl)-1H-indol-1-yl)benzonitrile (186): To a solution of XCIV (0.100 g, 0.250 mmol) in ethyl acetate (5 mL) was added tin(II) chloride (0.280 g, 1.20 mmol). The resultant mixture was heated at 70° C. for 5 h, before it was allowed to cool back to ambient temperature. The reaction mixture was neutralized with an aqueous solution of sodium carbonate, filtered through a pad of celite, and washed with ethyl acetate. The phases of the filtrate were separated and the organic layer was dried over anhydrous sodium sulfate, followed by concentration under vacuum to obtain the crude product. The crude product mixture was purified by column chromatography on neutral alumina, using 10% methanol in dichloromethane as the eluant, to afford 186 (0.050 g, 54%) as an off-white solid. $^1$H NMR (400 MHz, CDCl$_3$): δ 7.86 (d, J=8.4 Hz, 2H), 7.45 (d, J=8.4 Hz, 2H), 7.37 (d, J=2.0 Hz, 1H), 6.79 (d, J=8.6 Hz, 1H), 6.60 (dd, J=2.0, 8.6 Hz, 1H), 3.71 (s, 2H), 3.67 (brs, 2H), 2.62-2.55 (m, 7H), 1.68-1.62 (m, 4H), 1.48-1.47 (m, 2H); MS (ESI, positive mode) m/z 373 (MH$^+$).

Examples 34-35

N-(1-(4-Cyanophenyl)-2-methyl-3-(2-(piperidin-1-yl)acetyl)-1H-indol-5-yl)-N-methylacetamide (Compound 196), 4-(2-Methyl-5-(methylamino)-3-(2-(piperidin-1-yl)acetyl)-1H-indol-1-yl)benzonitrile (Compound 199)

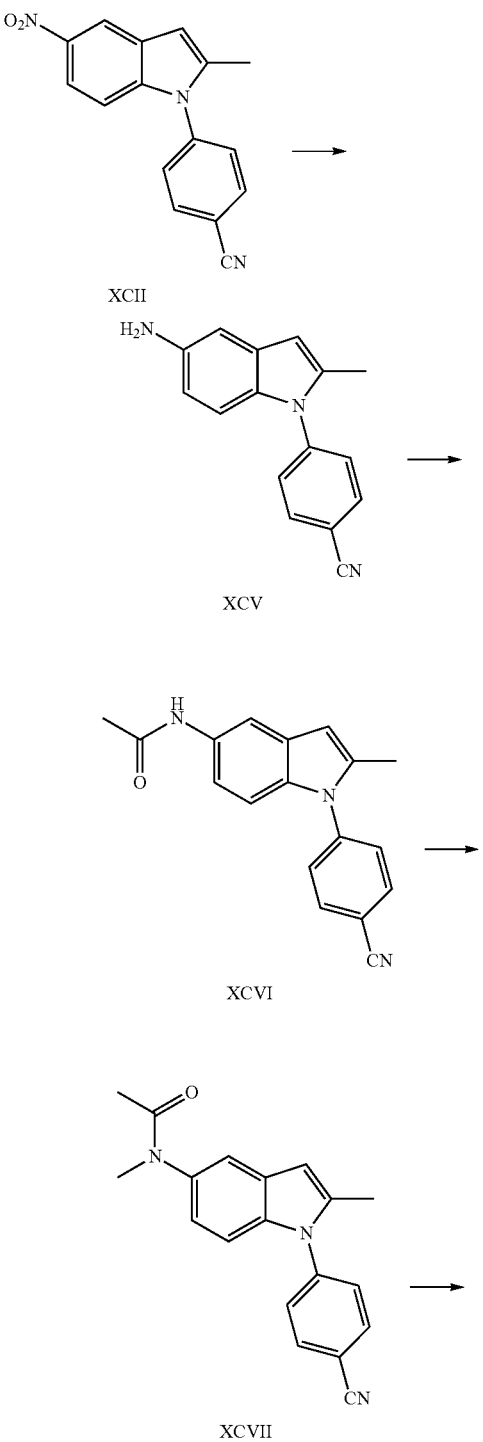

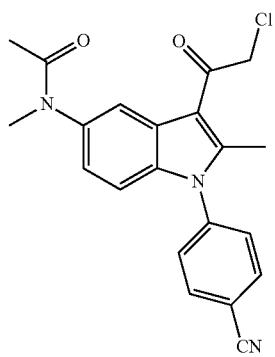

XCVIII

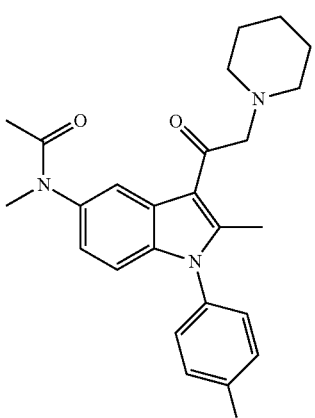

196

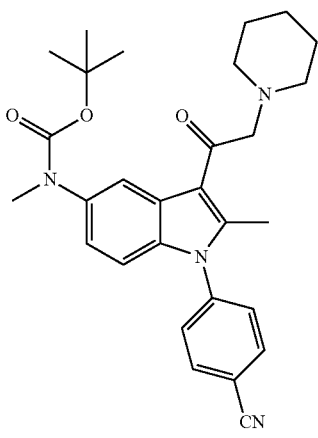

IC

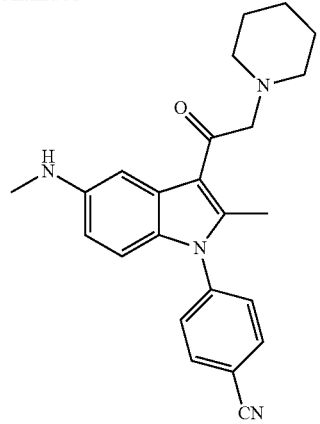

199

Synthesis of 4-(2-Methyl-5-amino-indol-1-yl)-benzonitrile (XCV): To a solution of compound XCII (1.0 g, 3.60 mmol) in ethyl acetate (40 mL) was added tin(II) chloride (4.9 g, 0.021 mol). The resultant mixture was heated at reflux for 24 h before cooling to room temperature. The reaction mixture was neutralized with an aqueous, saturated solution of sodium carbonate and the suspension that formed was filtered through a pad of celite. The filter pad was washed with ethyl acetate and the phases of the filtrate were separated. The organic layer was washed with water and brine, dried over sodium sulfate, and evaporated to afford the crude product as sticky mass. The crude product mixture was triturated with n-pentane and diethyl ether to afford compound XCV (0.5 g, 56%) as an off-white solid. $^1$H NMR (400 MHz, CDCl$_3$): δ 7.80 (d, J=8.4 Hz, 2H), 7.46 (d, J=8.5 Hz, 2H), 6.95 (d, J=8.6 Hz, 1H), 6.85 (d, J=1.8 Hz, 1H), 6.55 (dd, J=1.8, 8.6 Hz, 1H), 6.26 (s, 1H), 3.52 (brs, 2H), 2.29 (s, 3H); MS (ESI, positive mode) m/z 247 (MH$^+$).

Synthesis of N-[1-(4-Cyano-phenyl)-2-methyl-1H-indol-5-yl]acetamide (XCVI): To a solution of compound XCV (0.500 g, 2.02 mmol) in dichloromethane (10 mL) kept at 0° C. was added acetic anhydride (0.3 ml, 4.04 mmol) and triethylamine (0.3 mL, 6.06 mmol). The resulting mixture was allowed to stir at room temperature for 24 h. The reaction mixture was quenched with methanol (1 mL) and then poured onto ice-water. The aqueous mixture was extracted with dichloromethane (2×10 mL) and the organic layer was dried over anhydrous sodium sulfate. The organic layer was concentrated under vacuum to obtain the crude product mixture, which was further purified by column chromatography on neutral alumina using 50% ethyl acetate in hexanes as the eluant to afford compound XCVI (0.5 g, 85%) as an off-white solid. $^1$H NMR (400 MHz, CDCl$_3$): δ 8.82 (d, J=9.6 Hz, 2H), 7.76 (d, J=1.4 Hz, 1H), 7.47 (d, J=8.4 Hz, 2H), 7.17 (brs, 1H), 7.12 (dd, J=1.8, 8.4 Hz, 1H), 7.04 (d, J=8.4 Hz, 1H), 6.40 (s, 1H), 2.30 (s, 3H), 2.18 (s, 3H); MS (ESI, positive mode) m/z 290 (MH$^+$).

Synthesis of N-[1-(4-Cyano-phenyl)-2-methyl-1H-indol-5-yl]-N-methyl-acetamide (XCVII): To a solution of XCVI (1 g, 3.46 mmol) in anhydrous tetrahydrofuran (50 mL), kept at 0° C., was added sodium hydride (60% in oil, 0.5 g, 0.010 mol). The resulting mixture was allowed to stir at the reduced temperature for 0.5 h. Then methyl iodide (2.2 mL, 0.035 mol) was added and the reaction mixture was allowed to warm to room temperature and stir for 2 h. The reaction mixture was quenched with ice and then extracted with ethyl acetate (2×10 mL). The combined organic extracts were dried over anhydrous sodium sulfate and concentrated under vacuum to obtain compound XCVII (0.8 g, 80%) as an off-white solid. $^1$H NMR (400 MHz, CDCl$_3$): δ 7.86 (d, J=8.4 Hz, 2H), 7.50 (d, J=8.4 Hz, 2H), 7.36 (d, J=1.8 Hz, 1H), 7.10 (d, J=8.6 Hz, 1H), 6.91 (dd, J=1.8, 8.6 Hz, 1H), 6.45 (s, 1H), 3.28 (s, 3H), 2.33 (s, 3H), 1.86 (s, 3H); MS (ESI, positive mode) m/z 304 (MH$^+$).

Synthesis of N-[3-(2-Chloro-acetyl)-1-(4-cyano-phenyl)-2-methyl-1H-indol-5-yl]-N-methylacetamide (XCVIII): To a solution of XCVII (1.0 g, 3.30 mmol) in 1,2-dichloroethane (20 mL) was added chloro acetyl chloride (0.6 mL, 6.50 mmol). The reaction mixture was allowed to stir at room temperature for 0.5 h and then aluminum trichloride (0.879 g, 6.60 mmol) was added. The resultant mixture was heated at 60° C. for 24 h before cooling to room temperature. The reaction mixture was poured onto ice cold water and then filtered through celite. The filter pad was washed with dichloromethane and the phases of the filtrate were separated. The organic layer was washed with an aqueous 10%-sodium bicarbonate solution, dried over anhydrous sodium sulfate, and concentrated under vacuum to obtain the crude product. The crude product mixture was triturated with diethylether to afford XCVIII (0.6 g, 48%) as an off-white solid. $^1$H NMR (400 MHz, CDCl$_3$): δ 7.94 (d, J=8.5 Hz, 2H), 7.84 (d, J=8.4 Hz, 1H), 7.51 (d, J=8.4 Hz, 2H), 7.06-7.01 (m, 2H), 4.63 (s, 2H), 3.31 (s, 3H), 2.62 (s, 3H), 1.87 (s, 3H); MS (ESI, positive mode) m/z 380/382 (MH$^+$, $^{35/37}$Cl).

Synthesis of N-[1-(4-Cyano-phenyl)-2-methyl-3-(2-piperidin-1-yl-acetyl)-1H-indol-5-yl]-N-methyl-acetamide (196): To a solution of XCVIII (2.0 g, 5.30 mmol) in N,N-dimethylformamide (20 mL), kept at 0° C., was added solid potassium carbonate (1.46 g, 0.011 mol) and piperidine (1 mL, 0.011 mol). The reaction mixture was allowed to warm to room temperature and stir for 2 h. The reaction mixture was poured onto ice cold water and the precipitate that formed was collected via filtration. The filtered solid was washed with water and allowed to dry in a stream of air to afford 196 (1.5 g, 66%) as an off-white solid. $^1$H NMR (400 MHz, CDCl$_3$): δ 7.97 (s, 1H), 7.92 (d, J=8.5 Hz, 2H), 7.50 (d, J=8.4 Hz, 2H), 7.99 (d, 0.1=1.8, 8.6 Hz, 2H), 3.66 (s, 2H), 3.31 (s, 3H), 2.61-2.57 (m, 7H), 1.87 (s, 3H), 1.65-1.62 (m, 4H), 1.47-1.46 (m, 2H); MS (ESI, positive mode) m/z 429 (MH$^+$).

Synthesis of tert-Butyl (1-(4-Cyanophenyl)-2-methyl-3-(2-(piperidin-1-yl)acetyl)-1H-indol-5-yl)(methyl)carbamate (IC): A suspension of 196 (0.200 g, 0.470 mmol) in a 10% hydrochloric acid solution (5 mL) solution was heated at 70° C. for 12 h. The reaction mixture was condensed in vacuo and the remaining residue was suspended in dichloromethane (10 mL). The mixture was cooled to 0° C. and then treated with triethylamine (1.2 mL, 9.00 mmol), followed by di-tert-butyl-dicarbonate (0.8 mL, 0.036 mol). The reaction mixture was allowed to stir at room temperature for 24 h, before it was poured onto ice cold water and extracted with dichloromethane (2×20 mL). The combined organic extracts were washed with water and brine. The organic layer was then dried over anhydrous sodium sulfate and concentrated under vacuum to obtain the crude product. The crude product mixture was purified by column chromatography on basic alumina using 5% methanol in dichloromethane as the eluant to afford IC (0.150 g, 18%) as an off-white solid. $^1$H NMR (400 MHz, CDCl$_3$): δ 7.91-7.89 (m, 3H), 7.47 (d, J=8.4 Hz, 2H), 7.08-7.02 (m, 1H), 7.92 (d, J=8.6 Hz, 1H), 3.71 (s, 2H), 3.31 (s, 3H), 2.62-2.57 (m, 7H), 1.65-1.63 (m, 4H), 1.50-1.46 (m, 2H), 1.43 (s, 9H); MS (ESI, positive mode) m/z 487 (MH$^+$).

Synthesis of 4-(2-Methyl-5-(methylamino)-3-(2-(piperidin-1-yl)acetyl)-1H-indol-1-yl)benzonitrile (199): To a solution of IC (0.100 g, 0.200 mmol) in 1,4 dioxane (5 mL), kept at 0° C., was added a solution of hydrochloric acid 1,4-dioxane (1.0 M, 5 mL). The reaction mixture was allowed to warm to room temperature and stir for 24 h. The reaction mixture was condensed in vacuo and remaining crude material was basified with a saturated, aqueous solution of sodium bicarbonate. The aqueous layer was extracted with ethyl acetate (2×10 mL) and the combined organic extracts were washed with water and brine. The organic layer was condensed to afford a sticky mass, which was washed with n-pentane to obtain pure 199 (12 mg, 15%) as an off-white solid. $^1$H NMR (400 MHz, CDCl$_3$): δ 7.87 (d, J=8.6 Hz, 2H), 7.46 (d, J=8.4 Hz, 2H), 7.27 (brs, 1H), 6.82 (d, J=8.6 Hz, 1H), 6.55 (dd, J=2.8, 6.0 Hz, 1H), 3.72 (s, 2H), 2.91 (s, 3H), 2.65-2.55 (m, 7H), 1.65-1.62 (m, 4H), 1.48 (brs, 2H); MS (ESI, positive mode) m/z 387 (MH$^+$).

Examples 36-37

N-(1-(4-Cyanophenyl)-2-methyl-3-(2-(piperidin-1-yl)acetyl)-1H-indol-5-yl)pivalamide (187), N-(1-(4-Cyanophenyl)-2-methyl-3-(2-(piperidin-1-yl)acetyl)-1H-indol-5-yl)acetamide (191)

Compounds 187 and 191 was prepared using methods similar to those described in Examples 34 and 35.

Examples 38-40

Ethyl 3-(1-(4-Cyanophenyl)-2-methyl-3-(2-(piperidin-1-yl)acetyl)-1H-indol-6-yl)propanoate (Compound 133), 3-(1-(4-Cyanophenyl)-2-methyl-3-(2-(piperidin-1-yl)acetyl)-1H-indol-6-yl)propanoic Acid (Compound 201), 3-(1-(4-Cyanophenyl)-2-methyl-3-(2-(piperidin-1-yl)acetyl)-1H-indol-6-yl)propanamide (Compound 194)

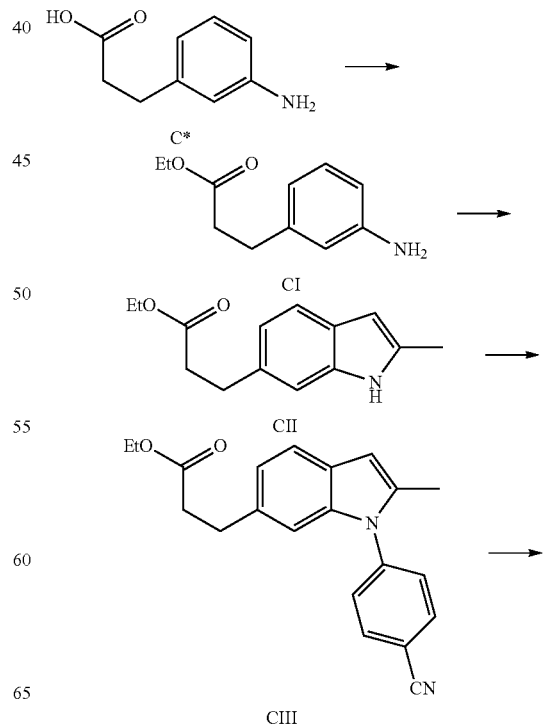

-continued

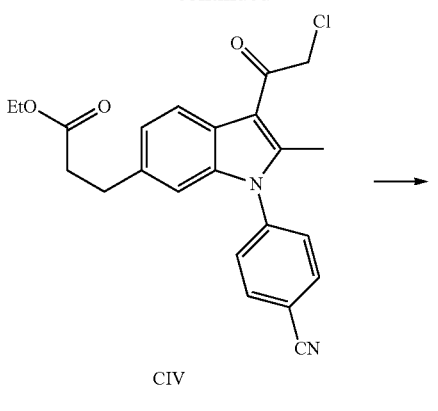

CIV

133

201

-continued

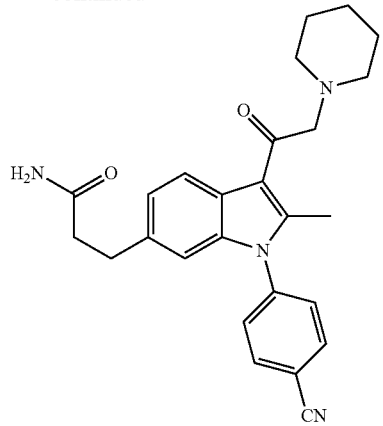

194

Synthesis of Ethyl 3-(3-Aminophenyl)propanoate (CI): To a suspension of compound C* (8.0 g, 0.048 mol) in ethanol (80 mL), kept at 0° C., was added thionyl chloride (23 g, 0.193 mol) and and a small quantity of N,N-dimethylformamide (0.2 mL). The reaction mixture was allowed to warm to room temperature and stir for 1 h. The reaction mixture was concentrated under reduced pressure and the residue was treated with a cold, aqueous, saturated solution of sodium bicarbonate. The aqueous mixture was extracted with ethyl acetate (3×50 mL) and the combined organic extracts were dried over anhydrous sodium sulfate. The organic layer was concentrated in vacuo to afford CI (8.0 g, 86%) as a pale brown, semi-solid. $^1$H NMR (400 MHz, CDCl$_3$): δ 7.08-7.04 (m, 1H), 6.61 (d, J=7.6 Hz, 1H), 6.55-6.54 (m, 2H), 4.10 (q, J=7.1 Hz, 2H), 2.85 (t, J=7.6 Hz, 2H), 2.58 (t, J=7.5 Hz, 2H), 1.23 (t, J=7.1 Hz, 3H); MS (ESI, positive mode) m/z 194 (MH$^+$).

Synthesis of Ethyl 3-(2-Methyl-1H-indol-6-yl)propanoate (CII): A solution of compound CI (0.5 g, 2.60 mmol) in dimethylsulfoxide (25 mL) and acetone (50 mL) was degassed for 10 minutes and then copper(II) acetate-hydrate (1.5 g, 7.70 mmol) and palladium(II) acetate (0.011 g, 0.500 mmol) were added. The resultant reaction mixture was heated at 100° C. for 15 h in sealed tube. After cooling the reaction mixture was concentrated under reduced pressure and the remaining residue was diluted with water. The aqueous mixture was extracted with ethyl acetate (3×150 mL) and the combined organic extracts were dried over anhydrous sodium sulfate. Concentrating the organic layer afforded the crude product mixture, which was purified by column chromatography (100-200 mesh) on silica gel using 5% ethyl acetate in hexanes as the eluant to afford CII (0.28 g, 48%) as a brown sticky mass. $^1$H NMR (400 MHz, CDCl$_3$): δ 7.77 (brs, 1H), 7.40 (d, J=8.0 Hz, 1H), 7.10 (s, 1H), 6.90 (dd, J=1.2, 8.1 Hz, 1H), 6.15 (s, 1H), 4.11 (q, J=7.2 Hz, 2H), 3.01 (t, J=7.6 Hz, 2H), 2.63 (t, J=8.2 Hz, 2H), 2.41 (s, 3H), 1.22 (t, J=7.2 Hz, 3H); MS (ESI, positive mode) m/z 232 (MH$^+$).

Synthesis of Ethyl 3-[1-(4-Cyano-phenyl)-2-methyl-1H-indol-6-yl]propanoate (CIII): A mixture of CII (0.250 g, 1.08 mmol), 4-iodo-benzonitrile (0.49 g, 2.16 mmol) and potassium phosphate (0.68 g, 3.20 mmol) in 1,4-dioxane (20 mL) was sparged with nitrogen gas for 0.5 h in a sealed tube. Then copper(I) iodide (0.02 g, 0.100 mmol) and trans-(+/−)-1,2-diamino-cyclohexane (0.012 g, 0.100 mmol) were added to the reaction mixture, which was then heated at 110° C. for 24 h. After cooling to room temperature, the reaction mixture was filtered through a bed of celite and the filter pad was washed with ethyl acetate. The filtrate was concentrated under vacuum and the remaining crude product mixture was purified by chromatography on (100-200 mesh) silica gel using 5% ethyl acetate in hexanes as the eluant to afford CIII (0.16 g, 45%) as an off-white solid. $^1$H NMR (400 MHz, CDCl$_3$): δ 7.84 (d, J=8.5 Hz, 2H), 7.48-7.45 (m, 3H), 6.98 (d, J=8.0 Hz, 1H), 6.94 (s, 1H), 6.39 (s, 1H), 4.19 (q, J=7.2 Hz, 2H), 2.97 (t, J=7.6 Hz, 2H), 2.57 (t, J=8.2 Hz, 2H), 2.29 (s, 3H), 1.19 (t, J=7.10 Hz, 3H); MS (ESI, positive mode) m/z 333 (MH$^+$).

Synthesis of Ethyl 3-[3-(2-Chloro-acetyl)-1-(4-cyano-phenyl)-2-methyl-1H-indol-6-yl]-propanoate (CIV): To a mixture of aluminum trichloride (0.20 g, 1.50 mmol) and chloro acetyl chloride (0.16 g, 1.50 mmol) in dichloroethane (3 mL) was added CIII (0.100 g, 0.304 mmol). The reaction mixture was allowed to stir at room temperature for 15 minutes and then the mixture was poured onto an ice-cold, aqueous saturated solution of sodium bicarbonate. The mixture was extracted with ethyl acetate (3×20 mL) and the combined organic extracts were dried over anhydrous sodium sulfate. After concentrating the organic layer the remaining crude product mixture was purified by column chromatography on neutral alumina using 20% ethyl acetate in hexanes as the eluant to afford CIV (0.08 g 33%) as an off-white solid. $^1$H NMR (400 MHz, CDCl$_3$): δ 7.92 (d, J=8.6 Hz, 2H), 7.80 (d, J=8.2 Hz 1H), 7.48 (d, J=8.2 Hz, 2H), 7.19 (dd, J=1.5, 8.3 Hz, 1H), 6.83 (s, 1H), 4.72 (s, 2H), 4.08 (q, J=7.2 Hz, 2H), 2.97 (d, J=7.6 Hz, 2H), 2.60-2.56 (m, 5H), 1.19 (t, J=7.1 Hz, 3H).

Synthesis of Ethyl 3-[1-(4-Cyano-phenyl)-2-methyl-3-(2-piperidin-1-yl-acetyl)-1H-indol-6-yl]propanoate (133): To a solution of CIV (0.08 g, 0.190 mmol) in N,N-dimethylformamide (1 mL), kept at 0° C., was added piperidine (0.03 g, 0.390 mmol). The reaction mixture was allowed to stir at the reduced temperature for 0.5 h and was then poured onto ice cold water. The precipitate that formed was collected by filtration and washed with water, followed by n-pentane. Drying the material in a stream of air afforded 133 (0.060 g, 67%) as a white solid. $^1$H NMR (400 MHz, DMSO-d$_6$): δ 8.15 (d, J=8.4 Hz, 2H), 7.98 (d, J=8.2 Hz, 1H), 7.72 (d, J=8.4 Hz, 2H), 7.13 (d, J=7.9 Hz, 1H), 6.85 (s, 1H), 3.97 (q, J=7.1 Hz, 2H), 3.61 (s, 2H), 2.86 (t, J=7.5 Hz, 2H), 2.57-2.46 (m, 9H), 1.55-1.45 (m, 4H), 1.42-1.38 (m, 2H), 1.08 (t, J=7.10 Hz, 3H); MS (ESI, positive mode) m/z 458 (MH$^+$).

Synthesis of 3-[1-(4-Cyano-phenyl)-2-methyl-3-(2-piperidin-1-yl-acetyl)-1H-indol-6-yl]-propionic acid Hydrochloride Salt (201): A suspension of 133 (0.3 g, 0.650 mmol) in an aqueous solution of 10% hydrochloric acid (6 mL) was heated at 70° C. for 1 h. After cooling to room temperature, the reaction mixture was concentrated under reduced pressure and the remaining residue was washed with diethylether to afford 201 (0.25 g, 89%) as a pale brown solid. $^1$H NMR (400 MHz, DMSO-d$_6$): δ 12.08 (brs, 1H), 9.72 (brs, 1H), 8.19 (d, J=8.3 Hz, 2H), 8.00 (d, J=8.2 Hz, 1H), 7.74 (d, J=8.4 Hz, 2H), 7.25 (d, J=8.3 Hz, 1H), 6.94 (s, 1H), 4.86 (d, J=4.6 Hz, 2H), 3.67-3.52 (m, 2H), 3.16-3.12 (m, 2H), 2.87-2.84 (m, 2H), 2.58 (s, 3H), 2.49-2.47 (m, 2H), 1.92-1.81 (m, 4H), 1.79-1.71 (m, 1H), 1.49-1.39 (m, 1H); MS (ESI, positive mode) m/z 430 (MH$^+$).

Synthesis of 3-[1-(4-Cyano-phenyl)-2-methyl-3-(2-piperidin-1-yl-acetyl)-1H-indol-6-yl]-propionamide (194): To a solution of compound 201 (0.25 g, 0.500 mmol) in dichloromethane (4 mL), kept at 0° C., was added thionyl chloride (0.13 g, 1.60 mmol). The reaction mixture was allowed to warm to room temperature and stir for 1 h. Then the reaction mixture was cooled to −20° C. and ammonia gas was passed through the mixture for 15 minutes. After warming to room temperature the reaction mixture was condensed in vacuo and the remaining residue treated with cold water. The precipitate that formed was collected by filtration and allowed to dry in a stream of air. The solid material was then purified by column chromatography on neutral alumina, using 0.8% methanol in dichloromethane as the eluant, to afford 194 (0.1 g, 41%) as an off-white solid. $^1$H NMR (400 MHz, DMSO-d$_6$): δ 8.15 (d, J=8.4 Hz, 2H), 7.97 (d, J=8.2 Hz, 1H), 7.73 (d, J=8.4 Hz, 2H), 7.23 (s, 1H), 7.12 (d, J=8.4 Hz, 1H), 6.85 (s, 1H), 6.73 (s, 1H), 3.61 (s, 2H), 2.81 (t, J=7.5 Hz, 2H), 2.53 (s, 3H), 2.49-2.41 (m, 4H), 2.31-2.27 (m, 2H), 1.52-1.48 (m, 4H), 1.41-1.38 (m, 2H); MS (ESI, positive mode) m/z 429 (MH$^+$).

Examples 41-42

2-(1-(4-Cyanophenyl)-2-methyl-3-(2-(piperidin-1-yl) acetyl)-1H-indol-6-yl)acetic Acid (Compound 198), 2-(1-(4-Cyanophenyl)-2-methyl-3-(2-(piperidin-1-yl) acetyl)-1H-indol-6-yl)acetamide (Compound 203)

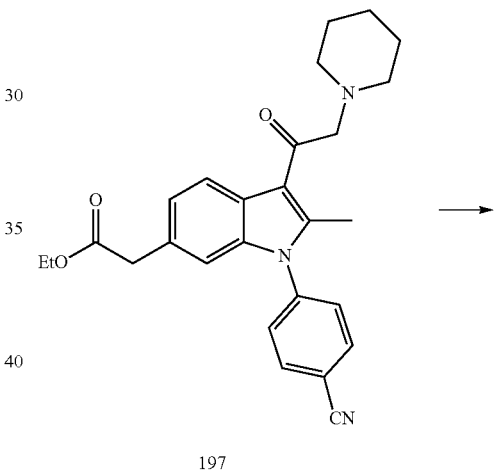

197

198

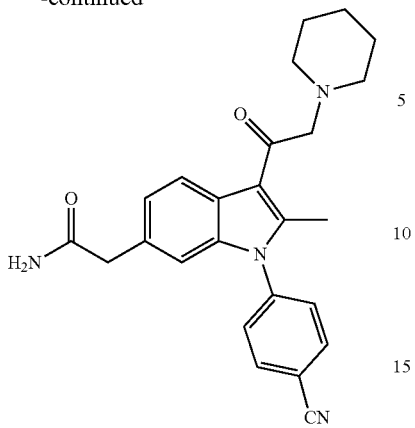

203

Synthesis of [1-(4-Cyano-phenyl)-2-methyl-3-(2-piperidin-1-yl-acetyl)-1H-indol-6-yl]acetic Acid Hydrochloride Salt (198): A solution of 197 (90 mg, 0.200 mmol) in an aqueous 10% hydrochloric acid solution (2 mL) was heated at 70° C. for 4 h. After cooling to room temperature, the reaction mixture was condensed to dryness. The remaining brown residue was washed with diethylether, filtered, and allowed to dry in a stream of air to afford 198 (50 mg, 59%) as a pale brown solid. $^1$H NMR (400 MHz, DMSO-$d_6$): δ 12.27 (brs, 1H), 9.66 (brs, 1H), 8.20 (d, J=8.4 Hz, 2H), 8.03 (d, J=8.2 Hz, 1H), 7.74 (d, J=8.4 Hz, 2H), 7.25 (d, J=8.2 Hz, 1H), 6.98 (s, 1H), 4.87 (d, J=8.7 Hz, 2H), 3.62 (s, 2H), 3.54-3.51 (m, 2H), 3.12-3.05 (m, 2H), 2.58 (s, 3H), 1.90-1.82 (m, 4H), 1.80-1.72 (m, 2H); MS (ESI, positive mode) m/z 416 (MH$^-$).

Synthesis of 2-[1-(4-Cyano-phenyl)-2-methyl-3-(2-piperidin-1-yl-acetyl)-1H-indol-6-yl]acetamide (203): To an ice-cooled solution of 198 (50 mg, 0.120 mmol) in dichloromethane (5 mL), maintained under a nitrogen atmosphere, was slowly added oxalyl chloride (0.1 mL, 1.2 mmol), followed by N,N-dimethylformamide (2 drops). The reaction mixture was allowed to stir at 0° C. for 1 h and was then cooled to −78° C. Dry ammonia gas was bubbled through the reaction mixture for 0.5 h and then the system was allowed to warm to room temperature. The reaction mixture as condensed in vacuo and the remaining material was partitioned between dichloromethane (10 mL) and ice-water (5 mL). The organic layer was dried over anhydrous sodium sulfate and then concentrated under vacuum to obtain a pale-brown sticky mass. The crude product mixture was purified by chromatography on neutral alumina, using 1% methanol in dichloromethane as the eluant, to afford 203 (25 mg, 25%) as a pale brown solid. $^1$H NMR (400 MHz, DMSO-$d_6$): δ 8.17 (d, J=8.3 Hz, 2H), 7.99 (d, J=8.2 Hz, 1H), 7.72 (d, J=8.3 Hz, 2H), 7.36 (brs, 1H), 7.16 (d, J=8.2 Hz, 2H), 6.92 (s, 1H), 6.79 (brs, 1H), 3.62 (s, 2H), 3.37 (s, 2H), 2.53 (s, 3H), 2.49-2.46 (m, 4H), 1.54-1.45 (m, 4H), 1.42-1.35 (m, 2H); MS (ESI, positive mode) m/z 415 (MH$^+$).

Examples 43-47

Ethyl 2-(1-(4-Cyanophenyl)-2-methyl-3-(2-(piperidin-1-yl)acetyl)-1H-pyrrolo[3,2-b]pyridin-6-yl)acetate (384), 2-(1-(4-Cyanophenyl)-2-methyl-3-(2-(piperidin-1-yl)acetyl)-1H-pyrrolo[3,2-b]pyridin-6-yl)-N-ethyl-N-methylacetamide (Compound 382), 2-(1-(4-Cyanophenyl)-2-methyl-3-(2-(piperidin-1-yl)acetyl)-1H-pyrrolo[3,2-b]pyridin-6-yl)-N-ethylacetamide (Compound 383), 2-(1-(4-Cyanophenyl)-2-methyl-3-(2-(piperidin-1-yl)acetyl)-1H-pyrrolo[3,2-b]pyridin-6-yl)-N-cyclopropylacetamide (Compound 381), 4-(2-Methyl-6-(2-oxo-2-(pyrrolidin-1-yl)ethyl)-3-(2-(piperidin-1-yl)acetyl)-1H-pyrrolo[3,2-b]pyridin-1-yl)benzonitrile (Compound 298)

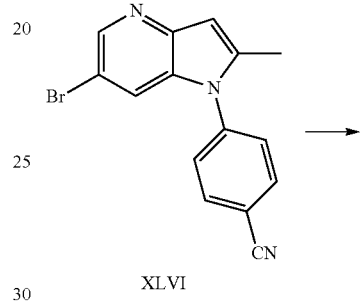

XLVI

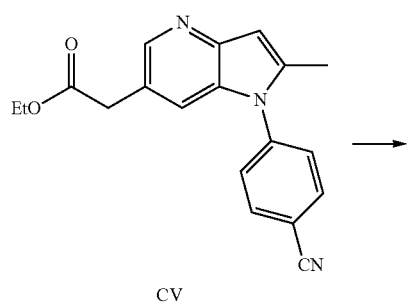

CV

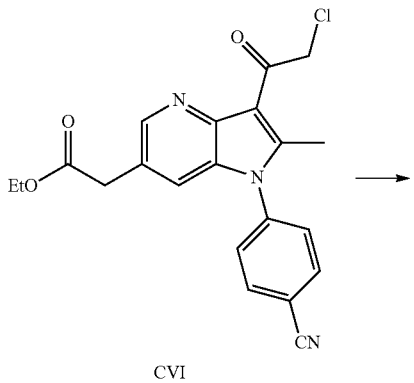

CVI

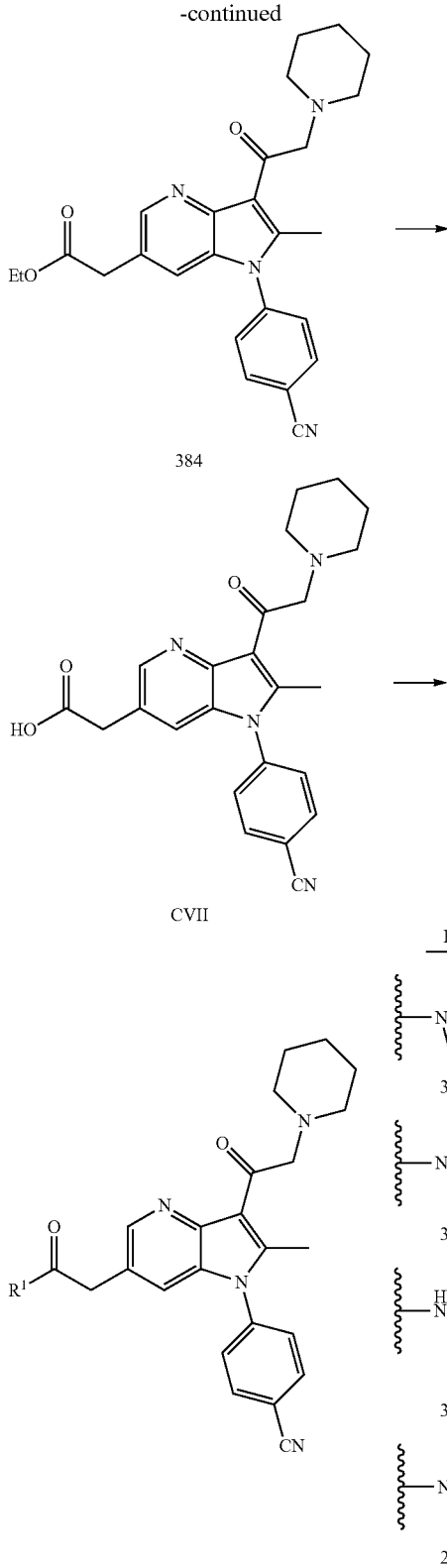

Synthesis of Ethyl [1-(4-Cyano-phenyl)-2-methyl-1H-pyrrolo[3,2-b]pyridin-6-yl]acetate (CV): To a degassed solution of ethyl acetoacetate (1.0 g, 7.68 mmol) and ethanol (0.354 g, 7.688 mmol) in dimethylsulfoxide (10 mL) were added potassium phosphate (1.63 g, 7.68 mmol), XLVI (0.800 g, 2.56 mmol) and copper(I) iodide (0.048 g, 0.250 mmol). The resulting mixture was heated at 40° C. for 1 h and then at 85° C. for 20 h. The progress of the reaction was monitored by TLC and HPLC. After cooling to room temperature, the reaction mixture was diluted with water (30 mL) and the mixture was extracted with ethyl acetate (30 mL×4). The combined organic extracts were dried over anhydrous sodium sulfate and concentrated under reduced pressure to obtain the crude product mixture. The crude product mixture was further purified by column chromatography on neutral alumina using 15% ethyl acetate in hexanes as eluent to afford CV (0.30 g, 36%) as an off-white, amorphous paste. $^1$H NMR (400 MHz, CDCl$_3$): δ 8.43 (s, 1H), 7.87 (d, J=8.4 Hz, 2H), 7.47 (d, J=8.4 Hz, 2H), 7.34 (s, 1H), 6.63 (s, 1H), 4.12 (q, J=7.1 Hz, 2H), 3.65 (s, 2H), 2.38 (s, 3H), 1.26 (t, J=7.1 Hz, 3H); MS (ESI, positive mode) m/z 320 (MH$^+$).

Synthesis of Ethyl [3-(2-Chloro-acetyl)-1-(4-cyano-phenyl)-2-methyl-1H-pyrrolo[3,2-b]pyridin-6-yl]acetate (CVI): To an ice-cooled solution of aluminum chloride (4.5 g, 34.4 mmol) in 1,2-dichloroethane (20 mL) was added chloroacetyl chloride (2.7 mL, 33.6 mmol) in a dropwise fashion. The reaction mixture was allowed to stir at 0° C. for 40 min. The reaction mixture was then treated with a solution of CV (0.55 g, 1.72 mmol) and heated at 60° C. for 14 h. Progress of the reaction was monitored by TLC. The reaction mixture was poured into an aqueous, saturated solution of sodium bicarbonate (500 mL) and extracted with dichloromethane (2×100 mL). The combined organic extracts were dried over sodium sulfate, filtered, and then concentrated in vacuo to afford the crude product. The crude product mixture was purified by column chromatography on neutral alumina, using 40% ethyl acetate in hexanes as the eluent, to afford CVI (0.32 g, 46%) as an off-white solid. $^1$H NMR (400 MHz, CDCl$_3$): δ 8.48 (d, J=1.7 Hz, 1H), 7.95 (d, J=8.4 Hz, 2H), 7.51 (d, J=8.4 Hz, 2H), 7.30 (d, J=1.6 Hz, 1H), 5.30 (s, 2H), 4.13 (q, J=7.1 Hz, 2H), 3.67 (s, 2H), 2.68 (s, 3H), 1.25 (t, J=7.0 Hz, 3H); MS (ESI, positive mode) m/z 396/398 (MH$^+$, $^{35/37}$Cl).

Synthesis of Ethyl 2-(1-(4-Cyanophenyl)-2-methyl-3-(2-(piperidin-1-yl)acetyl)-1H-pyrrolo[3,2-b]pyridin-6-yl)acetate (384): To an ice-cooled solution of CVI (0.32 g, 0.800 mmol) in acetonitrile (5 mL) was added piperidine (0.137 g, 1.61 mmol) and the reaction mixture was allowed to stir at room temperature for 2 h. Progress of the reaction was monitored by TLC. The reaction mixture was condensed in vacuo and the remaining crude product mixture was purified by column chromatography on neutral alumina using 1% methanol in dichloromethane as the eluent to afford 384 (0.21 g, 58%) as an off-white solid. $^1$H NMR (400 MHz, CDCl$_3$): δ 8.48 (d, J=1.8 Hz, 1H), 7.91 (d, J=8.5 Hz, 2H), 7.48 (d, J=8.5 Hz, 2H), 7.27 (d, J=1.8 Hz, 1H), 4.31 (s, 2H), 4.12 (q, J=7.1 Hz, 2H), 3.66 (s, 2H), 2.65 (s, 7H), 1.71-1.61 (m, 4H), 1.47 (brs, 2H), 1.24 (t, J=7.1 Hz, 3H); MS (ESI, positive mode) m/z 320 (MH$^+$).

Synthesis of [1-(4-Cyano-phenyl)-2-methyl-3-(2-piperidin-1-yl-acetyl)-1H-pyrrolo[3,2-b]pyridin-6-yl]acetic Acid (CVII): To a solution of 384 (0.15 g, 0.337 mmol) in 1,4-dioxane (5 mL) was added a solution of concentrated hydrochloric acid (0.15 mL) in water (3 mL). The reaction mixture was allowed to stir at room temperature for 15 h. The progress of the reaction was monitored by TLC. Upon completion, the reaction mixture was condensed in vacuo by azeotropic distillation with toluene to afford crude CVII (0.14 g), which was used as without any further purification. MS (ESI, positive mode) m/z 417 (MH$^+$).

General Procedure for Synthesis Target Compounds 381, 382, 383, 298: To a solution of CVII (0.05 g, 0.120 mmol)

in N,N-dimethylformamide (10 mL) was added diisopropylethylamine (0.046 g, 0.357 mmol) in a dropwise fashion and the reaction mixture was allowed to stir at room temperature for 10 min. The reaction mixture was then treated with propylphosphonic anhydride (T₃P; 0.19 g, 0.597 mmol), followed by an ethylamine solution (0.3 mL, 0.599 mmol, 2M in tetrahydrofuran). The reaction mixture was allowed to stir at room temperature for 20 h. The progress of the reaction was monitored by TLC. Upon completion, the reaction mixture was diluted with water (50 mL) and the mixture was extracted with ethyl acetate (2×25 mL). The combined organic extracts were washed with a brine solution (2×25 mL) and then dried over anhydrous sodium sulfate. The organic layer was condensed in vacuo to afford the crude product mixture, which was purified by column chromatography on neutral alumina using 2% methanol in dichloromethane as eluent to get afford the target compound. The following four compounds were prepared by this method.

2-(1-(4-Cyanophenyl)-2-methyl-3-(2-(piperidin-1-yl)acetyl)-1H-pyrrolo[3,2-b]pyridin-6-yl)-N-ethylacetamide (383): Yield: 43%; Off-white solid; ¹H NMR (400 MHz, CDCl₃): δ 8.45 (d, J=1.7 Hz, 1H), 7.91 (d, J=8.4 Hz, 2H), 7.47 (d, J=8.4 Hz, 2H), 7.31 (d, J=1.7 Hz, 1H), 5.41 (brs, 1H), 4.31 (s, 2H), 3.55 (s, 2H), 3.26-3.19 (m, 2H), 2.67-2.62 (m, 7H), 1.70-1.63 (m, 4H), 1.48 (brs, 2H), 1.07 (t, J=7.3 Hz, 3H), MS (ESI, positive mode) m/z 444 (MH⁺).

2-(1-(4-Cyanophenyl)-2-methyl-3-(2-(piperidin-1-yl)acetyl)-1H-pyrrolo[3,2-b]pyridin-6-yl)-N-ethyl-N-methylacetamide (382): Yield: 54%; Off-white solid; ¹H NMR at 100° C. (400 MHz, CDCl₃): δ 8.43 (s, 1H), 8.13-8.08 (m, 2H), 7.75-7.70 (m, 2H), 7.34 (s, 1H), 4.43 (brs, 2H), 3.78 (s, 2H), 3.36 (m, 2H), 2.93 (brs, 3H), 2.84 (brs, 4H), 2.60 (s, 3H), 1.74-1.60 (m, 4H), 1.51-1.47 (m, 2H), 1.05 (brs, 3H); MS (ESI, positive mode) m/z 458 (MH⁺).

2-(1-(4-Cyanophenyl)-2-methyl-3-(2-(piperidin-1-yl)acetyl)-1H-pyrrolo[3,2-b]pyridin-6-yl)-N-cyclopropylacetamide (381): Yield: 34%; Off-white solid; ¹H NMR (400 MHz, DMSO-d₆): δ 8.41 (d, J=1.6 Hz, 1H), 8.18 (d, J=8.3 Hz, 2H), 8.13 (d, J=3.8 Hz, 2H), 7.80 (d, J=8.5 Hz, 2H), 7.36 (d, J=1.3 Hz, 1H), 4.17 (s, 2H), 2.57 (s, 8H), 1.52 (brs, 4H), 1.41 (brs, 2H), 0.59-0.55 (m, 2H), 0.35-0.33 (m, 2H), MS (ESI, positive mode) m/z 456 (MH⁺).

4-(2-Methyl-6-(2-oxo-2-(pyrrolidin-1-yl)ethyl)-3-(2-(piperidin-1-yl)acetyl)-1H-pyrrolo[3,2-b]pyridin-1-yl)benzonitrile (298): Yield: 20%; Off-white solid; ¹H NMR (400 MHz, CDCl₃): δ 8.43 (d, J=1.6 Hz, 1H), 7.89 (d, J=8.4 Hz, 2H), 7.47 (d, J=8.4 Hz, 2H), 7.37 (d, J=1.5 Hz, 1H), 4.32 (s, 2H), 3.67 (s, 2H), 3.51-3.48 (m, 2H), 3.47-3.41 (m, 2H), 2.67-2.64 (m, 7H), 1.97-1.93 (m, 2H), 1.98-1.85 (m, 2H), 1.69 (brs, 4H), 1.48 (brs, 2H); MS (ESI, positive mode) m/z 468 (MH⁺).

Example 49

N-(2-(1-(4-Chlorophenyl)-2-methyl-3-(2-(piperidin-1-yl)acetyl)-1H-pyrrolo[3,2-b]pyridin-6-yl)ethyl)-N-ethylmethanesulfonamide (303)

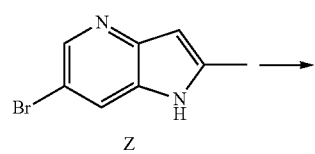

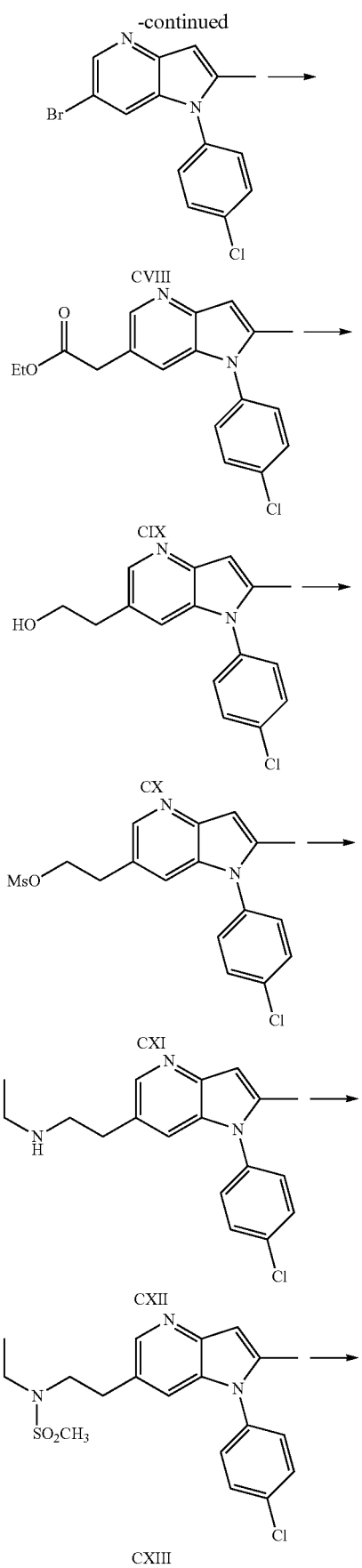

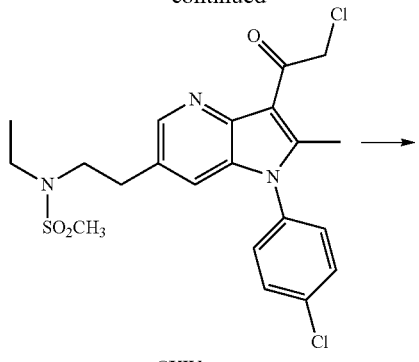

CXIV

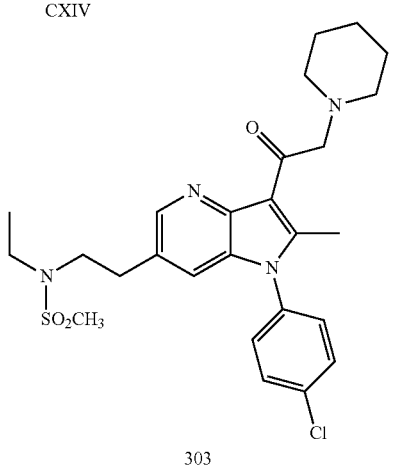

303

Synthesis of 6-Bromo-1-(4-chloro-phenyl)-2-methyl-1H-pyrrolo[3,2-b]pyridine (CVIII): To a degassed suspension of Z (1.0 g, 4.73 mmol), 1-chloro-4-iodobenze (11.3 g, 47.4 mmol) and potassium triphosphate (3.01 g, 14.2 mmol) in of 1,4-ioxane (80 mL) were added copper(I) iodide (0.090 g, 0.474 mmol) and trans-(+/−)-1,2-diaminocyclohexane (0.054 g, 0.470 mmol). The resulting reaction mixture was heated at 125° C. for 16 h. After cooling to room temperature the reaction mixture was filtered through a celite bed and the filter pad was washed with ethyl acetate. The filtrate was concentrated under reduced pressure to obtain crude product mixture, which was purified by column chromatography on neutral alumina using 2% ethyl acetate in hexanes as the eluent to afford compound CVIII (1.0 g, 65%) as an off-white solid. $^1$H NMR (400 MHz, CDCl$_3$): δ 8.45 (d, J=2.0 Hz, 1H), 7.53 (d, J=8.7 Hz, 2H), 7.44 (d, J=2.7 Hz, 1H), 7.26 (d, J=8.7 Hz, 2H), 6.57 (s, 1H), 2.32 (s, 3H); MS (ESI, positive mode) m/z 320/322 (MH$^+$, $^{35/37}$Cl, $^{79/81}$Br).

Synthesis of Ethyl [1-(4-Chloro-phenyl)-2-methyl-1H-pyrrolo[3,2-b]pyridin-6-yl]acetate (CIX): To a degassed solution of ethyl acetoacetate (10.5 g, 80.8 mmol) and ethanol (3.72 g, 80.8 mmol) in dimethylsulfoxide (10 mL) was added potassium phosphate (5.14 g, 24.3 mmol). The mixture was allowed to stir for 10 min and then the mixture was treated with a solution of CVIII (2.6 g, 8.08 mmol), followed by copper(I) iodide (0.153 g, 0.800 mmol). The resulting mixture was heated at 40° C. for 1 h and then at 90° C. for 16 h. After cooling to room temperature the reaction mixture was diluted with water and the mixture was extracted with ethyl acetate (150 mL×4). The combined organic extracts were dried over anhydrous sodium sulfate and concentrated under reduced pressure to obtain the crude product. The crude product mixture was purified by column chromatography on neutral alumina, using 15% ethyl acetate in hexanes as eluent, to obtain CIX (0.800 g, 30%) as a brown, viscous oil. $^1$H NMR (400 MHz, CDCl$_3$): δ 8.32 (d, J=1.8 Hz, 1H), 7.52 (d, J=8.6 Hz, 2H), 7.27-7.26 (m, occluded by solvent, 3H), 6.57 (s, 1H), 4.11 (q, J=7.1 Hz, 2H), 3.63 (s, 2H), 2.32 (s, 3H), 1.21 (t, J=7.1 Hz, 3H); MS (ESI, positive mode) m/z 320/322 (MH$^+$, $^{35/37}$Cl).

Synthesis of [2-[1-(4-Chloro-phenyl)-2-methyl-1H-pyrrolo[3,2-b]pyridin-6-yl]-ethanol (CX): To an ice-cooled solution of CIX (1.0 g, 3.04 mmol) in tetrahydrofuran (20 mL) under a nitrogen atmosphere was added solid lithium aluminum hydride (0.115 g, 3.04 mmol) in a portionwise manner. The mixture was allowed to stir at 0° C. for 45 min. The progress of the reaction was monitored by TLC. The reaction mixture was quenched through the addition of ethyl acetate (2 mL) and then filtered through a celite bed. The filter cake was washed with ethyl acetate (30 mL) and the filtrate was concentrated under reduced pressure to obtain CX (0.700 g, 80%) as a yellowish solid, which was used without further purification. $^1$H NMR (400 MHz, CDCl$_3$): δ 8.29 (d, J=1.7 Hz, 1H), 7.52 (d, J=8.6 Hz, 2H), 7.26 (d, J=8.6 Hz, 2H), 7.18 (s, 1H), 6.55 (s, 1H), 3.83 (t, J=6.5 Hz, 2H), 2.89 (t, J=6.5 Hz, 2H), 2.32 (s, 3H); MS (ESI, positive mode) m/z 287/289 (MH$^+$, $^{35/37}$Cl).

Synthesis of 2-(1-(4-Chlorophenyl)-2-methyl-1H-pyrrolo[3,2-b]pyridin-6-yl)ethyl methanesulfonate (CXI): To an ice-cooled solution of CX (0.700 g, 2.44 mmol) and triethylamine (0.680 mL, 4.88 mmol) in dichloromethane (50 mL) was added methanesulfonyl chloride (0.283 mL, 3.66 mmol) in a dropwise fashion. The resulting reaction mixture was allowed to stir at 0° C. for 1 h. The progress of the reaction was monitored by TLC. The reaction mixture was diluted with water (25 mL) and the mixture was extracted with dichloromethane (30 mL×4). The combined organic extracts were dried over sodium sulfate, filtered, and then concentrated in vacuo to obtain crude CXI (1.3 g) as a brown oil, which was used without further purification. MS (ESI, positive mode) m/z 365/367 (MH$^+$, $^{35/37}$Cl).

Synthesis of 2-(1-(4-Chlorophenyl)-2-methyl-1H-pyrrolo[3,2-b]pyridin-6-yl)-N-ethylethan-1-amine (CXII): To an ice-cooled solution of CXI (1.3 g, crude) in tetrahydrofuran (5 mL) under a nitrogen atmosphere was added ethylamine (10.7 mL, 21.4 mmol, 2M in tetrahydrofuran) and the resulting reaction mixture was heated at 70° C. for 16 h. Progress of the reaction was monitored by TLC. The reaction mixture was condensed in vacuo and the crude product mixture was purified by column chromatography on neutral alumina using 30% dichloromethane in hexanes and then 1% methanol in dichloromethane as eluant to afford CXII (0.650 g, 84% after two steps) as a brown, viscous oil. $^1$H NMR (400 MHz, CDCl$_3$): δ 8.30 (d, J=1.5 Hz, 1H), 7.51 (d, J=8.6 Hz, 2H), 7.26 (d, J=8.0 Hz, 2H), 7.15 (s, 1H), 6.56 (s, 1H), 2.84 (s, 3H), 2.63 (q, J=7.1 Hz, 2H), 2.32 (s, 3H), 1.05 (t, J=7.1 Hz, 3H); MS (ESI, positive mode) m/z 314/316 (MH$^+$, $^{35/37}$Cl).

Synthesis of N-(2-(1-(4-Chlorophenyl)-2-methyl-1H-pyrrolo[3,2-b]pyridin-6-yl)ethyl)-N-ethylmethanesulfonamide (CXIII): To an ice-cooled solution of CXII (0.100 g, 0.320 mmol) and triethylamine (0.089 mL, 0.64 mmol) in dichloromethane (5 mL) was added methane sulfonyl chloride (0.036 mL, 0.48 mmol) in a dropwise fashion. The reaction mixture was allowed to stir at 0° C. for 1 h. The progress of the reaction was monitored by TLC. The reaction mixture was diluted with water and the mixture was extracted with dichloromethane (25 mL×4). The combined organic extracts were dried over sodium sulfate, filtered, and concentrated in vacuo to obtain crude CXIII (0.110 g, 88%) as a brown oil.

¹H NMR (400 MHz, CDCl₃): δ 8.28 (d, J=1.8 Hz, 1H), 7.53 (d, J=9.4 Hz, 2H), 7.26 (d, J=9.4 Hz, 2H), 7.18 (s, 1H), 6.56 (s, 1H), 3.35-3.37 (m, 2H), 3.26 (q, J=7.1 Hz, 2H), 2.95 (t, J=7.8 Hz, 2H), 2.71 (s, 3H), 2.33 (s, 3H), 1.20 (t, J=7.2 Hz, 3H); MS (ESI, positive mode) m/z 392/394 (MH⁺, ³⁵/³⁷Cl).

Synthesis of N-(2-(3-(2-Chloroacetyl)-1-(4-chlorophenyl)-2-methyl-1H-pyrrolo[3,2-b]pyridin-6-yl)ethyl)-N-ethylmethanesulfonamide (CXIV): To an ice-cooled suspension of aluminum chloride (0.560 g, 4.21 mmol) in dichloroethane (10 mL) was added chloroacetyl chloride (0.475 g, 4.21 mmol) in a dropwise fashion and the resulting reaction mixture was allowed to stir for 45 min at 0° C. To the resulting reaction mixture was then added a solution of CXIII (0.110 g, 0.281 mmol) in 1,2-dichloroethane (7 mL) and t mixture was allowed to stir at room temperature for 1 h. The reaction mixture was then heated at 65° C. for 4 h. Progress of the reaction was monitored by TLC. After cooling, the reaction mixture was poured onto crushed ice and neutralized with an aqueous saturated solution of sodium bicarbonate (50 mL). The mixture was extracted with dichloromethane (30 mL×5). The combined organic extracts were dried over sodium sulfate, filtered and concentrated in vacuo to afford the crude product. The crude product mixture was purified by column chromatography on neutral alumina using dichloromethane as the eluent to afford CXIV (0.055 g, 41%) as a white solid. ¹H NMR (400 MHz, CDCl₃): δ 8.42 (d, J=1.9 Hz, 1H), 7.59 (d, J=8.6 Hz, 2H), 7.26 (d obscured by solvent signal, 2H), 7.20 (s, 1H), 5.30 (s, 2H), 3.37 (t, J=7.5 Hz, 2H), 3.26 (q, J=7.2 Hz, 2H), 2.98 (t, J=7 Hz, 2H), 2.75 (s, 3H), 2.66 (s, 3H), 1.17 (t, J=7.1 Hz, 3H); MS (ESI, positive mode) m/z 468/470 (MH⁺, ³⁵/³⁷Cl).

Synthesis of N-(2-(1-(4-Chlorophenyl)-2-methyl-3-(2-(piperidin-1-yl)acetyl)-1H-pyrrolo[3,2-b]pyridin-6-yl)ethyl)-N-ethylmethanesulfonamide (303): To an ice-cooled solution of CXIV (0.055 g, 0.117 mmol) in acetonitrile (5 mL) was added piperidine (0.019 g, 0.230 mmol) and the resulting reaction mixture was allowed to stir at room temperature for 16 h. The Progress of the reaction was monitored by TLC. The reaction mixture was condensed in vacuo and the remaining residue was diluted with water. The mixture was extracted with dichloromethane (15 mL×4) and the combined organic extracts were dried over anhydrous sodium sulfate. The organic layer was concentrated under reduced pressure to afford the crude product mixture, which was purified by column chromatography on neutral alumina using 1% methanol in dichloromethane as eluent to afford a solid. The solid was further washed with diethyl ether (1 mL) and allowed to dry in a stream of air to obtain 303 (0.032 g, 52%) as an off-white solid. ¹H NMR (400 MHz, CDCl₃): δ 8.42 (d, J=1.8 Hz, 1H), 7.58 (d, J=8.6 Hz, 2H), 7.25 (d, J=8.5 Hz, 2H), 7.15 (d, J=1.8 Hz, 1H), 4.30 (s, 2H), 3.36-3.37 (m, 2H), 3.26 (q, J=7.1 Hz, 2H), 2.96 (t, J=7.3 Hz, 2H), 2.74 (s, 3H), 2.66 (brs, 4H), 2.63 (s, 3H), 1.70-1.67 (m, 4H), 1.49 (m, 2H), 1.18 (t, J=7.2 Hz, 3H); MS (ESI, positive mode) m/z 517/519 (MH⁺, ³⁵/³⁷Cl).

Example 50

N-(2-(1-(4-Chlorophenyl)-3-(2-(4-hydroxypiperidin-1-yl)acetyl)-2-methyl-1H-pyrrolo[3,2-b]pyridin-6-yl)ethyl)methanesulfonamide (342)

Compound 342 was prepared using methods similar to those described in Example 49.

Examples 51-52

2-(1-(4-Cyanophenyl)-2-methyl-3-(2-(piperidin-1-yl)acetyl)-1H-indol-6-yl)ethyl Acetate (205), 4-(6-(2-Hydroxyethyl)-2-methyl-3-(2-(piperidin-1-yl)acetyl)-1H-indol-1-yl)benzonitrile (207)

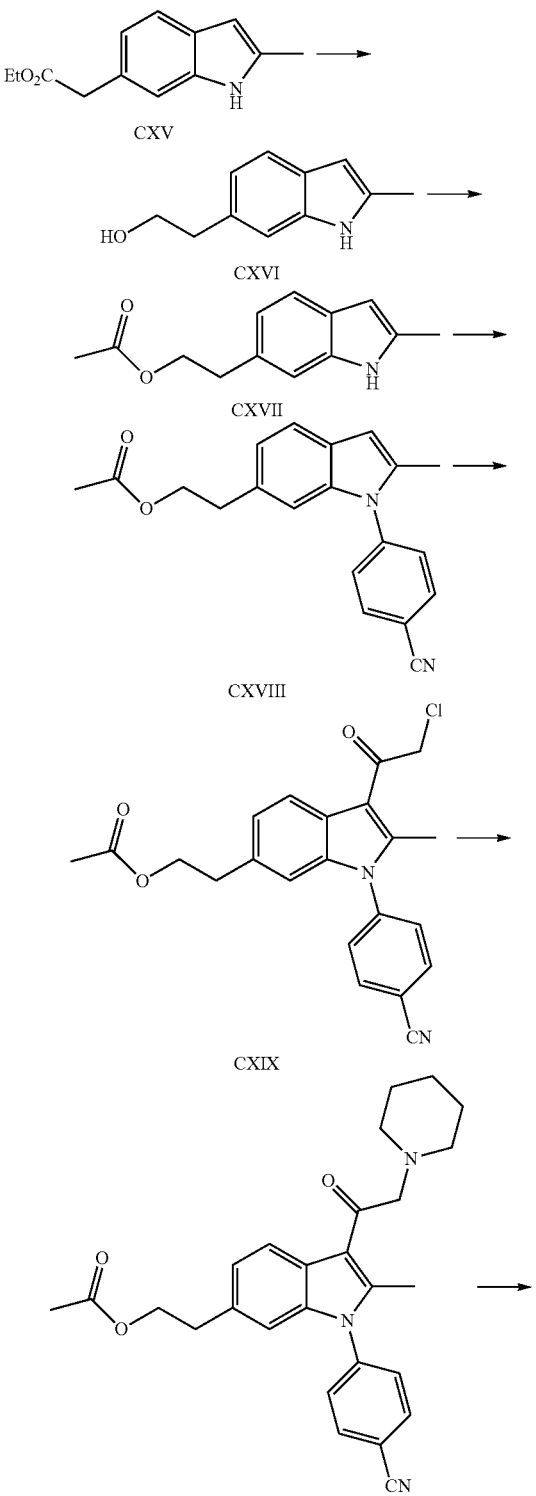

-continued

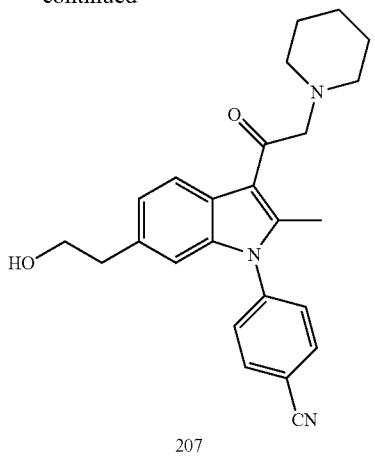

207

Synthesis of 2-(2-Methyl-1H-indol-6-yl)-ethanol (CXVI): To a stirred solution of CXV (0.80 g, 3.68 mmol) in dry tetrahydrofuran (35 mL), kept at 0° C., was slowly added a 1.0 M solution of lithium aluminum hydride in diethylether (7.4 mL, 7.40 mmol). The reaction mixture was allowed to stir at the reduced temperature for 0.5 h before the reaction was quenched with an aqueous, saturated solution of sodium sulfate (1 mL). Excess anhydrous sodium sulfate was added and then the reaction mixture was filtered through a pad of celite. The filtrate was concentrated in vacuo to obtain the crude CXVI as a pale yellow oil (0.69 g), which was used without any further purification. $^1$H NMR (400 MHz, CDCl$_3$): δ 7.82 (brs, 1H), 7.43 (d, J=7.9 Hz, 1H), 7.13 (s, 1H), 6.92 (d, J=8.0 Hz, 1H), 6.17 (s, 1H), 3.88-3.84 (m, 2H), 2.95-2.92 (m, 2H), 2.42 (s, 3H); MS (ESI, positive mode) m/z 176 (MH$^+$).

Synthesis of 2-(2-Methyl-1H-indol-6-yl)ethyl Acetate (CXVII): To an ice-cooled solution of CXVI (0.69 g, 3.94 mmol) in dichloromethane (30 mL) was added triethylamine (3.19 g, 31.5 mmol) and acetic anhydride (1.61 g, 15.8 mmol). The reaction mixture was allowed to warm to room temperature and stir for 3 h. The reaction mixture was condensed under reduced pressure and the remaining yellow mass was partitioned between dichloromethane (70 mL) and water (50 mL). The phases were separated and the organic layer was dried over anhydrous sodium sulfate. The organic layer was condensed in vacuo to afford CXVII (0.44 g, 51%) as a yellow oil. $^1$H NMR (400 MHz, CDCl$_3$): δ 7.79 (brs, 1H), 7.41 (d, J=8.1 Hz, 1H), 7.12 (s, 1H), 6.91 (d, J=8.0 Hz, 1H), 6.16 (s, 1H), 4.31-4.27 (m, 2H), 3.01-2.98 (m, 2H), 2.42 (s, 3H), 2.03 (s, 3H); MS (ESI, positive mode) m/z 218 (MH$^+$).

Synthesis of 2-(1-(4-Cyanophenyl)-2-methyl-1H-indol-6-yl)ethyl Acetate (CXVIII): A mixture of CXVII (0.20 g, 0.920 mmol), 4-iodo-benzonitrile (0.42 g, 1.84 mmol), potassium phosphate (0.352 g, 1.66 mmol) and copper(I) iodide (0.175 g, 0.92 mmol) in 1,4-dioxane (70 mL) was degassed with nitrogen gas for 0.5 h. Then trans-(+/−)-1,2-diamino-cyclohexane (0.011 g, 0.092 mmol) was added and the resulting mixture was heated at 100° C. for 24 h. After cooling to room temperature the reaction mixture was condensed in vacuo and the remaining residue was diluted with ice-water. The mixture was extracted with ethyl acetate and the combined extracts were then filtered through a pad of celite. The filtrate was dried over sodium sulfate and then concentrated under vacuum to afford the crude product. Analysis of the crude product mixture revealed some de-acetylated product was present, in addition to the target compound. The crude product mixture was treated with additional acetic anhydride and triethylamine in dichloromethane. After condensing, the crude product mixture was purified by column chromatography on (60-120 mesh) silica gel using 7% ethyl acetate in hexanes to afford CXVIII (0.18 g, 61%). $^1$H NMR (400 MHz, CDCl$_3$): δ 7.83-7.82 (m, 2H), 7.49-7.47 (m, 3H), 7.04-7.01 (m, 1H), 6.94 (s, 1H), 6.40 (s, 1H), 4.25-4.21 (m, 2H), 2.95-2.93 (m, 2H), 2.30 (s, 3H), 1.99 (s, 3H); MS (ESI, positive mode) m/z 319 (MH$^-$).

Synthesis of 2-(3-(2-Chloroacetyl)-1-(4-cyanophenyl)-2-methyl-1H-indol-6-yl)ethyl Acetate (CXIX): To an ice-cold solution of anhydrous aluminum chloride (0.40 g, 3.02 mmol) in 1,2-dichloroethane (20 mL) was added neat chloro-acetyl chloride (0.20 g, 1.81 mmol) in a dropwise fashion. The reaction mixture was allowed to stir at the reduced temperature for 0.5 h and then a solution of CXVIII (0.48 g, 1.51 mmol) in 1,2-dichloroethane was added to the reaction mixture at 0° C. The resultant reaction mixture was allowed to warm to room temperature and stir for 16 h. The reaction mixture was poured onto ice-cold water, neutralized with an aqueous, saturated solution of sodium bicarbonate and then extracted with dichloromethane. The organic layer was dried over sodium sulfate and then concentrated under vacuum to afford the crude product. The crude product mixture was purified by column chromatography on (60-120 mesh) silica gel using 20% ethyl acetate in hexanes to obtain CXIX (0.17 g, 29%) as an orange solid. $^1$H NMR (400 MHz, CDCl$_3$): δ 7.94-7.92 (m, 2H), 7.83 (d, J=8.3 Hz, 1H), 7.49-7.47 (m, 2H), 7.21 (dd, J=1.5, 8.1 Hz, 1H), 6.83 (s, 1H), 4.73 (s, 2H), 4.22 (t, J=7.1 Hz, 2H), 2.95 (t, J=7.0 Hz, 2H), 2.60 (s, 3H), 1.98 (s, 3H); MS (ESI, positive mode) m/z 395/397 (MH$^+$, $^{35/37}$Cl).

Synthesis of 2-(1-(4-Cyanophenyl)-2-methyl-3-(2-(piperidin-1-yl)acetyl)-1H-indol-6-yl)ethyl Acetate (205): To an ice-cold solution of CXIX (0.10 g, 0.250 mmol) in N,N-dimethylformamide (1.5 mL) was slowly added piperidine (0.03 mL, 1.01 mmol). The reaction mixture was allowed to stir at 0° C. for 1 h. The reaction mixture was poured onto ice and the precipitate that formed was collected by filtration. The filtered solid was washed with water and allowed to dry in a stream of air. The crude solid was purified by column chromatography on neutral alumina using 70% ethyl acetate in hexanes to afford 205 (0.06 g, 53%) as an off-white solid. $^1$H NMR (400 MHz, CDCl$_3$): δ 7.96-7.90 (m, 3H), 7.50-7.46 (m, 2H), 7.20-7.15 (m, 1H), 6.81 (s, 1H), 4.22 (t, J=7.1 Hz, 2H), 3.78 (s, 2H), 2.94 (t, J=7.1 Hz, 2H), 2.74-2.58 (m, 7H), 1.98 (s, 3H), 1.65-1.61 (m, 4H), 1.48-1.42 (m, 2H); MS (ESI, positive mode) m/z 444 (MH$^+$).

Synthesis of 4-(6-(2-Hydroxyethyl)-2-methyl-3-(2-(piperidin-1-yl)acetyl)-1H-indol-1-yl)benzonitrile (207): A hydrochloric acid solution (10% in water, 3 mL) was added to compound 205 (0.08 g, 0.180 mmol) and the resultant mixture was allowed to stir at room temperature for 26 h. The reaction mixture was condensed in vacuo and the remaining residue was neutralized with an aqueous saturated solution of sodium bicarbonate. The precipitate that formed was collected by filtration and washed with water. The solid was allowed to dry in a stream of air and was then purified by column chromatography on neutral alumina using 2% methanol in ethyl acetate to afford a solid (40 mg). The solid was triturated with diethylether and allowed to dry to obtain 207 (15 mg, 21%) as a grey solid. $^1$H NMR (400 MHz, CDCl$_3$): δ 7.96 (d, J=8.1 Hz, 1H), 7.91-7.89 (m, 2H), 7.50-7.46 (m, 2H), 7.18 (d, J=8.0 Hz, 1H), 6.84 (s, 1H), 3.84-3.81 (m, 4H), 2.90-2.87 (t, J=7.1 Hz, 2H), 2.70-2.64 (m, 4H), 2.58 (s, 3H), 1.72-1.62 (m, 4H), 1.52-1.44 (m, 2H); MS (ESI, positive mode) m/z 402 (MH$^+$).

Examples 53-56

Ethyl 3-(1-(4-Cyanophenyl)-2,5-dimethyl-3-(2-(piperidin-1-yl)acetyl)-1H-pyrrolo[3,2-b]pyridin-6-yl)propanoate (200), 3-(1-(4-Cyanophenyl)-2,5-dimethyl-3-(2-(piperidin-1-yl)acetyl)-1H-pyrrolo[3,2-b]pyridin-6-yl)propanoic Acid Hydrochloride Salt (202), 3-(1-(4-Cyanophenyl)-2,5-dimethyl-3-(2-(piperidin-1-yl)acetyl)-1H-pyrrolo[3,2-b]pyridin-6-yl)-N,N-diethylpropanamide (204), 3-(1-(4-Cyanophenyl)-2,5-dimethyl-3-(2-(piperidin-1-yl)acetyl)-1H-pyrrolo[3,2-b]pyridin-6-yl)propanamide (210)

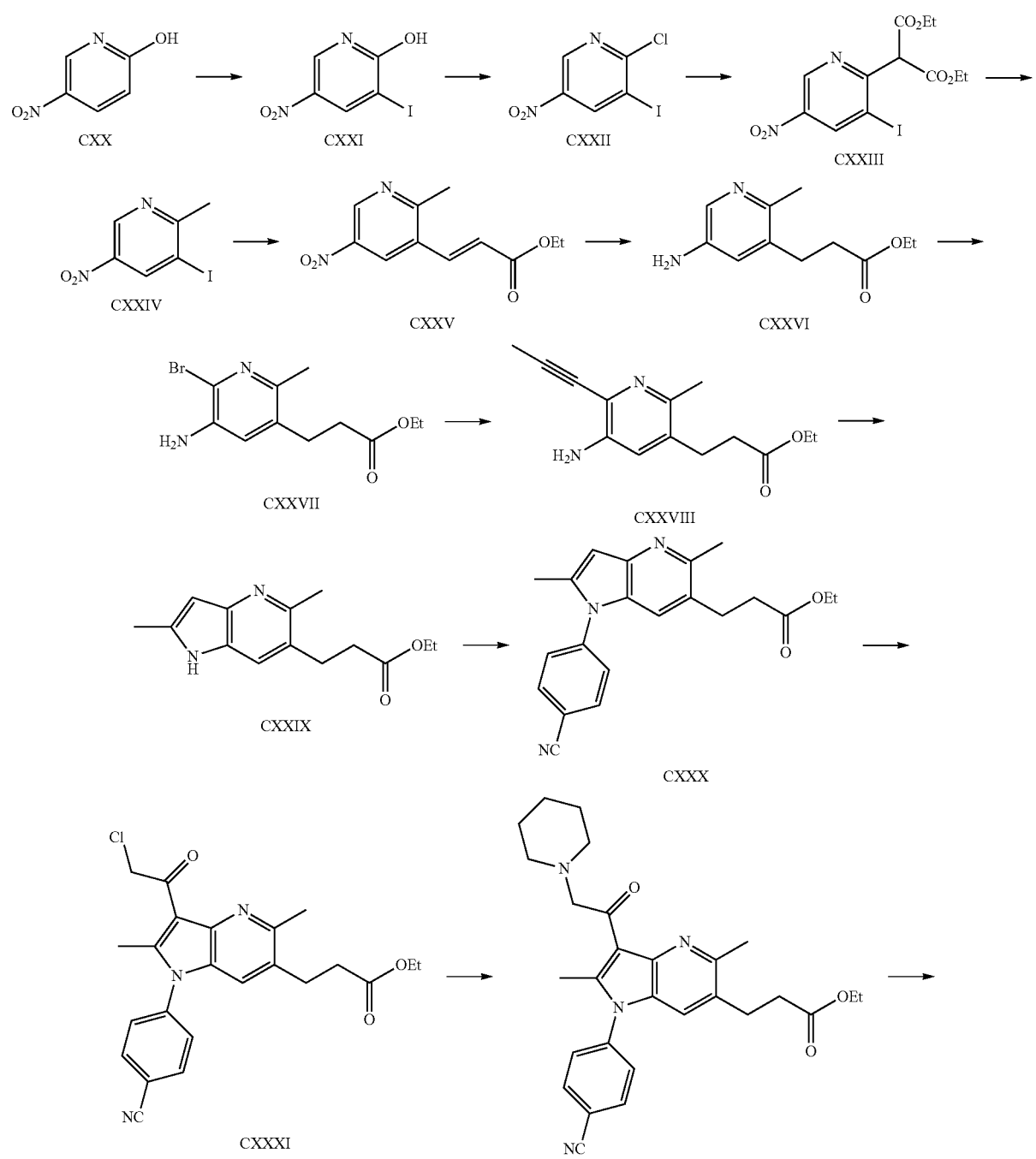

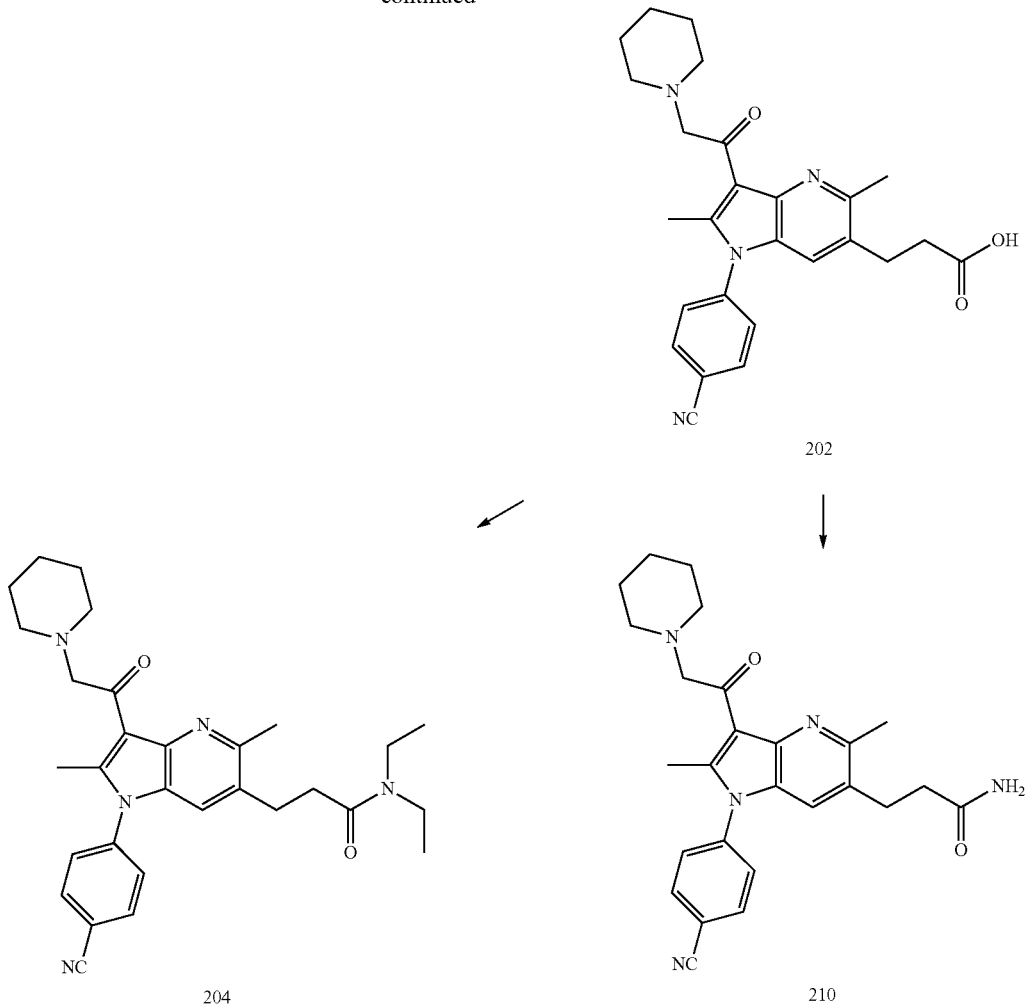

Synthesis of 3-Iodo-5-nitro-pyridin-2-ol (CXXI): To a mixture of 2-Hydroxy-5-nitro pyridine (14 g, 99.9 mmol) and potassium carbonate (13.8 g, 99.9 mmol) in N,N-dimethylformamide (100 mL) was added iodine (25.3 g, 99.7 mmol) in a portionwise fashion at room temperature. The resulting reaction mixture was heated at 85° C. for 15 h, before being allowed to cool to room temperature. The progress of the reaction was monitored by TLC. The reaction mixture was diluted with water (150 mL) and then extracted with ethyl acetate (75 mL×3). The combined organic extracts were washed with brine (150 mL×3), dried over anhydrous sodium sulfate and concentrated in vacuo. The remaining solid residue was washed with n-hexanes (50 mL×2) and allowed to dry in a stream of air to afford CXXI (14 g, 53%) as a brown solid, which was used without further purification.

Synthesis of 2-Chloro-3-iodo-5-nitro-pyridine (CXXII): To a solution of CXXI (14 g, 52.6 mmol) in quinoline (5 mL) was added phosphorous oxychloride (4.8 mL, 52.2 mmol). The resulting mixture was heated at 120° C. for 2 h. Progress of the reaction was monitored by TLC. After cooling to room temperature the reaction mixture was poured onto ice cold water (75 mL) and the precipitate that formed was collected by filtration. The filtered solid was washed with water and allowed to dry to obtain CXXII (12 g, 81%) as a brown solid. $^1$H NMR (400 MHz, CDCl$_3$): δ 9.12 (d, J=2.3 Hz, 1H), 8.84 (d, J=2.4 Hz, 1H).

Synthesis of 2-(3-Iodo-5-nitro-pyridin-2-yl)-malonic Acid Diethyl Ester (CXXIII): To an ice-cooled solution of diethylmalonate (2.2 g, 13.7 mmol) in N,N-dimethylformamide (30 mL) was added sodium hydride (0.72 g, 30.2 mmol) in a portionwise manner. The reaction mixture was allowed to stir for 15 min at 0° C. and then CXXII (2.0 g, 7.03 mmol) was added portionwise. The reaction mixture was allowed to warm to room temperature and stir for 2 h. The progress of the reaction was monitored by TLC. The reaction mixture was diluted with 2 N hydrochloric acid (20 mL) and the aqueous mixture was extracted with diethylether (50 mL×2). The combined organic extracts were washed with brine (75 mL×2) and dried over anhydrous sodium sulfate. The organic layer was condensed under reduced pressure to obtain CXXIII (2.5 g, 87%) as a brown oil, which was used without any further purification. MS (ESI, positive mode) m/z 407 (MH$^+$).

Synthesis of 3-Iodo-2-methyl-5-nitro-pyridine (CXXIV): A suspension of CXXIII (2.5 g, 6.12 mmol) in aqueous 7 N hydrochloric acid (40 mL) was heated at 110° C. for 4 h. After cooling to room temperature the reaction mixture was diluted with water (50 mL) and the pH of the mixture was adjusted to 10 through the addition of an aqueous 10% sodium hydroxide solution. The mixture was extracted with diethylether (50 mL×3) and the combined organic extracts were washed with brine (50 mL×3). The organic layer was dried over anhydrous sodium sulfate and concentrated under reduced pressure to obtain the crude product. The crude product mixture was purified by column chromatography on silica gel (100-200 mesh), using 8% ethyl acetate in hexanes as the eluent to afford CXXIV (1 g, 60%) as a pale yellow solid. $^1$H NMR (400 MHz, CDCl$_3$): δ 9.25 (d, J=2.3 Hz, 1H), 8.80 (d, J=2.4 Hz, 1H), 2.85 (s, 3H).

Synthesis of Ethyl (E)-3-(2-Methyl-5-nitropyridin-3-yl) acrylate (CXXV): To a degassed solution of CXXIV (3.2 g, 12.1 mmol) in N,N-dimethylformamide (50 mL) were added ethyl acrylate (2.4 g, 23.97 mmol), diisopropylethylamine (4.6 g, 35.7 mmol), tri(o-tolyl) phosphine (147 mg, 0.48 mmol) and palladium(II) acetate (54 mg, 0.24 mmol). The resulting reaction mixture was heated at 90° C. for 6 h. Upon cooling to room temperature, the reaction mixture was diluted with water (100 mL) and the mixture was extracted with ethyl acetate (75 mL×2). The combined organic extracts were washed with brine solution (100 mL×3), dried over anhydrous sodium sulfate, and concentrated under reduced pressure to obtain the crude product. The crude product mixture was washed with n-hexane (50 mL×2) and allowed dry to afford CXXV (2.2 g, 77%) as a brown solid. $^1$H NMR (400 MHz, CDCl$_3$): δ 9.28 (d, J=2.4 Hz, 1H), 8.55 (d, J=2.4 Hz, 1H), 7.88 (d, J=15.9 Hz, 1H), 6.53 (d, J=15.9 Hz, 1H), 4.30 (q, J=7.1 Hz, 2H), 2.77 (s, 3H), 1.35 (t, J=7.1 Hz, 3H); MS (ESI, positive mode) m/z 237 (MH$^-$).

Synthesis of Ethyl 3-(5-Amino-2-methyl-pyridin-3-yl) propionate (CXXVI): A mixture of CXXV (11.2 g, 47.4 mmol) and 10% palladium on carbon (4 g) in ethyl acetate (100 mL) was agitated under a hydrogen atmosphere (50 psi) for 15 h. The reaction mixture was then filtered through a celite bed and the filter pad was washed with ethyl acetate (100 mL×1). The filtrate was condensed in vacuo to obtain CXXVI (9 g, 91.18%) as pale-orange solid, which was used without further purification. $^1$H NMR (400 MHz, CDCl$_3$): δ 7.86 (d, J=2.6 Hz, 1H), 6.79 (d, J=2.5 Hz, 1H), 4.14 (q, J=7.1 Hz, 2H), 3.51 (brs, 2H), 2.85-2.81 (m, 2H), 2.56-2.52 (m, 2H), 2.41 (s, 3H), 1.24 (t, J=7.1 Hz, 3H); MS (ESI, positive mode) m/z 209 (MH$^+$).

Synthesis of Ethyl 3-(5-Amino-6-bromo-2-methyl-pyridin-3-yl)propionate (CXXVII): To an ice-cooled solution of CXXVI (1.5 g, 7.20 mmol) in acetic acid (20 mL) was added sodium acetate (1.1 g, 13.4 mmol) in a portionwise manner. The reaction mixture was allowed to stir for 10 min and then neat bromine (0.36 mL, 6.88 mmol) was added in a dropwise fashion. The reaction mixture was allowed to warm to room temperature and stir for 30 min. Progress of the reaction was monitored by TLC. The reaction mixture was diluted with water (100 mL) and the resulting aqueous mixture was extracted with ethyl acetate (75 mL×2). The combined organic extracts were washed with an aqueous, saturated solution of sodium bicarbonate (75 mL×2), dried over anhydrous sodium sulfate, and concentrated under reduced pressure to obtain the crude product. The crude product mixture was purified by column chromatography on silica gel (100-200 mesh), using 25% ethyl acetate in hexanes as the eluent, to afford CXXVII (1.4 g, 70%) as a pale orange solid. $^1$H NMR (400 MHz, CDCl$_3$): δ 6.85 (s, 1H), 4.17 (q, J=7.1 Hz, 2H), 3.93 (brs, 2H), 2.86-2.82 (m, 2H), 2.58-2.54 (m, 2H), 2.41 (s, 3H), 1.27 (t, J=7.1 Hz, 3H).

Synthesis of Ethyl 3-(5-Amino-2-methyl-6-prop-1-ynyl-pyridin-3-yl)propanoate (CXXVIII): To a degassed suspension of copper(I) iodide (0.039 g, 0.200 mmol) and CXXVII (1.2 g, 4.18 mmol) in triethylamine (30 mL) was added bis(triphenylphosphine)palladium(II) dichloride (0.146 g, 0.200 mmol). The resulting reaction mixture was cooled to −78° C. and propyne gas (1.3 g, 32.5 mmol) was passed through the reaction mixture. The reaction mixture was allowed to warm to room temperature and and stir for 48 h. The progress of the reaction was monitored by TLC. The reaction mixture was diluted with water (50 mL) and then filtered through a pad of celite. The filter cake was washed with ethyl acetate and the organic layer from the filtrate was dried over anhydrous sodium sulfate. The organic layer was concentrated in vacuo and the crude product mixture was purified by column chromatography on silica gel (100-200 mesh), using 50% ethyl acetate in hexanes as the eluent, to afford CXXVIII (0.85 g, 83%) as a viscous liquid. $^1$H NMR (400 MHz, CDCl$_3$): δ 6.79 (s, 1H), 4.14 (q, J=7.1 Hz, 2H), 3.96 (brs, 2H), 2.84 (t, J=7.6 Hz, 2H), 2.55 (t, J=7.6 Hz, 2H), 2.40 (s, 3H), 2.11 (s, 3H), 1.24 (t, J=7.1 Hz, 3H); MS (ESI, positive mode) m/z 248 (MH$^+$).

Synthesis of Ethyl 3-(2,5-Dimethyl-1H-pyrrolo[3,2-b]pyridin-6-yl)propanoate (CXXIX): To an ice-cooled solution of CXXVIII (2.60 g, 10.6 mmol) in 1,4-dioxane (50 mL) were added trifluoroacetic anhydride (3.7 mL, 26.2 mmol) and diisopropylethylamine (6.3 mL, 36.4 mmol). The reaction mixture was allowed to stir at room temperature for 3 h and then triethylamine (4.4 mL, 31.6 mmol) was added. The reaction mixture was heated at 60° C. for 15 h and the progress of the reaction was monitored by TLC. Upon cooling to room temperature the reaction mixture was diluted with water (50 mL) and the mixture was extracted with ethyl acetate (50 mL×2). The combined organic extracts were washed with brine (50 mL×3), dried over anhydrous sodium sulfate, and concentrated under reduced pressure to obtain the crude product. The crude product mixture was purified by column chromatography on silica gel (100-200 mesh), using 5% methanol in dichloromethane as the eluent, to afford CXXIX (1.8 g, 69%) as a brown solid. $^1$H NMR (400 MHz, CDCl$_3$): δ 8.22 (brs, 1H), 7.40 (s, 1H), 6.27 (s, 1H), 4.14 (q, J=7.1 Hz, 2H), 3.02 (t, J=7.5 Hz, 2H), 2.63-2.58 (m, 5H), 2.43 (s, 3H), 1.23 (t, J=7.1 Hz, 3H); MS (ESI, positive mode) m/z 247 (MH$^+$).

Synthesis of Ethyl 3-[1-(4-Cyano-phenyl)-2,5-dimethyl-1H-pyrrolo[3,2-b]pyridin-6-yl]propanoate (CXXX): To a degassed solution of CXXIX (1.6 g, 6.50 mmol), 4-iodobenzonitrile (2.9 g, 12.7 mmol), and potassium phosphate (4.1 g, 19.3 mmol) in 1,4 Dioxane (30 mL) were added copper(I) iodide (0.123 g, 0.640 mmol) and trans-(+/−)-1,2-cyclohexanediamine (0.074 g, 0.640 mmol). The reaction mixture was heated at 100° C. for 15 h and then allowed to cool to room temperature. The progress of the reaction was monitored by TLC. The reaction mixture was diluted with water (100 mL) and the mixture was extracted with ethyl acetate (75 mL×3). The combined organic extracts were washed with brine (100 mL×3), dried over anhydrous sodium sulfate, and concentrated under reduced pressure to obtain the crude product. The crude product mixture was purified by column chromatography on silica gel (100-200 mesh), using 2% methanol in dichloromethane as the eluent, to afford CXXX (1.5 g, 67%) as a pale orange solid. $^1$H NMR (400 MHz, CDCl$_3$): δ 7.87 (dd, J=6.7, 1.9 Hz, 2H), 7.46 (dd, J=6.7, 1.9 Hz, 2H), 7.23 (s, 1H), 4.11 (q, J=7.1 Hz, 2H), 3.00 (t, J=7.9 Hz, 2H), 2.69 (s, 3H), 2.57 (t, J=7.9 Hz, 2H), 2.36 (s, 3H), 1.20 (t, J=7.1 Hz, 3H); MS (ESI, positive mode) m/z 348 (MH$^+$).

Synthesis of Ethyl 3-[3-(2-Chloro-acetyl)-1-(4-cyano-phenyl)-2,5-dimethyl-1H-pyrrolo[3,2-b]pyridin-6-yl]propanoate (CXXXI): To an ice-cooled solution of aluminum trichloride (5.3 g, 39.7 mmol) in 1,2-dichloroethane (40 mL) was added neat chloroacetyl chloride (3.2 mL, 40.3 mmol) in a dropwise fashion. The reaction mixture was allowed to stir at 0° C. for 40 min and then a solution of CXXX (1.4 g, 4.03 mmol) in 1,2-dichloroethane (20 mL) was added. The reaction mixture was allowed to warm to room temperature and was then heated at 60° C. for 6 h. Progress of the reaction was monitored by TLC. After cooling, the reaction mixture was poured onto ice cold water (100 mL) and the mixture was extracted with dichloromethane (2×100 mL). The combined organic extracts were dried over sodium sulfate, filtered, and concentrated in vacuo to afford the crude product. The crude product mixture was purified by column chromatography on silica gel (100-200 mesh), using 30% ethyl acetate in hexanes as the eluent, to afford CXXXI (1.3 g, 76%) as a pale brown solid. $^1$H NMR (400 MHz, CDCl$_3$): δ 7.93 (dd, J=6.7, 1.9 Hz, 2H), 7.46 (dd, J=6.7, 1.9 Hz, 2H), 7.10 (s, 1H), 5.35 (s, 2H), 4.10 (q, J=7.1 Hz, 2H), 3.00 (t, J=7.9 Hz, 2H), 2.67 (s, 3H), 2.66 (s, 3H), 2.57 (t, J=7.9 Hz, 2H), 1.24 (t, J=7.1 Hz, 3H); MS (ESI, positive mode) m/z 424/426 (MH$^+$, $^{35/37}$Cl).

Synthesis of Ethyl 3-[1-(4-Cyano-phenyl)-2,5-dimethyl-3-(2-piperidin-1-yl-acetyl)-1H-pyrrolo[3,2-b]pyridin-6-yl]propanoate (200): To an ice-cooled solution of CXXXI (1.3 g, 3.06 mmol) in N,N-dimethylformamide (25 mL) was added piperidine (0.78 g, 9.19 mmol). The reaction mixture was allowed to stir at room temperature for 1 h before it was poured onto ice cold water. The precipitate that formed was collected by filtration and washed with water. After drying in a stream of air the solid was purified by column chromatography on silica gel (100-200 mesh) using 2% methanol in dichloromethane as the eluent to afford 200 (1.1 g, 76%) as an off white solid. $^1$H NMR (400 MHz, CDCl$_3$): δ 7.91 (d, J=8.4 Hz, 2H), 7.45 (d, J=8.4 Hz, 2H), 7.07 (s, 1H), 4.35 (s, 2H), 4.10-4.05 (m, 2H), 2.99 (t, J=7.6 Hz, 2H), 2.86-2.60 (m, 10H), 2.51 (t, J=7.6 Hz, 2H), 1.68 (m, 4H), 1.48 (m, 2H), 1.20 (t, J=7.2 Hz, 3H); MS (ESI, positive mode) m/z 473 (MH$^+$).

Synthesis of 3-[1-(4-Cyano-phenyl)-2,5-dimethyl-3-(2-piperidin-1-yl-acetyl)-1H-pyrrolo[3,2-b]pyridin-6-yl]propionic Acid Hydrochloride Salt (202): To a solution of 200 (0.75 g, 1.58 mmol) in 1,4-dioxane (20 mL) was added a solution of concentrated hydrochloric acid (2 mL) in water (4 mL). The mixture was heated at 70° C. for 3 h and then allowed to cool to room temperature. The progress of the reaction was monitored by TLC. The reaction mixture was condensed in vacuo through azeotropic distillation with toluene (10 mL×3). The remaining brown viscous liquid was purified by washing with diethylether (10 mL×3) to afford 202 (470 mg, 62%) as an off-white solid. $^1$H NMR (400 MHz, DMSO): δ 9.82 (brs, 1H), 8.19 (d, J=8.5 Hz, 2H), 7.80 (d, J=8.5 Hz, 2H), 7.42 (s, 1H), 5.10 (d, J=4.8 Hz, 2H), 3.58-3.53 (m, 2H), 3.19-3.17 (m, 2H), 2.92 (t, J=7.4 Hz, 2H), 2.68 (s, 3H), 2.64 (s, 3H), 2.53 (s, 2H), 1.88-1.84 (m, 4H), 1.74-1.71 (m, 1H), 1.47 (m, 1H); MS (ESI, positive mode) m/z 445 (MH$^-$).

Synthesis of 3-[1-(4-Cyano-phenyl)-2,5-dimethyl-3-(2-piperidin-1-yl-acetyl)-1H-pyrrolo[3,2-b]pyridin-6-yl]-propionamide (210): To a solution of 202 (0.45 g, 10.1 mmol) in N,N-dimethylformamide (20 mL) was added diisopropylethylamine (0.785 g, 6.08 mmol) in a dropwise fashion. The reaction mixture was allowed to stir at room temperature for 10 min and was then treated with HBTU (0.76 g, 2.02 mmol), followed by solid ammonium chloride (0.54 g, 10.1 mmol). The reaction mixture was allowed to stir for 3 h and was then diluted with water (100 mL). The mixture was extracted with ethyl acetate (50 mL×3) and the combined organic extracts were washed with brine (100 mL×3). The organic layer was dried over anhydrous sodium sulfate and then concentrated under reduced pressure to obtain the crude product. The crude product mixture was purified by column chromatography on neutral alumina, using 3% methanol in dichloromethane as eluent, to afford 210 (0.14 g, 31%) as an off-white solid. $^1$H NMR (400 MHz, DMSO-d$_6$): δ 8.15 (d, J=8.5 Hz, 2H), 7.76 (d, J=8.5 Hz, 2H), 7.25 (s, 2H), 6.78 (s, 1H), 4.18 (s, 2H), 2.85 (t, J=7.3 Hz, 2H), 2.60-2.50 (m, 10H), 2.32 (t, J=7.3 Hz, 2H), 1.55-1.47 (m, 4H), 1.41 (brs, 2H); MS (ESI, positive mode) m/z 444 (MH$^-$).

Synthesis of 3-[1-(4-Cyano-phenyl)-2,5-dimethyl-3-(2-piperidin-1-yl-acetyl)-1H-pyrrolo[3,2-b]pyridin-6-yl]-N,N-diethyl-propanamide (204): To a solution of 202 (70 mg, 0.158 mmol) in N,N-dimethylformamide (3 mL) was added diisopropylethylamine (0.08 mL, 0.472 mmol) in a dropwise fashion. The reaction mixture was allowed to stir at room temperature for 10 min and then HBTU (119 mg, 0.314 mmol), followed by diethylamine (34 mg, 0.465 mmol) was added. The reaction mixture was allowed to stir for 24 h and was then diluted with water (50 mL). The mixture was extracted with ethyl acetate (2×25 mL) and the combined organic extracts were washed with brine (3×50 mL), dried over anhydrous sodium sulfate, and concentrated under reduced pressure. The remaining crude product mixture was purified by column chromatography on neutral alumina, using 3% methanol in dichloromethane as the eluant, to afford to afford 204 (25 mg, 32%) as an off-white solid; $^1$H NMR (400 MHz, DMSO): δ 8.15 (d, J=8.5 Hz, 2H), 7.76 (d, J=8.5 Hz, 2H), 7.23 (s, 1H), 4.20 (brs, 2H), 3.23-3.16 (m, 4H), 2.88 (t, J=7.2 Hz, 2H), 2.67-2.61 (m, 5H), 2.56-2.44 (m, occluded by solvent, 6H), 1.53 (brs, 4H), 1.42 (brs, 2H), 0.97 (t, J=7.0 Hz, 3H), 0.89 (t, J=7.0 Hz, 3H); MS (ESI, positive mode) m/z 500 (MH$^+$).

Example 57

4-(2-Methyl-3-(2-(piperidin-1-yl)acetyl)-6-vinyl-1H-indol-1-yl)benzonitrile (206)

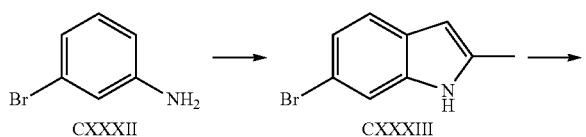

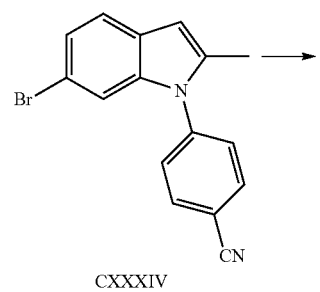

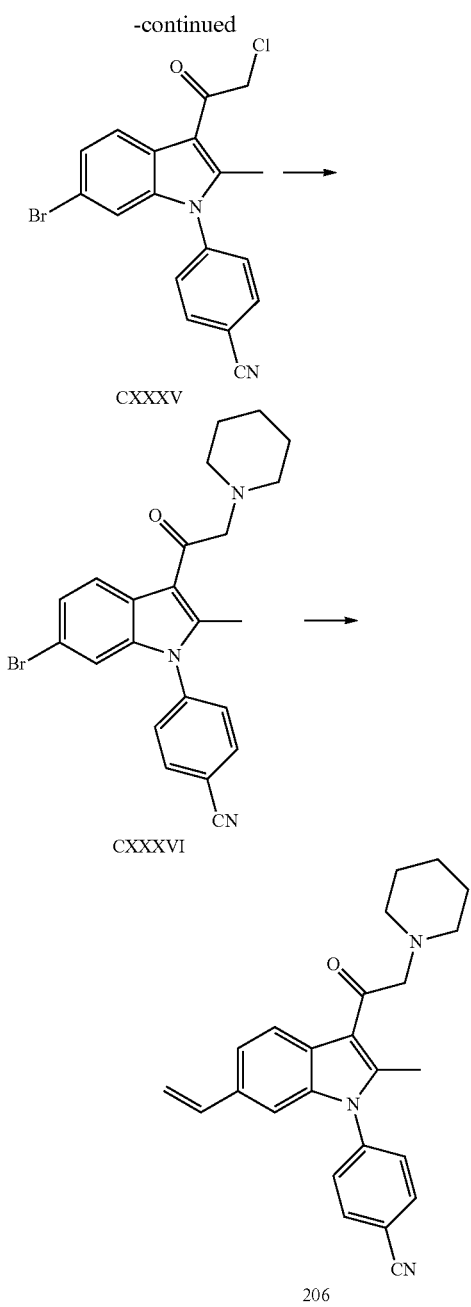

Synthesis of 6-Bromo-2-methyl-1H-indole (CXXXIII): A mixture of 3-bromo-aniline (4 g, 0.041 mmol), copper(II) acetate-monohydrate (14.0 g, 0.129 mmol), palladium(II) acetate (0.1 g, 0.000801 mmol) and acetone (100 mL) in dimethylsulfoxide (50 mL) was heated at 90° C. for 24 h. The reaction mixture was poured onto cold water and then extracted with ethyl acetate (2×250 mL). The organic layer was washed with water and brine, before drying over anhydrous sodium sulfate. The organic layer was concentrated under reduced pressure to afford the crude product, which was purified by column chromatography on (100-200 mesh) silica gel, using 5% ethyl acetate in hexanes, to afford CXXXIII (1.3 mg, 27%). $^1$H NMR (400 MHz, CDCl$_3$): δ 7.83 (brs, 1H), 7.40 (s, 1H), 7.34 (d, J=8.3 Hz, 1H), 7.14 (dd, J=8.5, 1.7 Hz, 1H), 6.17 (s, 1H), 2.41 (s, 3H); MS (ESI, positive mode) m/z 208/210 (MH$^+$, $^{79/81}$Br).

Synthesis of 4-(6-Bromo-2-methyl-indol-1-yl)-benzonitrile (CXXXIV): To a solution of CXXXIII (1.0 g, 4.70 mmol) in 1,4-dioxane (50 mL) was added potassium phosphate (2.98 g, 0.044 mol) and 4-iodo-benzonitrile (2.1 g, 0.010 mol). The mixture was sparged with nitrogen gas for 0.5 h at room temperature. Then copper(I) iodide (0.44 g, 0.230 mmol) and trans-(+/−)-1,2-diaminocyclohexane (0.054 g, 0.470 mmol) were added to the flask. The resultant reaction mixture was heated at 130° C. for 48 h. After cooling to room temperature, the reaction mixture was filtered through a bed of celite and the filter pad was washed with ethyl acetate. The filtrate was concentrated under reduced pressure and the remaining crude product mixture was purified by column chromatography on (100-200 mesh) silica gel, using 5% ethyl acetate in hexanes to afford CXXXIV (0.65 g, 44%) as an off-white solid. $^1$H NMR (400 MHz, CDCl$_3$): δ 7.85 (d, J=8.3 Hz, 2H), 7.4-7.45 (m, 2H), 7.42-7.39 (m, 1H), 7.24-7.22 (m, 2H), 6.41 (s, 1H), 2.29 (s, 3H).

Synthesis of 4-[6-Bromo-3-(2-chloro-acetyl)-2-methyl-indol-1-yl]-benzonitrile (CXXXV): To a solution of chloroacetyl chloride (1.32 g, 0.010 mol) in 1,2-dichloroethane (20 mL), kept at 0° C. under a nitrogen atmosphere, was added anhydrous aluminum chloride (1.4 g, 0.010 mol). The reaction mixture was allowed to warm to room temperature and stir for 0.5 h. Then a solution of CXXXIV (0.55 g, 1.70 mmol) in dry 1,2-dichloroethane (10 mL) was added to the reaction mixture. The reaction mixture was allowed to stir at room temperature for 1 h before it was poured onto cold water. The mixture was extracted with ethyl acetate (2×100 mL) and the combined organic extracts were dried over anhydrous sodium sulfate. The organic layer was concentrated under reduced pressure and the remaining crude product mixture was purified by column chromatography on (100-200 mesh) silica gel, using 10% ethyl acetate in hexanes, to afford CXXXV (0.380 g, 55%) as a brownish solid. $^1$H NMR (400 MHz, CDCl$_3$): δ 7.94 (d, J=8.4 Hz, 2H), 7.81 (d, J=8.6 Hz, 1H), 7.49-7.42 (m, 3H), 7.13 (d, J=1.5 Hz, 1H), 4.68 (s, 2H), 2.59 (s, 3H); MS (ESI, positive mode) m/z 385/387 (MH$^+$, $^{79/81}$Br/$^{35/37}$Cl).

Synthesis of 4-[6-Bromo-2-methyl-3-(2-piperidin-1-yl-acetyl)-indol-1-yl]-benzonitrile (CXXXVI): A mixture of CXXXV (0.35 g, 0.610 mmol) and piperidine (0.078 g, 0.910 mmol) in N,N-dimethylformamide (2 mL) was allowed to stir at room temperature for 1 h under a nitrogen atmosphere. The reaction mixture was poured onto cold water and the precipitate that formed was collected by filtration. The filtered solid was washed with water and, after drying, triturated with n-pentane to afford CXXXVI (0.27 g, 70%) as an off-white solid. $^1$H NMR (400 MHz, CDCl$_3$): δ 7.94-7.90 (m, 3H), 7.46 (d, J=8.4 Hz, 2H), 7.38 (dd, J=8.5, 1.6 Hz, 1H), 7.11 (d, J=1.5 Hz, 1H), 3.70 (s, 2H), 2.60-2.52 (m, 7H), 1.64-1.62 (m, 4H), 1.50-1.44 (m, 2H); MS (ESI, positive mode) m/z 436/438 (MH$^+$, $^{79/81}$Br).

Synthesis of 4-(2-Methyl-3-(2-(piperidin-1-yl)acetyl)-6-vinyl-1H-indol-1-yl)benzonitrile (206): To a solution of CXXXVI (0.15 g, 0.340 mmol) in toluene (10 mL) and ethanol (10 mL) was added an aqueous 2.0 M sodium bicarbonate solution (10 mL). The mixture was sparged with nitrogen gas for 0.5 h and then vinyl boronic acid pinacol ester (0.16 g, 0.001 mol) and tetrakis(triphenylphosphine)palladium(O) (2 mg, 0.017 mmol) was added. The reaction mixture was sparged with nitrogen for an additional 10 min before heating at 90° C. under a nitrogen atmosphere for 8 h. After cooling to room temperature the reaction mixture was filtered through celite and the filter pad was washed with ethyl acetate. The filtrate was extracted with ethyl acetate (2×50 mL) and the combined organic extracts were dried over anhydrous sodium sulfate. The organic layer was concentrated under reduced pressure and the remaining crude product mixture was purified by column chromatography on silica gel (100-200 mesh), using a gradient of ethyl acetate in hexanes. The solid obtained this way was further triturated with n-pentane and allowed to dry to afford 206 (44 mg, 38%) as a pale brown solid. $^1$H NMR (400 MHz, CDCl$_3$): δ 7.96 (d, J=8.4 Hz, 1H), 7.92-7.90 (m, 2H), 7.49-7.47 (m, 2H), 7.42-7.40 (dd, J=8.5 Hz, 1H), 6.95 (s, 1H), 6.70 (dd, J=17.5, 10.8 Hz, 1H), 5.66 (d, J=17.5 Hz, 1H), 5.18 (d, J=10.8 Hz, 1H), 3.77 (s, 2H), 2.60-2.59 (m, 7H), 1.68-1.62 (m, 4H), 1.50-1.45 (m, 2H); MS (ESI, positive mode) m/z 384 (MH$^+$).

Examples 58-59

4-(2-Methyl-3-(2-(piperidin-1-yl)acetyl)-5-(2H-1,2,3-triazol-2-yl)-1H-pyrrolo[3,2-b]pyridin-1-yl)benzonitrile (208), 4-(2-Methyl-3-(2-(piperidin-1-yl)acetyl)-5-(1H-1,2,3-triazol-1-yl)-1H-pyrrolo[3,2-b]pyridin-1-yl)benzonitrile (209)

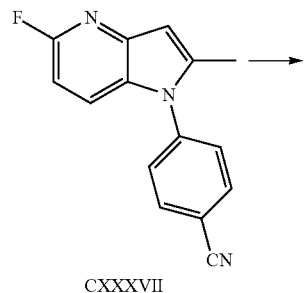

CXXXVII

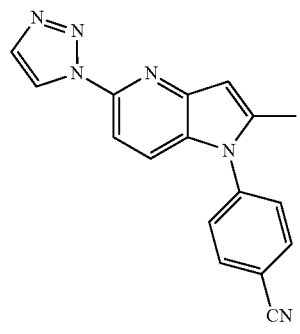

CXXXVIII

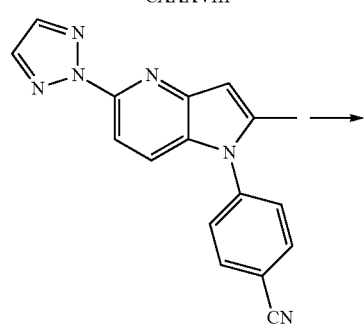

CXXXIX

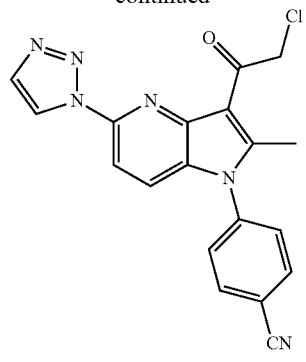

CXL

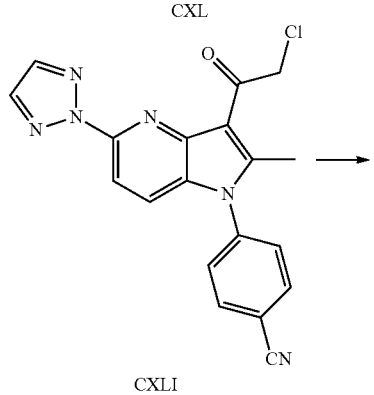

CXLI

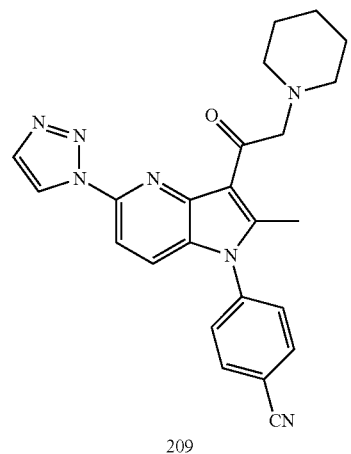

209

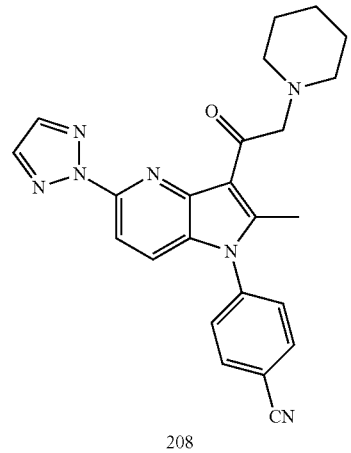

208

Synthesis of 4-(2-Methyl-5-(1H-1,2,3-triazol-1-yl)-1H-pyrrolo[3,2-b]pyridin-1-yl)benzonitrile (CXXXVIII) and 4-(2-Methyl-5-(2H-1,2,3-triazol-2-yl)-1H-pyrrolo[3,2-b]pyridin-1-yl)benzonitrile (CXXXIX): To a mixture of CXXXVII (0.025 g, 0.099 mmol) and 1,2,3-triazole (0.010 g, 0.149 mmol) in N,N-dimethylformamide (1 mL) was added potassium carbonate (0.041 g, 0.298 mmol). The resulting mixture was heated at 150° C. in a microwave for 2 h. Progress of the reaction was monitored by TLC. The reaction mixture was diluted with water (30 mL) and then extracted into ethyl acetate (30 mL×2). The combined organic extracts were washed with brine (25 mL×2), dried over anhydrous sodium sulfate, and concentrated in vacuo to obtain the crude product. The crude product mixture was purified by chromatography on silica using 8-10% ethyl acetate in hexanes to afford CXXXVIII (0.005 g, 17%) and CXXXIX (0.01 g, 17%) as off-white solids. MS (ESI, positive mode) m/z 301 (MH$^+$).

Synthesis of 4-(3-(2-Chloroacetyl)-2-methyl-5-(1H-1,2,3-triazol-1-yl)-1H-pyrrolo[3,2-b]pyridin-1-yl)benzonitrile (CXL) and 4-(3-(2-Chloroacetyl)-2-methyl-5-(2H-1,2,3-triazol-2-yl)-1H-pyrrolo[3,2-b]pyridin-1-yl)benzonitrile (CXLI), General Procedure: To an ice-cooled solution of aluminum trichloride (10 eq) in dichloromethane was added chloroacetyl chloride (10 eq) in a dropwise fashion. The reaction mixture was allowed to stir at 0° C. for 40 min and then to the mixture was added CXXXVIII or CXXXIX (1 eq). The reaction mixture was allowed to warm to room temperature and was then heated at 80° C. for 6 h. The progress of the reaction was monitored by TLC. After cooling, the reaction mixture was poured onto ice cold water and and the mixture was extracted with dichloromethane. The combined organic extracts were dried over sodium sulfate, filtered, and concentrated in vacuo to afford the crude product. The crude product mixture was purified by column chromatography on silica gel (100-200 mesh), using methanol in dichloromethane as the eluent to afford CXL and CXLI. The material were used without any further purification or characterization.

Synthesis of 4-(2-Methyl-3-(2-(piperidin-1-yl)acetyl)-5-(2H-1,2,3-triazol-2-yl)-1H-pyrrolo[3,2-b]pyridin-1-yl)benzonitrile (208): To an ice-cooled solution of CXLI (0.22 g, 0.584 mmol) in N,N-dimethylformamide (10 mL) were added piperidine (0.149 g, 1.75 mmol), potassium carbonate (0.16 g, 1.17 mmol) and stirred at room temperature for 2 h. Progress of the reaction was monitored by TLC. The reaction mixture was diluted with water (50 mL) and extracted with ethyl acetate (25 mL×2). The combined organic extracts were washed with brine (50 mL×2), dried over sodium sulfate, and concentrated in vacuo to obtain the crude product. The crude product mixture was purified by washing with diethyl ether (5 mL×2) and drying afforded 208 (0.14 g, 56%) as an off-white solid. $^1$H NMR (400 MHz, CDCl$_3$): δ 8.20 (t, J=4.2 Hz, 4H), 7.88 (d, J=8.6 Hz, 3H), 7.77 (d, J=8.8 Hz, 1H), 4.20 (s, 2H), 2.62 (brs, 7H), 1.48-1.46 (m, 4H), 1.39-1.38 (m, 2H); MS (ESI, positive mode) m/z 426 (MH$^+$).

Synthesis of 4-(2-Methyl-3-(2-(piperidin-1-yl)acetyl)-5-(1H-1,2,3-triazol-1-yl)-1H-pyrrolo[3,2-b]pyridin-1-yl)benzonitrile (209): To an ice-cooled solution of CXL (0.2 g, crude) in N,N-dimethylformamide (10 mL) was added piperidine (0.09 g). The mixture was allowed to stir at room temperature for 2 h and then the reaction mixture was poured onto ice cold water. The precipitate that formed was collected via filtration and the solids were washed with water. After drying, the solid was purified by column chromatography on neutral alumina, using 1% methanol in dichloromethane as eluent, to afford 209 (0.01 g, 3% after two steps) as an off-white solid. $^1$H NMR (400 MHz, CDCl$_3$): δ 8.88 (s, 1H), 8.20 (d, J=8.1 Hz, 2H), 8.04 (s, 1H), 7.97 (d, J=8.7 Hz, 1H), 7.88 (d, J=8.2 Hz, 2H), 7.83 (d, J=8.7 Hz, 1H), 4.21 (s, 2H), 2.62 (s, 7H), 1.52 (brs, 4H), 1.40 (brs, 2H); MS (ESI, positive mode) m/z 426 (MH$^+$).

Example 60

4-(2-Methyl-3-(2-(piperidin-1-yl)acetyl)-6-(pyrrolidin-1-ylmethyl)-1H-pyrrolo[3,2-b]pyridin-1-yl)benzonitrile (360)

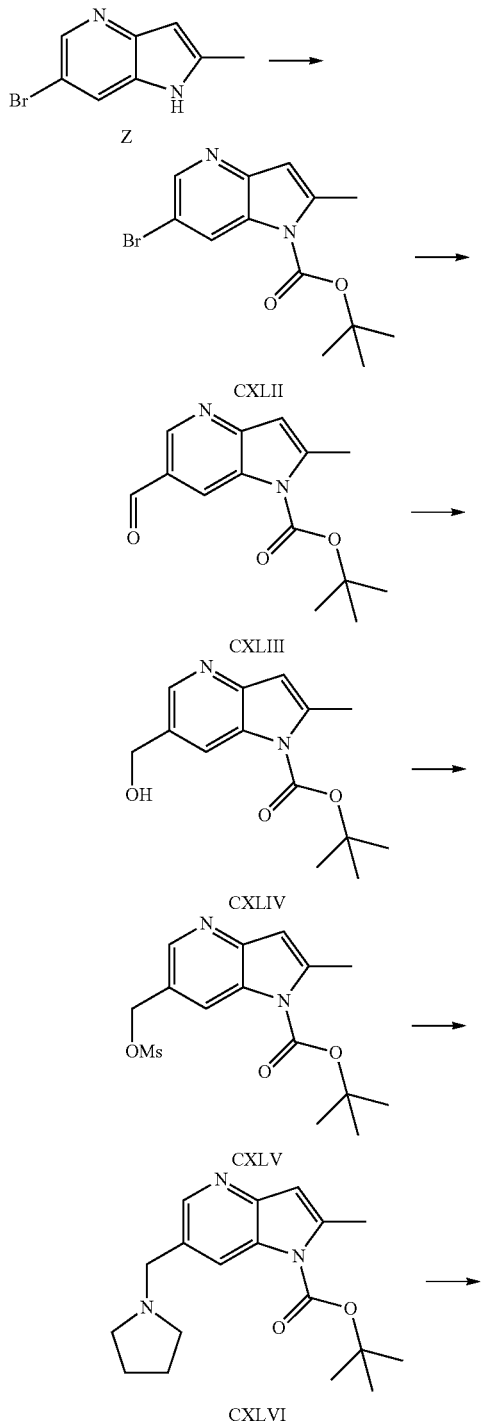

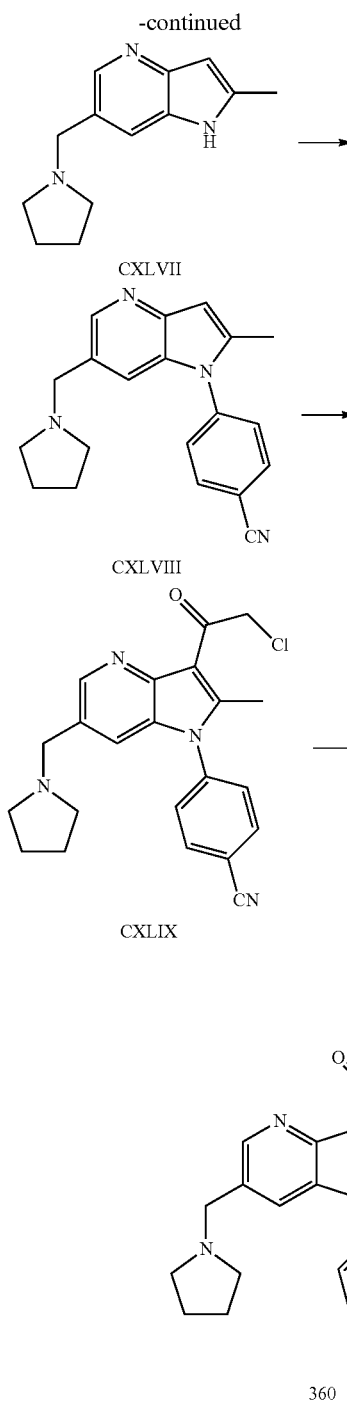

CXLVII

CXLVIII

CXLIX

360

Synthesis of tert-Butyl 6-bromo-2-methyl-1H-pyrrolo[3,2-b]pyridine-1-carboxylate (CXLII): To an ice-cooled solution of Z (4.5 g, 21.3 mmol) in dichloromethane (25 mL) were added 4-dimethylaminopyridine (2.60 g, 21.3 mmol) and di-tert-butyl dicarbonate (6.97 g, 32.0 mmol). The reaction mixture was allowed to stir at room temperature for 1 h. Progress of the reaction mixture was monitored by TLC. The reaction mixture was then poured onto cold water and the mixture was extracted with dichloromethane (2×50 mL). The combined organic extracts were dried over anhydrous sodium sulfate and concentrated under reduced pressure to afford CXLII (4.8 g, 73%) as an off-white solid. $^1$H NMR (400 MHz, CDCl$_3$): δ 8.49-8.48 (m, 2H), 6.47 (s, 1H), 2.62 (s, 3H), 1.67 (s, 9H); LC MS (ESI, positive mode) m/z 311/313 (MH$^+$, $^{79/81}$Br).

Synthesis of tert-Butyl 6-Formyl-2-methyl-1H-pyrrolo[3,2-b]pyridine-1-carboxylate (CXLIII): To a stirred solution of CXLII (4.8 g, 15.4 mmol) in dry diethylether (100 mL) was added tetramethylethylene diamine (2.14 g, 18.5 mmol) in a dropwise fashion. To the mixture was added n-butyl lithium (1.18 g, 18.5 mmol) in a dropwise fashion at −78° C. The reaction mixture was allowed to stir at −78° C. for 45 min and then dry N,N-dimethylformamide (5.07 g, 69.5 mmol) was added in a dropwise fashion. The reaction mixture was allowed to warm to room temperature and stir for 45 minutes. Progress of the reaction was monitored by TLC. The reaction mixture was quenched by through the addition of an aqueous ammonium chloride solution (50 mL) and then poured onto cold water (100 mL). The mixture was extracted with ethyl acetate (2×100 mL) and the combined organic extracts were dried over sodium sulfate, filtered, and concentrated in vaccuo. The remaining crude product mixture was purified by column chromatography on silica, using 30% ethyl acetate in hexanes as the eluant, to afford CXLIII (1.9 g, 47%) as an off-white solid. $^1$H NMR (400 MHz, DMSO-d$_6$): δ 10.14 (s, 1H), 8.93 (d, J=1.7 Hz 1H), 8.67 (d, J=1.7 Hz 1H), 6.77 (s, 1H), 2.67 (s, 3H), 1.66 (s, 9H); MS (ESI, positive mode) m/z 261 (MH$^+$).

Synthesis of tert-Butyl 6-(Hydroxymethyl)-2-methyl-1H-pyrrolo[3,2-h]pyridine-1-carboxylate (CXLIV): To an ice cooled solution of CXLIII (1.8 g, 6.92 mmol) in ethanol (20 mL) was added sodium borohydride (0.130 g, 3.46 mmol) in a portionwise manner. The reaction mixture was allowed to stir at room temperature for 1 h and was then condensed in vacuo. The reaction mixture was poured onto cold water (100 mL) and the mixture was extracted with ethyl acetate (2×100 mL). The combined organic extracts were dried over sodium sulfate, filtered, and concentrated in vaccuo to afford CXLIV (1.8 g, 99%) as an off-white solid. $^1$H NMR (400 MHz, DMSO-d$_6$): δ 8.34 (s, 1H), 8.28 (s, 1H), 6.57 (s, 1H), 5.31 (t, J=5.7 Hz, 1H), 4.62 (d, =5.6 Hz, 2H), 2.59 (s, 3H), 1.63 (s, 9H); MS (ESI, positive mode) m/z 263 (MH$^-$).

Synthesis of tert-Butyl 2-Methyl-6-(((methylsulfonyl)oxy)methyl)-1H-pyrrolo[3,2-b]pyridine-1-carboxylate (CXLV): To an ice cooled solution of CXLIV (1.8 g, 6.87 mmol) in dichloromethane (30 mL) were added triethylamine (4.17 g, 41.2 mmol) and methane sulfonyl chloride (1.88 g, 16.5 mmol) in a dropwise fashion. The reaction mixture was allowed to warm to room temperature and stir for 4 h. The progress of the reaction was monitored by TLC. The reaction mixture was then poured onto cold water (100 mL) and the mixture was extracted with dichloromethane (2×100 mL). The combined organic extracts were dried over sodium sulfate, filtered, and concentrated in vacuo to afford CXLV (1.9 g, crude) as pale-brown, viscous oil, which was used without further purification. MS (ESI, positive mode) m/z 281 (MH$^+$).

Synthesis of tert-Butyl 2-methyl-6-(pyrrolidin-1-ylmethyl)-1H-pyrrolo[3,2-b]pyridine-1-carboxylate (CXLVI): To a solution of CXLV (1.9 g, crude) in acetonitrile (30 mL) were added potassium carbonate (1.87 g, 13.6 mmol) and pyrrolidine (0.72 g, 10.2 mmol). The reaction mixture was allowed to stir at room temperature for 16 h. Progress of the reaction was monitored by TLC. The reaction mixture was condensed in vacuo and the remaining residue was diluted with cold water (100 mL). The mixture was extracted with dichloromethane (3×100 mL) and the combined organic extracts were dried over sodium sulfate, filtered, and concentrated in vacuo to afford CXLVI (0.750 g, crude) as a brown, viscous oil, which was used without any further purification. MS (ESI, positive mode) m/z 317 (MH+).

Synthesis of 2-Methyl-6-(pyrrolidin-1-ylmethyl)-1H-pyrrolo[3,2-b]pyridine (CXLVII): To an ice cooled solution of CXLVI (0.750 g, crude) in 1,4 dioxane (10 mL) is added concentrated hydrochloric acid (10 mL). The reaction mixture was allowed to warm to room temperature and stir for 16 h. Progress of the reaction was monitored by TLC. The reaction mixture was condensed in vacuo and the remaining material was diluted with cold water (50 mL). The mixture was neutralized through the addition of an aqueous, saturated sodium bicarbonate solution (15 mL) and then extracted with dichloromethane (4×100 mL). The combined organic extracts were dried over sodium sulfate, filtered, and concentrated in vacuo to afford CXLVII (0.300 g, 20% over three steps) as a brown, viscous oil. $^1$H NMR (400 MHz, DMSO-$d_6$); δ 11.02 (s, 1H), 8.13 (d, J=1.8 Hz, 1H), 7.48 (s, 1H), 6.20 (s, 1H), 4.26-4.20 (m, 1H), 4.02-3.96 (m 1H), 2.59-256 (m, 7H), 1.68-1.66 (m, 4H); MS (ESI, positive mode) m/z 216 (MH−).

Synthesis of 4-(2-methyl-6-(pyrrolidin-1-ylmethyl)-1H-pyrrolo[3,2-b]pyridin-1-yl)benzonitrile (CXLVIII): To a degassed mixture of CXLVII (0.300 g, 1.39 mmol), 4-iodobenzonitrile (1.27 g, 5.58 mmol), copper(I) iodide (0.132 g, 0.69 mmol) and potassium phosphate (1.77 g, 8.37 mmol) in 1,4-dioxane (15 mL) was added trans-(+/−)-1,2-cyclohexanediamine (0.079 g, 0.69 mol). The resulting reaction mixture was heated at 125° C. for 16 h in a sealed tube. After cooling, the reaction mixture was filtered through a bed of celite and the filter pad was washed with ethyl acetate. The filtrate was concentrated to afford the crude product, which was purified by column chromatography on neutral alumina, using 30% ethyl acetate in hexanes as eluent, to afford CXLVIII (0.300 g, 68%) as a viscous oil. $^1$H NMR (400 MHz, DMSO-$d_6$): δ 8.29 (d, J=1.6 Hz, 1H), 8.10 (d, J=8.5 Hz, 2H), 7.73 (d, J=8.5 Hz, 2H), 7.36 (s, 1H), 6.59 (s, 1H), 3.61 (s, 2H), 2.40-2.35 (m, 7H), 1.64 (brs, 4H); MS (ESI, positive mode) m/z 317 (MH+).

Synthesis of 4-(3-(2-Chloroacetyl)-2-methyl-6-(pyrrolidin-1-ylmethyl)-1H-pyrrolo[3,2-b]pyridin-1-yl)benzonitrile (CXLIX): To an ice cooled suspension of aluminum trichloride (1.58 g, 12.0 mmol) in 1,2-dichloroethane (20 mL) was added neat chloroacetyl chloride (1.34 g, 12.0 mmol) in a dropwise fashion. The reaction mixture was stirred for 45 min at 0° C. and then a solution of CXLVIII (0.190 g, 0.60 mmol) in 1,2-dichloroethane (20 mL) was added. The reaction was allowed to warm to room temperature and was then heated at 80° C. for 7 h. Progress of the reaction was monitored by TLC. The reaction mixture was poured onto an aqueous, saturated solution of sodium bicarbonate (500 mL) and the mixture was extracted with dichloromethane (2×100 mL). The combined organic extracts were dried over sodium sulfate, filtered and concentrated in vacuo to afford CXLIX (0.38 g, crude) as a pale-brown, viscous oil, which was used without further purification. MS (ESI, positive mode) m/z 393/395 (MH+, $^{35/37}$Cl).

Synthesis of 4-(2-Methyl-3-(2-(piperidin-1-yl)acetyl)-6-(pyrrolidin-1-ylmethyl)-1H-pyrrolo[3,2-b]pyridin-1-yl)benzonitrile (360): To a solution of CXLIX (0.38 g, crude) in acetonitrile (15 mL) was added piperidine (0.26 g). The reaction mixture was allowed to stir at room temperature for 5 h. The progress of the reaction was monitored by TLC. The reaction mixture was condensed in vacuo and the remaining material was diluted with cold water (100 mL). The mixture was extracted with dichloromethane (2×100 mL) and the combined organic extracts were dried over sodium sulfate. The organic layer was filtered and concentrated in vacuo to afford the crude product, which was purified by preperative HPLC to obtain 360 (0.030 g, 1.3% over two steps) as a pale brown solid. $^1$H NMR (400 MHz, DMSO-$d_6$): δ 8.48 (d, J=1.6 Hz, 1H), 8.17 (d, J=8.4 Hz 2H), 7.81 (d, J=8.5 Hz, 2H), 7.35 (d, J=1.4 Hz, 1H), 4.18 (s, 2H), 3.64 (s, 2H), 2.58-2.55 (m, 7H), 2.39 (s, 4H), 1.64 (brs, 4H), 1.53-1.49 (m, 4H), 1.41 (brs, 2H); MS (ESI, positive mode) m/z 442 (MH+).

Examples 61-62

Ethyl (E)-3-(1-(4-Cyanophenyl)-2-methyl-3-(2-(piperidin-1-yl)acetyl)-1H-pyrrolo[3,2-b]pyridin-6-yl) butanoate (350), Ethyl (S)-3-(1-(4-Cyanophenyl)-2-methyl-3-(2-(piperidin-1-yl)acetyl)-1H-pyrrolo[3,2-b]pyridin-6-yl)butanoate (351)

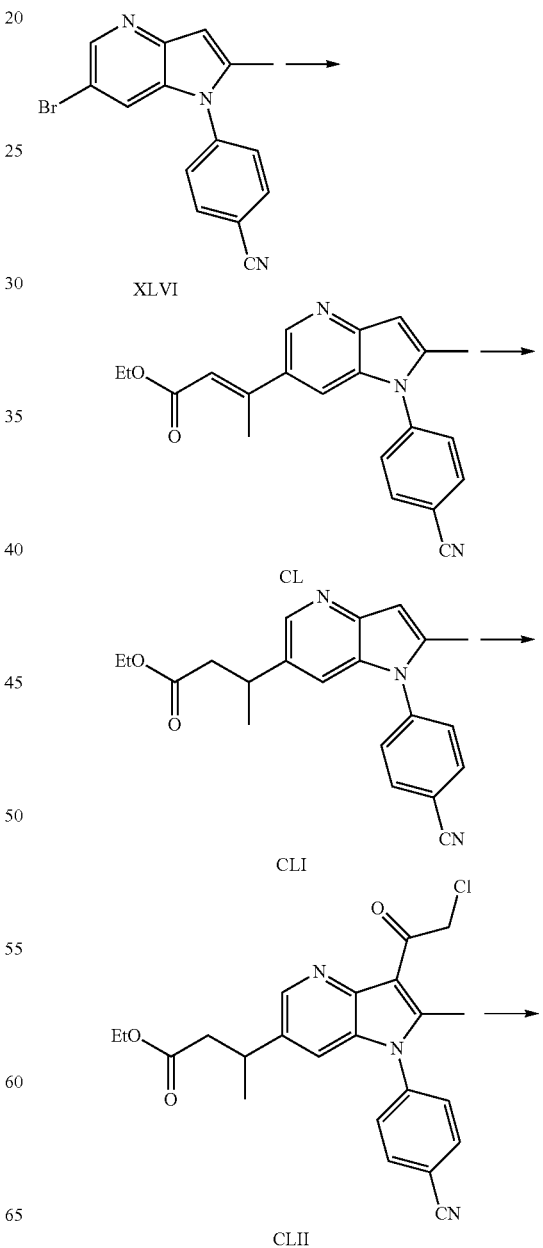

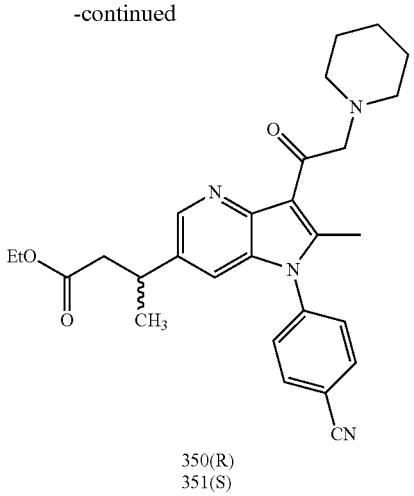

350(R)
351(S)

Synthesis of Ethyl (E)-3-[1-(4-Cyano-phenyl)-2-methyl-1H-pyrrolo[3,2-b]pyridin-6-yl]-but-2-enoate (CL): To a stirred solution of XLVI (1.1 g, 3.50 mmol) in N,N-dimethylformamide (20 mL) was added ethyl crotonate (1.2 ml, 0.011 mol), diisopropylethylamine (1.8 mL, 0.011 mol) and tri-o-tolylphosphine (21 mg, 0.141 mmol). The mixture was sparged with nitrogen gas for 20 minutes and then palladium (II) acetate (32 mg, 0.141 mmol) was added. The reaction mixture was heated at 100° C. for 12 h and then allowed to cool to room temperature. The reaction mixture was filtered through a bed of celite and the filtrate was diluted with ethyl acetate (20 mL). The mixture was washed with water (3×10 mL) and brine, dried over anhydrous sodium sulfate and concentrated under vacuum to afford crude product. The crude product mixture was purified by column chromatography on neutral alumina, using 30% ethyl acetate in hexanes as the eluant, to afford CL (0.300 g, 23%) as an off-white solid. $^1$H NMR (400 MHz, CDCl$_3$): δ 8.61 (d, J=1.8 Hz, 1H), 7.90 (d, J=8.5 Hz, 2H), 7.48 (d, J=8.5 Hz, 2H), 7.40 (d, J=1.8 Hz, 1H), 6.66 (s, 1H), 6.1 (s, 1H), 4.20 (q, J=7.1 Hz, 2H), 2.58 (s, 3H), 2.39 (s, 3H), 1.30 (t, J=7.1 Hz, 3H); MS (ESI, positive mode) m/z 346 (MH$^+$).

Synthesis of Ethyl 3-[1-(4-Cyano-phenyl)-2-methyl-1H-pyrrolo[3,2-b]pyridin-6-yl]-butanoate (CLI): To a stirred solution of CL (1.2 g, 3.50 mmol) in ethyl acetate (20 mL) was added palladium on carbon (10% wt/wt, 1.2 g). The reaction mixture was allowed to stir for 2 days under an atmosphere of hydrogen gas (50 psi). The reaction mixture was filtered through a bed of celite and the filtrate was concentrated under vacuum to obtain the crude product. The crude product mixture was purified by column chromatography on neutral alumina, using 30% ethyl acetate in hexanes as the eluant, to afforded CLI (0.400 g, 33%) as an off-white solid. $^1$H NMR (400 MHz, CDCl$_3$): δ 8.35 (d, J=1.8 Hz, 1H), 7.87 (d, J=8.4 Hz, 2H), 7.46 (d, J=8.4 Hz, 2H), 7.19 (d, J=1.8 Hz, 1H), 6.61 (s, 1H), 4.06-4.00 (m, 2H), 3.99-3.33 (m, 1H), 2.57 (dd, J=7.4, 1.0 Hz, 2H), 2.36 (s, 3H), 1.30 (d, J=7.0 Hz, 3H), 1.14 (t, J=7.2 Hz, 3H); MS (ESI, positive mode) m/z 348 (MH$^+$).

Synthesis of Ethyl 3-[3-(2-Chloro-acetyl)-1-(4-cyano-phenyl)-2-methyl-1H-pyrrolo[3,2-b]pyridin-6-yl]-butanoate (CLII): To a solution of CLI (600 mg, 1.70 mmol) in 1,2-dichloroethane (20 mL), kept at 0° C., was added aluminum trichloride (1.2 g, 8.60 mmol), followed by neat chloroacetyl chloride (0.88 mL, 8.60 mmol). The reaction mixture was allowed to warm to room temperature and was then heated at 60° C. for 16 h. After cooling, the reaction mixture was poured onto ice-cold water (50 mL) and extracted with dichloromethane (2×20 mL). The combined organic extracts were washed with an aqueous solution of sodium bicarbonate (2×20 mL), followed by brine. The organic layer was dried over sodium sulfate, filtered, and concentrated under vacuum to afford the crude product. The crude product mixture was purified by column chromatography on neutral alumina, using 30% ethyl acetate in hexanes as the elueant, to afford CLII (0.400 g, 55%) as an off-white solid. $^1$H NMR (400 MHz, CDCl$_3$): δ 8.49 (d, J=1.8 Hz, 1H), 7.94 (d, J=8.4 Hz, 2H), 7.48 (d, J=8.4 Hz, 2H), 7.15 (d, J=1.8 Hz, 1H), 5.30 (s, 2H), 4.06-4.00 (m, 2H), 3.40-3.35 (m, 1H), 2.67 (s, 3H), 2.58 (d, J=7.6 Hz, 2H), 1.31 (d, J=7.0 Hz, 3H), 1.15 (t, J=7.1 Hz, 3H); MS (ESI, positive mode) m/z 424/426 (MH$^+$, $^{35/37}$Cl).

Synthesis of Ethyl (R)-3-(1-(4-Cyanophenyl)-2-methyl-3-(2-(piperidin-1-yl)acetyl)-1H-pyrrolo[3,2-b]pyridin-6-yl) butanoate (350) and Ethyl (S)-3-(1-(4-Cyanophenyl)-2-methyl-3-(2-(piperidin-1-yl)acetyl)-1H-pyrrolo[3,2-b]pyridin-6-yl)butanoate (351): To a solution of CLII (100 mg, 0.240 mmol) in anhydrous N,N-dimethylformamide (5 mL), kept at 0° C., was added potassium carbonate (65 mg, 0.470 mmol) and piperidine (0.040 mL, 0.470 mmol). The reaction mixture was allowed to warm to room temperature at stir for 2 h. Progress of reaction was monitored by TLC. The reaction mixture was poured into ice cold water (20 mL) and the mixture was extracted with ethyl acetate (2×10 mL). Combined organic extracts were washed with water and brine, dried over sodium sulfate, and concentrated under vacuum to afford the crude product. The crude product mixture was purified by column chromatography on neutral alumina, using 30% ethyl acetate in hexanes as the eluant, to afford a racemic mixture of 350 and 351 (0.40 g, 36%) as an off-white solid. The enantiomers were separated by chiral stationary phase HPLC. $^1$H NMR (400 MHz, CDCl$_3$): δ 8.50 (d, J=1.8 Hz, 1H), 7.92 (d, J=8.4 Hz, 2H), 7.46 (d, J=8.4 Hz, 2H), 7.12 (d, J=1.8 Hz, 1H), 4.31 (s, 2H), 4.06-4.00 (m, 2H), 3.39-3.33 (m, 1H), 2.70-2.62 (m, 7H), 2.58 (d, J=7.6 Hz, 2H), 1.70-1.67 (m, 4H), 1.50-1.48 (m, 2H), 1.30 (d, J=7.0 Hz, 3H), 1.15 (t, J=7.2 Hz, 3H); MS (ESI, positive mode) m/z 473 (MH$^+$).

Examples 63-67

3-(1-(4-Cyanophenyl)-3-(2-(piperidin-1-yl)acetyl)-1H-pyrrolo[3,2-b]pyridin-6-yl)-N-(2,2-dimethoxyethyl)propanamide (296), N-(3-Azidopropyl)-3-(1-(4-cyanophenyl)-3-(2-(piperidin-1-yl)acetyl)-1H-pyrrolo[3,2-b]pyridin-6-yl)propanamide (299), N-(2-Azidoethyl)-3-(1-(4-cyanophenyl)-3-(2-(piperidin-1-yl)acetyl)-1H-pyrrolo[3,2-b]pyridin-6-yl)propanamide (304), 3-(1-(4-Cyanophenyl)-3-(2-(4-hydroxypiperidin-1-yl)acetyl)-1H-pyrrolo[3,2-b]pyridin-6-yl)-N-(pent-4-yn-1-yl)propanamide (361), 3-(1-(4-Cyanophenyl)-3-(2-(4-hydroxypiperidin-1-yl)acetyl)-1H-pyrrolo[3,2-b]pyridin-6-yl)-N-(3-cyanopropyl)propanamide (362)

Compounds 296, 299, 304, 361, and 362 were prepared using methods similar to those described in Examples 61 and 62, except ethyl acrolate was employed in the first step instead of ethyl crotonate. Conditions employed for the formation of the amide bonds are analogues to those described in Examples 53-56.

Example 68
4-(6-(Difluoromethyl)-2-methyl-3-(2-(piperidin-1-yl)acetyl)-1H-pyrrolo[3,2-b]pyridin-1-yl)benzonitrile (301)
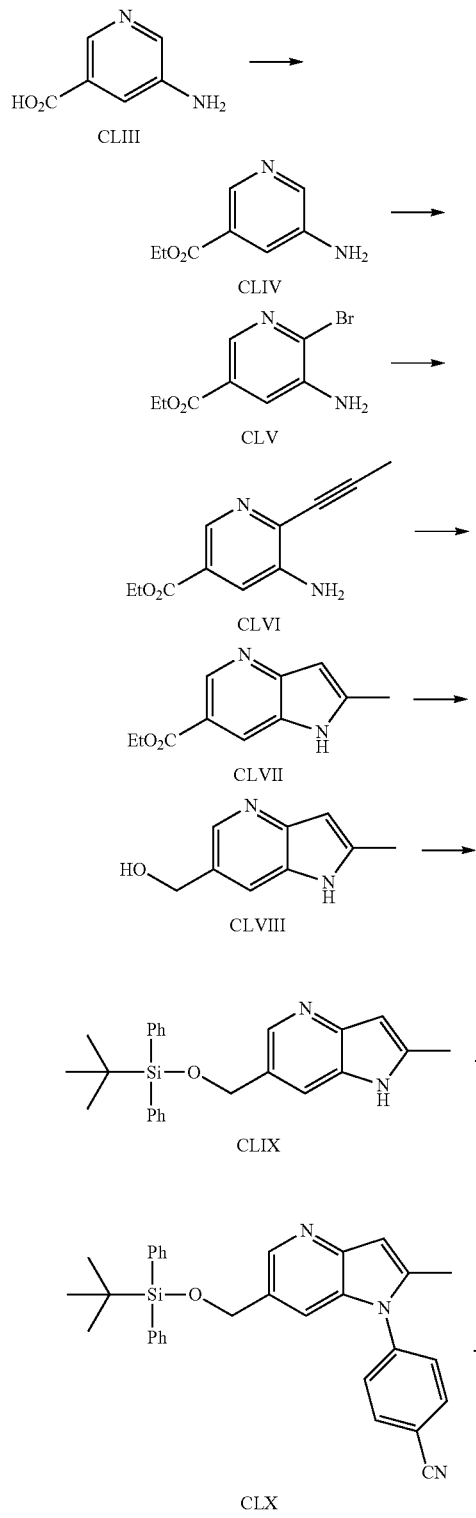
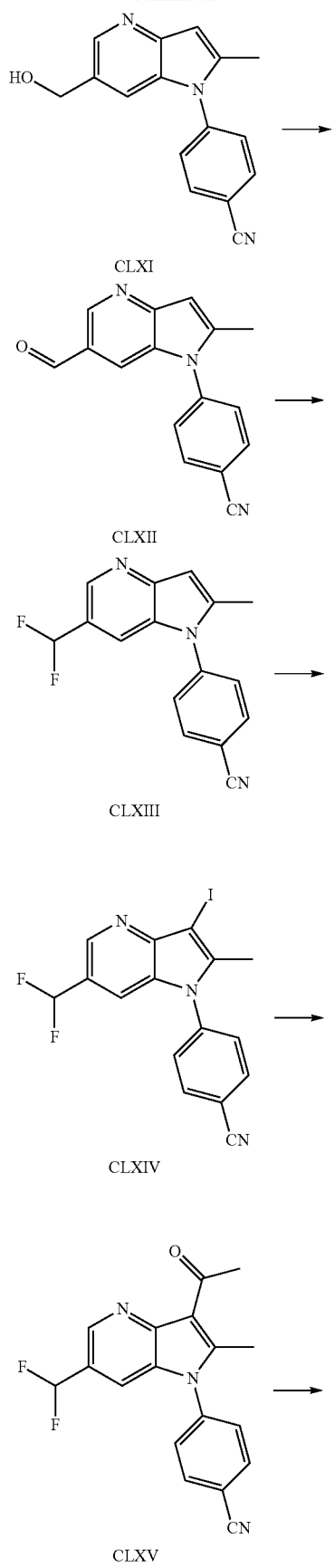

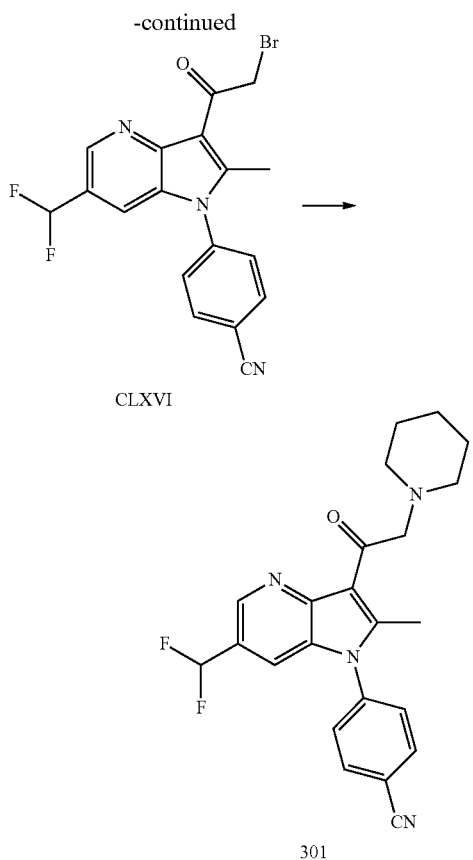

CLXVI

301

Synthesis of Ethyl 5-Amino-nicotinate (CLIV): To a solution of 5-amino-nicotinic acid (10 g, 72.3 mmol) in ethanol (400 mL) was added concentrated hydrochloric acid (100 mL). The reaction mixture was heated at reflux for 48 h and then allowed to cool to room temperature. The reaction mixture as condensed in vacuo and the remaining material was neutralized through the addition of an aqueous, saturated solution of sodium bicarbonate (200 mL). The aqueous mixture was extracted with ethyl acetate (200 mL×3) and the combined organic extracts were dried over sodium sulfate. The organic layer was concentrated in vacuo to afford CLIV (8.0 g, 67%) as a pale yellow solid. $^1$H NMR (400 MHz, CDCl$_3$): δ 8.61 (s, 1H), 8.22 (d, J=2.4 Hz, 1H), 7.55-7.54 (m, 1H), 4.36 (q, J=7.1 Hz, 2H), 3.83 (brs, 2H), 1.38 (t, J=7.1 Hz, 3H); MS (ESI, positive mode) m/z 167 (MH$^+$).

Synthesis of Ethyl 5-Amino-6-bromo-nicotinate (CLV): To an ice-cooled solution of CLIV (7.0 g, 42.1 mmol) in glacial acetic acid (100 mL) was added solid sodium acetate (6.9 g, 84.2 mmol), followed by bromine (6.0 g, 37.9 mmol). The resulting reaction mixture was allowed to warm to room temperature and stir for 1 h. Progress of the reaction was monitored by TLC. The reaction mixture was then diluted with water and extracted with ethyl acetate (100 mL×2). The combined organic extracts were washed with an aqueous, saturated solution of sodium bicarbonate and then dried over sodium sulfate. The organic layer was concentrated under reduced pressure to obtain the crude product, which was purified by column chromatography on silica gel (100-200 mesh), using 20% ethyl acetate in hexanes as eluent, to afford CLV (5.0 g, 50%) as an off-white solid. $^1$H NMR (400 MHz, CDCl$_3$): δ 8.34 (s, J=2.0 Hz, 1H), 7.56 (d, J=2.0 Hz, 1H), 4.36 (q, J=7.1 Hz, 2H), 4.26 (brs, 2H), 1.37 (t, J=7.1 Hz, 3H); MS (ESI, positive mode) m/z 245/247 (MH$^+$, $^{79/81}$Br).

Synthesis of Ethyl 5-Amino-6-prop-1-ynyl-nicotinate (CLVI): To a degassed suspension of CLV (5.0 g, 20.4 mmol) and copper(1) iodide (0.77 g, 4.08 mmol) in acetonitrile (50 mL) and triethylamine (25 mL) was added tetrakis (triphenylphosphine)palladium(0) (2.3 g, 0.204 mmol). The resulting mixture was cooled to −78° C. and propyne gas (6.5 g, 163 mmol) was bubbled through the system. The reaction mixture was allowed to warm to room temperature and stir for 18 h. Progress of the reaction was monitored by TLC. The reaction mixture was then filtered and the filtered material was washed with ethyl acetate (100 mL). The filtrate was concentrated under reduced pressure and the remaining material was purified by column chromatography on silica gel (100-200 mesh), using 40% ethyl acetate in hexanes as eluent, to afford CLVI (4 g, 98%) as a pale yellow solid. $^1$H NMR (400 MHz, CDCl$_3$): δ 8.53 (d, J=1.8 Hz, 1H), 7.56 (d, J=1.8 Hz, 1H), 4.36 (q, J=7.1 Hz, 2H), 4.27 (brs, 2H), 2.15 (s, 3H), 1.37 (t, J=7.1 Hz, 3H); MS (ESI, positive mode) m/z 205 (MH$^+$).

Synthesis of Ethyl 2-Methyl-1H-pyrrolo[3,2-b]pyridine-6-carboxylate (CLVII): To an ice-cooled solution of CLVI (3.0 g, 14.7 mmol) in N,N-dimethylformamide (100 mL) was added potassium tert-butoxide (3.2 g, 39.4 mmol). The reaction mixture was allowed to stir at room temperature for 1 h. The reaction was diluted with ice water and the aqueous mixture was extracted with ethyl acetate (50 mL×3). The emulsions that formed during the extractions were filtered through beds of celite to resolve the phases. The combined organic extracts were dried over sodium sulfate and concentrated under reduced pressure to obtain the crude product. The crude product mixture was purified by column chromatography on neutral alumina, using 30% ethyl acetate in hexanes as eluent, to afford CLVII (1.6 g, 57%) as a pale yellow solid. $^1$H NMR (400 MHz, DMSO-d$_6$): δ 11.58 (brs, 1H), 8.80 (d, J=1.8 Hz, 1H), 8.10 (s, 1H), 6.39 (s, 1H), 4.33 (q, J=7.1 Hz, 2H), 2.49 (s, obscured by solvent signal, 3H), 1.34 (t, J=7.1 Hz, 3H); MS (ESI, positive mode) m/z 205 (MH$^+$).

Synthesis of (2-Methyl-1H-pyrrolo[3,2-h]pyridin-6-yl)-methanol (CLVIII): To an ice cooled solution of lithium aluminum hydride (0.037 g, 0.96 mmol) in tetrahydrofuran (3 mL) was added a solution of CLVII (0.05 g, 0.24 mmol) in tetrahydrofuran (2 mL). The resulting mixture was allowed to warm to room temperature and stir for 2 h. Progress of the reaction was monitored by TLC. The reaction was quenched through the addition of an aqueous saturated solution of sodium thiosulfate and then filtered. The filtrate was concentrated in vacuo to afford CLVIII (0.03 g, 79%) as a pale-yellow, sticky mass. $^1$H NMR (400 MHz, DMSO-d$_6$): δ 11.07 (brs, 1H), 8.16 (d, J=1.5 Hz, 1H), 7.53 (s, 1H), 6.20 (s, 1H), 5.14 (t, J=5.7 Hz, 1H), 4.56 (d, J=5.6 Hz, 2H), 2.41 (s, 3H); MS (ESI, positive mode) m/z 163 (MH$^+$).

Synthesis of 6-(tert-Butyl-diphenyl-silanyloxymethyl)-2-methyl-1H-pyrrolo[3,2-b]pyridine (CLIX): To a solution of CLVIII (2.4 g, 14.7 mmol) in tetrahydrofuran (100 mL) were added tert-butyldiphenylsilyl chloride (8.1 g, 29.6 mmol) and imidazole (4 g, 58.8 mmol). The reaction mixture was allowed to stir at room temperature for 2 h. The reaction mixture was diluted with ice water and the mixture was extracted with ethyl acetate (100 mL×3). The combined organic extracts were dried over sodium sulfate and concentrated under reduced pressure to obtain the crude product. The crude product mixture was purified by column chromatography on neutral alumina, using 30% ethyl acetate in hexanes as the eluent, to afford partially pure CLIX (5.5 g, crude) as a white solid, which was used without further purification. MS (ESI, positive mode) m/z 402 (MH+).

Synthesis of 4-[6-(tert-Butyl-diphenyl-silanyloxymethyl)-2-methyl-pyrrolo[3,2-b]pyridin-1-yl]-benzonitrile (CLX): To a degassed solution of CLIX (5.5 g, 13.7 mmol) in 1,4-dioxane (150 mL) were added 4-iodobenzonitrile (6.2 g, 27.5 mmol), copper(I) iodide (0.130 g, 0.686 mmol), potassium phosphate (5.2 g, 24.7 mmol) and trans-(+/−)-1,2-diaminocyclohexane (2 mL). The reaction mixture was heated at reflux for 18 h and then allowed to cool to room temperature. Progress of the reaction was monitored by TLC. The reaction mixture was filtered and the filtrate was evaporated under reduced pressure to obtain the crude product. The crude product mixture was purified by column chromatography on neutral alumina, using 30% ethyl acetate in hexanes, as eluent to afford CLX (5.5 g, 74% over two steps) as a pale-yellow, sticky mass. $^1$H NMR (400 MHz, CDCl$_3$): δ 8.36 (d, J=1.1 Hz, 1H), 7.84 (d, J=8.4 Hz, 2H), 7.63 (d, J=7.8 Hz, 2H), 7.44-7.36 (m, 4H), 7.34-7.30 (m, 4H), 6.63 (s, 1H), 4.83 (s, 2H), 2.39 (s, 3H), 1.03 (s, 9H); MS (ESI, positive mode) m/z 502 (MH+).

Synthesis of 4-(6-Hydroxymethyl-2-methyl-pyrrolo[3,2-b]pyridin-1-yl)-benzonitrile (CLXI): To a solution of CLX (5.5 g, 10.9 mmol) in tetrahydrofuran (100 mL) was added a 1M solution of tetrabutylammonium fluoride in tetrahydrofuran (11.9 mL, 12 mmol). The reaction mixture was allowed to stir at room temperature for 2 h and then the mixture was diluted with water (50 mL). The mixture was extracted with ethyl acetate (50 mL×3) and the combined organic extracts were dried over sodium sulfate. The organic layer was concentrated under reduced pressure and the remaining material was washed with diethylether (20 mL×3) to afford CLXI (2.4 g, 71%) as a pale brown solid. $^1$H NMR (400 MHz, DMSO-d$_6$): δ 8.31 (d, J=1.5 Hz, 1H), 8.12 (d, J=8.5 Hz, 2H), 7.74 (d, J=8.5 Hz, 2H), 7.43 (s, 1H), 6.60 (s, 1H), 5.20 (brs, 1H), 4.56 (s, 2H), 2.37 (s, 3H); MS (ESI, positive mode) m/z 264 (MH+).

Synthesis of 4-(6-Formyl-2-methyl-pyrrolo[3,2-b]pyridin-1-yl)-benzonitrile (CLXII): To a solution of CLXI (1 g, 3.8 mmol) in dimethylsulfoxide (12 mL) was added 2-iodoxybenzoic acid (1.16 g, 4.17 mmol). The reaction mixture was allowed to stir at room temperature for 1 h and was then diluted with water (25 mL). The precipitate that formed was collected by filtration and washed with ethyl acetate (50 mL). The filtrate was evaporated and the remaining material was washed with diethyl ether (25 mL) to afford CLXII (0.9 g, 91%) as a pale yellow solid. $^1$H NMR (400 MHz, DMSO-d$_6$): δ 10.06 (s, 1H), 8.89 (d, J=1.7 Hz, 1H), 8.16 (d, J=8.6 Hz, 2H), 7.90 (d, J=0.8 Hz, 1H), 7.84 (d, J=8.6 Hz, 2H), 6.81 (s, 1H), 2.45 (s, 3H); MS (ESI, positive mode) m/z 262 (MH+).

Synthesis of 4-(6-Difluoromethyl-2-methyl-pyrrolo[3,2-b]pyridin-1-yl)-benzonitrile (CLXIII): To an ice-cooled solution of CLXII (1.5 g, 5.74 mmol) in dichloromethane (20 mL) was added diethylaminosulfur trifluoride (1.1 mL, 8.61 mmol). The reaction mixture was allowed to warm to room temperature and stir for 18 h. The reaction mixture was quenched through the addition of an aqueous, saturated solution of sodium bicarbonate (20 mL) and the mixture was extracted with dichloromethane (25 mL×3). The combined organic extracts were dried over sodium sulfate and condensed in vacuo to afford the crude product, which was purified by column chromatography on silica gel (100-200 mesh), using 60% ethyl acetate in hexanes, as the eluent to afford CLXIII (0.350 g, 22%) as a pale-yellow solid. $^1$H NMR (400 MHz, CDCl$_3$): δ 8.56 (s, 1H), 7.89 (d, J=8.1 Hz, 2H), 7.50-7.45 (overlapped d and s, 3H), 6.90-6.62 (overlapped t and s, 1H), 2.42 (s, 3H); MS (ESI, positive mode) m/z 284 (MH−).

Synthesis of 4-(6-Difluoromethyl-3-iodo-2-methyl-pyrrolo-[3,2-b]pyridin-1-yl)-benzonitrile (CLXIV): To a solution of CLXIII (0.12 g, 0.420 mmol) in N,N-dimethylformamide (5 mL) was added N-iodosuccinimide (0.143 g, 0.637 mmol). The reaction mixture was allowed to stir at room temperature for 3 h before it was diluted with cold water (20 mL). The precipitate that formed was collected by filtration and the solids were washed with cold water (20 mL). Drying the material afforded CLXIV (0.16 g, 94%) as a pale brown solid. $^1$H NMR (400 MHz, CDCl$_3$): δ 8.65 (s, 1H), 7.93 (d, J=8.4 Hz, 2H), 7.49-7.47 (overlapped d and s, 3H), 6.78 (t, J=5.6 Hz, 1H), 2.48 (s, 3H); MS (ESI, positive mode) m/z 410 (MH−).

Synthesis of 4-(3-Acetyl-6-difluoromethyl-2-methyl-pyrrolo-[3,2-b]-pyridin-1-yl)-benzonitrile (CLXV): To a solution of CLXIV (0.05 g, 0.120 mmol) in toluene (5 mL) was added tetrakis(triphenylphosphine)palladium(0) (0.042 g, 0.030 mmol), followed by tributyl(1-ethoxyvinyl)stannane (0.211 g, 0.660 mmol). The reaction mixture was heated at 120° C. for 1 h and then allowed to cool to room temperature. The reaction mixture was diluted with water (25 mL) and extracted with ethyl acetate (25 mL×3). The combined organic extracts were dried over sodium sulfate and concentrated under reduced pressure to obtain the crude product. The crude product mixture was was purified by column chromatography on silica gel (100-200 mesh), using 30% ethyl acetate in hexanes as eluent, to afford CLXV (0.010 g, crude) as a brown, viscous mass. MS (ESI, positive mode) m/z 326 (MH+).

Synthesis of 4-[3-(2-Bromo-acetyl)-6-difluoromethyl-2-methyl-pyrrolo[3,2-b]pyridin-1-yl]-benzonitrile (CLXVI): To a solution of CLXV (0.02 g, 0.061 mmol) in tetrahydrofuran (5 mL) was added phenyltrimethylammonium tribromide (0.023 g, 0.061 mmol). The reaction mixture was heated at 80° C. for 2 h before being allowed to cool to room temperature. The reaction mixture was condensed in vacuo and the remaining material was treated with an aqueous, saturated solution of sodium bicarbonate. The mixture was extracted with ethyl acetate (10 mL×3) and the combined organic extracts were dried over sodium sulfate. The organic layer was condensed in vacuo to afford CLXVI (0.02 g, crude) as a brown, viscous oil, which was used without purification. MS (ESI, positive mode) m/z 406/408 (MH+, $^{79/81}$Br).

Synthesis of 4-(6-(Difluoromethyl)-2-methyl-3-(2-(piperidin-1-yl)acetyl)-1H-pyrrolo[3,2-b]pyridin-1-yl)benzonitrile (301): To a solution of CLXVI (0.058 g, 0.178 mmol) in dichloromethane (5 mL) was added piperidine (0.028 mL, 0.28 mmol). The reaction mixture was allowed to stir at room temperature for 2 h, which was then diluted with water (25 mL). The phases were separated and the aqueous phase was extracted with dichloromethane (25 mL×3). The combined organic extracts were dried over sodium sulfate and concentrated under reduced pressure to obtain the crude product. The crude product mixture was purified by column chromatography on silica gel (100-200 mesh) using 4% methanol in dichloromethane as the eluent to afford 301 (0.010 g, 13% over two steps) as a pale-yellow solid. $^1$H NMR (400 MHz, CDCl$_3$): δ 8.68 (s, 1H), 7.94 (d, J=8.2 Hz, 2H), 7.49-7.45 (overlapped d and s, 3H), 6.78 (t, J=5.6 Hz, 1H), 4.45 (s, 2H), 2.85 (brs, 4H), 2.69 (s, 3H), 1.78 (brs, 4H), 1.53 (brs, 2H); MS (ESI, positive mode) m/z 409 (MH+).

Example 69

(E)-3-(1-(4-Cyanophenyl)-2-methyl-3-(2-(piperidin-1-yl)acetyl)-1H-pyrrolo[3,2-b]pyridin-6-yl)-N-ethyl-acrylamide (305)

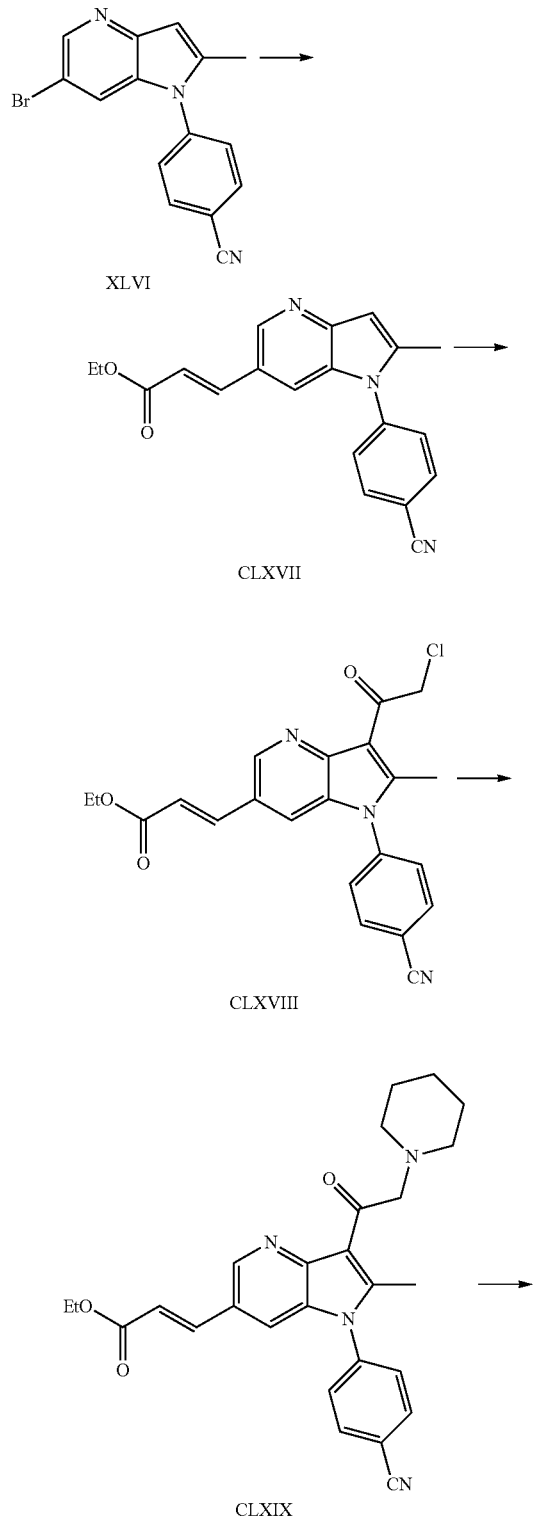

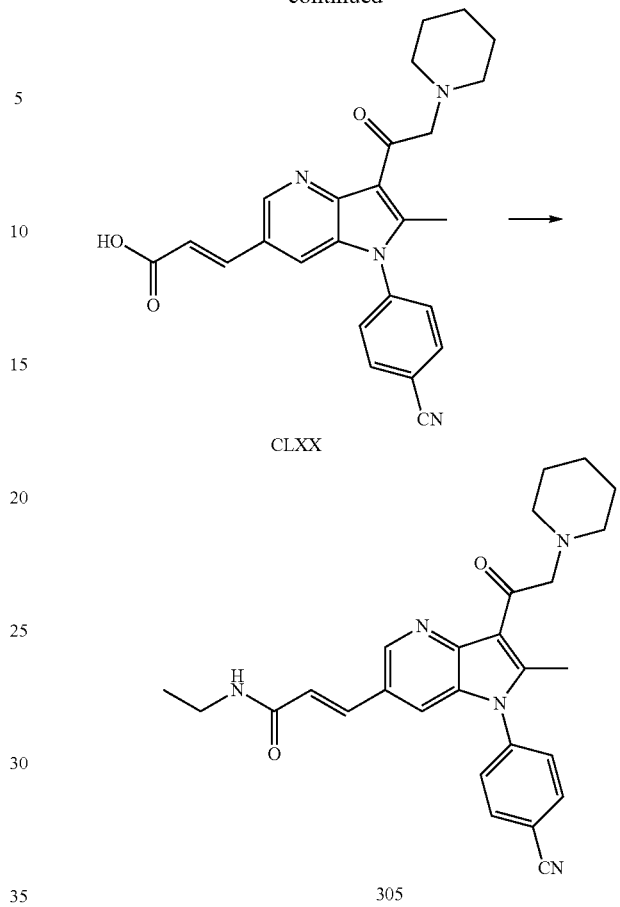

Synthesis of Ethyl (E)-3-(1-(4-Cyanophenyl)-2-methyl-1H-pyrrolo[3,2-b]pyridin-6-yl)acrylate (CLXVII): To a degassed solution of XLVI (2.0 g, 6.41 mmol), ethyl acrylate (8 mL), diisopropylethylamine (2.4 g, 19.2 mmol), and tri-o-tolylphosphine (0.195 g, 0.64 mmol) in N,N-dimethylformamide (100 mL) was added palladium(II) acetate (0.071 g, 0.31 mmol). The resulting reaction mixture was heated at 160° C. for 16 h in a sealed tube before being allowed to cool to room temperature. Progress of the reaction was monitored by TLC. The reaction mixture was diluted with water (150 mL) and the mixture was extracted with ethyl acetate (100 mL×2). The combined organic extracts were washed with brine (150 mL×3), dried over anhydrous sodium sulfate, and concentrated under reduced pressure to obtain the crude product. The crude product mixture was purified by column chromatography on silica gel (100-200 mesh) using 2% methanol in dichloromethane as the eluent to afford CLXVII (1.9 g, 89%), as a pale-yellow solid; $^1$H NMR (400 MHz, CDCl$_3$): δ 8.67 (s, 1H), 8.10 (d, J=8.4 Hz, 2H), 7.93 (s, 1H), 7.79-7.72 (m, 3H), 6.75-6.67 (m, 2H), 4.16 (q, J=7.1 Hz, 2H), 2.37 (s, 3H), 1.23 (t, J=7.1 Hz, 3H); MS (ESI, positive mode) m/z 332 (MH$^+$).

Synthesis of Ethyl (E)-3-(3-(2-Chloroacetyl)-1-(4-cyanophenyl)-2-methyl-1H-pyrrolo[3,2-b]pyridin-6-yl)acrylate (CLXVIII): To an ice-cooled solution of aluminum chloride (5.0 g, 37.5 mmol) in 1,2-dichloroethane (25 mL) was added chloroacetyl chloride (3 mL, 37.2 mmol) in a dropwise fashion. The reaction mixture was allowed to stir at 0° C. for 45 min and then a solution of CLXVII (0.5 g, 1.51 mmol) in 1,2-dichloroethane (10 mL) was added. The reaction mixture was allowed to warm to room temperature and was then heated at 60° C. for 12 h. Progress of the reaction was monitored by TLC. After cooling, the reaction mixture was poured onto an aqueous, saturated solution of sodium bicarbonate (500 mL). The aqueous mixture was extracted with dichloromethane (2×100 mL) and the combined organic extracts were dried over sodium sulfate. The organic layer was concentrated in vacuo and the remaining crude product mixture was purified by column chromatography on neutral alumina, using 40% ethyl acetate in hexanes, as the eluant to afford CLXVIII (0.38 g, 62%) as pale brown solid. $^1$H NMR (400 MHz, CDCl$_3$): δ 8.73 (d, J=1.8 Hz, 1H), 7.96 (d, J=8.6 Hz, 2H), 7.73 (d, J=16 Hz, 1H), 7.50 (d, J=8.5 Hz, 2H), 7.43 (d, J=1.8 Hz, 1H), 6.41 (d, J=16 Hz, 1H), 5.29 (s, 2H), 4.25 (q, J=7.1 Hz, 2H), 2.70 (s, 3H), 1.32 (t, J=7.1 Hz, 3H); MS (ESI, positive mode) m/z 409/411 (MH$^+$, $^{35/37}$Cl).

Synthesis of Ethyl (E)-3-(1-(4-Cyanophenyl)-2-methyl-3-(2-(piperidin-1-yl)acetyl)-1H-pyrrolo[3,2-b]pyridin-6-yl) acrylate (CLXIX): To an ice-cooled solution of CLXVIII (0.38 g, 0.930 mmol) in a mixture of acetonitrile and N,N-dimethylformamide (2:1, 30 mL) was added piperidine (0.23 g, 2.70 mmol). The reaction mixture was allowed to warm to room temperature and stir for 3 h. Progress of the reaction was monitored by TLC. The reaction mixture was condensed in vacuo to afford CLXIX (0.35 g, 82%) as a pale yellow solid, which was used without further purification. $^1$H NMR (400 MHz, CDCl$_3$): δ 8.72 (d, J=1.8 Hz, 1H), 7.94 (d, J=8.5 Hz, 2H), 7.73 (d, J=16 Hz, 1H), 7.46 (d, J=8.5 Hz, 2H), 7.41 (d, J=1.8 Hz, 1H), 6.40 (d, J=16 Hz, 1H), 4.31 (s, 2H), 4.26 (q, J=7.1 Hz, 2H), 2.67 (overlapped m and s, 7H), 1.67 (brs, 4H), 1.48 (brs, 2H), 1.31 (t, J=7.1 Hz, 3H); MS (ESI, positive mode) m/z 457 (MH$^+$).

Synthesis of (E)-3-(1-(4-Cyanophenyl)-2-methyl-3-(2-(piperidin-1-yl)acetyl)-1H-pyrrolo[3,2-b]pyridin-6-yl) acrylic acid (CLXX): To a solution of CLXIX (0.3 g, 0.650 mmol) in 1,4-dioxane (5 mL) was added a solution of concentrated hydrochloric acid (0.6 mL) in water (1.2 mL). The reaction mixture was heated at 60° C. for 15 h before cooling back to room temperature. Progress of the reaction was monitored by TLC. The reaction mixture was condensed in vacuo and the water was azeotropically distilled with toluene (10 mL×3) to obtain CLXX (0.32 g, crude) as a pale brown solid, which was used without further purification. MS (ESI, positive mode) m/z 429 (MH$^+$).

Synthesis of (E)-3-(1-(4-Cyanophenyl)-2-methyl-3-(2-(piperidin-1-yl)acetyl)-1H-pyrrolo[3,2-b]pyridin-6-yl)-N-ethylacrylamide (305): To a solution of CLXX (0.1 g, crude) in N,N-dimethylformamide (10 mL) was added diisopropylethylamine (0.15 g, 1.16 mmol) in a dropwise fashion. The reaction mixture was allowed to stir at room temperature for 10 min and then propylphosphonic acid anhydride (0.74 mL, 1.16 mmol) was added, followed by ethylamine (0.58 mL, 1.15 mmol, 1M in tetrahydrofuran). The reaction mixture was allowed to stir at room temperature for 15 h and was then diluted with water (50 mL). The aqueous mixture was extracted with ethyl acetate (25 mL×2) and the combined organic extracts were washed with brine (25 mL×2). The organic layer was dried over anhydrous sodium sulfate and then condensed in vacuo. The remaining residue was purified by preparative HPLC to afford 305 (0.021 g, 7% after two steps) as an off-white solid. $^1$H NMR (400 MHz, CDCl$_3$): δ 8.73 (d, J=1.8 Hz, 1H), 7.94 (d, J=8.4 Hz, 2H), 7.66 (d, J=15.6 Hz, 1H), 7.48 (d, J=8.4 Hz, 2H), 7.36 (d, J=1.8 Hz, 1H), 6.34 (d, J=15.6 Hz, 1H), 5.53 (t, J=5.0 Hz, 1H), 4.31 (s, 2H), 3.43-3.38 (m, 2H), 2.67 (overlapped m and s, 7H), 1.69 (brs, 4H), 1.48 (brs, 2H), 1.19 (t, J=7.2 Hz, 3H); MS (ESI, positive mode) m/z 456 (MH$^+$).

Example 70

3-(1-(4-Cyanophenyl)-2-methyl-3-(2-(piperidin-1-yl)acetyl)-1H-pyrrolo[3,2-b]pyridin-6-yl)prop-2-yn-1-yl Dimethylcarbamate (319)

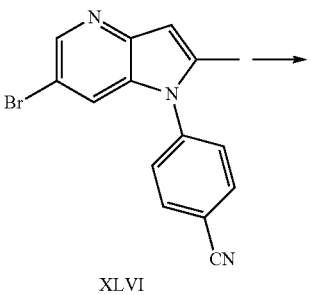

XLVI

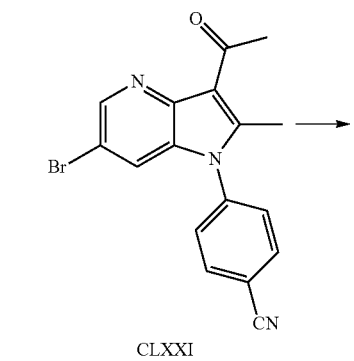

CLXXI

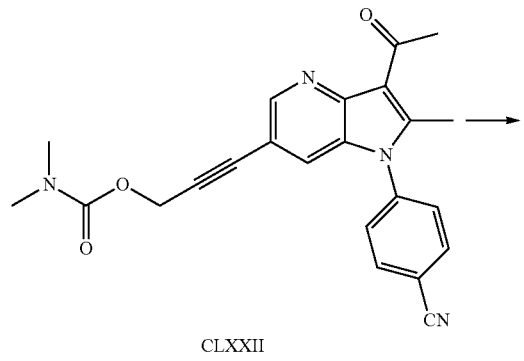

CLXXII

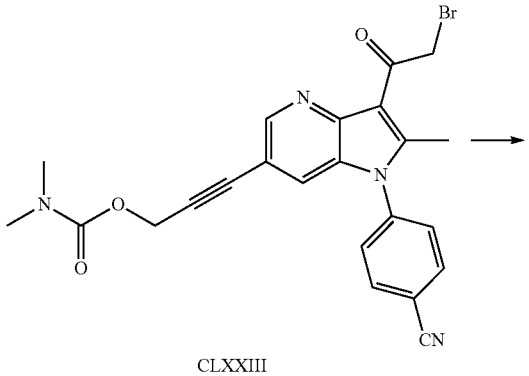

CLXXIII

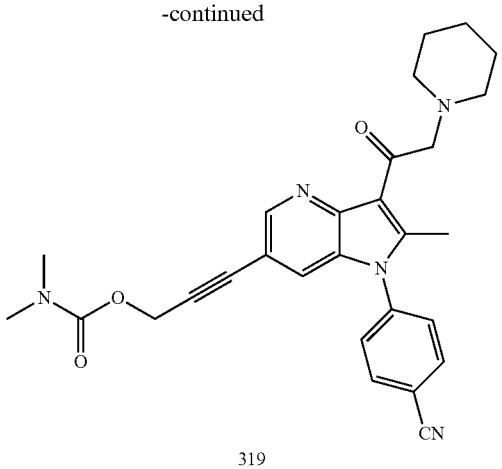

319

Synthesis of 4-(3-Acetyl-6-bromo-2-methyl-1H-pyrrolo[3,2-b]pyridin-1-yl)benzonitrile (CLXXI): To an ice-cooled suspension of aluminum chloride (4.2 g, 3.20 mmol) in 1,2-dichloroethane (20 mL) was added acetyl chloride (2.5 g, 0.032 mol). The reaction mixture was allowed to warm to room temperature and stir for 0.5 h. Then XLVI (2.0 g, 6.40 mmol) was added to the flask and the resulting mixture was allowed to stir at room temperature for 4 h. Progress of the reaction was monitored by TLC. The reaction mixture was poured onto ice-cold water neutralize with a sodium bicarbonate solution. The mixture was then extracted with dichloromethane (3×20 mL) and the combined organic extracts were dried over anhydrous sodium sulfate. The organic layer was concentrated under reduced pressure to obtain CLXXI (2.0 g, 88%) as an off-white solid. $^1$H NMR (400 MHz, DMSO-$d_6$): δ 8.64 (d, J=2.0 Hz, 1H), 8.17 (d, J=8.6 Hz, 2H), 7.83 (d, J=8.6 Hz, 2H), 7.78 (d, J=2.0 Hz, 1H), 2.84 (s, 3H), 2.56 (s, 3H); MS (ESI, positive mode) m/z 354/356 (MH$^+$, $^{79/81}$Br).

Synthesis of 3-(3-Acetyl-1-(4-cyanophenyl)-2-methyl-1H-pyrrolo[3,2-b]pyridin-6-yl)prop-2-yn-1-yl Dimethylcarbamate (CLXXII): A solution of CLXXI (2.0 g, 5.60 mmol) in acetonitrile (10 mL) and diisopropylethylamine (20 mL) was sparged with nitrogen gas for 0.5 h. Then copper(I) iodide (0.214 g, 1.20 mmol) and bis(triphenylphosphine) palladium(II) chloride (0.396 g, 0.560 mmol) was added to the flask, followed by prop-2-yn-1-yl dimethylcarbamate (4.3 g, 0.034 mol). The resultant mixture was heated at 80° C. for 16 h and then allowed to cool to room temperature. Progress of the reaction was monitored by TLC. The reaction mixture was filtered through a bed of celite and the filtrate was concentrated under vacuum to afford the crude product. The crude product mixture was purified by column chromatography on silica gel (100-200 mesh) using 50% ethyl acetate in hexanes as the eluant to afford CLXXII (0.450 g, 20%) as an off-white solid. $^1$H NMR (400 MHz, DMSO-$d_6$): δ 8.63 (d, J=1.7 Hz, 1H), 8.15 (d, J=6.7 Hz, 2H), 7.82 (d, J=6.7 Hz, 2H), 7.58 (d, J=1.8 Hz, 1H), 4.91 (s, 2H), 2.86 (s, 6H), 2.83 (s, 3H), 2.59 (s, 3H); MS (ESI, positive mode) m/z 401 (MH$^+$).

Synthesis of 3-(3-(2-Bromoacetyl)-1-(4-cyanophenyl)-2-methyl-1H-pyrrolo[3,2-b]pyridin-6-yl)prop-2-yn-1-yl Dimethylcarbamate (CLXXIII): To a solution of CLXXII (0.50 g, 1.20 mmol) in tetrahydrofuran (15 mL) was added phenyltrimethylammonium tribromide (0.46 g, 1.20 mmol). The reaction mixture was heated at 70° C. for 2 h and then allowed to cool to room temperature. The reaction mixture was condensed in vacuo and the remaining material was partitioned between ethyl acetate and water. The phases were separated and the organic layer was washed with water (10 mL×2), dried over anhydrous sodium sulfate, and concentrated under reduced pressure to obtain crude CLXXIII (700 mg), which was used without further purification. MS (ESI, positive mode) m/z 479/481 (MH$^+$, $^{79/81}$Br).

Synthesis of 3-(1-(4-Cyanophenyl)-2-methyl-3-(2-(piperidin-1-yl)acetyl)-1H-pyrrolo[3,2-b]pyridin-6-yl)prop-2-yn-1-yl Dimethylcarbamate (319): To an ice cooled solution of CLXXIII (0.700 g, crude) in dichloromethane (5 mL) was added piperidine (0.372 g, 4.30 mmol). The reaction mixture was allowed to warm to room temperature and stir for 3 h before it was poured onto ice-cold water. The phases were separated and the aqueous phase was extracted with dichloromethane (10 mL×3). The combined organic extracts were dried over anhydrous sodium sulfate and concentrated under reduced pressure to afford the crude product. The crude product mixture was purified by column chromatography on silica gel (100-200 mesh) using ethyl acetate as the eluent. The product was further purified by preparative HPLC to obtain 319 (20 mg, 3%) as an off-white solid. $^1$H NMR (400 MHz, DMSO-$d_6$): δ 8.61 (d, J=1.7 Hz, 1H), 8.14 (d, J=8.5 Hz, 2H), 7.82 (d, J=8.5 Hz, 2H), 7.57 (d, J=1.7 Hz, 1H), 4.91 (s, 2H), 4.15 (s, 2H), 2.85-2.83 (overlapped s, 6H), 2.58 (s, 3H), 2.55-2.44 (m, 4H), 1.54-1.49 (m, 4H), 1.42-1.37 (m, 2H); MS (ESI, positive mode) m/z 484 (MH$^+$).

Example 71

(E)-4-(3-(2-(4-Hydroxycyclohexyl)acetyl)-2-methyl-6-(2-(5-(trifluoromethyl)-1,3,4-oxadiazol-2-yl)vinyl)-1H-pyrrolo[3,2-b]pyridin-1-yl)benzonitrile (321)

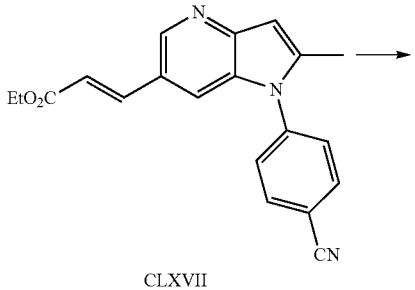

CLXVII

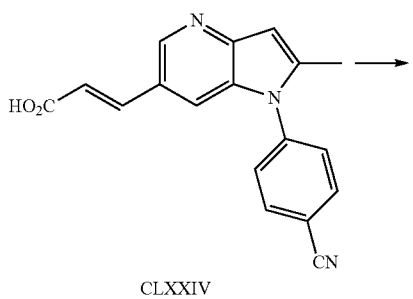

CLXXIV

-continued

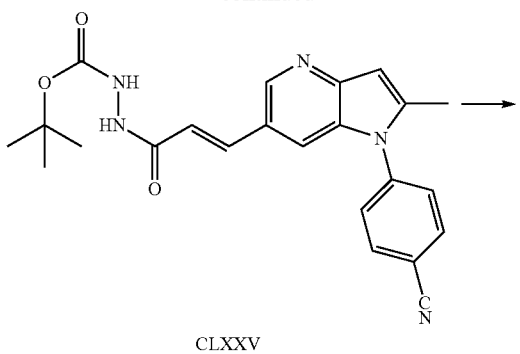

CLXXV

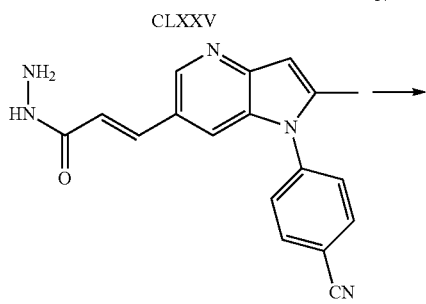

CLXXVI

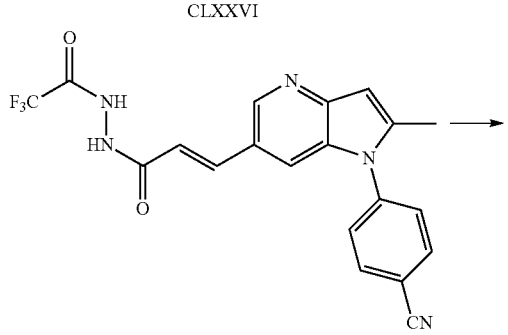

CLXXVII

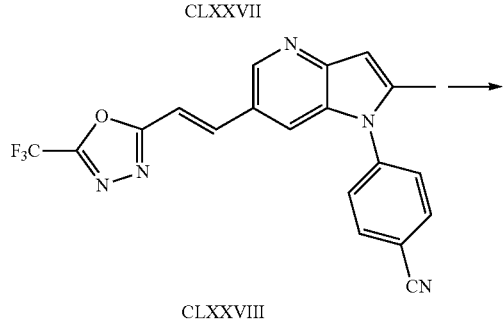

CLXXVIII

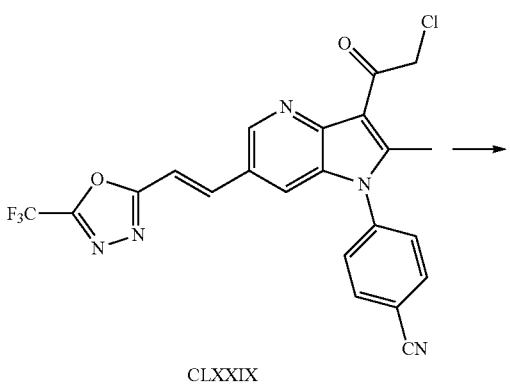

CLXXIX

-continued

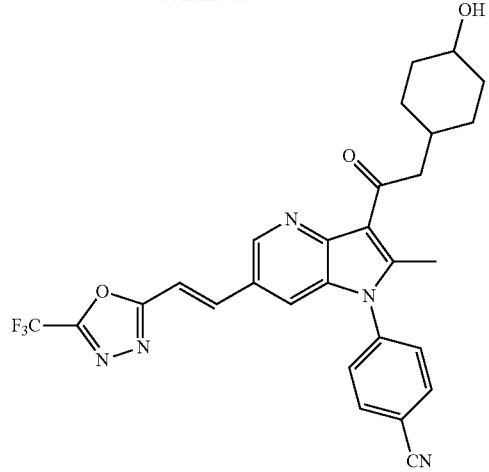

321

Synthesis of (E)-3-(1-(4-Cyanophenyl)-2-methyl-1H-pyrrolo[3,2-b]pyridin-6-yl)acrylic Acid (CLXXIV): To a solution of CLXVII (2.0 g, 6.03 mmol) in 1,4-dioxane (20 mL) was added an aqueous 30% hydrochloric acid solution (12 mL). The reaction mixture was heated at 80° C. for 15 h and then allowed to cool to room temperature. Progress of the reaction was monitored by TLC. The reaction mixture was condensed in vacuo and residual water was azeotropically distilled with toluene (10 mL×3) to obtain CLXXIV (2.0 g, crude) as an off-white solid, which was used without further purification. $^1$H NMR (400 MHz, DMSO-$d_6$): δ 8.97 (s, 1H), 8.48 (s, 1H), 8.18 (d, J=8.5 Hz, 2H), 7.84 (d, J=8.5 Hz, 2H), 7.76 (d, J=16 Hz, 1H), 6.96 (s, 1H), 6.82 (d, J=16 Hz, 1H), 2.45 (s, 3H); MS (ESI, positive mode) m/z 304 (MH$^+$).

Synthesis of tert-Butyl (E)-2-(3-(1-(4-Cyanophenyl)-2-methyl-1H-pyrrolo[3,2-b]pyridin-6-yl)acryloyl)hydrazine-1-carboxylate (CLXXV): To a mixture of CLXXIV (2.0 g, crude) in N,N-dimethylformamide and tetrahydrofuran (50 mL; 1:1) was added diisopropylethylamine (8.4 g, 65.1 mmol) in a dropwise fashion. The reaction mixture was allowed to stir at room temperature for 10 min and then propylphosphonic acid anhydride (20.9 mL, 31.4 mmol) was added, followed by tert-butyl hydrazinecarboxylate (1.7 g, 12.9 mmol). The reaction mixture was allowed to stir at room temperature for 15 h and then diluted with water (50 mL). The mixture was extracted with ethyl acetate (25 mL×2) and the combined organic extracts were washed with brine (25 mL×2). The organic layer was dried over anhydrous sodium sulfate and condensed in vacuo to obtain the crude product. The crude product mixture was purified by column chromatography on neutral alumina, using 2% methanol in dichloromethane as eluant, to afford CLXXV (1.3 g, crude) as an off-white solid. $^1$H NMR (400 MHz, DMSO-$d_6$) δ 8.53 (s, 1H), 7.89 (d, J=8.7 Hz, 2H), 7.84 (brs, 1H), 7.70 (d, J=15.4 Hz, 1H), 7.51 (d, J=8.7 Hz, 2H), 7.42 (s, 1H), 6.66 (s, 1H), 6.40 (d, J=15.9 Hz, 1H), 2.40 (s, 3H), 1.45 (s, 9H); MS (ESI, positive mode) m/z 418 (MH$^+$).

Synthesis of (E)-3-(1-(4-Cyanophenyl)-2-methyl-1H-pyrrolo[3,2-b]pyridin-6-yl)acrylohydrazide Hydrochloride (CLXXVI): To a solution of CLXXV (1.3 g, crude) in 1,4-dioxane (20 mL) was added concentrated hydrochloric acid (2 mL). The reaction mixture was allowed to stir at room temperature for 2 h. Progress of the reaction was monitored by TLC. The volatiles were removed under reduced pressure and the remaining material was azeotropically distilled with toluene (10 mL×3) to obtain CLXXVI (1.2 g, crude) as pale-yellow solid, which was used without further purification. $^1$H NMR (400 MHz, DMSO-d$_6$) δ 11.14 (s, 1H), 8.86 (s, 1H), 8.17-8.14 (overlapped d and s, 3H), 7.84 (d, J=8.5 Hz, 2H), 7.79 (d, J=15.9 Hz, 1H), 6.90 (s, 1H), 6.81 (d, J=15.9 Hz, 1H), 2.45 (s, 3H); MS (ESI, positive mode) m/z 318 (MH$^-$).

Synthesis of (E)-3-(1-(4-Cyanophenyl)-2-methyl-1H-pyrrolo[3,2-b]pyridin-6-yl)-N'-(2,2,2-trifluoroacetyl)acrylohydrazide (CLXXVII): To an ice-cooled solution of CLXXVI (1 g, 3.15 mmol) in dichloromethane (50 mL) was added pyridine (1.2 mL, 15.2 mmol), followed by diisopropylethylamine (1 mL, 6.20 mmol). The mixture was allowed to stir at 0° C. for 5 min and then trifluoroacetic anhydride (0.9 mL, 6.18 mmol) was added. The reaction mixture was allowed to stir 0° C. for 30 min and was then concentrated. The remaining residue was partitioned between ethyl acetate (100 mL) and water (75 mL). The organic layer was washed with brine (50 mL×2), dried over anhydrous sodium sulfate, and condensed in vacuo to afford crude CLXXVII (2.1 g, crude) as a yellow solid, which was used in the next step without further purification. $^1$H NMR (400 MHz, DMSO-d$_6$): δ 9.75 (s, 1H), 8.53 (d, J=1.7 Hz, 1H), 8.13 (d, J=8.5 Hz, 2H), 7.79 (d, J=8.5 Hz, 2H), 7.72 (s, 1H), 7.42 (d, J=15.6 Hz, 1H), 7.08-7.04 (d, J=16.8 Hz, 1H), 6.65 (s, 1H), 2.39 (s, 3H); MS (ESI, positive mode) m/z 414 (MH$^+$).

Synthesis of (E)-4-(2-Methyl-6-(2-(5-(trifluoromethyl)-1,3,4-oxadiazol-2-yl)vinyl)-1H-pyrrolo[3,2-b]pyridin-1-yl)benzonitrile (CLXXVIII): To a solution of CLXXVII (2.1 g, 5.08 mmol) in 1,4-dioxane (20 mL) was added phosphorus oxychloride (1 mL). The reaction mixture was heated at 90° C. for 15 h and then allowed to cool to room temperature. Progress of the reaction was monitored by TLC. The reaction mixture was condensed in vacuo and the remaining crude product was suspended in an aqueous, saturated solution of sodium bicarbonate (75 mL). The aqueous mixture was extracted with ethyl acetate (50 mL×2) and the combined organic extracts were washed with brine (50 mL×2). The organic layer was dried over anhydrous sodium sulfate and concentrated under reduced pressure to obtain the crude product, which was purified by column chromatography on neutral alumina, using 2% methanol in dichloromethane as eluent, to afford CLXXVIII (0.51 g, 25%) as a pale yellow solid. $^1$H NMR (400 MHz, CDCl$_3$): δ 8.67 (d, J=1.8 Hz, 1H), 7.93 (d, J=8.4 Hz, 2H), 7.77 (d, J=16.5 Hz, 1H), 7.53-7.50 (overlapped d and s, 3H), 7.01 (d, J=16.4 Hz, 1H), 6.71 (s, 1H), 2.42 (s, 3H); MS (ESI, positive mode) m/z 396 (MH$^+$).

Synthesis of (E)-4-(3-(2-Chloroacetyl)-2-methyl-6-(2-(5-(trifluoromethyl)-1,3,4-oxadiazol-2-yl)vinyl)-1H-pyrrolo[3,2-b]pyridin-1-yl)benzonitrile (CLXXIX): To an ice-cooled solution of aluminum trichloride (1.34 g, 10.1 mmol) in 1,2-dichloroethane (25 mL) was added chloroacetyl chloride (0.8 mL, 10.1 mmol) in a dropwise fashion. The reaction mixture was allowed to stir at 0° C. for 45 min and then a solution of CLXXVIII (0.2 g, 0.500 mmol) was added. The reaction mixture was allowed to warm to room temperature and was then heated at 70° C. for 15 h. Progress of the reaction was monitored by TLC. After cooling to room temperature, the reaction mixture was condensed in vacuo to obtain the crude product, which was suspended in a sodium bicarbonate solution (75 mL). The aqueous mixture was extracted with ethyl acetate (50 mL×2) and the combined organic extracts were washed with brine solution (50 mL×2). The organic layer was dried over anhydrous sodium sulfate and then concentrated under reduced pressure to obtain the crude product mixture, which was purified by column chromatography on neutral alumina, using 1% methanol in dichloromethane as eluant, to afford CLXXIX (0.14 g, 58%) as a pale brown solid. $^1$H NMR (400 MHz, CDCl$_3$): δ 9.02 (d, J=1.7 Hz, 1H), 8.21 (d, J=8.5 Hz, 2H), 8.16 (d, J=1.7 Hz, 1H), 7.94 (d, J=16.5 Hz, 1H), 7.86 (d, J=8.5 Hz, 2H), 7.68 (d, J=16.5 Hz, 1H), 5.39 (s, 2H), 2.64 (s, 3H); MS (ESI, negative mode) m/z 470/472 (M$^-$-H, $^{35/37}$Cl).

Synthesis of (E)-4-(3-(2-(4-Hydroxycyclohexyl)acetyl)-2-methyl-6-(2-(5-(trifluoromethyl)-1,3,4-oxadiazol-2-yl)vinyl)-1H-pyrrolo[3,2-b]pyridin-1-yl)benzonitrile (321): To a solution of CLXXIX (0.14 g, 0.290 mmol) in N,N-dimethylformamide (10 mL) was added 4-hydroxypiperidine (0.036 g, 0.350 mmol). The reaction mixture was allowed to stir at room temperature for 6 h, after which the reaction mixture was diluted with water (25 mL). The mixture was extracted with ethyl acetate (25 mL×2) and the combined organic extracts were washed with brine (25 mL×2). The organic layer was dried over anhydrous sodium sulfate and then concentrated under reduced pressure to obtain the compound product, which was purified by column chromatography on neutral alumina using 2% methanol in dichloromethane as eluent to afford 321 (0.03 g, 18%) as an off-white solid. $^1$H NMR (400 MHz, DMSO-d$_6$): δ 8.96 (d, J=1.7 Hz, 1H), 8.16 (d, J=8.5 Hz, 2H), 8.07 (d, J=1.7 Hz, 1H), 7.89 (d, J=16.4 Hz, 1H), 7.81 (d, J=8.4 Hz, 2H), 7.61 (d, J=16.4 Hz, 1H), 4.53 (d, J=4.3 Hz, 1H), 4.18 (s, 2H), 3.46-3.41 (m, 1H), 2.88-2.85 (m, 2H), 2.57 (s, 3H), 2.29-2.23 (m, 2H), 1.70-1.68 (m, 2H), 1.44-1.35 (m, 2H); MS (ESI, positive mode) m/z 537 (MH$^+$).

Example 72

1-(1-(4-Chlorophenyl)-2-methyl-6-(2-(pyrrolidin-1-yl)ethyl)-1H-pyrrolo[3,2-b]pyridin-3-yl)-2-(piperidin-1-yl)ethan-1-one (346)

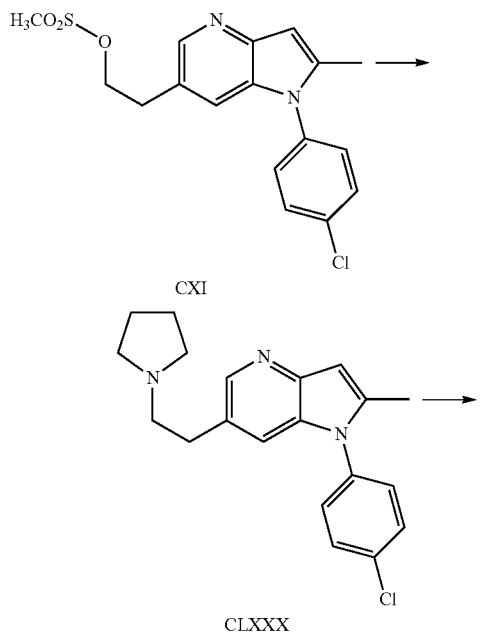

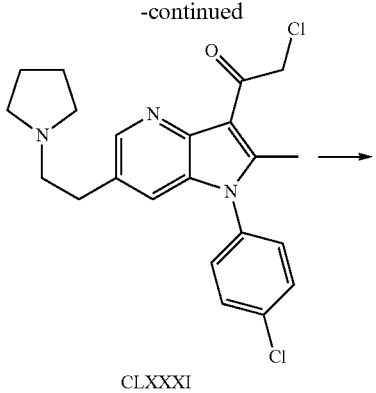

CLXXXI

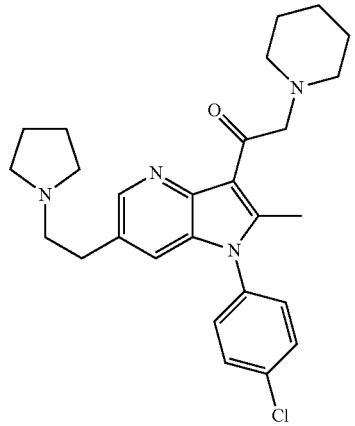

346

Synthesis of 1-(4-Chloro-phenyl)-2-methyl-6-(2-pyrrolidin-1-yl-ethyl)-1H-pyrrolo[3,2-b]pyridine (CLXXX): To a solution of CXI (0.2 g, 0.548 mmol) in tetrahydrofuran (5 mL) was added pyrrolidine (0.11 g, 1.64 mmol). The reaction mixture was heated at 70° C. for 16 h and then allowed to cool to room temperature. Progress of the reaction was monitored by TLC. The reaction mixture was diluted with cold water (20 mL) and the mixture was extracted with ethyl acetate (2×20 mL). The combined organic extracts was dried over sodium sulfate, filtered, and concentrated under reduced pressure to obtain the crude product. The crude product mixture was purified by column chromatography on silica, using 10% methanol in dichloromethane as the eluant, to afford CLXXX (0.18 g, 75% over two steps) as a white solid. $^1$H NMR (400 MHz, CDCl$_3$): δ 8.29 (d, J=1.8 Hz, 1H), 7.53-7.50 (m, 2H), 7.27-7.24 (m, 2H), 7.15 (s, 1H), 6.55 (s, 1H), 2.89 (t, J=7.5 Hz, 2H), 2.69 (t, J=8.7 Hz, 2H), 2.59 (brs, 4H), 2.32 (s, 3H), 1.85-1.80 (m, 4H); MS (ESI, positive mode) m/z 340/342 (MH$^+$, $^{35/37}$Cl).

Synthesis of 2-Chloro-1-[1-(4-chloro-phenyl)-2-methyl-6-(2-pyrrolidin-1-yl-ethyl)-1H-pyrrolo[3,2-b]pyridin-3-yl]-ethanone (CLXXXI): To an ice-cooled suspension of aluminum trichloride (1.2 g, 11.2 mmol) in 1,2-dichloroethane (15 mL) was added chloroacetyl chloride (1.2 g, 11.2 mmol) in a dropwise fashion. The reaction mixture was allowed to stir at 0° C. for 45 min and then a solution of CLXXX (0.19 g, 0.550 mmol) in 1,2-dichloroethane (5 mL) was added. The reaction mixture was heated at 80° C. for 2 h and then allowed to cool to room temperature. Progress of the reaction was monitored by TLC. The reaction mixture was poured onto crushed ice and mixture was neutralized with an aqueous, saturated solution of sodium bicarbonate. Then the aqueous phase was extracted with dichloromethane (3×30 mL) and the combined organic extracts were dried over sodium sulfate. The organic layer was concentrated under reduced pressure to afford the crude product. The crude product mixture was purified by column chromatography on neutral alumina, using 3% methanol in dichloromethane as the eluent, to afford CLXXXI (0.11 g, 48%) as an off white solid. $^1$H NMR (400 MHz, CDCl$_3$): δ 8.44 (d, J=1.7 Hz, 1H), 7.60-7.57 (m, 2H), 7.27-7.25 (m, 2H), 7.14 (s, 1H), 5.30 (s, 2H), 2.89 (t, J=7.6 Hz, 2H), 2.67 (t, J=8.6 Hz, 2H), 2.65 (s, 3H), 2.55 (brs, 4H), 1.78 (brs, 4H); MS (ESI, positive mode) m/z 416/418 (MH$^+$, $^{35/37}$Cl).

Synthesis of 1-(1-(4-Chlorophenyl)-2-methyl-6-(2-(pyrrolidin-1-yl)ethyl)-1H-pyrrolo[3,2-h]pyridin-3-yl)-2-(piperidin-1-yl)ethan-1-one (346): To a solution of CLXXXI (0.11 g, 0.264 mmol) in acetonitrile (5 mL) was added piperidine (0.045 g, 0.528 mmol). The reaction mixture was allowed to stir at room temperature for 30 min and was then condensed under reduced pressure. The remaining residue was diluted with water and the precipitate that formed was collected by filtration. The filtered solid was washed with water (2×5 mL), followed by hexanes (2×5 mL), and allowed to dry in a stream of air. The crude product was triturated with diethylether (2×5 mL) to afford 346 (0.06 g, 50%) as a brown solid. $^1$H NMR (400 MHz, DMSO-d$_6$): δ 8.43 (d, J=1.6 Hz, 1H), 7.73-7.71 (m, 2H), 7.57-7.55 (m, 2H), 7.32 (d, J=1.6 Hz 1H), 4.16 (s, 2H), 2.80 (t, J=7.2 Hz, 2H), 2.60-2.49 (m, 7H), 2.44-2.41 (m, 4H), 1.65-1.62 (m, 4H), 1.53-1.50 (m, 4H), 1.41-1.38 (m, 2H); MS (ESI, positive mode) m/z 465/467 (MH$^+$, $^{35/37}$Cl).

Example 73

2-(1-(4-Chlorophenyl)-3-(2-(4-hydroxypiperidin-1-yl)acetyl)-2-methyl-1H-pyrrolo[3,2-b]pyridin-6-yl)ethane-1-sulfonamide (357)

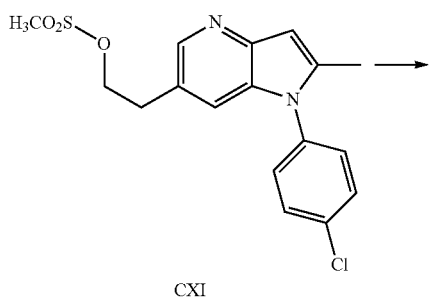

CXI

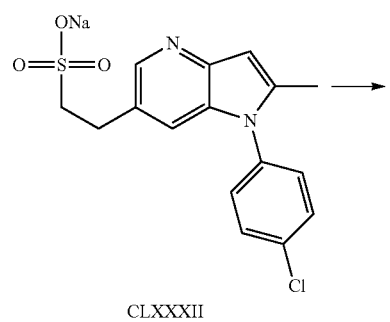

CLXXXII

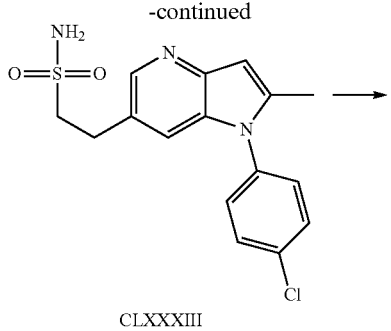

CLXXXIII

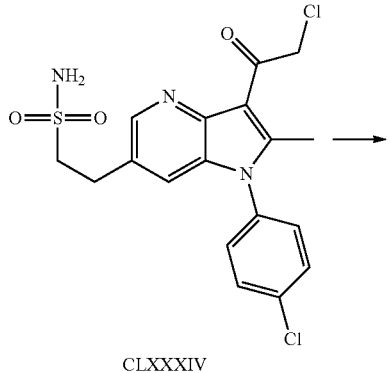

CLXXXIV

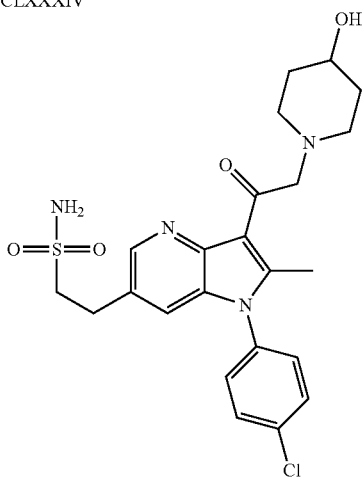

357

Synthesis of Sodium 2-(1-(4-Chlorophenyl)-2-methyl-1H-pyrrolo[3,2-b]pyridin-6-yl)ethane-1-sulfonate (CLXXXII): To a mixture of CXI (0.40 g, crude) in ethanol and water (1:1, 30 mL) was added tetrabutylammonium iodide (0.040 g, 0.110 mmol), followed by sodium sulfite (0.207 g, 1.64 mmol). The reaction mixture was heated at reflux for 16 h and then allowed too cool to room temperature. The reaction mixture was condensed under reduced pressure and the remaining material was diluted with water (50 mL). The aqueous mixture was extracted with dichloromethane (30 mL×3) and the combined organic extracts were concentrated under reduced pressure to obtain CLXXXII (0.50 g, crude) as an off-white solid. MS (ESI, positive mode) m/z 351/353 (MH$^+$, $^{35/37}$Cl).

Synthesis of 2-(1-(4-Chlorophenyl)-2-methyl-1H-pyrrolo[3,2-b]pyridin-6-yl)ethane-1-sulfonamide (CLXXXIII): To an ice-cooled suspension of CLXXXII (0.250 g, crude) in dichloromethane (40 mL) being maintained under a nitrogen atmosphere was added phosphorus pentachloride (0.558 g, 2.68 mmol) in a portionwise manner. The reaction mixture was allowed to stir at 0° C. for 16 h and was then cooled to −78° C. The mixture was treated with liquid ammonia (10 mL) and the resulting reaction mixture was allowed to warm to room temperature. The mixture was allowed to stir for 1 h and the mixture was filtered. The filtered solids were washed with dichloromethane and the filtrate was concentrated under reduced pressure to obtain the crude product. The crude product mixture was purified by column chromatography on neutral alumina using 5% methanol in dichloromethane as eluant to afford CLXXXIII (0.85 g) as an off-white solid. The product was used in the next step without further purification. MS (ESI, positive mode) m/z 350/352 (MH$^+$, $^{35/37}$Cl).

Synthesis of 2-(3-(2-Chloroacetyl)-1-(4-chlorophenyl)-2-methyl-1H-pyrrolo[3,2-b]pyridin-6-yl)ethane-1-sulfonamide (CLXXXIV): To an ice-cooled solution of aluminum trichloride (0.304 g, 2.28 mmol) in dry 1,2-dichloroethane (30 mL) was added chloroacetyl chloride (0.258 g, 2.28 mmol) in a dropwise fashion. The reaction mixture was allowed to stir at 0° C. for 45 min and then a solution of CLXXXIII (0.80 g, crude) in dry 1,2-dichloroethane (20 mL) was added. The reaction mixture was allowed to warm to room temperature and was then heated at 65° C. for 16 h. After cooling to room temperature the reaction mixture was poured onto crushed ice and neutralized with a solution of sodium bicarbonate. The mixture was extracted with ethyl acetate (25 mL×3) and the combined organic extracts were dried over sodium sulfate, filtered, and concentrated under reduced pressure. The remaining crude product mixture was purified by column chromatography on neutral alumina using 2% methanol in dichloromethane as the eluant to afford CLXXXIV (0.032 g, crude) as an off-white solid. The product was used in the next step without further purification. MS (ESI, positive mode) m/z 426/428 (MH$^+$, $^{35/37}$Cl).

Synthesis of 2-(1-(4-Chlorophenyl)-3-(2-(4-hydroxypiperidin-1-yl)acetyl)-2-methyl-1H-pyrrolo[3,2-b]pyridin-6-yl)ethane-1-sulfonamide (357): To a solution of CLXXXIV (0.030 g, crude) in acetonitrile (5 mL) was added 4-hydroxypiperidine (0.014 g, 0.14 mmol). The reaction mixture was allowed to stir at room temperature for 16 h. Progress of the reaction was monitored by TLC. The reaction mixture was condensed in vacuo to obtain the crude product mixture, which was purified by column chromatography on neutral alumina using 5% methanol in dichloromethane as the eluent. The material obtained after chromatography was further washed with diethyl ether (1 mL×2) and allowed to dry in a stream of air to afford 357 (0.011 g, 2% over five steps) as a pale brown solid. $^1$H NMR (400 MHz, CDCl$_3$): δ 8.47 (d, J=1.7 Hz, 1H), 7.73 (d, J=8.6 Hz, 2H), 7.58 (d, J=8.6 Hz, 2H), 7.41 (d, J=1.7 Hz, 1H), 6.83 (s, 2H), 4.55 (d, J=4.3 Hz, 1H), 4.18 (s, 2H), 3.46-3.43 (m, 1H), 3.29-3.25 (m, 2H), 3.10-3.06 (m, 2H), 2.90-2.86 (m, 2H), 2.55 (s, 3H), 2.29-2.24 (m, 2H), 1.71 (m, 2H), 1.45-1.37 (m, 2H); MS (ESI, positive mode) m/z 491/493 (MH$^+$, $^{35/37}$Cl).

The compounds shown below in Table 2 were prepared using the procedures similar to those described in Examples 1-73.

TABLE 2
| Compound No. | General Synthetic Route Number | Structure | ¹H NMR | LC-MS |
|---|---|---|---|---|
| 30 | 1 | 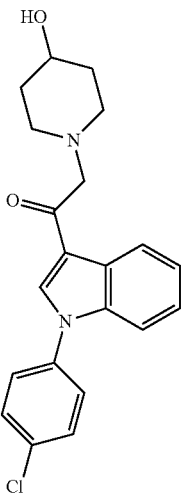 [SMILES: O=C(CN1CCC(O)CC1)c1cn(-c2ccc(Cl)cc2)c2ccccc12] | ¹H NMR (400 MHz, CDCl₃): δ 8.47 (dd, 1H), 8.39 (s, 1H), 7.52-7.58 (m, 2H), 7.40-7.48 (m, 3H), 7.28-7.38 (m, 2H), 3.68-3.78 (m, 1H), 3.65 (s, 2H), 2.88-2.95 (m, 2H), 2.28-2.38 (m, 2H), 1.88-1.97 (m, 2H), 1.60-1.70 (m, 2H) | LC $R_T$ = 8.9 min; MS: [M + H, $^{35/37}$Cl]$^+$ = 369/371 m/z |
| 31 | 1 | 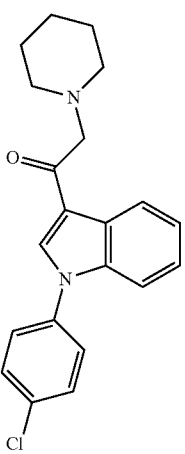 [SMILES: O=C(CN1CCCCC1)c1cn(-c2ccc(Cl)cc2)c2ccccc12] | ¹H NMR (400 MHz, CDCl₃): δ 8.48 (s, 1H), 8.40-8.47 (m, 1H), 7.52-7.58 (m, 2H), 7.45-7.50 (m, 2H), 7.40-7.44 (m, 1H), 7.26-7.37 (m, 2H), 3.60 (s, 2H), 2.40-2.60 (m, 4H), 1.58-1.64 (m, 4H), 1.40-1.50 (m, 2H) | LC $R_T$ = 9.7 min; MS: [M + H, $^{35/37}$Cl]$^+$ = 353/355 m/z |
| 34 | 1 | 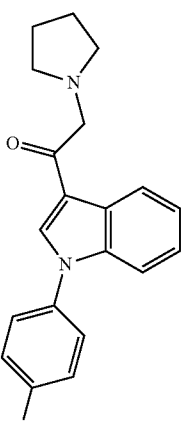 | ¹H NMR (400 MHz, CDCl₃): δ 8.45 (d, 1H), 8.24 (s, 1H), 7.50 (q, 4H), 7.42 (d, 1H), 7.34 (m, 1H), 3.85 (s, 2H), 2.70-2.73 (m, 4H), 1.79-1.91 (m, 4H) | LC $R_T$ = 9.9 min; MS: [M + H, $^{35/37}$Cl]$^+$ = 339/341 m/z |

TABLE 2-continued
| Compound No. | General Synthetic Route Number | Structure | ¹H NMR | LC-MS |
|---|---|---|---|---|
| 86 | 1 | 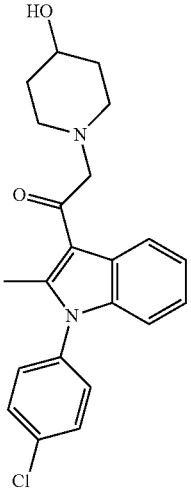 | ¹H NMR (400 MHz, CDCl₃): δ 7.99 (d, 1H), 7.55 (dd, 2H), 7.22-7.30 (m, 3H), 7.17 (t, 1H), 6.99 (d, 1H), 3.85 (s, 2H), 3.70-3.78 (m, 1H), 2.92-3.00 (m, 2H), 2.58 (s, 3H), 2.40-2.50 (m, 2H), 1.92-2.00 (m, 2H), 1.68-1.75 (m, 2H). | LC R$_T$ = 11.1 min; MS: [M + H, ³⁵/³⁷Cl]⁺ = 383/385 m/z |
| 87 | 1 | 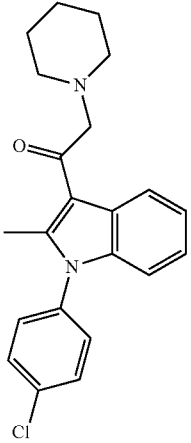 | ¹H NMR (400 MHz, CDCl₃): δ 8.01 (d, 1H), 7.55 (dd, 2H), 7.22-7.30 (m, 3H), 7.16 (t, 1H), 6.98 (d, 1H), 3.82 (s, 2H), 2.60-2.68 (m, 4H), 2.58 (s, 3H), 1.62-1.72 (m, 4H), 1.42-1.50 (m, 2H). | LC R$_T$ = 12.1 min; MS: [M + H, ³⁵/³⁷Cl]⁺ = 367/369 m/z |
| 88 | 1 | 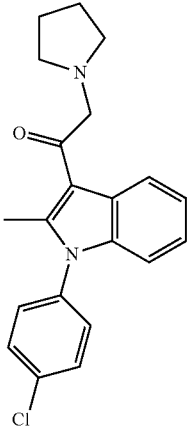 [SMILES: Cc1c(C(=O)CN2CCCC2)c2ccccc2n1-c1ccc(Cl)cc1] | ¹H NMR (400 MHz, CDCl₃): δ 7.98 (d, 1H), 7.54 (dd, 2H), 7.22-7.30 (m, 3H), 7.16 (t, 1H), 6.99 (d, 1H), 4.02 (s, 2H), 2.75-2.85 (m, 4H), 2.59 (s, 3H), 1.80-1.90 (m, 4H). | LC R$_T$ = 11.8 min; MS: [M + H, ³⁵/³⁷Cl]⁺ = 353/355 m/z |

TABLE 2-continued
| Compound No. | General Synthetic Route Number | Structure | ¹H NMR | LC-MS |
|---|---|---|---|---|
| 98 | 1 | 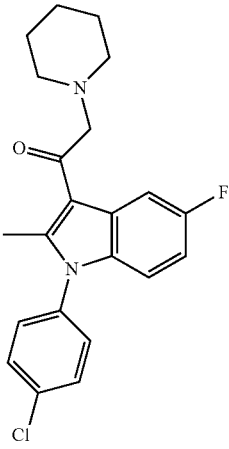 [SMILES: Cc1c(C(=O)CN2CCCCC2)c2cc(F)ccc2n1-c1ccc(Cl)cc1] | ¹H NMR (400 MHz, CDCl$_3$): δ 7.76 (d, 1H), 7.57 (d, 2H), 7.26 (d, 2H), 6.90 (d, 2H), 3.77 (s, 2H), 2.63-2.76 (m, 4H), 2.59 (s, 3H), 1.64-1.75 (m, 4H), 1.45-1.56 (m, 2H). | LC R$_T$ = 10.8 min; MS: [M + H, $^{35/37}$Cl]$^+$ = 385/387 m/z |
| 106 | | 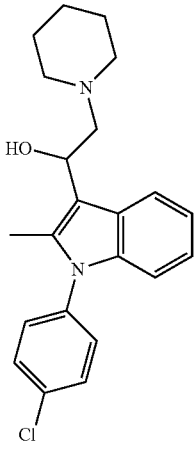 | ¹H NMR (400 MHz, DMSO-d$_6$): δ 7.73 (m, 1H), 7.65 (d, 2H), 7.42 (d, 2H), 7.00-7.04 (m, 3H), 5.06 (m, 1H), 4.75 (br s, 1H), 2.83 (m, 1H), 2.40-2.48 (m, 5H), 1.46-1.56 (m, 4H), 1.38-1.44 (m, 2H). | LC R$_T$ = 11.2 min; MS: [M + H, $^{35/37}$Cl]$^+$ − H$_2$O = 351/353 m/z |
| 108 | 1 | 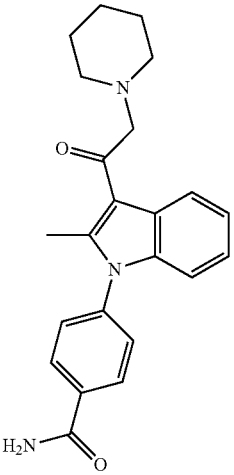 | ¹H NMR (400 MHz, DMSO-d$_6$): 8.19 (br s, 1H), 8.12 (d, 2H), 8.09 (s, 1H), 7.57-7.59 (m, 3H), 7.24 (t, 1H), 7.16 (t, 1H), 6.98 (d, 1H), 3.63 (s, 2H), 2.56 (s, 3H), 2.45-2.52 (brm, 4H), 1.47-1.55 (brm, 4H), 1.35-1.42 (m, 2H). | LC R$_T$ = 6.6 min; MS: [M + H]$^+$ = 376 m/z |

TABLE 2-continued

| Compound No. | General Synthetic Route Number | Structure | ¹H NMR | LC-MS |
|---|---|---|---|---|
| 115 | 1 | 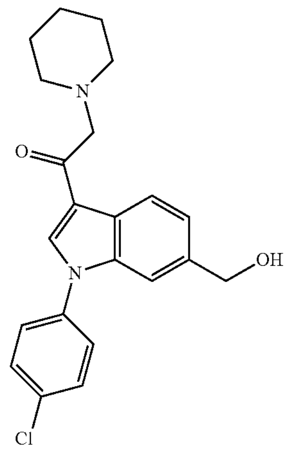 [SMILES: O=C(CN1CCCCC1)c1cn(-c2ccc(Cl)cc2)c2cc(CO)ccc12] | ¹H NMR (400 MHz, CDCl₃): δ 8.48 (s, 1H), 8.44 (d, 1H), 7.43-7.47 (m, 3H), 7.45 (d, 2H), 7.31 (d, 1H), 4.78 (s, 2H), 3.57 (s, 2H), 2.48-2.58 (m, 4H), 1.58-1.65 (m, 4H), 1.42-1.48 (m, 2H). | LC R$_T$ = 5.7 min; MS: [M + H, $^{35/37}$Cl]$^+$ = 383/385 m/z |
| 116 | | 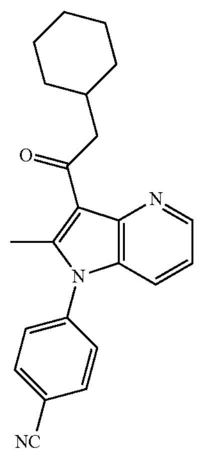 [SMILES: Cc1c(C(=O)CC2CCCCC2)c2ncccc2n1-c1ccc(C#N)cc1] | ¹H NMR (400 MHz, CDCl₃): δ 8.60 (dd, 1H), 7.90 (dd, 2H), 7.48 (dd, 2H), 7.31 (dd, 1H), 7.11 (dd, 1H), 3.39 (d, 2H), 2.65 (s, 3H), 1.83 (m, 1H), 1.62-1.72 (m, 4H), 1.15-1.28 (m, 4H), 1.08-1.12 (m, 2H). | LC R$_T$ = 10.1 min; MS: [M + H]$^+$ = 358 m/z |
| 118 | 1 | 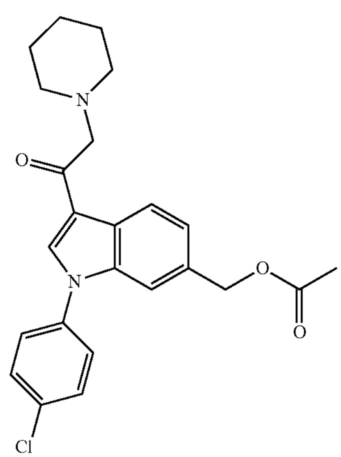 [SMILES: CC(=O)OCc1ccc2c(C(=O)CN3CCCCC3)cn(-c3ccc(Cl)cc3)c2c1] | ¹H NMR (400 MHz, CDCl₃): δ 8.51 (s, 1H), 8.46 (d, 1H), 7.57 (d, 2H), 7.46 (d, 2H), 7.40 (s, 1H), 7.35 (dd, 1H), 5.19 (s, 2H), 3.58 (s, 2H), 2.48-2.58 (m, 4H), 2.07 (s, 3H), 1.58-1.65 (m, 4H), 1.40-1.48 (m, 2H). | LC R$_T$ = 8.2 min; MS: [M + H, $^{35/37}$Cl]$^+$ = 425/427 m/z |

TABLE 2-continued

| Compound No. | General Synthetic Route Number | Structure | ¹H NMR | LC-MS |
|---|---|---|---|---|
| 119 | | 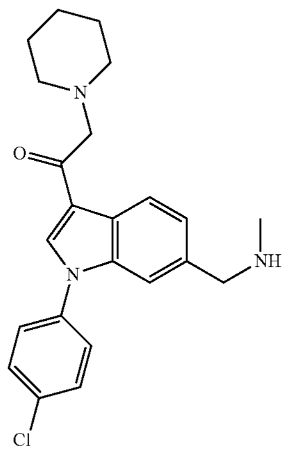 [SMILES: CNCc1ccc2c(C(=O)CN3CCCCC3)cn(-c3ccc(Cl)cc3)c2c1] | ¹H NMR (400 MHz, DMSO-$d_6$): δ 8.82 (s, 1H), 8.30 (d, 1H), 7.66-7.75 (m, 5H), 7.37 (d, 1H), 4.10 (s, 2H), 3.63 (s, 3H), 2.43-2.46 (4H), 1.49-1.52 (m, 4H), 1.38-1.40 (m, 2H). | LC $R_T$ = 4.9 min; MS: [M + H, $^{35/37}$Cl]$^+$ = 396/398 m/z |
| 120 | | 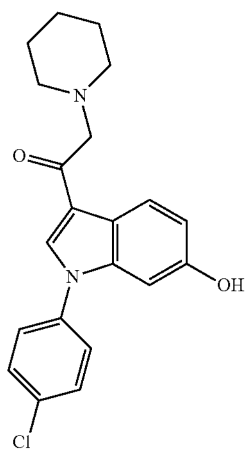 [SMILES: O=C(CN1CCCCC1)c1cn(-c2ccc(Cl)cc2)c2cc(O)ccc12] | ¹H NMR (400 MHz, DMSO-$d_6$): δ 9.44 (s, 1H), 8.56 (s, 1H), 8.06 (d, 1H), 7.69 (dd, 4H), 6.84 (m, 1H), 6.80 (dd, 1H), 3.56 (s, 2H), 2.46 (brs, 4H), 1.48-1.54 (m, 4H), 1.36-1.40 (m, 2H) | LC $R_T$ = 7.5 min; MS: [M + H, $^{35/37}$Cl]$^+$ = 369/371 m/z |
| 126 | | 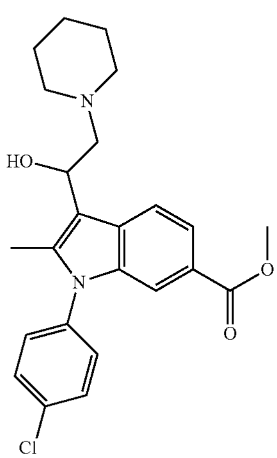 | ¹H NMR (400 MHz, CDCl$_3$): δ 7.79 (s, 2H), 7.70 (s, 1H), 7.52 (d, 2H), 7.23-7.25 (m, obscured by solvent, 2H), 5.26 (m, 1H), 3.86 (s, 3H), 3.09 (m, 1H), 2.84-2.88 (m, 2H), 2.55-2.70 (m, 3H), 2.29 (s, 3H), 1.70-1.80 (m, 6H) | LC $R_T$ = 8.1 min; MS: [M + H, $^{35/37}$Cl]$^+$ = 427/429 m/z |

TABLE 2-continued

| Compound No. | General Synthetic Route Number | Structure | ¹H NMR | LC-MS |
|---|---|---|---|---|
| 127 | 2 | 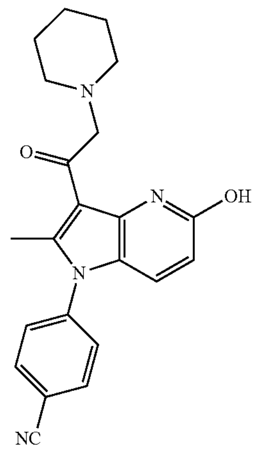 | ¹H NMR (400 MHz, CDCl₃): δ 13.87 (br s, 1H), 7.89 (d, 2H), 7.44 (d, 2H), 7.10 (d, 1H), 6.30 (d, 1H), 3.50 (s, 2H), 2.60-2.64 (m, 4H), 2.51 (s, 3H), 1.82 (s, 3H), 1.49-1.64 (m, 4H), 1.20-1.32 (m, 2H). | LC R$_T$ = 6.0 min; MS: [M + H]⁺ = 375 m/z |
| 128 | | 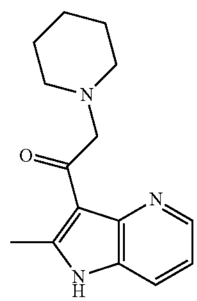 [SMILES: Cc1[nH]c2cccnc2c1C(=O)CN1CCCCC1] | ¹H NMR (400 MHz, CDCl₃): δ 8.47 (br s, 1H), 7.60 (m, 1H), 7.08 (m, 1H), 4.25 (s, 2H), 277 (s, 3H), 2.67 (br s, 4H), 1.62-1.69 (m, 4H), 1.44-1.48 (m, 2H). | LC R$_T$ = 5.0 min; MS: [M + H]⁺ = 258 m/z |
| 130 | | 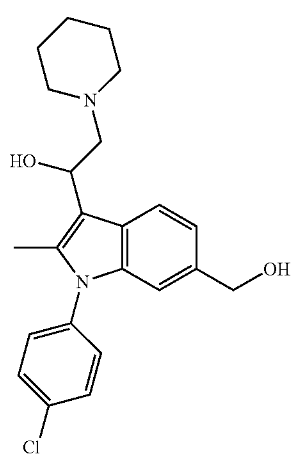 [SMILES: Cc1c(C(O)CN2CCCCC2)c2ccc(CO)cc2n1-c1ccc(Cl)cc1] | ¹H NMR (400 MHz, CDCl₃): δ 7.78 (d, 1 H), 7.51 (d, 2H), 7.26-7.23-7.25 (m, 2H, partially obscured by solvent), 7.11 (d, 1H), 7.03 (s, 1H), 5.23 (m, 1H), 4.69 (s, 2H), 3.14 (t, 1H), 2.86 (br s, 2H), 2.65 (br s, 2H), 2.55 (m, 1H) 2.26 (s, 3H), 1.71-1.75 (m, 4H) 1.53-1.55 (m, 2H). | LC R$_T$ = 6.4 min; MS: [M + H, ³⁵/³⁷Cl]⁺ = 399/401 m/z |

TABLE 2-continued

| Compound No. | General Synthetic Route Number | Structure | ¹H NMR | LC-MS |
|---|---|---|---|---|
| 131 | 3 | 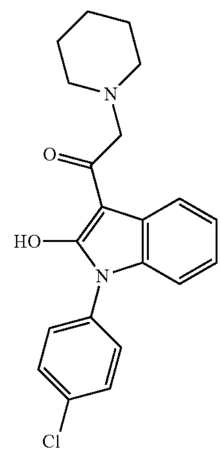 [SMILES: O=C(CN1CCCCC1)c1c(O)n(-c2ccc(Cl)cc2)c2ccccc12] | ¹H NMR (400 MHz, DMSO-d₆): δ 9.89 (br s, 1H), 7.95 (d, 2H), 7.55-7.53 (m, 2H), 7.46-7.44 (m, 2H), 6.87 (t, 1H), 6.78-6.75 (m, 2H), 4.29 (s, 2H), 3.32 (br s, 4H), 1.75-1.77 (m, 4H), 1.54 (br s, 2H). | LC R$_T$ = 11.1 min; MS: [M + H, $^{35/37}$Cl]⁺ = 369/371 m/z |
| 132 | 3 | 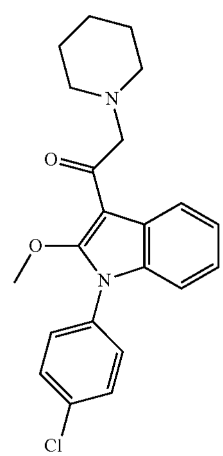 [SMILES: COc1c(C(=O)CN2CCCCC2)c2ccccc2n1-c1ccc(Cl)cc1] | ¹H NMR (400 MHz, CDCl₃); δ 8.15 (d, 1H), 7.40-7.43 (m, 4H), 7.05 (t, 1H), 6.97 (t, 1H), 6.82 (d, 1H), 4.89 (s, 2H), 3.84-3.89 (m, 2H), 3.31-3.36 (m, 5H), 2.03-2.09 (m, 2H), 1.82-1.91 (m, 2H), 1.65-1.78 (m, 2H) | LC R$_T$ = 7.5 min; MS: [M + H, $^{35/37}$Cl]⁺ = 383/385 m/z |
| 133 | 1 | 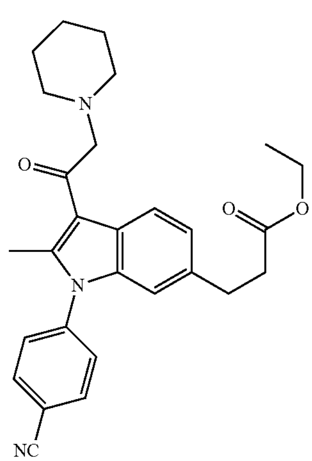 [SMILES: CCOC(=O)CCc1ccc2c(C(=O)CN3CCCCC3)c(C)n(-c3ccc(C#N)cc3)c2c1] | ¹H NMR (400 MHz, DMSO-d₆): δ 8.15 (d, 2H), 7.98 (d, 1H), 7.72 (d, 2H), 7.13 (d, 1H), 6.85 (s, 1H), 3.97 (q, 2H), 3.61 (s, 2H), 2.86 (t, 2H), 2.58-2.45 (m, 9H), 1.55-1.45 (m, 4H), 1.42-1.38 (m, 2H), 1.08 (t, 3H) | LC R$_T$ = 7.1 min; MS: [M + H]⁺ = 458 m/z |

TABLE 2-continued
| Compound No. | General Synthetic Route Number | Structure | $^1$H NMR | LC-MS |
|---|---|---|---|---|
| 141 | | 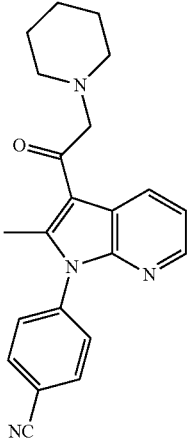 | $^1$H NMR (400 MHz, CDCl$_3$): δ 8.34 (d, 1H), 8.26 (m, 1H), 7.89 (d, 2H), 7.54 (d, 2H), 7.26-7.28 (m, 1H), 3.77 (s, 2H), 2.68 (s, 3H), 2.64 (br s, 4H), 1.63-1.68 (m, 4H), 1.45-1.50 (m, 2H). | LC R$_T$ = 9.3 min; MS: [M + H]$^+$ = 359 m/z |
| 142 | 1 | 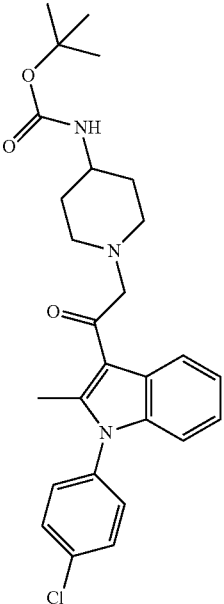 [SMILES: Cc1c(C(=O)CN2CCC(NC(=O)OC(C)(C)C)CC2)c2ccccc2n1-c1ccc(Cl)cc1] | $^1$H NMR (400 MHz, DMSO-d$_6$): δ 8.08 (d, 1H), 7.73 (d, 2H), 7.54 (d, 2H), 7.25 (t, 1H), 7.16 (t, 1H), 6.98 (d, 1H), 6.76 (m, 1H), 3.68 (s, 2H), 3.23 (m, 1H), 2.88-2.93 (m, 2H), 2.54 (s, 3H), 2.14-2.18 (m, 2H), 1.66-1.72 (m, 2H), 1.39-1.47 (m, 2H), 1.37 (s, 9H). | LC R$_T$ = 11.7 min; MS: [M + H, $^{35/37}$Cl]$^+$ = 482/484 m/z |
| 144 | | 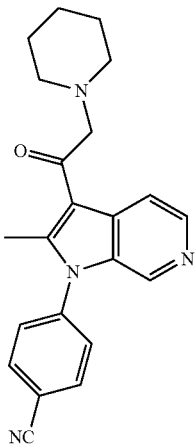 [SMILES: Cc1c(C(=O)CN2CCCCC2)c2ccncc2n1-c1ccc(C#N)cc1] | $^1$H NMR (400 MHz, CDCl$_3$): δ 8.44 (d, 1H), 8.39 (s, 1H), 7.94 (d, 2H), 7.88 (d, 1H), 7.52 (d, 2H), 3.75 (s, 2H), 2.65 (s, 3H), 2.56-2.61 (m, 4H), 1.60-1.67 (m, 4H), 1.46-1.49 (m, 2H). | LC R$_T$ = 8.3 min; MS: [M + H]$^+$ = 359 m/z |

TABLE 2-continued

| Compound No. | General Synthetic Route Number | Structure | ¹H NMR | LC-MS |
|---|---|---|---|---|
| 145 | 1 | 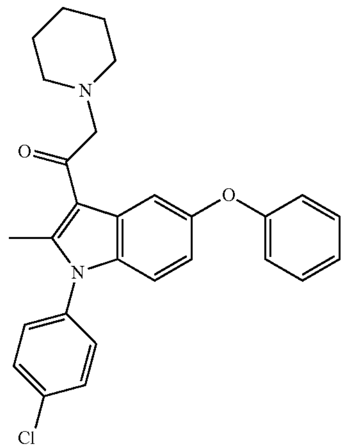 [SMILES: Cc1c(C(=O)CN2CCCCC2)c2cc(Oc3ccccc3)ccc2n1-c1ccc(Cl)cc1] | ¹H NMR (400 MHz, CDCl₃): δ 7.77 (m, 1H), 7.56 (d, 2H), 7.26-7.33 (m, 4H), 7.04 (t, 1H), 6.88-6.99 (m, 4H), 3.68 (s, 2H), 2.58 (s, 3H), 2.50-2.55 (m, 4H), 1.57-1.64 (m, 4H), 1.43-1.45 (m, 2H). | LC $R_T$ = 14.0 min; MS: $[M + H, {}^{35/37}Cl]^+$ = 459/461 m/z |
| 146 | 1 | 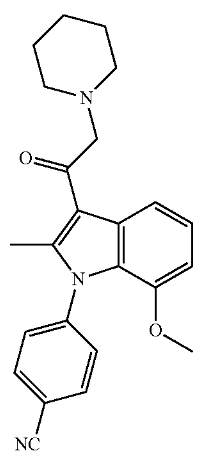 | ¹H NMR (400 MHz, CDCl₃) δ: 7.78 (d, 2H), 7.53 (d, 1H), 7.40-7.38 (d, 2H), 7.21 (m, 1H), 6.65 (d, 1H), 4.04 (s, 2H), 3.52 (S, 3H), 2.93 (br s, 4H), 2.46 (s, 3H), 1.75-1.79 (m, 4H), 1.29-1.31 (m, 2H). | LC $R_T$ = 7.4 min; MS: $[M + H]^+$ = 388 m/z |

TABLE 2-continued
| Compound No. | General Synthetic Route Number | Structure | $^1$H NMR | LC-MS |
|---|---|---|---|---|
| 147 | 1 | 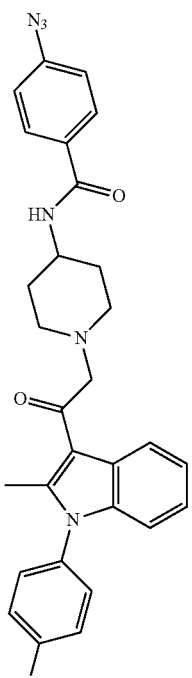 | $^1$H NMR (400 MHz, DMSO-$d_6$): δ 8.25 (d, 1H), 8.09 (d, 1H), 7.88 (d, 2H), 7.72 (d, 2H), 7.53 (d, 2H), 7.25 (t, 1H), 7.14-7.20 (m, 3H), 6.97 (d, 1H), 3.78 (m, 1H), 2.95-3.00 (m, 2H), 2.55 (s, 3H), 2.23 (t, 2H), 1.74-1.79 (m, 2H), 1.57-1.62 (m, 2H) | LC $R_T$ = 12.0 min; MS: [M + H, $^{35/37}$Cl]$^+$ = 527/529 m/z |
| 148 | 1 | 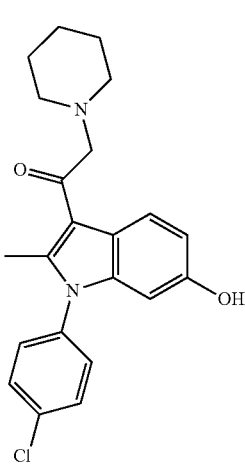 [SMILES: Cc1c(C(=O)CN2CCCCC2)c2ccc(O)cc2n1-c1ccc(Cl)cc1] | $^1$H NMR (400 MHz, CDCl$_3$): δ 7.87 (d, 1H), 7.53 (d, 2H), 7.23 (d, 2H), 6.80 (dd, 1H), 6.44 (d, 1H), 3.73 (s, 2H), 2.60 (bm, 4H), 2.54 (s, 3H), 1.40-1.67 (m, 6H) | LC $R_T$ = 10.4 min; MS: [M + H, $^{35/37}$Cl]$^+$ = 383/385 m/z |

TABLE 2-continued
| Compound No. | General Synthetic Route Number | Structure | ¹H NMR | LC-MS |
|---|---|---|---|---|
| 149 | 2 | 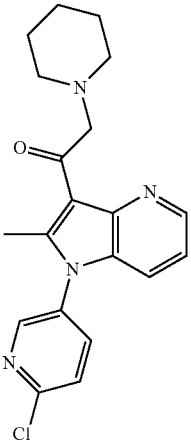 | ¹H NMR (400 MHz, CDCl₃) δ 8.59 (m, 1H), 8.43 (m, 1H), 7.65 (m, 1H), 7.59 (m, 1H), 7.29 (dd, 1H), 7.12 (dd, 1H), 4.33 (s, 2H), 2.65-2.69 (m, 7H), 1.65-1.72 (m, 4H), 1.45-1.51 (m, 2H) | LC $R_T$ = 9.3 min; MS: [M + H, $^{35/37}$Cl]⁺ = 369/371 m/z |
| 150 | 1 | 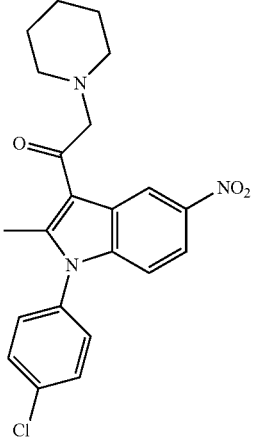 | ¹H NMR (400 MHz, DMSO-d₆): δ 9.10 (s, 1H), 8.06 (m, 1H), 7.76 (d, 2H), 7.61 (d, 2H), 7.17 (d, 1H), 3.63 (s, 2H), 2.58 (s, 3H), 2.50 (brs, 4H, occluded by solvent), 1.48-1.54 (m, 4H), 1.37-1.44 (m, 2H). | LC $R_T$ = 10.9 min; MS: [M + H, $^{35/37}$Cl]⁺ = 412/414 m/z |
| 151 |  | 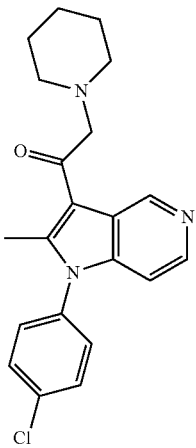 | ¹H NMR (400 MHz, CDCl₃): δ 9.34 (s, 1H), 8.36 (d, 1H), 7.93 (dd, 2H), 7.48 (dd, 2H), 6.95 (m, 1H), 3.77 (s, 2H), 2.62 (s, 3H), 2.42-2.60 (m, 4H), 1.60-1.67 (m, 4H) 1.47-1.51 (m, 2H). | LC $R_T$ = 9.6 min; MS: [M + H]⁺ = 359 m/z |

TABLE 2-continued

| Compound No. | General Synthetic Route Number | Structure | ¹H NMR | LC-MS |
|---|---|---|---|---|
| 152 | | 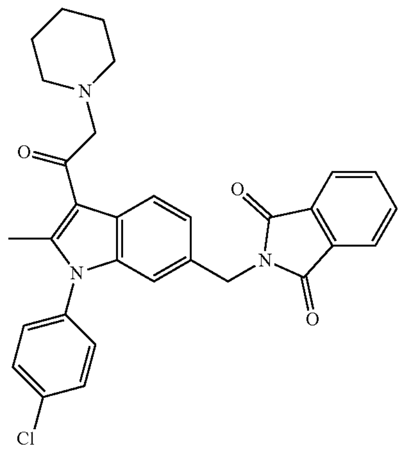 [SMILES: Cc1c(C(=O)CN2CCCCC2)c2ccc(CN3C(=O)c4ccccc4C3=O)cc2n1-c1ccc(Cl)cc1] | ¹H NMR (400 MHz, CDCl₃) δ 7.93 (d, 1H), 7.79-7.83 (m, 2H), 7.67-7.69 (m, 2H), 7.57 (d, 2H), 7.37 (d, 1H), 7.23-7.24 (d, 1H, occluded by solvent), 7.10 (s, 1H), 4.84 (s, 2H), 3.78 (bs, 2H), 2.61 (bs, 4H), 2.55 (s, 3H), 1.65 (bs, 4H), 1.49 (bs, 2H) | LC R$_T$ = 8.3 min; MS: [M + H, $^{35/37}$Cl]⁺ = 526/528 m/z |
| 153 | | 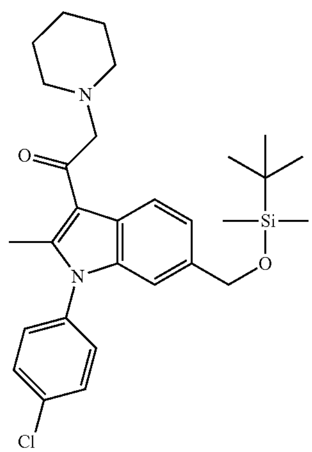 | ¹H NMR (400 MHz, CDCl₃) δ 7.93 (d, 1H), 7.54 (d, 2H), 7.25-7.23 (m, 2H partially obscured by solvent), 7.20 (d, 1H), 6.98 (s, 1H). 4.76 (S, 2H), 3.88 (s, 2H), 2.69-2.72 (m, 4H), 2.58 (s, 3H), 1.71-1.68 (m, 4H), 1.47-1.49 (m, 2H), 0.86 (s, 9H), 0.02 (s, 6H). | LC R$_T$ = 5.4 min; MS: [M + H, $^{35/37}$Cl]⁺ = 511/513 m/z |
| 155 | 1 | 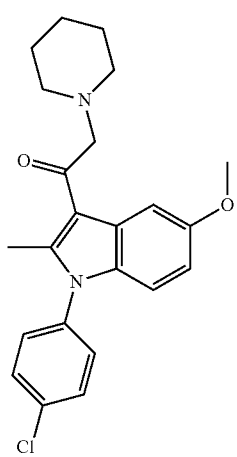 | ¹H NMR (400 MHz, CDCl₃): δ 7.63 (s, 1H), 7.55 (d, 2H), 7.26 (d, 2H), 6.84 (dd, 2H), 3.90 (s, 3H), 3.77 (s, 2H), 2.64-2.72 (m, 4H), 2.58 (s, 3H), 1.60-1.77 (m, 4H), 1.40-1.58 (m, 2H). | LC R$_T$ = 11.2 min; MS: [M + H, $^{35/37}$Cl]⁺ = 397/399 m/z |

TABLE 2-continued

| Compound No. | General Synthetic Route Number | Structure | ¹H NMR | LC-MS |
|---|---|---|---|---|
| 156 | 1 | 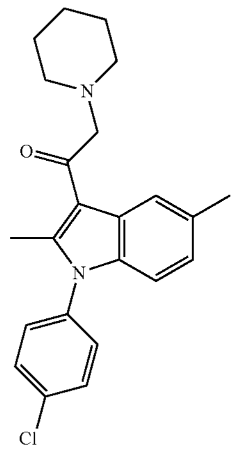 | ¹H NMR (400 MHz, CDCl₃): δ 7.79 (s, 1H), 7.56 (d, 2H), 7.25 (d, 2H), 7.01 (d, 1H), 6.88 (d, 1H), 3.96 (brs, 2H), 2.89 (br s, 4H), 2.58 (s, 3H), 2.49 (s, 3H), 1.71-1.88 (m, 4H), 1.47-1.70 (m, 2H). | LC R$_T$ = 11.4 min; MS: [M + H, $^{35/37}$Cl]⁺ = 381/383 m/z |
| 160 | 1 | 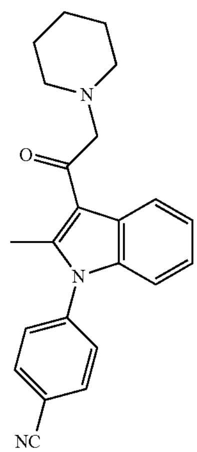 [SMILES: Cc1c(C(=O)CN2CCCCC2)c2ccccc2n1-c1ccc(C#N)cc1] | ¹H NMR (400 MHz, CDCl₃): δ 8.03 (d, 1H), 7.90 (d, 2H), 7.48 (d, 2H), 7.30 (t, 1H), 7.19 (t, 1H), 6.99 (d, 1H), 3.79 (s, 2H), 2.57-2.65 (bs, 7H), 1.62-1.70 (m, 4H), 1.42-1.50 (bm, 2H) | LC R$_T$ = 12.4 min; MS: [M + H]⁺ = 358 m/z |
| 161 | 2 | 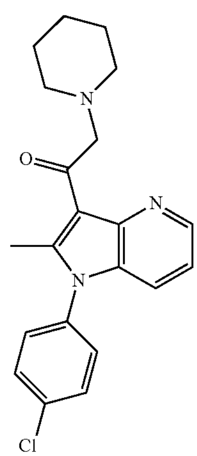 [SMILES: Cc1c(C(=O)CN2CCCCC2)c2ncccc2n1-c1ccc(Cl)cc1] | ¹H NMR (400 MHz, CDCl₃): δ 8.56 (dd, 1H), 7.56 (d, 2H), 7.24-7.30 (m, 3H, partially obscured by solvent), 7.08 (dd, 1H), 4.34 (s, 2H), 2.66-2.68 (m, 4H), 2.64 (s, 3H), 1.66-1.72 (m, 4H), 1.46-1.50 (m, 2H). | LC R$_T$ = 6.2 min; MS: [M + H, $^{35/37}$Cl]⁺ = 368/370 m/z |

TABLE 2-continued
| Compound No. | General Synthetic Route Number | Structure | ¹H NMR | LC-MS |
|---|---|---|---|---|
| 162 | 2 | 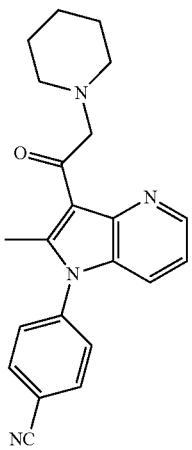 | ¹H NMR (400 MHz, CDCl₃): δ 8.59 (dd, 1H), 7.90 (d, 2H), 7.47 (d, 2H), 7.31 (dd, 1H), 7.11 (dd, 1H), 4.33 (s, 2H), 2.64-2.68 (bm, 7H), 1.64-1.72 (m, 4H), 1.42-1.50 (bm, 2H) | LC R$_T$ = 6.9 min; MS: [M + H]⁺ = 359 m/z |
| 163 | 1 | 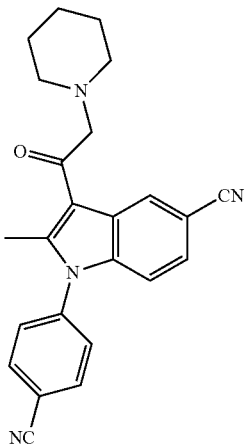 [SMILES: Cc1c(C(=O)CN2CCCCC2)c2cc(C#N)ccc2n1-c1ccc(C#N)cc1] | ¹H NMR (400 MHz, CDCl₃): δ 8.51 (s, 1H), 7.93 (d, 2H), 7.48 (d, 2H), 7.43 (dd, 1H), 7.03 (d, 1H), 3.67 (s, 2H), 2.61 (s, 3H), 2.55-2.59 (m, 3H), 1.65-1.60 (m, 4H), 1.45-1.49 (m, 2H) | LC R$_T$ = 7.6 min; MS: [M + H]⁺ = 383 m/z |
| 164 | 1 | 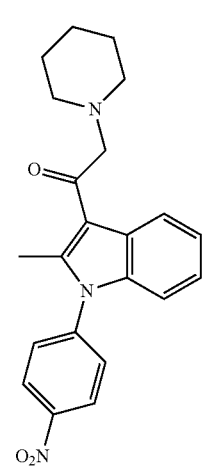 [SMILES: Cc1c(C(=O)CN2CCCCC2)c2ccccc2n1-c1ccc([N+](=O)[O-])cc1] | ¹H NMR (400 MHz, CDCl₃): δ 8.48 (d, 2H), 8.03 (d, 1H), 7.56 (d, 2H), 7.33 (t, 1H), 7.22 (t, 1H), 7.04 (d, 1H), 3.93 (brs, 2H), 2.70-2.88 (m, 4H), 2.64 (s, 3H), 1.75 (brs, 4H), 1.53 (brs, 2H). | LC R$_T$ = 10.2 min; MS: [M + H]⁺ = 378 m/z |

TABLE 2-continued

| Compound No. | General Synthetic Route Number | Structure | ¹H NMR | LC-MS |
|---|---|---|---|---|
| 165 | 2 | 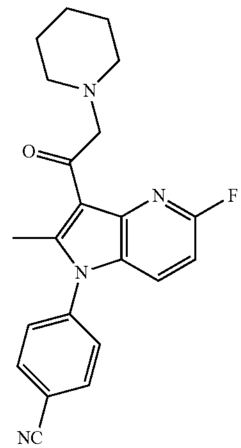 [SMILES: Cc1c(C(=O)CN2CCCCC2)c2nc(F)ccc2n1-c1ccc(C#N)cc1] | ¹H NMR (400 MHz, CDCl₃): δ 7.92 (d, 2H), 7.48 (d, 2H), 7.38 (m, 1H), 6.74 (m, 1H), 4.22 (s, 2H), 2.66-2.70 (m, 4H), 2.65 (s, 3H), 1.65-1.72 (m, 2H), 1.46-1.52 (m, 2H). | LC R$_T$ = 7.5 min; MS: [M + H]⁺ = 377 m/z |
| 167 | 1 | 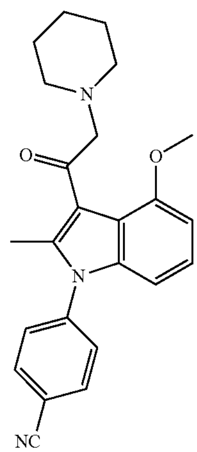 | ¹H NMR (400 MHz, CDCl₃): δ 7.86 (d, 2H), 7.47 (d, 2H), 7.10 (t, 1H), 6.66 (m, 1H), 3.94 (s, 3H), 3.88 (s, 2H), 2.53-2.57 (m, 4H), 2.32 (s, 3H), 1.60-1.66 (m, 4H), 1.43-1.47 (m, 2H) | LC R$_T$ = 8.1 min; MS: [M + H]⁺ = 388 m/z |
| 168 | 1 | 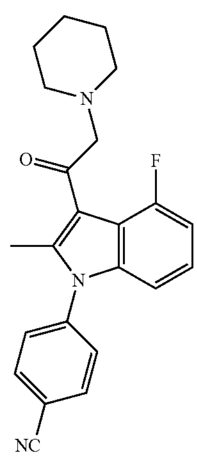 [SMILES: Cc1c(C(=O)CN2CCCCC2)c2c(F)cccc2n1-c1ccc(C#N)cc1] | ¹H NMR (400 MHz, CDCl₃): δ 7.89 (d, 2H), 7.47 (d, 2H), 7.10 (m, 1H), 6.94 (m, 1H), 6.79 (d, 2H), 3.85 (s, 2H), 2.54-2.58 (m, 4H), 2.44 (s, 3H), 1.58-1.63 (m, 2H), 1.42-1.45 (m, 2H) | LC R$_T$ = 11.0 min; MS: [M + H]⁺ = 376 m/z |

TABLE 2-continued
| Compound No. | General Synthetic Route Number | Structure | ¹H NMR | LC-MS |
|---|---|---|---|---|
| 169 | 1 | 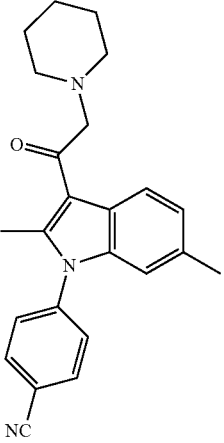 | ¹H NMR (400 MHz, CDCl$_3$): δ 7.95-7.87 (m, 3H), 7.46 (d, 2H), 7.12 (d, 1H), 6.77 (s, 1H), 3.78 (s, 2H), 2.60-2.57 (bm, 7H), 2.38 (s, 3H), 1.68-1.62 (m, 4H), 1.50-1.46 (bm, 2H) | LC R$_T$ = 10.9 min; MS: [M + H]$^+$ = 372 m/z |
| 170 | 1 | 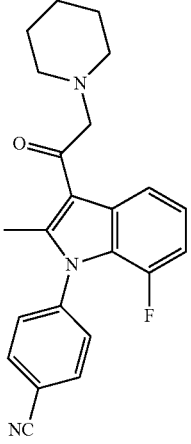 [SMILES: Cc1c(C(=O)CN2CCCCC2)c2cccc(F)c2n1-c1ccc(C#N)cc1] | ¹H NMR (400 MHz, CDCl$_3$): δ 7.82-7.85 (m, 3H), 7.48 (d, 2H), 7.19 (m, 1H), 6.88 (m, 1H), 3.75 (s, 2H), 2.59 (br s, 4H), 2.52 (s, 3H), 1.61-1.67 (m, 4H), 1.46-1.48 (m, 2H) | LC R$_T$ = 10.4 min; MS: [M + H]$^+$ = 376 m/z |
| 171 | 1 | 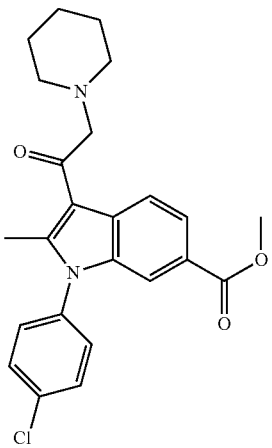 | ¹H NMR (400 MHz, CDCl$_3$): δ 8.06 (d, 1H), 7.96 (dd, 1H), 7.67 (m, 1H), 7.58 (d, 2H), 7.25-7.28 (m, 2H partially obscured by solvent), 3.87 (s, 3H), 3.77 (s, 2H), 2.57-2.63 (m, 7H), 1.61-68 (m, 4 H), 1.42-1.49 (m, 2H) | LC R$_T$ = 12.4 min; [M + H, $^{35/37}$Cl]$^+$ = 425/427 m/z |

TABLE 2-continued

| Compound No. | General Synthetic Route Number | Structure | ¹H NMR | LC-MS |
|---|---|---|---|---|
| 172 | | 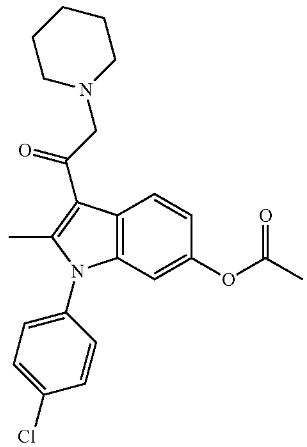 [SMILES: CC(=O)Oc1ccc2c(C(=O)CN3CCCCC3)c(C)n(-c3ccc(Cl)cc3)c2c1] | ¹H NMR (400 MHz, CDCl$_3$): δ 8.02 (d, 1H), 7.54 (d, 2H), 7.25 (d, 2H), 7.00 (d, 1H), 6.71 (s, 1H), 3.74 (s, 2H), 2.52-2.64 (bm, 7H), 2.25 (s, 3H), 1.58-1.68 (bm, 4H), 1.46 (bs, 2H) | LC R$_T$ = 14.4 min; [M + H, $^{35/37}$Cl]$^+$ = 425/427 m/z |
| 173 | 1 | 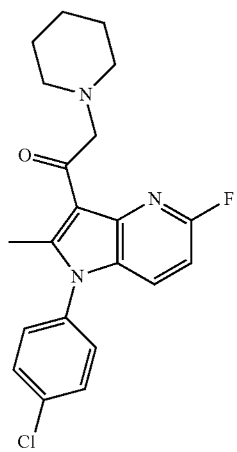 [SMILES: Cc1c(C(=O)CN2CCCCC2)c2nc(F)ccc2n1-c1ccc(Cl)cc1] | ¹H NMR (400 MHz, DMSO-d$_6$): δ 7.73 (d, 2H), 7.58-7.65 (m, 3H), 6.94 (d, 1H), 4.02 (s, 2H), 2.52-2.58 (m, 7H), 1.49-1.52 (m, 4H), 1.38-1.43 (m, 2H) | LC R$_T$ = 8.2 min; MS: [M + H, $^{35/37}$Cl]$^+$ = 386/388 m/z |
| 175 | 1 | 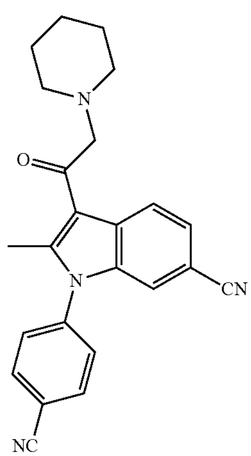 [SMILES: Cc1c(C(=O)CN2CCCCC2)c2ccc(C#N)cc2n1-c1ccc(C#N)cc1] | ¹H NMR (400 MHz, CDCl$_3$): δ 8.19 (d, 1H), 7.90-7.98 (m, 3H), 7.53 (m, 1H), 7.45-7.51 (m, 2H), 7.29 (s, 1H), 3.70 (s, 2H), 2.64 (s, 3H), 2.56-2.65 (m, 4H), 1.60-1.65 (m, 4H), 1.46-1.48 (m, 2H) | LC R$_T$ = 10.7 min; MS: [M + H]$^+$ = 383 m/z |

TABLE 2-continued

| Compound No. | General Synthetic Route Number | Structure | ¹H NMR | LC-MS |
|---|---|---|---|---|
| 176 | 1 | 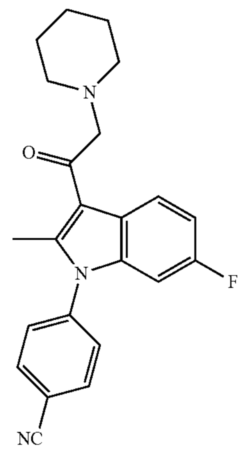 [SMILES: Cc1c(C(=O)CN2CCCCC2)c2ccc(F)cc2n1-c1ccc(C#N)cc1] | ¹H NMR (400 MHz, CDCl₃): δ 7.80 (dd, 1H), 7.91 (d, 2H), 7.47 (d, 2H), 7.05 (td, 1H), 6.68 (dd, 1H), 3.81 (s, 2H), 2.67-2.71 (m, 4H), 2.58 (s, 3H), 1.65-1.71 (m, 4H), 1.48-1.52 (m, 2H) | LC $R_T$ = 10.4 min; MS: [M + H]⁺ = 376 m/z |
| 177 | 1 | 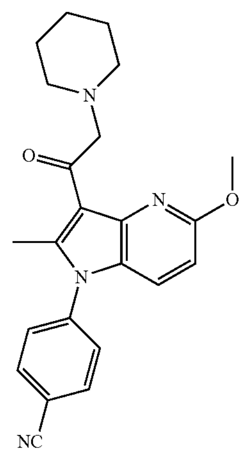 | ¹H NMR (400 MHz, CDCl₃) δ: 7.89 (d, 2H), 7.45 (d, 2H), 7.25 (d, 1H), 6.59 (d, 1H), 4.44 (bs, 2H), 4.04 (s, 3H), 2.79 (bs, 2H), 2.63 (s, 3H), 1.77 (bs, 4H), 1.60 (bs, 4H) | LC $R_T$ = 7.7 min; MS: [M + H]⁺ = 389 m/z |
| 178 | 1 | 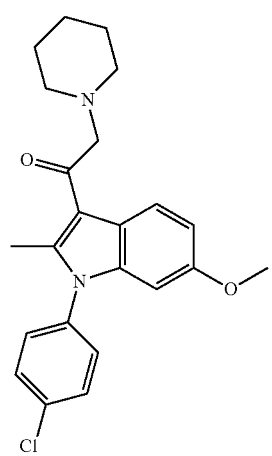 | ¹H NMR (400 MHz, CDCl₃): δ 7.91 (d, 1H), 7.55 (d, 2H), 7.25-7.27 (m, 2H, partially obscured by solvent), 6.92 (dd, 1H), 6.44 (m, 1H), 3.75 (br s, 2H), 3.74 (s, 3H), 2.59 (br s, 4H), 2.54 (s, 3H), 1.61-1.68 (m, 4H), 1.45-1.47 (m, 2H) | LC $R_T$ = 8.3 min; MS: [M + H, ³⁵/³⁷Cl]⁺ = 397/399 m/z |

TABLE 2-continued

| Compound No. | General Synthetic Route Number | Structure | ¹H NMR | LC-MS |
|---|---|---|---|---|
| 179 | | 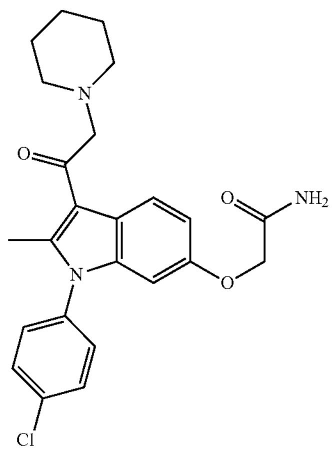 | ¹H NMR (400 MHz, CDCl₃): δ 7.99 (d, 1H), 7.57 (d, 2H), 7.24 (d, 2H), 6.93 (dd, 1H), 6.54 (bs, 1H), 6.47 (d, 1H), 5.53 (bs, 1H), 4.43 (s, 2H), 3.72 (s, 2H), 2.57-2.65 (bm, 4H), 2.55 (s, 3H), 1.60-1.68 (m, 4H), 1.42-1.50 (bm, 2H) | LC R$_T$ = 9.9 min; MS: [M + H, $^{35/37}$Cl]$^+$ = 440/442 m/z |
| 180 | 1 | 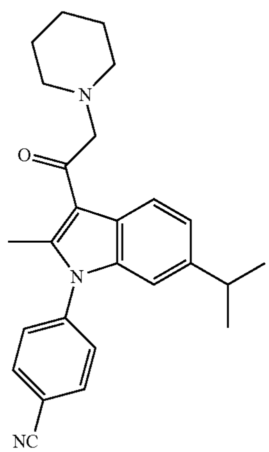 [SMILES: Cc1c(C(=O)CN2CCCCC2)c2ccc(C(C)C)cc2n1-c1ccc(C#N)cc1] | ¹H NMR (400 MHz, CDCl₃): δ 7.89-7.95 (m, 3H), 7.46 (d, 2H), 7.20 (d, 1H), 6.80 (s, 1H), 3.78 (s, 2H), 2.87-2.94 (bm, 1H), 2.57-2.65 (bm, 7H), 1.63-1.67 (bm, 4H), 1.47 (bs, 2H), 1.21 (d, 6H) | LC R$_T$ = 9.1 min; MS [M + H]$^+$ = 400 m/z |
| 181 | 2 | 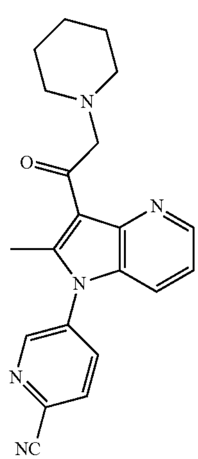 [SMILES: Cc1c(C(=O)CN2CCCCC2)c2ncccc2n1-c1ccc(C#N)nc1] | ¹H NMR (400 MHz, CDCl₃): δ 8.77 (m, 1H), 8.62 (m, 1H), 7.97 (d, 1H), 7.87 (dd, 1H), 7.33 (m, 1H), 7.16 (dd, 1H), 4.33 (s, 2H), 2.64-2.70 (m, 7H), 1.65-1.72 (m, 4H), 1.47-1.51 (m, 2H) | LC R$_T$ = 5.9 min; MS: [M + H]$^+$ = 360 m/z |

TABLE 2-continued
| Compound No. | General Synthetic Route Number | Structure | ¹H NMR | LC-MS |
|---|---|---|---|---|
| 182 | | 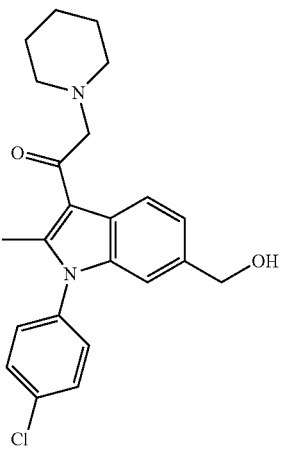 [SMILES: Cc1c(C(=O)CN2CCCCC2)c2ccc(CO)cc2n1-c1ccc(Cl)cc1] | ¹H NMR (400 MHz, CDCl₃): δ 7.99 (d, 1H), 7.56 (d, 2H), 2.24-7.27 (m, 3H partially obscured by solvent), 4.71 (s, 2H), 3.77 (s, 2H), 2.56-2.63 (m, 7H), 1.62-1.68 (m, 4H), 1.45-1.49 (m, 2H) | LC R$_T$ = 7.3 min; MS: [M + H, $^{35/37}$Cl]⁺ = 397/399 m/z |
| 183 | | 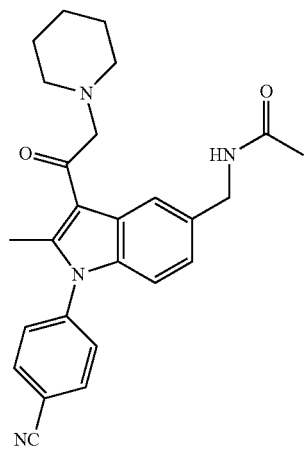 [SMILES: CC(=O)NCc1ccc2c(c1)c(C(=O)CN1CCCCC1)c(C)n2-c1ccc(C#N)cc1] | ¹H NMR (400 MHz, DMSO-d₆): δ 8.36 (t, 1H), 8.15 (d, 2H), 8.00 (s, 1H), 7.72 (d, 2H), 7.08 (d, 1H), 6.96 (d, 1H), 4.34 (d, 2H), 3.60 (s, 2H), 2.55 (s, 3H), 2.46 (s, 3H), 1.85 (s, 3H), 1.49-1.08 (m, 4H), 1.39 (brs, 2H) | LC R$_T$ = 6.9 min; MS: [M + H]⁺ = 429 m/z |
| 184 | 2 | 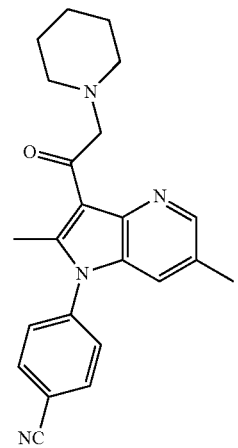 | ¹H NMR (400 MHz, CDCl₃): δ 8.42 (s, 1H), 7.90 (d, 2H), 7.46 (d, 2H), 7.09 (s, 1H), 4.35 (s, 2H), 2.69 (bs, 2H), 2.64 (s, 3H), 2.39 (s, 3H), 1.70 (bs, 4H), 1.61 (brs, 4H) | LC R$_T$ = 7.2 min; MS: [M + H]⁺ = 373 m/z |

TABLE 2-continued

| Compound No. | General Synthetic Route Number | Structure | ¹H NMR | LC-MS |
|---|---|---|---|---|
| 185 | | 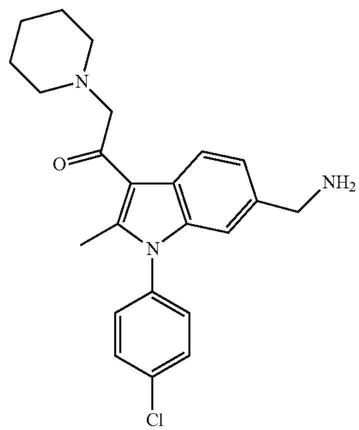 [SMILES: Cc1c(C(=O)CN2CCCCC2)c2ccc(CN)cc2n1-c1ccc(Cl)cc1] | ¹H NMR (400 MHz, CDCl₃): δ 7.96 (d, 1H), 7.55 (d, 2H), 7.26 (m, 2H, occluded by solvent), 7.21 (s, 1H), 6.93 (s, 1H), 3.89 (s, 2H), 3.79 (s, 2H), 2.62 (bs, 4H), 2.57 (s, 3H), 1.66-1.59 (m, 6H) | LC R$_T$ = 8.3 min; MS: [M + H, $^{35/37}$Cl]$^+$ = 396/398 m/z |
| 186 | | 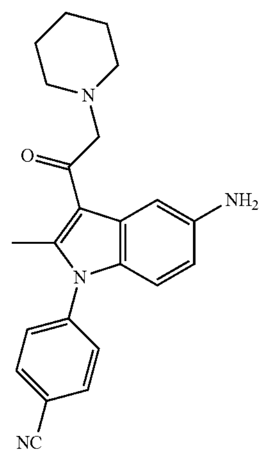 | ¹H NMR (400 MHz, CDCl₃): δ 7.87 (d, 2H), 7.46 (d, 2H), 7.38 (m, 1H), 6.80 (d, 1H), 6.60 (dd, 1H), 3.71 (s, 2H), 3.68 (br s, 2H), 2.56-2.62 (m 7H), 1.62-1.68 (m, 4H), 1.45-1.50 (m, 2H) | LC R$_T$ = 5.8 min; MS: [M + H]$^+$ = 373 m/z |
| 187 | | 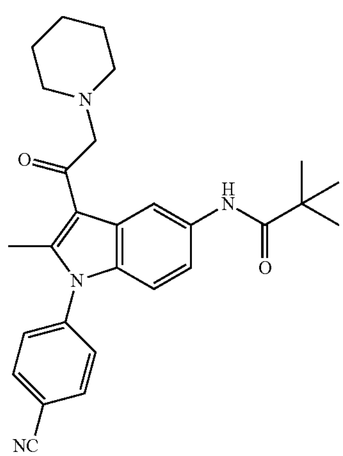 [SMILES: Cc1c(C(=O)CN2CCCCC2)c2cc(NC(=O)C(C)(C)C)ccc2n1-c1ccc(C#N)cc1] | ¹H NMR (400 MHz, CDCl₃): δ 8.11 (m, 1H), 7.90 (d, 2H), 7.57 (dd, 1H), 7.45-7.51 (m, 3H), 6.93 (d, 1H), 3.76 (s, 2H), 2.65 (br s, 4H), 2.60 (s, 3H), 1.61-1.66 (m, 4H), 1.47-1.50 (m, 2H), 1.34 (s, 9H) | LC R$_T$ = 6.4 min; MS: [M + H]$^+$ = 457 m/z |

TABLE 2-continued

| Compound No. | General Synthetic Route Number | Structure | ¹H NMR | LC-MS |
|---|---|---|---|---|
| 188 | | 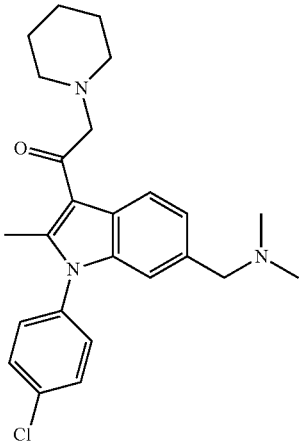 | ¹H NMR (400 MHz, DMSO-$d_6$): δ 8.03 (d, 1H), 7.74 (d, 2H), 7.53 (d, 2H), 7.20 (d, 1H), 6.92 (bs, 1H), 3.79-3.41 (m, 4H), 2.54 (s, 3H), 2.16 (bs, 6H), 1.54 (bs, 4H), 1.42 (bs 2H) | LC $R_T$ = 6.6 min; MS: [M + H, $^{35/37}$Cl]$^+$ = 424/426 m/z |
| 189 | 2 | 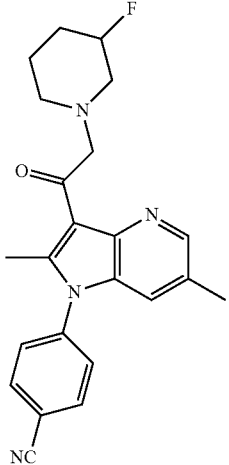 | ¹H NMR (400 MHz, CDCl$_3$): δ 8.42 (s, 1H), 7.91 (d, 2H), 7.47 (d, 2H), 7.10 (s, 1H), 4.66-4.82 (m, 1H), 4.40 (s, 2H), 3.20 (m, 1H), 2.90 (m, 1H), 2.59-2.64 (m, 4H), 2.45 (m, 1H), 2.39 (s, 3H), 1.98 (m, 1H), 1.86 (m, 1H), 1.59-1.69 (m, 2H partially obscured by solvent). | LC $R_T$ = 7.1 min; MS: [M + H]$^+$ = 391 m/z |
| 190 | 2 | 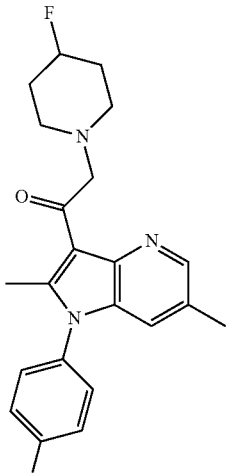 | ¹H NMR (400 MHz, DMSO-$d_6$): δ 8.41 (s, 1H), 8.15 (d, 2H), 7.79 (d, 2H), 7.33 (s, 1H), 4.62-4.76 (m, 1H), 4.25 (s, 2H), 2.74-2.78 (m, 2H), 2.55-2.57 (m, 4H), 2.36 (s, 3H), 1.84-1.91 (m, 2H), 1.70-1.74 (m, 2H) plus 1H obscured by solvent. | LC $R_T$ = 7.1 min; MS: [M + H]$^+$ = 391 m/z |

TABLE 2-continued

| Compound No. | General Synthetic Route Number | Structure | ¹H NMR | LC-MS |
|---|---|---|---|---|
| 191 | | 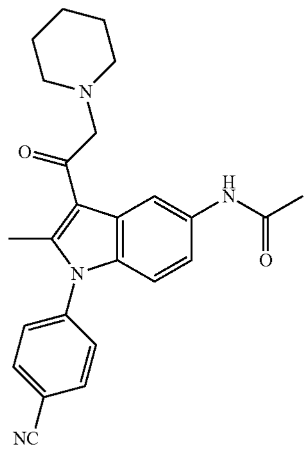 [SMILES: CC(=O)Nc1ccc2c(c1)c(C(=O)CN1CCCCC1)c(C)n2-c1ccc(C#N)cc1] | ¹H NMR (400 MHz, CDCl$_3$) δ 8.17 (brs, 1H), 7.89 (d, 2H), 7.48 (d, 2H), 7.40 (dd, 1H), 7.28 (brs, 1H), 6.94 (d, 1H), 3.75 (s, 2H), 2.57 (brs, 7H), 2.21 (s, 3H), 166-1.63 (m, 4H), 1.47 (brs, 2H) | LC R$_T$ = 5.9 min; MS: [M + H]$^+$ = 415 m/z |
| 192 | 3 | 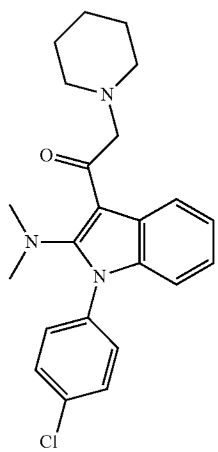 [SMILES: CN(C)c1c(C(=O)CN2CCCCC2)c2ccccc2n1-c1ccc(Cl)cc1] | ¹H NMR (400 MHz, DMSO-d$_6$) δ 7.93-7.91 (d, 1H), 7.70-7.68 (d, 2H), 7.54-7.52 (d, 1H), 7.19-7.15 (t, 1H), 7.10-7.06 (t, 1H), 6.91-6.89 (d, 1H), 3.59 (s, 2H), 2.68 (s, 2H), 2.47 (m, 4H), 1.50-1.48 (m, 4H), 1.38 (m, 2H) | LC R$_T$ = 7.4 min; MS [M + H, $^{35/37}$Cl]$^+$ 396/398 m/z |
| 193 | 1 | 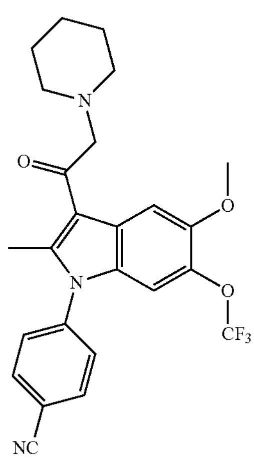 [SMILES: COc1cc2c(C(=O)CN3CCCCC3)c(C)n(-c3ccc(C#N)cc3)c2cc1OC(F)(F)F] | ¹H NMR (400 MHz, DMSO-d$_6$) δ 8.15 (d, 2H), 7.90 (s, 1H), 7.75 (d, 2H), 6.98 (s, 1H), 3.92 (s, 3H), 3.59 (s, 2H), 2.55 (s, 3H), 2.51-2.46 (brm, 4H, occluded by solvent), 1.50 (brs, 4H), 1.39 (brs, 2H) | LC R$_T$ = 10.0 min; MS [M + H]$^+$ 472 m/z |

TABLE 2-continued

| Compound No. | General Synthetic Route Number | Structure | ¹H NMR | LC-MS |
|---|---|---|---|---|
| 194 | | 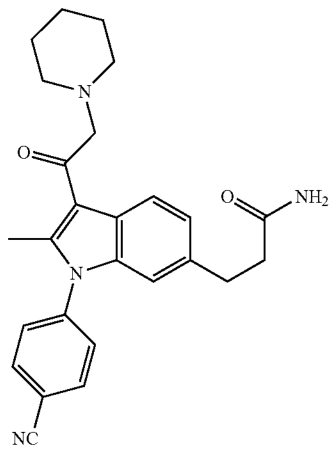 | ¹H NMR (400 MHz, DMSO-d₆): δ 8.15 (d, 2H), 7.97 (d, 1H), 7.73 (d, 2H), 7.23 (s, 1H), 7.12 (d, 1H), 6.85 (s, 1H), 6.74 (s, 1H), 3.61 (s, 2H), 2.81 (t, 2H), 2.53 (s, 3H), 2.49-2.41 (m, 4H, occluded by solvent), 2.29 (t, 2H), 1.52-1.48 (m, 4H), 1.41-1.38 (m, 2H) | LC R$_T$ = 5.5 min; MS: [M + H]⁺ = 429 m/z |
| 195 | 2 | 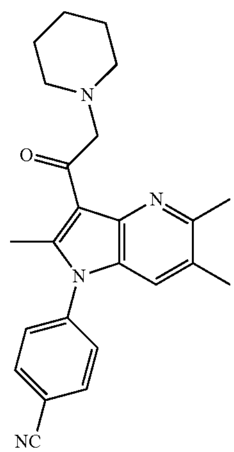 | ¹H NMR (400 MHz, DMSO-d₆): δ 7.89 (d, 2H), 7.45 (d, 2H), 7.03 (s, 1H), 4.36 (s, 2H), 2.70 (brs, 4H), 2.63 (s, 3H), 2.61 (s, 3H), 2.30 (s, 3H), 1.71-1.60 (m, 4H), 1.48 (brs, 2H) | LC R$_T$ = 7.3 min; MS: [M + H]⁺ = 387 m/z |
| 196 | | 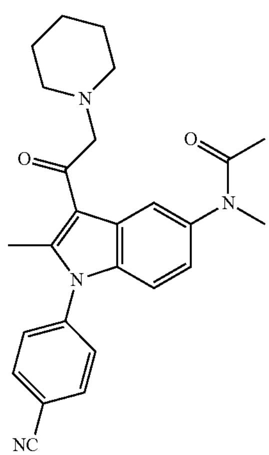 [SMILES: CC(=O)N(C)c1ccc2c(c1)c(C(=O)CN1CCCCC1)c(C)n2-c1ccc(C#N)cc1] | ¹H NMR (400 MHz, CDCl₃): δ 7.97 (s, 1H), 7.92 (d, 2H), 7.50 (d, 2H), 6.98 (d, 2H), 3.67 (s, 2H), 3.29 (s, 3H), 2.69 (s, 3H), 2.58 (brs, 4H), 1.88 (s, 3H), 1.67-1.56 (m, 4H), 1.24 (brs, 2H) | LC R$_T$ = 10.2 min; MS: [M + H]⁺ = 429 m/z |

TABLE 2-continued
| Compound No. | General Synthetic Route Number | Structure | ¹H NMR | LC-MS |
|---|---|---|---|---|
| 197 | 1 | 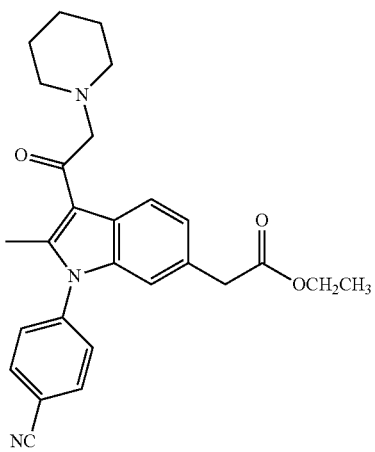 [SMILES: CCOC(=O)Cc1ccc2c(C(=O)CN3CCCCC3)c(C)n(-c3ccc(C#N)cc3)c2c1] | ¹H NMR (400 MHz, CDCl₃): δ 7.97 (d, 1H), 7.90 (d, 2H), 7.47 (d, 2H), 7.22 (d, 1H), 6.91 (s, 1H), 4.10 (q, 2H), 3.78 (s, 2H), 3.62 (s, 2H), 2.60 (brs, 4H), 2.58 (s, 3H), 1.69-1.45 (m, 6H), 1.21 (t, 3H) | LC R$_T$ = 7.8 min; MS: [M + H]⁺ = 444 m/z |
| 198 | | 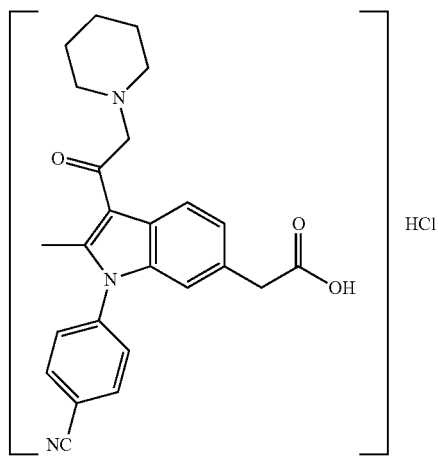 | ¹H NMR (400 MHz, DMSO-d₆): δ 12.27 (brs, 1H), 9.66 (brs, 1H), 8.21 (d, 2H), 8.03 (d, 1H), 7.75 (d, 2H), 7.25 (d, 1H), 6.98 (s, 1H), 4.87 (s, 2H), 3.62 (s, 2H), 3.53 (brd, 2H), 3.11 (brs, 2), 2.58 (s, 3H), 1.85 (brs, 4H), 1.74 (brd, 1H), 1.41 (brs, 2H) | LC R$_T$ = 5.9 min; MS: [M + H]⁺ = 416 m/z |
| 199 | | 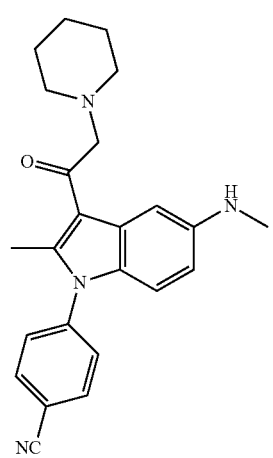 | ¹H NMR (400 MHz, CDCl₃): δ 7.86 (d, 2H), 7.46 (d, 2H), 7.28 (brs, 1H), 6.82 (d, 1H), 6.55 (dd, 1H), 3.73 (brs, 2H), 2.92 (s, 3H), 2.62 (brs, 4H), 2.58 (s, 3H), 1.66-1.42 (brm, 6H) | LC R$_T$ = 5.5 min; MS: [M + H]⁺ = 387 m/z |

TABLE 2-continued

| Compound No. | General Synthetic Route Number | Structure | ¹H NMR | LC-MS |
|---|---|---|---|---|
| 200 | 2 | 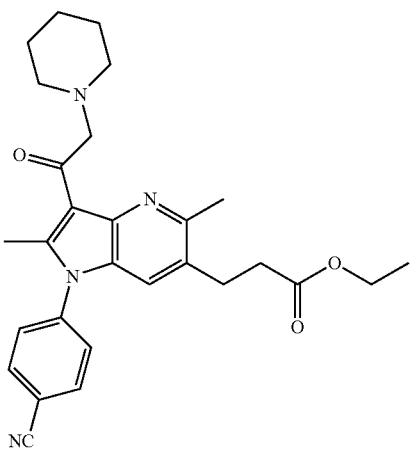 [SMILES: CCOC(=O)CCc1cc2c(nc1C)c(C(=O)CN1CCCCC1)c(C)n2-c1ccc(C#N)cc1] | ¹H NMR (400 MHz, CDCl₃): δ 7.90 (d, 2H), 7.44 (d, 2H), 7.07 (s, 1H), 4.36 (s, 2H), 4.08 (q, 2H), 2.98 (t, 2H), 2.79 (brs, 4H), 2.67 (3H), 2.63 (s, 3H), 2.55 (t, 2H), 1.68 (brs, 4H), 1.49 (brs, 2H), 1.20 (t, 3H) | LC R$_T$ = 13.1 min; MS: [M + H]⁺ = 473 m/z |
| 201 | | 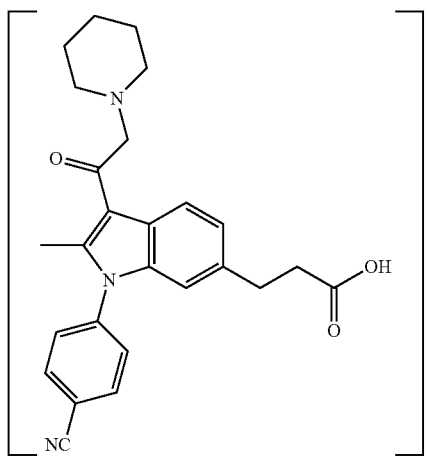 | ¹H NMR (400 MHz, DMSO-d₆): δ 12.09 (brs, 1H), 9.67 (brs, 1H), 8.18 (d, 2H), 7.99 (d, 1H), 7.73 (d, 2H), 7.21 (brs, 1H), 6.93 (brs, 1H), 4.87 (brs, 2H), 3.48 (dd, 1H), 3.42 (dd, 1H), 3.02 (brs, 2H), 2.85 (t, 2H), 2.56 (s, 3H), 2.53 (s, 2H, occluded by solvent), 1.95-1.42 (brm, 6H) | LC R$_T$ = 2.3 min; MS: [M + H]⁺ = 430 m/z |
| 202 | | 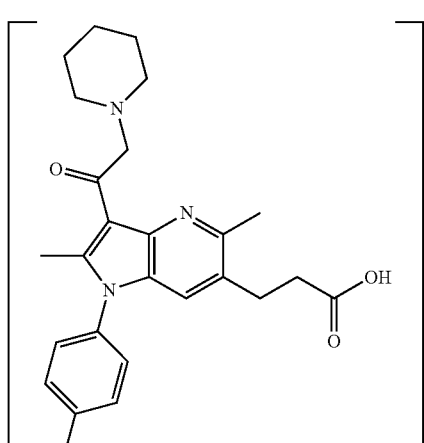 | ¹H NMR (400 MHz, DMSO-d₆): δ 9.83 (brs, 1H), 8.19 (d, 2H), 7.79 (d, 2H), 7.43 (s, 1H), 5.10 (d, 2H), 3.55 (brd, 2H), 3.18 (brd, 2H), 2.91 (t, 2H), 2.68 (s, 3H), 2.65 (s, 3H), 2.53 (t, 2H, occluded by solvent), 1.88 (brs, 4H), 1.84 (brd, 1H), 1.47 (brd, 1H) | LC R$_T$ = 6.4 min; MS: [M + H]⁺ = 445 m/z |

TABLE 2-continued
| Compound No. | General Synthetic Route Number | Structure | ¹H NMR | LC-MS |
|---|---|---|---|---|
| 203 | | 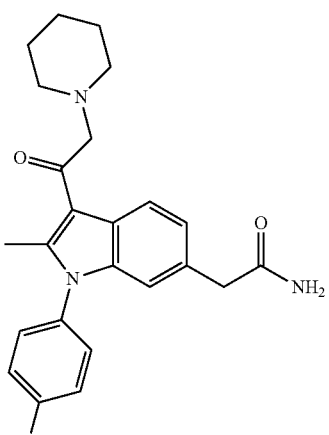 | ¹H NMR (400 MHz, DMSO-d₆): δ 8.17 (d, 2H), 7.99 (d, 1H), 7.73 (d, 2H), 7.36 (brs, 1H), 7.16 (d, 1H), 6.92 (s, 1H), 6.80 (s, 1H), 3.63 (s, 2H), 3.37 (s, 2H), 2.54 (2, 3H), 2.46 (brs, 4H, occluded by solvent), 1.50 (brs, 4H), 1.40 (brs, 2H) | LC $R_T$ = 6.5 min; MS: $[M + H]^+$ = 415 m/z |
| 204 | | 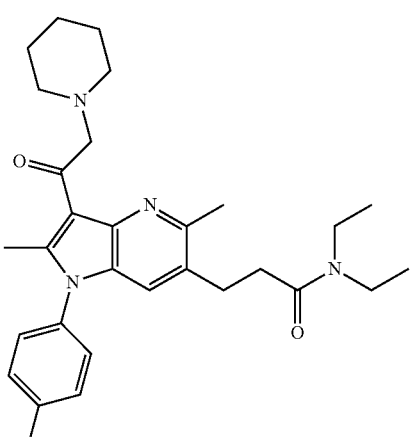 | ¹H NMR (400 MHz, DMSO-δ 8.14 (d, 2H), 7.75 (d, 2H), 7.23 (s, 1H), 4.20 (brs, 2H), 3.23-3.16 (m, 4H), 2.88 (t, 2H), 2.62 (brs, 4H), 2.56 (s, 3H), 2.54 (d, 2H), 1.54 (brs, 4H), 1.42 (brs, 2H), 0.97 (t, 3H), 0.88 (t, 3H) | LC $R_T$ = 11.4 min; MS: $[M + H]^+$ = 500 m/z |
| 205 | | 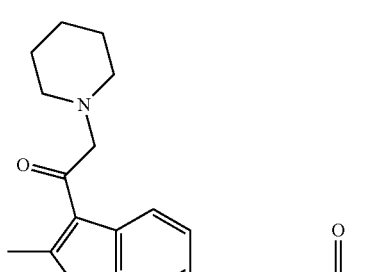 | ¹H NMR (400 MHz, CDCl₃): δ 7.95 (d, 1H), 7.91 (d, 2H), 7.47 (d, 2H), 7.16 (dd, 1H), 6.82 (s, 1H), 4.22 (t, 2H), 3.78 (s, 2H), 2.95 (t, 2H), 2.62 (brs, 4H), 2.59 (s, 3H), 1.99 (s, 3H), 1.67 (brs, 4H), 1.47 (brs, 2H) | LC $R_T$ = 7.7 min; MS: $[M + H]^+$ = 444 m/z |

TABLE 2-continued

| Compound No. | General Synthetic Route Number | Structure | ¹H NMR | LC-MS |
|---|---|---|---|---|
| 206 | | 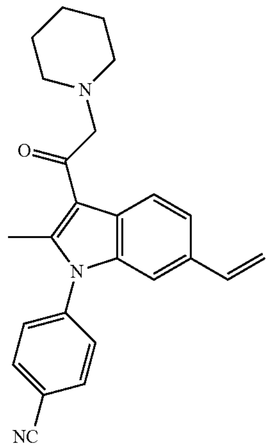 [SMILES: C=Cc1ccc2c(C(=O)CN3CCCCC3)c(C)n(-c3ccc(C#N)cc3)c2c1] | ¹H NMR (400 MHz, CDCl₃): δ 7.97 (d, 1H), 7.91 (d, 2H), 7.48 (d, 2H), 7.41 (dd, 1H), 6.95 (s, 1H), 6.70 (dd, 1H), 5.67 (d, 2H), 5.18 (d, 1H), 3.77 (s, 2H), 2.61 (brs, 4H), 2.59 (s, 3H), 1.69-1.60 (m, 4H), 1.48 (brs, 2H) | LC R$_T$ = 7.8 min; MS: [M + H]⁺ = 384 m/z |
| 207 | | 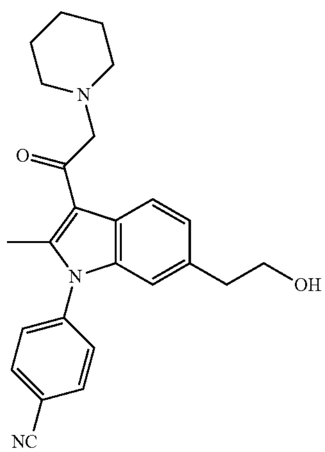 [SMILES: Cc1c(C(=O)CN2CCCCC2)c2ccc(CCO)cc2n1-c1ccc(C#N)cc1] | ¹H NMR (400 MHz, CDCl₃): δ 7.96 (d, 1H), 7.90 (d, 2H), 7.47 (d, 2H), 7.18 (d, 1H), 6.85 (s, 1H), 3.85-3.82 (m, 4H), 2.89 (t, 2H), 2.64 (brs, 4H), 2.59 (s, 3H), 1.69-1.37 (brm, 6H, partially occluded by solvent) | LC R$_T$ = 6.9 min; MS: [M + H]⁺ = 402 m/z |
| 208 | | 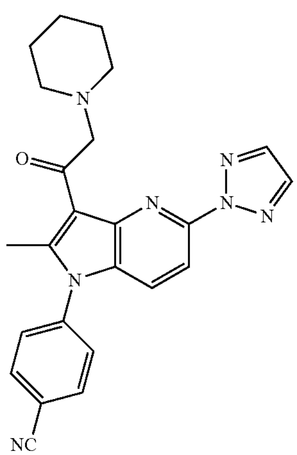 [SMILES: Cc1c(C(=O)CN2CCCCC2)c2nc(-n3nccn3)ccc2n1-c1ccc(C#N)cc1] | ¹H NMR (400 MHz, DMSO-d₆): δ 8.20-8.17 (m, 4H), 7.89-7.86 (m, 3H), 7.76 (d, 1H), 4.20 (s, 2H), 2.63 (brs, 4H), 2.62 (s, 3H), 1.47 (brs, 4H), 1.38 (brs, 2H) | LC R$_T$ = 8.9 min; MS: [M + H]⁺ = 426 m/z |

TABLE 2-continued

| Compound No. | General Synthetic Route Number | Structure | ¹H NMR | LC-MS |
|---|---|---|---|---|
| 209 | | 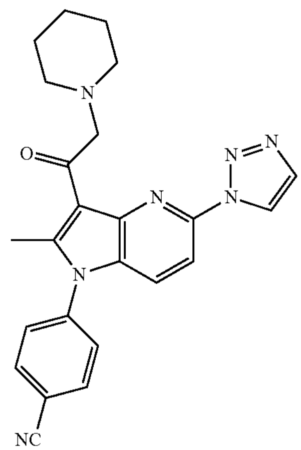 [SMILES: Cc1c(C(=O)CN2CCCCC2)c2nc(-n3ccnn3)ccc2n1-c1ccc(C#N)cc1] | ¹H NMR (400 MHz, DMSO-d$_6$): δ 8.88 (s, 1H), 8.19 (d, 2H), 8.04 (s, 1H), 7.96 (d, 1H), 7.87 (d, 2H), 7.82 (d, 1H), 4.21 (s, 2H), 2.65 (s, 3H), 2.62 (brs, 4H), 1.52 (brs, 4H), 1.41 (brs, 2H) | LC R$_T$ = 8.7 min; MS: [M + H]$^+$ = 426 m/z |
| 210 | | 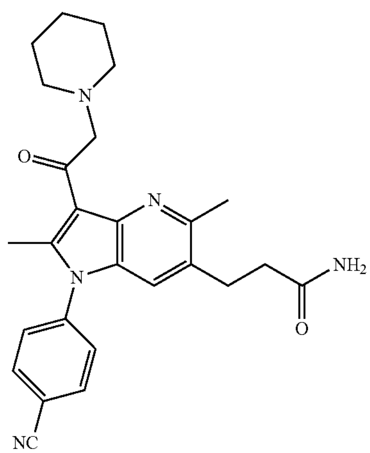 [SMILES: Cc1nc2c(C(=O)CN3CCCCC3)c(C)n(-c3ccc(C#N)cc3)c2cc1CCC(N)=O] | ¹H NMR (400 MHz, DMSO-d$_6$): δ 8.14 (d, 2H), 7.75 (d, 2H), 7.25 (s, 2H), 6.78 (s, 1H), 4.18 (brs, 2H), 2.85 (t, 2H), 2.61-2.51 (m, 10H), 2.30 (t, 2H), 1.51 (brs, 4H), 1.41 (brs, 2H) | LC R$_T$ = 7.2 min; MS: [M + H]$^+$ = 444 m/z |
| 296 | | 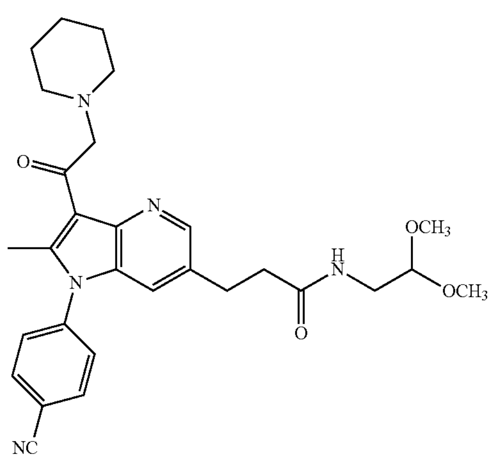 [SMILES: COC(CNC(=O)CCc1cnc2c(C(=O)CN3CCCCC3)c(C)n(-c3ccc(C#N)cc3)c2c1)OC] | ¹H NMR (400 MHz, DMSO): δ 8.45 (d, 1H), 7.92 (d, 2H), 7.44 (d, 2H), 7.15 (d, 1H), 5.53 (s, 1H), 4.30 (s, 2H), 4.26 (t, 1H) 3.39-3.33 (m, 8H), 3.02 (t, 2H), 2.72-2.64 (overlapped s and m, 7H), 2.46 (t, 2H), 1.71-1.65 (m, 4H), 1.48-1.47 (m, 2H) | LC R$_T$ = 10.0 min; MS: [M + H]$^+$ 518 m/z |

TABLE 2-continued

| Compound No. | General Synthetic Route Number | Structure | ¹H NMR | LC-MS |
|---|---|---|---|---|
| 297 | 4 | 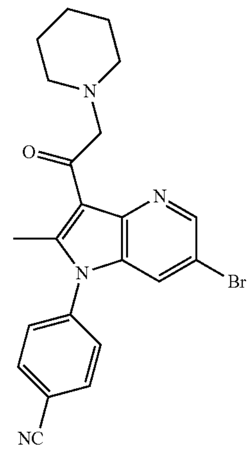 [SMILES: Cc1c(C(=O)CN2CCCCC2)c2ncc(Br)cc2n1-c1ccc(C#N)cc1] | ¹H NMR (400 MHz, CDCl₃) δ 8.61 (d, 1H), 7.93 (d, 2H), 7.46 (d, 2H), 7.44 (d, 1H), 4.26 (s, 2H), 2.72-2.70 (m, 4H), 2.64 (s, 3H), 1.69-1.67 (m, 4H), 1.49-1.48 (m, 2H) | LC R$_T$ = 10.7 min; MS [M + H]⁺ 437 m/z |
| 298 | | 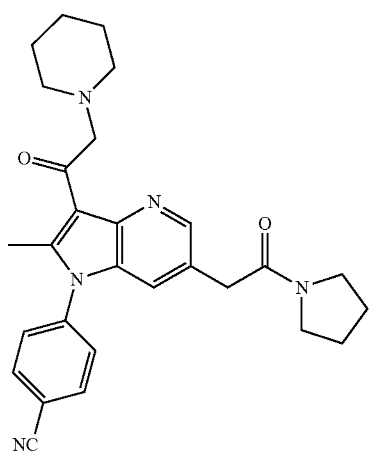 [SMILES: Cc1c(C(=O)CN2CCCCC2)c2ncc(CC(=O)N3CCCC3)cc2n1-c1ccc(C#N)cc1] | ¹H NMR (400 MHz, CDCl₃): δ 8.43 (d, 1H), 7.89 (d, 2H), 7.47 (d, 2H), 7.37 (d, 1H), 4.32 (s, 2H), 3.67 (s, 2H), 3.51-3.48 (m, 2H), 3.47-3.41 (m, 2H), 2.67-2.64 (m, 7H), 1.97-1.93 (m, 2H), 1.98-1.85 (m, 2H), 1.69 (m, 4H), 1.48 (m, 2H), 1.25-1.21 (t, 3H) | LC R$_T$ = 7.5 min; MS: [M + H]⁺ = 468 m/z |
| 299 | | 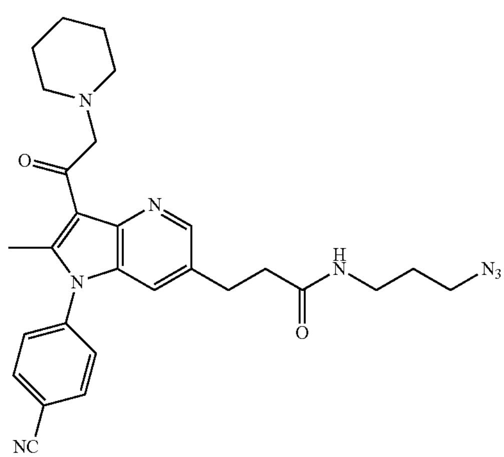 [SMILES: Cc1c(C(=O)CN2CCCCC2)c2ncc(CCC(=O)NCCCN=[N+]=[N-])cc2n1-c1ccc(C#N)cc1] | ¹H NMR (400 MHz, CDCl₃): δ 8.45 (d, 1H), 7.91 (d, 2H), 7.46 (d, 2H), 7.16 (d, 1H), 5.51 (brs, 1H), 4.30 (s, 2H), 3.28-3.23 (m, 4H), 3.02 (t, 2H), 2.66-2.64 (overlapped m and s, 7H), 2.45 (t, 2H), 1.71-1.66 (m, 6H), 1.49-1.47 (m, 2H) | LC R$_T$ = 7.6 min; MS: [M + H]⁺ 513 m/z |

TABLE 2-continued

| Compound No. | General Synthetic Route Number | Structure | ¹H NMR | LC-MS |
|---|---|---|---|---|
| 300 | 2 | 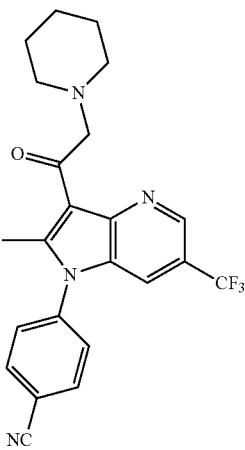 | ¹H NMR (400 MHz, CDCl₃): δ 8.85 (s, 1H), 7.96 (d, J = 8.5 Hz, 2H), 7.50-7.48 (overlapped d and s, 3H), 4.34 (s, 2H), 2.83-2.75 (m, 4H), 2.69 (s, 3H), 1.79-1.64 (m, 4H), 1.54 (m obscured by solvent signal, 2H) | LC R$_T$ = 10.2 min; MS: [M + H]⁺ 427 m/z |
| 301 | | 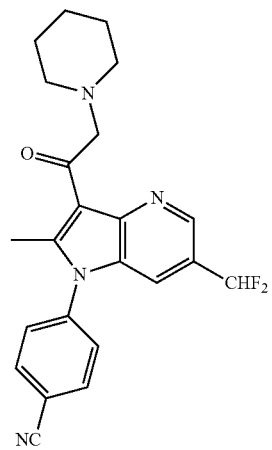 [SMILES: Cc1c(C(=O)CN2CCCCC2)c2ncc(C(F)F)cc2n1-c1ccc(C#N)cc1] | ¹H NMR (400 MHz, CDCl₃): δ 8.68 (s, 1H), 7.95-7.93 (d, 2H), 7.49-7.45 (overlapped d and s, 3H), 6.78 (t, 1H), 4.45 (s, 2H), 2.85 (m, 4H), 2.69 (s, 3H), 1.78 (m, 4H), 1.53 (m, 2H) | LC R$_T$ = 8.4 min; MS: (M + H) = 409 m/z |
| 302 | 2 | 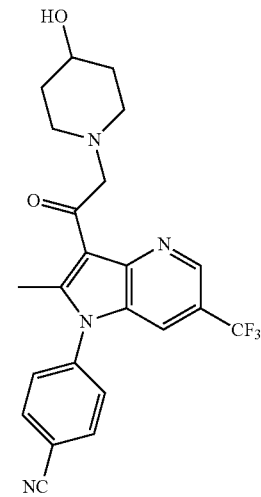 [SMILES: Cc1c(C(=O)CN2CCC(O)CC2)c2ncc(C(F)(F)F)cc2n1-c1ccc(C#N)cc1] | ¹H NMR (400 MHz, CDCl₃): δ 8.92 (s, 1H), 8.18 (d, 2H), 7.86-7.84 (overlapped d and s, 3H), 4.61 (brs obscured by occluded solvent signal, 1H, D2O exchangable), 4.28 (m, 2H), 3.49-3.41 (overlapped m, 2H), 2.94 (m, 2H), 2.62 (s, 3H), 2.35 (m, 2H), 1.75 (m, 2H), 1.46 (m, 2H) | LC R$_T$ = 5.8 min; MS: [M + H]⁺ 443 m/z |

TABLE 2-continued

| Compound No. | General Synthetic Route Number | Structure | ¹H NMR | LC-MS |
|---|---|---|---|---|
| 303 | | 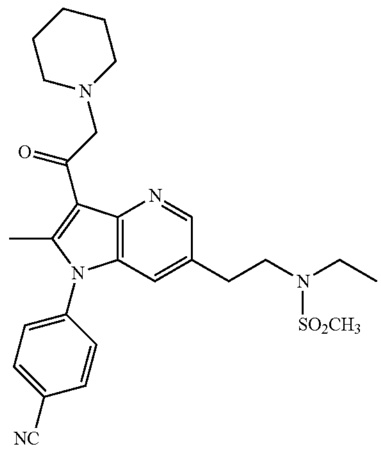 | ¹H NMR (400 MHz, CDCl₃): δ 8.42 (d, 1H), 7.58 (d, 2H), 7.25 (d, 2H), 7.15 (d, 1H), 4.30 (s, 2H), 3.36-3.37 (m, 2H), 3.26 (q, 2H), 2.96 (t, 2H), 2.74 (s, 3H), 2.66 (brs, 4H), 2.63 (s, 3H), 1.70-1.67 (m, 4H), 1.49 (m, 2H), 1.18 (t, 3H) | LC R$_T$ = 8.1 min; MS: [M + H]⁺ = 517 m/z |
| 304 | | 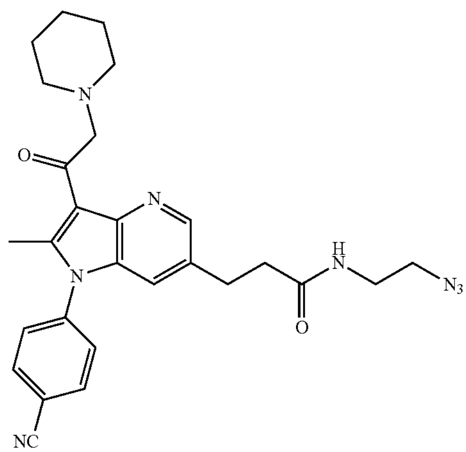 [SMILES: Cc1c(C(=O)CN2CCCCC2)c2ncc(CCC(=O)NCCN=[N+]=[N-])cc2n1-c1ccc(C#N)cc1] | ¹H NMR (400 MHz, CDCl₃): δ 8.46 (d, 1H), 7.92 (d, 2H), 7.46 (d, 2H), 7.15 (d, 1H), 5.63 (brs, 1H), 4.32 (s, 2H), 3.35 (s, 4H), 3.03 (t, 2H), 2.74-2.66 (m, 4H), 2.64 (s, 2H), 2.48 (t, 2H), 1.70-1.66 (m, 4H), 1.49-1.48 (m, 2H) | LC R$_T$ = 8.1 min; MS: [M + H]⁺ = 499 m/z |
| 305 | | 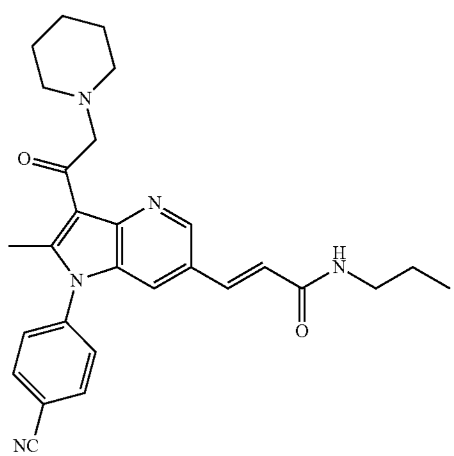 | ¹H NMR (400 MHz, CDCl₃): δ 8.73 (d, 1H), 7.94 (d, 2H), 7.66 (d, 1H), 7.48 (d, 2H), 7.36 (d, 1H), 6.34 (d, 1H), 5.53 (t, 1H), 4.31 (s, 2H), 3.43-3.38 (m, 2H), 2.67(overlapped m and s, 7H), 1.69 (m, 4H), 1.48 (m, 2H), 1.19 (t, 3H) | LC R$_T$ = 8.8 min; MS: [M + H]⁺ = 456 m/z |

TABLE 2-continued

| Compound No. | General Synthetic Route Number | Structure | ¹H NMR | LC-MS |
|---|---|---|---|---|
| 306 | 4 | 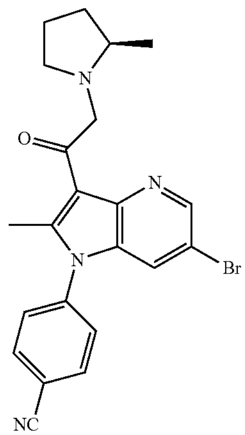 [SMILES: Cc1c(C(=O)CN2CCC[C@H]2C)c2ncc(Br)cc2n1-c1ccc(C#N)cc1] | ¹H NMR (400 MHz, DMSO-$d_6$): δ 8.65 (d, 1H), 8.15 (d, 2H), 7.82 (d, 2H), 7.77 (d, 1H), 4.72-4.67 (d, 1H), 3.92-3.87 (d, 1H) geminal coupling, 3.28 (obscured by solvent signal, 1H), 2.63-2.56 (m, 1H), 2.56 (s, 3H), 2.28-2.26 (m, 1H), 1.94-1.87 (m, 1H), 1.72-1.64 (m, 2H), 1.33-1.27 (m, 1H), 1.07 (d, 3H) | LC $R_T$ = 10.7 min; MS: [M + H, $^{79/81}$Br]$^+$ = 437/439 m/z |
| 307 | 4 | 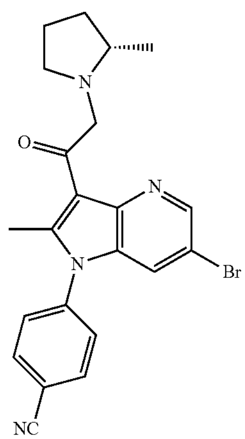 [SMILES: Cc1c(C(=O)CN2CCC[C@@H]2C)c2ncc(Br)cc2n1-c1ccc(C#N)cc1] | ¹H NMR (400 MHz, DMSO-$d_6$): δ 8.65 (d, 1H), 8.15 (d, 2H), 7.82 (d, 2H), 7.77 (d, 1H), 4.69 (d, 1H), 3.88 (d, 1H) geminal coupling, 3.33-3.25 (m, 1H), 2.62-2.56 (m, 1H), 2.56 (s, 3H), 2.28-2.26 (m, 1H), 1.92-1.86 (m, 1H), 1.72-1.63 (m, 2H), 1.35-1.30 (m, 1H), 1.06 (d, 3H) | LC RT = 10.7 min; MS: [M + H, $^{79/81}$Br]$^+$ = 437/439 m/z |
| 308 | 4 | 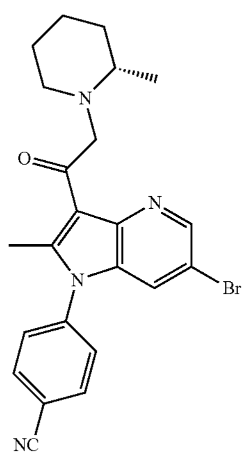 [SMILES: Cc1c(C(=O)CN2CCCC[C@@H]2C)c2ncc(Br)cc2n1-c1ccc(C#N)cc1] | ¹H NMR (400 MHz, DMSO-$d_6$): δ 8.64 (d, 1H), 8.15 (d, 2H), 7.82 (d, 2H), 7.77 (d, 1H), 4.39, 4.27 (q, 2H), 2.91-2.87 (m, 1H), 2.73-2.66 (m, 1H), 2.59-2.55 (m, 1H), 2.55 (s, 3H), 1.65-1.62 (m, 2H), 1.59-1.42 (m, 2H), 1.33-1.15 (overlapped m, 2H), 1.01 (d, 3H) | LC $R_T$ = 11.0 min; MS: [M + H, $^{79/81}$Br]$^+$ = 451/453 m/z |

TABLE 2-continued

| Compound No. | General Synthetic Route Number | Structure | ¹H NMR | LC-MS |
|---|---|---|---|---|
| 309 | 4 | 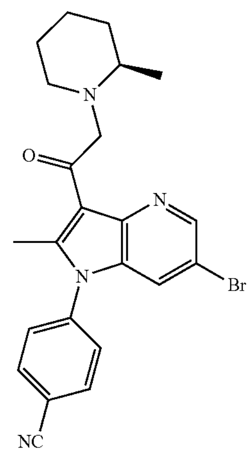 [SMILES: Cc1c(C(=O)CN2CCCC[C@H]2C)c2ncc(Br)cc2n1-c1ccc(C#N)cc1] | ¹H NMR (400 MHz, DMSO-$d_6$): δ 8.64 (d, 1H), 8.15 (d, 2H), 7.81 (d, 2H), 7.77 (d, 1H), 4.39, 4.27 (q, 2H), 2.91-2.88 (m, 1H), 2.73-2.69 (m, 1H), 2.60-2.59 (m, 1H), 2.59-2.55 (m, 1H), 2.55 (s, 3H), 1.66-1.62 (m, 2H), 1.59-1.42 (m, 2H), 1.33-1.17 (m, 2H), 1.01 (d, 3H) | LC $R_T$ = 11.0 min; MS: [M + H, $^{79/81}$Br]$^+$ = 451/453 m/z |
| 310 | 4 | 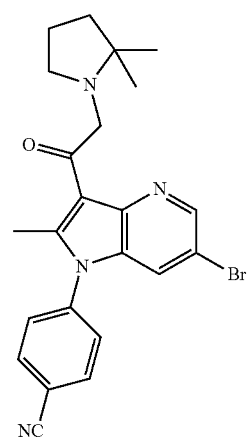 [SMILES: Cc1c(C(=O)CN2CCCC2(C)C)c2ncc(Br)cc2n1-c1ccc(C#N)cc1] | ¹H NMR (400 MHz, CDCl$_3$): δ 8.64 (d, 1H), 8.15 (d, 2H), 7.82 (d, 2H), 7.77 (d, 1H), 4.21 (s, 2H), 2.87-2.83 (m, 2H), 2.55 (s, 3H), 1.74-1.67 (m, 2H), 1.63-1.55 (m, 2H), 1.03 (s, 6H) | LC $R_T$ = 10.8 min; MS: [M + H, $^{79/81}$Br]$^+$ = 451/453 m/z |
| 311 | 4 | 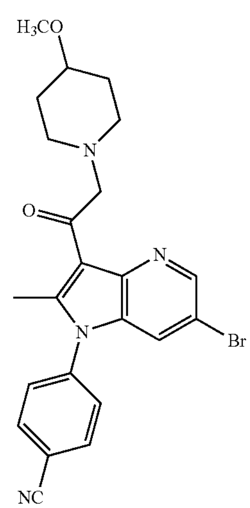 [SMILES: COC1CCN(CC(=O)c2c(C)n(-c3ccc(C#N)cc3)c3cc(Br)cnc23)CC1] | ¹H NMR (400 MHz, DMSO-$d_6$): δ 8.64 (d, 1H), 8.15 (d, 2H), 7.82 (d, 2H), 7.77 (d, 1H), 4.16 (s, 2H), 3.23 (s, 3H), 3.19-3.17 (m, 1H), 2.88-2.85 (m, 2H), 2.56 (s, 3H), 2.33 (bs, 2H), 1.85-1.82 (m, 2H), 1.45-1.42 (m, 2H) | LC $R_T$ = 11.1 min; MS: [M + H, $^{79/81}$Br]$^+$ = 467/469 m/z |

TABLE 2-continued
| Compound No. | General Synthetic Route Number | Structure | ¹H NMR | LC-MS |
|---|---|---|---|---|
| 312 | 4 | 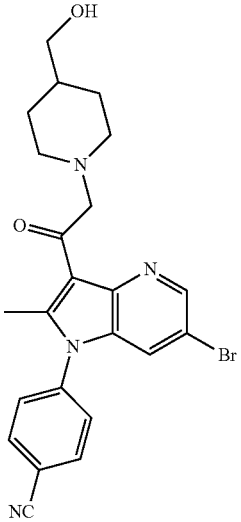 [SMILES: Cc1c(C(=O)CN2CCC(CO)CC2)c2ncc(Br)cc2n1-c1ccc(C#N)cc1] | ¹H NMR (400 MHz, DMSO-$d_6$): δ 8.64 (d, 1H), 8.15 (d, 2H), 7.82 (d, 2H), 7.77 (d, 1H), 4.41 (t, 1H), 4.16 (s, 2H), 3.24 (t, 2H), 2.99 (m, 2H), 2.57 (s, 3H), 2.15-2.09 (m, 2H), 1.64-1.62 (m, 2H), 1.40-1.33 (m, 1H), 1.18-1.15 (m, 2H) | LC $R_T$ = 7.8 min; MS: [M + H, $^{79/81}$Br]$^+$ = 467/469 m/z |
| 314 | 4 | 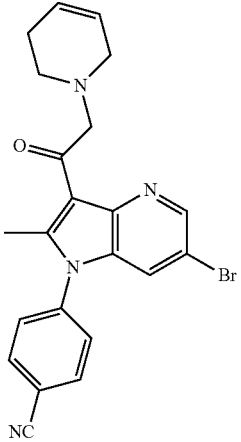 [SMILES: Cc1c(C(=O)CN2CC=CCC2)c2ncc(Br)cc2n1-c1ccc(C#N)cc1] | ¹H NMR (400 MHz, DMSO-$d_6$): δ 8.65 (d, 1H), 8.15 (d, 2H), 7.82 (d, 2H), 7.77 (d, 1H), 5.72-5.65 (m, 2H), 4.24 (s, 2H), 3.13 (s, 2H), 2.74-2.71 (t, 2H), 2.57 (s, 3H), 2.09 (s, 2H) | LC $R_T$ = 7.4 min; MS: [M + H, $^{79/81}$Br]$^+$ = 435/437 m/z |
| 315 | 4 | 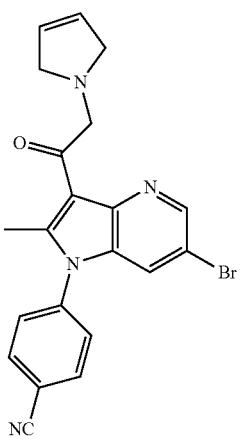 [SMILES: Cc1c(C(=O)CN2CC=CC2)c2ncc(Br)cc2n1-c1ccc(C#N)cc1] | ¹H NMR (400 MHz, DMSO-$d_6$): δ 8.65 (d, 1H), 8.15 (d, 2H), 7.82 (d, 2H), 7.77 (d, 1H), 5.82 (s, 2H), 4.48 (s, 2H), 3.65 (s, 4H), 2.57 (s, 3H) | LC $R_T$ = 7.9 min; MS: [M + H, $^{79/81}$Br]$^+$ = 421/423 m/z |

TABLE 2-continued
| Compound No. | General Synthetic Route Number | Structure | ¹H NMR | LC-MS |
|---|---|---|---|---|
| 318 | 4 | 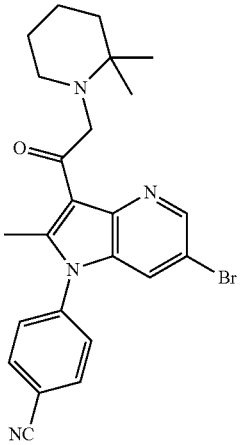 [SMILES: Cc1c(C(=O)CN2CCCCC2(C)C)c2ncc(Br)cc2n1-c1ccc(C#N)cc1] | ¹H NMR (400 MHz, CDCl$_3$): δ 8.62 (d, 1H), 7.92 (d, 2H), 7.51-7.43 (overlapped d and s, 2H), 4.32 (s, 2H), 2.67-2.65 (m, 2H), 2.63 (s, 3H), 1.65-1.55 (m, 6H), 1.14 (s, 6H) | LC R$_T$ = 10.9 min; MS: [M + H, $^{79/81}$Br]$^+$ = 465/467 m/z |
| 319 | | 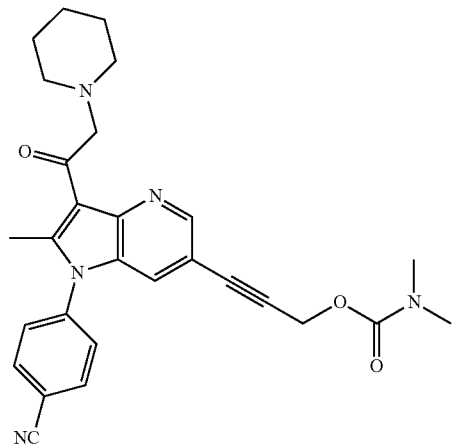 | ¹H NMR (400 MHz, DMSO-d$_6$): δ 8.61 (d, 1H), 8.14 (d, 2H), 7.82 (d, 2H), 7.57 (d, 1H), 4.91 (s, 2H), 4.15 (s, 2H), 2.85-2.83 (overlapped s, 6H), 2.58 (s, 3H), 2.55-2.44 (m, 4H), 1.54-1.49 (m, 4H), 1.42-1.37 (m, 2H) | LC R$_T$ = 6.6 min; MS: [M + H]$^+$ = 484 m/z |
| 320 | 4 | 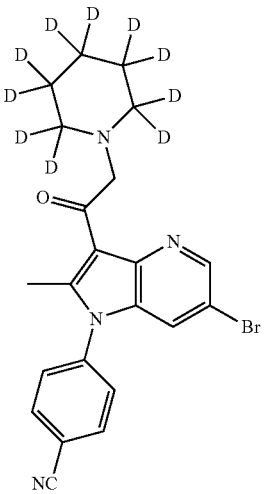 [SMILES: [2H]C1([2H])N(CC(=O)c2c(C)n(-c3ccc(C#N)cc3)c3cc(Br)cnc23)C([2H])([2H])C([2H])([2H])C([2H])([2H])C1([2H])[2H]] | ¹H NMR (400 MHz, DMSO-d$_6$): δ 8.64 (d, 1H), 8.15 (d, 2H), 7.82 (d, 2H), 7.77 (d, 1H), 4.12 (s, 2H), 2.56-2.55 (m, 2H) reduced split signal for CH$_3$ | LC R$_T$ = 8.0 min; MS: [M+H, $^{79/81}$Br]$^+$ = 447/449 m/z |

TABLE 2-continued

| Compound No. | General Synthetic Route Number | Structure | ¹H NMR | LC-MS |
|---|---|---|---|---|
| 321 | | 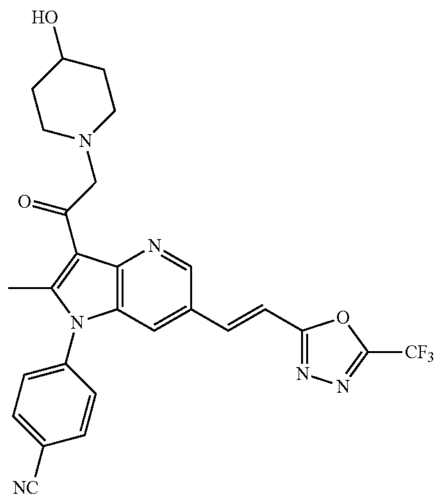 [SMILES: Cc1c(C(=O)CN2CCC(O)CC2)c2ncc(/C=C/c3nnc(C(F)(F)F)o3)cc2n1-c1ccc(C#N)cc1] | ¹H NMR (400 MHz, DMSO-$d_6$): δ 8.96 (d, 1H), 8.16 (d, 2H), 8.07 (d, 1H), 7.89 (d, 1H), 7.81 (d, 2H), 7.61 (d, 1H), 4.53 (d, 1H), 4.18 (s, 2H), 3.46-3.41 (m, 1H), 2.88-2.85 (m, 2H), 2.57 (s, 3H), 2.29-2.23 (m, 2H), 1.70-1.68 (m, 2H), 1.44-1.35 (m, 2H) | LC $R_T$ = 6.1 min; MS: [M + H]⁺ = 537 m/z |
| 324 | 4 | 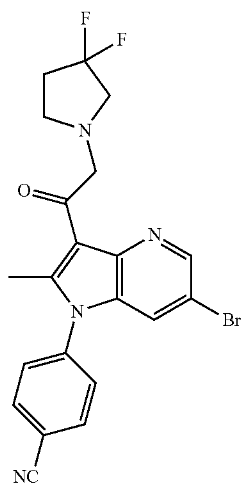 [SMILES: Cc1c(C(=O)CN2CCC(F)(F)C2)c2ncc(Br)cc2n1-c1ccc(C#N)cc1] | ¹H NMR (400 MHz, DMSO-$d_6$): δ 8.65 (d, 1H), 8.16 (d, 2H), 7.82 (d, 2H), 7.79 (d, 1H), 4.36 (s, 2H), 3.15 (t, 2H), 2.95 (t, 2H), 2.58 (s, 3H), 2.32-2.21 (m, 2H) | LC $R_T$ = 9.0 min; MS: [M + H, ⁷⁹/⁸¹Br]⁺ = 459/461 m/z |
| 325 | 4 | 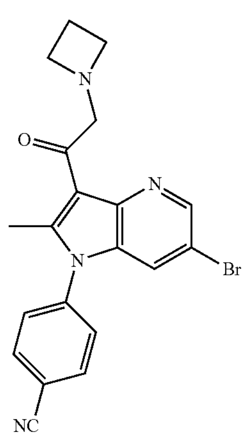 [SMILES: Cc1c(C(=O)CN2CCC2)c2ncc(Br)cc2n1-c1ccc(C#N)cc1] | ¹H NMR (400 MHz, CDCl₃): δ 8.60 (d, 1H), 7.93 (dd, 2H), 7.47-7.44 (overlapped d and s, 3H), 4.36 (s, 2H), 3.50 (t, 4H), 2.63 (s, 3H), 2.21 (quin, 2H) | LC $R_T$ = 6.6 min; MS: [M+H, ⁷⁹/⁸¹Br]⁺ = 409/411 m/z |

TABLE 2-continued

| Compound No. | General Synthetic Route Number | Structure | ¹H NMR | LC-MS |
|---|---|---|---|---|
| 326 | 5 | 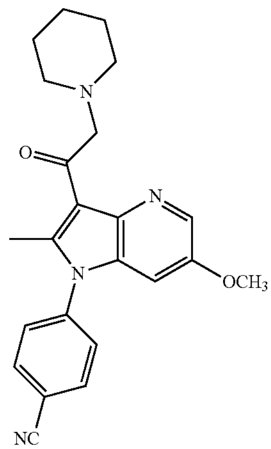 [SMILES: COc1cnc2c(C(=O)CN3CCCCC3)c(C)n(-c3ccc(C#N)cc3)c2c1] | ¹H NMR (400 MHz, CDCl₃): δ 8.34 (d, 1H), 7.94 (d, 2H), 7.48 (d, 2H), 6.77 (d, 1H), 4.62 (s, 2H), 3.81 (s, 3H), 3.08 (m, 4H), 2.63 (s, 3H), 1.92 (m, 6H) | LC R$_T$ = 5.1 min; MS: [M − H]⁺ = 389 m/z |
| 327 | 4 | 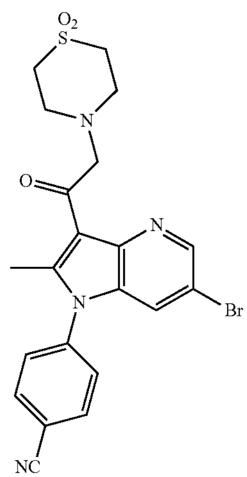 [SMILES: Cc1c(C(=O)CN2CCS(=O)(=O)CC2)c2ncc(Br)cc2n1-c1ccc(C#N)cc1] | ¹H NMR (400 MHz, DMSO-d₆): δ 8.65 (d, 1H), 8.16 (d, 2H), 7.81 (d, 2H), 7.79 (d, 1H), 4.43 (s, 2H), 3.20-3.19 (m, 4H), 3.12-3.11 (m, 4H), 2.58 (s, 3H) | LC R$_T$ = 6.6 min; MS: [M + H, ⁷⁹/⁸¹Br]⁺ = 487/489 m/z |
| 328 | 4 | 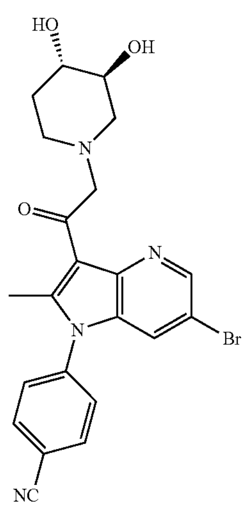 [SMILES: Cc1c(C(=O)CN2CC[C@H](O)[C@@H](O)C2)c2ncc(Br)cc2n1-c1ccc(C#N)cc1] | ¹H NMR (400 MHz, DMSO-d₆): δ 8.64 (d, 1H), 8.15 (d, 2H), 7.82 (d, 2H), 7.77 (d, 1H), 4.67 (d, 1H), 4.64 (d, 1H), 4.17 (q, 2H), 3.25-3.22 (m, 1H), 3.15-3.10 (m, 1H), 3.02-2.98 (m, 1H), 2.87-2.84 (m, 1H), 2.57 (s, 3H), 2.20-2.19 (m, 1H), 2.01 (t, 1H), 1.72-1.70 (m, 1H), 1.45-1.38 (m, 1H) | LC R$_T$ = 5.8 min; MS: [M + H, ⁷⁹/⁸¹Br]⁺ = 469/471 m/z |

TABLE 2-continued
| Compound No. | General Synthetic Route Number | Structure | ¹H NMR | LC-MS |
|---|---|---|---|---|
| 329 | 4 | 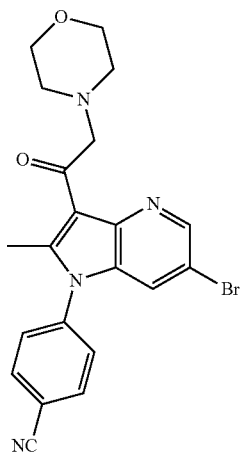 | ¹H NMR (400 MHz, CDCl₃): δ 8.61 (d, 1H), 7.93 (d, 2H), 7.47 (d, 2H), 7.45 (d, 1H), 4.29 (s, 2H), 3.83-3.81 (m, 4H), 2.75-2.73 (m, 4H), 2.64 (s, 3H) | LC $R_T$ = 6.8 min; MS: [M + H, $^{79/81}$Br]$^+$ = 439/441 m/z |
| 330 | 4 | 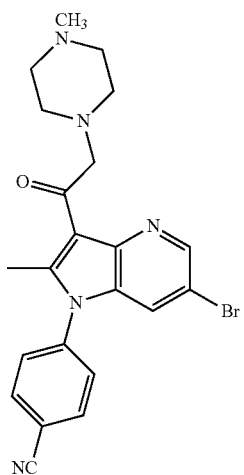 | ¹H NMR (400 MHz, CDCl₃): δ 8.61 (d, 1H), 7.93 (d, 2H), 7.46 (d, 2H), 7.44 (d, 1H), 4.29 (s, 2H), 2.77 (br s, 4H), 2.64 (s, 3H), 2.55 (br s, 4H), 2.31 (s, 3H) | LC $R_T$ = 5.8 min; MS: [M + H, $^{79/81}$Br]$^+$ = 452/454 m/z |
| 331 | 4 | 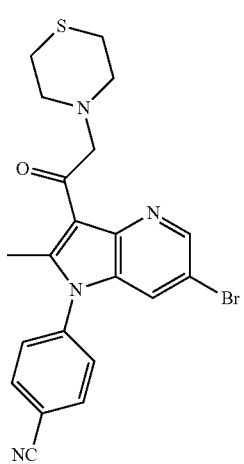 | ¹H NMR (400 MHz, CDCl₃): δ 8.61 (d, 1H), 7.93 (d, 2H), 7.47 (d, 2H), 7.45 (d, 1H), 4.31 (s, 2H), 2.99-2.97 (m, 4H), 2.79-2.76 (m, 4H), 2.64 (s, 3H) | LC $R_T$ = 8.1 min; MS: [M + H, $^{79/81}$Br]$^+$ = 455/457 m/z |

TABLE 2-continued

| Compound No. | General Synthetic Route Number | Structure | ¹H NMR | LC-MS |
|---|---|---|---|---|
| 332 | 4 | 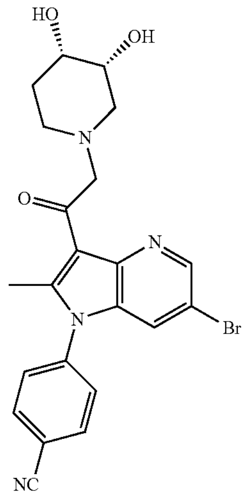 [SMILES: Cc1c(C(=O)CN2CC[C@H](O)[C@H](O)C2)c2ncc(Br)cc2n1-c1ccc(C#N)cc1] | ¹H NMR (400 MHz, DMSO-d₆): δ 8.65 (d, 1H), 8.15 (d, 2H), 7.82 (d, 2H), 7.77 (d, 1H), 4.32 (d, 1H), 4.23 (d, 1H), 4.17 (d, 2H), 3.65 (s, 1H), 3.52 (br s, 1H), 2.67-2.63 (m, 1H), 2.57 (s, 3H), 2.56 (s, obscured by solvent signal, 1H) 1.68-1.63 (m, 1H), 1.58-1.53 (m, 1H) | LC R$_T$ = 5.8 min; MS: [M + H, $^{79/81}$Br]$^+$ = 469/471 m/z |
| 335 | 2 | 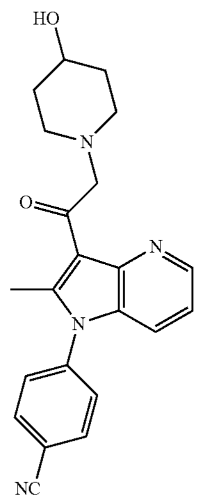 [SMILES: Cc1c(C(=O)CN2CCC(O)CC2)c2ncccc2n1-c1ccc(C#N)cc1] | ¹H NMR (400 MHz, CDCl₃): δ 8.58 (d, 1H), 7.91 (d, 2H), 7.47 (d, 2H), 7.31 (d, 1H), 7.13-7.12 (m, 1H), 4.39 (s, 2H), 3.76 (m, 1H), 3.07-3.04 (m, 2H), 2.67 (s, 3H), 2.50-2.42 (m, 2H), 1.99-1.96 (m, 2H), 1.78-1.72 (m, 2H), 1.39 (brs, 1H) | LC R$_T$ = 6.4 min; MS: [M + H]$^+$ = 375 m/z |
| 336 | 2 | 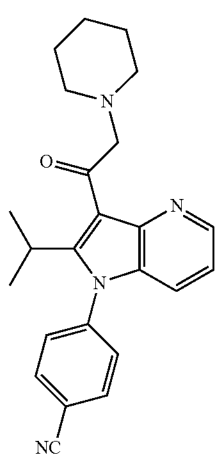 [SMILES: CC(C)c1c(C(=O)CN2CCCCC2)c2ncccc2n1-c1ccc(C#N)cc1] | ¹H NMR (400 MHz, DMSO-d₆): δ 8.56 (d, 1H), 8.17 (d, 2H), 7.79 (d, 2H), 7.31-7.15 (m, 3H), 4.24 (brs, 2H), 3.34-3.21 (m, 1H, occluded by solvent peak), 2.53 (brs, 4H), 1.54 (brs, 4H), 1.42 (brs, 2H), 1.28 (d, 6H) | LC R$_T$ = 1.7 min; MS: [M + H]$^+$ 387 m/z |

TABLE 2-continued
| Compound No. | General Synthetic Route Number | Structure | ¹H NMR | LC-MS |
|---|---|---|---|---|
| 337 | 1 | 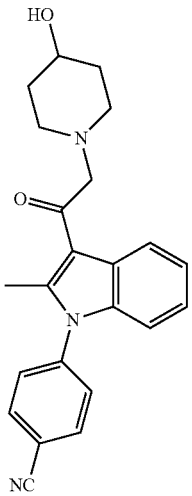 | ¹H NMR (400 MHz, CDCl₃): δ 7.99 (d, 1H), 7.90 (d, 1H), 7.48 (d, 2H), 7.33-7.29 (m, 1H), 7.22-7.17 (m, 1H), 7.00 (d, 1H), 3.90 (s, 2H), 3.81-3.77 (m, 1H), 3.04-3.01 (m, 2H), 2.60 (s, 3H), 2.54-2.50 (m, 2H), 2.09 (s, 1H), 1.99-1.97 (br, 2H), 1.76-1.68 (m, 2H) | LC R$_T$ = 6.4 min; MS: [M + H]⁺ 374 m/z |
| 338 | 4 | 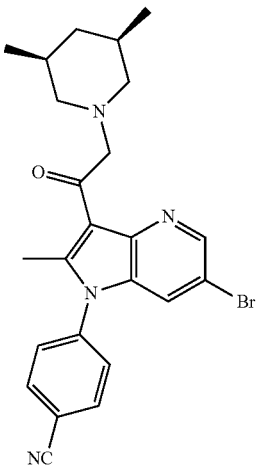 [SMILES: Cc1c(C(=O)CN2C[C@H](C)C[C@H](C)C2)c2ncc(Br)cc2n1-c1ccc(C#N)cc1] | ¹H NMR (400 MHz, CDCl₃): δ 8.60 (d, 1H), 7.93 (d, 2H), 7.47 (d, 2H), 7.44 (d, 1H), 4.29 (s, 2H), 3.09-3.07 (m, 2H), 2.64 (s, 3H), 2.03-2.00 (m, 2H), 1.78-1.72 (m, 3H), 0.86 (d, 6H), 0.61-0.55 (m, 1H) | LC R$_T$ = 10.7 min; MS: [M + H, $^{79/81}$Br]⁺ = 465/467 m/z |
| 339 | 5 | 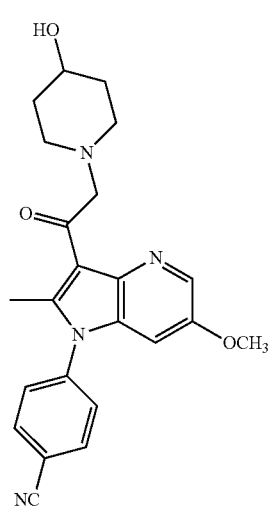 [SMILES: COc1cnc2c(C(=O)CN3CCC(O)CC3)c(C)n(-c3ccc(C#N)cc3)c2c1] | ¹H NMR (400 MHz, CDCl₃): δ 8.29 (d, 1H), 7.93 (d, 2H), 7.47 (d, 2H), 6.75 (d, 1H), 4.79 (s, 2H), 4.1 (overlapped signals, 2H), 3.78 (s, 3H), 3.71-3.70 (m, 1H), 3.59-3.57 (m, 1H), 3.50 (br, 2H), 2.62 (s, 3H), 1.99-1.84 (br, 4H) | LC R$_T$ = 5.9 min; MS: [M + H]⁺ = 405 m/z |

TABLE 2-continued

| Compound No. | General Synthetic Route Number | Structure | ¹H NMR | LC-MS |
|---|---|---|---|---|
| 340 | 5 | 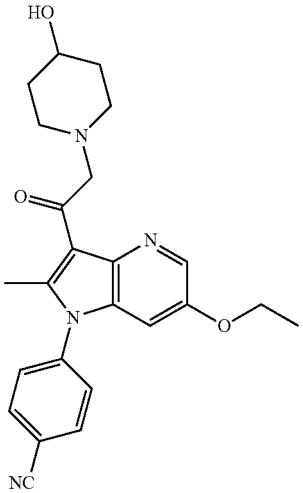 [SMILES: CCOc1cnc2c(C(=O)CN3CCC(O)CC3)c(C)n(-c3ccc(C#N)cc3)c2c1] | ¹H NMR (400 MHz, CDCl₃): δ 8.32 (d, 1H), 7.93 (d, 2H), 7.48 (d, 2H), 6.77 (d, 1H), 4.59 (m, 2H), 4.00 (q, 2H), 3.34 (m, 4H), 3.10 (m, 1H), 2.63 (s, 3H), 1.87 (m, 2H), 1.57 (m obscured by solvent signal, 2H), 1.44 (signal obscured by adjacent t, 1H), 1.41 (t, 3H) | LC R$_T$ = 6.4 min; MS: [M − H]⁺ = 419 m/z |
| 341 | 5 | 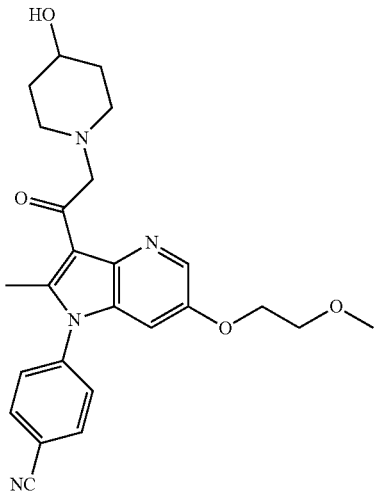 | ¹H NMR (400 MHz, CDCl₃): δ 8.38 (s, 1H), 7.90 (d, 2H), 7.45 (d, 2H), 6.86 (s, 1H), 4.33 (s, 2H), 4.10 (brt, 2H), 3.75-3.71 (brm, 3H), 3.43 (s, 3H), 3.07-3.02 (brm, 2H), 2.62 (s, 3H), 2.46 (t, 2H), 1.99-1.92 (brm, 2H), 1.73 (q, 2H) | LC R$_T$ = 6.8 min; MS: [M + H]⁺ = 448 m/z |
| 342 | | 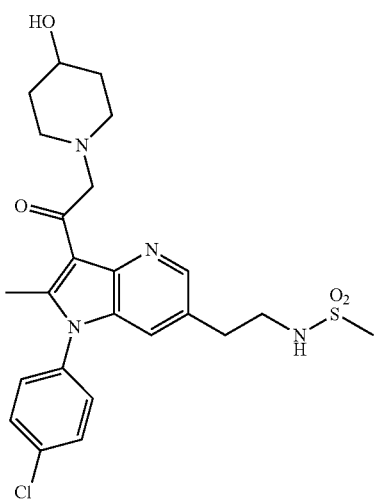 | ¹H NMR (400 MHz, CDCl₃): δ 8.44 (d, 1H), 7.73-7.71 (m, 2H), 7.58-7.56 (m, 2H), 7.37 (d, 1H), 7.04 (t, 1H), 4.54 (d, 1H), 4.18 (s, 2H), 3.46-3.43 (m, 1H), 3.19-3.14 (m, 2H), 2.89-2.83 (m, 4H), 2.81 (s, 3H), 2.55 (s obscured by solvent signal, 3H), 2.29-2.24 (m, 2H), 1.71-1.70 (m, 2H), 1.46-1.38 (m, 2H) | LC R$_T$ = 7.2 min; MS: [M + H, ³⁵/³⁷Cl]⁺ = 505/507 m/z |

TABLE 2-continued
| Compound No. | General Synthetic Route Number | Structure | ¹H NMR | LC-MS |
|---|---|---|---|---|
| 343 | 4 | 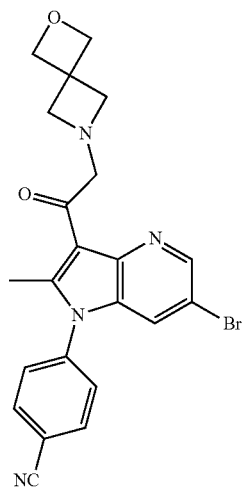 [SMILES: Cc1c(C(=O)CN2CC3(COC3)C2)c2ncc(Br)cc2n1-c1ccc(C#N)cc1] | ¹H NMR (300 MHz, DMSO-d₆): δ 8.63 (s, 1H), 8.15 (d, J = 8.4 Hz, 2H), 7.80 (d, J = 8.1 Hz, 2H), 7.76 (s, 1H), 4.63 (s, 4H), 4.23 (s, 2H), 3.48 (s, 4H), 2.56 (s, 3H) | LC R$_T$ = 2.2 min; MS: [M + H, $^{79/81}$Br] = 451/453 m/z |
| 344 | 4 | 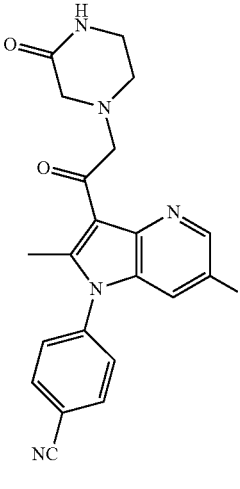 | ¹H NMR (300 MHz, DMSO-d₆): δ 8.65 (s, 1H), 8.16 (d, J = 8.4 Hz, 2H), 7.82 (d, 2H), 7.78 (s, 1H), 7.74 (s, 1H), 4.28 (s, 2H), 3.20 (brs, 4H), 2.83 (t, 2H), 2.58 (s, 3H) | LC R$_T$ = 2.4 min; MS: [M + H, $^{79/81}$Br] = 452/454 m/z |
| 345 | 4 | 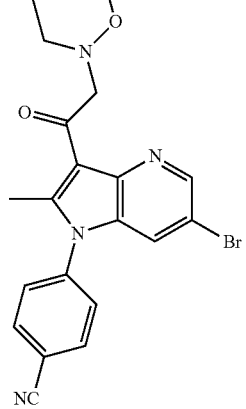 | ¹H NMR (300 MHz, DMSO-d₆): δ 8.65 (s, 1H), 8.15 (d, 2H), 7.82 (d, 2H), 7.77 (s, 1H), 4.46 (s, 2H), 3.82 (t, 2H), 2.90 (s, 2H), 2.57 (s, 3H), 1.76-1.71 (m, 2H), 1.53-1.48 (m, 2H) | LC R$_T$ = 2.3 min; MS: [M + H, $^{79/81}$Br] = 439/441 m/z |

TABLE 2-continued
| Compound No. | General Synthetic Route Number | Structure | ¹H NMR | LC-MS |
|---|---|---|---|---|
| 346 | | 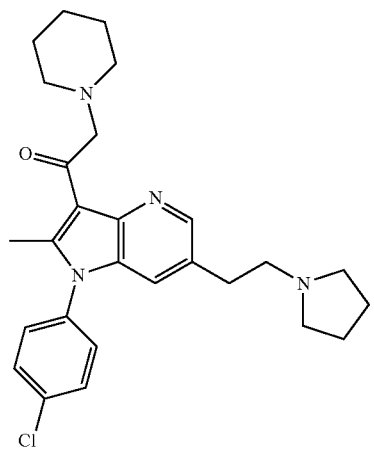 [SMILES: Cc1c(C(=O)CN2CCCCC2)c2ncc(CCN3CCCC3)cc2n1-c1ccc(Cl)cc1] | ¹H NMR (400 MHz, DMSO-d₆): δ 8.43 (d, 1H), 7.72 (d, 2H), 7.56 (d, 2H), 7.32 (d, 1H), 4.17 (s, 2H), 2.80 (t, 2H), 2.60-2.50 (m, 9H), 2.43 (brs, 4H), 1.64 (brs, 4H), 1.54-1.49 (brm, 4H), 1.42-1.37 (brm, 2H) | LC R$_T$ = 5.0 min; MS: [M + H]⁺ = 465 m/z |
| 347 | 5 | 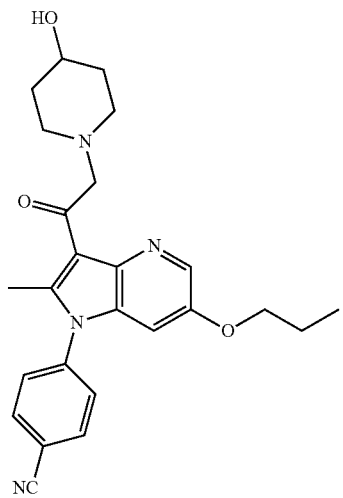 [SMILES: CCCOc1cnc2c(C(=O)CN3CCC(O)CC3)c(C)n(-c3ccc(C#N)cc3)c2c1] | ¹H NMR (400 MHz, CDCl₃): δ 8.33 (d, 1H), 7.91 (d, 2H), 7.46 (d, 2H), 6.77 (d, 1H), 4.42 (s, 2H), 3.89 (t, 2H), 3.81 (s, 1H), 3.12 (s, 1H), 2.61 (s, 5H), 2.03 (br, 2H), 1.84-1.75 (m, 4H), 1.02 (t, 3H), 0.88 (m, 2H) | LC R$_T$ = 10.9 min; MS: [M + H]⁺ = 433 m/z |
| 348 | 4 | 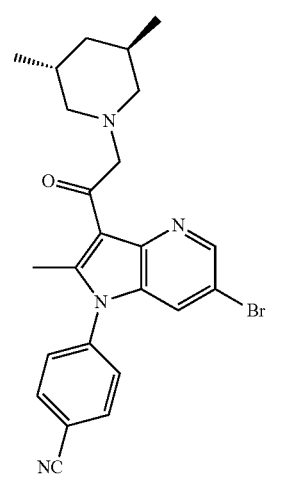 [SMILES: Cc1c(C(=O)CN2C[C@H](C)C[C@@H](C)C2)c2ncc(Br)cc2n1-c1ccc(C#N)cc1] | ¹H NMR (400 MHz, CDCl₃): δ 8.60 (d, 1H), 7.92 (d, 2H), 7.92 (d, 2H), 7.44 (d, 1H), 4.19 (s, 2H), 2.63 (s, 3H), 2.59 (br s, 1H), 2.36-2.31 (m, 2H), 1.99-1.96 (m, 2H), 1.41 (obscured by solvent signal, 1H), 1.30-1.24 (m, 2H), 0.99 (d, 6H) | LC R$_T$ = 8.1 min; MS: [M + H, ⁷⁹/⁸¹Br] = 465/467 m/z |

TABLE 2-continued
| Compound No. | General Synthetic Route Number | Structure | ¹H NMR | LC-MS |
|---|---|---|---|---|
| 349 | 4 | 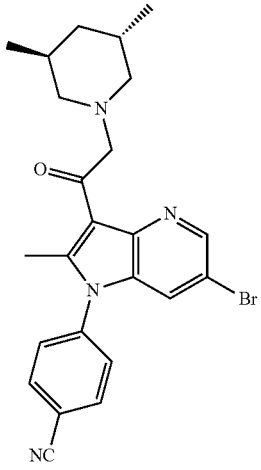 [SMILES: Cc1c(C(=O)CN2C[C@@H](C)C[C@H](C)C2)c2ncc(Br)cc2n1-c1ccc(C#N)cc1] | ¹H NMR (400 MHz, CDCl₃): δ 8.60 (d, 1H), 7.93 (d, 2H), 7.93 (d, 2H), 7.44 (d, 1H), 4.22 (s, 2H), 2.63 (s, 4H), 2.39 (br s, 2H), 1.99-1.97 (m, 2H), 1.55 (obscured by solvent signal, 1H), 1.31-1.24 (m, 2H), 0.99 (d, 6H) | LC R$_T$ = 8.1 min; MS: [M + H, $^{79/81}$Br] = 465/467 m/z |
| 350 | | 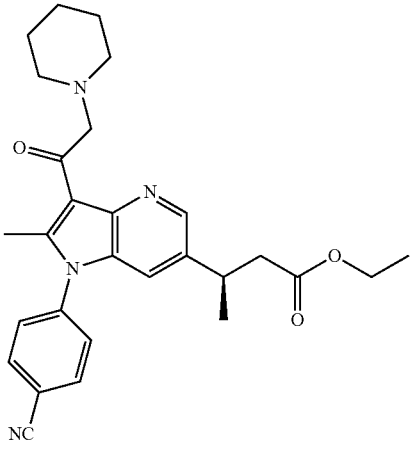 | ¹H NMR (400 MHz, CDCl₃): δ 8.50 (s, 1H), 7.92 (d, 2H), 7.46 (d, 2H), 7.12 (s, 1H), 4.33 (s, 2H), 4.08-3.99 (m, 2H), 3.36 (dt, 1H), 2.72-2.56 (m, 10H), 1.70 (brs, 2H), 1.49 (brs, 2H), 1.30 (d, 3H), 1.15 (t, 3H) | LC R$_T$ = 5.7 min; MS: [M + H]⁺ = 473 m/z |
| 351 | | 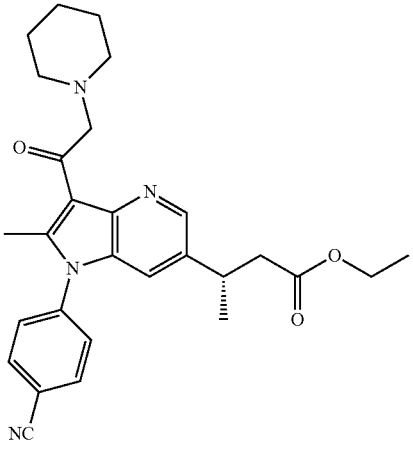 [SMILES: CCOC(=O)C[C@H](C)c1cnc2c(C(=O)CN3CCCCC3)c(C)n(-c3ccc(C#N)cc3)c2c1] | ¹H NMR (400 MHz, CDCl₃): δ 8.50 (s, 1H), 7.92 (d, 2H), 7.46 (d, 2H), 7.12 (s, 1H), 4.33 (s, 2H), 4.05-4.02 (m, 2H), 3.40-3.33 (brm, 1H), 2.68 (brs, 4H), 2.64 (s, 3H), 2.58 (d, 2H), 1.70 (brs, 4H), 1.49 (brs, 2H), 1.30 (d, 3H), 1.15 (t, 3H) | LC R$_T$ = 5.7 min; MS: [M + H]⁺ = 473 m/z |

TABLE 2-continued
| Compound No. | General Synthetic Route Number | Structure | ¹H NMR | LC-MS |
|---|---|---|---|---|
| 352 | 4 | 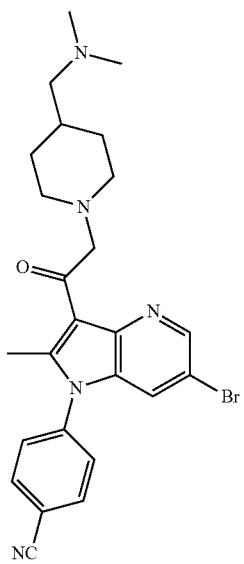 [SMILES: Cc1c(C(=O)CN2CCC(CN(C)C)CC2)c2ncc(Br)cc2n1-c1ccc(C#N)cc1] | ¹H NMR (400 MHz, DMSO-$d_6$): δ 8.64 (d, 1H), 8.15 (d, 2H), 7.82 (d, 2H), 7.77 (d, 1H), 4.17 (brs, 2H), 2.99 (brd, 2H), 2.57 (s, 3H), 2.14 (brs, 10 H), 1.65 (brd, J = 12.5 Hz, 2H), 1.45 (brs, 1H), 1..18-1.11 (brm, 2H) | LC $R_T$ = 6.9 min; MS: [M + H, $^{79/81}$Br] = 494/496 m/z |
| 353 | 4 | 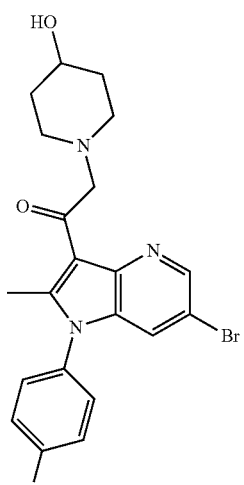 | ¹H NMR (400 MHz, CDCl₃): δ 8.60 (d, 1H), 7.93 (d, 2H), 7.46 (d, 2H), 7.45 (d, 1H), 4.37 (s, 2H), 3.80 (brs, 1H), 3.08 (brs, 2H), 2.65 (s, 3H), 2.57 (brs, 2H), 2.06 (brs, 2H), 1.79-1.72 (m, 2H) | LC $R_T$ = 6.3 min; MS: [M + H, $^{79/81}$Br] = 453/455 m/z |

TABLE 2-continued
| Compound No. | General Synthetic Route Number | Structure | ¹H NMR | LC-MS |
|---|---|---|---|---|
| 354 | 4 | 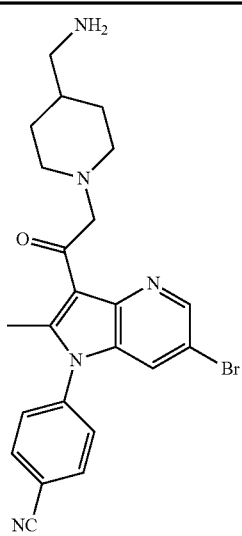 | ¹H NMR (400 MHz, CDCl₃): δ 8.63 (d, 1H), 7.96 (d, 2H), 7.49 (d, 2H), 7.47 (d, 1H), 4.31 (s, 2H), 3.21 (brd, 2H), 2.67 (s, 3H), 2.63 (d, 2H), 2.26 (t, 2H), 1.78 (brs, 1H), 1.75 (brs, 1H), 1.50-1.38 (brm, 3H) | LC R$_T$ = 6.3 min; MS: [M + H, $^{79/81}$Br]= 466/468 m/z |
| 355 | 4 | 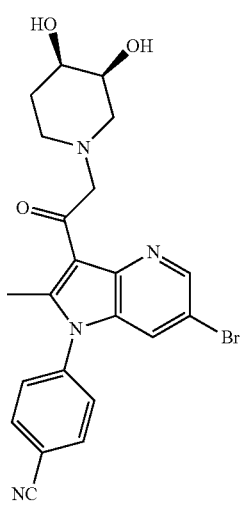 [SMILES: Cc1c(C(=O)CN2CC[C@@H](O)[C@@H](O)C2)c2ncc(Br)cc2n1-c1ccc(C#N)cc1] | ¹H NMR (400 MHz, CDCl₃): δ 8.61 (s, 1H), 7.93 (d, 2H), 7.48-7.46 (m, 3H), 4.35 (d, 1H), 4.23 (d, 1H), 3.84 (s, 1H), 3.58 (s, 1H), 3.08, (brd, 1H), 2.90 (brs, 1H), 2.64 (brs, 4H), 2.52-2.45 (brm, 1H), 1.84-1.76 (brm, 3H), 1.24 (s, 2H) | LC R$_T$ = 8.0 min; MS: [M + H, $^{79/81}$Br] = 469/471 m/z |
| 356 | 4 | 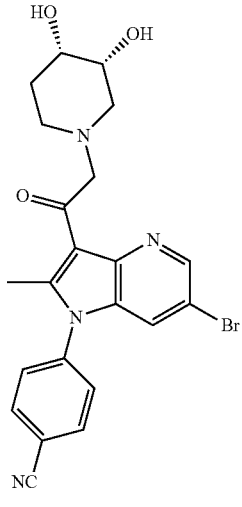 [SMILES: Cc1c(C(=O)CN2CC[C@H](O)[C@H](O)C2)c2ncc(Br)cc2n1-c1ccc(C#N)cc1] | ¹H NMR (400 MHz, CDCl₃): δ 8.61 (s, 1H), 7.93 (d, 2H), 7.48-7.46 (m, 3H), 4.35 (d, 1H), 4.23 (d, 1H), 3.84 (s, 1H), 3.61-3.57 (m, 1H), 3.11-3.07, (m, 1H), 2.93-2.89 (m, 1H), 2.66-2.62 (m, 4H), 2.49 (dt, 1H), 1.84-1.76 (brm, 3H), 1.24 (s, 2H) | LC R$_T$ = 8.0 min; MS: [M + H]⁺ = 469/471 m/z |

TABLE 2-continued
| Compound No. | General Synthetic Route Number | Structure | ¹H NMR | LC-MS |
|---|---|---|---|---|
| 357 | | 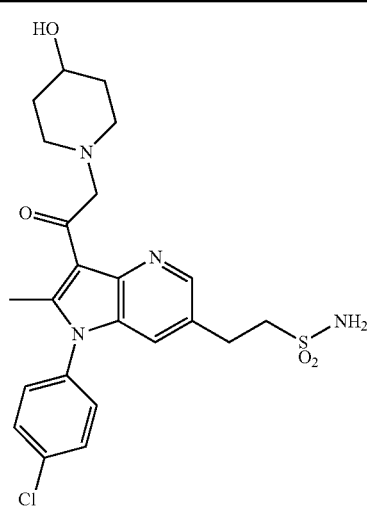 | ¹H NMR (400 MHz, DMSO-$d_6$): δ 8.46 (s, 1H), 7.72 (d, 2H), 7.57 (d, 2H), 7.41 (s, 1H), 6.83 (s, 2H), 4.55 (d, 1H), 4.18 (s, 2H), 3.47-3.24 (m, 4H, occluded by solvent peak); 3.10-3.06 (m, 2H), 2.90-2.86 (m, 2H), 2.55 (s, 3H), 2.26 (t, 2H), 1.73-1.69 (m, 2H), 1.45-1.36 (m, 2H) | LC $R_T$ = 6.7 min; MS: [M + H, $^{35/37}$Cl]$^+$ = 491/493 m/z |
| 359 | 4 | 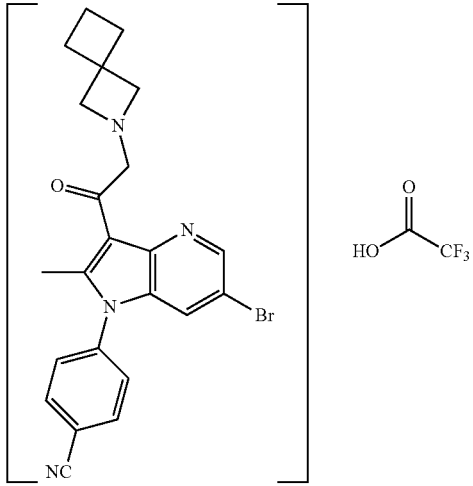 | ¹H NMR (300 MHz, MeOH-$d_4$): δ 8.61 (s, 1H), 8.03 (d, 2H), 7.71 (s, 1H), 7.65 (d, 2H), 5.13 (s, 2H), 4.43 (d, 2H), 4.18 (d, 2H), 2.65 (s, 3H), 2.40 (t, 2H), 2.27 (t, 2H), 1.91-1.83 (m, 2H) | LC $R_T$ = 1.8 min; MS: [M + H]$^+$ = 451 m/z |
| 360 | | 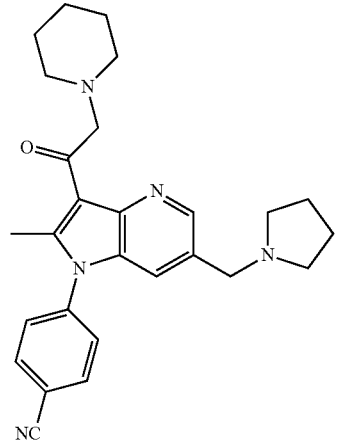 [SMILES: Cc1c(C(=O)CN2CCCCC2)c2ncc(CN3CCCC3)cc2n1-c1ccc(C#N)cc1] | ¹H NMR (400 MHz, DMSO-$d_6$): δ 8.49 (s, 1H), 8.17 (d, 2H), 7.80 (d, 2H), 7.36 (s, 1H), 4.18 (s, 2H), 3.64 (s, 2H), 2.58-2.49 (m, 7H), 2.39 (brs, 4H), 1.65 (brs, 4H), 1.55-1.48 (m, 4H), 1.42-1.38 (brm, 2H) | LC $R_T$ = 7.7 min; MS: [M + H]$^+$ = 442 m/z |

TABLE 2-continued

| Compound No. | General Synthetic Route Number | Structure | ¹H NMR | LC-MS |
|---|---|---|---|---|
| 361 | | 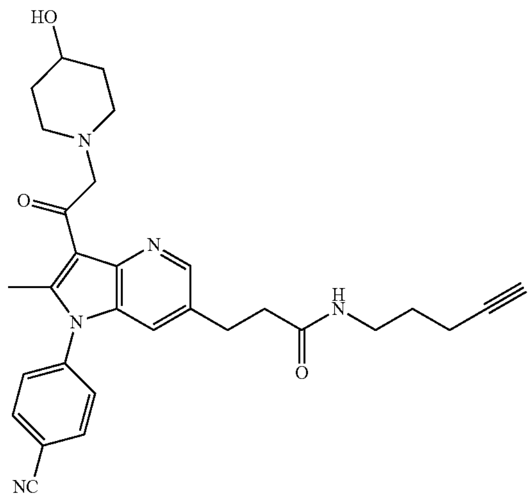 [SMILES: C#CCCCNC(=O)CCc1cnc2c(C(=O)CN3CCC(O)CC3)c(C)n(-c3ccc(C#N)cc3)c2c1] | ¹H NMR (300 MHz, DMSO-$d_6$): δ 8.42 (s, 1H), 8.16 (d, 2H), 7.76 (apparent d, 2H), 7.75 (brs, 1H), 7.30 (s, 1H), 4.54 (d, 1H), 4.19 (s, 2H), 3.45 (brs, 1H), 3.01 (dd, 2H), 2.89 (t, 4H), 2.74 (t, 1H), 2.56 (s, 3H), 2.38 (t, 2H), 2.29 (brs, 2H), 2.01 (dt, 2H), 1.75-1.69 (m, 2H), 1.49-1.33 (m, 2H) | LC $R_T$ = 1.8 min; MS: [M + H]⁺ = 512 m/z |
| 362 | | 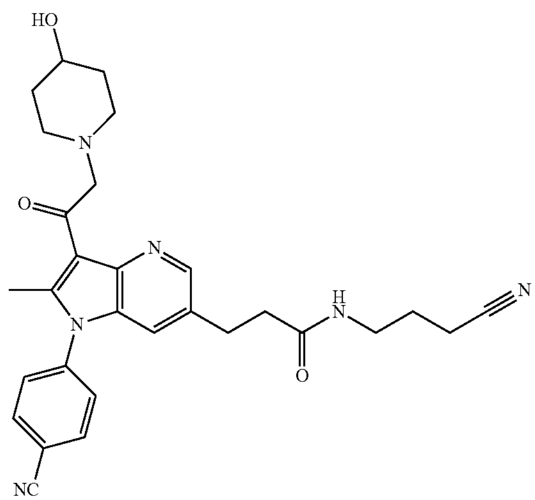 [SMILES: Cc1c(C(=O)CN2CCC(O)CC2)c2ncc(CCC(=O)NCCCC#N)cc2n1-c1ccc(C#N)cc1] | ¹H NMR (300 MHz, DMSO-$d_6$): δ 8.42 (s, 1H), 8.16 (d, 2H), 7.85 (t, 1H), 7.77 (d, 2H), 7.31 (s, 1H), 4.55 (brs, 1H), 4.21 (brs, 2H), 3.46 (brs, 2H), 3.03 (dd, 2H), 2.90 (t, 4H), 2.57 (s, 3H), 2.37 (t, 2H), 2.31 (t, 2H), 1.75-1.70 (brm, 2H), 1.55 (q, 2H), 1.47-1.36 (m, 2H) | LC $R_T$ = 2.7 min; MS: [M + H]⁺ = 513 m/z |
| 363 | 5 | 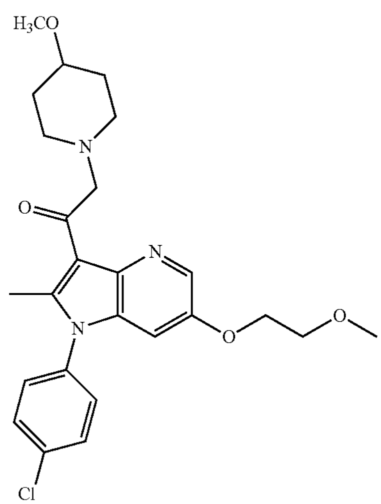 | ¹H NMR (400 MHz, DMSO-$d_6$): δ 8.30 (s, 1H), 7.71 (d, 2H), 7.57 (d, 2H), 7.01 (s, 1H), 4.16 (s, 2H), 4.10 (brs, 2H), 3.63 (brs, 2H), 3.28 (s, 3H), 3.23 (s, 3H), 3.17 (brs, 1H), 2.89-2.84 (m, 2H), 2.51 (s, 3H, occluded by solvent peak), 2.31 (t, 2H), 1.87-1.81 (m, 2H), 1.45-1.41 (m, 2H) | LC $R_T$ = 20.3 min; MS: [M + H, ³⁵/³⁷Cl]⁺ = 472/474 m/z |

TABLE 2-continued

| Compound No. | General Synthetic Route Number | Structure | $^1$H NMR | LC-MS |
|---|---|---|---|---|
| 364 | 5 | 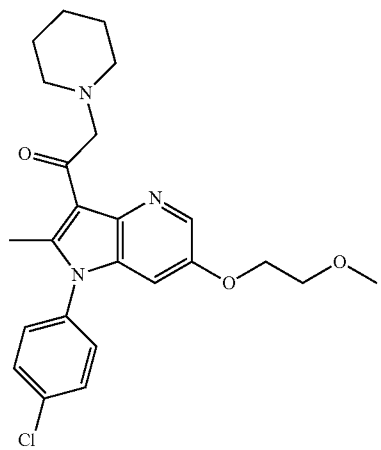 | $^1$H NMR (400 MHz, DMSO-d$_6$): δ 8.31 (s, 1H), 7.71 (d, 2H), 7.57 (d, 2H), 7.00 (s, 1H), 4.14 (s, 2H), 4.12-4.08 (m, 2H), 3.64-3.61 (m, 2H), 3.31 (s, 2H, occluded by solvent), 3.28 (s, 3H), 2.54 (brs, 2H), 2.50 (s, 3H, occluded by solvent), 1.53-1.49 (m, 4H), 1.40 (brs, 2H) | LC R$_T$ = 10.8 min; MS: [M + H, $^{35/37}$Cl]$^+$ = 442/444 m/z |
| 365 | 4 | 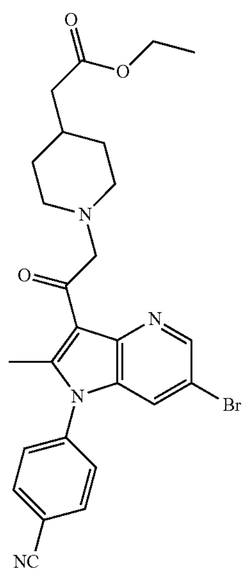 [SMILES: CCOC(=O)CC1CCN(CC(=O)c2c(C)n(-c3ccc(C#N)cc3)c3cc(Br)cnc23)CC1] | $^1$H NMR (400 MHz, CDCl$_3$): δ 8.58 (s, 1H), 7.59-7.56 (m, 2H), 7.41 (d, 1H), 7.23 (m, 2H), 4.27 (s, 2H), 4.12 (q, 2H), 3.13 (d, 2H), 2.62 (s, 3H), 2.29-2.23 (m, 4H), 1.85, brs, 1H), 1.74 (brs, 1H), 1.71 (brs, 1H), 1.54-1.45 (m, 2H), 1.24 (t, 3H) | LC R$_T$ = 10.4 min; MS: [M + H, $^{79/81}$Br] = 523/525 m/z |
| 366 | 4 | 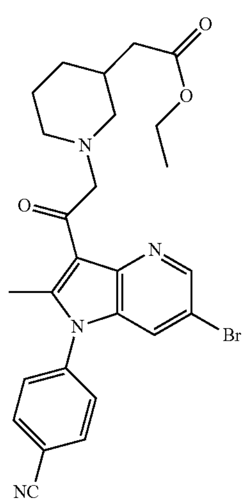 [SMILES: CCOC(=O)CC1CCCN(CC(=O)c2c(C)n(-c3ccc(C#N)cc3)c3cc(Br)cnc23)C1] | $^1$H NMR (400 MHz, CDCl$_3$): δ 8.57 (s, 1H), 7.59-7.56 (m, 2H), 7.41 (d, 1H), 7.26-7.23 (m, 2H, occluded by solvent), 4.27 (s, 2H), 4.11 (q, 2H), 3.07 (brd, 2H), 2.61 (s, 3H), 2.27-2.15 (m, 4H), 2.07-2.03 (m, 1H), 1.82-1.59 (m, 3H), 1.24 (t, 3H), 1.03 (brs, 1H) | LC R$_T$ = 12.6 min; MS: [M + H, $^{79/81}$Br] = 523/525 m/z |

TABLE 2-continued
| Compound No. | General Synthetic Route Number | Structure | ¹H NMR | LC-MS |
|---|---|---|---|---|
| 367 | 4 | 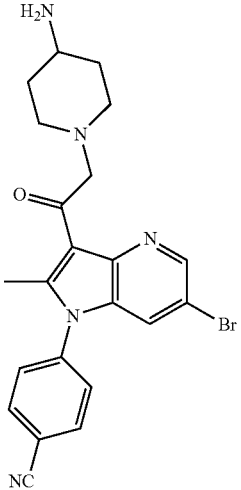 | ¹H NMR (400 MHz, CDCl₃): δ 8.57 (s, 1H), 7.60-7.56 (m, 2H), 7.42 (d, 1H), 7.26-7.22 (m, 2H), occluded by solvent), 4.29 (s, 2H), 3.12 (brd, 2H), 2.85-2.76 (m, 1H), 2.62 (s, 3H), 2.33 (t, 2H), 1.92 (brd, 2H), 1.70-1.59 (m, 2H) | LC R$_T$ = 8.6 min; MS: [M + H, $^{79/81}$Br] = 452/454 m/z |
| 368 | 4 | 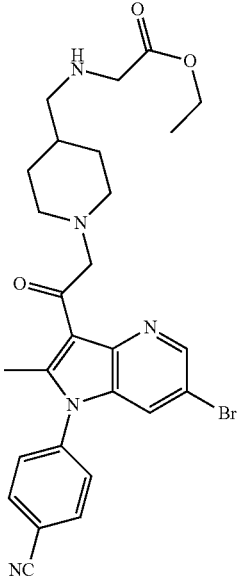 [SMILES: CCOC(=O)CNCC1CCN(CC(=O)c2c(C)n(-c3ccc(C#N)cc3)c3cc(Br)cnc23)CC1] | ¹H NMR (400 MHz, CDCl₃): δ 8.58 (s, 1H), 7.59-7.54 (m, 2H), 7.41 (d, 1H), 7.26-7.21 (m, 2H, occluded by solvent), 4.28 (s, 2H), 4.18 (q, J = 7.2 Hz, 2H), 3.39 (s, 2H), 3.17 (brd, 2H), 2.23 (brt, 2H), 1.76 (brd, 2H), 1.49-1.42 (m, 3H), 1.27 (t, 3H) | LC R$_T$ = 8.0 min; MS: [M + H, $^{79/81}$Br] = 552/554 m/z |

TABLE 2-continued

| Compound No. | General Synthetic Route Number | Structure | $^1$H NMR | LC-MS |
|---|---|---|---|---|
| 369 | 5 | 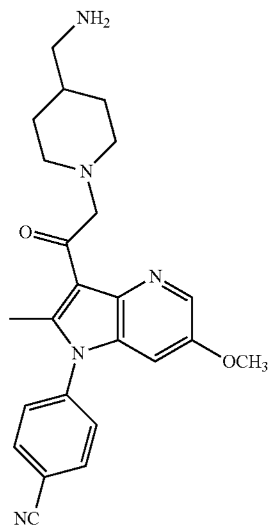 [SMILES: COc1cnc2c(C(=O)CN3CCC(CN)CC3)c(C)n(-c3ccc(C#N)cc3)c2c1] | $^1$H NMR (400 MHz, DMSO-$d_6$): δ 8.32 (d, 1H), 8.15 (d, 2H), 7.79 (d, 2H), 7.71 (brs, 1H), 7.04 (d, 1H), 4.18 (s, 2H), 3.77 (s, 3H), 3.39-3.33 (m, 1H), 3.03 (d, 2H), 2.70-2.67 (m, 2H), 2.53 (s, 3H), 2.20-2.13 (m, 2H), 1.70 (brs, 1H), 1.67 (brs, 1H), 1.55 (brs, 1H), 1.28-1.10 (m, 2H) | LC $R_T$ = 7.1 min; MS: [M + H]$^+$ = 418 m/z |
| 370 | 5 | 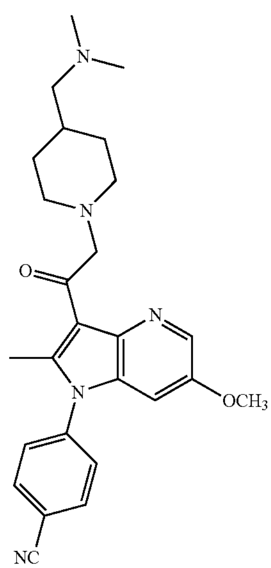 [SMILES: COc1cnc2c(C(=O)CN3CCC(CN(C)C)CC3)c(C)n(-c3ccc(C#N)cc3)c2c1] | $^1$H NMR (400 MHz, DMSO-$d_6$): δ 8.33 (s, 1H), 8.15 (d, 2H), 7.79 (d, 2H), 7.03 (s, 1H), 4.15 (s, 2H), 3.77 (s, 3H), 2.98 (brd, 2H), 2.53 (s, 3H), 2.14 (brt, 2H), 2.09 (s, 6H), 2.03 (d, 2H), 1.64 (brd, 2H), 1.41 (brs, 1H), 1.16-1.06 (m, 2H) | LC $R_T$ = 11.4 min; MS: [M + H]$^+$ = 446 m/z |

TABLE 2-continued
| Compound No. | General Synthetic Route Number | Structure | ¹H NMR | LC-MS |
|---|---|---|---|---|
| 371 | 4 | 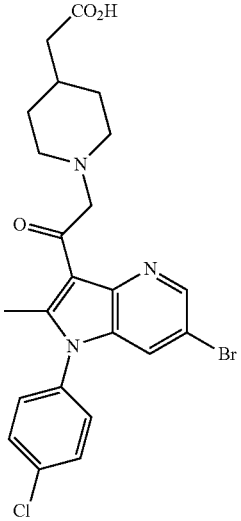 [SMILES: Cc1c(C(=O)CN2CCC(CC(=O)O)CC2)c2ncc(Br)cc2n1-c1ccc(Cl)cc1] | ¹H NMR (400 MHz, MeOH-d₆): δ 8.63 (s, 1H), 7.73-7.67 (m, 3H), 7.49 (brs, 2H), 5.05 (brs, 2H), 3.65 (brs, 2H), 3.21 (brs, 2H), 2.69 (s, 3H), 2.27 (s, 2H), 2.08-1.95 (m, 7H), 1.70-1.64 (m, 2H), 1.29 (brs, 1H) | LC $R_T$ = 7.0 min; MS: [M + H, $^{79/81}$Br] = 504/506 m/z |
| 372 | 2 | 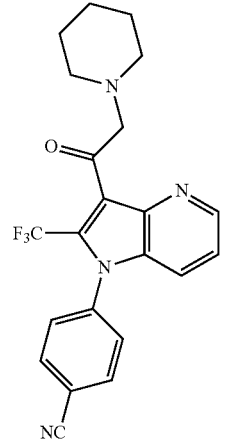 [SMILES: N#Cc1ccc(-n2c(C(F)(F)F)c(C(=O)CN3CCCCC3)c3ncccc32)cc1] | ¹H NMR (400 MHz, DMSO-d₆): δ 8.67 (d, 1H), 8.54 (d, 1H), 8.18 (d, 2H), 7.94 (d, 2H), 7.56 (dd, 1H), 2.90 (s, 3H), 2.07 (brs, 4H), 1.30 (brs, 6H) | LC $R_T$ = 1.9 min; MS: [M + H]⁺ = 413 m/z |
| 373 | 4 | 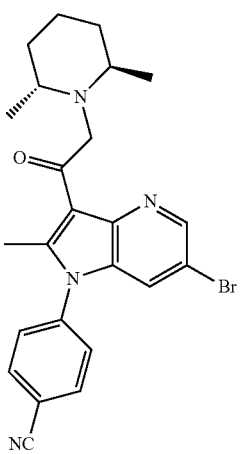 [SMILES: Cc1c(C(=O)CN2[C@H](C)CCC[C@H]2C)c2ncc(Br)cc2n1-c1ccc(C#N)cc1] | ¹H NMR (400 MHz, CDCl₃): δ 8.61 (d, 1H), 7.93 (d, 2H), 7.47 (d, 2H), 7.45 (d, 1H), 4.64 (brs, 1H), 4.43 (brs, 1H), 3.27 (brs, 1H), 2.62 (s, 3H), 1.78 (brs, 2H), 1.66 (brs, 2H), 1.57 (brs, 2H), 1.15 (brs, 6H) | LC $R_T$ = 6.6 min; MS: [M + H, $^{79/81}$Br] = 465/467 m/z |

TABLE 2-continued
| Compound No. | General Synthetic Route Number | Structure | ¹H NMR | LC-MS |
|---|---|---|---|---|
| 374 | 4 | 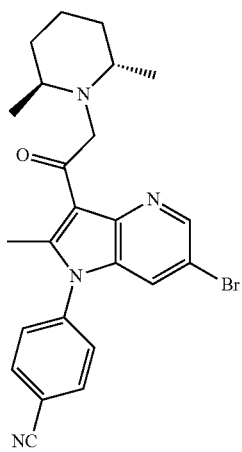 [SMILES: Cc1c(C(=O)CN2[C@@H](C)CCC[C@@H]2C)c2ncc(Br)cc2n1-c1ccc(C#N)cc1] | ¹H NMR (400 MHz, CDCl₃): δ 8.61 (d, 1H), 7.93 (d, 2H), 7.46 (d, 2H), 7.45 (d, 1H), 4.67-4.61 (m, 1H), 4.45-4.38 (m, 1H), 3.30 (brs, 2H), 2.62 (s, 3H), 1.78 (brs, 2H), 1.75-1.40 (brm, 4H), 1.15 (brs, 6H) | LC R$_T$ = 6.6 min; MS: [M + H, $^{79/81}$Br] = 465/467 m/z |
| 381 | | 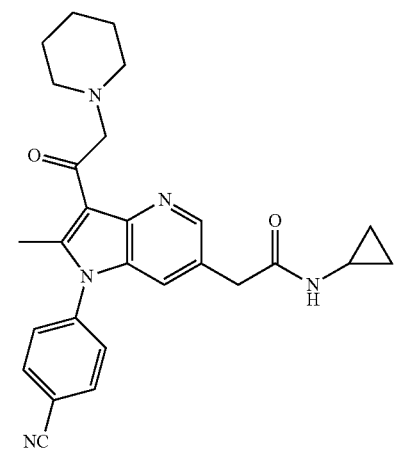 [SMILES: Cc1c(C(=O)CN2CCCCC2)c2ncc(CC(=O)NC3CC3)cc2n1-c1ccc(C#N)cc1] | ¹H NMR (400 MHz, DMSO-d₆): δ 8.41 (d, 1H), 8.18 (d, 2H), 8.13 (d, 2H), 7.80 (d, 2H), 7.36 (d, 1H), 4.17 (s, 2H), 2.57 (s, 8H), 1.52 (m, 4H), 1.41 (m, 2H), 0.59-0.55 (m, 2H), 0.35-0.33 (m, 2H) | LC R$_T$ = 7.6 min; MS [M + H]⁺ = 456 m/z |
| 382 | | 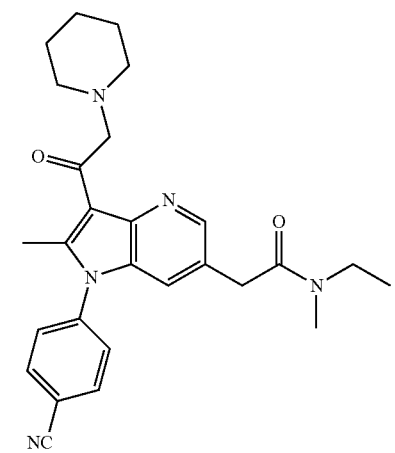 [SMILES: CCN(C)C(=O)Cc1cnc2c(C(=O)CN3CCCCC3)c(C)n(-c3ccc(C#N)cc3)c2c1] | ¹H NMR at 100°C. (400 MHz, CDCl₃): δ 8.43 (s, 1H), 8.12 (m, 2H), 7.74 (m, 2H), 7.34 (s, 1H), 4.43 (s, 2H), 3.78 (s, 1H), 3.36 (m, 2H), 2.93 (m, 7H), 2.60 (s, 3H), 1.74-1.60 (m, 4H), 1.51-1.47 (m, 2H), 1.13 (t, 3H) | LC R$_T$ = 6.4 min; MS [M + H]⁺ = 458 m/z |

TABLE 2-continued

| Compound No. | General Synthetic Route Number | Structure | ¹H NMR | LC-MS |
|---|---|---|---|---|
| 383 | | 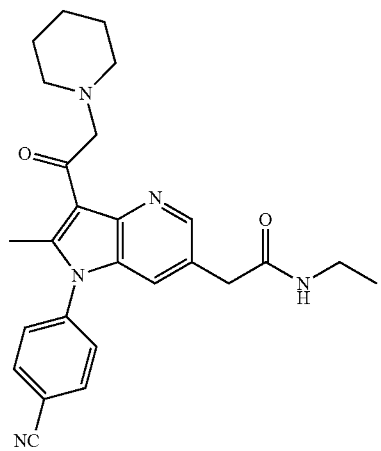 [SMILES: CCNC(=O)Cc1cnc2c(C(=O)CN3CCCCC3)c(C)n(-c3ccc(C#N)cc3)c2c1] | ¹H NMR (400 MHz, CDCl₃): δ 8.45 (d, 1H), 7.91 (d, 2H), 7.47 (d, 2H), 7.31 (d, 1H), 5.41 (brs, 1H), 4.31 (s, 2H), 3.55 (s, 2H), 3.26-3.19 (m, 2H), 2.67-2.62 (m, 7H), 1.70-1.63 (m, 4H), 1.48 (m, 2H), 1.07 (t, 3H) | LC R$_T$ = 10.3 min; MS [M + H]⁺ = 444 m/z |
| 384 | | 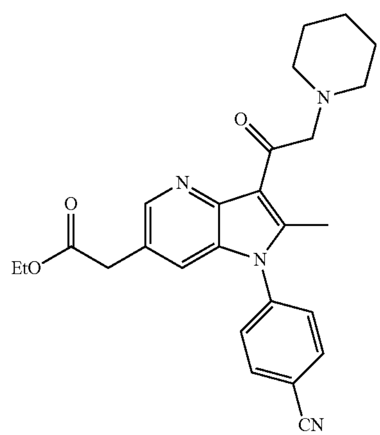 [SMILES: CCOC(=O)Cc1cnc2c(C(=O)CN3CCCCC3)c(C)n(-c3ccc(C#N)cc3)c2c1] | ¹H NMR (400 MHz, CDCl₃): δ 8.48 (d, 1H), 7.91 (d, 2H), 7.48 (d, 2H), 7.27 (d, 1H), 4.31 (s, 2H), 4.12 (q, 2H), 3.66 (s, 2H), 2.65 (s, 7H), 1.71-1.61 (m, 4H), 1.47 (brs, 2H), 1.24 (t, 3H) | LC R$_T$ = 8.1 min; MS [M + H]⁺ = 445 m/z |
| 385 | 2 | 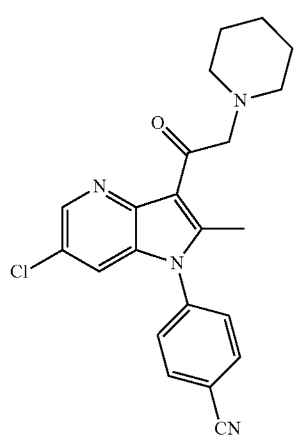 [SMILES: Cc1c(C(=O)CN2CCCCC2)c2ncc(Cl)cc2n1-c1ccc(C#N)cc1] | ¹H NMR (400 MHz, DMSO-d₆): δ 8.58 (d, 1H), 8.16 (d, 2H), 7.82 (d, 2H), 7.68 (d, 1H), 4.17 (brs, 2H), 2.58-2.50 (m, 7H), 1.54 (brs, 4H), 1.41 (brs, 2H) | LC R$_T$ = 6.3 min; MS: [M + H, ³⁵/³⁷Cl]⁺ = 393/395 m/z |

TABLE 2-continued

| Compound No. | General Synthetic Route Number | Structure | ¹H NMR | LC-MS |
|---|---|---|---|---|
| 386 | 4 | 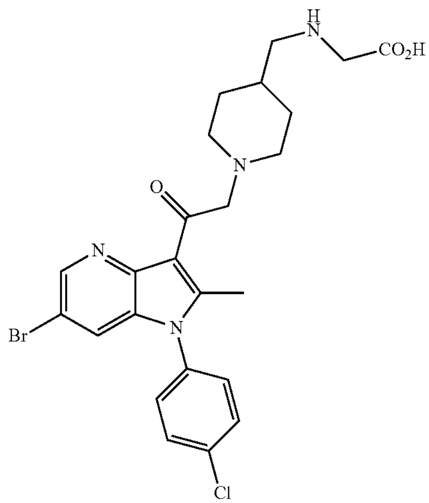 [SMILES: Cc1c(C(=O)CN2CCC(CNCC(=O)O)CC2)c2ncc(Br)cc2n1-c1ccc(Cl)cc1] | ¹H NMR (400 MHz, DMSO-$d_6$ at 80 °C.): δ 8.62 (s, 1H), 7.74-7.67 (m, 3H), 7.59 (d, 2H), 4.15 (s, 2H), 3.01 (brs, 4H), 2.75-2.63 (m, 2H), 2.55 (s, 3H), 2.33-2.24 (m, 2H), 1.91 (s, 1H), 1.78 (brs, 1H), 1.70 (brd, 2H), 1.58 (brs, 1H), 1.27-1.19 (m, 2H) | LC $R_T$ = 6.3 min; MS: [M + H, $^{35/37}$Cl, $^{79/81}$Br]$^+$ = 535/537 m/z |
| 387 | 2 | 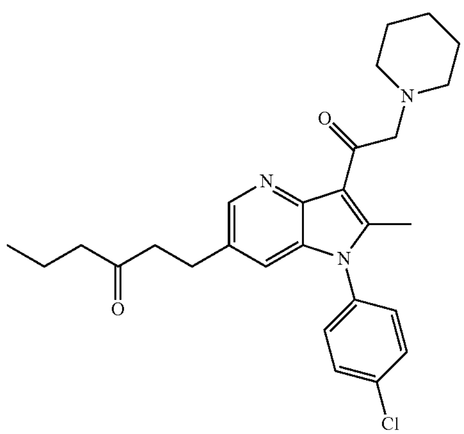 [SMILES: CCCC(=O)CCc1cnc2c(C(=O)CN3CCCCC3)c(C)n(-c3ccc(Cl)cc3)c2c1] | ¹H NMR (400 MHz, CDCl$_3$): δ 8.42 (s, 1H), 7.56 (d, 2H), 7.22 (d, occluded by solvent, 2H), 7.09 (s, 1H), 4.30 (s, 2H), 2.93 (t, 2H), 2.73-2.62 (m, 6H), 2.61 (s, 3H), 2.33 (t, 2H), 1.71-1.64 (m, 4H), 1.58-1.51 (m, 2H), 1.47 (brs, 2H), 0.85 (t, 3H), | LC $R_T$ = 9.6 min; MS: [M + H, $^{35/37}$Cl]$^+$ = 466/468 m/z |
| 388 | 2 | 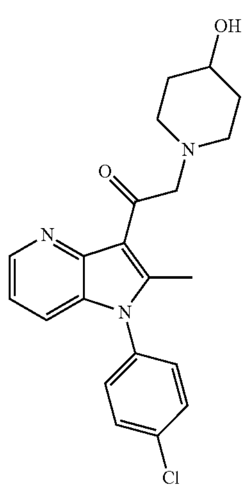 [SMILES: Cc1c(C(=O)CN2CCC(O)CC2)c2ncccc2n1-c1ccc(Cl)cc1] | ¹H NMR (400 MHz, DMSO-$d_6$): δ 8.53 (d, 1H), 7.72 (d, 2H), 7.58 (d, 2H), 7.45 (d, 1H), 7.20 (dd, 1H), 4.54 (d, 1H), 4.20 (s, 2H), 3.46 (brs, 1H), 2.91-2.86 (m, 2H), 2.56 (s, 3H), 2.28 (t, 2H), 1.72 (brd, 2H), 1.46-1.37 (m, 2H) | LC $R_T$ = 5.5 min; MS: [M + H, $^{35/37}$Cl]$^+$ = 384/386 m/z |

TABLE 2-continued
| Compound No. | General Synthetic Route Number | Structure | ¹H NMR | LC-MS |
|---|---|---|---|---|
| 389 | 1 | 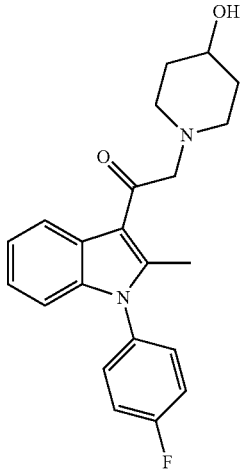 [SMILES: Cc1c(C(=O)CN2CCC(O)CC2)c2ccccc2n1-c1ccc(F)cc1] | ¹H NMR (400 MHz, DMSO-d$_6$): δ 8.08 (d, 1H), 7.56-7.46 (m, 4H), 7.23 (t, 1H), 7.16 (t, 1H), 6.93 (d, 1H), 3.65 (s, 2H), 3.45 (brs, 1H), 2.80 (brd, 2H), 2.53 (s, 3H), 2.22 (t, 2H), 1.71 (brd, 2H), 1.41-1.37 (m, 2H) | LC R$_T$ = 10.2 min; MS: [M + H]$^+$ = 367 m/z |
| 390 | 1 | 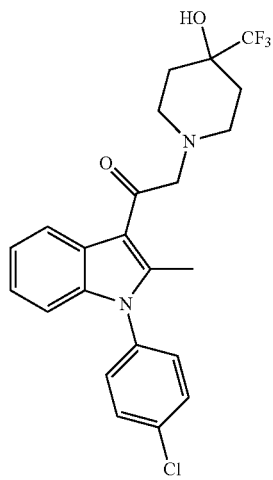 [SMILES: Cc1c(C(=O)CN2CCC(O)(C(F)(F)F)CC2)c2ccccc2n1-c1ccc(Cl)cc1] | ¹H NMR (400 MHz, CDCl$_3$): δ 7.97 (d, 1H), 7.56 (d, 2H), 7.31-7.25 (m, 3H), 7.17 (t, 1H), 7.00 (d, 1H), 3.91 (s, 2H), 3.03 (d, 2H), 2.61-2.54 (m, 5H), 2.14 (dt, 2H), 1.82 (s, 1H), 1.74 (d, 2H) | LC R$_T$ = 13.7 min; MS: [M + H, $^{35/37}$Cl]$^+$ = 451/453 m/z |
| 391 | 1 | 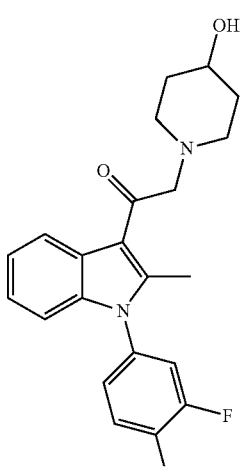 | ¹H NMR (400 MHz, DMSO-d$_6$): δ 8.08 (d, 1H), 7.83-7.70 (m, 2H), 7.40 (brd, 1H), 7.25 (t, 1H), 7.17 (t, 1H), 7.00 (d, 1H), 4.55 (d, 1H), 3.65 (s, 2H), 3.45 (brs, 1H), 2.80 (brd, 2H), 2.55 (s, 3H), 2.22 (t, 2H), 1.71 (brd, 2H), 1.44-1.35 (m, 2H) | LC R$_T$ = 10.1 min; MS: [M + H]$^+$ = 385 m/z |

TABLE 2-continued
| Compound No. | General Synthetic Route Number | Structure | ¹H NMR | LC-MS |
|---|---|---|---|---|
| 392 | 1 | 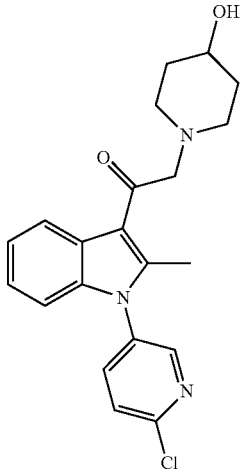 | ¹H NMR (400 MHz, DMSO-δ 8.62 (d, 1H), 8.11 (d, 1H), 8.09 (d, 1H), 7.83 (d, 1H), 7.25 (t, 1H), 7.17 (t, 1H), 7.03 (d, 1H), 4.54 (d, 1H), 3.66 (s, 2H), 3.49-3.41 (m, 1H), 2.80 (brd, 2H), 2.52 (s, 3H), 2.22 (t, 2H), 1.70 (brd, 2H), 1.45-1.35 (m, 2H) | LC $R_T$ = 1.0 min; MS: [M + H, $^{35/37}Cl]^+$ = 384/386 m/z |
| 393 | 1 | 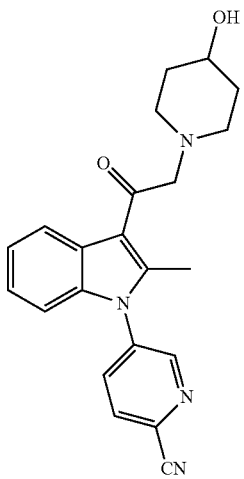 [SMILES: Cc1c(C(=O)CN2CCC(O)CC2)c2ccccc2n1-c1ccc(C#N)nc1] | ¹H NMR (400 MHz, DMSO-$d_6$): δ 8.95 (s, 1H), 8.43-8.35 (m, 2H), 8.09 (d, 1H), 7.28 (t, 1H), 7.21 (t, 1H), 7.07 (d, 1H), 4.54 (d, 2H), 3.67 (s, 2H), 3.50-3.39 (m, 1H), 2.83-2.75 (m, 2H), 2.55 (s, 3H), 2.22 (dt, 2H), 1.76-1.68 (m, 2H), 1.49-1.31 (m, 2H) | LC $R_T$ = 1.5 min; MS: [M + H]⁺ = 375 m/z |
| 394 | 1 | 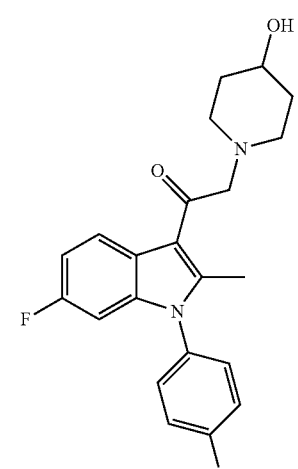 | ¹H NMR (400 MHz, DMSO-$d_6$): δ 8.11 (dd, 1H), 7.18 (d, 2H), 7.54 (d, 2H), 7.10 (dt, 1H), 6.77 (dd, 1H), 4.56 (d, 1H), 3.62 (s, 3H), 3.46-3.42 (m, 1H), 2.79 (brd, 1H), 2.53 (s, 3H), 2.21 (dt, 2H), 1.70 (brd, 2H), 1.43-1.33 (m, 2H) | LC $R_T$ = 5.6 min; MS: [M + H, $^{35/37}Cl]^+$ = 401/403 m/z |

TABLE 2-continued
| Compound No. | General Synthetic Route Number | Structure | ¹H NMR | LC-MS |
|---|---|---|---|---|
| 395 | 1 | 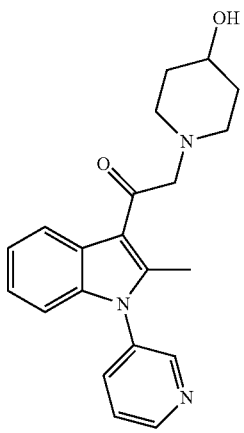 [SMILES: Cc1c(C(=O)CN2CCC(O)CC2)c2ccccc2n1-c1cccnc1] | ¹H NMR (400 MHz, DMSO-d₆): δ 8.81 (d, 1H), 8.73 (s, 1H), 8.10 (d, 1H), 8.02 (dt, 1H), 7.72 (dd, 1H), 7.26 (t, 1H), 7.18 (t, 1H), 6.96 (d, 1H), 4.54 (d, 1H), 3.66 (s, 2H), 3.48-3.43 (m, 1H), 2.80 (brd, 2H), 2.55 (s, 3H), 2.23 (t, 2H), 1.73 (brd, 2H), 1.44-1.35 (m, 2H) | LC R$_T$ = 1.0 min; MS: [M + H]⁺ = 350 m/z |
| 396 | 1 | 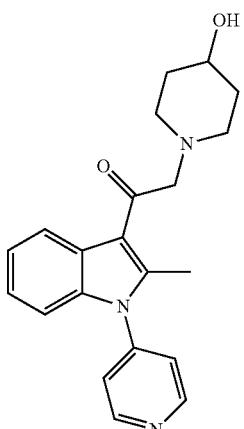 | ¹H NMR (400 MHz, DMSO-d₆): δ 8.87 (d, 2H), 8.10 (d, 1H), 7.61 (d, 2H), 7.27 (t, 1H), 7.19 (t, 1H), 7.10 (d, 1H), 4.54 (d, 1H), 3.66 (s, 2H), 3.48-3.43 (m, 1H), 2.80 (brd, 2H), 2.59 (s, 3H), 2.23 (s, 3H), 1.71 (brd, 2H), 1.44-1.35 (m, 2H) | LC R$_T$ = 0.7 min; MS: [M + H]⁺ = 350 m/z |
| 397 | 1 | 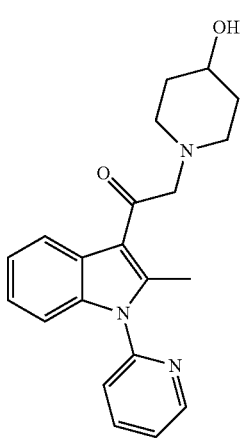 [SMILES: Cc1c(C(=O)CN2CCC(O)CC2)c2ccccc2n1-c1ccccn1] | ¹H NMR (400 MHz, DMSO-d₆): δ 8.75 (d, 2H), 8.20-8.07 (m, 2H), 7.69-7.61 (m, 2H, 7.27-7.10 (m, 3H), 4.54 (d, 1H), 3.66 (s, 2H), 3.46 (brs, 1H), 2.80 (brd, 2H), 2.61 (s, 3H), 2.28 (t, 2H), 1.71 (brd, 2H), 1.44-1.23 (m, 2H) | LC R$_T$ = 1.4 min; MS: [M + H]⁺ = 350 m/z |

TABLE 2-continued

| Compound No. | General Synthetic Route Number | Structure | ¹H NMR | LC-MS |
|---|---|---|---|---|
| 398 | 1 | 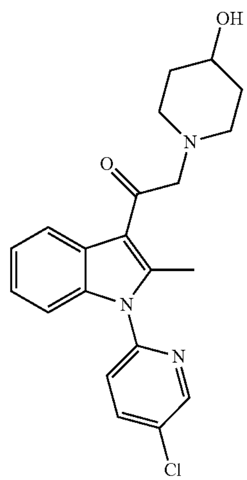 [SMILES: Cc1c(C(=O)CN2CCC(O)CC2)c2ccccc2n1-c1ccc(Cl)cn1] | ¹H NMR (400 MHz, DMSO-d₆): δ 8.82 (d, 1H), 8.29 (dd, 1H), 8.09 (d, 1H), 7.75 (d, 1H), 7.29-7.17 (m, 3H), 4.54 (d, 1H), 3.65 (s, 2H), 3.48-3.42 (m, 1H), 2.81-2.76 (m, 2H), 2.67 (s, 3H), 2.22 (t, 2H), 1.70 (brd, 2H), 1.43-1.34 (m, 2H) | LC $R_T$ = 2.0 min; MS: [M + H, $^{35/37}$Cl]⁺ = 384/386 m/z |
| 399 | 1 | 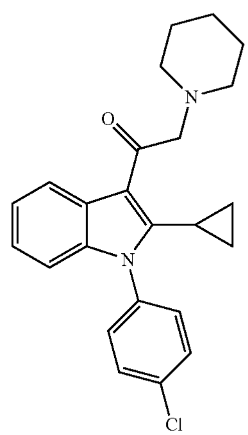 [SMILES: O=C(CN1CCCCC1)c1c(C2CC2)n(-c2ccc(Cl)cc2)c2ccccc12] | ¹H NMR (400 MHz, DMSO-d₆): δ 8.10 (d, 1H), 7.70 (d, 2H), 7.59 (d, 2H), 7.24-7.16 (m, 2H), 7.06 (d, 1H), 3.80 (s, 2H), 2.49 (brs, occluded by solvent, 4H), 2.31-2.27 (m, 1H), 1.50 (brs, 2H), 1.41 (brs, 2H), 0.87-0.83 (m, 2H), 0.44-0.41 (m, 2H) | LC $R_T$ = 2.0 min; MS: [M + H, $^{35/37}$Cl]⁺: 393/395 m/z |
| 400 | 1 | 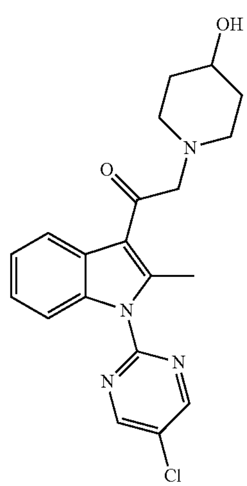 [SMILES: Cc1c(C(=O)CN2CCC(O)CC2)c2ccccc2n1-c1ncc(Cl)cn1] | ¹H NMR (400 MHz, DMSO-d₆): δ 9.19 (s, 2H), 8.08 (d, 1H), 7.74 (d, 1H), 7.29-7.22 (m, 2H), 4.53 (brs, 1H), 3.68 (s, 2H), 3.44 (brs, 1H), 2.80-2.73 (m, 5H), 2.22 (brt, 2H), 1.70 (brd, 2H), 1.40-1.33 (m, 2H) | LC $R_T$ = 1.6 min; MS: [M + H, $^{35/37}$Cl]⁺ = 385/387 m/z |

TABLE 2-continued

| Compound No. | General Synthetic Route Number | Structure | ¹H NMR | LC-MS |
|---|---|---|---|---|
| 401 | 1 | 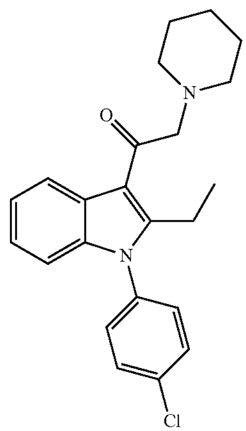 [SMILES: CCc1c(C(=O)CN2CCCCC2)c2ccccc2n1-c1ccc(Cl)cc1] | ¹H NMR (400 MHz, DMSO-$d_6$): δ 7.99 (d, 1H), 7.72 (d, 2H), 7.55 (d, 2H), 7.25 (t, 1H), 7.16 (t, 1H), 6.90 (d, 1H), 3.70 (s, 2H), 2.96-2.89 (m, 2H), 2.50 (brs, occluded by solvent, 4H), 1.51 (brs, 4H), 1.43 (brs, 2H), 1.05 (t, 3H) | LC $R_T$ = 1.9 min; MS: [M + H, $^{35/37}$Cl]$^+$ = 381/383 m/z |
| 402 | 1 | 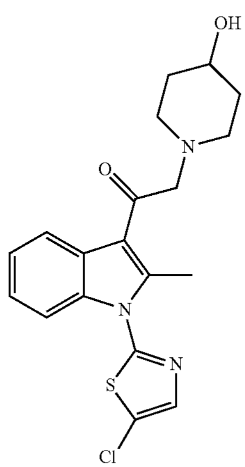 [SMILES: Cc1c(C(=O)CN2CCC(O)CC2)c2ccccc2n1-c1ncc(Cl)s1] | ¹H NMR (400 MHz, DMSO-$d_6$): δ 8.11 (s, 1H), 8.10 (d, 1H), 7.40 (d, 1H), 7.33-7.25 (m, 2H), 4.54 (brs, 1H), 3.66 (brs, 2H), 3.45 (brs, 1H), 2.78 (brs, 2H), 2.68 (s, 3H), 2.22 (brs, 2H), 1.70 (brd, 2H), 1.39-1.22 (m, 2H) | LC $R_T$ = 1.2 min; MS: [M + H, $^{35/37}$Cl]$^+$ = 390/392 m/z |

Example 17

USP14 Inhibition Assay

Using previously described methodology [B. H. Lee et al. Nature 2010, 467 (9), 179, the contents of which are expressly incorporated by reference herein], select compounds described herein were found to inhibit USP14 as delineated in Table 3. "I" in the Table below designates an $IC_{50}$ of >5 μM, "II" in the Table below designates and $IC_{50}$ between 0.5 and 5 μM, and "III" designates an $IC_{50}$<0.5 μM. The $IC_{50}$ values in the Table below represent the average value from a minimum of two experimental determinations.

TABLE 3
| Compound No. | Chemical Structure | IC$_{50}$ Category |
|---|---|---|
| 30 | 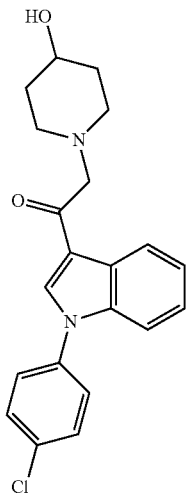 [SMILES: O=C(CN1CCC(O)CC1)c1cn(-c2ccc(Cl)cc2)c2ccccc12] | I |
| 31 | 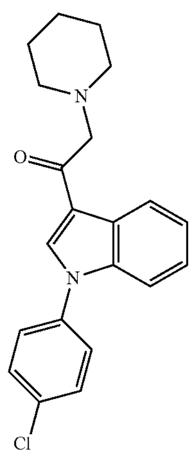 [SMILES: O=C(CN1CCCCC1)c1cn(-c2ccc(Cl)cc2)c2ccccc12] | I |
| 34 | 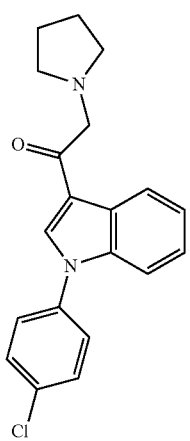 [SMILES: O=C(CN1CCCC1)c1cn(-c2ccc(Cl)cc2)c2ccccc12] | I |

TABLE 3-continued
| Compound No. | Chemical Structure | IC$_{50}$ Category |
|---|---|---|
| 86 | 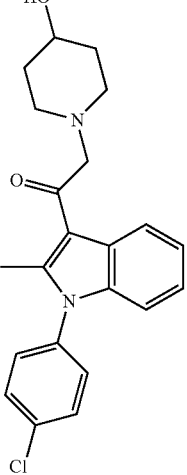 | III |
| 87 | 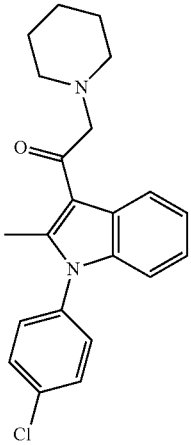 [SMILES: Cc1c(C(=O)CN2CCCCC2)c2ccccc2n1-c1ccc(Cl)cc1] | III |
| 88 | 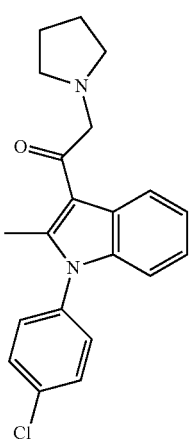 [SMILES: Cc1c(C(=O)CN2CCCC2)c2ccccc2n1-c1ccc(Cl)cc1] | III |

TABLE 3-continued

| Compound No. | Chemical Structure | IC$_{50}$ Category |
| --- | --- | --- |
| 98 | 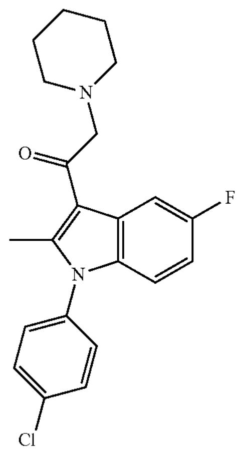 | III |
| 106 | 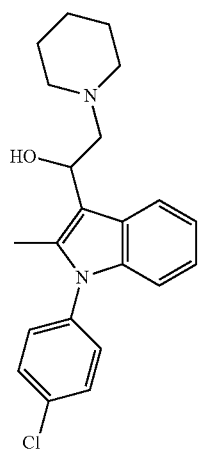 [SMILES: Cc1c(C(O)CN2CCCCC2)c2ccccc2n1-c1ccc(Cl)cc1] | I |
| 108 | 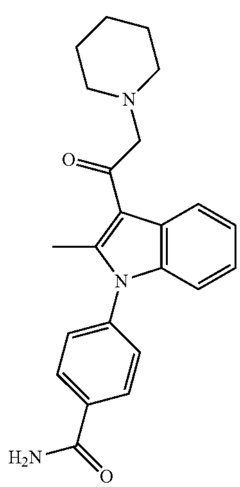 [SMILES: Cc1c(C(=O)CN2CCCCC2)c2ccccc2n1-c1ccc(C(N)=O)cc1] | I |

TABLE 3-continued
| Compound No. | Chemical Structure | IC$_{50}$ Category |
|---|---|---|
| 115 | 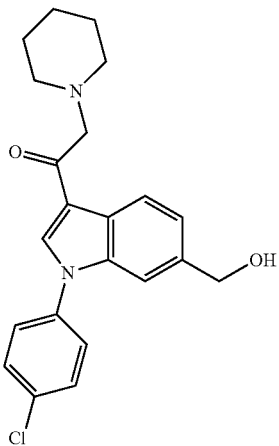 [SMILES: O=C(CN1CCCCC1)c1cn(-c2ccc(Cl)cc2)c2cc(CO)ccc12] | I |
| 116 | 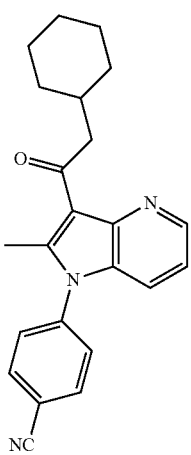 [SMILES: Cc1c(C(=O)CC2CCCCC2)c2ncccc2n1-c1ccc(C#N)cc1] | I |
| 118 | 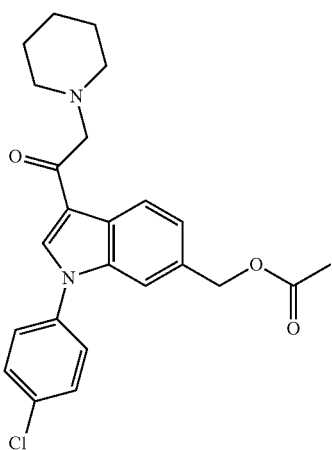 [SMILES: CC(=O)OCc1ccc2c(C(=O)CN3CCCCC3)cn(-c3ccc(Cl)cc3)c2c1] | I |

TABLE 3-continued

| Compound No. | Chemical Structure | IC$_{50}$ Category |
|---|---|---|
| 119 | 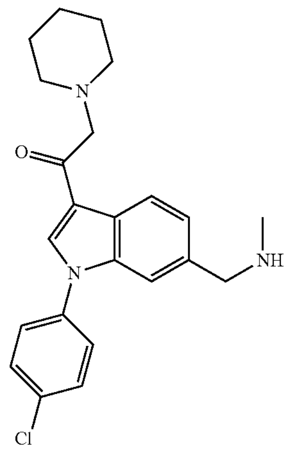 | I |
| 120 | 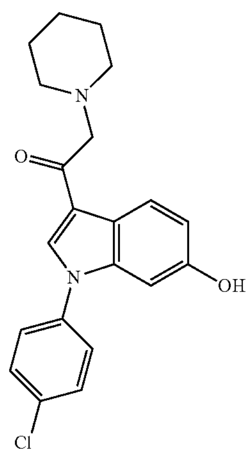 [SMILES: O=C(CN1CCCCC1)c1cn(-c2ccc(Cl)cc2)c2cc(O)ccc12] | I |
| 126 | 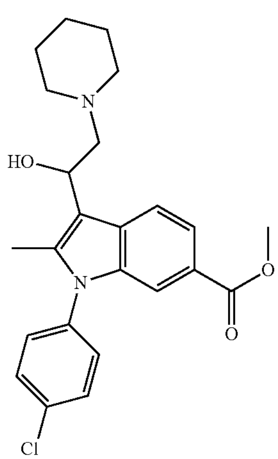 | I |

TABLE 3-continued
| Compound No. | Chemical Structure | IC$_{50}$ Category |
|---|---|---|
| 127 | 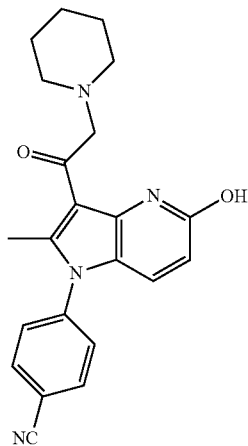 | I |
| 128 | 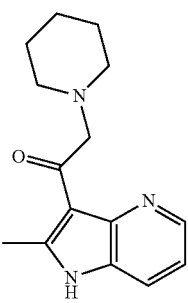 | I |
| 130 | 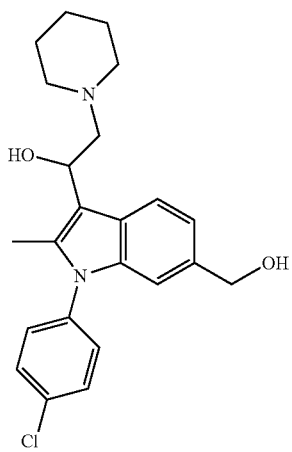 [SMILES: Cc1c(C(O)CN2CCCCC2)c2ccc(CO)cc2n1-c1ccc(Cl)cc1] | I |

TABLE 3-continued
| Compound No. | Chemical Structure | IC$_{50}$ Category |
|---|---|---|
| 131 | 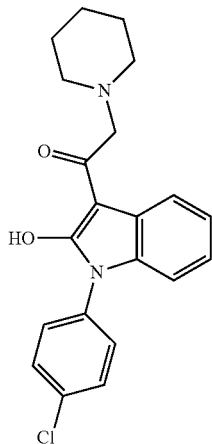 | I |
| 132 | 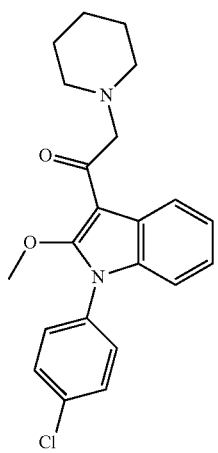 | I |
| 133 | 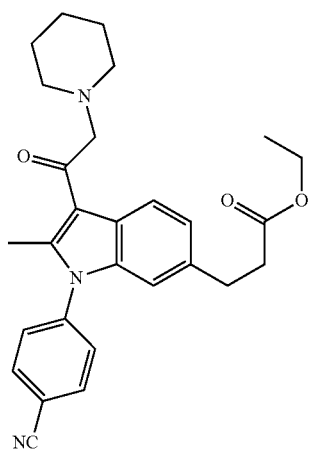 [SMILES: CCOC(=O)CCc1ccc2c(C(=O)CN3CCCCC3)c(C)n(-c3ccc(C#N)cc3)c2c1] | III |

TABLE 3-continued
| Compound No. | Chemical Structure | IC$_{50}$ Category |
|---|---|---|
| 141 | 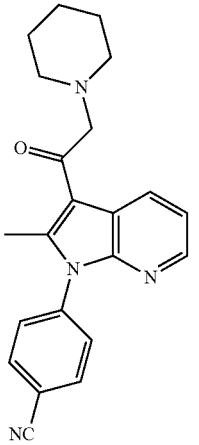 [SMILES: Cc1c(C(=O)CN2CCCCC2)c2cccnc2n1-c1ccc(C#N)cc1] | II |
| 142 | 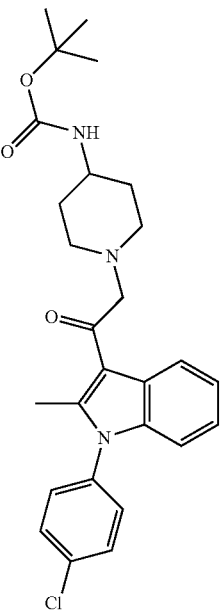 [SMILES: Cc1c(C(=O)CN2CCC(NC(=O)OC(C)(C)C)CC2)c2ccccc2n1-c1ccc(Cl)cc1] | II |
| 144 | 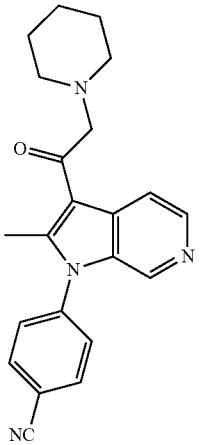 [SMILES: Cc1c(C(=O)CN2CCCCC2)c2ccncc2n1-c1ccc(C#N)cc1] | II |

TABLE 3-continued
| Compound No. | Chemical Structure | IC$_{50}$ Category |
|---|---|---|
| 145 | 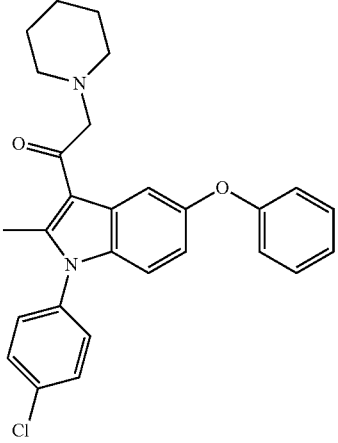 [SMILES: Cc1c(C(=O)CN2CCCCC2)c2cc(Oc3ccccc3)ccc2n1-c1ccc(Cl)cc1] | II |
| 146 | 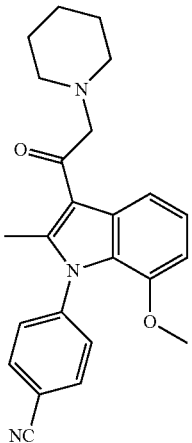 | II |
| 147 | 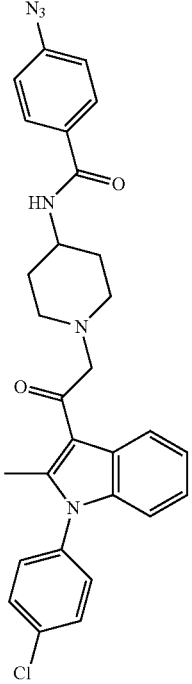 [SMILES: Cc1c(C(=O)CN2CCC(NC(=O)c3ccc(N=[N+]=[N-])cc3)CC2)c2ccccc2n1-c1ccc(Cl)cc1] | II |

TABLE 3-continued

| Compound No. | Chemical Structure | IC$_{50}$ Category |
|---|---|---|
| 148 | 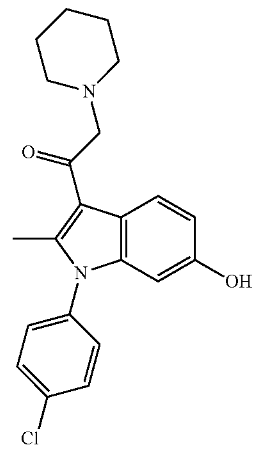 | II |
| 149 | 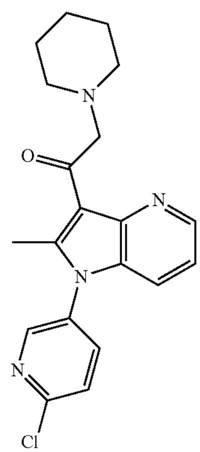 [SMILES: Cc1c(C(=O)CN2CCCCC2)c2ncccc2n1-c1ccc(Cl)nc1] | II |
| 150 | 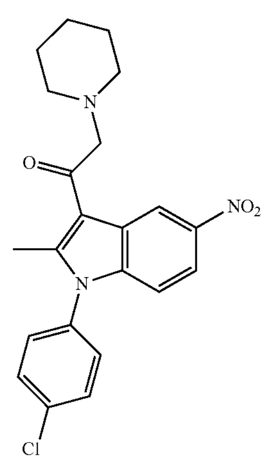 [SMILES: Cc1c(C(=O)CN2CCCCC2)c2cc([N+](=O)[O-])ccc2n1-c1ccc(Cl)cc1] | II |

TABLE 3-continued
| Compound No. | Chemical Structure | IC$_{50}$ Category |
|---|---|---|
| 151 | 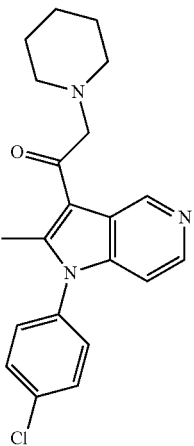 [SMILES: Cc1c(C(=O)CN2CCCCC2)c2cnccc2n1-c1ccc(Cl)cc1] | II |
| 152 | 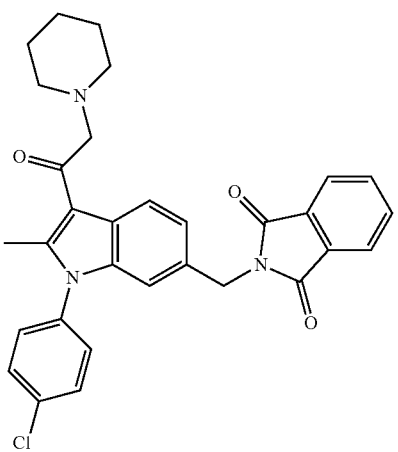 [SMILES: Cc1c(C(=O)CN2CCCCC2)c2ccc(CN3C(=O)c4ccccc4C3=O)cc2n1-c1ccc(Cl)cc1] | II |
| 153 | 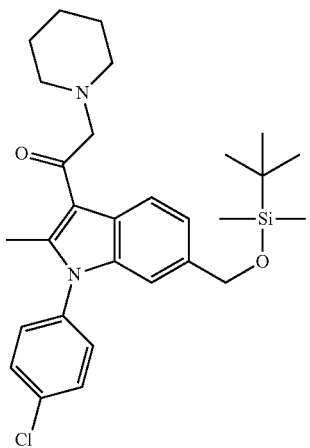 | II |

TABLE 3-continued
| Compound No. | Chemical Structure | IC$_{50}$ Category |
|---|---|---|
| 155 | 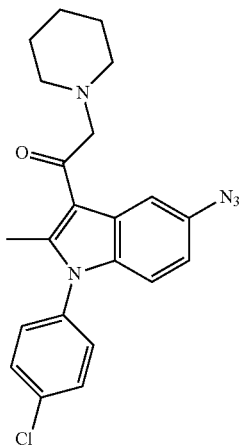 [SMILES: Cc1c(C(=O)CN2CCCCC2)c2cc(N=[N+]=[N-])ccc2n1-c1ccc(Cl)cc1] | III |
| 156 | 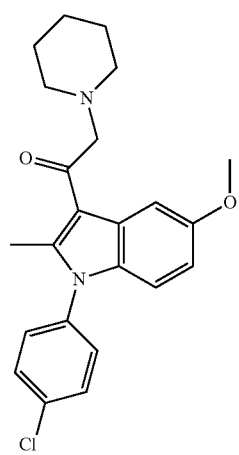 | III |
| 160 | 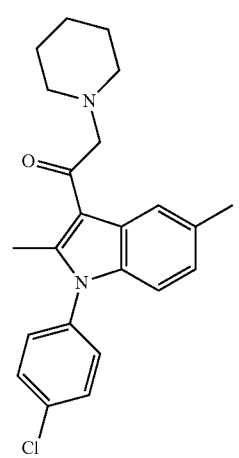 | III |

TABLE 3-continued
| Compound No. | Chemical Structure | IC$_{50}$ Category |
|---|---|---|
| 161 | 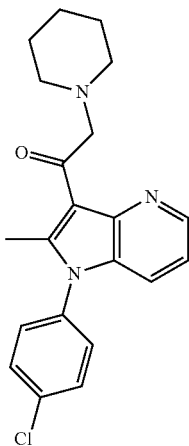 | III |
| 162 | 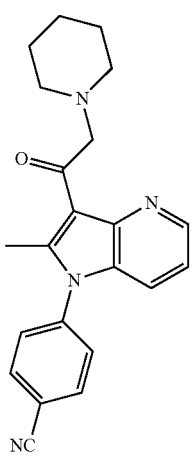 | III |
| 163 | 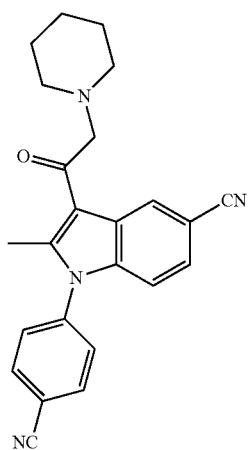 [SMILES: Cc1c(C(=O)CN2CCCCC2)c2cc(C#N)ccc2n1-c1ccc(C#N)cc1] | III |

TABLE 3-continued
| Compound No. | Chemical Structure | IC$_{50}$ Category |
|---|---|---|
| 164 | 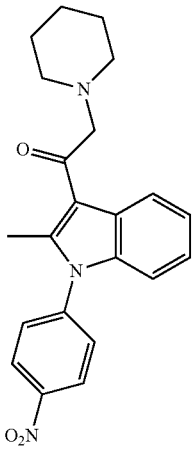 [SMILES: Cc1c(C(=O)CN2CCCCC2)c2ccccc2n1-c1ccc([N+](=O)[O-])cc1] | III |
| 165 | 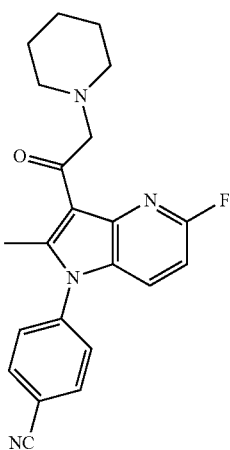 | III |
| 167 | 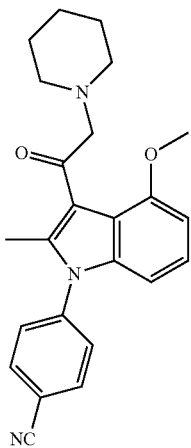 | III |

TABLE 3-continued
| Compound No. | Chemical Structure | IC$_{50}$ Category |
|---|---|---|
| 168 | 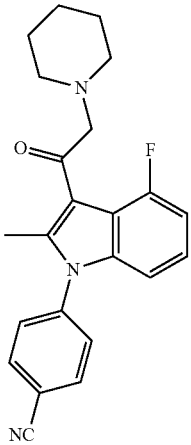 [SMILES: Cc1c(C(=O)CN2CCCCC2)c2c(F)cccc2n1-c1ccc(C#N)cc1] | III |
| 169 | 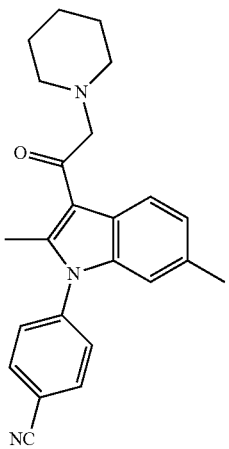 | III |
| 170 | 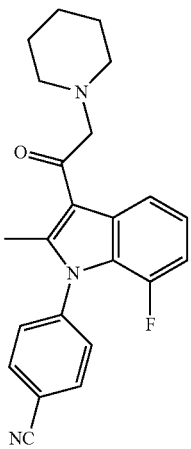 [SMILES: Cc1c(C(=O)CN2CCCCC2)c2cccc(F)c2n1-c1ccc(C#N)cc1] | III |

TABLE 3-continued
| Compound No. | Chemical Structure | IC$_{50}$ Category |
|---|---|---|
| 171 | 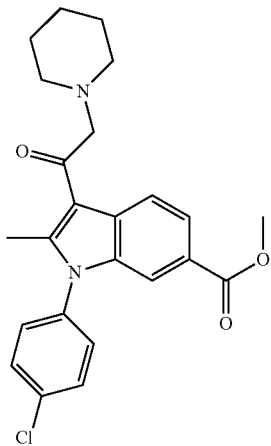 | III |
| 172 | 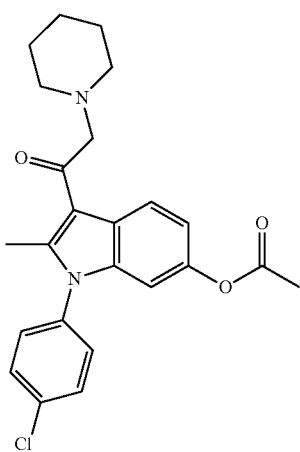 [SMILES: CC(=O)Oc1ccc2c(C(=O)CN3CCCCC3)c(C)n(-c3ccc(Cl)cc3)c2c1] | III |
| 173 | 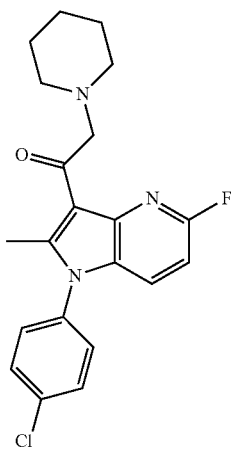 | III |

TABLE 3-continued
| Compound No. | Chemical Structure | IC$_{50}$ Category |
|---|---|---|
| 175 | 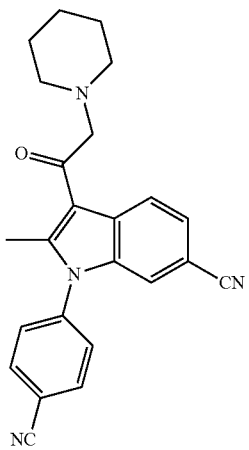 | III |
| 176 | 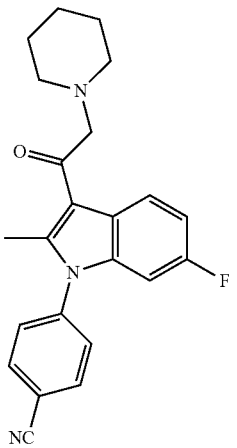 [SMILES: Cc1c(C(=O)CN2CCCCC2)c2ccc(F)cc2n1-c1ccc(C#N)cc1] | III |
| 177 | 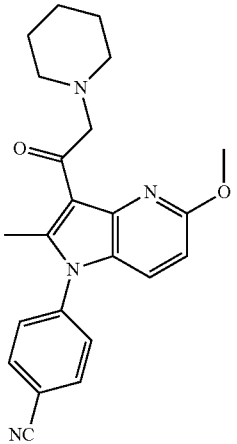 | III |

TABLE 3-continued
| Compound No. | Chemical Structure | IC$_{50}$ Category |
|---|---|---|
| 178 | 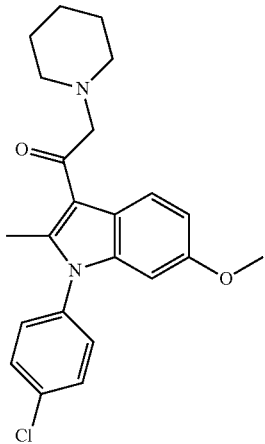 | III |
| 179 | 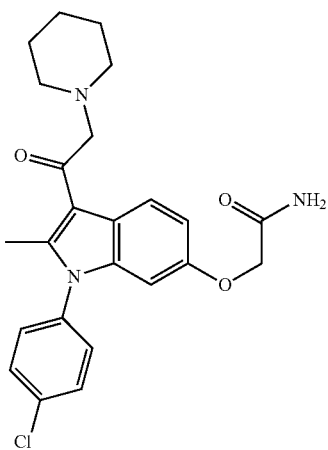 [SMILES: Cc1c(C(=O)CN2CCCCC2)c2ccc(OCC(N)=O)cc2n1-c1ccc(Cl)cc1] | III |
| 180 | 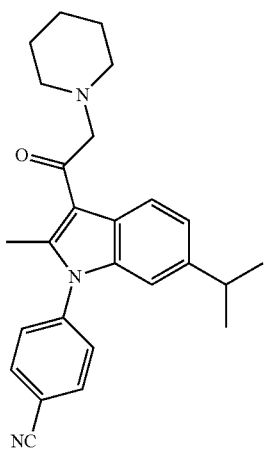 [SMILES: Cc1c(C(=O)CN2CCCCC2)c2ccc(C(C)C)cc2n1-c1ccc(C#N)cc1] | III |

TABLE 3-continued
| Compound No. | Chemical Structure | IC$_{50}$ Category |
|---|---|---|
| 181 | 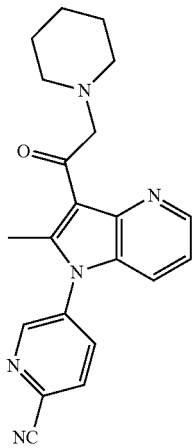 | III |
| 182 | 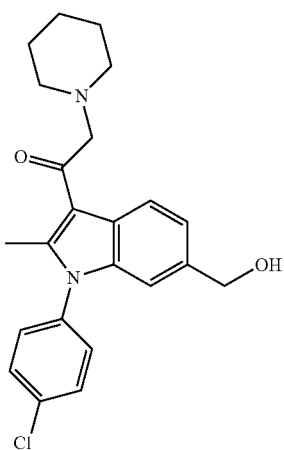 [SMILES: Cc1c(C(=O)CN2CCCCC2)c2ccc(CO)cc2n1-c1ccc(Cl)cc1] | III |
| 183 | 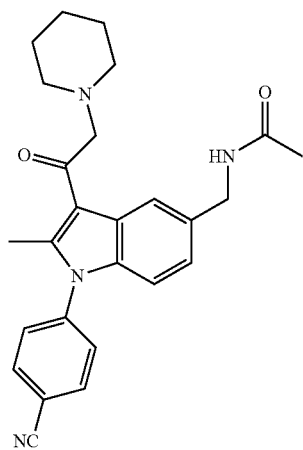 [SMILES: CC(=O)NCc1ccc2c(c1)c(C(=O)CN1CCCCC1)c(C)n2-c1ccc(C#N)cc1] | III |

TABLE 3-continued
| Compound No. | Chemical Structure | IC$_{50}$ Category |
|---|---|---|
| 184 | 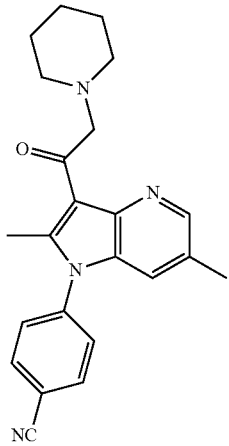 | III |
| 185 | 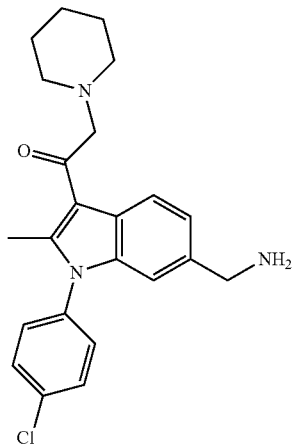 [SMILES: Cc1c(C(=O)CN2CCCCC2)c2ccc(CN)cc2n1-c1ccc(Cl)cc1] | III |
| 186 | 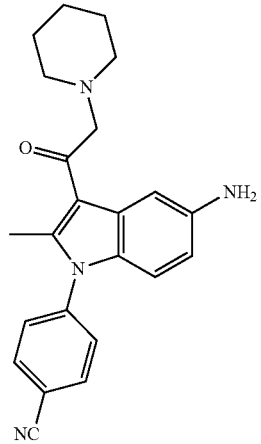 [SMILES: Cc1c(C(=O)CN2CCCCC2)c2cc(N)ccc2n1-c1ccc(C#N)cc1] | III |

TABLE 3-continued

| Compound No. | Chemical Structure | IC$_{50}$ Category |
|---|---|---|
| 187 | 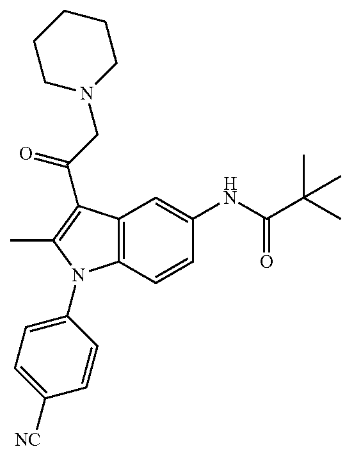 [SMILES: Cc1c(C(=O)CN2CCCCC2)c2cc(NC(=O)C(C)(C)C)ccc2n1-c1ccc(C#N)cc1] | III |
| 188 | 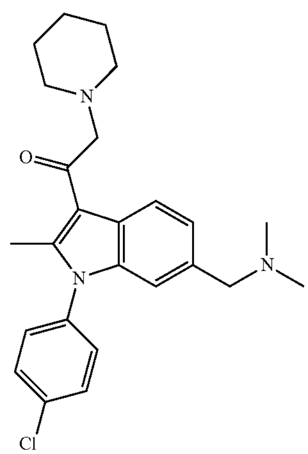 | III |
| 189 | 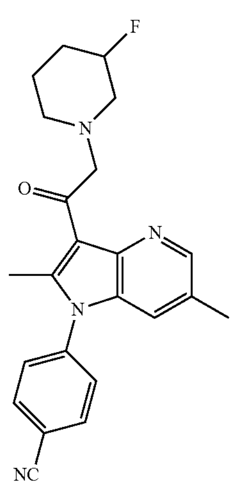 | III |

TABLE 3-continued

| Compound No. | Chemical Structure | IC$_{50}$ Category |
|---|---|---|
| 190 | 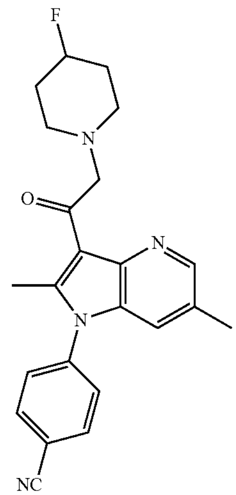 | III |
| 191 | 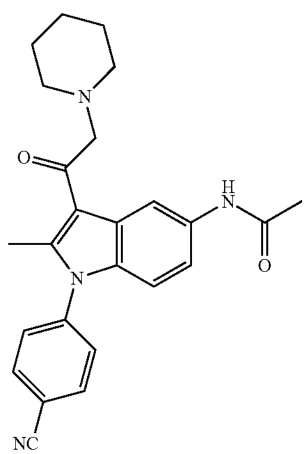 [SMILES: CC(=O)Nc1ccc2c(c1)c(C(=O)CN1CCCCC1)c(C)n2-c1ccc(C#N)cc1] | III |
| 192 | 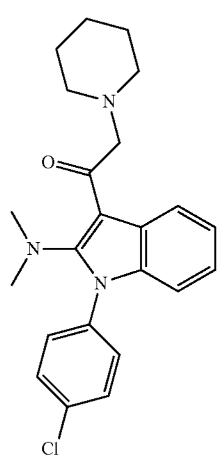 [SMILES: CN(C)c1c(C(=O)CN2CCCCC2)c2ccccc2n1-c1ccc(Cl)cc1] | I |

TABLE 3-continued
| Compound No. | Chemical Structure | IC$_{50}$ Category |
|---|---|---|
| 193 | 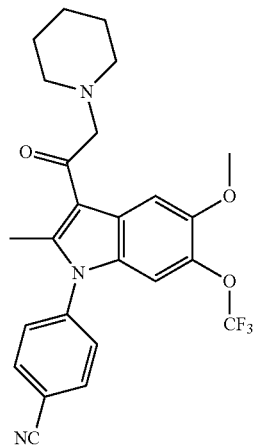 [SMILES: COc1cc2c(C(=O)CN3CCCCC3)c(C)n(-c3ccc(C#N)cc3)c2cc1OC(F)(F)F] | II |
| 194 | 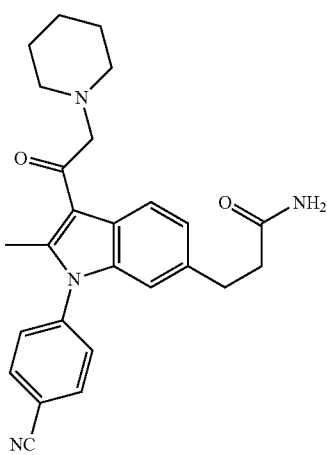 [SMILES: Cc1c(C(=O)CN2CCCCC2)c2ccc(CCC(N)=O)cc2n1-c1ccc(C#N)cc1] | III |
| 195 | 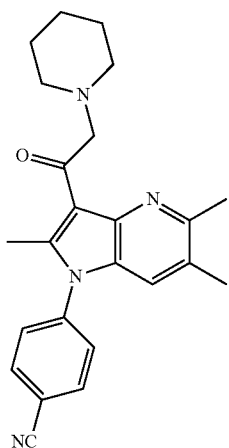 | III |

TABLE 3-continued
| Compound No. | Chemical Structure | IC$_{50}$ Category |
|---|---|---|
| 196 | 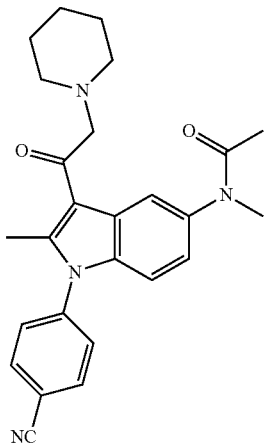 [SMILES: CC(=O)N(C)c1ccc2c(c1)c(C(=O)CN1CCCCC1)c(C)n2-c1ccc(C#N)cc1] | III |
| 197 | 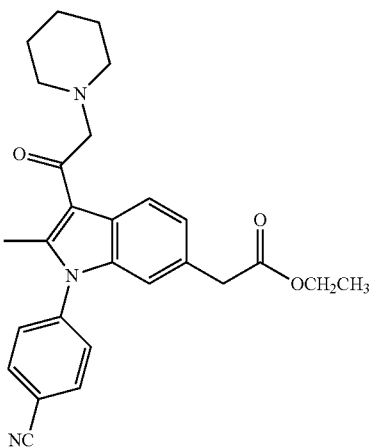 [SMILES: CCOC(=O)Cc1ccc2c(C(=O)CN3CCCCC3)c(C)n(-c3ccc(C#N)cc3)c2c1] | III |
| 198 | 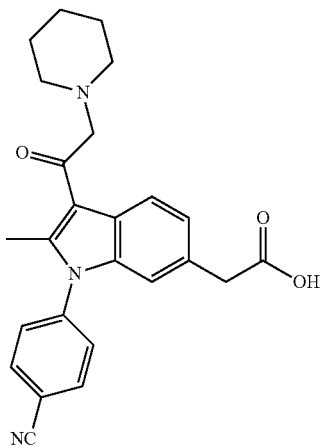 [SMILES: Cc1c(C(=O)CN2CCCCC2)c2ccc(CC(=O)O)cc2n1-c1ccc(C#N)cc1] | III |

TABLE 3-continued
| Compound No. | Chemical Structure | IC$_{50}$ Category |
|---|---|---|
| 199 | 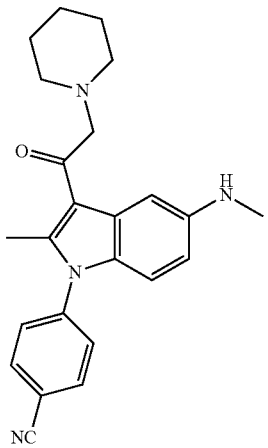 | III |
| 200 | 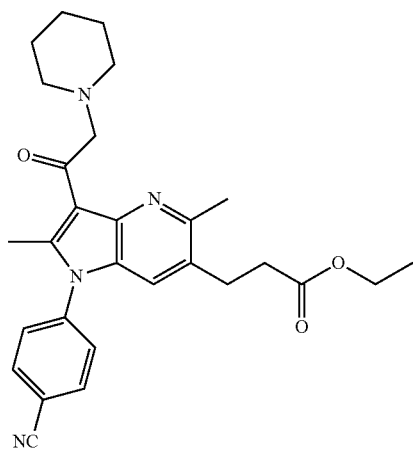 [SMILES: CCOC(=O)CCc1cc2c(nc1C)c(C(=O)CN1CCCCC1)c(C)n2-c1ccc(C#N)cc1] | III |
| 201 | 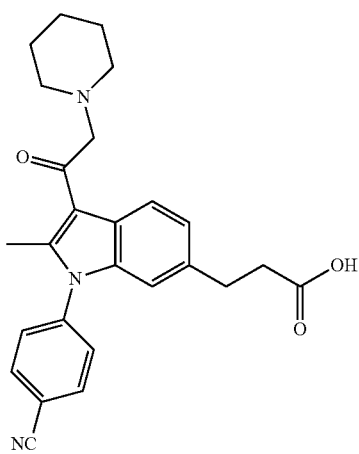 [SMILES: Cc1c(C(=O)CN2CCCCC2)c2ccc(CCC(=O)O)cc2n1-c1ccc(C#N)cc1] | III |

TABLE 3-continued
| Compound No. | Chemical Structure | IC$_{50}$ Category |
|---|---|---|
| 202 | 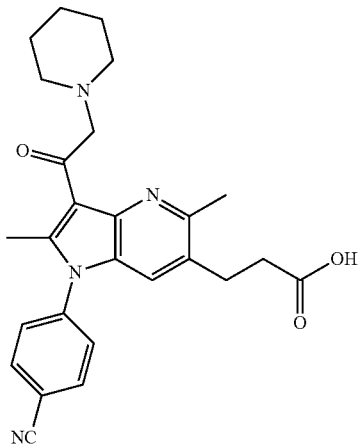 [SMILES: Cc1nc2c(C(=O)CN3CCCCC3)c(C)n(-c3ccc(C#N)cc3)c2cc1CCC(=O)O] | III |
| 203 | 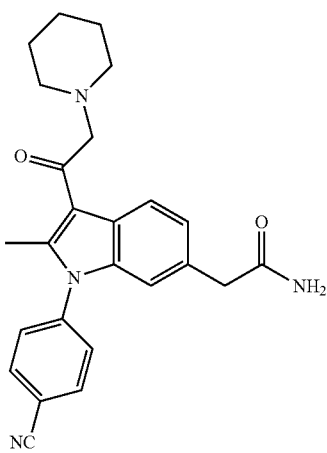 [SMILES: Cc1c(C(=O)CN2CCCCC2)c2ccc(CC(N)=O)cc2n1-c1ccc(C#N)cc1] | III |
| 204 | 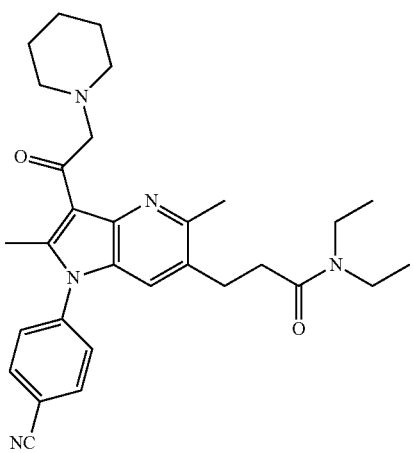 [SMILES: CCN(CC)C(=O)CCc1cc2c(nc1C)c(C(=O)CN1CCCCC1)c(C)n2-c1ccc(C#N)cc1] | III |

TABLE 3-continued
| Compound No. | Chemical Structure | IC$_{50}$ Category |
|---|---|---|
| 205 | 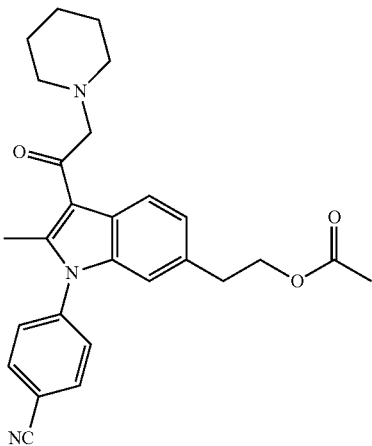 [SMILES: CC(=O)OCCc1ccc2c(C(=O)CN3CCCCC3)c(C)n(-c3ccc(C#N)cc3)c2c1] | III |
| 206 | 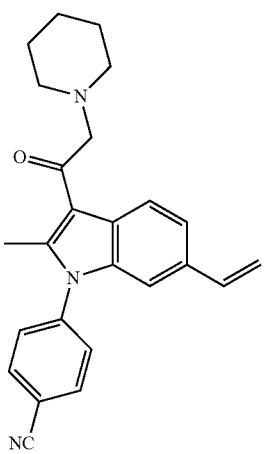 [SMILES: C=Cc1ccc2c(C(=O)CN3CCCCC3)c(C)n(-c3ccc(C#N)cc3)c2c1] | III |
| 207 | 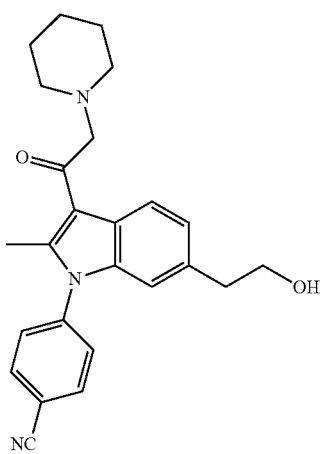 [SMILES: Cc1c(C(=O)CN2CCCCC2)c2ccc(CCO)cc2n1-c1ccc(C#N)cc1] | III |

TABLE 3-continued
| Compound No. | Chemical Structure | IC$_{50}$ Category |
|---|---|---|
| 208 | 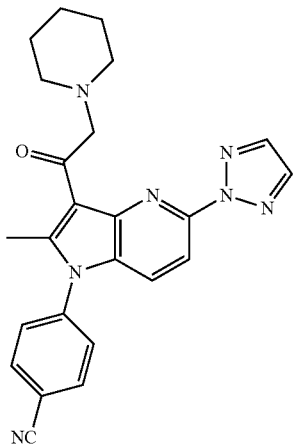 [SMILES: Cc1c(C(=O)CN2CCCCC2)c2nc(-n3nccn3)ccc2n1-c1ccc(C#N)cc1] | III |
| 209 | 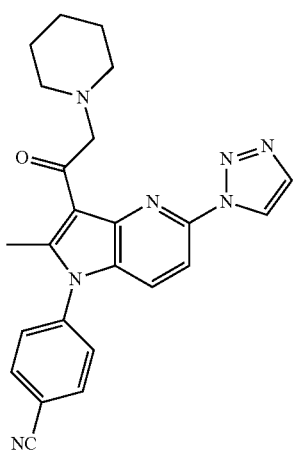 [SMILES: Cc1c(C(=O)CN2CCCCC2)c2nc(-n3ccnn3)ccc2n1-c1ccc(C#N)cc1] | III |
| 210 | 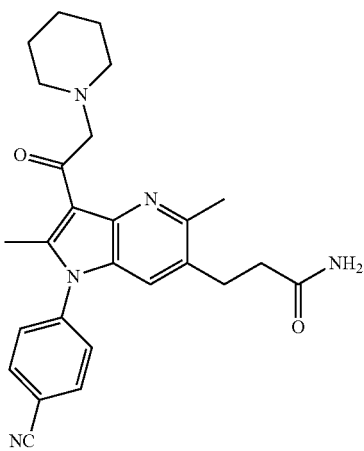 [SMILES: Cc1nc2c(C(=O)CN3CCCCC3)c(C)n(-c3ccc(C#N)cc3)c2cc1CCC(N)=O] | III |

TABLE 3-continued
| Compound No. | Chemical Structure | IC$_{50}$ Category |
|---|---|---|
| 296 | 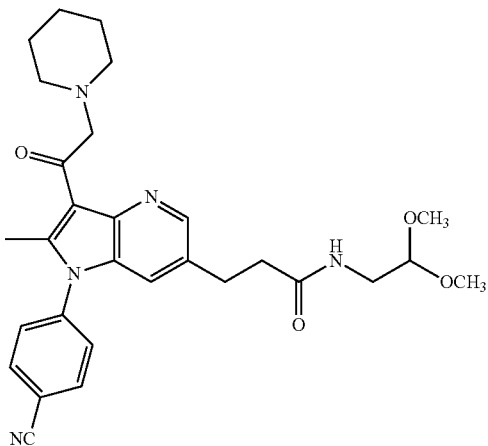 [SMILES: COC(CNC(=O)CCc1cnc2c(C(=O)CN3CCCCC3)c(C)n(-c3ccc(C#N)cc3)c2c1)OC] | III |
| 297 | 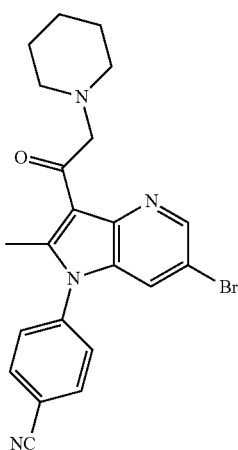 [SMILES: Cc1c(C(=O)CN2CCCCC2)c2ncc(Br)cc2n1-c1ccc(C#N)cc1] | III |
| 298 | 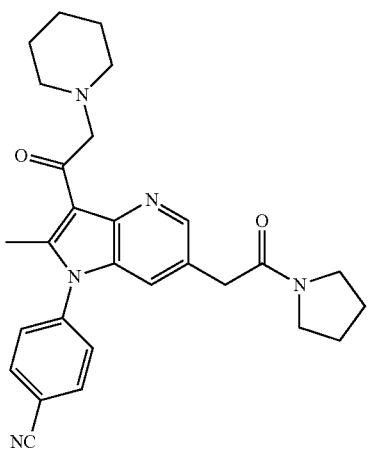 [SMILES: Cc1c(C(=O)CN2CCCCC2)c2ncc(CC(=O)N3CCCC3)cc2n1-c1ccc(C#N)cc1] | III |

TABLE 3-continued
| Compound No. | Chemical Structure | IC$_{50}$ Category |
|---|---|---|
| 299 | 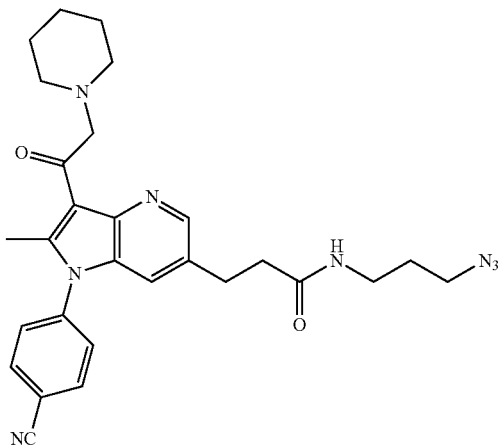 [SMILES: Cc1c(C(=O)CN2CCCCC2)c2ncc(CCC(=O)NCCCN=[N+]=[N-])cc2n1-c1ccc(C#N)cc1] | III |
| 300 | 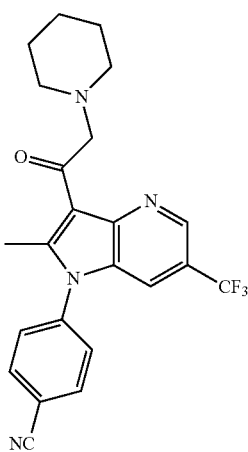 [SMILES: Cc1c(C(=O)CN2CCCCC2)c2ncc(C(F)(F)F)cc2n1-c1ccc(C#N)cc1] | III |
| 301 | 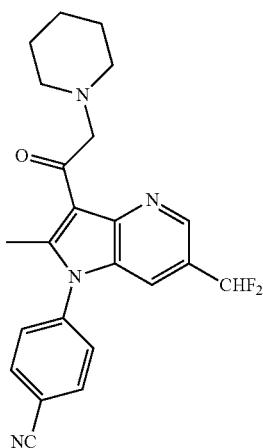 [SMILES: Cc1c(C(=O)CN2CCCCC2)c2ncc(C(F)F)cc2n1-c1ccc(C#N)cc1] | III |

TABLE 3-continued
| Compound No. | Chemical Structure | IC$_{50}$ Category |
|---|---|---|
| 302 | 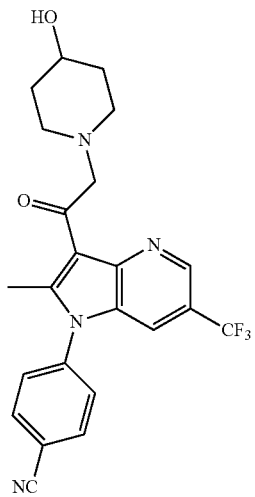 [SMILES: Cc1c(C(=O)CN2CCC(O)CC2)c2ncc(C(F)(F)F)cc2n1-c1ccc(C#N)cc1] | III |
| 303 | 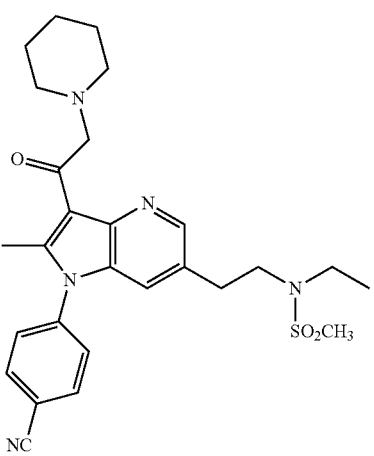 [SMILES: CCN(CCc1cnc2c(C(=O)CN3CCCCC3)c(C)n(-c3ccc(C#N)cc3)c2c1)S(C)(=O)=O] | III |
| 304 | 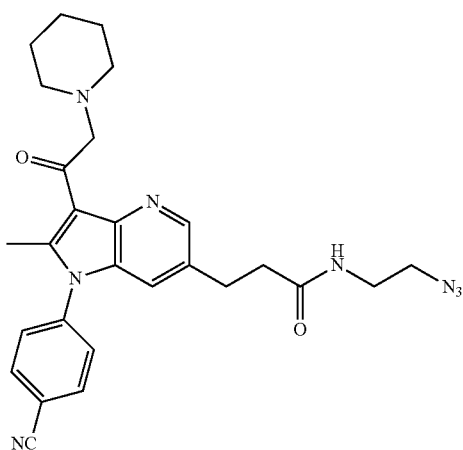 [SMILES: Cc1c(C(=O)CN2CCCCC2)c2ncc(CCC(=O)NCCN=[N+]=[N-])cc2n1-c1ccc(C#N)cc1] | III |

TABLE 3-continued
| Compound No. | Chemical Structure | IC$_{50}$ Category |
|---|---|---|
| 305 | 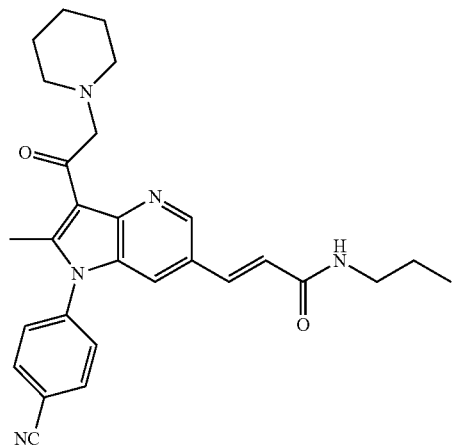 [SMILES: CCCNC(=O)/C=C/c1cnc2c(C(=O)CN3CCCCC3)c(C)n(-c3ccc(C#N)cc3)c2c1] | III |
| 306 | 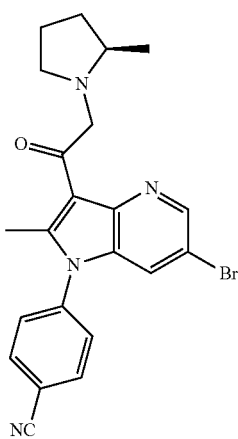 [SMILES: Cc1c(C(=O)CN2CCC[C@H]2C)c2ncc(Br)cc2n1-c1ccc(C#N)cc1] | III |
| 307 | 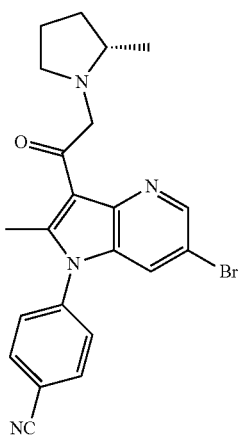 [SMILES: Cc1c(C(=O)CN2CCC[C@@H]2C)c2ncc(Br)cc2n1-c1ccc(C#N)cc1] | III |

TABLE 3-continued
| Compound No. | Chemical Structure | IC$_{50}$ Category |
|---|---|---|
| 308 | 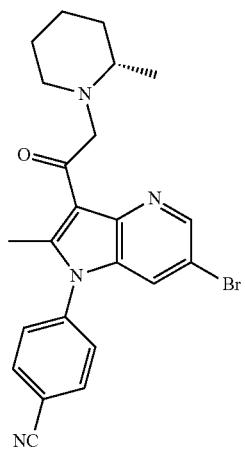 [SMILES: Cc1c(C(=O)CN2CCCC[C@@H]2C)c2ncc(Br)cc2n1-c1ccc(C#N)cc1] | III |
| 309 | 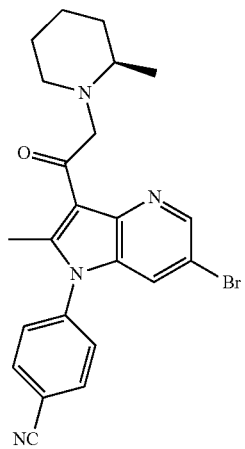 [SMILES: Cc1c(C(=O)CN2CCCC[C@H]2C)c2ncc(Br)cc2n1-c1ccc(C#N)cc1] | III |
| 310 | 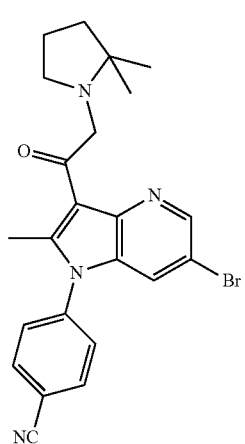 [SMILES: Cc1c(C(=O)CN2CCCC2(C)C)c2ncc(Br)cc2n1-c1ccc(C#N)cc1] | III |

TABLE 3-continued
| Compound No. | Chemical Structure | IC$_{50}$ Category |
|---|---|---|
| 311 | 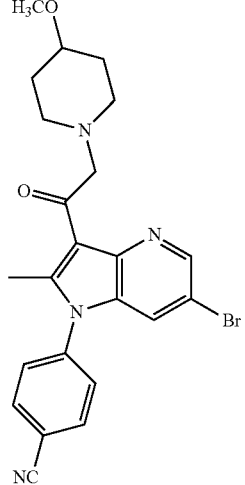 [SMILES: COC1CCN(CC(=O)c2c(C)n(-c3ccc(C#N)cc3)c3cc(Br)cnc23)CC1] | III |
| 312 | 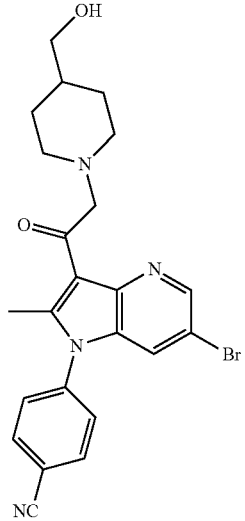 | II |
| 314 | 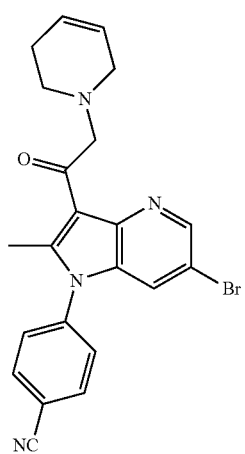 [SMILES: Cc1c(C(=O)CN2CC=CCC2)c2ncc(Br)cc2n1-c1ccc(C#N)cc1] | II |

TABLE 3-continued

| Compound No. | Chemical Structure | IC$_{50}$ Category |
|---|---|---|
| 315 | 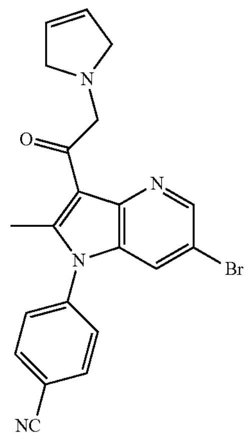 [SMILES: Cc1c(C(=O)CN2CC=CC2)c2ncc(Br)cc2n1-c1ccc(C#N)cc1] | III |
| 318 | 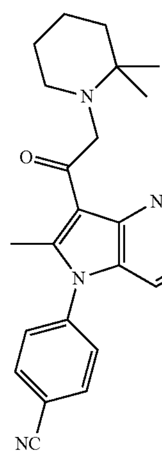 | III |
| 319 | 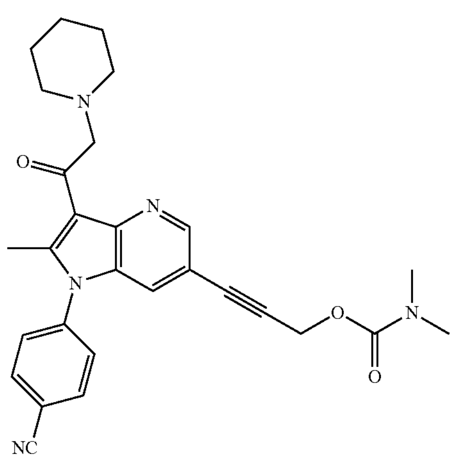 | III |

TABLE 3-continued

| Compound No. | Chemical Structure | IC$_{50}$ Category |
|---|---|---|
| 320 | 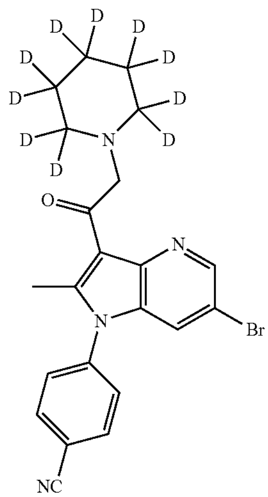 [SMILES: [2H]C1([2H])N(CC(=O)c2c(C)n(-c3ccc(C#N)cc3)c3cc(Br)cnc23)C([2H])([2H])C([2H])([2H])C([2H])([2H])C1([2H])[2H]] | III |
| 321 | 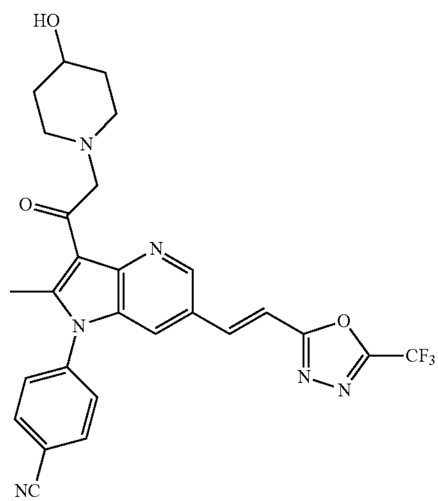 [SMILES: Cc1c(C(=O)CN2CCC(O)CC2)c2ncc(/C=C/c3nnc(C(F)(F)F)o3)cc2n1-c1ccc(C#N)cc1] | III |
| 324 | 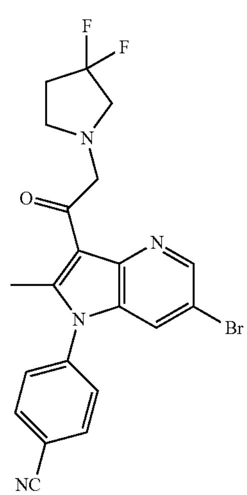 [SMILES: Cc1c(C(=O)CN2CCC(F)(F)C2)c2ncc(Br)cc2n1-c1ccc(C#N)cc1] | I |

TABLE 3-continued

| Compound No. | Chemical Structure | IC$_{50}$ Category |
|---|---|---|
| 325 | 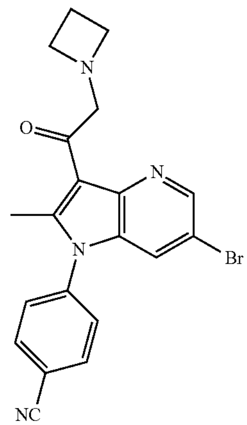 [SMILES: Cc1c(C(=O)CN2CCC2)c2ncc(Br)cc2n1-c1ccc(C#N)cc1] | I |
| 326 | 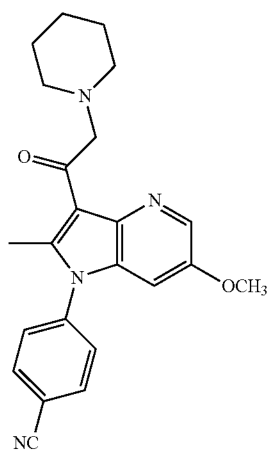 [SMILES: COc1cnc2c(C(=O)CN3CCCCC3)c(C)n(-c3ccc(C#N)cc3)c2c1] | III |
| 327 | 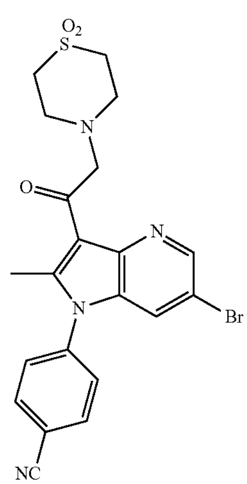 | I |

TABLE 3-continued
| Compound No. | Chemical Structure | IC$_{50}$ Category |
|---|---|---|
| 328 | 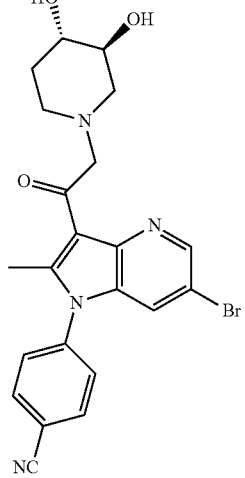 | I |
| 329 | 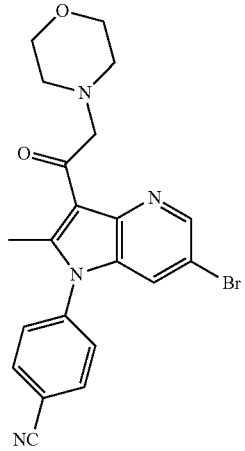 | I |
| 330 | 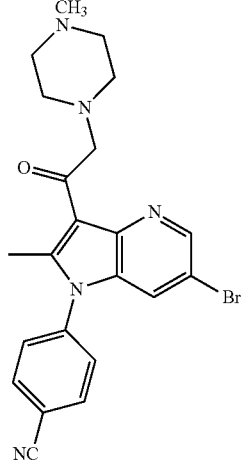 | I |

TABLE 3-continued

| Compound No. | Chemical Structure | IC$_{50}$ Category |
|---|---|---|
| 331 | 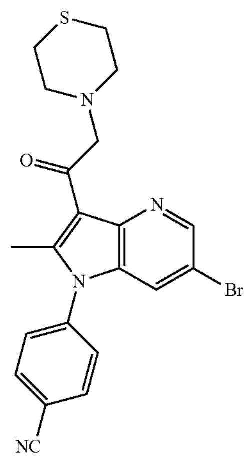 | III |
| 332 | 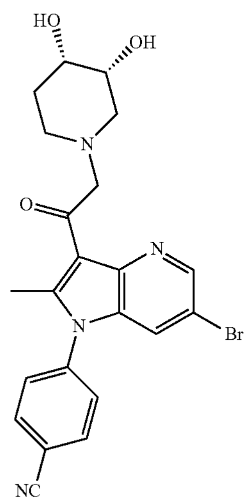 [SMILES: Cc1c(C(=O)CN2CC[C@H](O)[C@H](O)C2)c2ncc(Br)cc2n1-c1ccc(C#N)cc1] | III |
| 335 | 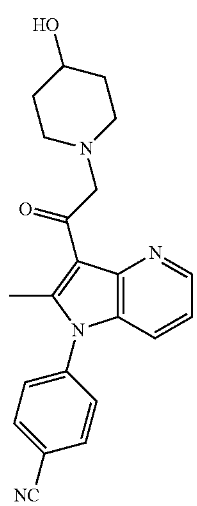 | III |

TABLE 3-continued
| Compound No. | Chemical Structure | IC$_{50}$ Category |
|---|---|---|
| 336 | 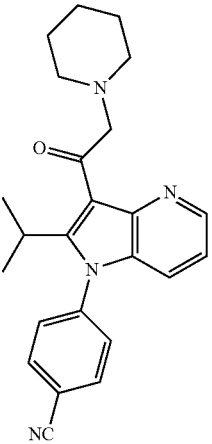 [SMILES: CC(C)c1c(C(=O)CN2CCCCC2)c2ncccc2n1-c1ccc(C#N)cc1] | I |
| 337 | 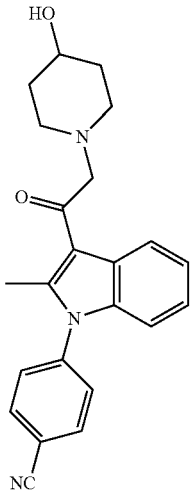 [SMILES: Cc1c(C(=O)CN2CCC(O)CC2)c2ccccc2n1-c1ccc(C#N)cc1] | III |
| 338 | 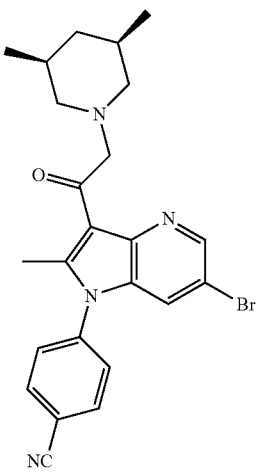 [SMILES: Cc1c(C(=O)CN2C[C@H](C)C[C@H](C)C2)c2ncc(Br)cc2n1-c1ccc(C#N)cc1] | I |

TABLE 3-continued
| Compound No. | Chemical Structure | IC$_{50}$ Category |
|---|---|---|
| 339 | 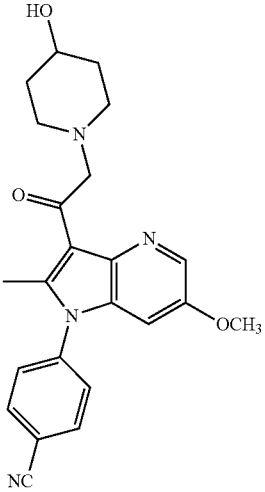 [SMILES: COc1cnc2c(C(=O)CN3CCC(O)CC3)c(C)n(-c3ccc(C#N)cc3)c2c1] | III |
| 340 | 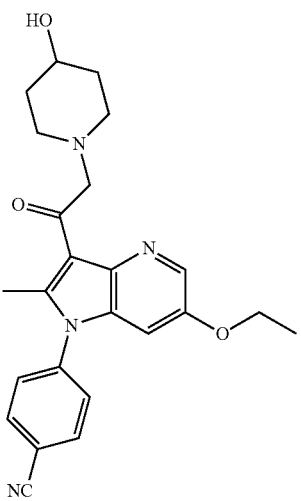 [SMILES: CCOc1cnc2c(C(=O)CN3CCC(O)CC3)c(C)n(-c3ccc(C#N)cc3)c2c1] | III |
| 341 | 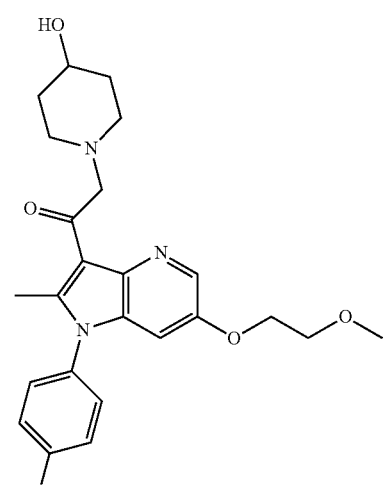 | III |

TABLE 3-continued
| Compound No. | Chemical Structure | IC$_{50}$ Category |
| --- | --- | --- |
| 342 | 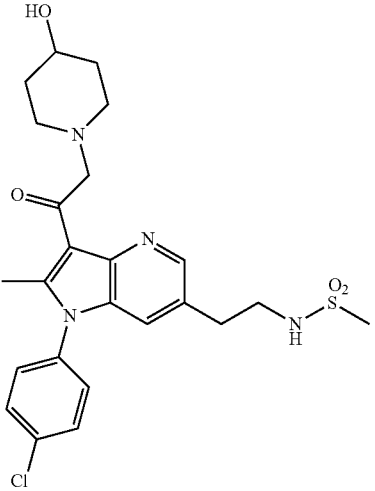 | III |
| 343 | 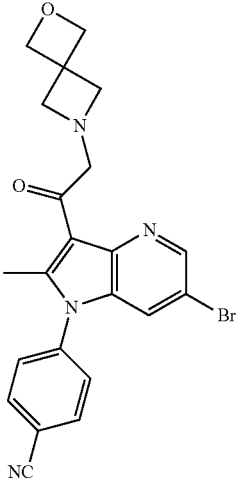 [SMILES: Cc1c(C(=O)CN2CC3(COC3)C2)c2ncc(Br)cc2n1-c1ccc(C#N)cc1] | I |
| 344 | 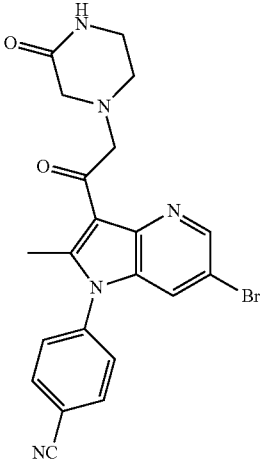 [SMILES: Cc1c(C(=O)CN2CCNC(=O)C2)c2ncc(Br)cc2n1-c1ccc(C#N)cc1] | I |

TABLE 3-continued
| Compound No. | Chemical Structure | IC$_{50}$ Category |
|---|---|---|
| 345 | 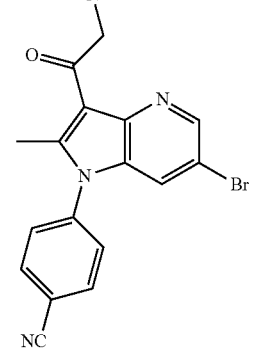 | I |
| 346 | 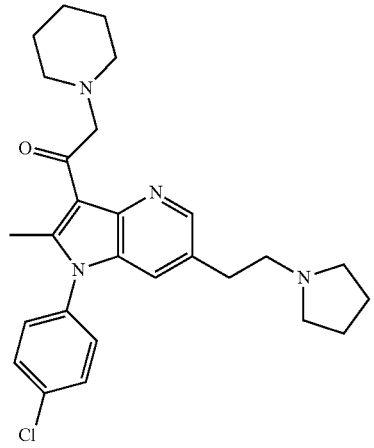 [SMILES: Cc1c(C(=O)CN2CCCCC2)c2ncc(CCN3CCCC3)cc2n1-c1ccc(Cl)cc1] | III |
| 347 | 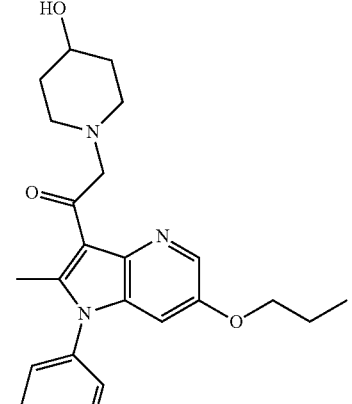 | III |

TABLE 3-continued

| Compound No. | Chemical Structure | IC$_{50}$ Category |
|---|---|---|
| 348 | 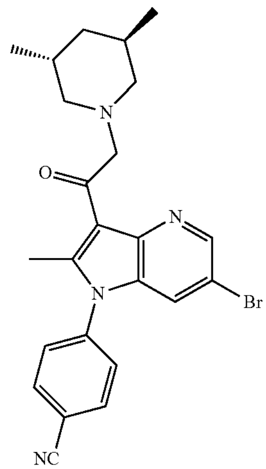 [SMILES: Cc1c(C(=O)CN2C[C@H](C)C[C@@H](C)C2)c2ncc(Br)cc2n1-c1ccc(C#N)cc1] | I |
| 349 | 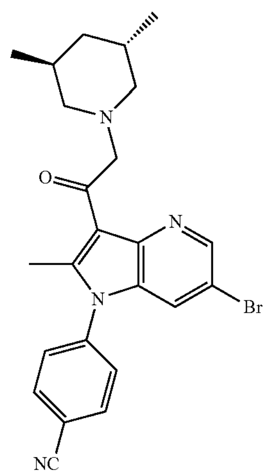 [SMILES: Cc1c(C(=O)CN2C[C@@H](C)C[C@H](C)C2)c2ncc(Br)cc2n1-c1ccc(C#N)cc1] | III |
| 350 | 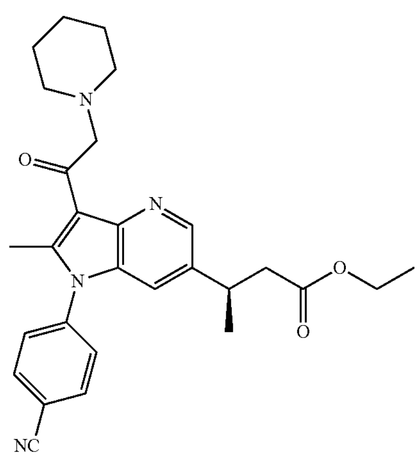 [SMILES: CCOC(=O)C[C@@H](C)c1cnc2c(C(=O)CN3CCCCC3)c(C)n(-c3ccc(C#N)cc3)c2c1] | III |

TABLE 3-continued

| Compound No. | Chemical Structure | IC$_{50}$ Category |
|---|---|---|
| 351 | 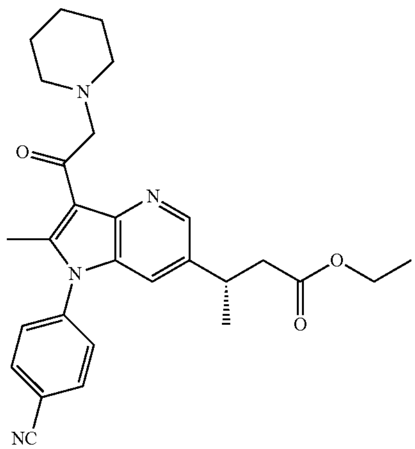 [SMILES: CCOC(=O)C[C@H](C)c1cnc2c(C(=O)CN3CCCCC3)c(C)n(-c3ccc(C#N)cc3)c2c1] | III |
| 352 | 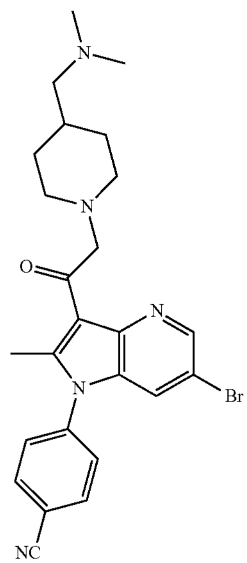 [SMILES: Cc1c(C(=O)CN2CCC(CN(C)C)CC2)c2ncc(Br)cc2n1-c1ccc(C#N)cc1] | III |
| 353 | 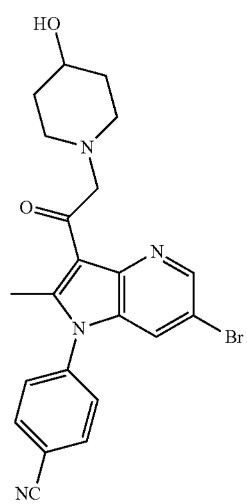 [SMILES: Cc1c(C(=O)CN2CCC(O)CC2)c2ncc(Br)cc2n1-c1ccc(C#N)cc1] | III |

TABLE 3-continued

| Compound No. | Chemical Structure | IC$_{50}$ Category |
|---|---|---|
| 354 | 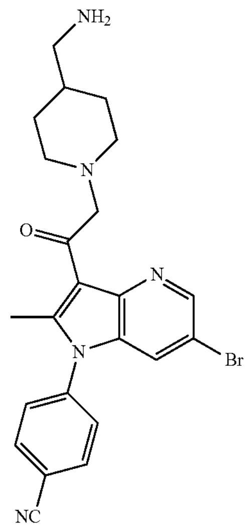 | III |
| 355 | 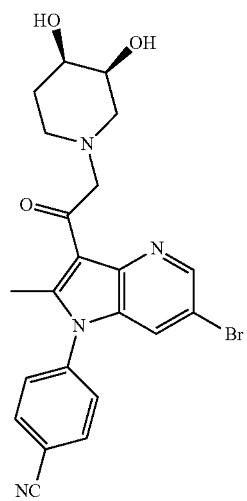 [SMILES: Cc1c(C(=O)CN2CC[C@@H](O)[C@@H](O)C2)c2ncc(Br)cc2n1-c1ccc(C#N)cc1] | III |
| 356 | 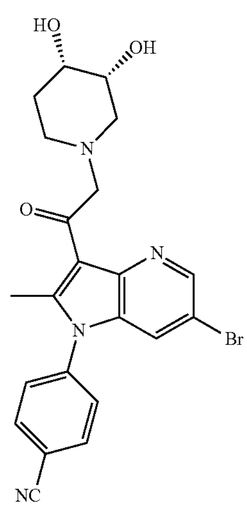 [SMILES: Cc1c(C(=O)CN2CC[C@H](O)[C@H](O)C2)c2ncc(Br)cc2n1-c1ccc(C#N)cc1] | III |

TABLE 3-continued
| Compound No. | Chemical Structure | IC$_{50}$ Category |
|---|---|---|
| 357 | 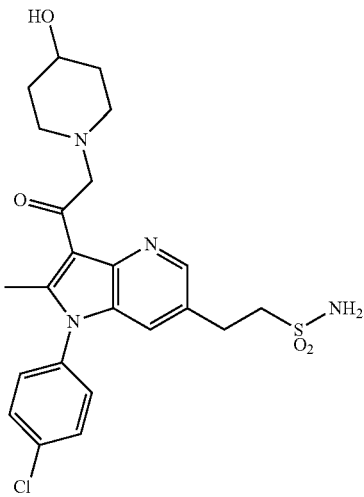 [SMILES: Cc1c(C(=O)CN2CCC(O)CC2)c2ncc(CCS(N)(=O)=O)cc2n1-c1ccc(Cl)cc1] | III |
| 359 | 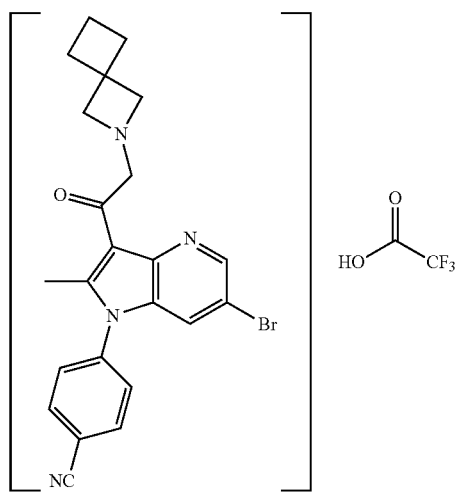 | I |
| 360 | 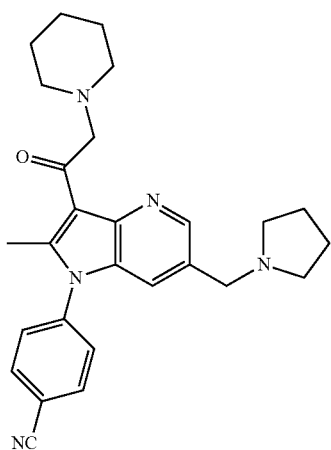 [SMILES: Cc1c(C(=O)CN2CCCCC2)c2ncc(CN3CCCC3)cc2n1-c1ccc(C#N)cc1] | III |

TABLE 3-continued

| Compound No. | Chemical Structure | IC$_{50}$ Category |
|---|---|---|
| 361 | 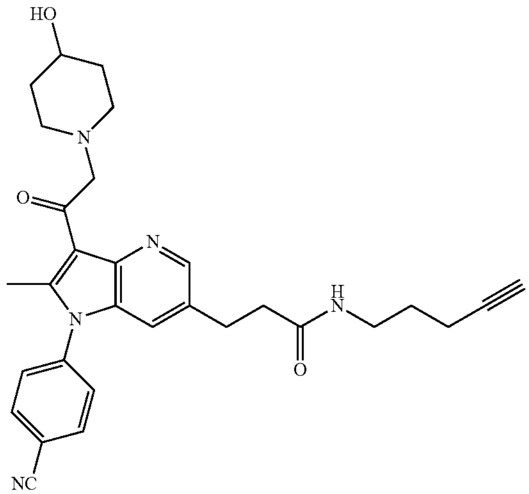 [SMILES: C#CCCCNC(=O)CCc1cnc2c(C(=O)CN3CCC(O)CC3)c(C)n(-c3ccc(C#N)cc3)c2c1] | III |
| 362 | 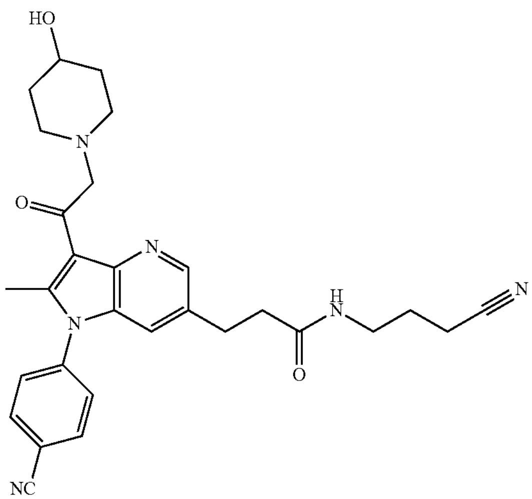 [SMILES: Cc1c(C(=O)CN2CCC(O)CC2)c2ncc(CCC(=O)NCCCC#N)cc2n1-c1ccc(C#N)cc1] | III |
| 363 | 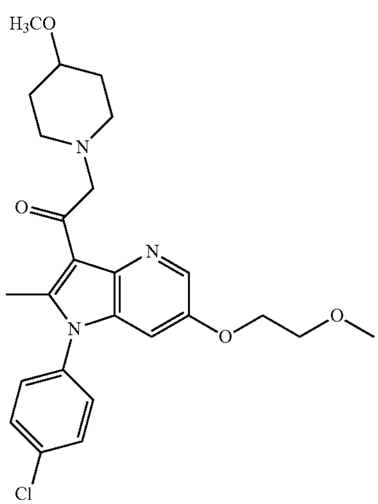 | III |

TABLE 3-continued

| Compound No. | Chemical Structure | IC$_{50}$ Category |
|---|---|---|
| 364 | 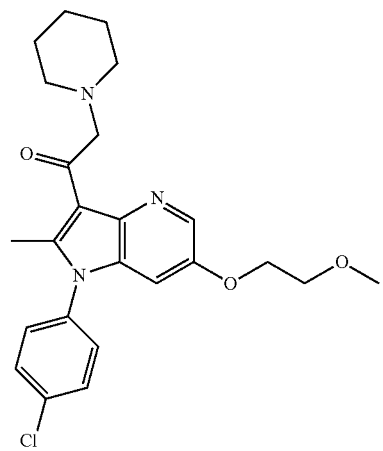 | III |
| 365 | 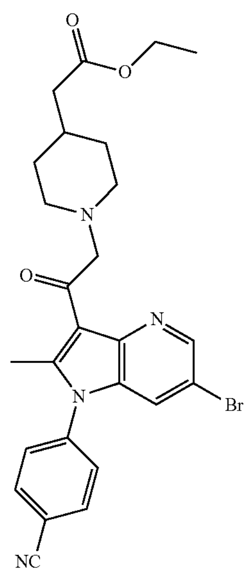 [SMILES: CCOC(=O)CC1CCN(CC(=O)c2c(C)n(-c3ccc(C#N)cc3)c3cc(Br)cnc23)CC1] | II |
| 366 | 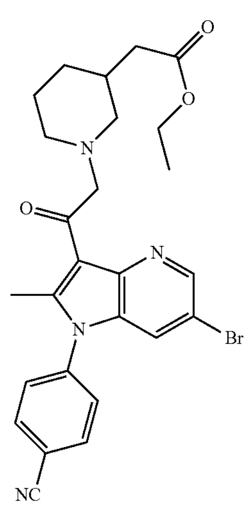 [SMILES: CCOC(=O)CC1CCCN(CC(=O)c2c(C)n(-c3ccc(C#N)cc3)c3cc(Br)cnc23)C1] | II |

TABLE 3-continued
| Compound No. | Chemical Structure | IC$_{50}$ Category |
|---|---|---|
| 367 | 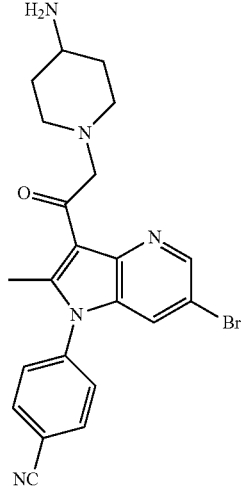 | II |
| 368 | 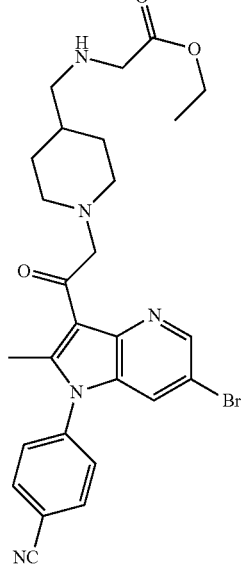 | II |
| 369 | 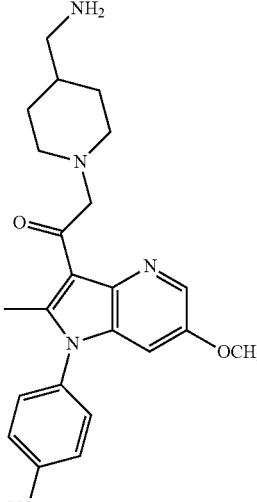 | III |

TABLE 3-continued
| Compound No. | Chemical Structure | IC$_{50}$ Category |
|---|---|---|
| 370 | 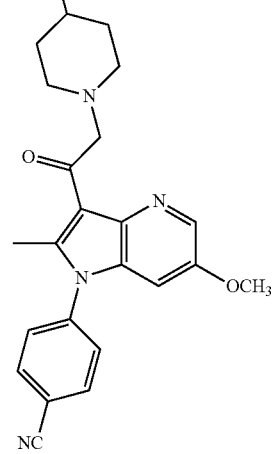 | III |
| 371 | 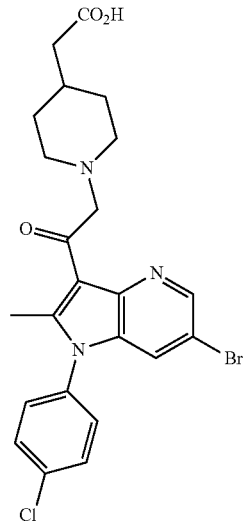 [SMILES: Cc1c(C(=O)CN2CCC(CC(=O)O)CC2)c2ncc(Br)cc2n1-c1ccc(Cl)cc1] | I |
| 372 | 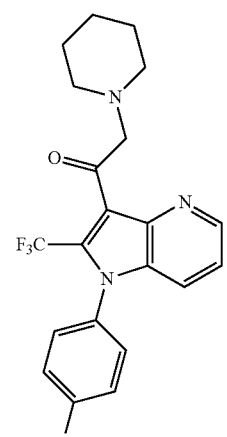 | I |

TABLE 3-continued
| Compound No. | Chemical Structure | IC$_{50}$ Category |
|---|---|---|
| 373 | 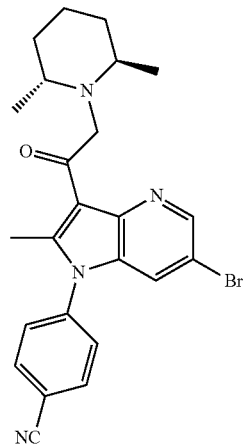 [SMILES: Cc1c(C(=O)CN2[C@H](C)CCC[C@H]2C)c2ncc(Br)cc2n1-c1ccc(C#N)cc1] | II |
| 374 | 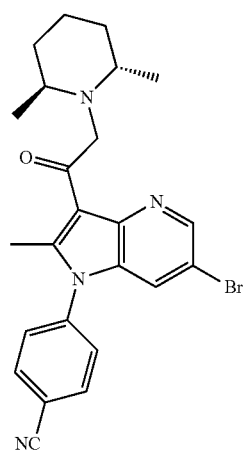 [SMILES: Cc1c(C(=O)CN2[C@@H](C)CCC[C@@H]2C)c2ncc(Br)cc2n1-c1ccc(C#N)cc1] | II |
| 381 | 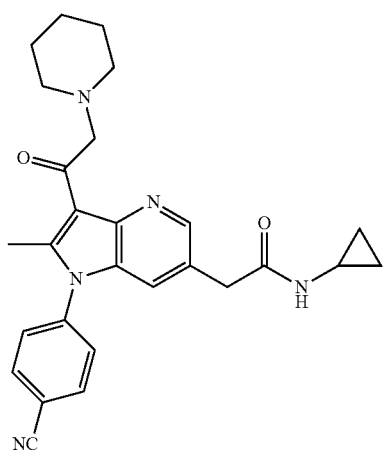 [SMILES: Cc1c(C(=O)CN2CCCCC2)c2ncc(CC(=O)NC3CC3)cc2n1-c1ccc(C#N)cc1] | III |

TABLE 3-continued
| Compound No. | Chemical Structure | IC$_{50}$ Category |
|---|---|---|
| 382 | 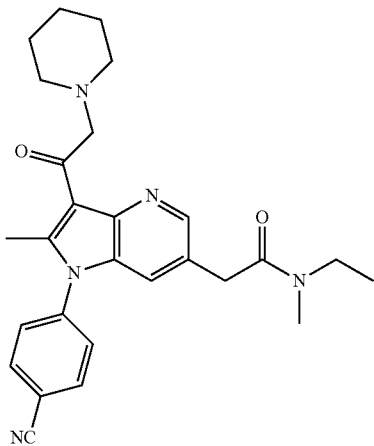 [SMILES: CCN(C)C(=O)Cc1cnc2c(C(=O)CN3CCCCC3)c(C)n(-c3ccc(C#N)cc3)c2c1] | III |
| 383 | 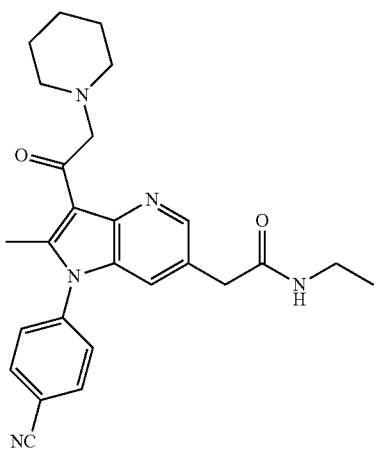 [SMILES: CCNC(=O)Cc1cnc2c(C(=O)CN3CCCCC3)c(C)n(-c3ccc(C#N)cc3)c2c1] | III |
| 384 | 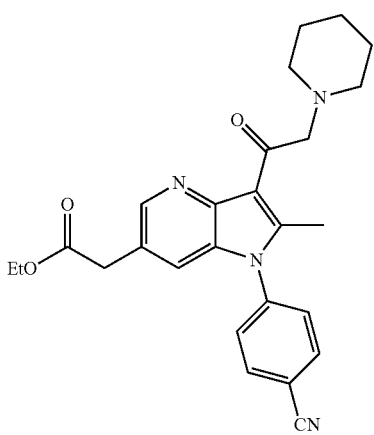 [SMILES: CCOC(=O)Cc1cnc2c(C(=O)CN3CCCCC3)c(C)n(-c3ccc(C#N)cc3)c2c1] | III |

TABLE 3-continued

| Compound No. | Chemical Structure | IC$_{50}$ Category |
| --- | --- | --- |
| 385 | 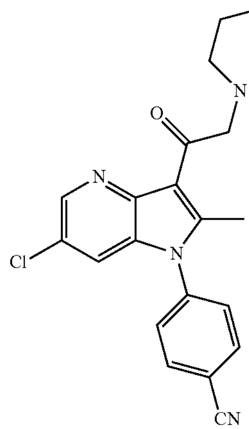 | III |
| 386 | 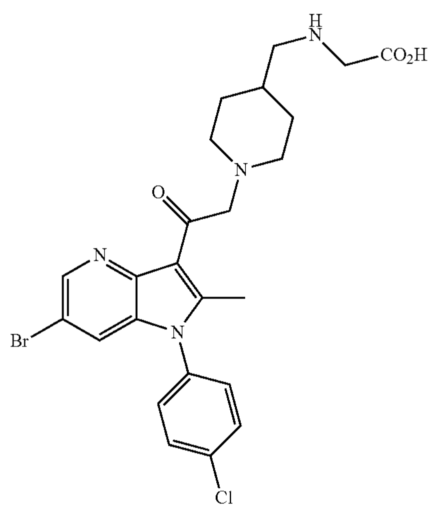 [SMILES: Cc1c(C(=O)CN2CCC(CNCC(=O)O)CC2)c2ncc(Br)cc2n1-c1ccc(Cl)cc1] | I |
| 387 | 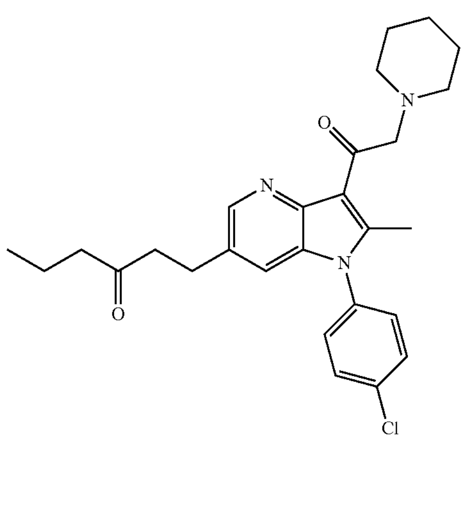 [SMILES: CCCC(=O)CCc1cnc2c(C(=O)CN3CCCCC3)c(C)n(-c3ccc(Cl)cc3)c2c1] | III |

TABLE 3-continued

| Compound No. | Chemical Structure | IC$_{50}$ Category |
|---|---|---|
| 388 | 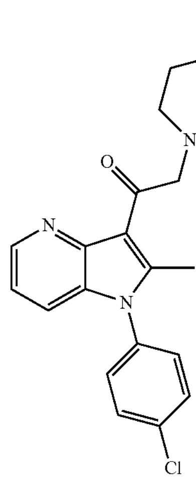 | III |
| 389 | 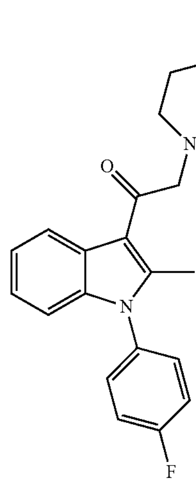 | III |
| 390 | 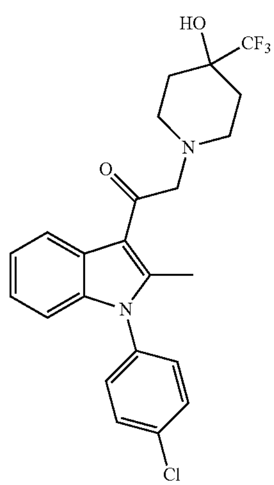 [SMILES: Cc1c(C(=O)CN2CCC(O)(C(F)(F)F)CC2)c2ccccc2n1-c1ccc(Cl)cc1] | I |

TABLE 3-continued

| Compound No. | Chemical Structure | IC$_{50}$ Category |
|---|---|---|
| 391 | 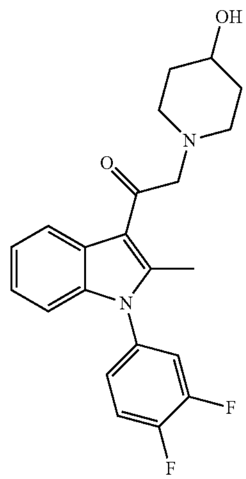 [SMILES: Cc1c(C(=O)CN2CCC(O)CC2)c2ccccc2n1-c1ccc(F)c(F)c1] | II |
| 392 | 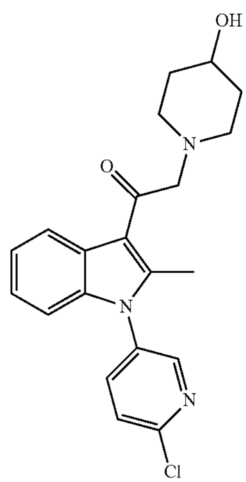 [SMILES: Cc1c(C(=O)CN2CCC(O)CC2)c2ccccc2n1-c1ccc(Cl)nc1] | II |
| 393 | 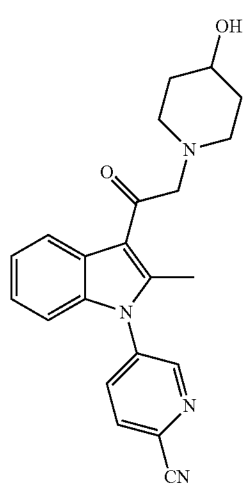 [SMILES: Cc1c(C(=O)CN2CCC(O)CC2)c2ccccc2n1-c1ccc(C#N)nc1] | II |

TABLE 3-continued

| Compound No. | Chemical Structure | IC$_{50}$ Category |
|---|---|---|
| 394 | 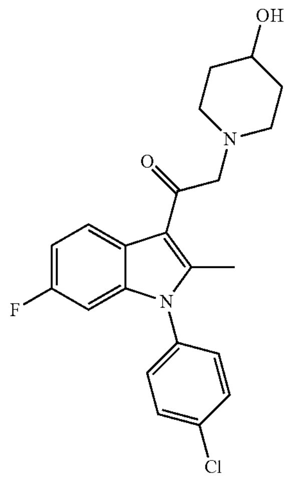 [SMILES: Cc1c(C(=O)CN2CCC(O)CC2)c2ccc(F)cc2n1-c1ccc(Cl)cc1] | I |
| 395 | 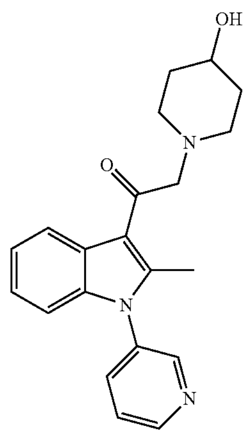 [SMILES: Cc1c(C(=O)CN2CCC(O)CC2)c2ccccc2n1-c1cccnc1] | I |
| 396 | 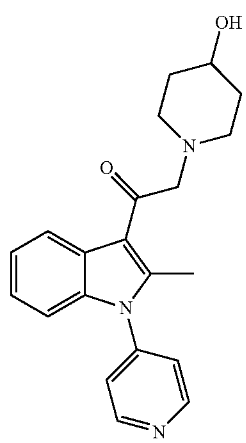 [SMILES: Cc1c(C(=O)CN2CCC(O)CC2)c2ccccc2n1-c1ccncc1] | I |

TABLE 3-continued
| Compound No. | Chemical Structure | IC$_{50}$ Category |
|---|---|---|
| 397 | 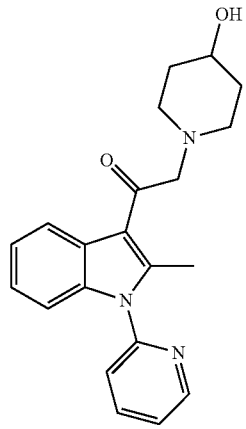 [SMILES: Cc1c(C(=O)CN2CCC(O)CC2)c2ccccc2n1-c1ccccn1] | I |
| 398 | 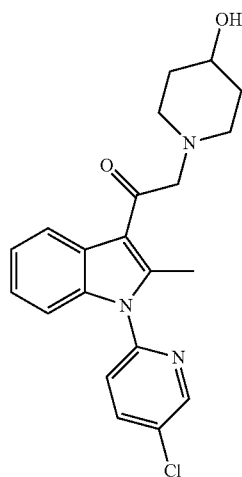 [SMILES: Cc1c(C(=O)CN2CCC(O)CC2)c2ccccc2n1-c1ccc(Cl)cn1] | II |
| 399 | 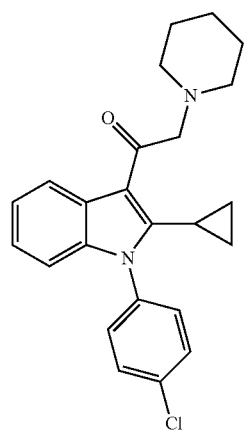 [SMILES: O=C(CN1CCCCC1)c1c(C2CC2)n(-c2ccc(Cl)cc2)c2ccccc12] | I |

TABLE 3-continued

| Compound No. | Chemical Structure | IC$_{50}$ Category |
|---|---|---|
| 400 | 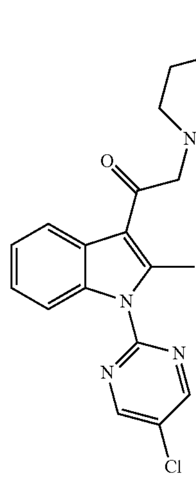 | I |
| 401 | 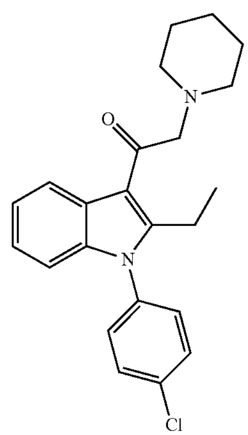 [SMILES: CCc1c(C(=O)CN2CCCCC2)c2ccccc2n1-c1ccc(Cl)cc1] | II |
| 402 | 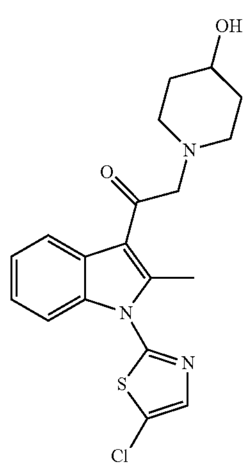 [SMILES: Cc1c(C(=O)CN2CCC(O)CC2)c2ccccc2n1-c1ncc(Cl)s1] | I |

493

While this invention has been particularly shown and described with references to preferred embodiments thereof, it will be understood by those skilled in the art that various changes in form and details may be made therein without departing from the scope of the invention encompassed by the appended claims.

What is claimed is:
1. A compound having the Formula (IV):

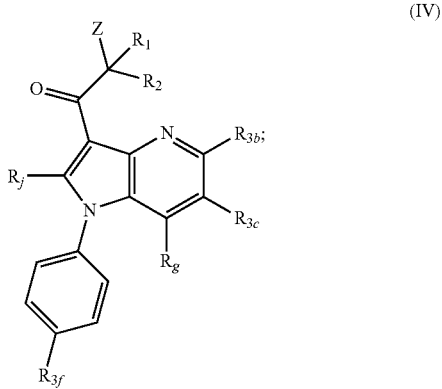

(IV)

or a pharmaceutically acceptable salt, solvate, clathrate or prodrug thereof; wherein Z is an optionally substituted N-heterocyclic;

$R_1$ and $R_2$ are each independently selected from hydrogen and optionally substituted $C_1$-$C_{10}$ alkyl;

$R_{3f}$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)C(O)OR_c$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c(C=NR_d)R_c$, $OC(O)R_c$, optionally substituted heterocyclic and optionally substituted heteroaryl;

each of $R_{3b}$ and $R_{3c}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)C(O)OR_c$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c(C=NR_d)R_c$, $OC(O)R_c$, optionally substituted heterocyclic and optionally substituted heteroaryl; and $R_g$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)C(O)OR_c$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c(C=NR_d)R_c$,

494

$OC(O)R_c$, optionally substituted heterocyclic and optionally substituted heteroaryl;

$R_j$ is optionally substituted $C_1$-$C_4$ alkyl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or two geminal $R_d$ groups are taken together with the nitrogen atom to which they are attached to form an optionally substituted heterocyclic or an optionally substituted heteroaryl; and each n is independently, 1 or 2.

2. The compound of claim 1, wherein $R_1$ and $R_2$ are each hydrogen.

3. The compound of claim 1, wherein each of $R_{3b}$ and $R_{3c}$ is independently selected from the group consisting of hydrogen, halo, $NR_dR_d$, $NO_2$, CN, optionally substituted $C_1$-$C_{10}$ alkyl, $C(O)OR_c$, $C(O)R_c$, $NR_dC(O)R_c$, $OC(O)R_c$, and $OR_c$.

4. The compound of claim 1, wherein $R_g$ and $R_{3b}$ are both hydrogen and $R_{3c}$ is selected from the group consisting of optionally substituted $C_1$-$C_6$ alkyl, CN, and $OR_c$.

5. The compound of claim 1, wherein $R_g$ and $R_{3c}$ are both hydrogen and $R_{3b}$ is selected from the group consisting of optionally substituted $C_1$-$C_6$ alkyl, CN, and $OR_c$.

6. The compound of claim 1, wherein $R_{3f}$ is selected from the group consisting of hydrogen, halo, $N_3$, $C(O)OR_c$, CN, $C(O)R_c$, $C(O)C(O)R_c$, $C(O)NR_dR_d$, $NO_2$, and $NR_dR_d$.

7. The compound of claim 6, wherein $R_{3f}$ is selected from the group consisting of halo and CN.

8. The compound of claim 1, wherein Z is selected from the group consisting of optionally substituted 1-pyrrolidinyl and optionally substituted 1-piperidinyl.

9. The compound of claim 8, wherein Z is optionally substituted 1-piperidinyl.

10. The compound of claim 1, wherein $R_j$ is methyl, and $R_{3f}$ is selected from the group consisting of halo, $N_3$, $C(O)OR_c$, CN, $C(O)R_c$, $C(O)C(O)R_c$, $C(O)NR_dR_d$, $NO_2$ and $NR_dR_d$.

11. The compound of claim 1, wherein Z is:

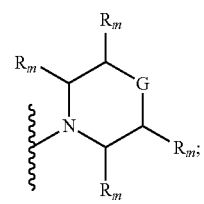

wherein G is absent, $C(R_n)$, O or S;

each $R_m$ and $R_n$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NRR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C{=}NR_d)R_c$, $OC(O)R_c$, optionally substituted heterocyclic, and optionally substituted heteroaryl.

12. The compound of claim 11 wherein each $R_m$ and $R_n$ are each independently selected from the group consisting of hydrogen and optionally substituted $C_1$-$C_{10}$ alkyl.

13. The compound of claim 11 wherein G is O.

14. The compound of claim 11, wherein G is S.

15. A pharmaceutical composition comprising a pharmaceutically acceptable carrier or excipient and a compound of claim 1, or a pharmaceutically acceptable salt, solvate, clathrate or prodrug thereof.

16. A compound having the Formula (V):

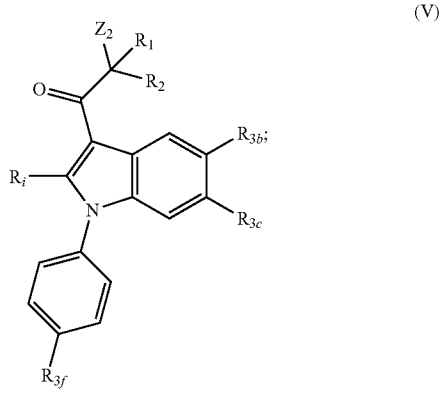

(V)

or a pharmaceutically salt, solvate, clathrate or prodrug thereof, wherein
$R_i$ is an optionally substituted $C_1$-$C_4$ alkyl;
$R_{3f}$ is selected from the group consisting of halo, $N_3$, $C(O)OR_c$, CN, $C(O)R_c$, $C(O)C(O)R_c$, $C(O)NR_dR_d$, $NO_2$ and $NR_dR_d$;
$R_1$ and $R_2$ are each independently selected from hydrogen and optionally substituted $C_1$-$C_{10}$ alkyl;
one of $R_{3b}$ and $R_{3c}$ is hydrogen and the other of $R_{3b}$ and $R_{3c}$ is selected from the group consisting of optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)C(O)OR_c$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C{=}NR_d)R_c$, $OC(O)R_c$, optionally substituted heterocyclic and optionally substituted heteroaryl;
$Z_2$ is selected from the group consisting of optionally substituted 1-pyrrolidinyl and 1-piperdinyl;
each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;
each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or two terminal $R_d$ groups are taken together with the nitrogen atom to which they are attached to form an optionally substituted heterocyclic or an optionally substituted heteroaryl; and
each n is independently 0, 1 or 2.

17. The compound of claim 16, wherein $Z_2$ is an optionally substituted 1-piperidinyl.

18. The compound of claim 16, wherein $R_{3b}$ is hydrogen, and $R_{3c}$ is selected from the group consisting of optionally substituted $C_1$-$C_6$ alkyl, CN, and $OR_c$.

19. The compound of claim 16, wherein $R_{3c}$ is hydrogen, and $R_{3b}$ is selected from the group consisting of optionally substituted $C_1$-$C_6$ alkyl, CN, and $OR_c$.

20. The compound of claim 16, wherein $R_i$ is methyl or ethyl.

21. The compound of claim 20, wherein $R_i$ is methyl.

22. The compound of claim 16, wherein $R_i$ is methyl, $R_{3f}$ is selected from the group consisting of halo and CN, and $Z_2$ is an optionally substituted 1-piperidinyl.

23. The compound of claim 16, wherein $Z_2$ is an optionally substituted 1-pyrrolidinyl.

24. A pharmaceutical composition comprising a pharmaceutically acceptable carrier or excipient and a compound of claim 16, or a pharmaceutically acceptable salt, solvate, clathrate or prodrug thereof.

25. A compound selected from the group consisting of those shown in the Table below, or a pharmaceutically acceptable salt thereof:

30

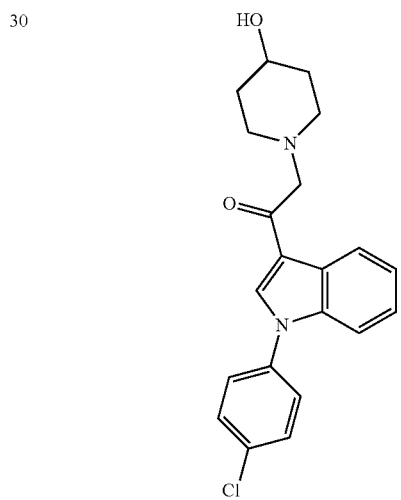

-continued
31 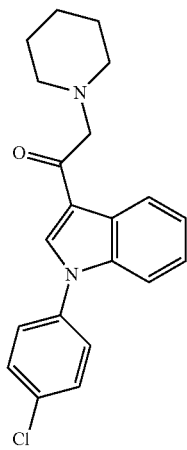 [SMILES: O=C(CN1CCCCC1)c1cn(-c2ccc(Cl)cc2)c2ccccc12]
34 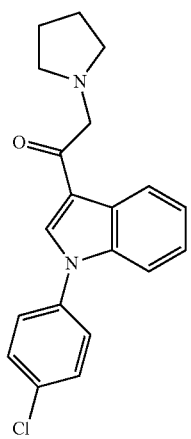 [SMILES: O=C(CN1CCCC1)c1cn(-c2ccc(Cl)cc2)c2ccccc12]
86 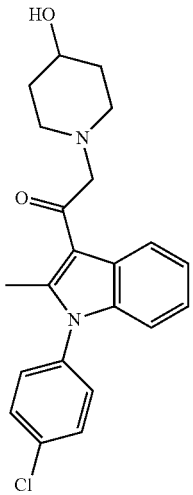
-continued
87 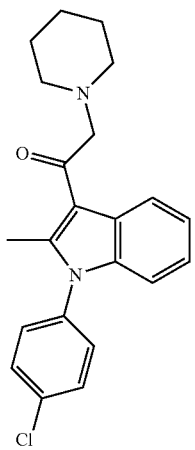 [SMILES: Cc1c(C(=O)CN2CCCCC2)c2ccccc2n1-c1ccc(Cl)cc1]
88 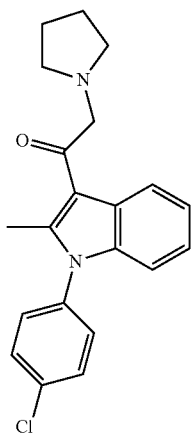 [SMILES: Cc1c(C(=O)CN2CCCC2)c2ccccc2n1-c1ccc(Cl)cc1]
98 
104 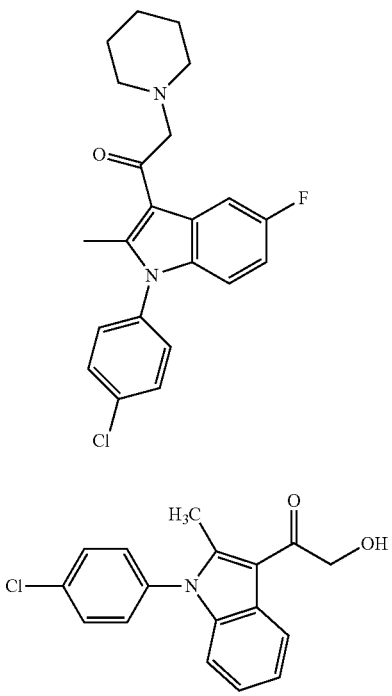

| 499 -continued | 500 -continued |
|---|---|
| 106 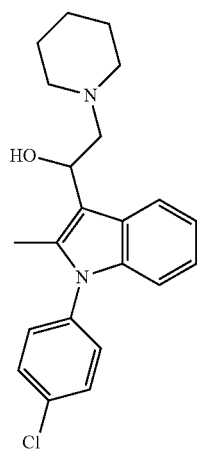 [SMILES: Cc1c(C(O)CN2CCCCC2)c2ccccc2n1-c1ccc(Cl)cc1] | 116 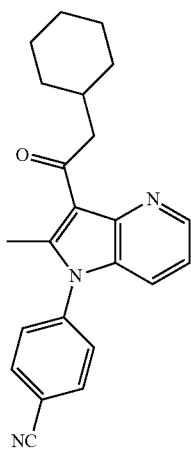 [SMILES: Cc1c(C(=O)CC2CCCCC2)c2ncccc2n1-c1ccc(C#N)cc1] |
| 108 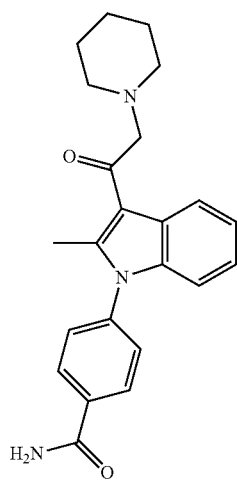 | 118 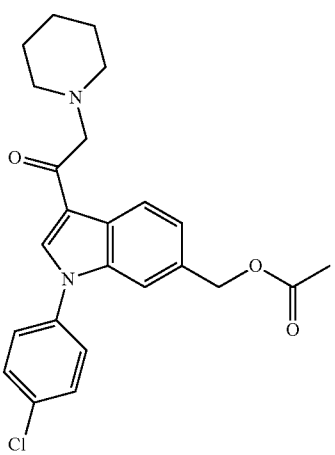 [SMILES: CC(=O)OCc1ccc2c(C(=O)CN3CCCCC3)cn(-c3ccc(Cl)cc3)c2c1] |
| 115 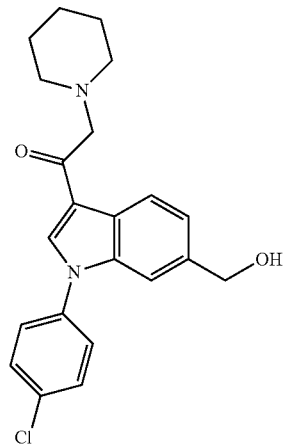 | 119 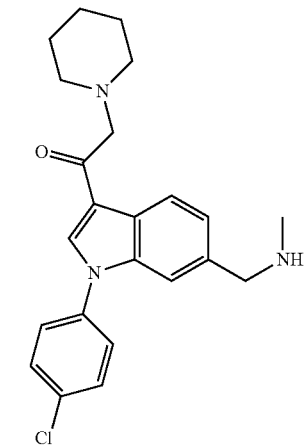 [SMILES: CNCc1ccc2c(C(=O)CN3CCCCC3)cn(-c3ccc(Cl)cc3)c2c1] |

| 501 -continued | 502 -continued |
|---|---|
| 120  | 127 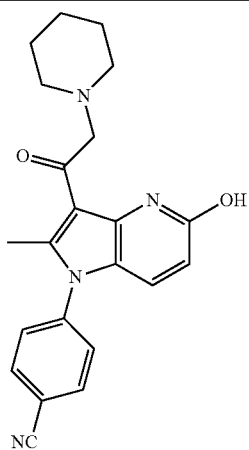 |
| 123 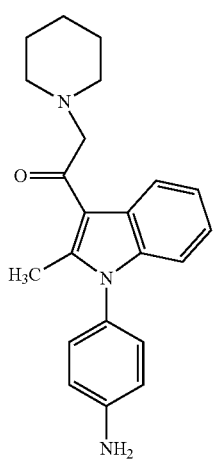 [SMILES: Cc1c(C(=O)CN2CCCCC2)c2ccccc2n1-c1ccc(N)cc1] | 128 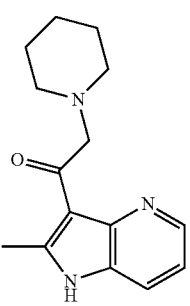 |
| 125 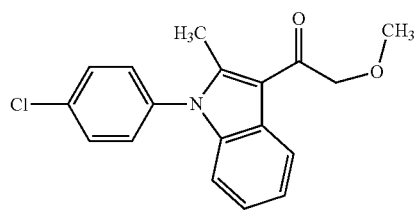 [SMILES: COCC(=O)c1c(C)n(-c2ccc(Cl)cc2)c2ccccc12] | 130 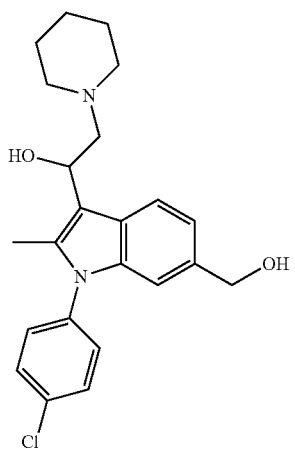 |
| 126 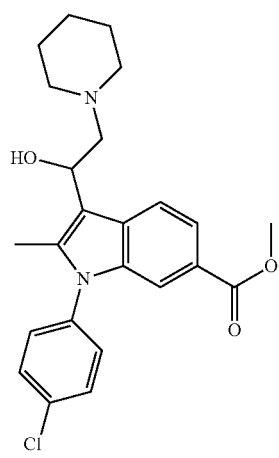 | 131 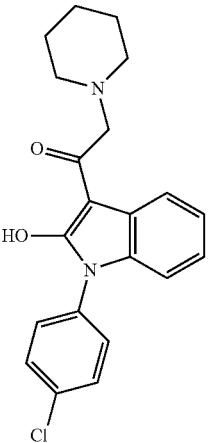 [SMILES: O=C(CN1CCCCC1)c1c(O)n(-c2ccc(Cl)cc2)c2ccccc12] |

503
-continued
132 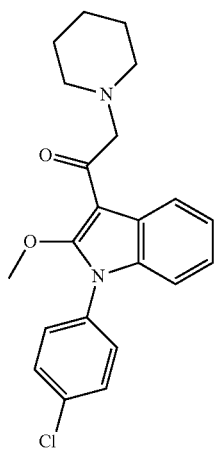 [SMILES: COc1c(C(=O)CN2CCCCC2)c2ccccc2n1-c1ccc(Cl)cc1]
133 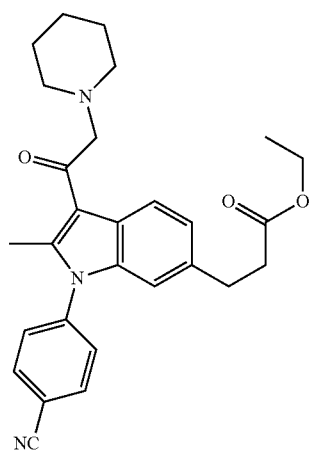 [SMILES: CCOC(=O)CCc1ccc2c(C(=O)CN3CCCCC3)c(C)n(-c3ccc(C#N)cc3)c2c1]
141 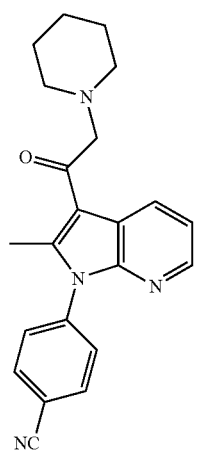
504
-continued
142 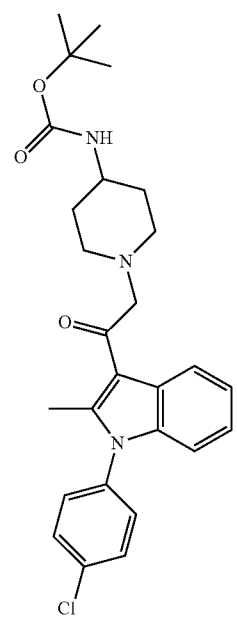
144 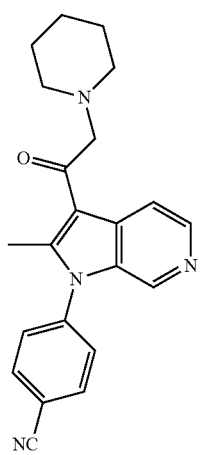 [SMILES: Cc1c(C(=O)CN2CCCCC2)c2ccncc2n1-c1ccc(C#N)cc1]
145 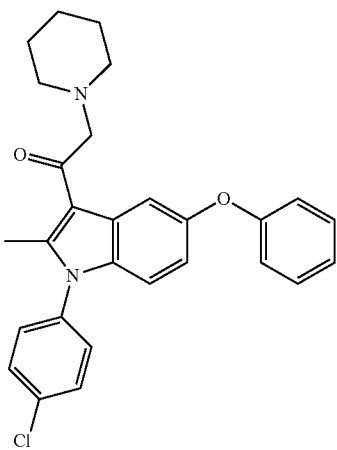 [SMILES: Cc1c(C(=O)CN2CCCCC2)c2cc(Oc3ccccc3)ccc2n1-c1ccc(Cl)cc1]

| 505 -continued | 506 -continued |
|---|---|
| 146 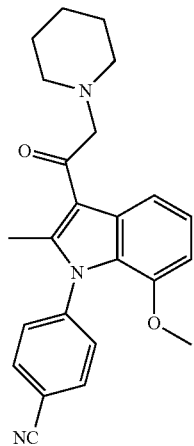 | 149 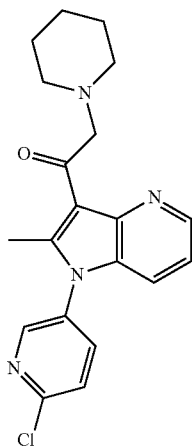 |
| 147 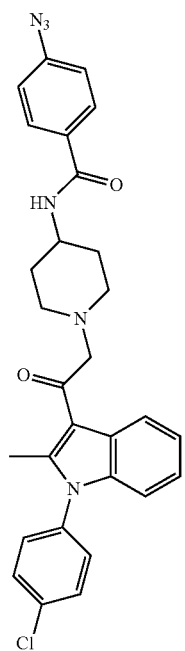 [SMILES: Cc1c(C(=O)CN2CCC(NC(=O)c3ccc(N=[N+]=[N-])cc3)CC2)c2ccccc2n1-c1ccc(Cl)cc1] | 150 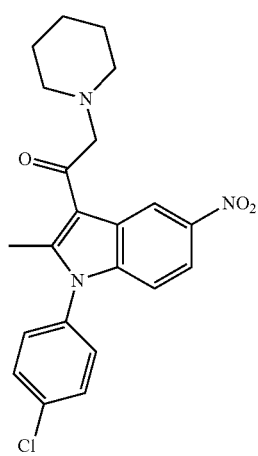 |
| 148 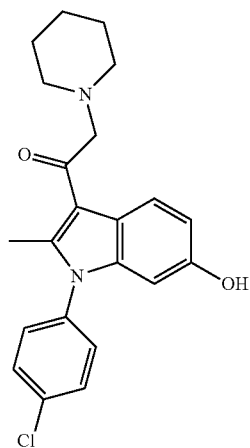 [SMILES: Cc1c(C(=O)CN2CCCCC2)c2ccc(O)cc2n1-c1ccc(Cl)cc1] | 151 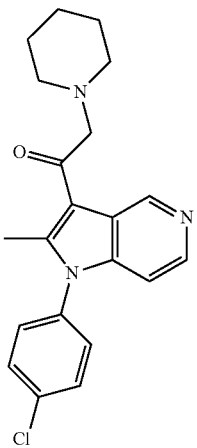 |

| 507 -continued | 508 -continued |
|---|---|
| 152 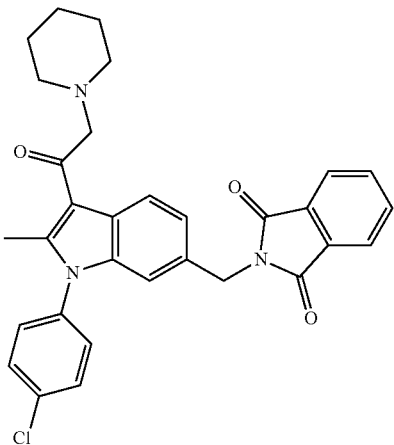 [SMILES: Cc1c(C(=O)CN2CCCCC2)c2ccc(CN3C(=O)c4ccccc4C3=O)cc2n1-c1ccc(Cl)cc1] | 155 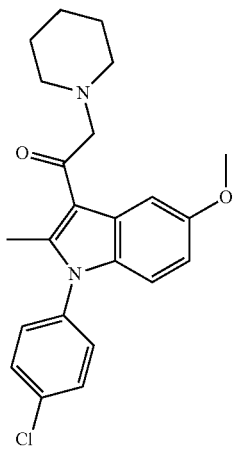 |
| 153 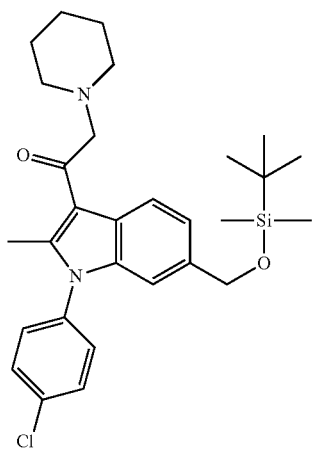 | 156 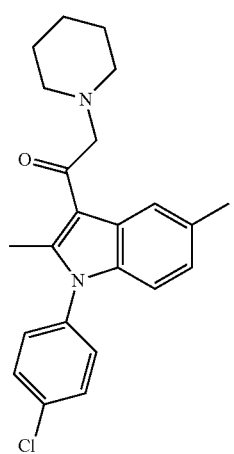 |
| 154 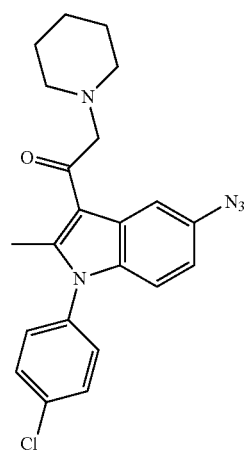 [SMILES: Cc1c(C(=O)CN2CCCCC2)c2cc(N=[N+]=[N-])ccc2n1-c1ccc(Cl)cc1] | 160 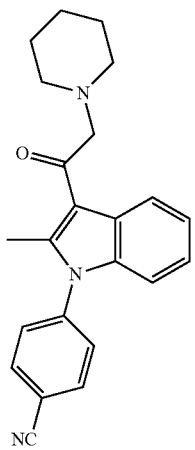 [SMILES: Cc1c(C(=O)CN2CCCCC2)c2ccccc2n1-c1ccc(C#N)cc1] |

| 509 -continued | 510 -continued |
|---|---|
| 161 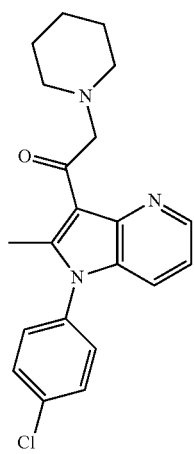 | 164 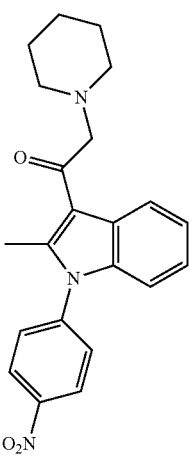 |
| 162 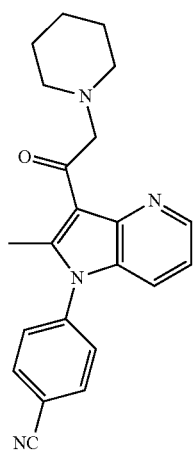 | 165 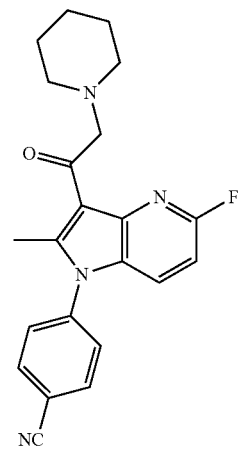 |
| 163 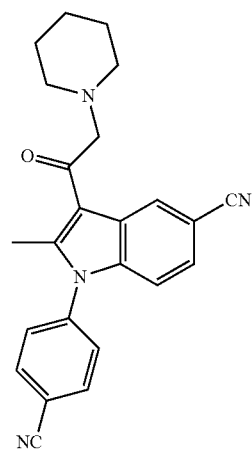 [SMILES: Cc1c(C(=O)CN2CCCCC2)c2cc(C#N)ccc2n1-c1ccc(C#N)cc1] | 166 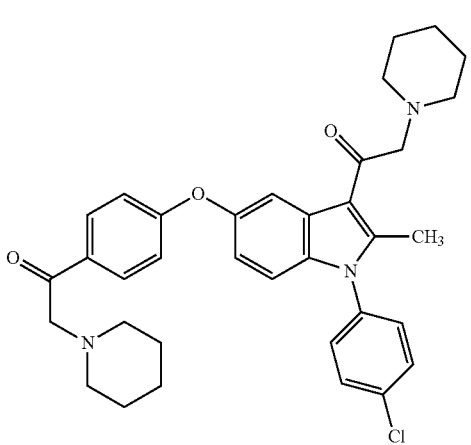 [SMILES: Cc1c(C(=O)CN2CCCCC2)c2cc(Oc3ccc(C(=O)CN4CCCCC4)cc3)ccc2n1-c1ccc(Cl)cc1] |

| 511 -continued | 512 -continued |
|---|---|
| 167 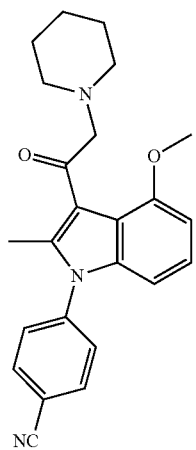 | 170 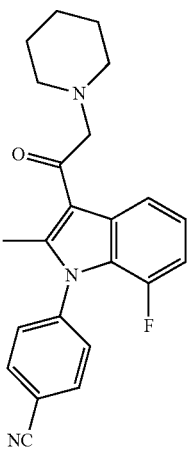 [SMILES: Cc1c(C(=O)CN2CCCCC2)c2cccc(F)c2n1-c1ccc(C#N)cc1] |
| 168 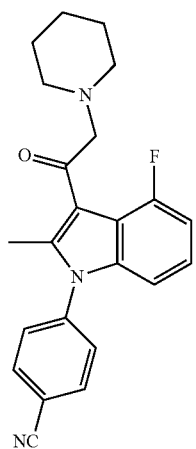 | 171 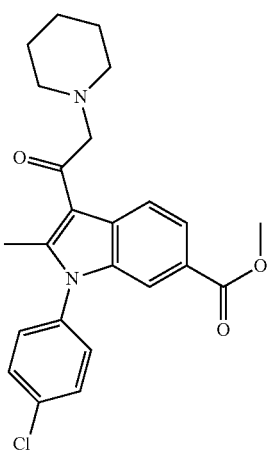 |
| 169 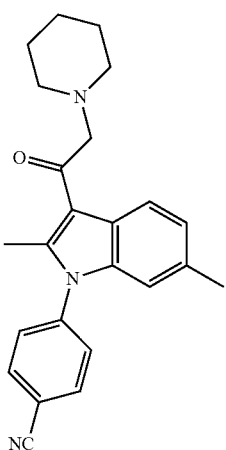 | 172 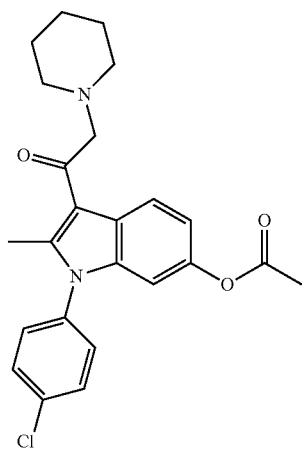 [SMILES: CC(=O)Oc1ccc2c(C(=O)CN3CCCCC3)c(C)n(-c3ccc(Cl)cc3)c2c1] |

| 513 -continued | 514 -continued |
|---|---|
| 173 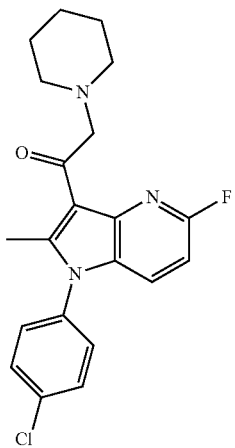 | 177 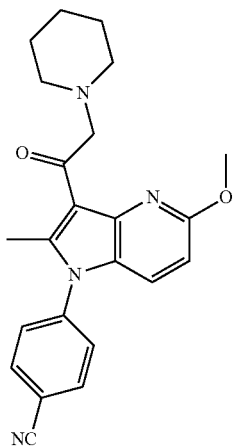 |
| 174 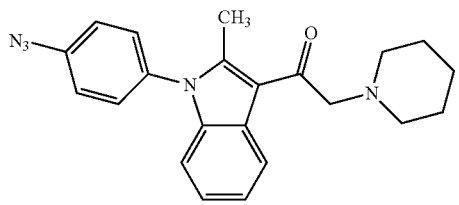 [SMILES: Cc1c(C(=O)CN2CCCCC2)c2ccccc2n1-c1ccc(N=[N+]=[N-])cc1] | |
| 175 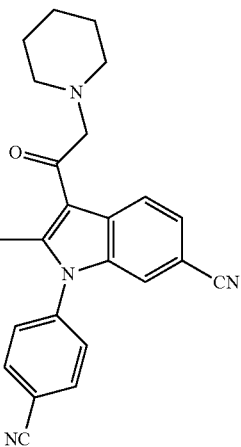 [SMILES: Cc1c(C(=O)CN2CCCCC2)c2ccc(C#N)cc2n1-c1ccc(C#N)cc1] | 178 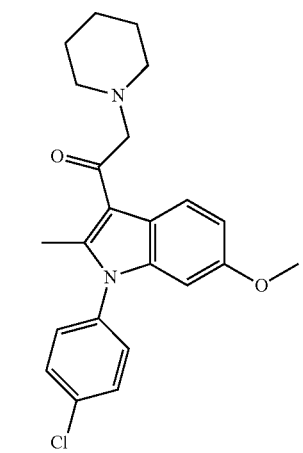 |
| 176 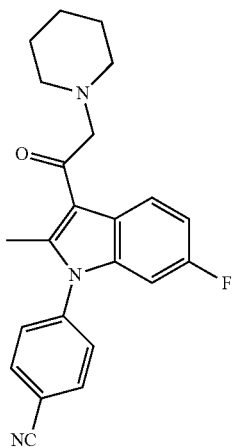 [SMILES: Cc1c(C(=O)CN2CCCCC2)c2ccc(F)cc2n1-c1ccc(C#N)cc1] | 179 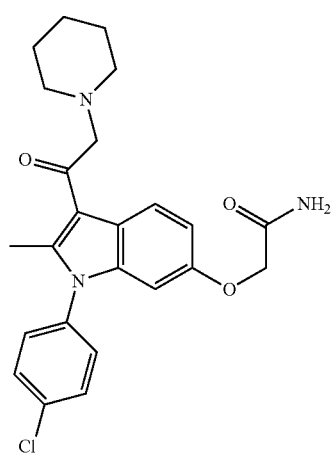 [SMILES: Cc1c(C(=O)CN2CCCCC2)c2ccc(OCC(N)=O)cc2n1-c1ccc(Cl)cc1] |

| 515 -continued | 516 -continued |
|---|---|
| 180 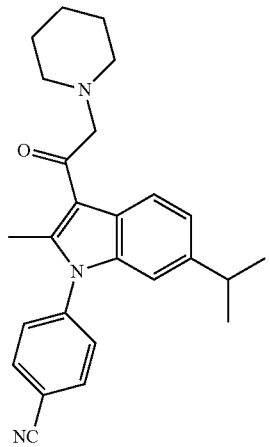 [SMILES: Cc1c(C(=O)CN2CCCCC2)c2ccc(C(C)C)cc2n1-c1ccc(C#N)cc1] | 183 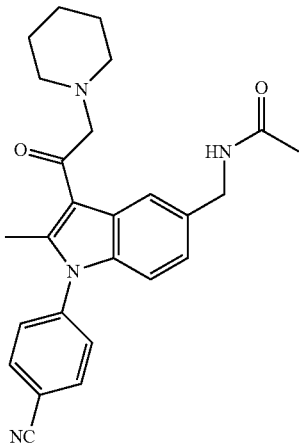 [SMILES: CC(=O)NCc1ccc2c(c1)c(C(=O)CN1CCCCC1)c(C)n2-c1ccc(C#N)cc1] |
| 181 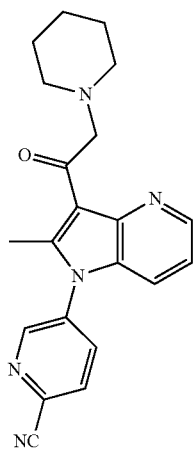 | 184 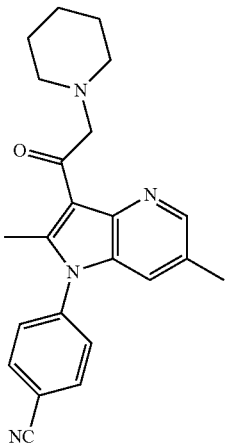 |
| 182 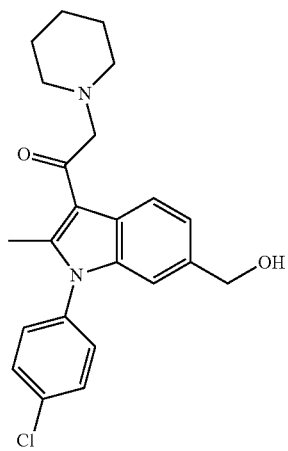 | 185 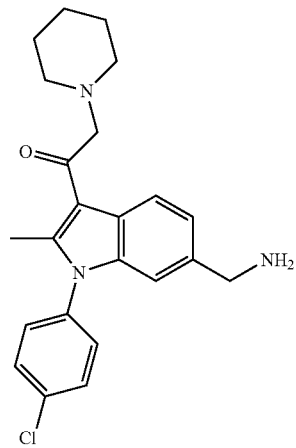 [SMILES: Cc1c(C(=O)CN2CCCCC2)c2ccc(CN)cc2n1-c1ccc(Cl)cc1] |

| 517 -continued | 518 -continued |
|---|---|
| 186 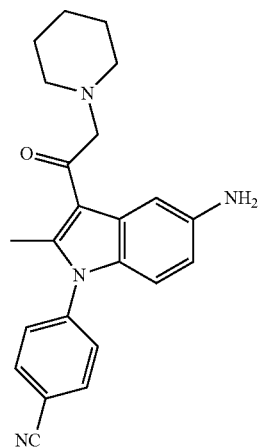 | 189 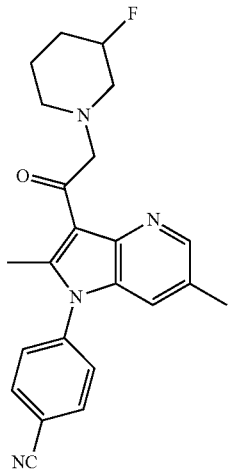 |
| 187 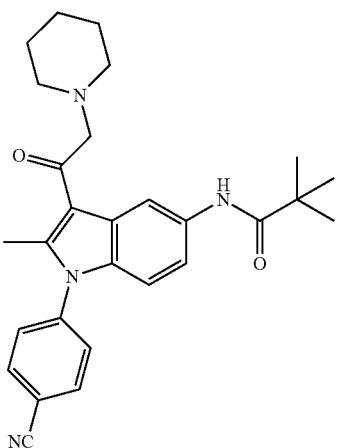 [SMILES: Cc1c(C(=O)CN2CCCCC2)c2cc(NC(=O)C(C)(C)C)ccc2n1-c1ccc(C#N)cc1] | 190 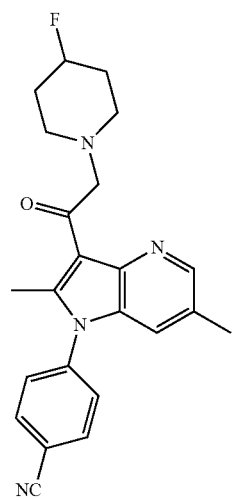 |
| 188 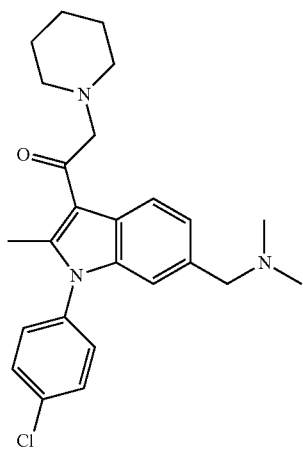 | 191 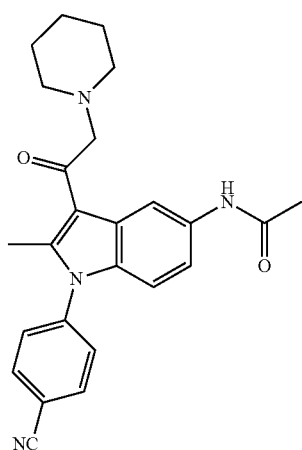 [SMILES: CC(=O)Nc1ccc2c(c1)c(C(=O)CN1CCCCC1)c(C)n2-c1ccc(C#N)cc1] |

| 519 -continued | 520 -continued |
|---|---|
| 192 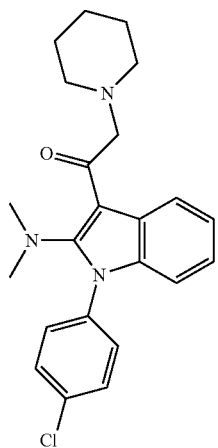 [SMILES: CN(C)c1c(C(=O)CN2CCCCC2)c2ccccc2n1-c1ccc(Cl)cc1] | 195 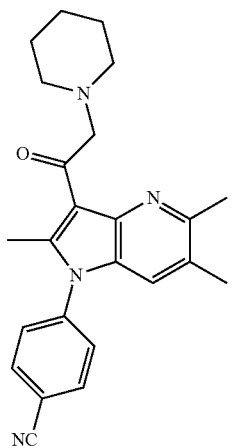 |
| 193 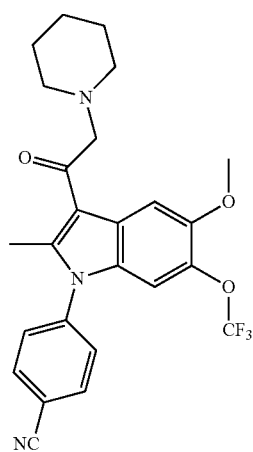 [SMILES: COc1cc2c(C(=O)CN3CCCCC3)c(C)n(-c3ccc(C#N)cc3)c2cc1OC(F)(F)F] | 196 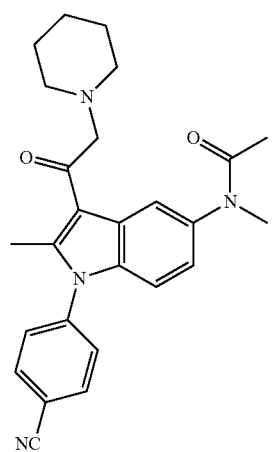 |
| 194 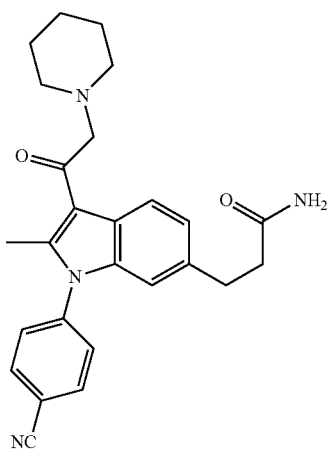 [SMILES: Cc1c(C(=O)CN2CCCCC2)c2ccc(CCC(N)=O)cc2n1-c1ccc(C#N)cc1] | 197 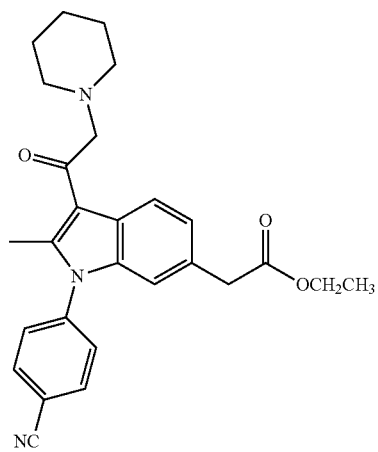 [SMILES: CCOC(=O)Cc1ccc2c(C(=O)CN3CCCCC3)c(C)n(-c3ccc(C#N)cc3)c2c1] |

| 521 -continued | 522 -continued |
|---|---|
| 198 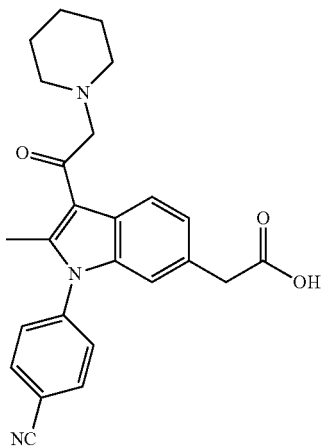 [SMILES: Cc1c(C(=O)CN2CCCCC2)c2ccc(CC(=O)O)cc2n1-c1ccc(C#N)cc1] | 201 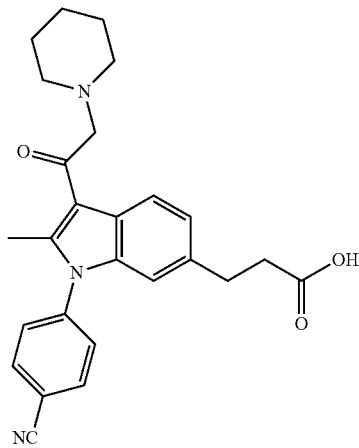 [SMILES: Cc1c(C(=O)CN2CCCCC2)c2ccc(CCC(=O)O)cc2n1-c1ccc(C#N)cc1] |
| 199 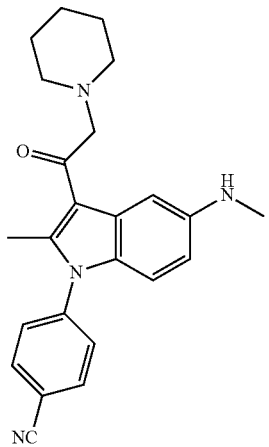 | 202 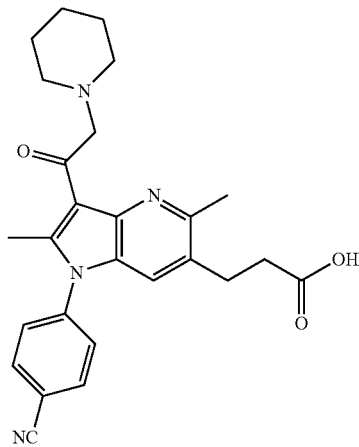 [SMILES: Cc1nc2c(C(=O)CN3CCCCC3)c(C)n(-c3ccc(C#N)cc3)c2cc1CCC(=O)O] |
| 200 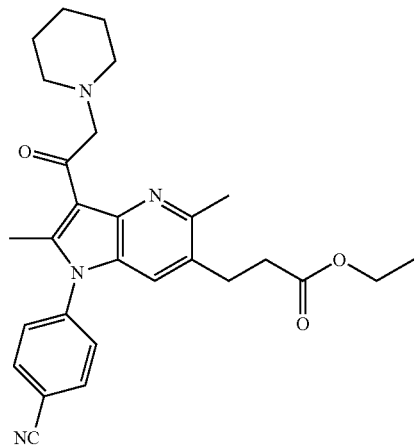 | 203 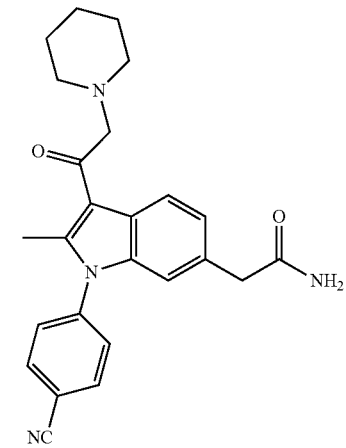 [SMILES: Cc1c(C(=O)CN2CCCCC2)c2ccc(CC(N)=O)cc2n1-c1ccc(C#N)cc1] |

| 523 -continued | 524 -continued |
|---|---|
| 204 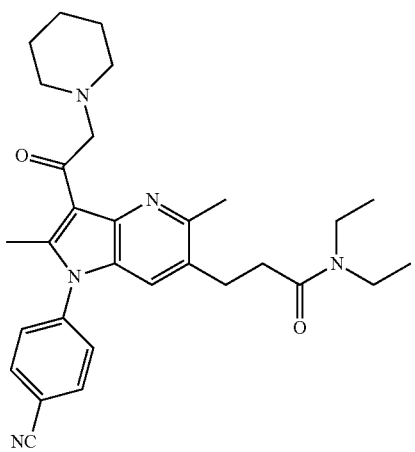 [SMILES: CCN(CC)C(=O)CCc1cc2c(nc1C)c(C(=O)CN1CCCCC1)c(C)n2-c1ccc(C#N)cc1] | 207 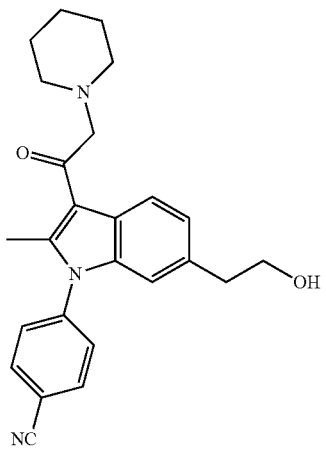 |
| 205 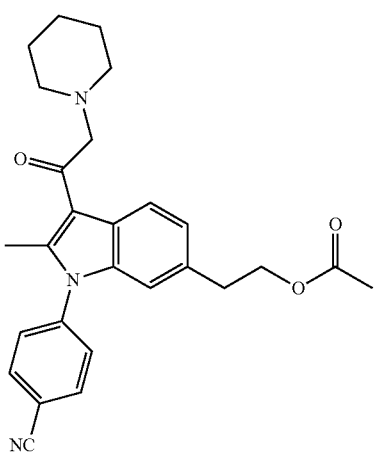 [SMILES: CC(=O)OCCc1ccc2c(C(=O)CN3CCCCC3)c(C)n(-c3ccc(C#N)cc3)c2c1] | 208 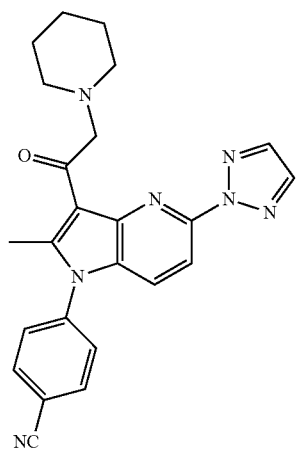 |
| 206 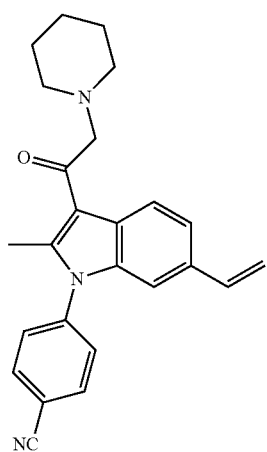 [SMILES: C=Cc1ccc2c(C(=O)CN3CCCCC3)c(C)n(-c3ccc(C#N)cc3)c2c1] | 209 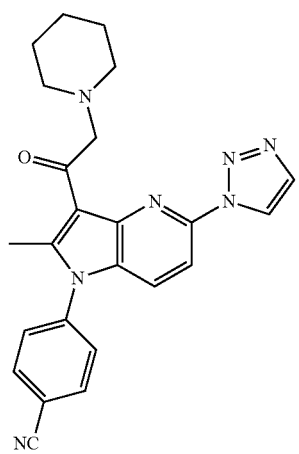 [SMILES: Cc1c(C(=O)CN2CCCCC2)c2nc(-n3ccnn3)ccc2n1-c1ccc(C#N)cc1] |

| 525 -continued | 526 -continued |
|---|---|
| 210 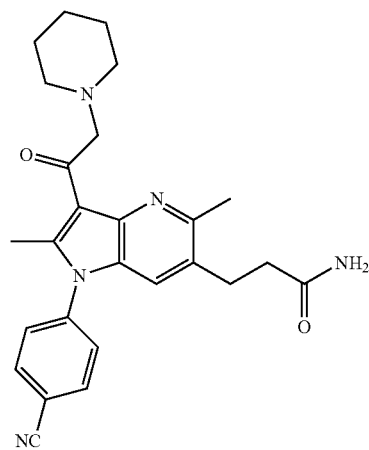 [SMILES: Cc1nc2c(C(=O)CN3CCCCC3)c(C)n(-c3ccc(C#N)cc3)c2cc1CCC(N)=O] | 213 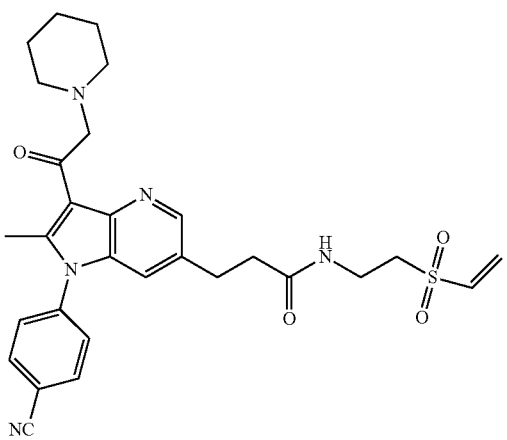 |
| 211 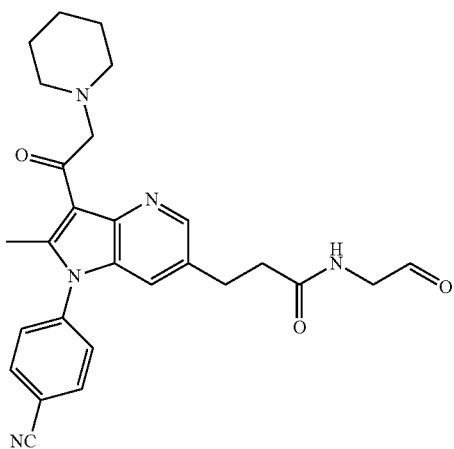 [SMILES: Cc1c(C(=O)CN2CCCCC2)c2ncc(CCC(=O)NCC=O)cc2n1-c1ccc(C#N)cc1] | 214 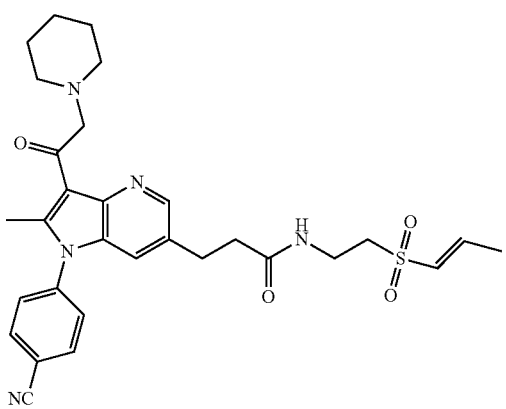 |
| 212 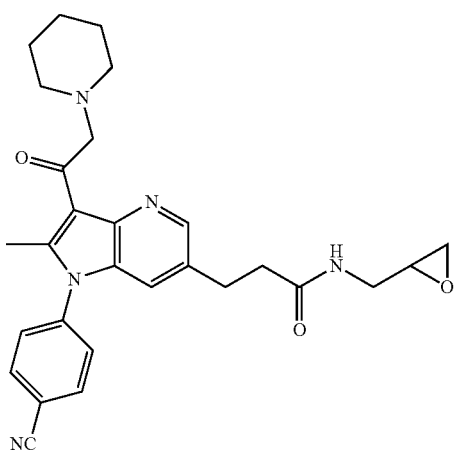 [SMILES: Cc1c(C(=O)CN2CCCCC2)c2ncc(CCC(=O)NCC3CO3)cc2n1-c1ccc(C#N)cc1] | 215 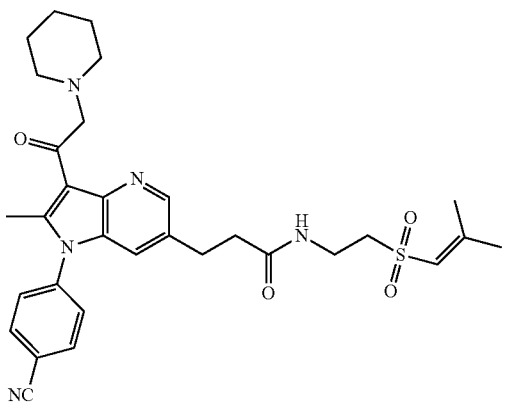 [SMILES: CC(C)=CS(=O)(=O)CCNC(=O)CCc1cnc2c(C(=O)CN3CCCCC3)c(C)n(-c3ccc(C#N)cc3)c2c1] |

527
-continued
216
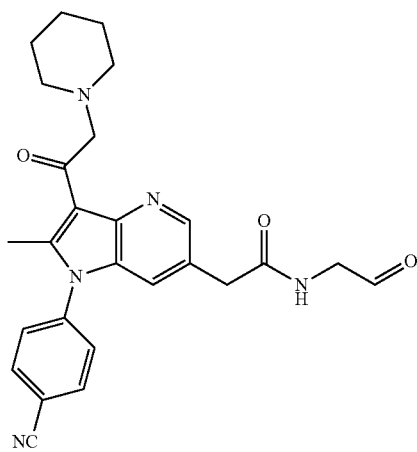 [SMILES: Cc1c(C(=O)CN2CCCCC2)c2ncc(CC(=O)NCC=O)cc2n1-c1ccc(C#N)cc1]
217
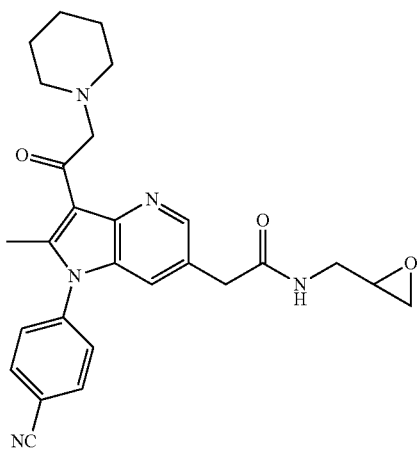 [SMILES: Cc1c(C(=O)CN2CCCCC2)c2ncc(CC(=O)NCC3CO3)cc2n1-c1ccc(C#N)cc1]
218
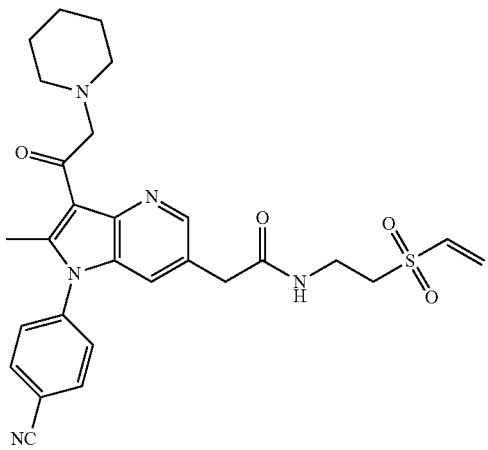 [SMILES: C=CS(=O)(=O)CCNC(=O)Cc1cnc2c(C(=O)CN3CCCCC3)c(C)n(-c3ccc(C#N)cc3)c2c1]
528
-continued
219
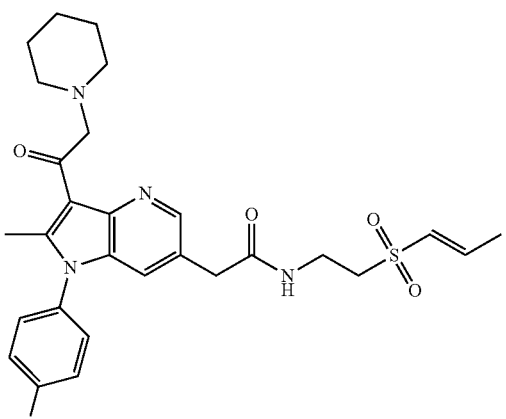
220
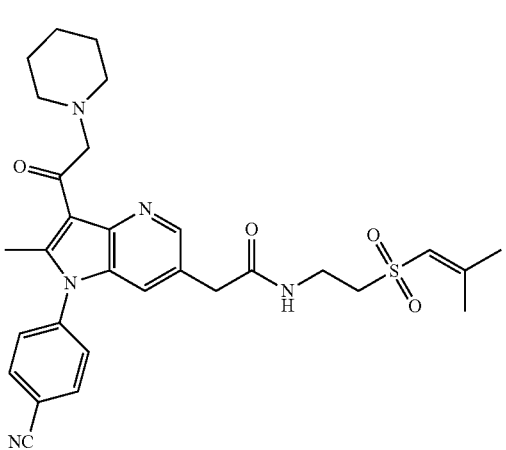 [SMILES: CC(C)=CS(=O)(=O)CCNC(=O)Cc1cnc2c(C(=O)CN3CCCCC3)c(C)n(-c3ccc(C#N)cc3)c2c1]
230
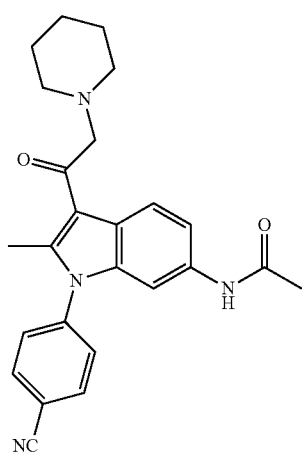 [SMILES: CC(=O)Nc1ccc2c(C(=O)CN3CCCCC3)c(C)n(-c3ccc(C#N)cc3)c2c1]

| 529 -continued | 530 -continued |
|---|---|
| 231 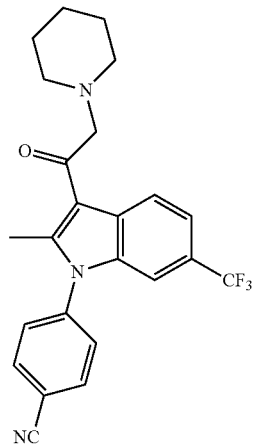 [SMILES: Cc1c(C(=O)CN2CCCCC2)c2ccc(C(F)(F)F)cc2n1-c1ccc(C#N)cc1] | 235 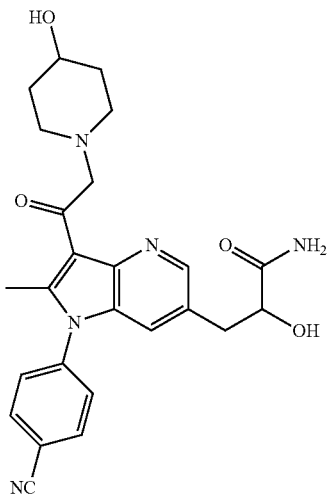 |
| 233 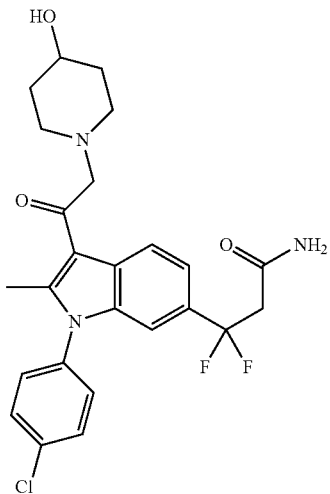 [SMILES: Cc1c(C(=O)CN2CCC(O)CC2)c2ccc(C(F)(F)CC(N)=O)cc2n1-c1ccc(Cl)cc1] | 236 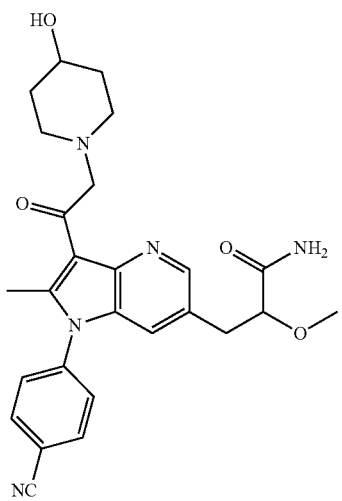 |
| 234 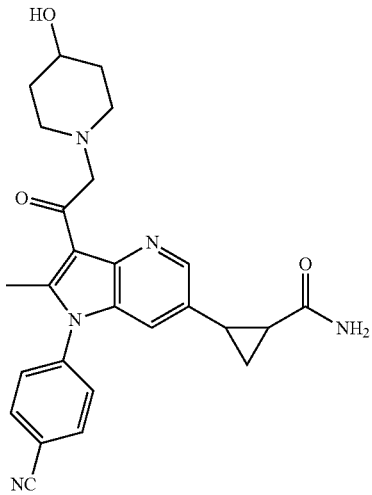 [SMILES: Cc1c(C(=O)CN2CCC(O)CC2)c2ncc(C3CC3C(N)=O)cc2n1-c1ccc(C#N)cc1] | 237 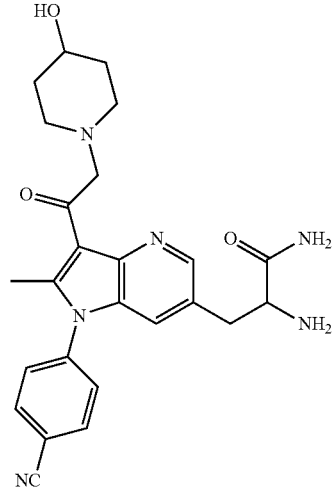 [SMILES: Cc1c(C(=O)CN2CCC(O)CC2)c2ncc(CC(N)C(N)=O)cc2n1-c1ccc(C#N)cc1] |

| 531 -continued | 532 -continued |
|---|---|
| 238 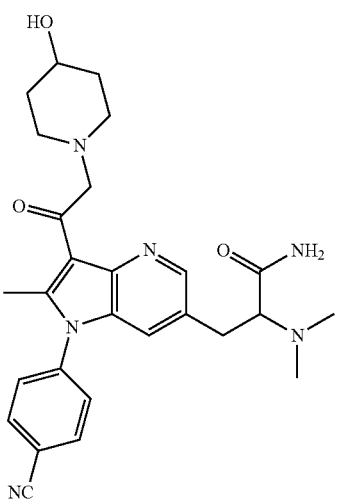 | 241 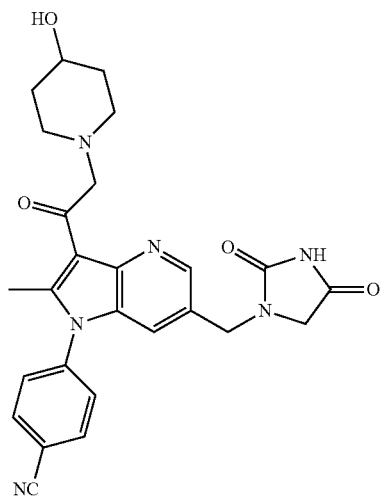 |
| 239 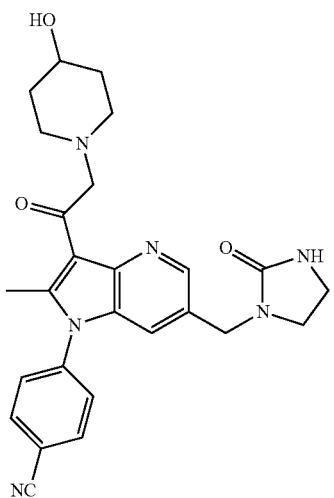 | 242 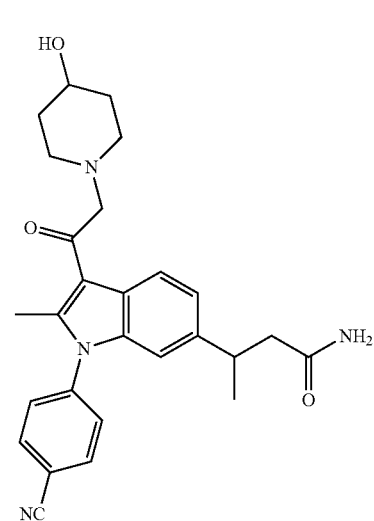 |
| 240 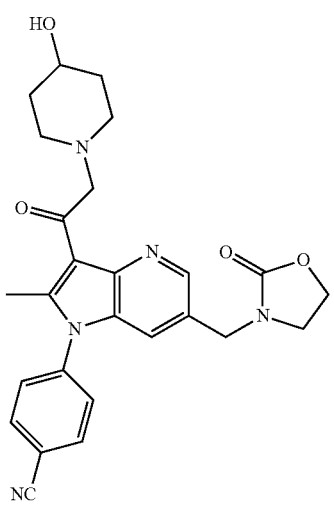 [SMILES: Cc1c(C(=O)CN2CCC(O)CC2)c2ncc(CN3CCOC3=O)cc2n1-c1ccc(C#N)cc1] | 243 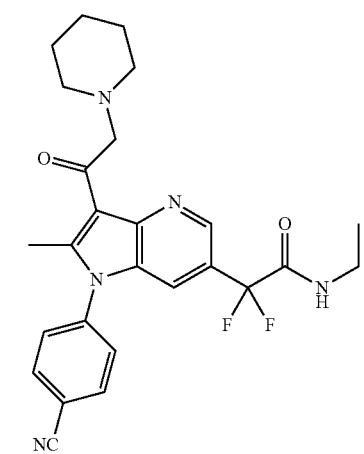 [SMILES: CCNC(=O)C(F)(F)c1cnc2c(C(=O)CN3CCCCC3)c(C)n(-c3ccc(C#N)cc3)c2c1] |

| 244 | 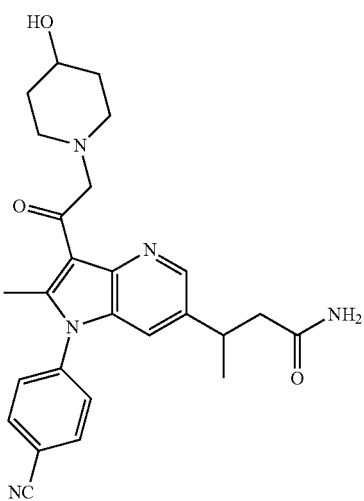 [SMILES: Cc1c(C(=O)CN2CCC(O)CC2)c2ncc(C(C)CC(N)=O)cc2n1-c1ccc(C#N)cc1] | 247 | 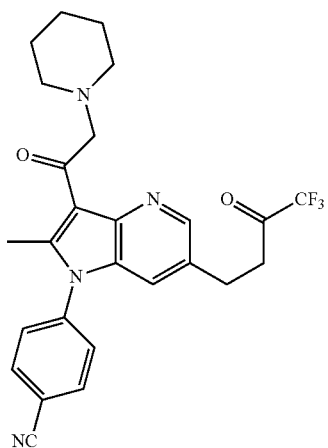 |
|---|---|---|---|
| 245 | 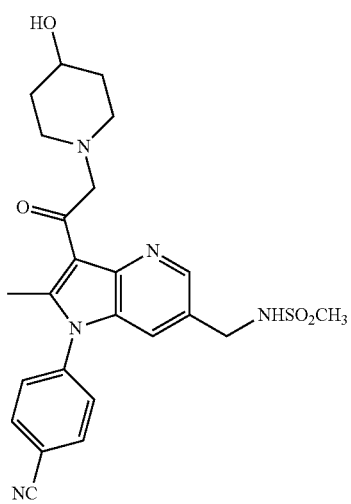 | 248 | 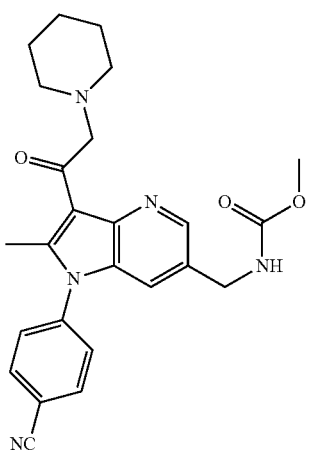 |
| 246 | 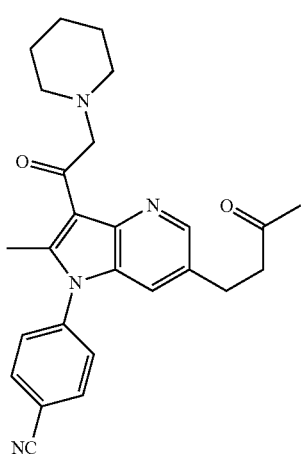 [SMILES: CC(=O)CCc1cnc2c(C(=O)CN3CCCCC3)c(C)n(-c3ccc(C#N)cc3)c2c1] | 249 | 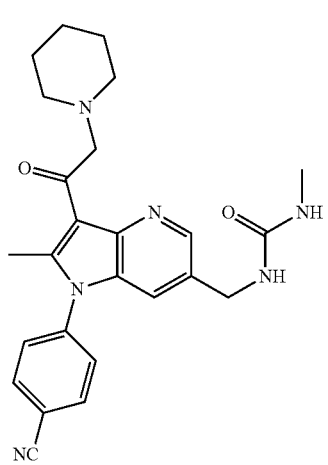 |

| 250 | 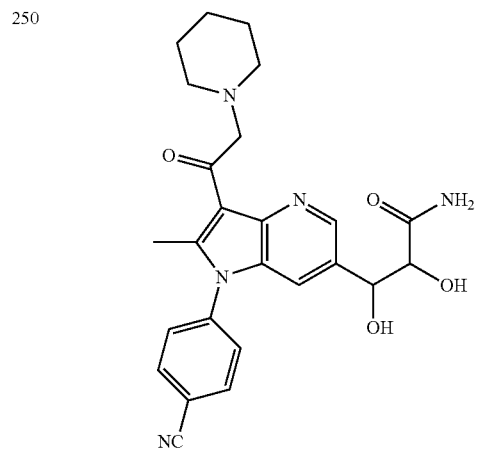 | 253 | 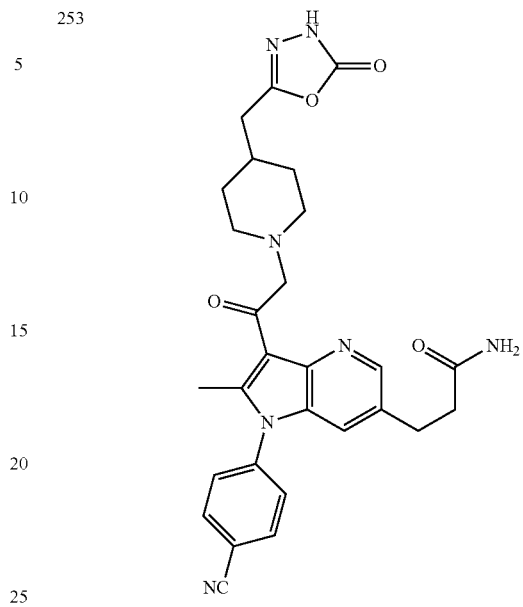 |
| --- | --- | --- | --- |
| 251 | 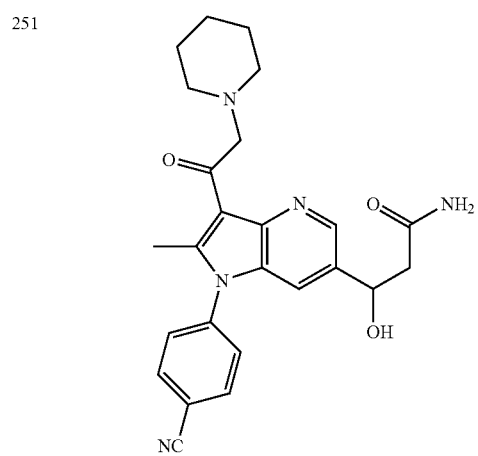 | 254 | 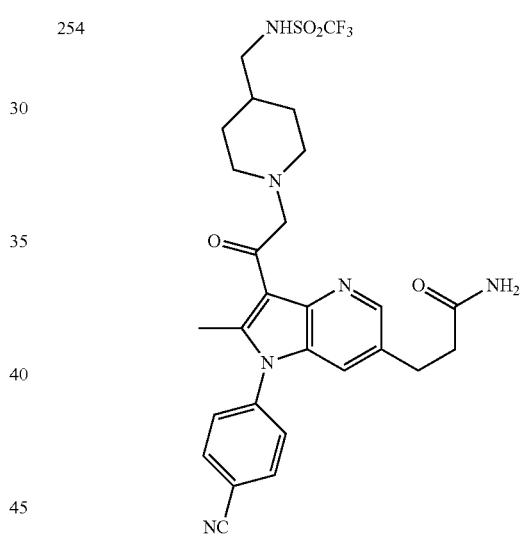 |
| 252 | 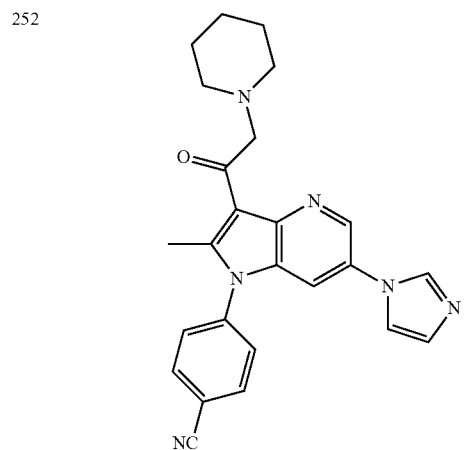 | 255 | 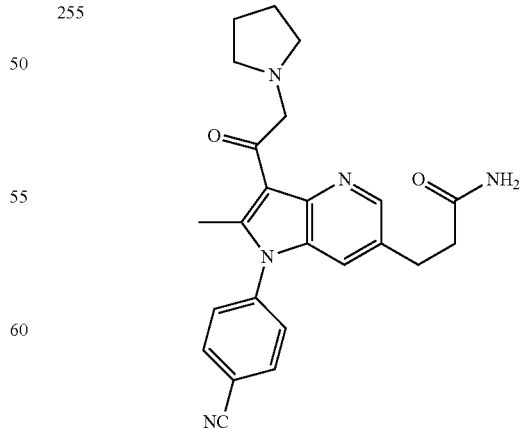 |

256 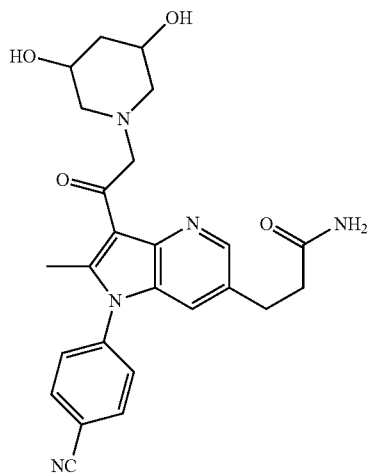 [SMILES: Cc1c(C(=O)CN2CC(O)CC(O)C2)c2ncc(CCC(N)=O)cc2n1-c1ccc(C#N)cc1]
257 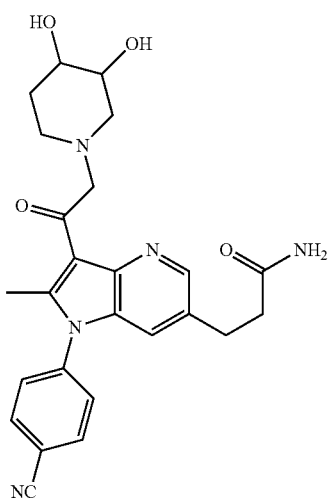 [SMILES: Cc1c(C(=O)CN2CCC(O)C(O)C2)c2ncc(CCC(N)=O)cc2n1-c1ccc(C#N)cc1]
258 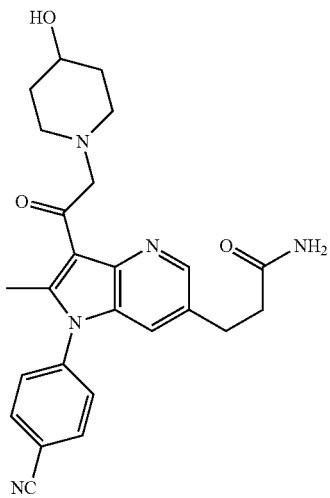 [SMILES: Cc1c(C(=O)CN2CCC(O)CC2)c2ncc(CCC(N)=O)cc2n1-c1ccc(C#N)cc1]
259 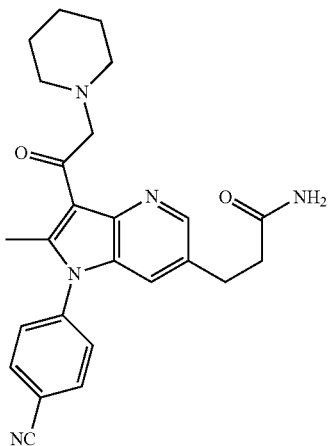 [SMILES: Cc1c(C(=O)CN2CCCCC2)c2ncc(CCC(N)=O)cc2n1-c1ccc(C#N)cc1]
260 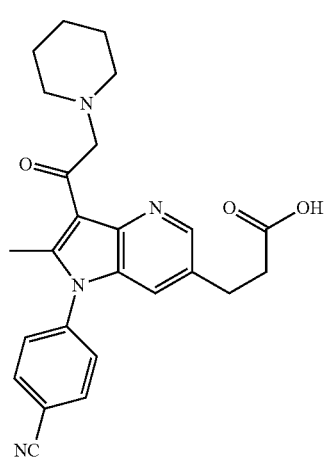 [SMILES: Cc1c(C(=O)CN2CCCCC2)c2ncc(CCC(=O)O)cc2n1-c1ccc(C#N)cc1]
261 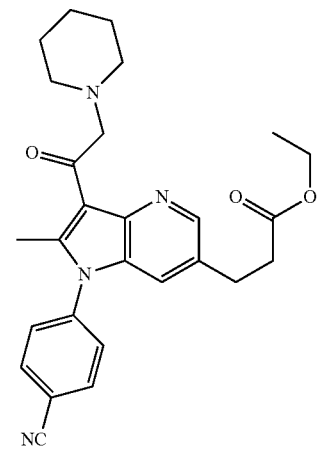 [SMILES: CCOC(=O)CCc1cnc2c(C(=O)CN3CCCCC3)c(C)n(-c3ccc(C#N)cc3)c2c1]

262 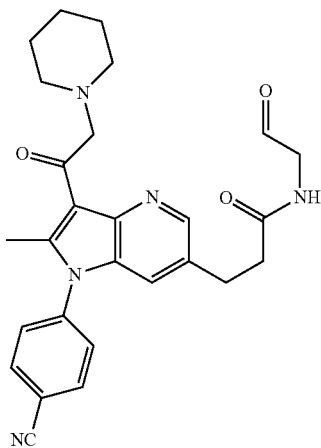 [SMILES: Cc1c(C(=O)CN2CCCCC2)c2ncc(CCC(=O)NCC=O)cc2n1-c1ccc(C#N)cc1]
265 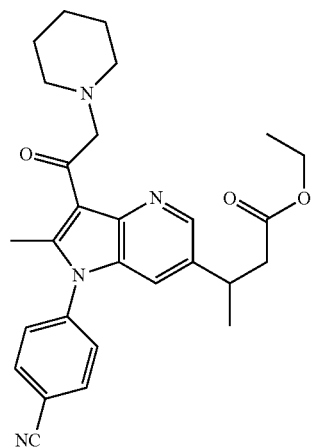
263 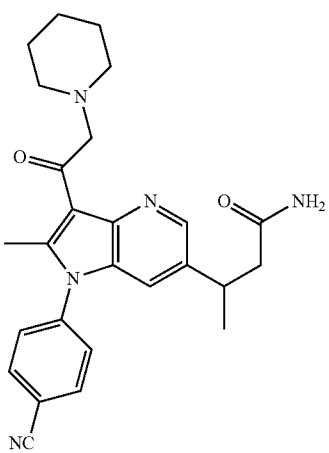 [SMILES: Cc1c(C(=O)CN2CCCCC2)c2ncc(C(C)CC(N)=O)cc2n1-c1ccc(C#N)cc1]
266 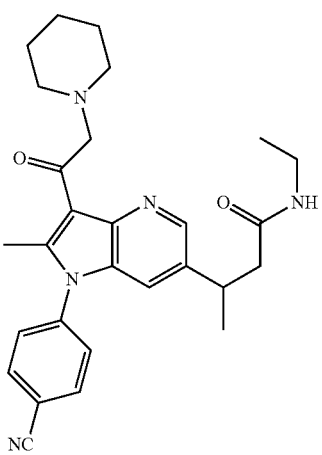
264 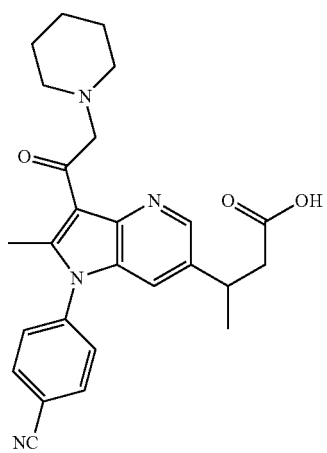 [SMILES: Cc1c(C(=O)CN2CCCCC2)c2ncc(C(C)CC(=O)O)cc2n1-c1ccc(C#N)cc1]
267 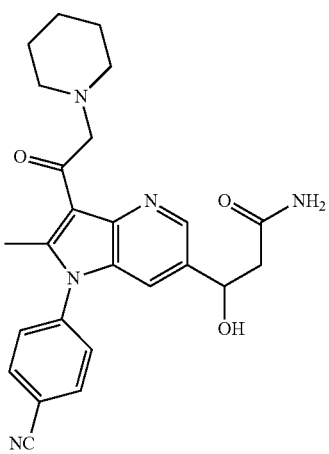 [SMILES: Cc1c(C(=O)CN2CCCCC2)c2ncc(C(O)CC(N)=O)cc2n1-c1ccc(C#N)cc1]

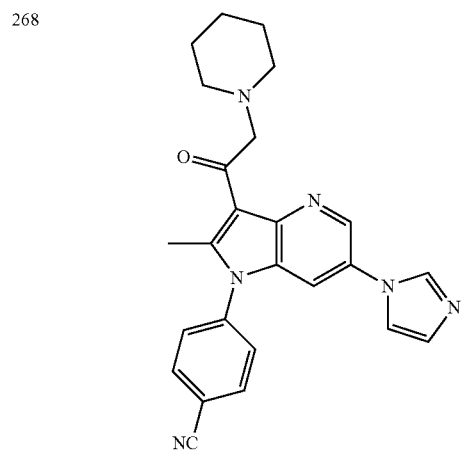
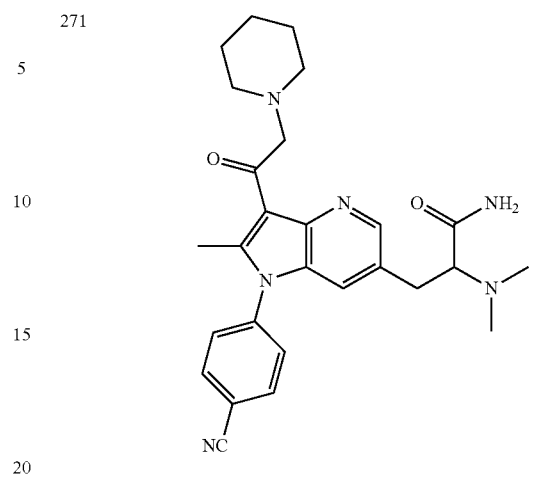

| 274 | 277 |
|---|---|
| 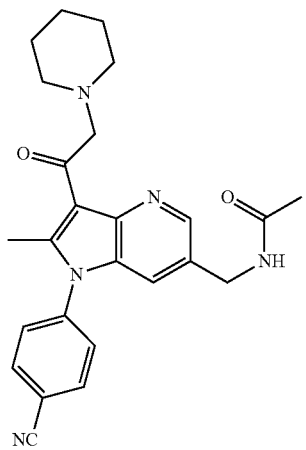 [SMILES: CC(=O)NCc1cnc2c(C(=O)CN3CCCCC3)c(C)n(-c3ccc(C#N)cc3)c2c1] | 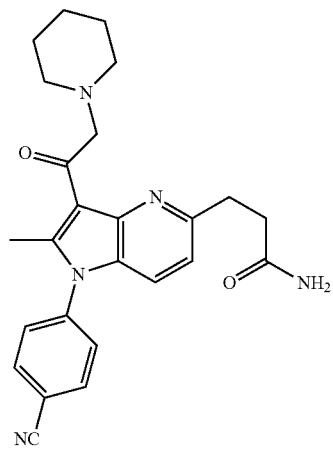 |
| 275 | 278 |
| 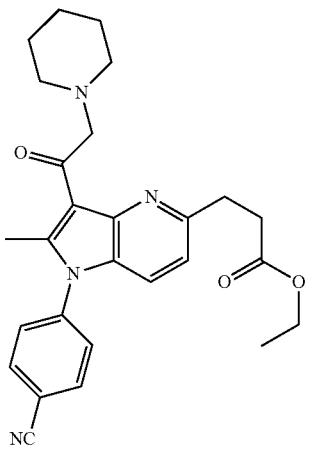 [SMILES: CCOC(=O)CCc1ccc2c(n1)c(C(=O)CN1CCCCC1)c(C)n2-c1ccc(C#N)cc1] | 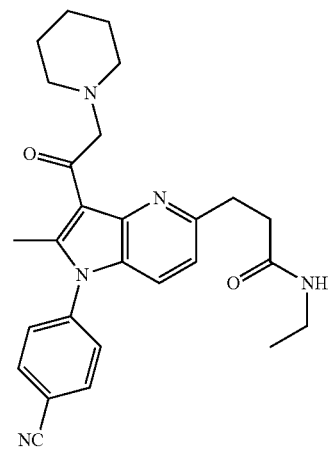 |
| 276 | 279 |
| 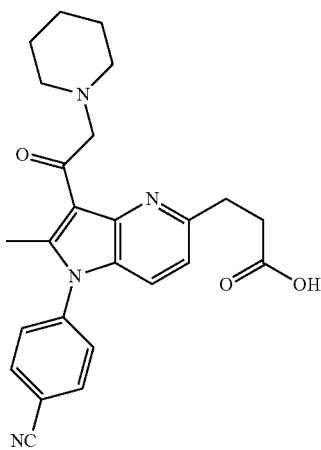 [SMILES: Cc1c(C(=O)CN2CCCCC2)c2nc(CCC(=O)O)ccc2n1-c1ccc(C#N)cc1] | 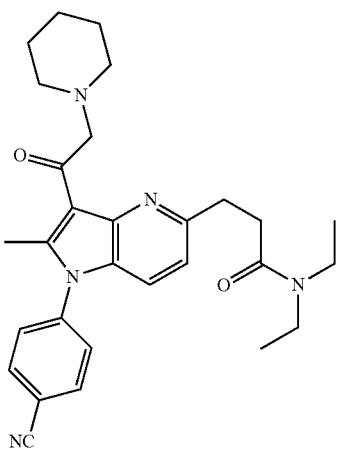 [SMILES: CCN(CC)C(=O)CCc1ccc2c(n1)c(C(=O)CN1CCCCC1)c(C)n2-c1ccc(C#N)cc1] |

| 545 -continued | 546 -continued |
|---|---|
| 280 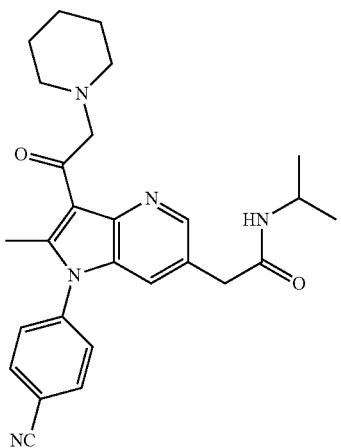 [SMILES: Cc1c(C(=O)CN2CCCCC2)c2ncc(CC(=O)NC(C)C)cc2n1-c1ccc(C#N)cc1] | 283 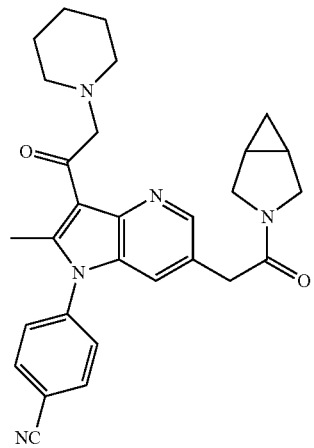 |
| 281 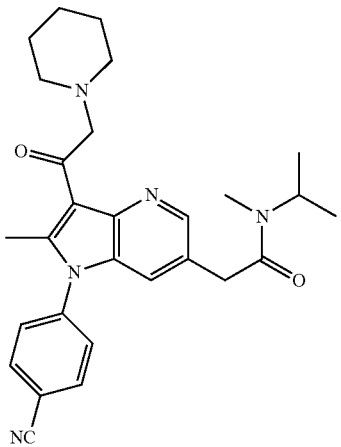 [SMILES: Cc1c(C(=O)CN2CCCCC2)c2ncc(CC(=O)N(C)C(C)C)cc2n1-c1ccc(C#N)cc1] | 284 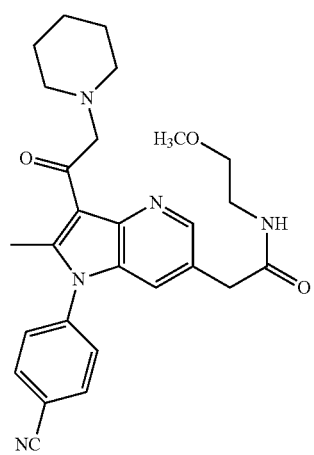 [SMILES: COCCNC(=O)Cc1cnc2c(C(=O)CN3CCCCC3)c(C)n(-c3ccc(C#N)cc3)c2c1] |
| 282 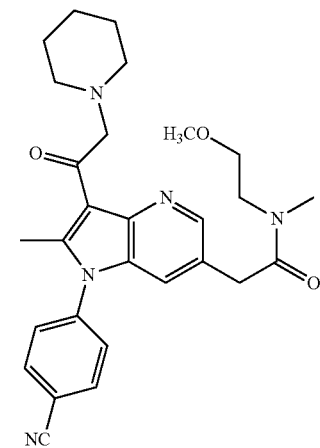 | 285 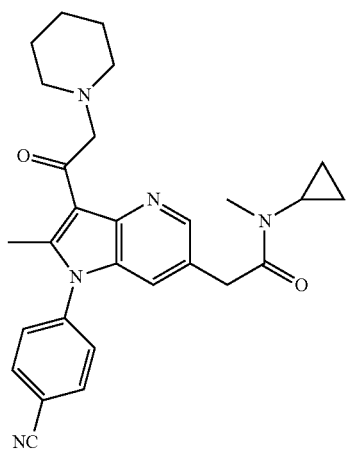 [SMILES: Cc1c(C(=O)CN2CCCCC2)c2ncc(CC(=O)N(C)C3CC3)cc2n1-c1ccc(C#N)cc1] |

| 547 -continued | 548 -continued |
|---|---|
| 286 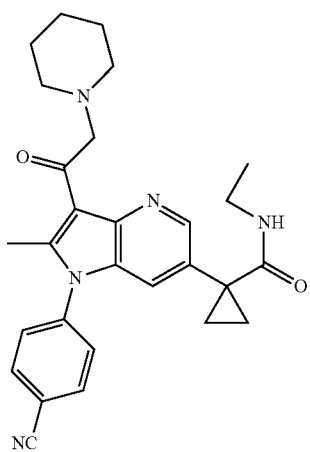 [SMILES: CCNC(=O)C1(c2cnc3c(C(=O)CN4CCCCC4)c(C)n(-c4ccc(C#N)cc4)c3c2)CC1] | 289 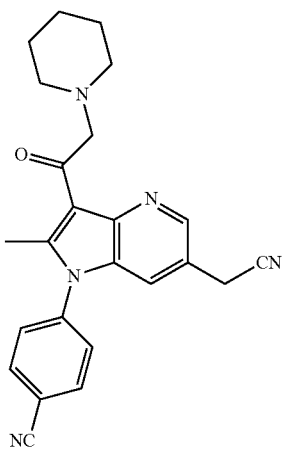 |
| 287 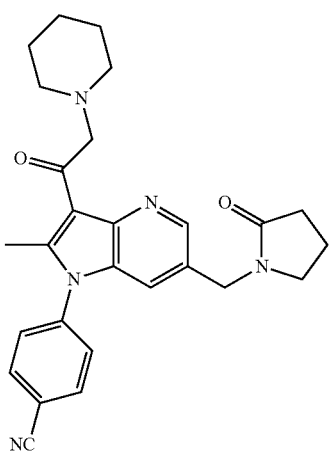 [SMILES: Cc1c(C(=O)CN2CCCCC2)c2ncc(CN3CCCC3=O)cc2n1-c1ccc(C#N)cc1] | 290 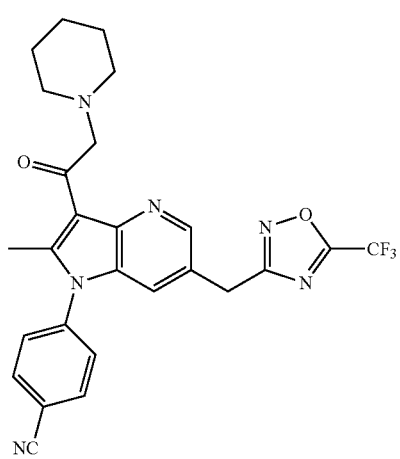 |
| 288 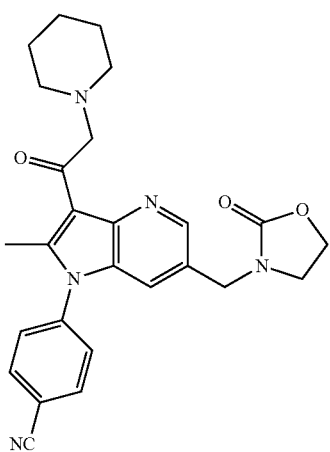 | 291 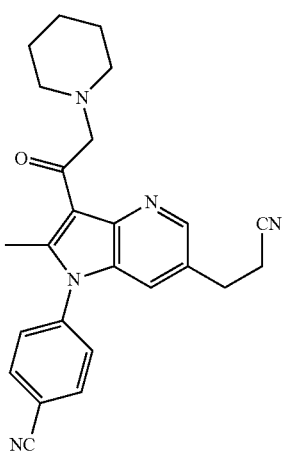 [SMILES: Cc1c(C(=O)CN2CCCCC2)c2ncc(CCC#N)cc2n1-c1ccc(C#N)cc1] |

292 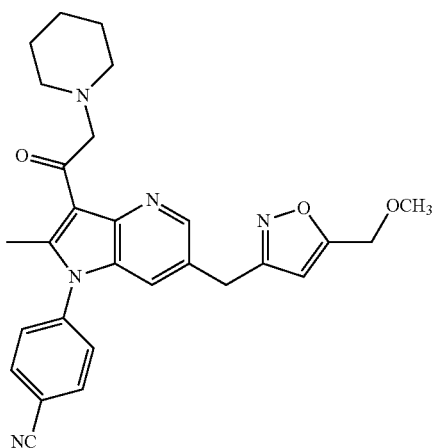 [SMILES: COCc1cc(Cc2cnc3c(C(=O)CN4CCCCC4)c(C)n(-c4ccc(C#N)cc4)c3c2)no1]
296 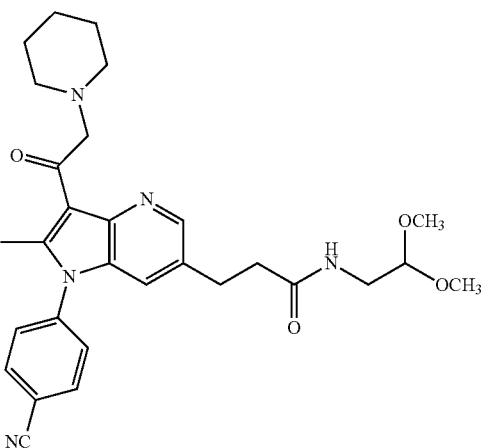
294 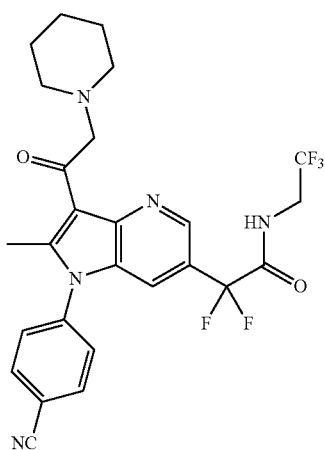 [SMILES: Cc1c(C(=O)CN2CCCCC2)c2ncc(C(F)(F)C(=O)NCC(F)(F)F)cc2n1-c1ccc(C#N)cc1]
297 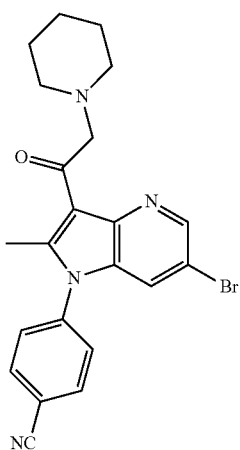
295 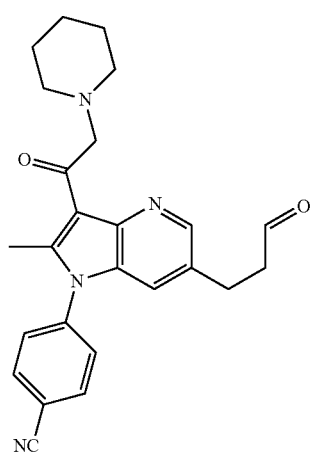 [SMILES: Cc1c(C(=O)CN2CCCCC2)c2ncc(CCC=O)cc2n1-c1ccc(C#N)cc1]
298 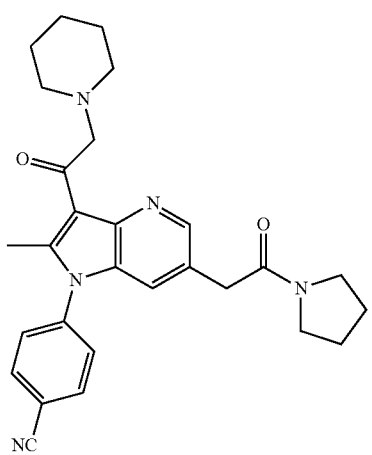 [SMILES: Cc1c(C(=O)CN2CCCCC2)c2ncc(CC(=O)N3CCCC3)cc2n1-c1ccc(C#N)cc1]

| 551 -continued | 552 -continued |
|---|---|
| 299 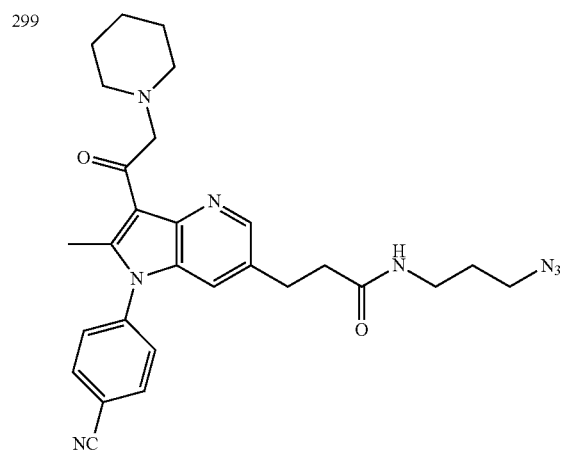 | 302 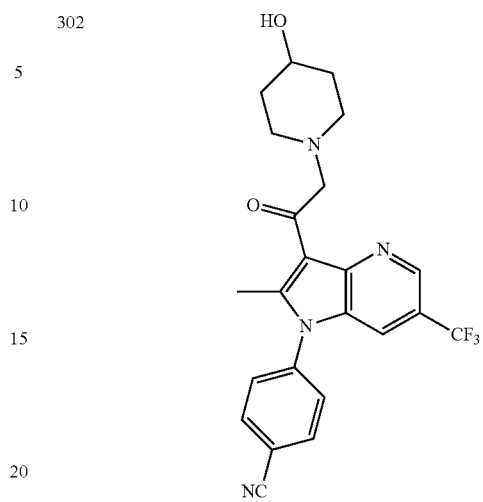 |
| 300 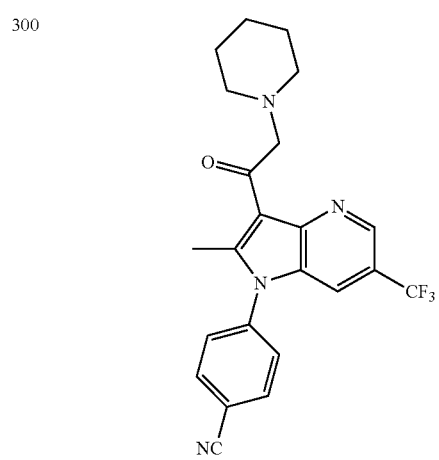 | 303 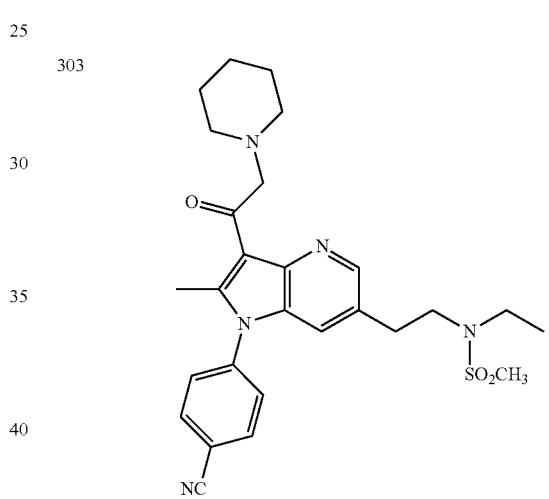 |
| 301 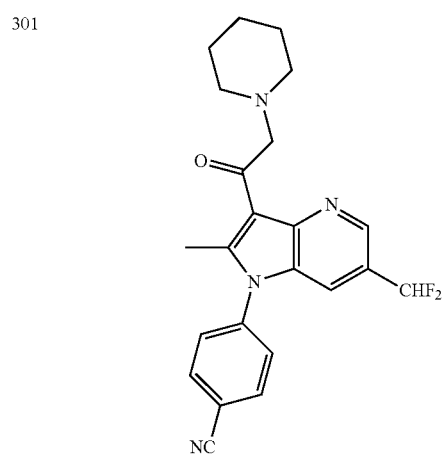 | 304 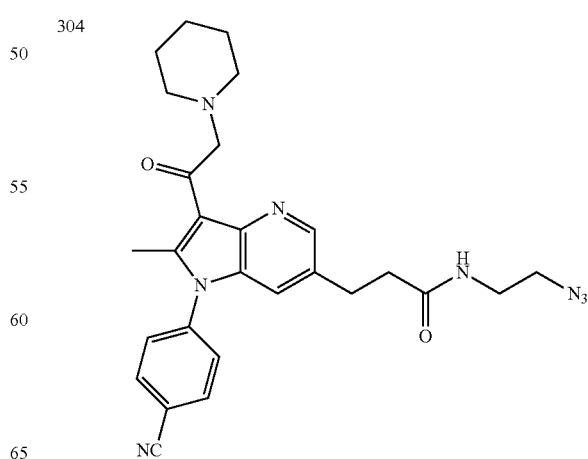 |

553
-continued
305 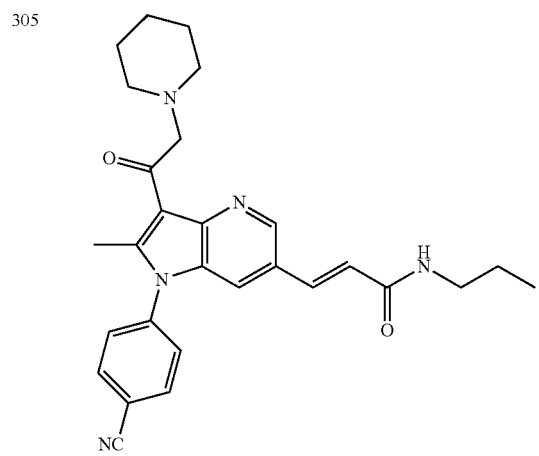
306 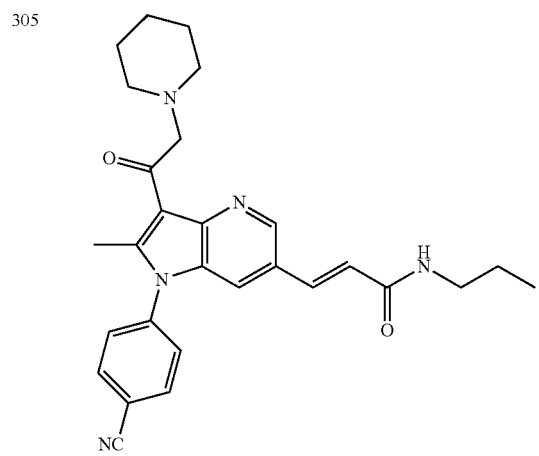
307 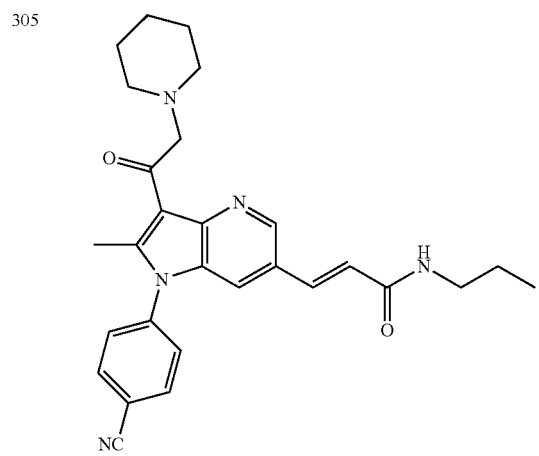
554
-continued
308 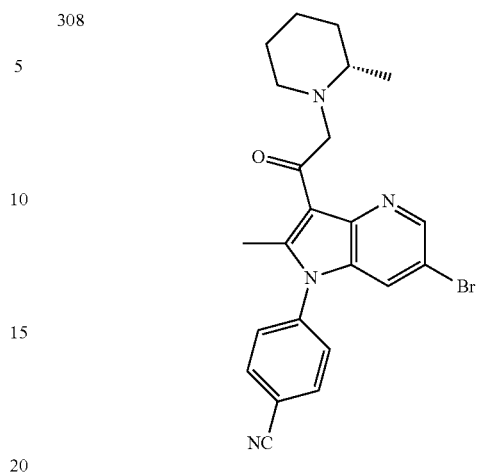
309 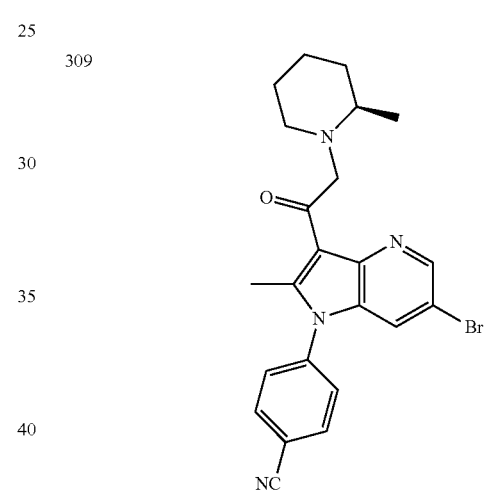
310 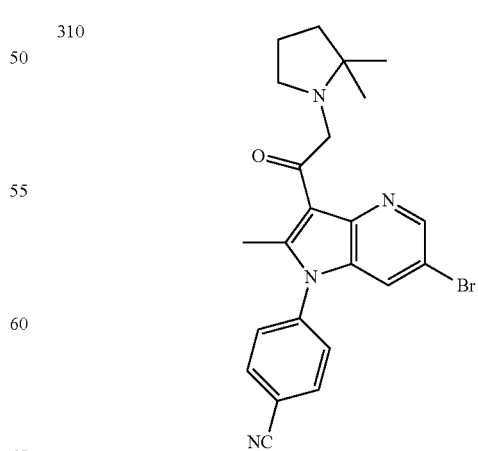

| 555 -continued | 556 -continued |
|---|---|
| 311 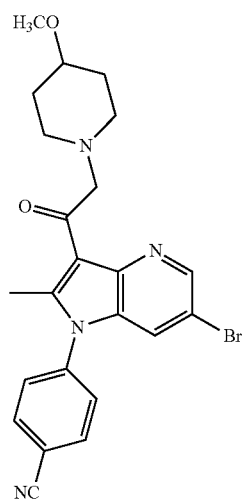 [SMILES: COC1CCN(CC(=O)c2c(C)n(-c3ccc(C#N)cc3)c3cc(Br)cnc23)CC1] | 315 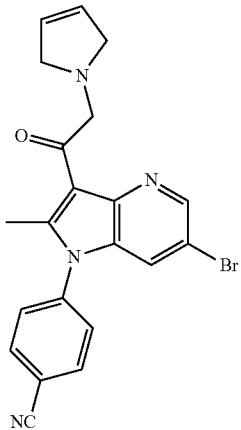 |
| 312 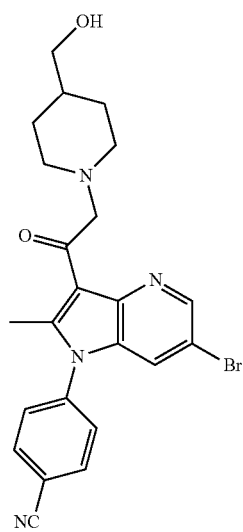 [SMILES: Cc1c(C(=O)CN2CCC(CO)CC2)c2ncc(Br)cc2n1-c1ccc(C#N)cc1] | 318 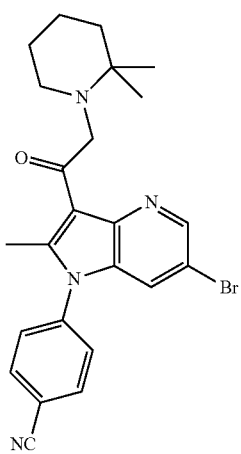 |
| 314 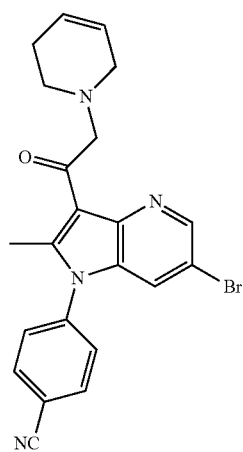 [SMILES: Cc1c(C(=O)CN2CC=CCC2)c2ncc(Br)cc2n1-c1ccc(C#N)cc1] | 319 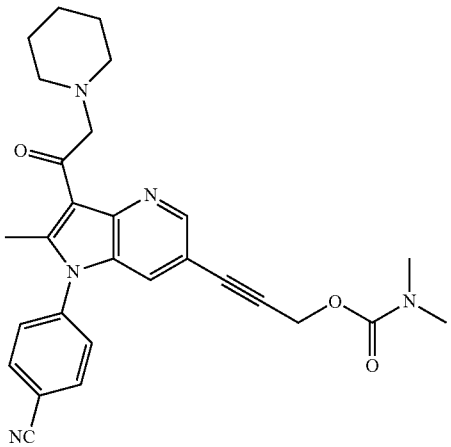 |

| 320 | 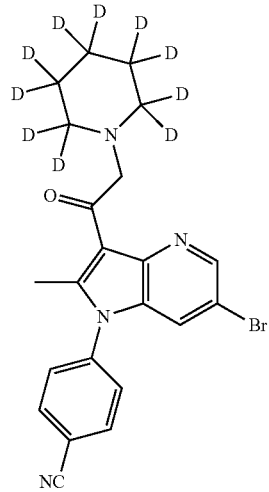 | 325 | 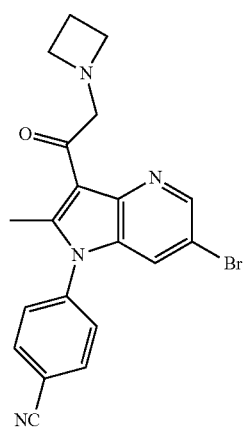 |
| 321 | 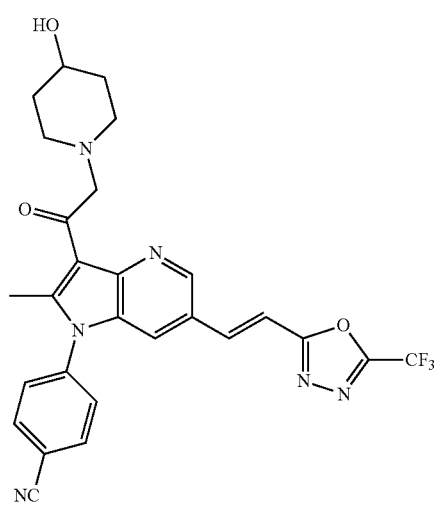 [SMILES: Cc1c(C(=O)CN2CCC(O)CC2)c2ncc(/C=C/c3nnc(C(F)(F)F)o3)cc2n1-c1ccc(C#N)cc1] | 326 | 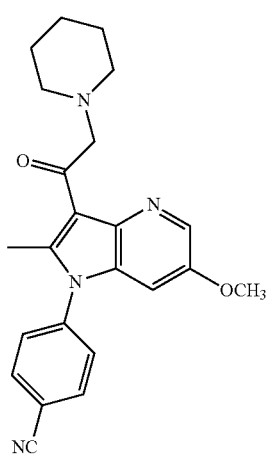 |
| 324 | 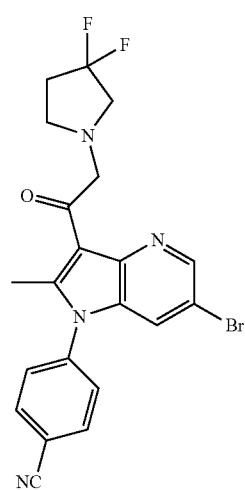 [SMILES: Cc1c(C(=O)CN2CCC(F)(F)C2)c2ncc(Br)cc2n1-c1ccc(C#N)cc1] | 327 | 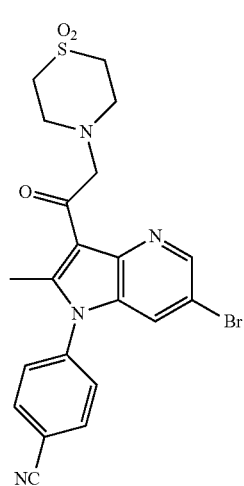 [SMILES: Cc1c(C(=O)CN2CCS(=O)(=O)CC2)c2ncc(Br)cc2n1-c1ccc(C#N)cc1] |

| 328 | 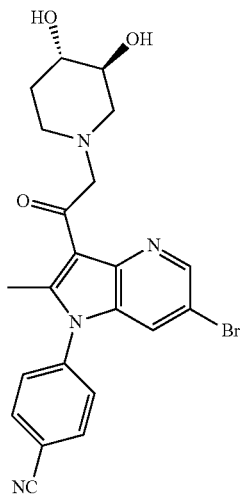 [SMILES: Cc1c(C(=O)CN2CC[C@H](O)[C@@H](O)C2)c2ncc(Br)cc2n1-c1ccc(C#N)cc1] | 331 | 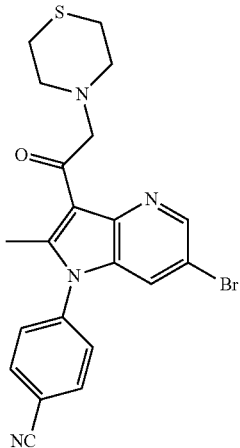 |
|---|---|---|---|
| 329 | 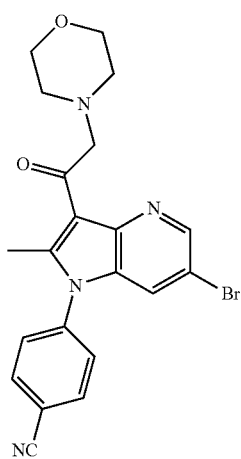 [SMILES: Cc1c(C(=O)CN2CCOCC2)c2ncc(Br)cc2n1-c1ccc(C#N)cc1] | 332 | 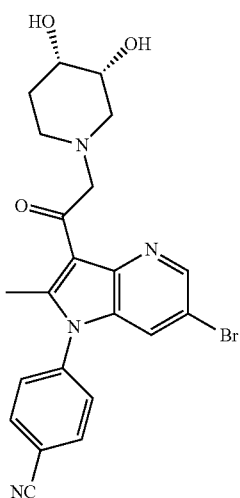 |
| 330 | 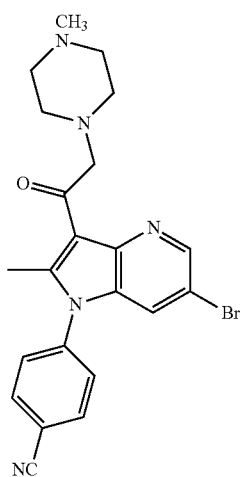 | 335 | 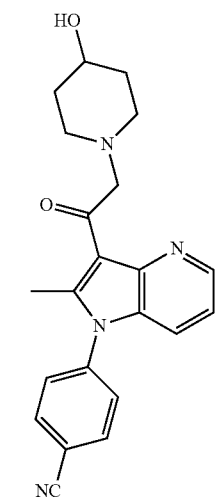 [SMILES: Cc1c(C(=O)CN2CCC(O)CC2)c2ncccc2n1-c1ccc(C#N)cc1] |

| 336 | 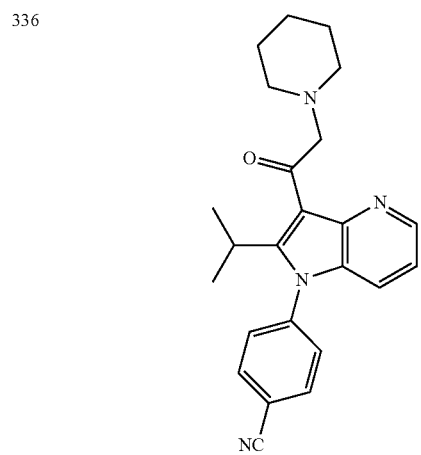 | 339 | 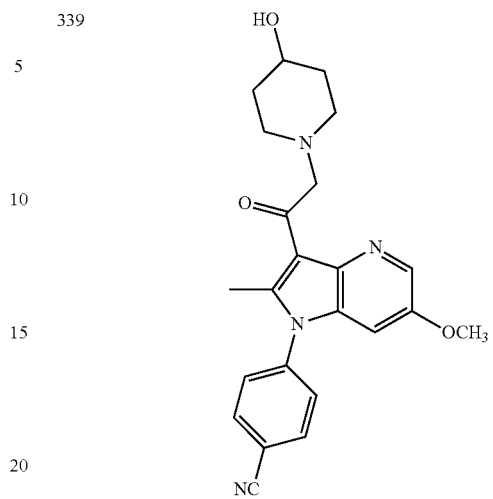 |
| 337 | 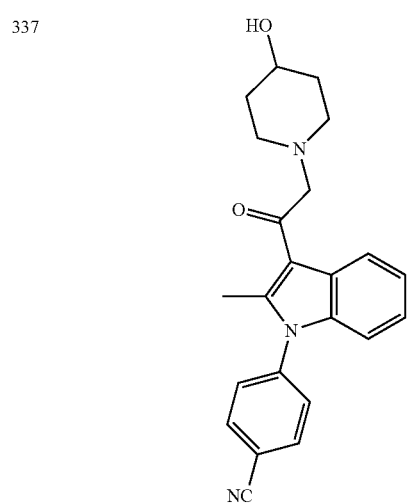 | 340 | 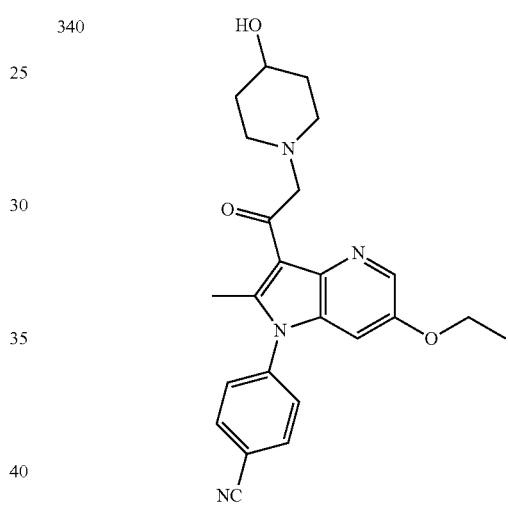 |
| 338 | 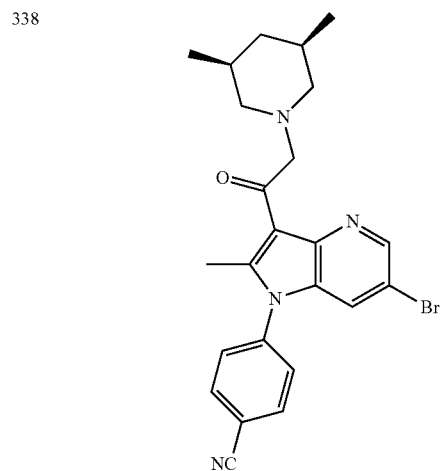 | 341 | 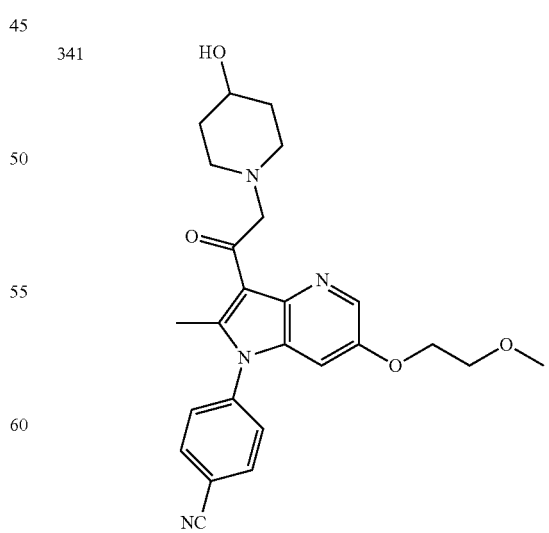 |

| 563 -continued | 564 -continued |
|---|---|
| 342 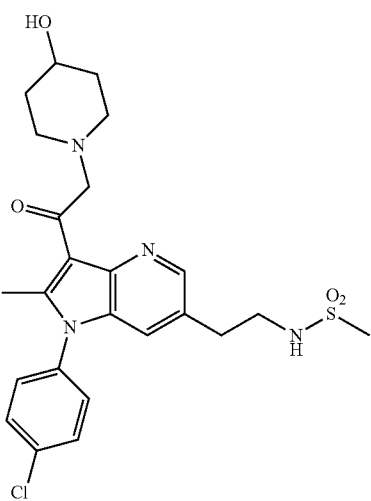 | 345 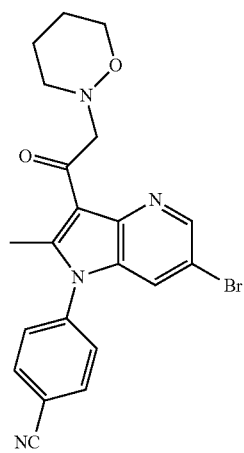 |
| 343 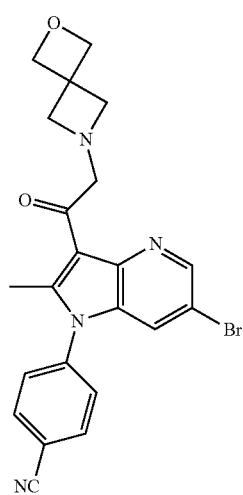 [SMILES: Cc1c(C(=O)CN2CC3(COC3)C2)c2ncc(Br)cc2n1-c1ccc(C#N)cc1] | 346 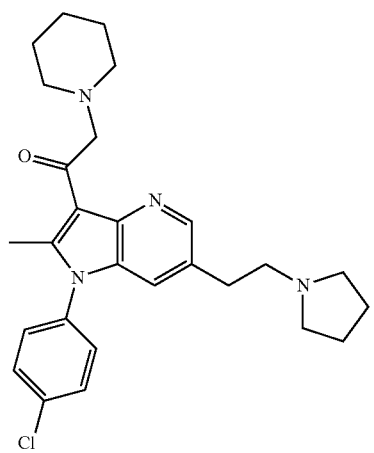 |
| 344 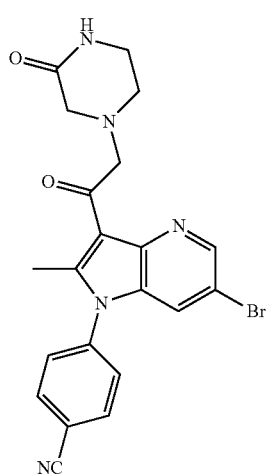 [SMILES: Cc1c(C(=O)CN2CCNC(=O)C2)c2ncc(Br)cc2n1-c1ccc(C#N)cc1] | 347 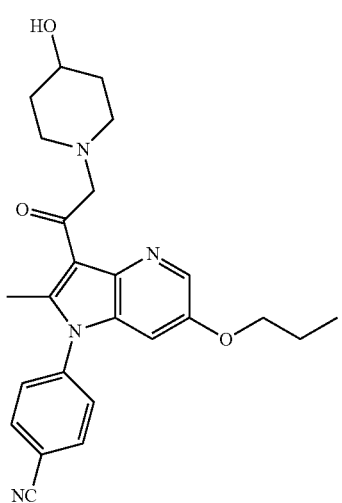 [SMILES: CCCOc1cnc2c(C(=O)CN3CCC(O)CC3)c(C)n(-c3ccc(C#N)cc3)c2c1] |

| 348 | 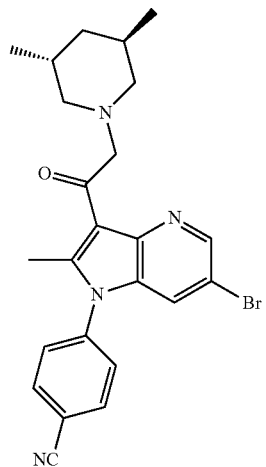 [SMILES: Cc1c(C(=O)CN2C[C@H](C)C[C@@H](C)C2)c2ncc(Br)cc2n1-c1ccc(C#N)cc1] | 351 | 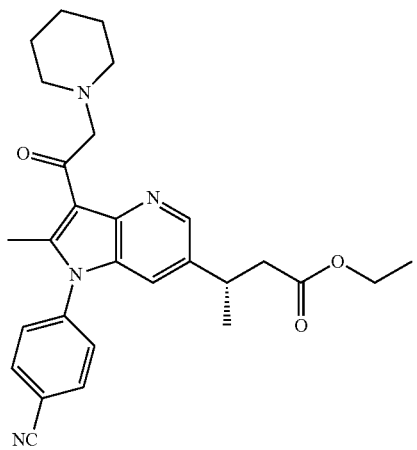 |
| --- | --- | --- | --- |
| 349 | 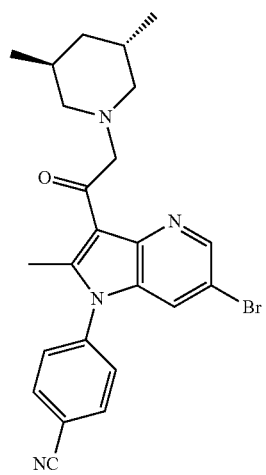 [SMILES: Cc1c(C(=O)CN2C[C@@H](C)C[C@H](C)C2)c2ncc(Br)cc2n1-c1ccc(C#N)cc1] | 352 | 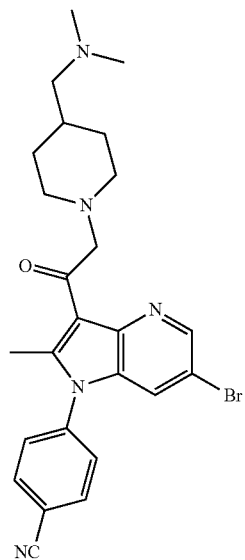 |
| 350 | 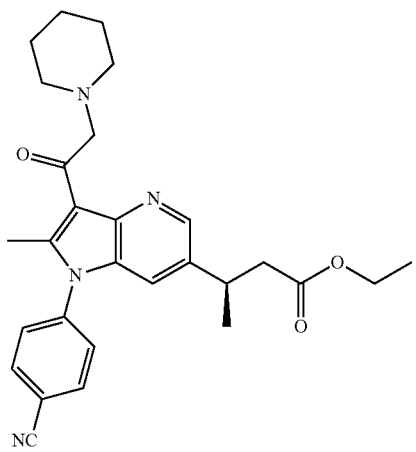 | 353 | 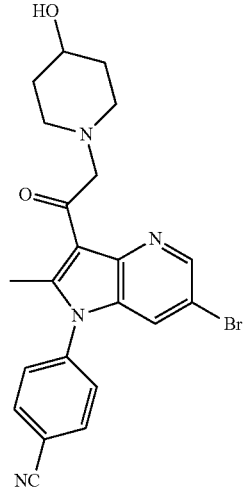 [SMILES: Cc1c(C(=O)CN2CCC(O)CC2)c2ncc(Br)cc2n1-c1ccc(C#N)cc1] |

| 567 -continued | 568 -continued |
|---|---|
| 354 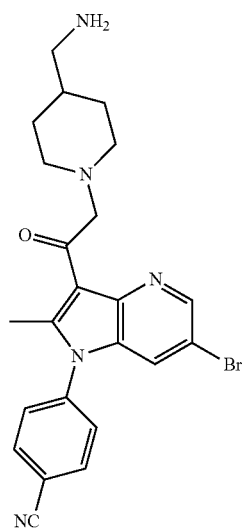 [SMILES: Cc1c(C(=O)CN2CCC(CN)CC2)c2ncc(Br)cc2n1-c1ccc(C#N)cc1] | 357 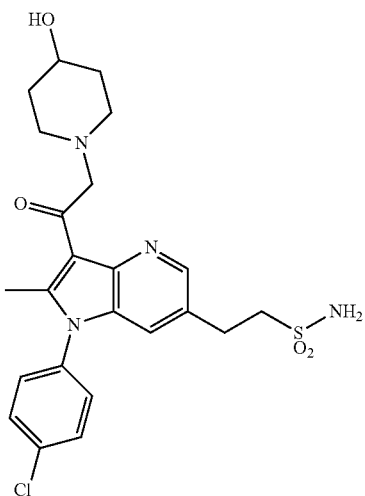 |
| 355 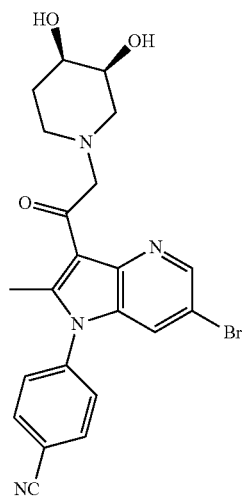 [SMILES: Cc1c(C(=O)CN2CC[C@@H](O)[C@@H](O)C2)c2ncc(Br)cc2n1-c1ccc(C#N)cc1] | 359 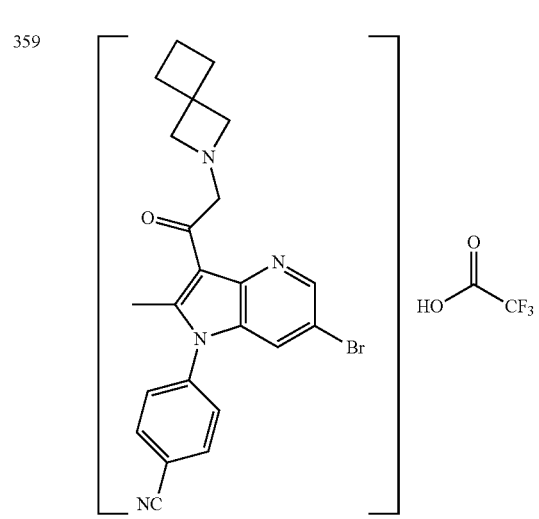 |
| 356 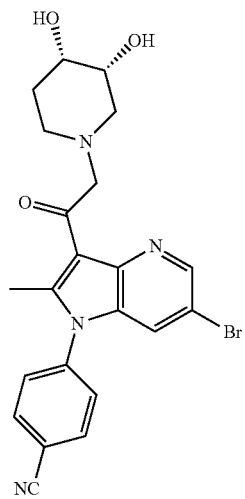 [SMILES: Cc1c(C(=O)CN2CC[C@H](O)[C@H](O)C2)c2ncc(Br)cc2n1-c1ccc(C#N)cc1] | 360 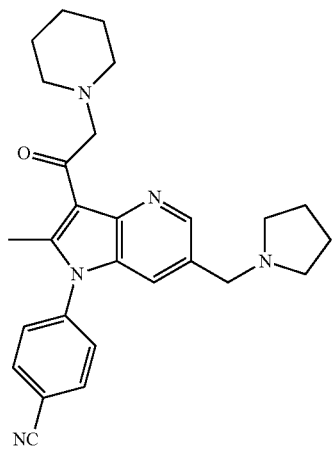 [SMILES: Cc1c(C(=O)CN2CCCCC2)c2ncc(CN3CCCC3)cc2n1-c1ccc(C#N)cc1] |

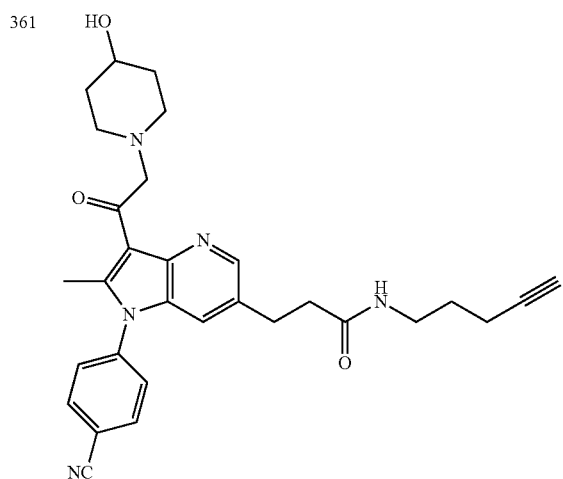
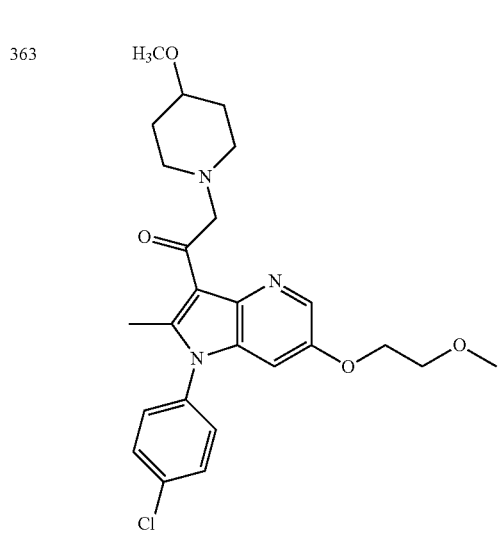
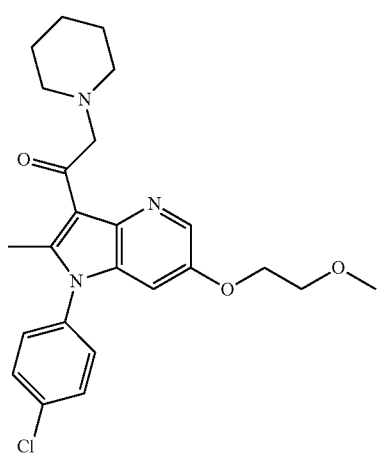
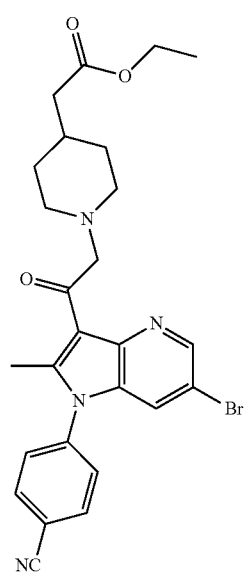 [SMILES: CCOC(=O)CC1CCN(CC(=O)c2c(C)n(-c3ccc(C#N)cc3)c3cc(Br)cnc23)CC1]
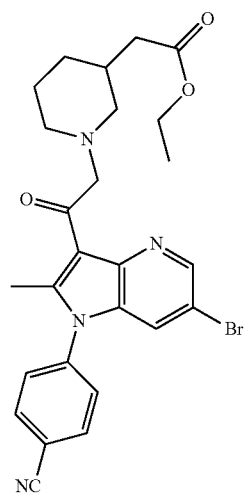 [SMILES: CCOC(=O)CC1CCCN(CC(=O)c2c(C)n(-c3ccc(C#N)cc3)c3cc(Br)cnc23)C1]

| | |
|---|---|
| 367 | 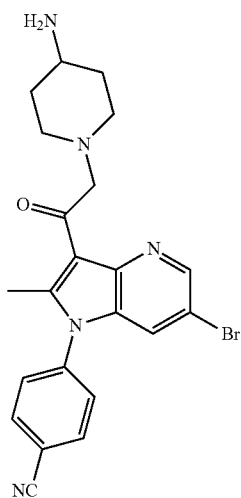 [SMILES: Cc1c(C(=O)CN2CCC(N)CC2)c2ncc(Br)cc2n1-c1ccc(C#N)cc1] |
| 368 | 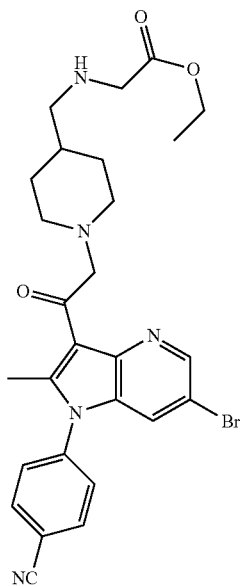 [SMILES: CCOC(=O)CNCC1CCN(CC(=O)c2c(C)n(-c3ccc(C#N)cc3)c3cc(Br)cnc23)CC1] |
| 369 | 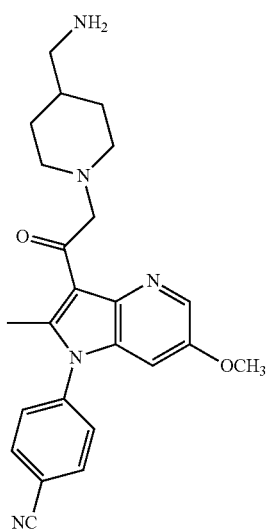 [SMILES: COc1cnc2c(C(=O)CN3CCC(CN)CC3)c(C)n(-c3ccc(C#N)cc3)c2c1] |
| 370 | 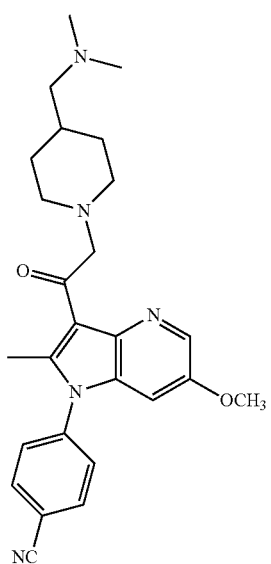 [SMILES: COc1cnc2c(C(=O)CN3CCC(CN(C)C)CC3)c(C)n(-c3ccc(C#N)cc3)c2c1] |
| 371 | 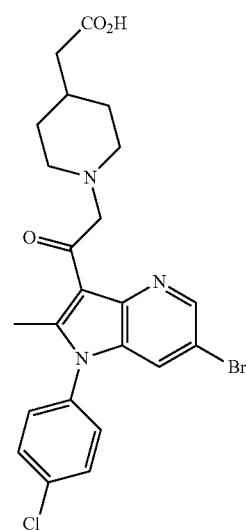 [SMILES: Cc1c(C(=O)CN2CCC(CC(=O)O)CC2)c2ncc(Br)cc2n1-c1ccc(Cl)cc1] |
| 372 | 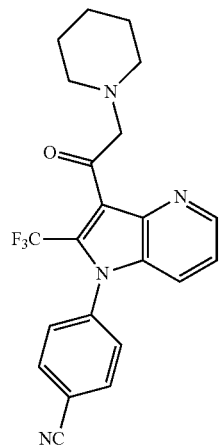 |

| 573 -continued | 574 -continued |
|---|---|
| 373 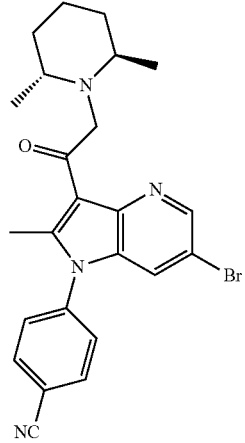 [SMILES: Cc1c(C(=O)CN2[C@H](C)CCC[C@H]2C)c2ncc(Br)cc2n1-c1ccc(C#N)cc1] | 382 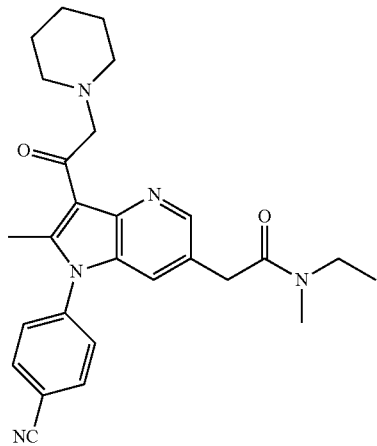 |
| 374 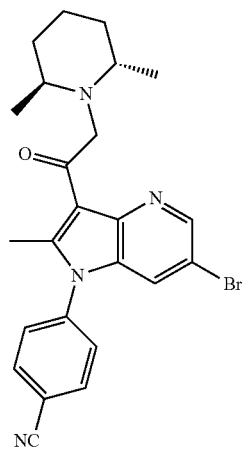 [SMILES: Cc1c(C(=O)CN2[C@@H](C)CCC[C@@H]2C)c2ncc(Br)cc2n1-c1ccc(C#N)cc1] | 383 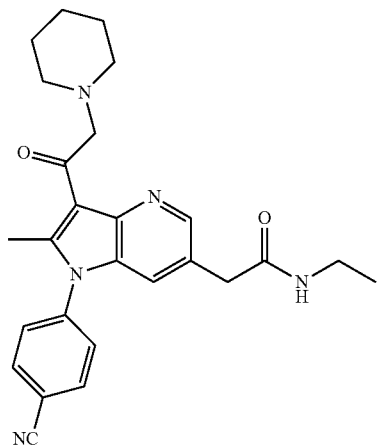 |
| 381 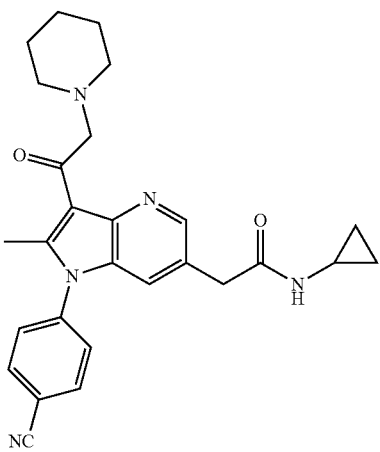 [SMILES: Cc1c(C(=O)CN2CCCCC2)c2ncc(CC(=O)NC3CC3)cc2n1-c1ccc(C#N)cc1] | 384 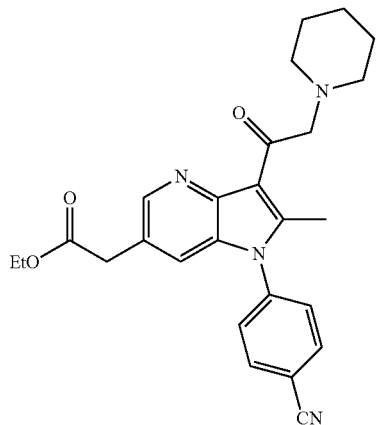 [SMILES: CCOC(=O)Cc1cnc2c(C(=O)CN3CCCCC3)c(C)n(-c3ccc(C#N)cc3)c2c1] |

| 385 | 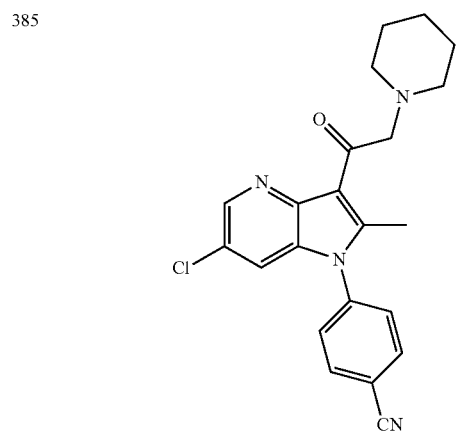 | 388 | 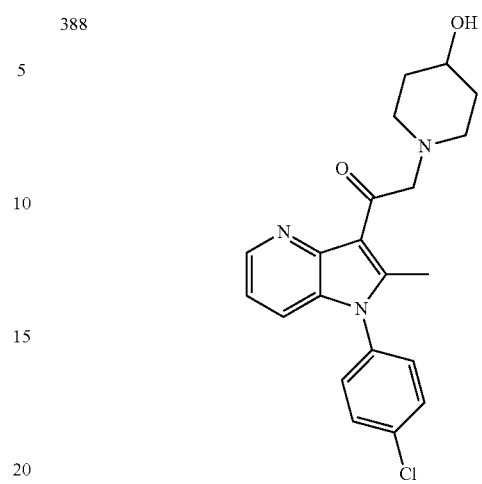 |
| 386 | 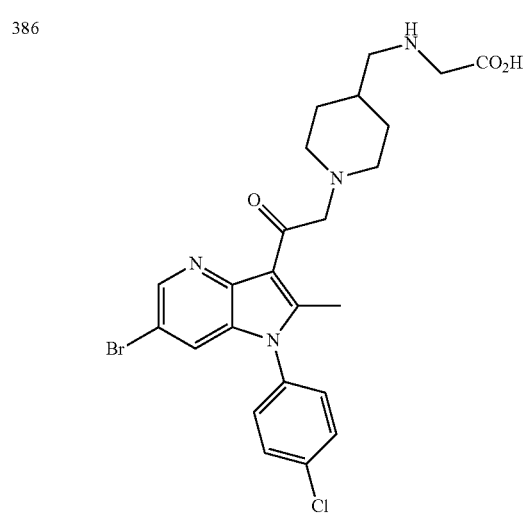 | 389 | 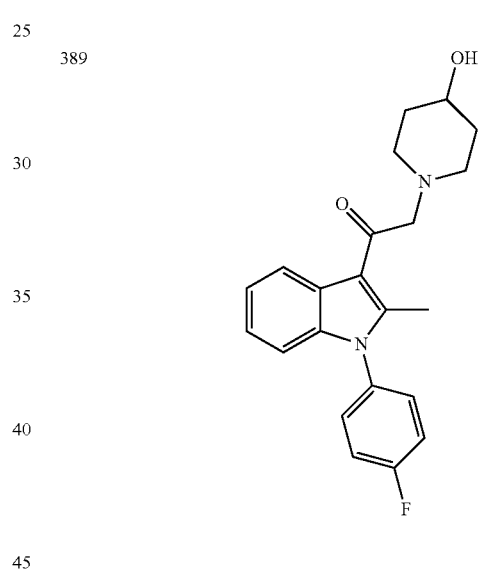 |
| 387 | 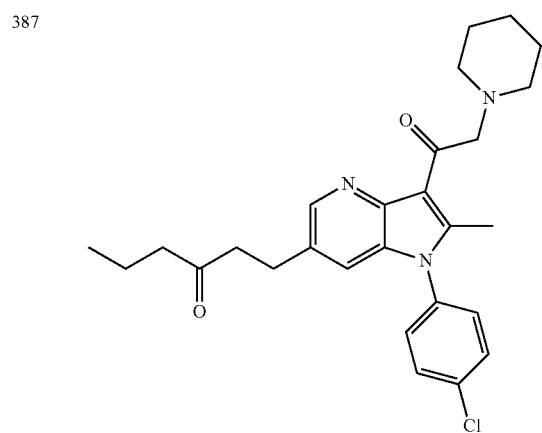 | 390 | 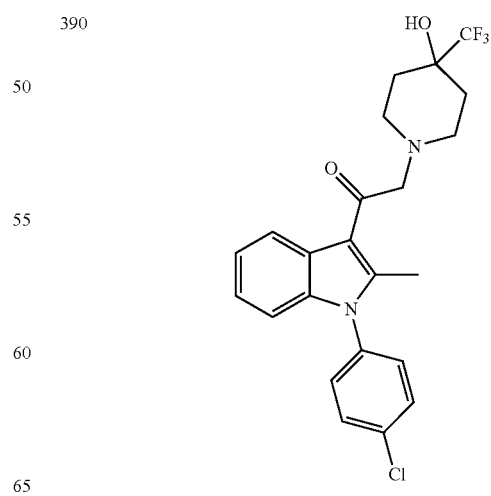 |

| 391 | 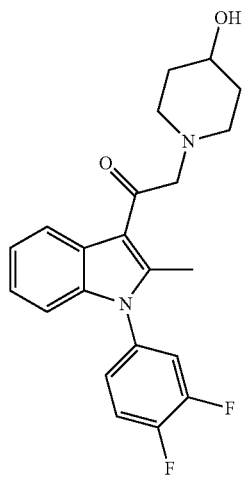 [SMILES: Cc1c(C(=O)CN2CCC(O)CC2)c2ccccc2n1-c1ccc(F)c(F)c1] |
|---|---|
| 392 | 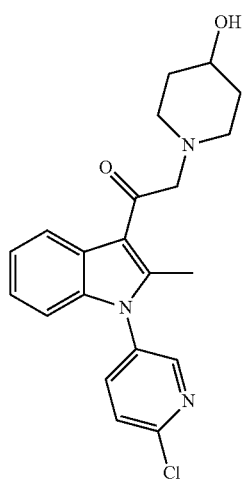 |
| 393 | 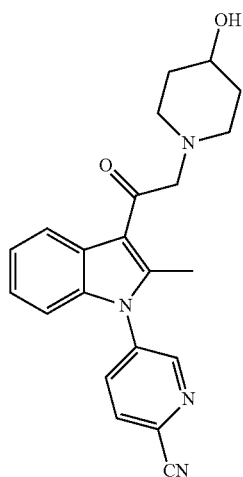 |
| 394 | 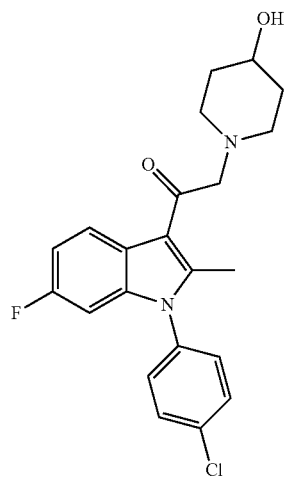 [SMILES: Cc1c(C(=O)CN2CCC(O)CC2)c2ccc(F)cc2n1-c1ccc(Cl)cc1] |
| 395 | 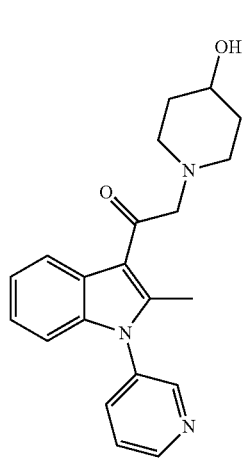 [SMILES: Cc1c(C(=O)CN2CCC(O)CC2)c2ccccc2n1-c1cccnc1] |
| 396 | 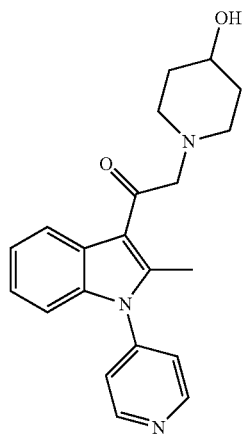 [SMILES: Cc1c(C(=O)CN2CCC(O)CC2)c2ccccc2n1-c1ccncc1] |

| 397 | 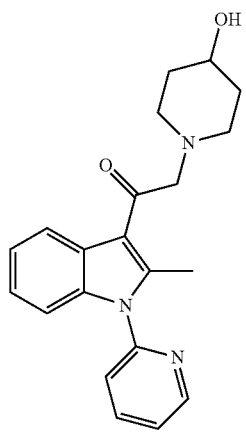 [SMILES: Cc1c(C(=O)CN2CCC(O)CC2)c2ccccc2n1-c1ccccn1] |
| --- | --- |
| 398 | 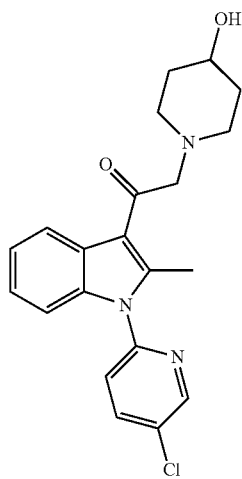 |
| 399 | 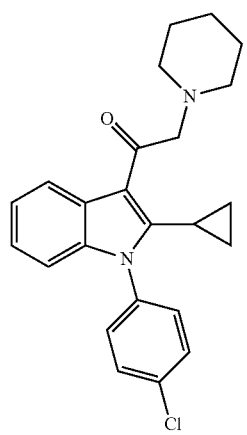 [SMILES: O=C(CN1CCCCC1)c1c(C2CC2)n(-c2ccc(Cl)cc2)c2ccccc12] |
| 400 | 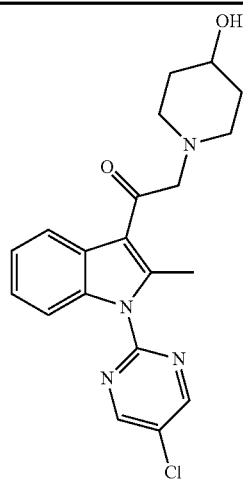 |
| --- | --- |
| 401 | 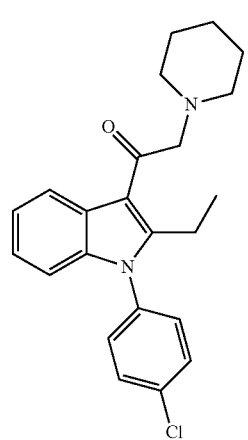 [SMILES: CCc1c(C(=O)CN2CCCCC2)c2ccccc2n1-c1ccc(Cl)cc1] |
| 402 | 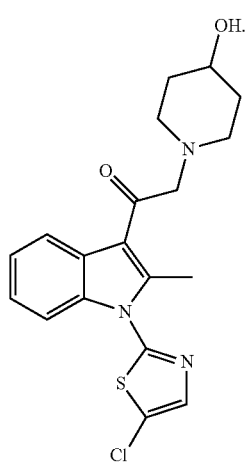 [SMILES: Cc1c(C(=O)CN2CCC(O)CC2)c2ccccc2n1-c1ncc(Cl)s1] |
* * * * *

UNITED STATES PATENT AND TRADEMARK OFFICE
CERTIFICATE OF CORRECTION

| | | |
|---|---|---|
| PATENT NO. | : 9,850,262 B2 | Page 1 of 1 |
| APPLICATION NO. | : 15/153379 | |
| DATED | : December 26, 2017 | |
| INVENTOR(S) | : Matthew Cullen et al. | |

It is certified that error appears in the above-identified patent and that said Letters Patent is hereby corrected as shown below:

In the Claims

<u>At Column 494</u>
In Claim 1, Line 23, after "independently" please insert --0--; and <u>At Column 495</u>
In Claim 11, Line 3, delete "$NRR_d$," and replace with --$\mathbf{NR_dR_d}$,--.

Signed and Sealed this
Twenty-second Day of May, 2018

Andrei Iancu
*Director of the United States Patent and Trademark Office*